US008263545B2

(12) United States Patent  
Levy et al.

(10) Patent No.: US 8,263,545 B2
(45) Date of Patent: Sep. 11, 2012

(54) GIP ANALOG AND HYBRID POLYPEPTIDES WITH SELECTABLE PROPERTIES

(75) Inventors: Odile Esther Levy, San Diego, CA (US); Alain D. Baron, San Diego, CA (US); Lawrence J. D'Souza, San Diego, CA (US); Mary Erickson, San Diego, CA (US); Soumitra S. Ghosh, San Diego, CA (US); Michael R. Hanley, San Diego, CA (US); Samuel Janssen, San Diego, CA (US); Carolyn M. Jodka, San Diego, CA (US); Diana Y. Lewis, San Diego, CA (US); Christine M. Mack, San Diego, CA (US); David G. Parkes, San Diego, CA (US); Richard A. Pittner, San Diego, CA (US); Christopher J. Soares, San Diego, CA (US); Ved Srivastava, San Diego, CA (US); Andrew A. Young, San Diego, CA (US); Thao Le, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 650 days.

(21) Appl. No.: 11/840,921

(22) Filed: Aug. 17, 2007

(65) Prior Publication Data

US 2008/0312157 A1    Dec. 18, 2008

Related U.S. Application Data

(63) Continuation-in-part of application No. 11/507,081, filed on Aug. 17, 2006, now abandoned.

(51) Int. Cl.
*A61K 38/00* (2006.01)
*A61P 3/10* (2006.01)

(52) U.S. Cl. .......................... 514/1.1; 514/6.8; 514/11.7

(58) Field of Classification Search ........................ None
See application file for complete search history.

(56) References Cited

U.S. PATENT DOCUMENTS

| | | | |
|---|---|---|---|
| 4,397,780 A | 8/1983 | Orlowski et al. |
| 4,401,593 A | 8/1983 | Orlowski et al. |
| 4,414,149 A | 11/1983 | Orlowski et al. |
| 4,444,981 A | 4/1984 | Goudie |
| 4,495,097 A | 1/1985 | Orlowski et al. |
| 4,497,731 A | 2/1985 | Orlowski et al. |
| 4,537,716 A | 8/1985 | Orlowski et al. |
| 4,597,900 A | 7/1986 | Orlowski et al. |
| 4,604,238 A | 8/1986 | Orlowski et al. |
| 4,606,856 A | 8/1986 | Seyler et al. |
| 4,652,627 A | 3/1987 | Kempe et al. |
| 4,687,839 A | 8/1987 | Kempe |
| 4,697,002 A | 9/1987 | Kempe |
| 5,188,666 A | 2/1993 | Boccardo |
| 5,234,906 A | 8/1993 | Young et al. |
| 5,512,549 A | 4/1996 | Chen et al. |
| 5,521,283 A | 5/1996 | DiMarchi et al. |
| 5,532,336 A | 7/1996 | DiMarchi et al. |
| 5,545,618 A | 8/1996 | Buckley et al. |
| 5,686,511 A | 11/1997 | Bobo |
| 5,739,106 A | 4/1998 | Rink et al. |
| 5,824,778 A | 10/1998 | Ishikawa et al. |
| 5,824,784 A | 10/1998 | Kinstler et al. |
| 5,846,937 A | 12/1998 | Drucker et al. |
| 5,998,204 A | 12/1999 | Tsien et al. |
| 5,998,367 A | 12/1999 | Gaeta et al. |
| 6,077,822 A | 6/2000 | Dyrsting et al. |
| 6,087,476 A | 7/2000 | Kenten et al. |
| 6,303,661 B1 | 10/2001 | Demuth et al. |
| 6,410,508 B1 | 6/2002 | Isales et al. |
| 6,514,500 B1 | 2/2003 | Bridon et al. |
| 6,528,486 B1 | 3/2003 | Larsen et al. |
| 6,747,006 B2 | 6/2004 | Efendic |
| 6,849,714 B1 | 2/2005 | Bridon et al. |
| 6,852,690 B1 | 2/2005 | Nauck et al. |
| 6,921,748 B1 | 7/2005 | O'Harte |
| 2002/0151495 A1 | 10/2002 | Wolfe et al. |
| 2003/0157107 A1 | 8/2003 | Miyawaki et al. |
| 2003/0186846 A1 | 10/2003 | Hoeg-Jensen et al. |
| 2003/0204063 A1 | 10/2003 | Gravel et al. |
| 2003/0221201 A1 | 11/2003 | Prior et al. |
| 2003/0232761 A1 | 12/2003 | Hinke et al. |
| 2004/0029805 A1 | 2/2004 | Wolfe et al. |
| 2004/0209803 A1 | 10/2004 | Baron et al. |
| 2004/0228846 A1 | 11/2004 | Pang et al. |

(Continued)

FOREIGN PATENT DOCUMENTS

DE    19616486 A1    7/1998

(Continued)

OTHER PUBLICATIONS

Bowie, Science, 247, 1306-1310, 1990.*
Vilsboll, T., Dan. Med Bull. vol. 51 364-370, 2004.*
Reda et al., Obesity Res. 10: 1087-1091, 2002.*
Wells, Biochemistry 29:8509-8517, 1990.
Ngo, et al., The Protein Folding Problem and Tertiary Structure Prediction, pp. 492-49, 1994.
Bork, Genome Research 10:398-400, 2000.
Skolnick, et al., Trends in Biotech. 18(1): 34-39, 2000.

(Continued)

*Primary Examiner* — Gyan Chandra

(57) ABSTRACT

The present invention relates generally to novel GIP analogs and GIP hybrid polypeptides with selectable properties, useful as agents for the treatment and prevention of metabolic diseases and disorders, for example those which can be alleviated by control plasma glucose levels, insulin levels, and/or insulin secretion, positive inotropic effects, reduction of catabolic effects, slowing of gastric emptying. Such conditions and disorders include, but are not limited to, hypertension, dyslipidemia, cardiovascular disease, eating disorders, critical care, insulin-resistance, obesity, and diabetes mellitus of any kind, including type 1, type 2, and gestational diabetes.

3 Claims, 88 Drawing Sheets

U.S. PATENT DOCUMENTS

| | | | |
|---|---|---|---|
| 2004/0242853 A1 | 12/2004 | Greig et al. | |
| 2005/0009147 A1 | 1/2005 | Bauer et al. | |
| 2005/0049177 A1 | 3/2005 | Bachovchin et al. | |

FOREIGN PATENT DOCUMENTS

| | | |
|---|---|---|
| DE | 19921537 A1 | 11/2000 |
| EP | 00479210 B1 | 8/1992 |
| EP | 0658568 A1 | 6/1995 |
| EP | 0708179 A1 | 4/1996 |
| EP | 0733644 A1 | 9/1996 |
| EP | 00869135 A1 | 10/1998 |
| EP | 0851763 B1 | 10/2002 |
| EP | 1421950 A1 | 5/2004 |
| EP | 1171465 B1 | 11/2007 |
| EP | 1283058 A1 | 11/2007 |
| WO | WO9111457 A1 | 8/1991 |
| WO | WO9210576 A1 | 6/1992 |
| WO | WO9519785 A1 | 7/1995 |
| WO | WO9605309 A2 | 2/1996 |
| WO | WO9622308 A2 | 7/1996 |
| WO | WO9622308 A3 | 7/1996 |
| WO | WO9640196 A1 | 12/1996 |
| WO | WO9702004 A2 | 1/1997 |
| WO | WO9715322 A1 | 5/1997 |
| WO | WO9727286 A1 | 7/1997 |
| WO | WO 9721980 A2 | 8/1997 |
| WO | WO9731621 A1 | 9/1997 |
| WO | WO9805351 A1 | 2/1998 |
| WO | WO9812224 A1 | 3/1998 |
| WO | WO9818486 A1 | 5/1998 |
| WO | WO9830231 A1 | 7/1998 |
| WO | WO9836763 A1 | 8/1998 |
| WO | WO9840477 A1 | 9/1998 |
| WO | WO9848831 A1 | 11/1998 |
| WO | WO9855139 A1 | 12/1998 |
| WO | WO9907404 A1 | 2/1999 |
| WO | WO9925727 A2 | 5/1999 |
| WO | WO9925728 A1 | 5/1999 |
| WO | WO9925728 A1 | 5/1999 |
| WO | WO0020592 A2 | 4/2000 |
| WO | WO0073331 A2 | 12/2000 |
| WO | WO01/44284 A2 | 6/2001 |
| WO | WO01/51078 A1 | 7/2001 |
| WO | WO0181919 A2 | 11/2001 |
| WO | WO0187341 A1 | 11/2001 |
| WO | WO0210195 A2 | 2/2002 |
| WO | WO03011892 A2 | 2/2003 |
| WO | WO03022304 A1 | 3/2003 |
| WO | WO03026591 A2 | 4/2003 |
| WO | WO 03/059934 * | 7/2003 |
| WO | WO03057235 A2 | 7/2003 |
| WO | WO030829898 A2 | 10/2003 |
| WO | WO03103572 A2 | 12/2003 |
| WO | WO03105760 A2 | 12/2003 |
| WO | WO031036972 A2 | 12/2003 |
| WO | WO2004037195 A2 | 5/2004 |
| WO | WO2004039832 A2 | 5/2004 |
| WO | WO2004/056313 A2 | 7/2004 |
| WO | WO2004067548 A2 | 8/2004 |
| WO | WO2004078127 A2 | 9/2004 |
| WO | WO2004103390 A2 | 12/2004 |
| WO | WO2005077072 A2 | 8/2005 |
| WO | WO2005082938 A2 | 9/2005 |
| WO | WO2006086769 A2 | 8/2006 |
| WO | WO2007/018619 | 2/2007 |
| WO | WO2007022123 A2 | 2/2007 |
| WO | WO0058360 A2 | 11/2007 |
| WO | WO2008021560 | 2/2008 |

OTHER PUBLICATIONS

ISR-PCT/US07/018, May 26, 2008, Amylin Pharmaceuticals, Inc.
Al-Sabah et al., "A Model for Receptor-Peptide Binding at the Glucagon-like Peptide-1-(GLP-1) . . . " British Journ. of Pharm. (2003) 140:339-346.
Anderson et al., "Medium-Dependence of the Second Structure of Exendin-4 & Glucagon-Like Peptide-1", Bioorganic & Med. Chem (2002) pp. 79-85.
Conlon et al., "Purification & Characterization of Insulin, Glucagon & Two Glucagon-Like Peptides . . . " (1998) Endocrinology 139:3442-3448.
Delmeire et al., "Prior in vitro exposure to GLP-1 with or without GIP can influence the subsequent . . . " (2004) Biochemical Pharm. 68, pp. 33-39.
Doyle et al., "Insertion of an N-Terminal 6-Aminohexaoic Acid after the 7 Amino Acid Position . . . " (2001) Endocrinology 142: 4462-4468.
Doyle et al., "The Importance of the Nine-Amino Acid C-Terminal Sequence for Binding to the GLP-1 . . . " (2003) Regulatory Peptides 114:153-158.
Elahi et al., "The Insulinotropic Action of Glucose Dependent Insulinoropic Polypeptide (GIP) and Glucagon-Like . . . " (1994) Regulatory Peptides 51:63-74.
Eng, John, "Prolonged Effect of Exendin 4 on Hyperglycemia of db/db mice", Diabetes (1996) 45:152A Abstract 554.
Fehmann et al., "Cell & Molecular Biology of the Incretin Hormones Glucagon Like Peptide-I . . . " Endocrine Reviews (1995) vol. 16, No. 3: 390-410.
Furman et al., "Targeting B-Cell Cyclic 3'5' Adenosine Monophosphate . . . " Journ. of Pharmacy and Pharmacology (2004) 56:1477-1492.
Gallwitz et al., "Binding Specificity and Signal Transduction of Receptors for Glucagon-Like Peptide . . . " Journ. of Molec. Endocr. (1993) 10: 259-268.
Gallwitz et al., "GLP-1/GIP Chimeric Peptides Define the Structural Requirements for Specific Ligand . . . " Regulatory Peptides (1996) 63:17-22.
Gault et al., "Stability of GIP and Amino-Terminally Modified GIP Analogues to DPP IV . . . " Univ. of Ulster #10; Digestion (1999) 60:501-513.
Gault et al., "Glucose-Dependent Insulinotropic Polypeptide Analogues and their Therapeutic . . . " Biochem & Biophys. Res. Comm (2003) 308:207-213.
Green et al., "Comparative effects of GLP-1 and GIP on cAMP Production Insulin Secretion . . . " Biochem. & Biophys. (2004) 428:136-143.
Hinke et al, "Dipeptidyl Peptidase IV-Resistant [D-Ala2] Glucose-Dependent . . . " Diabetes (2002) 51:652-661.
Hinke et al., "In Depth Analysis of the N-Terminal Bioactive Domain of Gastric Inhibitory . . . " Life Sciences (2004) 75:1857-1870.
Hinke et al., [Ser2] and [Ser(P)2] Incretin Analogs (2004) Journal of Biological Chemistry, vol. 279:3998-4006.
Holst, et al., The Pathogeneisis of NIDDM Involves a Defective Expression of the GIP Receptor, Diabetologia (1997) 40:984-986.
Hudson et al., "Exenatide: NMR/CD Evaluation of the Medium Dependence of Conformation and Aggregation State" Biopolymers (2004) 76:298-308.
Hupe-Sodmann et al., "Characterization of the Processing of Human Neutral Endopeptidase 24.11 of GLP . . . " Regulatory Peptides (1995) 58:149-156.
Irwin et al., "Degradation, Insulin Secretion and Antihyperglycemic Actions of Two Palmitate . . . " J. Med. Chem (2005) 48:1244-1250.
Irwin et al., "GIP (LYS16PAL) and GIP (LYS37PAL) Novel Long-Acting Acylated Analogues . . . " J. Med. (2006 49:1047-1054.
Kieffer et al., "Degradation of Glucose-Dependent Insulinotropic Polypeptide and Truncated . . . " Endocrinology (1995) 136:3585-3596.
Kuhn-Wache et al., "Analogs of Glucose-Dependent Insulinotropic Polypeptide with Increased . . . " Cell Peptidases (2000) 2:187-195.
Lin et al., "The Helical Alanine Controversy: An (Ala)6 Insertion Dramatically . . . " J. Am. Chem. Soc. (2004) 126:13679-13684.
Manhart et al., "Structure-Function Analysis of a Series of Novel GIP Analogues . . . " Biochemistry (2003) 42:3081-3088.
Meier et al., "Glucose-Dependent Insulinotropic Polypeptide/Gastric . . ." Best Prac. & Res. Clin. Endocrin. & Metab. (2004) 18(4):587-606.
Meier et al., "Stimulation of Insulin Secretion by Intravenous Bolus . . . " Diabetes 53( Supp. 3) 2004:S220-S224.
Montrose et al., "High Potency Antagonists for the Pancreatic Glucagon . . . " The Jour. of Bio. Chem. (1997) vol. 272, No. 34:21201-21206.

Morrow et al., "The Insulinotropic Region of Gastric Inhibitory . . ." Can. J. Physiol. Pharmacol. (1996) 74:65-72.

Nauck et al., "Preserved Incretin Activity of Glucagon-Like Peptide . . ." J. Clin. Invest. (1993) 91:301-307.

Neidigh et al., "Exendin-4 and Glucagon-like Peptide-1: NMR Structural . . ." Biochemistry (2001) 40:13188-13200.

O'Harte et al., "Effects of Non-Glycated and Glycated Glucagon-Like . . ." Peptides (1997) vol. 18, No. 9:1327-1333.

O'Harte et al., "Amino Terminal Glycation of Gastric Inhibitory Polypeptide . . ." Biochimica et Biophysica Act (1998) 1425:319-327.

O'Harte et al., "Glycation of Glucagon-Like Peptide-1(7-36) amide: . . ." Diabetologias (1998) 41:1187-1193.

O'Harte et al., "NH2-Terminally Modified Gastric Inhibitory Polypeptide . . ." Diabetes (1999) 48:758-765.

O'Harte et al.., "Degradation and Glycemic Effects of His7-Glucitol . . ." Regulatory Peptides (2001) 96:95-104.

Pauly et al., "Investigation of Glucose-Dependent Insulinotropic . . ." The Journ. of Bio. Chem. (1996) vol. 271, No. 38:23222-23229.

Pederson et al., "The Exteroinsular Axis in Depeptidyl Peptidase IV . . ." Metabolism 1996) vol. 45, No. 11: 1335-1341.

Plamboeck et al., "Neutral Endopeptidase 24.11 and Dipeptidyl Petidase . . ." Dipeptidyl Aminopeptidases in Health and Disease (2003) pp. 303-312.

Siegal et al., "Comparison of the Effect of Native Glucagon-Like Peptide . . . " European Journal of Clinical Investigation (1999) 29:610-614.

Thum et al., "Endoproteolysis by Isolated Membrane Peptidases Reveal . . . " Exp. Clin. Endocrinol. Diabetes (2002) 110:113-118.

Gault et al., "DPP IV Resistance & Insulin Releasing Activity of a Novel Di-Substituted . . . " Cell Biol. Int'l. (2003) 27:41-46.

Gault et al., "Degradation, Cyclic Adenosine Monophosphate Production, Insulin Secretion . . . " Metabolism (2003) 52:679-687.

Gault et al., "Improved Biological Activity of Gly2-and Ser2-Substituted Analogues . . . " Journ. of Endocr. (2003) 176:133-141.

Gault et al., "Glucose-Dependent Insulinotropic Polypeptide (GIP): Anti-Diabetic and Anti-Obesity . . >" Neuropeptides (2003) 37:253-263.

Gault et al., "Characterization of the Cellular and Metabolic Effects of a Novel Enzyme . . . " Biochem. & Biophys. Res. Comm. (2002) 290:1420-1426.

Hinke et al., "Structure-Activity Relationships of Glucose-Dependent Insulinotiropic.." Biol. Chem., (2003) 384:403-407.

Demuth, et al., Chemical Abstracts 127;69 abstract 341803D (1997).

Clodfelter, Dean K., et al., "Effects of Non-Covalent Self-Association on the Subcutaneous Absorption of a Therapeutic Peptide", Pharmaceutical Research, vol. 15, No. 2, 1998, pp. 254-262.

Deacon, C.F., et al., "Dipeptidyl Peptidase IV Resistant Analogues of Glucagon-Like Peptide-1 Which Have Extended Metabolic Stability and Improved Biological Activity", Diabetologia (1998) 41, pp. 271-278.

Deacon, C.F., et al., "Dipeptidyl Peptidase IV Inhibition Potentiates the Insulinotropic Effect of Glucoagon-Like Peptide 1 in the Anesthetized Pig", Diabetes, vol. 47, May 1998, pp. 764-769.

Frohman, Lawrence A., et al., "Rapid Enymatic Degradation of Growth Hormone-releasing Hormone by Plasma In Vitro and In Vivo to a Biologically Inactive Product Cleaved at the NH2 Terminus", J. Clin. Invest, vol. 78, Oct. 1986, pp. 906-913.

Frohman, Lawrence A., et al., "Dipeptidylpeptidase IV and Trypsin-like Enzymatic Degradation of Human Growth Hormone-releasing Hormone in Plasma", J. Clin. Invest, vol. 83, May 1989, pp. 1533-1540.

Pederson, Raymond A., et al., "Improved Glucose Tolerance in Zucker Fatty Rats in Oral Administration of the Dipeptidyl Peptidase IV Inhibitor Isoleucine Thiazolidide", Diabetes, vol. 47, Aug. 1998, pp. 1253-1258.

Rossowski, Wojciech J., et al., "Reduced Gastric Acid Inhibory Effect of a pGIP(1-30)NH2 Fragment with Potent Pancreatic Amylase Inhibitory Activity", Regulatory Peptides, vol. 39, 1992, pp. 9-17.

Wheeler, Michael B., et al., "Functional Expression of the Rat Pancreatic Islet Glucose-Dependent Insulinotropic Polypeptide Receptor: Ligand Binding and Intracellular Signaling Properties", Endocrinology, vol. 136, No. 10, 1995, pp. 4629-4639.

Andreu, David, et al "Shortened Cecropin A-Melittin Hybrids", FEBS (1992) 190-194, 296 (2).

Aponte, Gregory W., et al "Meal-Induced Peptide Tyrosine Tyrosine Inhibition of Pancreatic Secretion in the Rat", FASEB J (1989) 1949-1955, 3.

Becker, K. L., et al "Procalcitonin and the Calcitonin Gene Family of Peptides in Inflammation . . . ", JCEM (2004) 1512-1525, 89 (4).

Bhavsar, Sunil, et al "Synergy Between Amylin and Cholecystokinin for Inhibition of Food Intake in Mice", Physiol. & Behavior (1998) 557-561, 64.

Campfield, L. Arthur, et al "Recombinant Mouse OB Protein: Evidence for a Peripheral Signal Linking Adiposity and Central Neural Networks", Science (1995) 546-549, 269.

Cooper, G. J. S., et al "Amylin and the Amylin Gene: Structure, Function and Relationship to Islet Amyloid and to Diabetes Mellitus", Biochim Biophys Acta (1989) 247-258, 1014.

Cooper, G. J. S., et al "Purification and Characterization of a Peptide from Amyloid-Rich Pancreases of Type 2 Diabetic Patients", Proc. Natl. Acad. Sci. (1987) 8628-8632, 84.

Cox, James E., "Inhibitory Effects of Cholecystokinin Develop Through Interaction With Duodenal Signals", Behav Brain Res (1990) 35-44, 38.

Crawley, Jacqueline N., et al "Biological Actions of Cholecystokinin", Peptides (1994) 731-755, 15 (4).

Dasgupta, P., et al "Antiproliferative and GH-Inhibitory Activity of Chimeric Peptides Consisting of GHRP-6 and Somatostatin", Biochem Biophys Res Commun (1999) 379-384, 259.

Dulawa, Stephanie C., et al "Cholecystokinin and Estradiol Synergistically Potentiate Satiety in Rats" Peptides (1994) 913-918, 15(5).

Eberlein, Gert A., et al "A New Molecular Form of PYY: Structural Characterization of Human PYY(3-36) and PYY (1-36)" Peptides (1989) 797-803, 10.

Farquhar, Michelle, et al "Novel Mastoparan Analogs Induce Differential Secretion from Mast Cells", Chem Biol (2002) 63-70, 9.

Goke, R., et al "Glucagon-Like Peptide-1 (7-36) Amide is a New Incretin/Enterogastrone Candidate" J Biol Chem (1991) 135-144, 21.

Goke, R., et al "Exendin-4 is a High Potency Agonist and Truncated Exendin-(9-39)-amide an Antagonist . . . ", J Biol Chem (1993) 19650-19655, 268(26).

Grandt, D., et al "Two Molecular Forms of Peptide YY (PYY) are Abundant in Human Blood: Characterization . . . ", Regulatory Peptides (1994) 151-159, 51.

Halaas, Jeffrey L., et al "Weight-Reducing Effects of the Plasma Protein Encoded by the Obese Gene", Science (1995) 543-546, 269.

Hinson, Joy P., et al "Adrenomedullin, a Multifunctional Regulatory Peptide", Endocrine Reviews (2000) 138-167, 21(2).

Hinton, Veronica, et al "Combined Injection Potentiates the Satiety Effects of Pancreatic Glucagon, Cholecystokinin, and Bombesin", Brain Res Bull (1986) 615-619, 17.

Hojo, Keiko, et al "Amino Acids and Peptides. Part 39:A Bivalent Poly(ethylene glycol) Hybrid Containing . . . " Bioorg Med Chem Lett (2001) 1429-1432, 11.

Howl, John, et al "Chimeric Hormones and Neuropeptides", Clin Sci (1997) 605-606, 93.

Howl, John, et al "Chimeric Strategies for the Rational Design of Bioactive Analogs of Small Peptide Hormones", FASEB J. (1997) 582-590, 11.

Keire, David A., et al "Solution Structure of Monomeric Peptide YY Supports the Functional Significance of the PP-Fold", Biochemistry (2600) 9935-9942, 39.

Kimmel, Joe R., et al "Isolation and Characterization of chicken Insulin" Endocrinology (1968) 1323-1330, 83.

Le Sauter, Joseph, et al "Pancreatic Glucagon and Cholecystokinin Synergistically Inhibit Sham Feeding in Rats" Am J Physiol (1987) R719-R725, 253.

Lieverse, R. J., et al "Role of Cholecystokinin in the Regulation of Satiation and Satiety in Humans", Ann N.Y. Acad Sci (1994) 268-272, 713.

Lutz, T. A., et al "Different Influence of CGRP (8-37), an Amylin and CGRP Antagonist, on the Anorectic Effects . . . " Peptides (1997) 643-649, 18(5).

Mezna, Mokdad, et al "Calcium-Mobilizing Actions of Chimeric Hormone-Mastoparan Peptides" Biochem Soc Trans (1997) 450S, 25.

Mohri, Hiroshi, et al "Effects of Hybrid Peptide Analogs to Receptor Recognition Domains on . . ." Thromb Haemost (1993) 490-495, 69.

Mojsov, Svetlana "Structural Requirements for Biological Activity of Glucagon-like Peptide-1" Int J Pept Protein Res (1992) 333-343, 40.

Montrose-Rafizadeh, C., et al "Structure-Function Analysis of Exendin-4 GLP-1 Analogs", Diabetes (1996) 152A, 45 (abstract 553).

Pelleymounter, Mary Ann, et al "Effects of the Obese Gene Product on Body Weight Regulation in Ob/Ob Mice", Science (1995) 540-543, 269.

Raufman, Jean-Pierre, et al "Exendin-3, a Novel Peptide from Heloderma Horridum Venom, Interacts with Vasoactive . . .", J. Biol Chem (1991) 2897-2902, 266.

Roh, Jaesook, et al "Intermedin Is a Calcitonin/Calcitonin Gene-related Peptide Family Peptide Acting through the Calcitonin . . .", J Biol Chem (2004) 7264-7274, 279.

Sexton, P. M., et al "Calcitonin", Current Medicinal Chemistry (1999) 1067-1093, 6.

Schepp, Wolfgang, et al "Exendin-4 and Exendin-(9-39) NH2:Agonist and Antagonist, Respectively . . .", Eur J Pharmacol (1994) 183-191, 269.

Shin, Song Yub, et al "Cecropin A-Magainin 2 Hybrid Peptides Having Potent Antimicrobial Activity with Low Hemolytic Effect" Biochem Mol Biol Int (1998) 1119-1126, 44(6).

Smith, G. P., et al "Satiating Effect of Cholecystokinin" Ann N.Y. Acad Sci (1994) 236-241, 713.

Tatemoto, Kazuhiko "Isolation and Characterization of Peptide YY (PYY), a Candidate Gut Hormone that Inhibits Pancreatic . . ." Proc Natl Acad Sci (1982) 2514-2518, 79(8).

Tatemoto, Kuzahiko, et al "Neuropeptide Y: Complete Amino Acid Sequence of the Brain Peptide" Proc Natl Acad Sci (1982) 5485-5489, 79(18).

Tatemoto, Kazuhiko, et al "Neuropeptide Y—A Novel Brain Peptide with Structural Similarities to Peptide YY and Pancreatic Polypeptide", Nature (1982) 659-660, 296.

Teyssen, Stephan, et al "Inhibition of Canine Exocrine Pancreatic Secretion by Peptide YY is Mediated by PYY-Preferring Y2 Receptors", Pancreas (1996) 80-88, 13(1).

Udvardy, M., et al "Hybrid Peptide Containing RGDF (Arg-Gly-Asp-Phe) Coupled with the Carboxy Terminal . . ." Blood Coagul Fibrinolysis (1995) 11-16, 6.

Wade, D., et al "Antibacterial Peptides Designed as Analogs or Hybrids of Cecropins and Melittin" Int J Pept Protein Res (1992) 429-436, 40.

Walsh, John H. "Gastrointestinal Hormones", Johnson, L.R., New York:Raven Press (1994) 1-128, 3rd Edition.

Weigle, David S., et al "Recombinant ob Protein Reduces Feeding and Body Weight in the ob/ob Mouse", J Clin Invest (1995) 2065-2070, 96.

Wimalawansa, Sunil J., et al "Amylin, Calcitonin Gene-Related Peptide, Calcitonin, and Adrenomedullin: A Peptide Superfamily", Crit Rev Neurobiol (1997) 167-239, 11(2-3).

Zhang, Lianshan, et al "Preparation of Functionally Active Cell-Permeable Peptides by Single-Step Ligation of Two Peptide Modules" Proc Natl Acad Sci (1998) 9184-9189, 95.

Fuji et al., "Studies on Peptides. CXXXIX. Solution Synthesis of a 42-Residue Peptide . . . " Chem. Pharm. Bull 34*6):2397-2410 (1986).

Gelling, et al., "Minor-N-Terminal Modification of Glucose-Dependent Insulinotropic Polyeptpide (GIP) . . . " AbstractP-2-29, Tenth Int'l. Congress of Endo. Jun. 12-13, 1996. SF.

Fujii et al., "Studies on Peptides. CXXXIX. Solution Synthesis of a 42-Residue Peptide Corresponding to the Entire Amino Acid . . . " Chem. Pharm. Bull. 34(6):2397-2410 (1986).

Gallwitz et al., "Binding Specificity and Signal Transduction of Receptors for Glucagon-like Peptide-1(7-36) Amide and Gastric . . . " J. Mol. Endocrinology 10:259-268 (1993).

Gelling et al., "Minor N-Terminal Modification of Glucose-Dependent Insulin . . ."Abstract P2-29, Tenth International Congress of Endocrinology, Jun. 12, 13, 1996, San Francisco.

Gelling et al., "Localization of the Domains Involved in Ligand Binding and Activation of the Glucose-Department . . . " Endocrinology 138:2640-2643 (1997)

Gelling et al., "GIP6-30 Amide Contains the High Affinity Binding Region of GIP and is a Potent Inhibitor of GIP1-42 Action in Vitro" Regulatory Peptides 69:151-154 (1997).

Gelling, Ph.D. "Structure-Function Studies of the Gastric Inhibitory Polypeptide/glucose Dependent Insulinotropic Polypeptide (GIP) Receptor" Thesis, Oct. 1998.

Jornvall et al., "Amino acid sequence and heterogeneity of gastric inhibitory polypeptide (GIP)" FEBS Letters 123:205-210 (1981).

Kurtzhals et al., "Albumin Binding of Insulins Acylated with Fatty Acids: Characterization of the Ligand-Protein Interaction . . . " Biochem. J. 312:725-731 (1995).

McIntosh et al., "GIP Receptors and Signal-transduction Mechanisms" Acta Physiol. Scand. 157:361-365 (1996).

Mentlein, "Proline Residues in the Maturation and Degradation of Peptide Hormones and Neuropeptides" FEBS Letters 234:251-256 (1988).

Mentlein et al., "Dipeptidyl-peptidase IV hydrolyses gastric inhibitory polypeptide, glucagon-like peptide-1(7-36)amide, peptide . . . " Eur. J. Biochem. 214:829-835 (1993).

Mooney et al., "Effect of Tyr1-Glucitol GIP on Insulin Release and Glucose Homeostasis in Obese Diabetic Mice," Scientific Meeting; Digestion 60:505 (1999).

Mohri, Hiroshi, et al., "Effects of Hybrid Peptide Analogs to Receptor Recognition Domains on . . . " Thromb. Haemost (1993) 490-495, 69.

Irwin et al., "A Novel, Long-Acting Agonist of Glucose-Dependent . . . " Journ. of Pharm. and Exper. Therapeutics; vol. 314(3) (2005).

O'Harte et al., "Gastric Inhibitory Polypeptide and Effects of Glycation on Glucose . . . " Journal of Endocrinology (1998) 156, 237-243.

O'Harte et al., "NH2-Terminally Modified Gastric Inhibitory Polypeptide Exhibits Aminopeptidase Resistance . . . " Chemical Abstracts 131:122 (1999).

O'Harte et al., "Improved Glycaemic Control in Obese Diabetic OB/OB Mice Using N-Terminally Modified Gastric Inhibitory Polypeptide . . . " J. Endocrinology 165:639-648 (2000).

Schmidt et al., "Commercially Available Preparations of Porcine Glucose-Dependent Insulinotropic . . . " Endocrinology 120:835-837 (1987).

Shin, Song Yu et al., "Cecropin A-Magainin 2 Hybrid Peptides Having a Potent Antimicrobial . . . " Biochem. Mol. Biol. Int. (1998) 1119-1126,44(6).

Smith, G.P. et al., "Satiating Effect of Cholecystokinin" Ann. N.Y. Acad. Sci. (1994) 236-241, 713.

Udvardy, M., et al., "Hybrid Peptide Containing RGDF (Arg-Gly-Asp-Phe) Coupled with the Carboxy Terminal . . . " Blood Coagul Fibrinolysis (1995) 11-16, 6.

Walsh, John H. "Gastrointestinal Hormones", Johnson, L.R., New York: Raven Press (1994) 1-128, 3rd Edition.

Zhang L. et al., Preparation of Functionally Active Cell-Permeable Peptides Proc. Natl. Acad. Sci. USA, vol. 95, pp. 9184-9189, (1998).

* cited by examiner

Fig. 2

| SEQ ID NO: | Name | Sequence | GIP RBA | GLP RBA | Glucagon RBA | OGTT glucose lowering (%) |
|---|---|---|---|---|---|---|
| 2 | GIP Human | YAEGTFISDYSIAMDKIHQQDFVNWLLAQKGKKNDWKHNITQ-OH | 0.29 | | | -10 |
| 413 | GIP (1-30), Amide, Porcine | YAEGTFISDYSIAMDKIRQQDFVNWLLAQK-NH2 | 0.30 | >1000 | >1000 | TBD |
| 3 | GIP(1-30), Acid, Human | YAEGTFISDYSIAMDKIHQQDFVNWLLAQK-OH | 23 | >1000 | >1000 | 1 |
| 293 | GIP(1-30), Amide, Human | YAEGTFISDYSIAMDKIHQQDFVNWLLAQK-NH2 | 1.0 | >1000 | >1000 | -9 |
| 414 | GIP(1-30)-EX (31-39), Amide, Human | YAEGTFISDYSIAMDKIHQQDFVNWLLAQKPSSGAPPPS-NH2 | 3.1 | >1000 | >1000 | -22 |
| 294 | HG-GIP(1-30), Amide, Human | HGEGTFISDYSIAMDKIHQQDFVNWLLAQK-NH2 | 361 | >1000 | >1000 | -10 |
| 415 | HG-GIP(1-30)-EX (31-39), Amide, Human | HGEGTFISDYSIAMDKIHQQDFVNWLLAQKPSSGAPPPS-NH2 | 351 | >1000 | >1000 | -12 |
| 295 | YS-GIP(1-30), Acid, Human | YSEGTFISDYSIAMDKIHQQDFVNWLLAQK-OH | >1000 | >1000 | >1000 | TBD |
| 296 | [Ser2] GIP-(1-30) human, amide | YSEGTFISDYSIAMDKIHQQDFVNWLLAQK-NH2 | 2.6 | >1000 | >1000 | TBD |
| 416 | YS-GIP(1-30)-EX (31-39), Amide, Human | YSEGTFISDYSIAMDKIHQQDFVNWLLAQKPSSGAPPPS-NH2 | 3.1 | >1000 | >1000 | -26 |
| 297 | YG-GIP(1-30), Amide, Human | YGEGTFISDYSIAMDKIHQQDFVNWLLAQK-OH | >1000 | >1000 | >1000 | TBD |
| 417 | YG-GIP(1-30)-EX (31-39), Amide, Human | YGEGTFISDYSIAMDKIHQQDFVNWLLAQKPSSGAPPPS-NH2 | 8.1 | >1000 | >1000 | TBD |
| 3 | Ya-GIP(1-30), Acid, Human | YaEGTFISDYSIAMDKIHQQDFVNWLLAQK-OH | >1000 | >1000 | >1000 | TBD |
| 186 | Ya-GIP(1-30)-EX (31-39), Amide, Human | YaEGTFISDYSIAMDKIHQQDFVNWLLAQKPSSGAPPPS-NH2 | 3.8 | >1000 | >1000 | -23 |
| 298 | AcGIP(1-42)-COOH | Ac-YAEGTFISDYSIAMDKIHQQDFVNWLLAQKGKKNDWKHNITQ-OH | TBD | TBD | TBD | TBD |
| 291 | Pro3[GIP(1-42)]-COOH | YAPGTFISDYSIAMDKIHQQDFVNWLLAQKGKKNDWKHNITQ-OH | TBD | TBD | TBD | TBD |
| 292 | Pro3[GIP(1-30)]-NH2 | YAPGTFISDYSIAMDKIHQQDFVNWLLAQK-NH2 | TBD | TBD | TBD | TBD |
| 418 | Pro3[GIP(1-30)-EX (31-39)], Amide, Human | YAPGTFISDYSIAMDKIHQQDFVNWLLAQKPSSGAPPPS-NH2 | TBD | TBD | >1000 | TBD |
| 419 | GIP (1-26)-EX(27-39) | YGEGTFISDYSIAMDKIHQQDFVNWLKNGGPSSGAPPPS-NH2 | 10 | 153 | >1000 | TBD |
| 299 | Gly2 GIP (1-26)-EX(27-39) | YGEGTFISDYSIAMDKIHQQDFVNWLKNGGPSSGAPPPS-NH2 | 95 | >1000 | >1000 | TBD |

Fig. 5A

| SEQ ID NO: | Compound No. | Sequence |
|---|---|---|
| 100 | 0601GIP231 | YAEGTFISDYSIAMDKIRQQDFVNWLLAQK-Linker-KCNTATCVLGKLSQELHRLQTYPRTNTGSNTY |
| 101 | 0601GIP232 | YAEGTFISDYSIAMDKIRQQDFVNWLLAQK-Linker-KCNTATCVLGRLSQELHRLQTLPRTNTGSNTY |
| 102 | 0601GIP233 | YAEGTFISDYSIAMDKIRQQDFVNWLLAQK-Linker-KCNTATCVLGRLSQELHRLQTYPPTNTGSNTY |
| 103 | 0601GIP234 | YAEGTFISDYSIAMDKIRQQDFVNWLLAQK-Linker-KCNTATCVLGRLSQELHRLQTYPRTNVGSNTY |
| 104 | 0601GIP235 | YAEGTFISDYSIAMDKIRQQDFVNWLLAQK-Linker-KCNTATCVLGRLSQELHRLQTLPPTNVGSNTY |
| 105 | 0601GIP237 | YAEGTFISDYSIAMDKIRQQDFVNWLLAQK-Linker-KCNTATCVLGRLANFLHRLQTYPRTNTGSNTY |
| 106 | 0601GIP245 | YAEGTFISDYSIAMDKIRQQDFVNWLLAQK-Linker-ACNTATCVLGRLSQELHRLQTYPRTNTGSNTY |
| 107 | 0601GIP247 | YAEGTFISDYSIAMDKIRQQDFVNWLLAQK-Linker-KCNAATCVLGRLSQELHRLQTYPRTNTGSNTY |
| 108 | 0601GIP248 | YAEGTFISDYSIAMDKIRQQDFVNWLLAQK-Linker-KCNTAACVLGRLSQELHRLQTYPRTNTGSNTY |
| 109 | 0601GIP249 | YAEGTFISDYSIAMDKIRQQDFVNWLLAQK-Linker-CANLSTCVLGRLSQELHRLQTYPRTNTGSNTY |
| 110 | 0601GIP259 | YAEGTFISDYSIAMDKIRQQDFVNWLLAQK-Linker-CSNLSACVLGRLSQELHRLQTYPRTNTGSNTY |
| 111 | 0601GIP260 | YAEGTFISDYSIAMDKIRQQDFVNWLLAQK-Linker-CSNLATCVLGRLSQELHRLQTYPRTNTGSNTY |
| 112 | 0601GIP261 | YAEGTFISDYSIAMDKIRQQDFVNWLLAQK-Linker-CSNLSTCVLGRLSQELHKLQTYPRTNTGSNTY |
| 113 | 0601GIP262 | YAEGTFISDYSIAMDKIRQQDFVNWLLAQK-Linker-CSNASTCVLGRLSQELHRLQTYPRTNTGSTP |
| 114 | 0601GIP276 | YAEGTFISDYSIAMDKIRQQDFVNWLLAQK-Linker-KCNTATCVLGRLSQELHRLQTYPRTNTGSNTY |
| 115 | 0601GIP354 | YAEGTFISDYSIAMDKIRQQDFVNWLLAQK-Linker-CSALSTCVLGRLSQELHRLQTYPRTNTGSNTY |
| 116 | 0601GIP378 | YAEGTFISDYSIAMDKIRQQDFVNWLLAQK-Linker-KCNTATCLLQQLKLLQQLKQYPRTNTGSNTY |
| 117 | 0601GIP379 | YAEGTFISDYSIAMDKIRQQDFVNWLLAQK-Linker-KCNTASCVLGRLSQELHRLQTYPRTNTGSNTY |
| 118 | 0601GIP380 | YAEGTFISDYSIAMDKIRQQDFVNWLLAQK-Linker-KCNTAVCVLGRLSQELHRLQTYPRTNTGSNTY |
| 119 | 0601GIP417 | YAEGTFISDYSIAMDKIRQQDFVNWLLAQK-Linker-KCNTATCVLGRLSQELHRYPRTNTGSNTY |
| 120 | 0601GIP425 | YAEGTFISDYSIAMDKIRQQDFVNWLLAQK-Linker-KCNTATCVLGK(For)LSQELHK(For)LQTYPRTNTGSNTY |
| 457 | 0601GIP426 | YAEGTFISDYSIAMDKIRQQDFVNWLLAQK-Linker-KCNTA(d-Thr)CVLGRLSQELHRLQTYPRTNTGSNTY |
| 458 | 0601GIP427 | YAEGTFISDYSIAMDKIRQQDFVNWLLAQK-Linker-KCNTA(dAh)CVLGRLSQELHRLQTYPRTNTGSNTY |
| 121 | 0601GIP440 | YAEGTFISDYSIAMDKIRQQDFVNWLLAQK-Linker-ACNTATCVLGRLSQELHK(PEG5000)LQTYPRTNTGSNTY |
| 122 | 0601GIP441 | YAEGTFISDYSIAMDKIRQQDFVNWLLAQK-Linker-KCNTATCVLGRLSQELHRLQTLQTYPRTNTGSNTY |
| 123 | 0601GIP442 | YAEGTFISDYSIAMDKIRQQDFVNWLLAQK-Linker-KCNTATCVLGRLSQELHRLQTLLQTYPRTNTGSNTY |
| 124 | 0601GIP464 | YAEGTFISDYSIAMDKIRQQDFVNWLLAQK-Linker-KCNTATCVLGKLSQELHKLQTYPRTNTGSNTY |

Fig. 5B

| SEQ ID NO: | Compound No. | Sequence | | |
|---|---|---|---|---|
| 125 | 0601GIP465 | YAEGTFISDYSIAMDKIRQQDFVNWLLAQK | -Linker- | KCNTSTCVLGRLSQELHRLQTYPRTNTGSNTY |
| 126 | 0601GIP466 | YAEGTFISDYSIAMDKIRQQDFVNWLLAQK | -Linker- | KCNTATCATQRLSQELHRLQTYPRTNTGSNTY |
| 127 | 0601GIP467 | YAEGTFISDYSIAMDKIRQQDFVNWLLAQK | -Linker- | KCNTATCATQRLSQELHRLQTYPRTNVGSNTY |
| 128 | 0601GIP468 | YAEGTFISDYSIAMDKIRQQDFVNWLLAQK | -Linker- | KCNTSTCVLGRLANELVRLQTYPRTNVGSNTY |
| 129 | 0601GIP498 | YAEGTFISDYSIAMDKIRQQDFVNWLLAQK | -Linker- | KCNTA(Hse)CVLGRLSQELHRLQTYPRTNTGSNTY |
| 130 | 0601GIP499 | YAEGTFISDYSIAMDKIRQQDFVNWLLAQK | -Linker- | KCNTA(Ahb)CVLGRLSQELHRLQTYPRTNTGSNTY |
| 131 | 0601GIP500 | YAEGTFISDYSIAMDKIRQQDFVNWLLAQK | -Linker- | KCNTA(Ahp)CVLGRLSQELHRLQTYPRTNTGSNTY |
| 132 | 0601GIP501 | YAEGTFISDYSIAMDKIRQQDFVNWLLAQK | -Linker- | KCNTAT(OPO3H2)CVLGRLSQELHRLQTYPRTNTGSNTY |
| 133 | 0601GIP539 | YAEGTFISDYSIAMDKIRQQDFVNWLLAQK | -Linker- | KCNTATCVLG(Orn)LSQELHRLQTYPRTNTGSNTY |
| 134 | 0601GIP540 | YAEGTFISDYSIAMDKIRQQDFVNWLLAQK | -Linker- | KCNTATCVLG(Cit)LSQELHRLQTYPRTNTGSNTY |
| 135 | 0601GIP553 | YAEGTFISDYSIAMDKIRQQDFVNWLLAQK | -Linker- | KCNTATCVLG(homoK)LSQELH(homoK)LQTYPRTNTGSNTY |
| 136 | 0601GIP564 | YAEGTFISDYSIAMDKIRQQDFVNWLLAQK | -Linker- | KCNTATCMLGRYTQDFHRLQTYPRTNTGSNTY |
| 137 | 0601GIP567 | YAEGTFISDYSIAMDKIRQQDFVNWLLAQK | -Linker- | DSNLSTKVLGRLSQELHRLQTYPRTNTGSNTY |
| 138 | 0601GIP568 | YAEGTFISDYSIAMDKIRQQDFVNWLLAQK | -Linker- | KDNTATKVLGRLSQELHRLQTYPRTNTGSNTY |
| 139 | 0601GIP594 | YAEGTFISDYSIAMDKIRQQDFVNWLLAQK | -Linker- | CNTATCVLGRLSQELHRLQTYPRTNTGSNTY |
| 140 | 0601GIP602 | YAEGTFISDYSIAMDKIRQQDFVNWLLAQK | -Linker- | KCNTATCVLGRLSQELHRLQTYPRTNTGSNTY(9Anc) |
| 141 | 0601GIP603 | YAEGTFISDYSIAMDKIRQQDFVNWLLAQK | -Linker- | KCNTATCVLGRLSQELHRLQTYPRTNTGSNTY(L-octylglycine) |
| 142 | 0601GIP623 | YAEGTFISDYSIAMDKIRQQDFVNWLLAQK | -Linker- | KCNTATCVLG(homoR)LSQELH(homoR)LQTYPRTNTGSNTY |
| 143 | 0601GIP634 | YAEGTFISDYSIAMDKIRQQDFVNWLLAQK | -Linker- | FCNTATCVLGRLSQELHRLQTYPRTNTGSNTY |
| 144 | 0601GIP640 | YAEGTFISDYSIAMDKIRQQDFVNWLLAQK | -Linker- | KCNTATCVLGRLSQELH(Cit)LQTYPRTNTGSNTY |
| 145 | 0601GIP641 | YAEGTFISDYSIAMDKIRQQDFVNWLLAQK | -Linker- | KCNTATCVLGRLSQELH(Orn)LQTYPRTNTGSNTY |
| 146 | 0601GIP642 | YAEGTFISDYSIAMDKIRQQDFVNWLLAQK | -Linker- | ICNTATCVLGRLSQELHRLQTYPRTNTGSNTY |
| 147 | 0601GIP661 | YAEGTFISDYSIAMDKIRQQDFVNWLLAQK | -Linker- | KCNTATCVLG(Cit)LSQELHRLQTYPRTNTGSNTY |
| 148 | 0601GIP665 | YAEGTFISDYSIAMDKIRQQDFVNWLLAQK | -Linker- | KCNTATCVLGRLSQELHRLQTYPRTNTGSNTY(4ABU) |
| 149 | 0601GIP715 | YAEGTFISDYSIAMDKIRQQDFVNWLLAQK | -Linker- | KCNTSTCATQRLANELVRLQTYPRTNVGSEAF |
| 150 | 0601GIP716 | YAEGTFISDYSIAMDKIRQQDFVNWLLAQK | -Linker- | KCNTATCVLGRLSQELHRLQTYPTNVGSEAF |

Fig. 5C

| SEQ ID NO: | Compound No. | Sequence |
|---|---|---|
| 151 | 0601GIP717 | YAEGTFISDYSIAMDKIRQQDFVNWLLAQK-Linker-KCNTATCVLGRLSRSLHRLQTYPRTNTGSNTY |
| 152 | 060-1GIP718 | YAEGTFISDYSIAMDKIRQQDFVNWLLAQK-Linker-KCNTATCVTHRLSQELHRLQTYPRTNTGSNTY |
| 153 | 0601GIP719 | YAEGTFISDYSIAMDKIRQQDFVNWLLAQK-Linker-KCNTATCVLGRLADFLHRLQTYPRTNTGSNTY |
| 154 | 0601GIP737 | YAEGTFISDYSIAMDKIRQQDFVNWLLAQK-Linker-CNTATCVLGRLSQELHRLQTYPRTNTGSNT |
| 155 | 0601GIP742 | YAEGTFISDYSIAMDKIRQQDFVNWLLAQK-Linker-KCNTATCVLGRLSQELHRLQNFVPRTNTGSNTY |
| 156 | 0601GIP760 | YAEGTFISDYSIAMDKIRQQDFVNWLLAQK-Linker-KCNTATCVLGRLSQELHRLQTYPRTNTGSETF |
| 157 | 0601GIP761 | YAEGTFISDYSIAMDKIRQQDFVNWLLAQK-Linker-ACDTATCVLGRLSQELHRLQTYPRTNTGSNTY |
| 158 | 0601GIP769 | YAEGTFISDYSIAMDKIRQQDFVNWLLAQK-Linker-KCNTATCVLGRLSQELHRLQTYPRTNTGSKAF |
| 159 | 0601GIP775 | YAEGTFISDYSIAMDKIRQQDFVNWLLAQK-Linker-KCDTATCVTHRLAGLLSRSQTYPRTNTGSNTY |
| 160 | 0601GIP776 | YAEGTFISDYSIAMDKIRQQDFVNWLLAQK-Linker-KCNTATCVLGRLADALHRLQTYPRTNTGSNTY |
| 161 | 0601GIP777 | YAEGTFISDYSIAMDKIRQQDFVNWLLAQK-Linker-KCNTATCVLGRLAAFLHRLQTYPRTNTGSNTY |
| 162 | 0601GIP784 | YAEGTFISDYSIAMDKIRQQDFVNWLLAQK-Linker-SCNTATCVLGRLSQELHRLQTYPRTNTGSNTY |
| 163 | 0601GIP797 | YAEGTFISDYSIAMDKIRQQDFVNWLLAQK-Linker-KCNTATCVLGRLSQELHRLQTMPRTNTGSNTY |
| 164 | 0601GIP798 | YAEGTFISDYSIAMDKIRQQDFVNWLLAQK-Linker-KCNTATCVLGRLNEYLHRLQTYPRTNTGSNTY |
| 165 | 0601GIP799 | YAEGTFISDYSIAMDKIRQQDFVNWLLAQK-Linker-SCNTATCVLGRLSQELHRLQTYPRTNTGSNTY |
| 166 | 0601GIP802 | YAEGTFISDYSIAMDKIRQQDFVNWLLAQK-Linker-KCNTATCVLGRLTEFLHRLQTYPRTNTGSNTY |
| 167 | 0601GIP810 | YAEGTFISDYSIAMDKIRQQDFVNWLLAQK-Linker-KCNTATCVLGRLAEFLHRLQTYPRTNTGSNTY |
| 168 | 0601GIP843 | YAEGTFISDYSIAMDKIRQQDFVNWLLAQK-Linker-KCNTATCVLGRLTDYLHRLQTYPRTNTGSNTY |
| 169 | 0601GIP844 | YAEGTFISDYSIAMDKIRQQDFVNWLLAQK-Linker-KCNTATCVLGRLAQFLHRLQTYPRTNTGSNTY |
| 170 | 0601GIP845 | YAEGTFISDYSIAMDKIRQQDFVNWLLAQK-Linker-KCNTATCVLGRLADFLHRFHTFPRTNTGSNTY |
| 171 | 0601GIP847 | YAEGTFISDYSIAMDKIRQQDFVNWLLAQK-Linker-KCNTATCVLGRLADFLHRFQTFPRTNTGSGTP |
| 172 | 0601GIP848 | YAEGTFISDYSIAMDKIRQQDFVNWLLAQK-Linker-KCNTATCVLGRLADFLHRFQTFPRTNTGSNTY |
| 173 | 0601GIP849 | YAEGTFISDYSIAMDKIRQQDFVNWLLAQK-Linker-CNTATCVLGRLADFLHRFQTFPRTNTGSGTP |
| 174 | 0601GIP850 | YAEGTFISDYSIAMDKIRQQDFVNWLLAQK-Linker-KCDTATCVLGRLSQELHRLQTYPRTNTGSNTY |
| 175 | 0601GIP851 | YAEGTFISDYSIAMDKIRQQDFVNWLLAQK-Linker-KCNTATCVLGRLFDFLHRLQTYPRTNTGSNTY |
| 176 | 0601GIP852 | YAEGTFISDYSIAMDKIRQQDFVNWLLAQK-Linker-KCNTATCVLGRLAALHRLQTYPRTNTGSNTY |
| 177 | 0601GIP865 | YAEGTFISDYSIAMDKIRQQDFVNWLLAQK-Linker-KCNTATCVLGRLAAALHRLQTYPRTNTGSNTY |

Fig. 5D

| SEQ ID NO: | Compound No. | Sequence |
|---|---|---|
| 178 | 0601GIP866 | YAEGTFISDYSIAMDKIRQQDFVNWLLAQK-Linker- TCDTATCVLGRLSQELHRLQTYPRTNTGSNTY |
| 179 | 0601GIP1820 | YAEGTFISDYSIAMDKIRQQDFVNWLLAQK-Linker- CSNLSTCATQRLANELVRLQTYPRTNVGSNTY |
| 180 | 0601GIP2221 | YAEGTFISDYSIAMDKIRQQDFVNWLLAQK-Linker- KCNTATCATQRLANELVRLQTYPRTNVGSNTY |
| 181 | 0601GIP2306 | YAEGTFISDYSIAMDKIRQQDFVNWLLAQK-Linker- CSNLSTCVLGRLSQELHRLQTYPRTNTGSNTY |
| 182 | 0601GIP2307 | YAEGTFISDYSIAMDKIRQQDFVNWLLAQK-Linker- KCNTATCVLGRLSQELHRLQTYPRTNTGSNTY |

Fig. 6

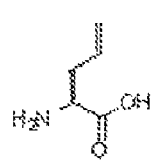

Agy = Allylglycine

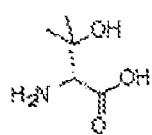

D-Ah = (R)-2-amino-3-hydroxy-3-methylbutanoic acid

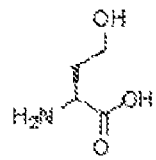

Hse = L-Homoserine

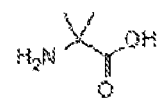

Aib = Aminoisobutyric acid

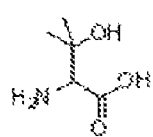

Ahb = (S)-2-amino-3-hydroxy-methylbutanoic acid

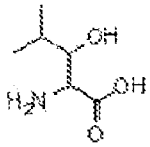

Ahp = (2S,3R)-2-amino-3-hydroxy-methylpentanoic acid

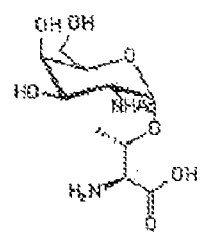

Thr(GalNAcα)

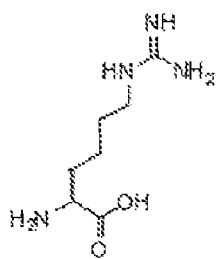

hR = L-homoarginine

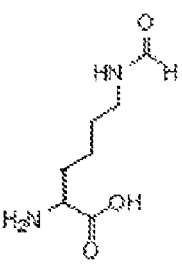

Lys(For) = L-N$^\epsilon$-formyllysine

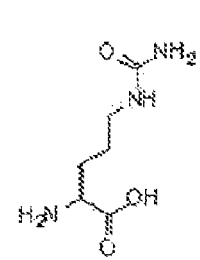

Cit = L- Citrulline

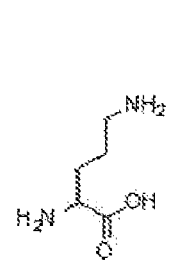

Orn = L-Ornithine

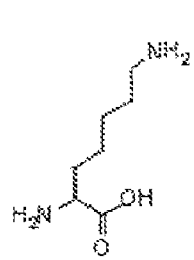

hK = L-Homolysine

9-AMINONONANOIC ACID (ANC)

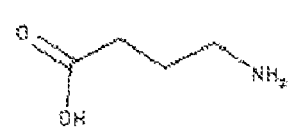

4-AMINOBUTYRIC ACID (ABU)

Fig. 7
5 Apa = Fmoc- 5 amino pentanoic acid
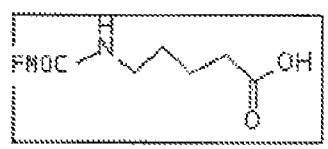
12 Ado = Fmoc-12 amino dodecanoic acid
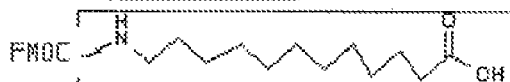
mini peg(8) = Fmoc- 3, 6-dioxyoctanoic acid
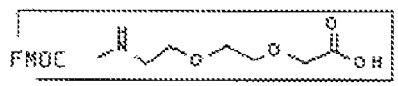
mini peg (13) = Fmoc-1-amino-4,7,10-trioxa-13-tridecanamine succinimic acid
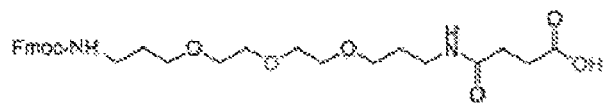

Fig. 8
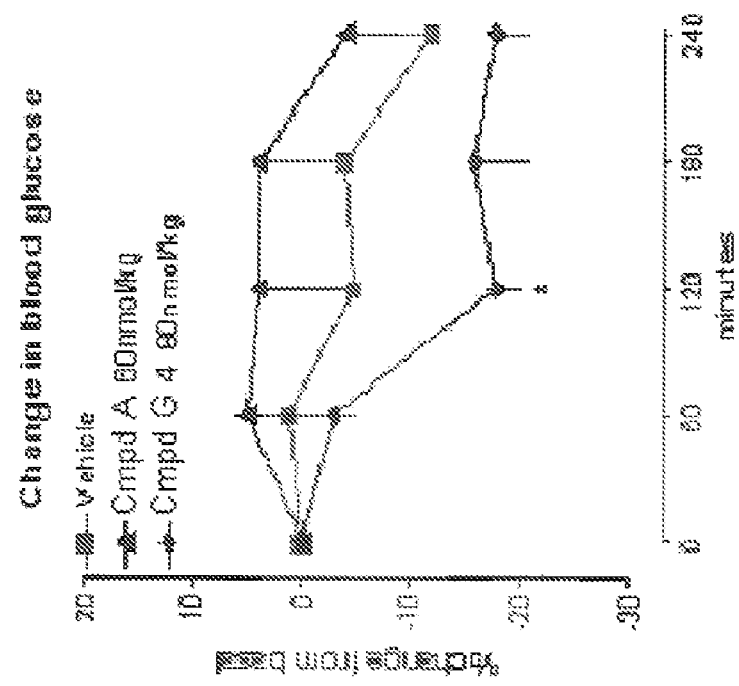
A
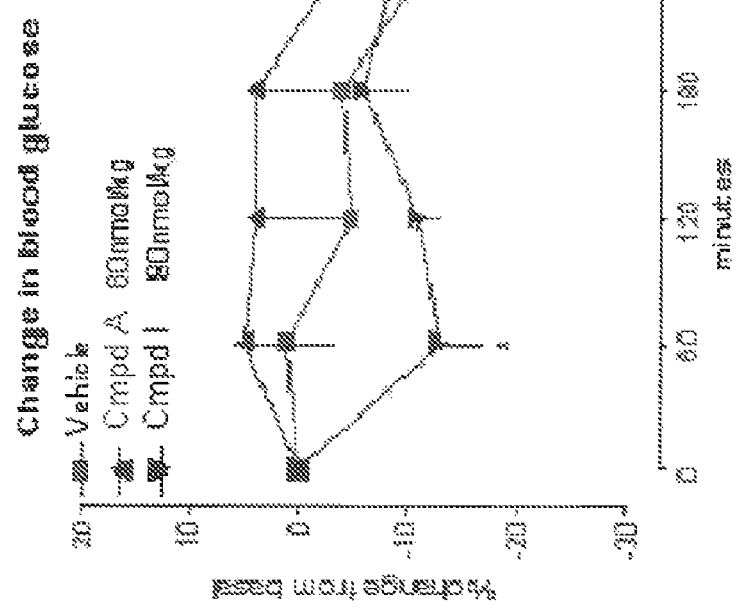
B

Fig. 12.15

| SEQ ID NO: | SEQ # | N | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 307 |  |  | Y | A | E | G | T | F | I | S | D | Y | S | I | A | M | D | K | I | H | Q | Q | D | F | V | N | W | L | L | A | Q | K | G | K | N | D | W | K | H | N | I | T | Q |  |
| 308 | 060 1GI P41 24 | Ac | Y | A | E | G | T | F |  | S | D | Y | S | I | A | M | D | K | I | H | Q | Q | D | F | V | N | W | L | L | A | Q | K | G | K | N | D | W | K | H | N | I | T | Q |  |
| 739 | 060 1GI P40 42 |  | Y | a | E | G | T | F |  | S | D | Y | S | I | A | M | D | K | I | H | Q | Q | D | F | V | N | W | L | L | A | Q | K | G | K | N | D | W | K(al a) | H | N | I | T | Q |  |
| 309 | 060 1GI P40 84 | Ac | Y | A | E | G | T | F |  | S | D | Y | S | I | A | M | D | K | I | H | Q | Q | D | F | V | N | W | L | L | A | Q | K | G | K | N | D | W | K | H | N | I | T | Q |  |
| 310 | 060 1GI P39 06 |  | Y | A | P | G | T | F |  | S | D | Y | S | I | A | M | D | K | I | H | Q | Q | D | F | V | N | W | L | L | A | Q | K | G | K | N | D | W | K | H | N | I | T | Q |  |
| 311 | 060 1GI P37 83 |  | Y | A | E | G | T | F |  | S | D | Y | S | I | A | M | D | K | I | H | Q | Q | D | F | V | N | W | L | L | A | Q | K |  |  |  |  |  |  |  |  |  |  | Q |  |
| 312 | 060 1GI P38 23 |  | Y | S | E | G | T | F |  | S | D | Y | S | I | A | M | D | K | I | H | Q | Q | D | F | V | N | W | L | L | A | Q | K |  |  |  |  |  |  |  |  |  |  | Q |  |
| 313 | 060 1GI P38 22 |  | Y | G | E | G | T | F |  | S | D | Y | S | I | A | M | D | K | I | H | Q | Q | D | F | V | N | W | L | L | A | Q | K |  |  |  |  |  |  |  |  |  |  | Q |  |
| 3 | 060 1GI P38 |  | Y | a | E | G | T | F |  | S | D | Y | S | I | A | M | D | K | I | H | Q | Q | D | F | V | N | W | L | L | A | Q | K |  |  |  |  |  |  |  |  |  |  | Q |  |

Fig. 12.16

| SEQ ID NO. | # | N | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 314 | 42 | | Y | A | E | G | T | F | | S | D | Y | S | I | A | M | D | K | I | H | Q | D | F | V | N | W | L | L | A | Q | K | NH2 | | | | | | | | | | | | |
| 315 | 060 1GI P37 39 | | H | G | E | G | T | F | | S | D | Y | S | I | A | M | D | K | I | H | Q | D | F | V | N | W | L | L | A | Q | K | NH2 | | | | | | | | | | | | |
| 316 | 060 1GI P37 41 | | Y | S | E | G | T | F | | S | D | Y | S | I | A | M | D | K | I | H | Q | D | F | V | N | W | L | L | A | Q | K | NH2 | | | | | | | | | | | | |
| 3 | 060 1GI P39 42 | | Y | a | P | G | T | F | | S | D | Y | S | I | A | M | D | K | I | H | Q | D | F | V | N | W | L | L | A | Q | K | NH2 | | | | | | | | | | | | |
| 317 | 060 1GI P40 58 | | Y | A | E | G | T | F | | S | D | Y | S | I | A | M | D | K | I | H | Q | D | F | V | N | W | L | L | A | Q | K | NH2 | | | | | | | | | | | | |
| 318 | 060 1GI P37 57 | | Y | A | E | G | T | F | | S | D | Y | S | I | A | M | D | K | I | H | Q | D | F | V | N | W | L | L | A | Q | K | P | S | S | G | A | P | P | S | NH2 | | | | |
| 319 | 060 1GI P40 44 | Ac | Y | A | E | G | T | F | | S | A | Y | S | I | A | M | D | K | I | H | Q | D | F | V | N | W | L | L | A | Q | K | P | S | S | G | A | P | P | S | NH2 | | | | |
| 320 | 060 1GI P40 45 | | Y | A | E | G | T | F | | S | A | Y | S | I | A | M | D | K | I | H | Q | D | F | V | N | W | L | L | A | Q | K | P | S | S | G | A | P | P | S | NH2 | | | | |

Fig. 12.17

| SEQ ID NO. | # | N | 1 | 2 | 3 | 4 | 5 | 6 | 7 | 8 | 9 | 10 | 11 | 12 | 113 | 114 | 115 | 116 | 117 | 118 | 119 | 120 | 121 | 122 | 123 | 124 | 125 | 126 | 127 | 128 | 129 | 130 | 131 | 332 | 333 | 334 | 335 | 336 | 337 | 338 | 339 | 340 | 345 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 106 | 060 1GI P37 94** |  | Y | a | E | G | T | F | - | S | D | Y | S | - | A | M | D | K | I | H | Q | Q | D | F | V | N | W | L | L | A | Q | K | P | S | S | G | A | P | P | P | S | NH2 |  |
| 740 | 060 1GI P40 46 | A c | Y | a | E | G | T | F | - | S | D | Y | S | - | A | M | D | K | I | H | Q | Q | D | F | V | N | W | L | L | A | Q | K | P | S | S | G | A | P | P | P | S | NH2 |  |
| 321 | 060 1GI P37 93 |  | Y | S | E | G | T | F | - | S | D | Y | S | - | A | M | D | K | I | H | Q | Q | D | F | V | N | W | L | L | A | Q | K | P | S | S | G | A | P | P | P | S | NH2 |  |
| 322 | 060 1GI P37 91 |  | Y | G | E | G | T | F | - | S | D | Y | S | - | A | M | D | K | I | H | Q | Q | D | F | V | N | W | L | L | A | Q | K | P | S | S | G | A | P | P | P | S | NH2 |  |
| 323 | 060 1GI P37 56 |  | Y | G | E | G | T | F | - | S | D | Y | S | - | A | M | D | K | I | H | Q | Q | D | F | V | N | W | L | L | A | Q | K | P | S | S | G | A | P | P | P | S | NH2 |  |
| 324 | 060 1GI P39 74 |  | H | A | E | P | G | T | F | - | S | D | Y | S | - | A | M | D | K | I | H | Q | Q | D | F | V | N | W | L | K | N | G | G | P | S | S | G | A | P | P | P | S | NH2 |
| 325 | 060 1GI P37 86 |  | Y | A | E | G | T | F | - | S | D | Y | S | - | A | M | D | K | I | H | Q | Q | D | F | V | N | W | L | K | N | G | G | P | S | S | G | A | P | P | P | S | NH2 |  |
| 326 | 060 1GI P37 85 |  | Y | G | E | G | T | F | - | S | D | Y | S | - | A | M | D | K | I | H | Q | Q | D | F | V | N | W | L | L | A | Q | G | G | P | S | S | G | A | P | P | P | S | NH2 |  |
| 741 | 060 1GI P44 28 |  | Y | a | E | G | T | F | - | S | D | Y | S | - | A | M | D | K | I | H | Q | Q | D | F | V | N | W | F | L | L | A | Q | K | P | S | S | G | A | P | P | P | S | NH2 |  |

Fig. 12.18

| SEQ ID NO: | # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 327 | 060 1GI P44 29 | Y | A | E | G | T | F | I | S | D | Y | S | I | A | M | D | K | I | H | Q | Q | D | F | V | N | F | L | L | A | Q | K | P | S | G | A | P | P | S | NH2 | | | |
| 590 | 060 1GI P41 92 | Y | a | E | G | T | F | T | S | D | Y | S | I | A | M | D | K | I | H | Q | Q | D | F | V | N | W | L | L | A | Q | K | P | S | G | A | P | P | S | NH2 | | | |
| 742 | 060 1GI P41 66 | Y | a | E | G | T | F | T | S | D | Y | S | I | A | L | D | K | I | H | Q | Q | D | F | V | N | W | L | L | V | K | G | R | P | S | G | A | P | P | S | NH2 | | | |
| 660 | 060 1GI P42 82 also AA A | Y | a | E | G | T | F | T | S | D | Y | S | I | A | M | D | K | I | H | Q | Q | D | E | F | V | N | W | L | V | K | G | R | P | S | G | A | P | P | S | NH2 | | | |
| 743 | 060 1GI P43 98 | Y | a | E | G | T | F | T | S | E | Y | S | I | A | M | D | K | I | H | Q | Q | E | F | V | N | W | L | L | A | Q | K | P | S | G | A | P | P | S | NH2 | | | |
| 744 | 060 1GI P42 81 | Y | a | E | G | T | F | T | S | D | Y | S | I | A | M | E | E | A | Q | Q | E | F | V | N | W | L | V | K | G | R | P | S | G | A | P | P | S | NH2 | | | | |
| 745 | 060 1GI P42 80 | Y | a | E | G | T | F | T | S | D | Y | S | I | A | M | E | G | G | A | Q | Q | E | F | V | N | W | L | V | K | G | R | P | S | G | A | P | P | S | NH2 | | | |

Fig. 12.19

| ID | Clone | Sequence |
|---|---|---|
| 746 | | Y a E G T F T S E Y S I A M E K I A Q E F V N W L L A Q K P S G A P P S -NH2 |
| 597 | 060 1GI P41 86 | Y a E G T F T S D Y S I A M D K I H Q V K F V N W L L A Q K P S G A P P S -NH2 |
| 603 | 060 1GI P42 35 | Y a E G T F T S D Y S I A L D K I R Q Q E F V N W L L A Q K P S G A P P S -NH2 |
| 604 | 060 1GI P42 83 | Y a E G T F T S D Y S I A L D K I K Q Q E F V N W L L A Q K P S G A P P S -NH2 |
| 328 | 060 1GI P42 84** | Y a E G T F T S D Y S I A L D K I K Q Q E F V N W L L A Q K P S G A P P S -NH2 |
| 329 | 060 1GI P44 05 | Y A E G T F T S D Y S I A L D K I K Q Q E F V N W L L A Q K P S G A P P S -NH2 |
| 330 | 060 1GI P44 06 | Y A E G T F T S D Y S I A L D K I K Q Q E F V N W L L A Q K P S G A P P S -NH2 |
| 331 | 060 1GI P44 04 | G , Y A E G T F T S D Y S I A M D K I H Q Q F V N W L L A Q K P S G A P P S -NH2 |

Fig. 12.20

| | | | | | | | | | | | | | | | | | | | | | | | | | |
|---|---|---|---|---|---|---|---|---|---|---|---|---|---|---|---|---|---|---|---|---|---|---|---|---|---|
| 605 | 060 1GI P42 85 | Y | a | E | G | T | F | I | S | Y | D | Y | S | I | A | L | D | K | I | A | Q | E | F | V | N W L L A Q K P S G A P P S NH2 |
| 748 | UU U | Y | a | E | G | T | F | I | S | D | Y | S | I | A | M | D | K | I | A | R | Q | E | F | V | N W L L A Q H P S G A P P S NH2 |
| 606 | 060 1GI P42 86 | Y | a | E | G | T | F | I | S | D | Y | S | I | A | L | D | K | I | A | R | Q | Q | F | V | N W L L A Q K P S G A P P S NH2 |
| 607 | 060 1GI P42 87 | Y | a | E | G | T | F | T | A | D | Y | S | K | A | L | D | K | I | H | Q | Q | F | V | N W L L A Q K P S G A P P S NH2 |
| 749 | BB B | Y | a | E | G | T | F | T | S | D | Y | S | K | A | L | D | K | I | H | Q | Q | F | V | N W L L A Q K P S G A P P S NH2 |
| 750 | 060 1GI P43 13 | Y | a | E | G | T | F | T | S | D | Y | S | K | A | L | D | K | I | H | Q | Q | F | V | N W L L A Q K P S G A P P S NH2 |
| 608 | 060 1GI P42 88 | Y | a | E | G | T | F | T | S | D | Y | S | I | A | L | E | K | I | R | Q | Q | E | F | V | N W L L A Q K P S G A P P S NH2 |
| 751 | CC C | Y | a | E | G | T | F | I | S | D | Y | S | I | A | L | E | K | I | H | Q | Q | K | F | V | N W L L A Q K P S G A P P S NH2 |
| 752 | 060 1GI P43 44 | Y | a | E | G | T | F | I | S | D | Y | S | I | A | L | D | K | I | R | Q | Q | E | F | V | N W L L A Q K P S G A P P S NH2 |
| 609 | 060 1GI P42 89** | Y | a | E | G | T | F | I | S | D | Y | S | I | A | L | D | K | I | R | Q | Q | G | F | V | E W L L A Q K P S G A P P S NH2 |

| # | ID | Sequence |
|---|---|---|
| 341 | | Y A E G T F I S D Y S I A M D K I R Q Q D F V N W L L A Q K G K K S D W K H N I T Q, OH |
| 342 | 060 1GI P39 43 | Y A E G T F I S D Y S I A M D K I R Q Q D F V N W L L A Q K G —OH |
| 343 | 060 1GI P23 50 | Y A E G T F I S D Y S I A M D K I R Q Q D F V N W L L A Q K G K K S D W K H N, OH |
| 344 | | Y A E G T F I S D Y S I A M D K I R Q Q D F V N W L L A Q K G NH2 |
| 345 | | Y S E A T L A S D Y S R T M D N M L K K N F K N F V E W L L A R R E K G QEPPRRMRLSSAPGYPREAKPIKFK-OH |
| 346 | | Y S E A I L A S D Y S R S V D N M L K K N F V D W L L A R R E K S D N V I E P Y K, OH |
| 347 | | Y a E S T I A S D I S K I V D S M V Q K N F V N F L L N Q R E K S E N T S E A T OH |
| 588 | 060 1GI P90 | Y a E G T F I S D Y S I A L D K I H Q Q D F V N W L L A Q K P S S G A P P P S NH2 |
| 581 | 060 1GI P41 51 | Y a E G T F I E Y S I A M D K I H Q Q D F V N W L L A Q K P S S G A P P P S NH2 |
| 582 | 060 1GI P41 52 | Y a E G T F I S D Y S I A M D K I H Q Q D F V N W L L A Q K P S S G A P P P S NH2 |

Fig. 12.23

| ID | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| 580 / 060 1GI P41 50 | Y | a | E | G | T | F | I | S | D | Y | S | I | A | M | D | K | I | A | Q | D | F | V | N | W | L | L | A | Q | K | P | S | S | G | A | P | P | S | NH2 |
| 583 / 060 1GI P41 53 | Y | a | E | G | T | F | I | S | D | Y | S | I | A | M | D | K | I | R | Q | D | F | V | N | W | L | L | A | Q | K | P | S | S | G | A | P | P | S | NH2 |
| 579 / 060 1GI P41 49 | Y | a | E | G | T | F | I | S | D | Y | S | I | A | M | D | K | I | K | Q | D | F | V | N | W | L | L | A | Q | A | P | S | S | G | A | P | P | S | NH2 |
| 584 / 060 1GI P41 65 | Y | a | E | G | T | F | I | S | D | Y | S | I | A | M | D | K | I | H | Q | D | F | V | N | W | L | L | A | Q | R | P | S | S | G | A | P | P | S | NH2 |
| 585 / 060 1GI P41 76 | Y | a | E | G | T | F | I | S | D | Y | S | I | A | M | D | K | I | H | Q | D | F | V | N | W | L | L | A | Q | H | P | S | S | G | A | P | P | S | NH2 |
| 586 / 060 1GI P41 77 | Y | a | E | G | T | F | I | S | D | Y | S | I | A | M | D | K | I | H | Q | D | F | V | N | W | L | L | A | C | K | P | S | S | G | A | P | P | S | NH2 |
| 582 / 060 1GI P42 13 | Y | a | E | G | T | F | I | S | D | Y | S | I | A | M | D | K | I | H | Q | D | F | V | N | W | L | L | A | C | K | P | S | S | G | A | P | P | S | NH2 |
| 593 / 060 1GI P42 14 | Y | a | E | G | T | F | I | S | D | Y | S | I | A | M | D | K | I | K | Q | D | F | V | N | W | L | L | S | C | K | P | S | S | G | A | P | P | S | NH2 |
| 600 / 060 1GI P42 63 | Y | a | E | G | T | F | I | S | D | Y | S | I | A | L | D | K | I | A | Q | D | F | V | N | W | L | L | A | C | R | P | S | S | G | A | P | P | S | NH2 |

Fig. 12.24

| # | ID | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|
| 601 | 060 1GI P4278 | Y | a | E | G | T | F | I | S | D | Y | S | I | A | L | D | K | I | R | Q | Q | E | F | V | N | W | L | L | A | Q | R | P | S |   | S | G | A | P | P | S | NH2 |
| 653 | 060 1GI P4264 | Y | a | E | G | T | F | I | S | D | Y | S | I | A | L | D | K | I | K | Q | Q | E | F | V | N | W | L | L | A | Q | R | P | S |   | S | G | A | P | P | S | NH2 |
| 602 | 060 1GI P4279 | Y | a | E | G | T | F | I | S | D | Y | S | I | A | L | D | K | I | A | Q | Q | E | F | V | N | W | L | L | A | Q | H | P | S |   | S | G | A | P | P | S | NH2 |
| 753 | 060 1GI P4314 also QQQ | Y | a | E | G | T | F | I | S | D | Y | S | I | A | L | D | K | I | R | Q | Q | E | F | V | N | W | L | L | A | Q | H | P | S |   | S | G | A | P | P |   | NH2 |
| 754 | 060 1GI P4306 also RRR | Y | a | E | G | T | F | I | S | D | Y | S | I | A | L | D | K | I | K | Q | Q | E | F | V | N | W | L | L | A | Q | H | P | S |   | S | G | A | P | P | S | NH2 |
| 348 | Xenopus | Y | S | E | A | I | L | S | D | Y | S | R | S | V | D | N | M | L | K | K | Q | N | F | V | D | W | L | L | A | R | R | P | E | K | S | E | A | N | T | S | OH |
| 349 | 060 1GI P4503 | Y | S | E | A | L | L | S | D | Y | S | R | S | V | D | N | M | L | Q | Q | Q | N | F | V | D | W | L | L | A | Q | K | P | S |   | S | G | A | P | P | S | NH2 |
| 350 | 060 1GI P4504 | Y | S | D | A | L | L | S | D | Y | S | R | S | V | D | N | M | L | Q | Q | Q | N | F | V | D | W | L | L | A | Q | K | P | S |   | S | G | A | P | P | S | NH2 |
| 755 | 060 1GI P4505 | Y | a | E | A | L | L | S | D | Y | S | R | S | V | D | N | M | L | Q | Q | Q | N | F | V | D | W | L | L | A | Q | K | P | S |   | S | G | A | P | P | S | NH2 |

Fig. 12.25

| # | ID | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 756 | 060 1GI P45 06 | Y | a | E | G | T | F | S | D | Y | S | I | A | M | D | K | I | H | Q | Q | D | F | V | N | W | L | L | A | Q | K | P | S | S | G | A | P | P | S | NH2 |
| 757 | VV V | Y | a | E | G | T | F | S | D | Y | S | I | A | M | D | K | I | H | Q | Q | D | F | V | N | W | L | L | A | Q | K | P | S | S | G | A | P | P | S | NH2 |
| 758 | WW W | Y | a | E | G | T | F | S | D | Y | S | I | A | M | D | K | M | H | Q | Q | D | F | V | N | W | L | L | A | Q | K | P | S | S | G | A | P | P | S | NH2 |
| 759 | XX X | Y | a | E | G | T | F | S | D | Y | S | I | A | M | D | K | I | H | Q | Q | D | F | V | Q | W | L | L | A | Q | K | P | S | S | G | A | P | P | S | NH2 |
| 351 | chicken | Y | S | E | A | T | L | A | S | D | Y | S | R | T | M | D | N | L | K | K | N | F | V | V | E | W | L | L | A | R | R | E | K | S | Q | N | L | V | EPYK,OH |
| 760 | 060 1GI P44 65 | Y | a | E | G | T | F | I | S | D | Y | S | I | A | M | D | K | I | H | Q | Q | D | F | V | N | W | L | L | A | Q | K | P | S | S | G | A | P | P | S | NH2 |
| 761 | 060 1GI P44 66 | Y | a | E | G | T | F | L | S | D | Y | S | I | A | M | D | K | I | H | Q | Q | D | F | V | N | W | L | L | A | Q | K | P | S | S | G | A | P | P | S | NH2 |
| 762 | 060 1GI P44 78 | Y | a | E | G | T | F | A | S | D | Y | S | I | A | M | D | K | I | H | Q | Q | D | F | V | N | W | L | L | A | Q | K | P | S | S | G | A | P | P | S | NH2 |
| 763 | 060 1GI P44 67 | Y | a | E | G | T | F | F | S | D | Y | S | I | A | M | D | K | I | H | Q | Q | D | F | V | N | W | L | L | A | Q | K | P | S | S | G | A | P | P | S | NH2 |
| 764 | 060 1GI P44 79 | Y | a | E | G | T | F | I | S | D | Y | S | I | T | M | D | K | I | H | Q | Q | D | F | V | N | W | L | L | A | Q | K | P | S | S | G | A | P | P | S | NH2 |
| 765 | 060 1GI P44 80 | Y | a | E | G | T | F | L | S | D | Y | S | I | A | M | D | N | I | H | Q | Q | D | F | V | N | W | L | L | A | Q | K | P | S | S | G | A | P | P | S | NH2 |

Fig. 12.26

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 766 | YYY | Y | a | E | G | T | F | S | D | Y | S | I | A | M | D | K | I | L | Q | F | V | N | W | L | A | Q | K | P | G S P S G A P P S NH2 |
| 767 | 060 1GI P45 51 | Y | a | E | A | T | L | A | S | D | Y | S | R | Y | M | D | K | I | H | Q | F | V | N | W | L | A | Q | K | P S G A P P S NH2 |
| 352 | ZZZ | Y | A | E | G | T | F | I | S | D | Y | S | R | R | M | D | K | I | H | Q | F | V | N | W | L | A | Q | K | P S G A P P S NH2 |
| 353 | 060 1GI P44 07 | Y | A | E | G | T | F | I | S | D | Y | S | R | A | L | D | K | I | H | Q | F | V | N | W | L | A | Q | K | P S G A P P S NH2 |
| 354 | AB B | Y | A | E | G | T | F | I | S | D | Y | S | I | A | M | D | K | I | H | Q | F | V | N | W | L | A | Q | K | P S G A P P S NH2 |
| 355 | AC C | Y | S | E | G | T | F | I | S | D | Y | S | R | A | M | D | K | I | H | Q | F | V | N | W | L | A | Q | K | P S G A P P S NH2 |
| 356 | AD D | Y | S | E | G | T | F | I | S | D | Y | S | I | T | M | D | K | I | H | Q | F | N | V | N | W | L | A | Q | K | P S G A P P S |
| 357 | | Y | A | E | S | T | I | A | S | D | I | S | K | L | V | D | S | M | V | Q | K | N | F | L | N | F | L | N | Q R E K S K E | 
| 768 | 060 1GI P45 07 | Y | a | E | G | T | F | I | S | D | Y | S | I | A | M | D | K | I | H | Q | D | F | V | N | W | L | A | Q | K | P S G A P P S NH2 |
| 769 | 060 1GI P45 36 | Y | a | E | G | T | F | I | S | D | Y | S | I | A | M | D | K | I | H | Q | D | F | V | N | W | L | A | Q | K | P S G A P P S NH2 |
| 770 | 060 1GI P45 37 | Y | a | E | G | T | F | I | S | D | Y | S | I | A | M | D | K | I | H | Q | D | F | V | N | W | L | A | Q | K | P S G A P P S NH2 |
| 771 | AE E | Y | a | E | G | T | F | I | S | D | Y | S | K | A | M | D | K | I | H | Q | D | F | V | N | W | L | A | Q | K | P S G A P P S NH2 |

| | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|
| 364 | also DDD | Y | Abu | E | G | T | F | T | S | D | Y | S | - | I | A | M | D | K | I | H | Q | Q | D | F | V | N | W | L | L | A | Q | K | P | S | G | A | P | P | P | S | NH2 |
| 365 | 060 1GI P41 86 | Y | homoSer | E | G | T | F | T | S | D | Y | S | - | I | A | M | D | K | I | H | Q | Q | D | F | V | N | W | L | L | A | Q | K | P | S | G | A | P | P | P | S | NH2 |
| 776 | 060 1GI P41 95 | Y | homoSer-P | E | G | T | F | T | S | D | Y | S | - | I | A | M | D | K | I | H | Q | Q | D | F | V | N | W | L | L | A | Q | K | P | S | G | A | P | P | P | S | NH2 |
| 366 | 060 1GI P41 64 | Y | P | E | G | T | F | T | S | D | Y | S | - | I | A | M | D | K | I | H | Q | Q | D | F | V | N | W | L | L | A | Q | K | P | S | G | A | P | P | P | S | NH2 |
| 367 | 060 1GI P41 87 | Y | cyclopropylAla | E | G | T | F | T | S | D | Y | S | - | I | A | M | D | K | I | H | Q | Q | D | F | V | N | W | L | L | A | Q | K | P | S | G | A | P | P | P | S | NH2 |

Fig. 12.29

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 777 | 060 1GI P41 88 | Y | d-γGlu-γGlu-Ala | E | G | T | F | I | S | D | Y | S | I | A | M | D | K | I | H | Q | D | F | V | N | W | L | L | A | P | K | P P P | A | G | S | P P P | S | NH2 |
| 368 | 080 1GI P41 81 also EEE | Y | cycloHex-Ala | E | G | T | F | | S | D | Y | S | I | A | M | D | K | I | H | Q | D | F | V | N | W | L | L | A | P | K | P P P | A | G | S | P P P | S | NH2 |
| 778 | 060 1GI P41 82 | Y | d-γGlu-γGlu-Ala | E | G | T | F | | S | D | Y | S | I | A | M | D | K | I | H | Q | D | F | V | N | W | L | L | A | P | K | P P P | A | G | S | P P P | S | NH2 |
| 369 | 080 1GI P42 37 | Y | A-(NMe)-A | E | G | T | F | | S | Y | D | S | I | A | M | D | K | I | H | Q | D | F | V | N | W | L | L | A | P | K | P P P | A | G | S | P P P | S | NH2 |
| 370 | FFF | Y | A | E | G | T | F | | S | D | Y | S | I | A | M | D | K | I | H | Q | D | F | V | N | W | L | L | A | P | K | P P P | A | G | S | P P P | S | N |

Fig. 12.30

| # | ID | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| 371 | 060 1GI P43 24 also GG G HH H | Y | A (Me) | E | G | T | F | I | S | D | Y | S | I | A | M | D | K | I | H | Q | Q | D | F | V | N | W | L | L |
| 372 | | Y | ib | E | G | T | F | | S | D | Y | S | I | A | M | D | K | I | H | Q | Q | D | F | V | N | W | L | L |
| 373 | 060 1GI P44 58 | Y | c v d p l o a G | E | G | T | F | I | S | D | Y | S | I | A | M | D | K | I | H | Q | Q | D | F | V | N | W | L | L |
| 374 | 060 1GI P42 15 | Y | b et a | D | G | T | F | I | S | D | Y | S | I | A | M | D | K | I | H | Q | Q | D | F | V | N | W | L | L |
| 375 | 060 1GI P43 89 | Y | A | D | G | T | F | I | S | D | Y | S | I | A | M | D | K | I | H | Q | Q | D | F | V | N | W | L | L |
| 376 | 060 1GI P43 99 | Y | A | D | G | T | F | I | S | D | Y | S | I | A | M | D | K | I | H | Q | Q | D | F | V | N | W | L | L |
| 377 | 060 1GI | Y | A | D | | T | F | | S | D | Y | S | I | A | M | D | K | I | H | Q | Q | D | F | V | N | W | L | L |

| # | | | | | | | | | | |
|---|---|---|---|---|---|---|---|---|---|---|
| 371 | A | Q | K | P | S | S | G | A | P | P P P S -NH2 |
| 372 | A | Q | K | P | S | S | G | A | P | P P P S -NH2 |
| 373 | A | Q | K | P | S | S | G | A | P | P P P S -NH2 |
| 374 | A | Q | K | P | S | S | G | A | P | P P P S -NH2 |
| 375 | A | Q | K | P | S | S | G | A | P | P P P S -NH2 |
| 376 | A | Q | K | P | S | S | G | A | P | P P P S -NH2 |
| 377 | A | Q | K | P | K | I | - | R | Y | R V P P S -NH |

(O ct yl gly cine)

Fig. 12.31

| # | ID | Sequence |
|---|---|---|
| 378 | P43 90 | Y S DGTF T F I S DY S I A M DK H Q DF V N W L L A Q K P(bAla) P S S G A C A P P S NH2 |
| 379 | 060 1GI P43 95 | Y S DGTF T F I S DY S I A M DK H Q DF V N W L L A Q K P S S G A P P S NH2 |
| 380 | 060 1GI P43 87 | Y S(α-hydroxy-glycine) DGTF T F I S DY S I A M DK H Q DF V N W L L A Q K P K KI RY A P P NH2 |
| 381 | 060 1GI P41 86 | Y A EGTF T F I S DY S I A M DK H Q DF V N W L L A Q K P S S G A P P S NH2 |
| 382 | 060 1GI P41 96 | Y A EGTF T F I S DY S I A M DK H Q DF V N W L L A Q K P(isoGlu-isoGlu-OCC) S S G A P P S NH2 |
| 779 | 060 1GI P41 80 also JJJ | Y a EGTF T F I S DY S I A M DK H Q DF V N W L L A Q K P S S G A P P S NH2 |
| 383 | 060 1GI P42 38** | Y(NMe) A EGTF T F I S EY S I A M DK H Q DF V N W L L A Q K P S S G A P P S |
|  | 060 1GI P43 92 | Y(NMe) A EGTF T F I S DY S I A L DK K K Q EF V N W L L A Q K P S S G A P P S |

Fig. 12.32

| # | Y-mod | A | E | G | T | F | I | S | D | Y | S | I | A | M | D/L | K | I | H | Q | D/E/Q | F | V | N | W | L | L | A | K | P | S | G | A | P | P | P | S | NH |
|---|---|---|---|---|---|---|---|---|---|---|---|---|---|---|---|---|---|---|---|---|---|---|---|---|---|---|---|---|---|---|---|---|---|---|---|---|
| 384 | Y(NMe) | A | E | G | T | F | I | S | D | Y | S | I | A | M | D | K | I | H | Q | D | F | V | N | W | L | L | A | K | P | S | G | A | P | P | P | S | NH2 |
| 780 | Y(NMe) Succinoyl | | E | G | T | F | I | S | D | Y | S | I | A | M | D | K | I | H | Q | D | F | V | N | W | L | L | A | K | P | S | G | A | P | P | P | S | NH2 |
| 781 | Y Succinoyl | | E | G | T | F | I | S | D | Y | S | I | A | M | D | K | I | H | Q | D | F | V | N | W | L | L | A | K | P | S | G | A | P | P | P | S | NH2 |
| 782 | Y Glutaroyl | | E | G | T | F | I | S | D | Y | S | I | A | M | D | K | I | H | Q | D | F | V | N | W | L | L | A | K | P | S | G | A | P | P | P | S | NH2 |
| 783 | Y Glutaroyl | | E | G | T | F | I | S | D | Y | S | I | A | M | D | K | I | H | R | Q | F | V | N | W | L | L | A | K | P | S | G | A | P | P | P | S | NH2 |
| 784 | Y Glutaroyl | | E | G | T | F | I | S | D | Y | S | I | A | L | D | K | I | R | Q | E | F | V | N | W | L | L | A | K | P | S | G | A | P | P | P | S | NH2 |
| 385 | Y | A | E | G | T | F | I | S | D | Y | S | I | A | L | D | K | I | R | Q | E | F | V | N | W | L | L | A | K | P | S | G | A | P | P | P | S | NH |

| | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| 389 | ALL | Y | A | E | G | T | F | I | S | D | Y | S | I | A | M | D | K | I | H | Q | D | F | V | N | W | L | L | A | Q | K | P | S | G | A | P | P | P | S | NH2 |
| 788 | 060 1Gi P43 84 | 4-hydroxy Phen Prop | | E | G | T | F | I | S | D | Y | S | I | A | M | D | K | I | H | Q | Q | D | F | V | N | W | L | L | A | Q | K | P | S | G | A | P | P | P | S | NH2 |
| 390 | 060 1Gi P43 85 | 4-hydroxy Phen Prop | A | E | G | T | F | I | S | D | Y | S | I | A | M | D | K | I | H | Q | Q | D | F | V | N | W | L | L | A | Q | K | P | S | G | A | P | P | P | S | NH2 |
| 391 | 060 1Gi P41 78 | Oct yl gly cin e | A | E | G | T | F | I | S | D | Y | S | I | A | M | D | K | I | H | Q | D | F | V | N | W | L | L | A | Q | K | P | S | G | A | P | P | P | S | NH2 |
| 392 | 060 1Gi P42 93 | Oct yl gly cin e | A | E | G | T | F | I | S | D | Y | S | I | A | M | D | K | I | R | Q | D | F | V | N | W | L | L | A | Q | K | P | S | G | A | P | P | P | S | NH2 |
| 393 | 060 1Gi P42 92** | Oct yl gly cin e | A | E | G | T | F | T | S | D | Y | S | I | A | L | D | K | I | R | Q | E | F | V | N | W | L | L | A | H | H | P | S | G | A | P | P | P | S | NH2 |

Fig. 12.35

| ID | AM | | | Sequence | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|
| 394 | AMM | Y | A | E | G | T | F | I | S | D | Y | S | I | A | M | D | K | I | R | Q | E | F | V | N | W | L | L | A | H | P | S | S | G | A | P P P S NH2 |
| 391 | 060 1GI P41 78 | Y | a | E | G | T | F | T | S | D | Y | S | I | A | M | D | K | I | H | Q | Q | D | F | V | N | W | L | L | A | K | P | S | S | G | A P P P S NH2 |
| 392 | 060 1GI P42 93 | Y | a | E | G | T | F | T | S | D | Y | S | I | A | M | D | K | I | R | Q | Q | D | F | V | N | W | L | L | A | K | P | S | S | G | A P P P S NH2 |
| 393 | 060 1GI P42'' 92'' | Y | a | E | G | T | F | T | S | D | Y | S | I | A | L | D | K | I | R | Q | Q | E | F | V | N | W | L | L | A | H | P | S | S | G | A P P P S NH2 |
| 395 | 060 1GI P45 43 | Y | A | P | G | T | F | T | S | D | Y | S | I | A | L | D | K | I | R | Q | Q | E | F | V | N | W | L | L | A | H | P | S | S | G | A P P P S NH2 |
| 789 | 060 1GI | Y | a | P | G | T | F | T | S | D | Y | S | I | A | L | D | K | I | R | Q | Q | E | F | V | N | W | L | L | A | H | P | S | S | G | A P P P S NH |

| | Y | S | E | G | T | F | I | S | D | Y | S | I | A | M | D | K | I | H | Q | Q | D | F | V | N | W | L | L | A | Q | K | P | S | S | Gcitrulline-lysGlupheglugluala | A | P | P | P | S | NH2 | 060 1GI P45 49 | 397 |
| --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| | Y | S | E | G | T | F | I | S | D | Y | S | I | A | M | D | K | I | H | Q | Q | D | F | V | N | W | L | L | A | Q | K | P | S | S | Gcitrulline-lysGlupheglugluala | A | P | P | P | S | NH2 | 060 1GI P45 50 | 398 |
| | Y | a | E | G | T | F | I | S | D | Y | S | I | A | L | D | K | I | H | Q | Q | D | F | V | N | W | L | L | A | Q | K | P | S | S | Gcitrulline-lysGlupheglualaala | A | P | P | P | S | NH2 | AN N | 790 |
| | Y | a | E | G | T | F | I | S | D | Y | S | I | A | L | D | K | I | R | Q | Q | D | F | V | N | W | L | L | A | Q | K | P | S | S | Gcitrulline-lysG | A | P | P | P | S | NH2 | AO O | 791 |

Fig. 12-38

| | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| 399 | 060 1GI P43 25 also MM M | Y | A | E | G | T | F | I | S | D | Y | S | I | A Q K L G K Q | | | | | | | | | | | | | | | | | | I Y Q G L |
| 400 | JA also NN N | Y | A | E | G | T | F | I | S | D | Y | S | I | A | | | | | | | | | | | | | | | | | |
| 611 | 060 1GI P43 26 also OO O | Y | a | E | G | T | F | I | S | D | Y | S | I | A Q K L G K Q | D | K | I | H | Q | D | F | V | N | W | L | L | A | Q | K | NH2 | |
| 619 | 080 1GI P45 47 also PP P | Y | a | E | G | T | F | I | S | D | Y | S | I | A | D | K | I | H | Q | D | F | V | N | W | L | L | A | Q | K | NH2 | |
| 401 | 060 1GI P44 61 | Y | A | E | G | T | F | I | S | D | Y | S | I | A M D K I H Q D F V N W L L A Q K P S G A P P S NH2 I Y Q G L | | | | | | | | | | | | | | | | | |

| | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| 94** | | Y | a | Q | P | G | T | F | S | D | Y | S | I | A | L | D | K | I | H | Q | Q | I | D | F | V | N | W | L | L |
| 617 | 060 1GI P45 42 | Y | A | P | | G | T | F | | S | D | Y | S | I | A | L | D | K | I | H | Q | Q | I | D | F | V | N | W | L | L |
| 403 | 060 1GI P45 41 | Y | | | | | | | S | D | Y | S | I | A | L | D | K | I | H | Q | Q | | D | F | V | N | W | L | L |
| 589 | 060 1GI P41 91 | Y | a | E | | G | T | F | | S | D | Y | S | I | A | L | D | K | I | H | Q | Q | | D | F | V | N | W | L | L |
| 645 | 060 1GI P44 62 | Y | a | E | | G | T | F | D(N-al-N2) | S | D | Y | S | I | A | M | D | K | I | H | Q | Q | | D | F | V | N | W | L | L |
| 798 | 060 1GI P44 14 | Y | a | E | | G | T | F | | S | D | Y | S | I | A | M | * | K | I | H | Q | Q | | D | F | V | N | W | L | L |
| 789 | 060 1GI P44 15 | Y | a | E | | G | T | F | | S | D | Y | S | I | A | | * | D | K | I | H | Q | Q | | D | F | V | N | W | L | L |

| | A | Q | K | (sidechain) | P | S | G | A | P | P | S | NH2 |
|---|---|---|---|---|---|---|---|---|---|---|---|---|
| 94** | A | Q | K | | P | S | G | A | P | P | S | NH2 |
| 617 | A | Q | K | bAla bAla | P | S | G | A | P | P | S | NH2 |
| 403 | A | Q | K | bAla bAla | P | S | G | A | P | P | S | NH2 |
| 589 | A | Q | K | 8-amino-3,6-dioxao-ctanoyl | P | S | G | A | P | P | S | NH2 |
| 645 | A | Q | K | | P | S | | | A | P | P | S NH2 |
| 798 | A | Q | K | | P | | S | G | A | P | P | S NH2 |
| 789 | A | Q | K | | P | | S | G | A | P | P | S NH2 |

| | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 404 | AZZ | Y | * | E | G | T | F | – | S | D | Y | S | – | I | A | M | D | K | – | H | Q | Q | D | F | V | N | W | L | L | A | Q | K | P | S | K | G | S | A | P | P | P | S | NH2 |
| 811 | BAA | Y | a | E | G | T | F | – | S | D | Y | S | – | I | A | M | D | K | – | H | Q | Q | D | F | V | N | W | L | L | A | Q | K | P | S | K | G | S | A | P | P | P | S | NH2 |
| 594 | 060 1GI P42 16 | Y | a | E | G | T | F | – | S | D | Y | S | – | I | A | M | D | K | – | H | Q | Q | L | F | I | E | W | L | L | K | N | G | G | P | S | S | G | A | P | P | P | S | NH2 |
| 595 | 060 1GI P42 33 | Y | a | E | G | T | F | – | S | D | Y | S | – | I | A | M | D | K | – | H | Q | Q | D | F | V | N | W | L | L | A | Q | K | P | S | K | G | S | A | P | P | P | |
| 405 | 060 1GI P42 27 also SSS | Y | A | E | G | T | F | – | S | D | Y | S | – | I | A | M | D | K | – | H | Q | Q | D | F | V | N | W | L | L | A | Q | K | P | K | K | I | R | Y | S | NH2 | | |
| 406 | 060 1GI P43 86 | Y | S | D | G | T | F | – | S | D | Y | S | – | I | A | M | D | K | – | H | Q | Q | D | F | V | N | W | L | L | A | Q | K | P | K | K | I | R | Y | S | NH2 | | |
| 407 | 060 1GI P45 38 | Y | S | E | G | T | F | – | S | D | Y | S | – | I | A | M | D | K | – | H | Q | Q | D | F | V | N | W | L | L | A | Q | K | P | K | K | I | R | Y | S | NH2 | | |
| 615 | 060 1GI P45 39 | Y | a | E | G | T | F | – | S | D | Y | S | – | I | A | L | D | K | – | R | Q | Q | D | F | V | N | W | L | L | A | Q | K | P | K | K | I | R | Y | S | NH2 | | |
| 616 | 060 1GI P45 40 | Y | a | E | G | T | F | – | S | D | Y | S | – | I | A | L | D | K | – | R | Q | Q | E | F | V | E | W | L | L | A | Q | K | P | K | K | I | R | Y | S | NH2 | | |
| 685 | 060 1GI P45 61 OctG | Y | a | E | G | T | F | – | S | D | Y | S | – | I | A | M | D | K | – | R | Q | Q | E | F | V | N | W | L | L | A | Q | K | P | K | K | I | R | Y | S | NH2 | | |

Fig. 12.43

| # | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 | Code |
|---|---|---|---|---|---|---|---|---|---|---|---|---|---|---|---|---|---|---|---|---|---|---|---|---|---|---|---|---|---|---|---|---|---|---|---|---|---|---|
| 596 | Y | a | E | G | T | F | I | S | D | Y | S | I | A | M | D | K | I | H | Q | Q | D | F | V | N | W | L | L | A | Q | K | P | S | K | E | I | L | S-NH2 | 060 1GI P42 34 |
| 598 | Y | a | G | T | F | I | S | D | Y | S | I | A | M | D | K | I | H | Q | Q | D | F | V | N | W | L | L | A | Q | K | T | S | PR | PR | P | P | S-NH2 | | 060 1GI P42 36 |
| 408 | Y | A | G | T | F | I | S | D | Y | S | I | A | M | D | K | I | H | Q | Q | D | F | V | N | W | L | L | A | Q | K | T | S | PR | R | P | P | S-NH2 | | 060 1GI P43 28 also TTT |
| 612 | Y | a | E | G | T | F | I | S | D | Y | S | I | A | M | D | K | I | H | Q | Q | D | F | V | N | W | L | L | A | Q | K | T | P | P | NH2 | | | | 060 1GI P43 45 |
| 409 | Y | A | E | G | T | F | I | S | D | Y | S | I | A | M | D | K | I | H | Q | Q | D | F | V | N | W | L | L | A | Q | K | T | S | PR | R | P | P | S-NH2 | 060 1GI P44 01 |
| 613 | Y | a | E | G | T | F | I | S | D | Y | S | I | A | M | D | K | I | H | Q | Q | D | F | V | N | W | L | L | A | Q | K | P | K | L | L | K | L | K-NH2 | 060 1GI P43 46 |
| 410 | Y | A | E | G | T | F | I | S | D | Y | S | I | A | M | D | K | I | H | Q | Q | D | F | V | N | W | L | L | A | Q | K | Aun | Ado | Ado | K | | | | 060 1GI P44 00 |

Ado is 8-Amino 3,6 dioxaoctanoic acid; Aun is 11-Amino Undecanoic acid

Fig. 12.44
| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| [Lys30,N-e]GIP-(1-30)-Exendin-4-(31-39) (SEQ ID No. 614) | 0601G IP4402 | Y | a | E | G | T | F | I | S | D | Y | S | I | A | M | D | K | I | H | Q | D | F | V | N | W | L | L | A | Q | K | -linker- | P | S | S | G | A | P | P | P | S | NH2 |
| [Lys(Biotin)37]GIP-(1-42), acid (SEQ ID NO: 411) | 0601G IP4545 | Y | A | E | G | T | F | I | S | D | Y | S | I | A | M | D | K | I | H | Q | D | F | V | N | W | L | L | A | Q | K | Q | K | N | D | W | K(-biotin-) | H | NH-OH |
| [Lys(Biotin)16]GIP-(1-42), acid (SEQ ID NO: 412) | 0601G IP4546 | Y | A | E | G | T | F | I | S | D | Y | S | I | A | M | D | K | I | H | Q | D | F | V | N | W | L | L | A | Q | K(-biotin-) | Q | K | N | D | W | K | H | NH-OH |
| 812 | BCC | Y | a | E | G | T | F | I | S | D | Y | S | I | A | M | cyclo D-K | | H | Q | D | F | V | N | W | L | L | A | Q | K | P | S | G | A | P | P | P | S | NH2 |
Linker in 0601GIP4402 is
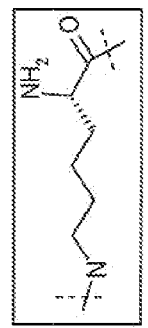

Fig. 12.45

| SEQ ID NO. | Description or Category | Compound # |
|---|---|---|
| | Parent Reference Peptides | |
| 307 | GIP(1-42)-OH, human | |
| 308 | Ac-[Lys37(palmitoyl)]GIP(1-42)-OH | 0601GIP4124 |
| | Human GIP and Analogs | |
| - | [a2]GIP(1-42)-OH | 0601GIP4042 |
| 309 | Ac-GIP(1-42)-OH | 0601GIP3984 |
| 310 | [Pro3]GIP(1-42)-OH | 0601GIP4006 |
| 311 | GIP(1-30)-OH, human | 0601GIP3783 |
| 312 | [Ser2]GIP(1-30)-OH | 0601GIP3823 |
| 313 | [Gly2]GIP(1-30)-OH | 0601GIP3822 |
| - | [dAla2]GIP(1-30)-OH | 0601GIP3842 |

Fig. 12.46

| SEQ ID NO. | Description or Category | Compound # |
|---|---|---|
| 314 | GIP(1-30)-NH2, human | 0601GIP3739 |
| 315 | [His1, Gly2]GIP(1-30)-NH2 | 0601GIP3741 |
| 316 | [Ser2]GIP(1-30)-NH2 | 0601GIP3942 |
| - | [dAla2]GIP(1-30)-NH2 | 0601GIP4058 |
| 317 | [Pro3]GIP(1-30)-NH2 | 0601GIP3979 |
|  | GIP-Exendin tail |  |
| 318 | GIP(1-30)-Ex(31-39)-NH2 | 0601GIP3757 |
| 319 | Ac-[A10]GIP(1-30)-Ex(31-39)-NH2 | 0601GIP4044 |
| 320 | [A10]GIP(1-30)-Ex(31-39)-NH2 | 0601GIP4045 |
| - | [dAla2]GIP(1-30)-Ex(31-39)-NH2 | 0601GIP3794*** |
| - | Ac-[dAla2]GIP(1-30)-Ex(31-39)-NH2 | 0601GIP4046 |

Fig. 12.47

| SEQ ID NO. | Description or Category | Compound # |
|---|---|---|
| 321 | [Ser2]GIP(1-30)-Ex(31-39)-NH2 | 0601GIP3793 |
| 322 | [Gly2]GIP(1-30)-Ex(31-39)-NH2 | 0601GIP3791 |
| 323 | [His1,Gly2]GIP(1-30)-Ex(31-39)-NH2 | 0601GIP3756 |
| 324 | [Pro3]GIP(1-30)-Ex(31-39)-NH2 | 0601GIP3974 |
| 325 | GIP(1-26)-Ex(27-39)-NH2 | 0601GIP3786 |
| 326 | [Gly2]GIP(1-26)-Ex(27-39)-NH2 | 0601GIP3785 |
| - | Additional analogs | 0601GIP4428 |
| 327 |  | 0601GIP4429 |

Fig. 12.48

| SEQ ID NO. | Description or Category | Compound # |
|---|---|---|
| | | 0601GIP4192 |
| | | 0601GIP4166 |
| | [dA2,E21,V27,K28,G29,R30]GIP(1-30) also [dA2,E21]GIP(1-26)-GLP1(33-36) | 0601GIP4282 also AAA |
| | [dA2,E21,V27,K28,G29,R30]GIP(1-30)-EX(31-39) also [dA2,E21,V27,K28,G29,R30]GIP(1-30) also [dA2,E21]GIP(1-26)-GLP1(33-36)-EX(31-39) | 0601GIP4398 |
| | [dA2,E15,E16,E17,A18]GIP(1-30)-EX(31-39) | 0601GIP4281 |
| | [dA2,E15,G16,Q17,A18,E21,V27,K28,G29,R30]GIP(1-30)-EX(31-39) | 0601GIP4280 |
| | [d-Ala2,Glu9,Glu15,Ala18,Glu21]GIP-(1-30)-Exendin-4-(31-39) | 0601GIP4198 |
| | [dA2,V19,K20]GIP(1-30)-EX(31-39) | 0601GIP4235 |

Fig. 12.49

| SEQ ID NO. | Description or Category | Compound # |
|---|---|---|
| - | [dAla2,Leu14,Arg18,Glu21]GIP-(1-30)-Exendin-4-(31-39) | 0601GIP4283 |
| - | [dAla2,Leu14,Lys18,Glu21]GIP-(1-30)-Exendin-4-(31-39) | 0601GIP4284*** |
| 328 | | 0601GIP4405 |
| 329 | | 0601GIP4406 |
| 330 | | 0601GIP4403 |
| 331 | [dAla2,Leu14,Ala18,Glu21]GIP-(1-30)-Exendin-4-(31-39) | 0601GIP4404 |
| - | | 0601GIP4285 |
| - | | UUU |
| - | [dAla2,Leu14,Arg18,Glu21,His30]GIP-(1-30)-Exendin-4-(31-39) | 0601GIP4286 |
| - | [dAla2,Thr7,Ala8,Lys12,Leu14]GIP-(1-30)-Exendin-4-(31-39) | 0601GIP4287 |
| - | | BBB |

Fig. 12.50

| SEQ ID NO. | Description or Category | Compound # |
|---|---|---|
| - | [dAla2,Arg18,Glu21]GIP-(1-30)-Exendin-4-(31-39) | 0601GIP4313 |
| - |  | 0601GIP4288 |
| - |  | CCC |
| - | [dAla2,Leu14,Arg18,Glu24]GIP-(1-30)-Exendin-4-(31-39) | 0601GIP4344 |
| - |  | 0601GIP4289*** |
| - | [dAla2,leu14,Arg18,Glu21,beta-Ala31]GIP-(1-31)-Exendin-4-(31-39) | 0601GIP4290 |
| 332 |  | 0601GIP4456 |
| 333 |  | 0601GIP4457 |
| 334 |  | 0601GIP4460 |
|  | Analogs incorporating modifications from different species and GIP from different species |  |
| 335 | GIP(1-42)-OH, human |  |
| 336 | GIP(3-42)-OH, human |  |
| 337 | GIP(1-42)-OH, cattle | 0601GIP3300 |

Fig. 12.51

| SEQ ID NO. | Description or Category | Compound # |
|---|---|---|
| 338 | GIP(1-42)-OH, rat | |
| 339 | GIP(1-42)-OH, mouse | |
| 340 | GIP(1-42)-OH, opossum | |
| 341 | GIP(1-42)-OH, porcine | |
| 342 | GIP (1-39)-OH, porcine | 0601GIP3943 |
| 343 | GIP (1-30)-NH2, Porcine | 0601GIP2350 |
| 344 | GIP, dog | |
| 345 | GIP, chicken | |
| 346 | GIP, Xenopus | |
| 347 | GIP, zebrafish (partial) | |
| - | [dAla2, Leu14]GIP(1-30)-Exendin(31-39) | 0601GIP4190 |
| - | [dAla2, Glu9]GIP(1-30)-Exendin(31-39) | 0601GIP4151 |

Fig. 12.52

| SEQ ID NO. | Description or Category | Compound # |
|---|---|---|
| - | [dAla2, Glu21]GIP(1-30)-Exendin(31-39) | 0601GIP4152 |
| - | [dAla2, Ala18]GIP(1-30)-Exendin(31-39) | 0601GIP4150 |
| - | [dAla2, Arg18]GIP(1-30)-Exendin(31-39) | 0601GIP4153 |
| - | [dAla2, Lys18]GIP(1-30)-Exendin(31-39) | 0601GIP4149 |
| - | [dAla2, Ala30]GIP(1-30)-Exendin(31-39) | 0601GIP4165 |
| - | [dAla2, Arg30]GIP(1-30)-Exendin(31-39) | 0601GIP4176 |
| - | [dAla2, His30]GIP(1-30)-Exendin(31-39) | 0601GIP4177 |
| - | | 0601GIP4213 |

Fig. 12.53

| SEQ ID NO. | Description or Category | Compound # |
|---|---|---|
| - | | 0601GIP4214 |
| - | | 0601GIP4263 |
| - | [dAla2,Leu14,Arg18,Glu21,Arg30]GIP-(1-30)-Exendin-4-(31-39) | 0601GIP4278 |
| - | | 0601GIP4264 |
| - | [dAla2,Leu14,Ala18,Glu21,His30]GIP-(1-30)-Exendin-4-(31-39) | 0601GIP4279 |
| - | | 0601GIP4314 also QQQ |
| - | | 0601GIP4306 also RRR |
| 348 | | Xenopus |
| 349 | | 0601GIP4503 |
| 350 | | 0601GIP4504 |
| - | | 0601GIP4505 |
| - | | 0601GIP4506 |
| - | | VVV |

Fig. 12.54

| SEQ ID NO. | Description or Category | Compound # |
|---|---|---|
|  |  | www |
| 351 |  | xxx |
|  |  | chicken |
|  |  | 0601GIP4465 |
|  |  | 0601GIP4466 |
|  |  | 0601GIP4478 |
|  |  | 0601GIP4467 |
|  |  | 0601GIP4479 |
|  |  | 0601GIP4480 |
|  |  | YYY |
|  |  | 0601GIP4551 |
| 352 |  | ZZZ |
| 353 |  | 0601GIP4407 |
| 354 |  | ABB |
| 355 |  | ACC |

Fig. 12.55

| SEQ ID NO. | Description or Category | Compound # |
|---|---|---|
| 356 | Zebra fish (partial) | ADD |
| 357 | | 0601GIP4507 |
| , | | 0601GIP4536 |
| , | | 0601GIP4537 |
| , | | AEE |
| 358 | | 0601GIP4391 |
| 359 | | 0601GIP4459 |
| , | | AFF |
| , | | AGG |
| | Exemplary Modifications at positions 1 and/or 2 and 0601GIP3794 analogs modified at position 2 and/or position 3 | |
| 360 | [Val2]GIP(1-30)Exendin(31-39) LD | 0601GIP4189 |

Fig. 12.56

| SEQ ID NO. | Description or Category | Compound # |
|---|---|---|
| - | [dnorval2]GIP(1-30)Exendin(31-39) RN | 0601GIP4145 |
| - | [dSer2]GIP(1-30)Exendin(31-39) RN | 0601GIP4146 |
| 361 | [Abu2]GIP(1-30)Exendin(31-39) RN | 0601GIP4147 |
| 362 | | 0601GIP4318 |
| 363 | | 0601GIP4362 also DDD |
| 364 | [dAbu2]GIP(1-30)Exendin(31-39) RN | 0601GIP4148 |
| 365 | [hSer]GIP(1-30)Exendin(31-39) RN | 0601GIP4186 |
| - | | 0601GIP4195 |
| 366 | [dPro2]GIP(1-30)Exendin(31-39) LD | 0601GIP4164 |
| 367 | [CyclopropA]GIP(1-30)Exendin(31-39) RN | 0601GIP4187 |

Fig. 12.57

| SEQ ID NO. | Description or Category | Compound # |
|---|---|---|
| - | [dCyclopropA]GIP(1-30)Exendin(31-39) RN | 0601GIP4188 |
| 368 | | 0601GIP4181 also EEE |
| - | | 0601GIP4182 |
| 369 | | 0601GIP4237 FFF |
| 370 | | |
| 371 | | 0601GIP4324 also GGG HHH |
| 372 | | |
| 373 | | 0601GIP4458 |
| 374 | | 0601GIP4215 |
| 375 | | 0601GIP4389 |
| 376 | | 0601GIP4399 |
| 377 | fGLP1 tail added | 0601GIP4390 |
| 378 | | 0601GIP4395 |

Fig. 12.58

| SEQ ID NO. | Description or Category | Compound # |
|---|---|---|
| 379 | | 0601GIP4387 |
| 380 | | 0601GIP4386 |
| | Exemplary N-terminus modifications and N-terminus Modified 0601GIP3794 analogs | |
| 381 | | 0601GIP4196 |
| 382 | | 0601GIP4180 also JJJ |
| , | | 0601GIP4238*** |
| 383 | | 0601GIP4392 |
| 384 | | 0601GIP4369 also KKK |
| , | | LLL |
| , | (N-Succinoyl)[dAla2]GIP-(1-30)-Exendin-4-(31-39) | 0601GIP4291 |
| , | | 0601GIP4330 |
| , | | AHH |
| , | | 0601GIP4331 |
| 385 | | AII |

Fig. 12.59

| SEQ ID NO. | Description or Category | Compound # |
|---|---|---|
| 386 | | AJJ |
| | | 0601GIP4359 |
| 387 | | 0601GIP4347 |
| | | 0601GIP4348 |
| 388 | | 0601GIP4349 |
| | | AKK |
| 389 | | ALL |
| | | 0601GIP4384 |
| 390 | | 0601GIP4385 |
| | Fatty acid/Linker substitution | |
| 391 | Octylglycine-GIP(1-30)Exendin(31-39) | 0601GIP4178 |
| 392 | (N-Octylglycine)-[Arg18]GIP-(1-30)-Exendin-4-(31-39) | 0601GIP4293 |
| 393 | (N-Octylglycine)-[Leu14,Arg18,Glu21,His30]GIP-(1-30)-Exendin-4-(31-39) | 0601GIP4292*** |
| 394 | | AMM |
| | | 0601GIP4178 |

Fig. 12.60

| SEQ ID NO. | Description or Category | Compound # |
|---|---|---|
| | | 0601GIP4293 |
| | | 0601GIP4292*** |
| | | 0601GIP4543 |
| | | 0601GIP4544 |
| 395 | | 0601GIP4194 |
| | | 0601GIP4252 |
| | | 0601GIP4548 |
| | | 0601GIP4549 |
| 396 | | 0601GIP4550 |
| 397 | | |
| 398 | | ANN |

Fig. 12.61

| SEQ ID NO. | Description or Category | Compound # |
|---|---|---|
| - | | AOO |
| 399 | | 0601GIP4325 also MMM |
| 400 | | JA also NNN |
| - | | 0601GIP4326 also OOO |
| - | | 0601GIP4547 also PPP |
| 401 | | 0601GIP4461 |
| - | | APP |
| - | | 0601GIP4179 |
| - | | AQQ |
| 402 | | ARR |

Fig. 12.62

| SEQ ID NO. | Description or Category | Compound # |
|---|---|---|
| - | | ASS |
| - | | ATT |
| - | | AUU |
| - | | AVV |
| - | (N-Octylglycine)-[dAla2,Leu14,beta-Ala31,beta-Ala32]GIP-(1-32)-Exendin-4-(31-39) | 0601GIP4294*** |
| - | | 0601GIP4542 |
| 403 | | 0601GIP4541 |
| - | | 0601GIP4191 |
| - | | 0601GIP4562 |
| - | [Lys30,N-e] GIP-(1-30)]-Exendin-4-(31-39) | 0601GIP4402 |
| | Deletions | |
| - | | 0601GIP4414 |
| - | | 0601GIP4415 |
| - | | 0601GIP4434 |
| - | | 0601GIP4416 |

Fig. 12.63

| SEQ ID NO. | Description or Category | Compound # |
|---|---|---|
| | | 0601GIP4417 |
| | | 0601GIP4435 |
| | | 0601GIP4436 |
| | | 0601GIP4437 |
| | | 0601GIP4438 |
| | | 0601GIP4439 |
| | | AWW |
| | | AXX |
| | | AYY |
| 404 | | AZZ |
| | | BAA |
| | 0601GIP3794 incorporating a "Trp Cage" from Exendin: Leu21-Pro38 | 0601GIP4216 |
| | Tail (Trp-cage) Modifications | |
| | fGLP1 tail | 0601GIP4233 |

Fig. 12.64

| SEQ ID NO. | Description or Category | Compound # |
|---|---|---|
| 405 | | 0601GIP4327 also SSS |
| 406 | | 0601GIP4386 |
| 407 | | 0601GIP4538 |
| | | 0601GIP4539 |
| | | 0601GIP4540 |
| | | 0601GIP4561 |
| | fGLP1 tail variant | 0601GIP4234 |
| | [dA2]GIP(1-30)-HS2(31-39); HS=HELOSPECTIN-2 | 0601GIP4236 |
| 408 | | 0601GIP4328 also TTT |
| | [dA2]GIP(1-30)-Helodermin(31-35) | 0601GIP4345 |
| 409 | GIP(1-30)helospectin1(31-38) | 0601GIP4401 |
| | | 0601GIP4346 |

Fig. 12.65

| SEQ ID NO. | Description or Category | Compound # |
|---|---|---|
| 410 | | 0601GIP4400 |

Effect of Compounds of the Invention in Food Intake Assay

Effect of Compounds of the Invention on Blood Glucose (Oral Glucose Tolerance Test)

Effect of Compounds of the Invention in Food Intake Assay

Figure Legend:
- Vehicle
- Cmpd 2  3 nmol/kg
- Cmpd 2  10 nmol/kg
- Cmpd 2  30 nmol/kg
- Cmpd 2  100 nmol/kg
- Cmpd 2  300 nmol/kg Effect of Compounds of the Invention in Food Intake Assay Effect of sCT (amide form) in Food Intake Assay Effect of Compounds of the Invention on Blood Glucose

Fig. 22

Mammalian and Non-Mammalian GIP Alignment

|  |  | (1) 1 10 20 30 42 | SEQ ID NO: |
|---|---|---|---|
| BOVINE_GIBO | (1) | | 13 |
| COW_XP_588333 | (1) | | 420 |
| MOUSE_NP_032145 | (1) | | 10 |
| PIG_2_GIP_AY609506 | (1) | | 12 |
| CHICKEN_XP_418111 | (1) | LA RT LKKN E R E NVI PYR | 300 |
| Xenopus_Trop_GIP | (1) | ILA R N LKKN E E NTSEA K | 301 |
| ZEBRAFISH_POTENTIAL_GIP | (1) | ES IA ISK T V KN E N E ———— | 302 |
| MONKEY_GIP | (1) | N A E H PP N P | 303 |
| Opussum_GIP_peptide | (1) | N T K M N NS E | 304 |
| HUMAN_NP_004114 | (1) | | 2 |
| HAMSTER_GDIP_TRANSLATION | (1) | | 305 |
| NP_062604_RAT_GIP | (1) | | 11 |
| Consensus | (1) | YAEGTFISDYSIAMDKIRQQDFVNWLLAQKGKKSDWKHNITQ | 306 |
|  |  | ☆☆   ☆☆  ☆   ☆☆ ☆☆  ☆ |  |

Positions Y1, E3, D9, S11, D15, F22, V23, L26, L27, and K32 are conserved across all species.

Fig. 24
Additional Linkers
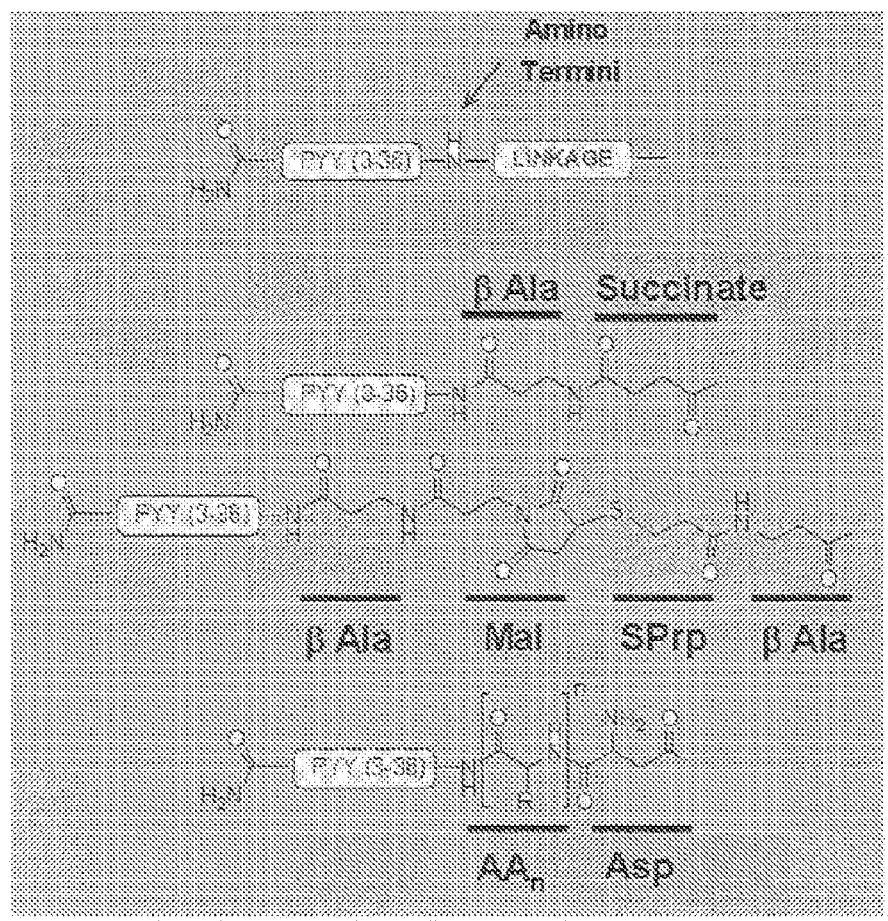
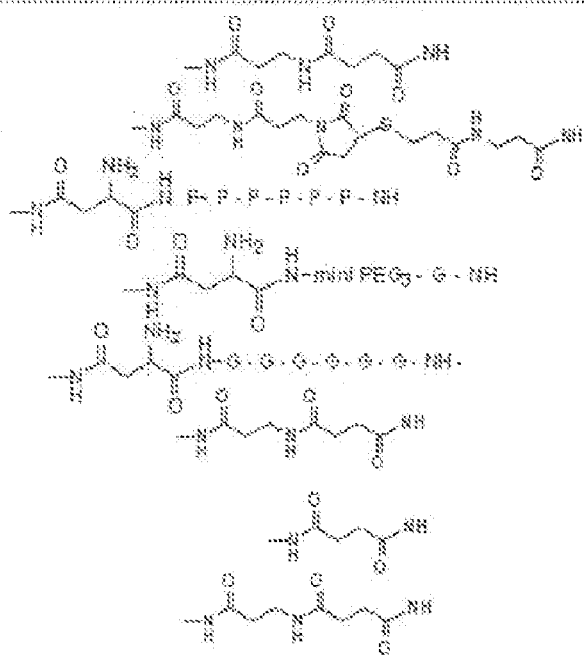

Fig. 27
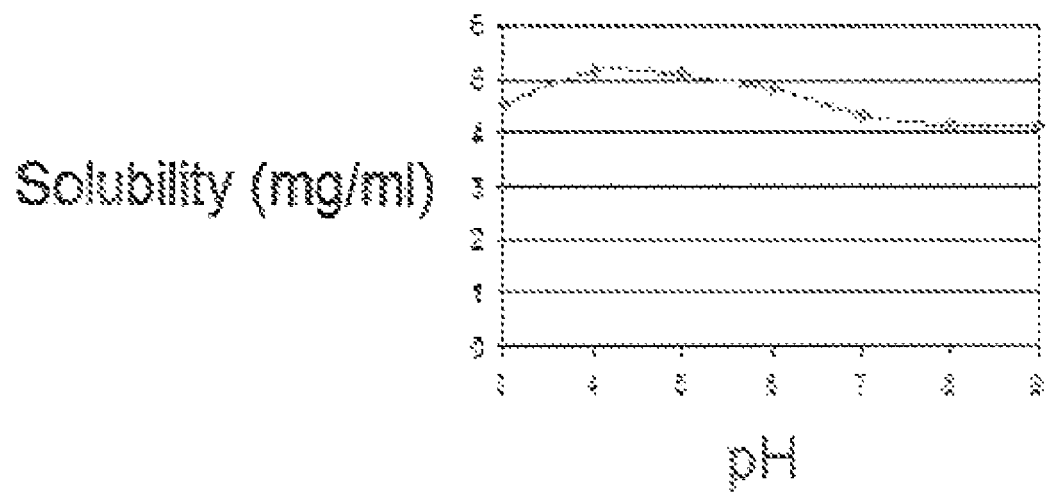
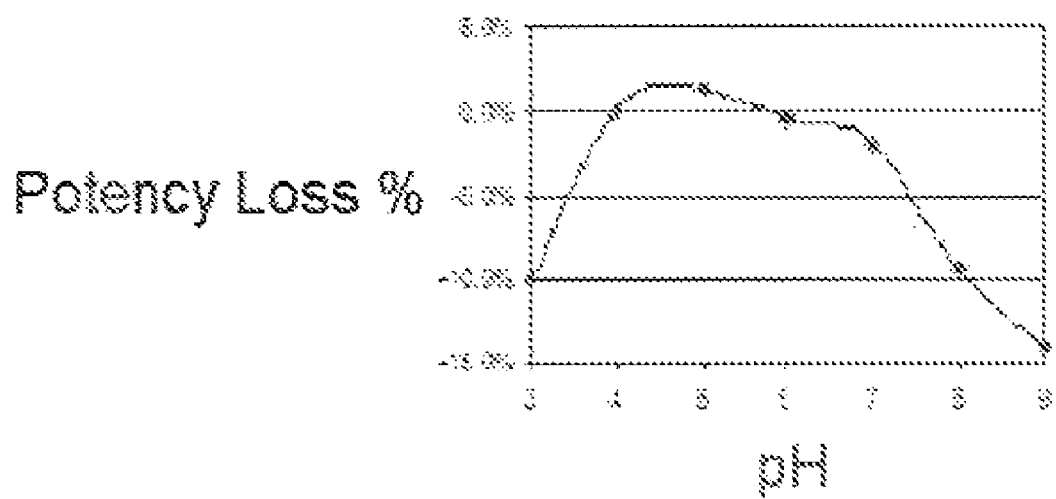

```
                        SEQUENCE LISTING

<160> NUMBER OF SEQ ID NOS: 933

<210> SEQ ID NO 1
    <211> LENGTH: 9
    <212> TYPE: PRT
    <213> ORGANISM: Artificial Sequence
    <220> FEATURE:
    <223> OTHER INFORMATION: synthetic peptide

<400> SEQUENCE: 1

Pro Ser Ser Gly Ala Pro Pro Pro Ser
    1               5

<210> SEQ ID NO 2
    <211> LENGTH: 42
    <212> TYPE: PRT
    <213> ORGANISM: Homo sapiens

<400> SEQUENCE: 2

Tyr Ala Glu Gly Thr Phe Ile Ser Asp Tyr Ser Ile Ala Met Asp Lys
    1               5                   10                  15

Ile His Gln Gln Asp Phe Val Asn Trp Leu Leu Ala Gln Lys Gly Lys
                20                  25                  30

Lys Asn Asp Trp Lys His Asn Ile Thr Gln
            35                  40

<210> SEQ ID NO 3
    <211> LENGTH: 30
    <212> TYPE: PRT
    <213> ORGANISM: Homo sapiens

<400> SEQUENCE: 3

Tyr Ala Glu Gly Thr Phe Ile Ser Asp Tyr Ser Ile Ala Met Asp Lys
    1               5                   10                  15

Ile His Gln Gln Asp Phe Val Asn Trp Leu Leu Ala Gln Lys
                20                  25                  30

<210> SEQ ID NO 4
    <211> LENGTH: 30
    <212> TYPE: PRT
    <213> ORGANISM: Artificial Sequence
    <220> FEATURE:
    <223> OTHER INFORMATION: synthetic peptide

<400> SEQUENCE: 4

His Ala Glu Gly Thr Phe Thr Ser Asp Val Ser Ser Tyr Leu Glu Gly
    1               5                   10                  15
```

```
Gln Ala Ala Lys Glu Phe Ile Ala Trp Leu Val Lys Gly Arg
            20                  25                  30

<210> SEQ ID NO 5
<211> LENGTH: 39
<212> TYPE: PRT
<213> ORGANISM: Artificial Sequence
<220> FEATURE:
<223> OTHER INFORMATION: synthetic peptide

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 13
<212> TYPE: PRT
<213> ORGANISM: Artificial Sequence
<220> FEATURE:
<223> OTHER INFORMATION: synthetic peptide

<400> SEQUENCE: 6

Lys Asn Gly Gly Pro Ser Ser Gly Ala Pro Pro Pro Ser
1               5                   10

<210> SEQ ID NO 7
<211> LENGTH: 18
<212> TYPE: PRT
<213> ORGANISM: Artificial Sequence
<220> FEATURE:
<223> OTHER INFORMATION: synthetic peptide

<400> SEQUENCE: 7

Phe Ile Glu Trp Leu Lys Asn Gly Gly Pro Ser Ser Gly Ala Pro Pro
1               5                   10                  15

Pro Ser

<210> SEQ ID NO 8
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (13)..(13)
<223> OTHER INFORMATION: Xaa is homoserine

<400> SEQUENCE: 8

Gly Lys Lys Asn Asp Trp Lys His Asn Ile Thr Gln Xaa
1               5                   10

<210> SEQ ID NO 9
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (13)..(13)
<223> OTHER INFORMATION: Xaa is homoserine

<400> SEQUENCE: 9
```

```
Gly Lys Lys Asn Asp Trp Lys His Asn Ile Thr Gln Xaa
1               5                   10
```

<210> SEQ ID NO 10
<211> LENGTH: 42
<212> TYPE: PRT
<213> ORGANISM: Mus musculus

<400> SEQUENCE: 10

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Ile Thr Gln
        35                  40
```

<210> SEQ ID NO 11
<211> LENGTH: 42
<212> TYPE: PRT
<213> ORGANISM: Rattus rattus

<400> SEQUENCE: 11

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln
        35                  40
```

<210> SEQ ID NO 12
<211> LENGTH: 42
<212> TYPE: PRT
<213> ORGANISM: Sus scrofa

<400> SEQUENCE: 12

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln
        35                  40
```

<210> SEQ ID NO 13
<211> LENGTH: 42
<212> TYPE: PRT
<213> ORGANISM: Bos taurus

<400> SEQUENCE: 13

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln
        35                  40
```

<210> SEQ ID NO 14
<211> LENGTH: 14
<212> TYPE: PRT
<213> ORGANISM: Artificial Sequence
<220> FEATURE:
<223> OTHER INFORMATION: synthetic peptide

```
<400> SEQUENCE: 14

Tyr Ala Glu Gly Thr Phe Ile Ser Asp Tyr Ser Ile Ala Met
1               5                   10

<210> SEQ ID NO 15
<211> LENGTH: 12
<212> TYPE: PRT
<213> ORGANISM: Artificial Sequence
<220> FEATURE:
<223> OTHER INFORMATION: synthetic peptide

<400> SEQUENCE: 15

Gln Gln Asp Phe Val Asn Trp Leu Leu Ala Gln Lys
1               5                   10

<210> SEQ ID NO 16
<211> LENGTH: 40
<212> TYPE: PRT
<213> ORGANISM: Artificial Sequence
<220> FEATURE:
<223> OTHER INFORMATION: synthetic peptide

<400> SEQUENCE: 16

Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Gly Lys Lys Asn
            20                  25                  30

Asp Trp Lys His Asn Ile Thr Gln
        35                  40

<210> SEQ ID NO 17
<211> LENGTH: 30
<212> TYPE: PRT
<213> ORGANISM: Artificial Sequence
<220> FEATURE:
<223> OTHER INFORMATION: synthetic peptide

<400> SEQUENCE: 17

Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys
            20                  25                  30

<210> SEQ ID NO 18
<211> LENGTH: 48
<212> TYPE: PRT
<213> ORGANISM: Artificial Sequence
<220> FEATURE:
<223> OTHER INFORMATION: synthetic peptide

<400> SEQUENCE: 18

Thr Gln Ala Gln Leu Leu Arg Val Gly Cys Gly Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45

<210> SEQ ID NO 19
<211> LENGTH: 47
<212> TYPE: PRT
<213> ORGANISM: Artificial Sequence
<220> FEATURE:
<223> OTHER INFORMATION: synthetic peptide
```

-continued

```
<400> SEQUENCE: 19

Thr Gln Ala Gln Leu Leu Arg Val Gly Cys Asp Thr Ala Thr Cys Gln
1               5                   10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
            35                  40                  45

<210> SEQ ID NO 20
<211> LENGTH: 47
<212> TYPE: PRT
<213> ORGANISM: Artificial Sequence
<220> FEATURE:
<223> OTHER INFORMATION: synthetic peptide

<400> SEQUENCE: 20

Thr Gln Ala Gln Leu Leu Arg Val Gly Met Val Leu Gly Thr Met Gln
1               5                   10                  15

Val Gln Asn Leu Ser His Arg Leu Trp Gln Leu Met Gly Pro Ala Gly
                20                  25                  30

Arg Gln Asp Ser Ala Pro Val Asp Pro Ser Ser Pro His Ser Tyr
            35                  40                  45

<210> SEQ ID NO 21
<211> LENGTH: 47
<212> TYPE: PRT
<213> ORGANISM: Artificial Sequence
<220> FEATURE:
<223> OTHER INFORMATION: synthetic peptide

<400> SEQUENCE: 21

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
                20                  25                  30

Arg Gln Asp Ser Ala Pro Val Glu Pro Ser Ser Pro His Ser Tyr
            35                  40                  45

<210> SEQ ID NO 22
<211> LENGTH: 47
<212> TYPE: PRT
<213> ORGANISM: Artificial Sequence
<220> FEATURE:
<223> OTHER INFORMATION: synthetic peptide

<400> SEQUENCE: 22

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
                20                  25                  30

Arg Gln Glu Ser Ala Pro Val Glu Pro Ser Ser Pro His Ser Tyr
            35                  40                  45

<210> SEQ ID NO 23
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: SULFATATION
```

```
<400> SEQUENCE: 23

Asp Tyr Met Gly Trp Met Asp Phe
1               5

<210> SEQ ID NO 24
<211> LENGTH: 8
<212> TYPE: PRT
<213> ORGANISM: Artificial Sequence
<220> FEATURE:
<223> OTHER INFORMATION: synthetic peptide

<400> SEQUENCE: 24

Asp Tyr Met Gly Trp Met Asp Phe
1               5

<210> SEQ ID NO 25
<211> LENGTH: 6
<212> TYPE: PRT
<213> ORGANISM: Artificial Sequence
<220> FEATURE:
<223> OTHER INFORMATION: synthetic peptide

<400> SEQUENCE: 25

Met Gly Trp Met Asp Phe
1               5

<210> SEQ ID NO 26
<211> LENGTH: 5
<212> TYPE: PRT
<213> ORGANISM: Artificial Sequence
<220> FEATURE:
<223> OTHER INFORMATION: synthetic peptide

<400> SEQUENCE: 26

Gly Trp Met Asp Phe
1               5

<210> SEQ ID NO 27
<211> LENGTH: 4
<212> TYPE: PRT
<213> ORGANISM: Artificial Sequence
<220> FEATURE:
<223> OTHER INFORMATION: synthetic peptide

<400> SEQUENCE: 27

Trp Met Asp Phe
1

<210> SEQ ID NO 28
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: SULFATATION

<400> SEQUENCE: 28

Lys Asp Tyr Met Gly Trp Met Asp Phe
1               5

<210> SEQ ID NO 29
<211> LENGTH: 9
<212> TYPE: PRT
<213> ORGANISM: Artificial Sequence
<220> FEATURE:
```

```
<223> OTHER INFORMATION: synthetic peptide

<400> SEQUENCE: 29

Lys Asp Tyr Met Gly Trp Met Asp Phe
1               5

<210> SEQ ID NO 30
<211> LENGTH: 7
<212> TYPE: PRT
<213> ORGANISM: Artificial Sequence
<220> FEATURE:
<223> OTHER INFORMATION: synthetic peptide

<400> SEQUENCE: 30

Lys Met Gly Trp Met Asp Phe
1               5

<210> SEQ ID NO 31
<211> LENGTH: 6
<212> TYPE: PRT
<213> ORGANISM: Artificial Sequence
<220> FEATURE:
<223> OTHER INFORMATION: synthetic peptide

<400> SEQUENCE: 31

Lys Gly Trp Met Asp Phe
1               5

<210> SEQ ID NO 32
<211> LENGTH: 5
<212> TYPE: PRT
<213> ORGANISM: Artificial Sequence
<220> FEATURE:
<223> OTHER INFORMATION: synthetic peptide

<400> SEQUENCE: 32

Lys Trp Met Asp Phe
1               5

<210> SEQ ID NO 33
<211> LENGTH: 37
<212> TYPE: PRT
<213> ORGANISM: Rattus rattus

<400> SEQUENCE: 33

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 34
<211> LENGTH: 37
<212> TYPE: PRT
<213> ORGANISM: Homo sapiens

<400> SEQUENCE: 34

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35
```

```
<210> SEQ ID NO 35
<211> LENGTH: 52
<212> TYPE: PRT
<213> ORGANISM: Homo sapiens

<400> SEQUENCE: 35

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 36
<211> LENGTH: 32
<212> TYPE: PRT
<213> ORGANISM: Artificial Sequence
<220> FEATURE:
<223> OTHER INFORMATION: synthetic peptide

<400> SEQUENCE: 36

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 37
<211> LENGTH: 32
<212> TYPE: PRT
<213> ORGANISM: Homo sapiens

<400> SEQUENCE: 37

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 38
<211> LENGTH: 37
<212> TYPE: PRT
<213> ORGANISM: Homo sapiens

<400> SEQUENCE: 38

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 39
<211> LENGTH: 37
<212> TYPE: PRT
<213> ORGANISM: Homo sapiens

<400> SEQUENCE: 39

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30
```

Gly Ser Lys Ala Phe
        35

<210> SEQ ID NO 40
<211> LENGTH: 47
<212> TYPE: PRT
<213> ORGANISM: Homo sapiens

<400> SEQUENCE: 40

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 41
<211> LENGTH: 40
<212> TYPE: PRT
<213> ORGANISM: Homo sapiens

<400> SEQUENCE: 41

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40

<210> SEQ ID NO 42
<211> LENGTH: 47
<212> TYPE: PRT
<213> ORGANISM: Mus musculus

<400> SEQUENCE: 42

Pro His Ala Gln Leu Leu Arg Val Gly Cys Val Leu Gly Thr Cys Gln
1               5                   10                  15

Val Gln Asn Leu Ser His Arg Leu Trp Gln Leu Val Arg Pro Ala Gly
            20                  25                  30

Arg Arg Asp Ser Ala Pro Val Asp Pro Ser Ser Pro His Ser Tyr
        35                  40                  45

<210> SEQ ID NO 43
<211> LENGTH: 40
<212> TYPE: PRT
<213> ORGANISM: Mus musculus

<400> SEQUENCE: 43

Val Gly Cys Val Leu Gly Thr Cys Gln Val Gln Asn Leu Ser His Arg
1               5                   10                  15

Leu Trp Gln Leu Val Arg Pro Ala Gly Arg Arg Asp Ser Ala Pro Val
            20                  25                  30

Asp Pro Ser Ser Pro His Ser Tyr
        35                  40

<210> SEQ ID NO 44
<211> LENGTH: 8
<212> TYPE: PRT
<213> ORGANISM: Artificial Sequence
<220> FEATURE:
<223> OTHER INFORMATION: synthetic peptide
<220> FEATURE:

```
<221> NAME/KEY: MOD_RES
<222> LOCATION: (2)..(2)
<223> OTHER INFORMATION: SULFATATION

<400> SEQUENCE: 44

Asp Tyr Met Gly Trp Met Asp Phe
1               5

<210> SEQ ID NO 45
<211> LENGTH: 167
<212> TYPE: PRT
<213> ORGANISM: Homo sapiens

<400> SEQUENCE: 45

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
    130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 46
<211> LENGTH: 36
<212> TYPE: PRT
<213> ORGANISM: Homo sapiens

<400> SEQUENCE: 46

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
                20                  25                  30

Arg Gln Arg Tyr
            35

<210> SEQ ID NO 47
<211> LENGTH: 34
<212> TYPE: PRT
<213> ORGANISM: Homo sapiens

<400> SEQUENCE: 47

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
                20                  25                  30
```

Arg Tyr

<210> SEQ ID NO 48
<211> LENGTH: 37
<212> TYPE: PRT
<213> ORGANISM: Homo sapiens

<400> SEQUENCE: 48

His Asp Glu Phe Glu Arg His Ala Glu Gly Thr Phe Thr Ser Asp Val
1               5                   10                  15

Ser Ser Thr Leu Glu Gly Gln Ala Ala Leu Glu Phe Ile Ala Trp Leu
            20                  25                  30

Val Lys Gly Arg Gly
        35

<210> SEQ ID NO 49
<211> LENGTH: 37
<212> TYPE: PRT
<213> ORGANISM: Xenopus sp.

<400> SEQUENCE: 49

His Ala Glu Gly Thr Tyr Thr Asn Asp Val Thr Glu Tyr Leu Glu Glu
1               5                   10                  15

Lys Ala Ala Lys Glu Phe Ile Glu Trp Leu Ile Lys Gly Lys Pro Lys
            20                  25                  30

Lys Ile Arg Tyr Ser
        35

<210> SEQ ID NO 50
<211> LENGTH: 37
<212> TYPE: PRT
<213> ORGANISM: Xenopus sp.

<400> SEQUENCE: 50

His Ala Glu Gly Thr Phe Thr Ser Asp Val Thr Gln Gln Leu Asp Glu
1               5                   10                  15

Lys Ala Ala Lys Glu Phe Ile Asp Trp Leu Ile Asn Gly Gly Pro Ser
            20                  25                  30

Lys Glu Ile Ile Ser
        35

<210> SEQ ID NO 51
<211> LENGTH: 30
<212> TYPE: PRT
<213> ORGANISM: Homo sapiens

<400> SEQUENCE: 51

His Ala Glu Gly Thr Phe Thr Ser Asp Val Ser Ser Tyr Leu Glu Gly
1               5                   10                  15

Gln Ala Ala Leu Glu Phe Ile Ala Trp Leu Val Lys Gly Arg
            20                  25                  30

<210> SEQ ID NO 52
<211> LENGTH: 33
<212> TYPE: PRT
<213> ORGANISM: Homo sapiens

<400> SEQUENCE: 52

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Glu Thr Lys Ile Thr

```
                     20                  25                  30

Asp

<210> SEQ ID NO 53
<211> LENGTH: 31
<212> TYPE: PRT
<213> ORGANISM: Xenopus sp.

<400> SEQUENCE: 53

His Ala Glu Gly Thr Phe Thr Asn Asp Met Thr Asn Tyr Leu Glu Glu
1               5                   10                  15

Lys Ala Ala Lys Glu Phe Val Gly Trp Leu Ile Lys Gly Arg Pro
            20                  25                  30

<210> SEQ ID NO 54
<211> LENGTH: 37
<212> TYPE: PRT
<213> ORGANISM: Artificial Sequence
<220> FEATURE:
<223> OTHER INFORMATION: synthetic peptide

<400> SEQUENCE: 54

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 55
<211> LENGTH: 39
<212> TYPE: PRT
<213> ORGANISM: Artificial Sequence
<220> FEATURE:
<223> OTHER INFORMATION: synthetic peptide

<400> SEQUENCE: 55

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 56
<211> LENGTH: 42
<212> TYPE: PRT
<213> ORGANISM: Artificial Sequence
<220> FEATURE:
<223> OTHER INFORMATION: synthetic peptide

<400> SEQUENCE: 56

Thr Gln Ala Gln Leu Leu Arg Val Gly Cys Val Leu Gly Thr Cys Gln
1               5                   10                  15

Val Gln Asn Leu Ser His Arg Leu Trp Gln Leu Arg Gln Asp Ser Ala
            20                  25                  30

Pro Val Asp Pro Ser Ser Pro His Ser Tyr
        35                  40

<210> SEQ ID NO 57
<211> LENGTH: 40
<212> TYPE: PRT
<213> ORGANISM: Artificial Sequence
```

<220> FEATURE:
<223> OTHER INFORMATION: synthetic peptide

<400> SEQUENCE: 57

Thr Gln Ala Gln Leu Leu Arg Val Gly Cys Val Leu Gly Thr Cys Gln
1               5                   10                  15

Val Gln Asn Leu Ser His Arg Leu Trp Gln Leu Asp Ser Ala Pro Val
            20                  25                  30

Asp Pro Ser Ser Pro His Ser Tyr
        35                  40

<210> SEQ ID NO 58
<211> LENGTH: 41
<212> TYPE: PRT
<213> ORGANISM: Artificial Sequence
<220> FEATURE:
<223> OTHER INFORMATION: synthetic peptide

<400> SEQUENCE: 58

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr
        35                  40

<210> SEQ ID NO 59
<211> LENGTH: 40
<212> TYPE: PRT
<213> ORGANISM: Artificial Sequence
<220> FEATURE:
<223> OTHER INFORMATION: synthetic peptide

<400> SEQUENCE: 59

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Glu Pro Ser Ser Pro His Ser Tyr
        35                  40

<210> SEQ ID NO 60
<211> LENGTH: 35
<212> TYPE: PRT
<213> ORGANISM: Artificial Sequence
<220> FEATURE:
<223> OTHER INFORMATION: synthetic peptide

<400> SEQUENCE: 60

Val Gly Cys Val Leu Gly Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 61
<211> LENGTH: 39
<212> TYPE: PRT
<213> ORGANISM: Artificial Sequence
<220> FEATURE:
<223> OTHER INFORMATION: synthetic peptide

<400> SEQUENCE: 61

-continued

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
            35

<210> SEQ ID NO 62
<211> LENGTH: 34
<212> TYPE: PRT
<213> ORGANISM: Artificial Sequence
<220> FEATURE:
<223> OTHER INFORMATION: synthetic peptide

<400> SEQUENCE: 62

Gly Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 63
<211> LENGTH: 34
<212> TYPE: PRT
<213> ORGANISM: Artificial Sequence
<220> FEATURE:
<223> OTHER INFORMATION: synthetic peptide

<400> SEQUENCE: 63

Gly Cys Asn Thr Ala Thr Cys Gln Val Gln Asn Leu Ser His Arg Leu
1               5                   10                  15

Trp Gln Leu Arg Gln Asp Ser Ala Pro Val Glu Pro Ser Ser Pro His
            20                  25                  30

Ser Tyr

<210> SEQ ID NO 64
<211> LENGTH: 35
<212> TYPE: PRT
<213> ORGANISM: Artificial Sequence
<220> FEATURE:
<223> OTHER INFORMATION: synthetic peptide

<400> SEQUENCE: 64

Gly Cys Ser Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
            35

<210> SEQ ID NO 65
<211> LENGTH: 35
<212> TYPE: PRT
<213> ORGANISM: Artificial Sequence
<220> FEATURE:
<223> OTHER INFORMATION: synthetic peptide

<400> SEQUENCE: 65

Gly Cys Gly Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

```
His Ser Tyr
        35

<210> SEQ ID NO 66
<211> LENGTH: 34
<212> TYPE: PRT
<213> ORGANISM: Artificial Sequence
<220> FEATURE:
<223> OTHER INFORMATION: synthetic peptide

<400> SEQUENCE: 66

Gly Cys Val Leu Gly Thr Cys Gln Val Gln Asn Leu Ser His Arg Leu
1               5                   10                  15

Trp Gln Leu Arg Gln Glu Ser Ala Pro Val Glu Pro Ser Ser Pro His
            20                  25                  30

Ser Tyr

<210> SEQ ID NO 67
<211> LENGTH: 38
<212> TYPE: PRT
<213> ORGANISM: Artificial Sequence
<220> FEATURE:
<223> OTHER INFORMATION: synthetic peptide

<400> SEQUENCE: 67

Cys Val Leu Gly Thr Cys Gln Val Gln Asn Leu Ser His Arg Leu Trp
1               5                   10                  15

Gln Leu Met Gly Pro Ala Gly Arg Gln Asp Ser Ala Pro Val Asp Pro
            20                  25                  30

Ser Ser Pro His Ser Tyr
        35

<210> SEQ ID NO 68
<211> LENGTH: 32
<212> TYPE: PRT
<213> ORGANISM: Artificial Sequence
<220> FEATURE:
<223> OTHER INFORMATION: synthetic peptide

<400> SEQUENCE: 68

Gln Val Gln Asn Leu Ser His Arg Leu Trp Gln Leu Met Gly Pro Ala
1               5                   10                  15

Gly Arg Gln Asp Ser Ala Pro Val Asp Pro Ser Ser Pro His Ser Tyr
            20                  25                  30

<210> SEQ ID NO 69
<211> LENGTH: 31
<212> TYPE: PRT
<213> ORGANISM: Artificial Sequence
<220> FEATURE:
<223> OTHER INFORMATION: synthetic peptide

<400> SEQUENCE: 69

Val Gln Asn Leu Ser His Arg Leu Trp Gln Leu Met Gly Pro Ala Gly
1               5                   10                  15

Arg Gln Asp Ser Ala Pro Val Asp Pro Ser Ser Pro His Ser Tyr
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: synthetic peptide
```

<400> SEQUENCE: 70

Val Gln Asn Leu Ser His Arg Leu Gln Leu Met Gly Pro Ala Gly Arg
1               5                   10                  15

Gln Asp Ser Ala Pro Val Asp Pro Ser Ser Pro His Ser Tyr
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: synthetic peptide

<400> SEQUENCE: 71

Gly Thr Met Gln Val Gln Asn Leu Ser His Arg Leu Trp Gln Leu Arg
1               5                   10                  15

Gln Asp Ser Ala Pro Val Glu Pro Ser Ser Pro His Ser Tyr
            20                  25                  30

<210> SEQ ID NO 72
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: SULFATATION

<400> SEQUENCE: 72

Asp Tyr Met Gly Trp Met Asp Phe
1               5

<210> SEQ ID NO 73
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: SULFATATION

<400> SEQUENCE: 73

Lys Asp Tyr Met Gly Trp Met Asp Phe
1               5

<210> SEQ ID NO 74
<211> LENGTH: 39
<212> TYPE: PRT
<213> ORGANISM: Artificial Sequence
<220> FEATURE:
<223> OTHER INFORMATION: synthetic peptide

<400> SEQUENCE: 74

His Gly Glu Gly Thr Phe Thr Ser Asp Val Ser Ser Tyr Leu Glu Gly
1               5                   10                  15

Gln Ala Ala Lys Leu Phe Ile Glu Trp Leu Lys Asn Gly Gly Pro Ser
            20                  25                  30

Ser Gly Ala Pro Pro Pro Ser
        35

<210> SEQ ID NO 75

```
<211> LENGTH: 39
<212> TYPE: PRT
<213> ORGANISM: Artificial Sequence
<220> FEATURE:
<223> OTHER INFORMATION: synthetic peptide

<400> SEQUENCE: 75

His Gly Glu Gly Thr Phe Thr Ser Asp Val Ser Ser Tyr Leu Glu Gly
1               5                   10                  15

Gln Ala Ala Lys Glu Phe Ile Glu Trp Leu Lys Asn Gly Gly Pro Ser
            20                  25                  30

Ser Gly Ala Pro Pro Pro Ser
        35

<210> SEQ ID NO 76
<211> LENGTH: 39
<212> TYPE: PRT
<213> ORGANISM: Artificial Sequence
<220> FEATURE:
<223> OTHER INFORMATION: synthetic peptide

<400> SEQUENCE: 76

His Gly Glu Gly Thr Phe Thr Ser Asp Val Ser Ser Tyr Leu Glu Gly
1               5                   10                  15

Gln Ala Ala Lys Glu Phe Ile Ala Trp Leu Lys Asn Gly Gly Pro Ser
            20                  25                  30

Ser Gly Ala Pro Pro Pro Ser
        35

<210> SEQ ID NO 77
<211> LENGTH: 39
<212> TYPE: PRT
<213> ORGANISM: Artificial Sequence
<220> FEATURE:
<223> OTHER INFORMATION: synthetic peptide

<400> SEQUENCE: 77

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Asn Gly Gly Pro Ser
            20                  25                  30

Ser Gly Ala Pro Pro Pro Ser
        35

<210> SEQ ID NO 78
<211> LENGTH: 39
<212> TYPE: PRT
<213> ORGANISM: Artificial Sequence
<220> FEATURE:
<223> OTHER INFORMATION: synthetic peptide

<400> SEQUENCE: 78

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Pro Ser
        35

<210> SEQ ID NO 79
<211> LENGTH: 23
<212> TYPE: PRT
<213> ORGANISM: Mus musculus
```

<400> SEQUENCE: 79

Arg Ser Met Arg Leu Ser Phe Arg Thr Arg Gly Tyr Gly Phe Arg Asp
1               5                   10                  15

Pro Gly Leu Gln Leu Arg Arg
            20

<210> SEQ ID NO 80
<211> LENGTH: 23
<212> TYPE: PRT
<213> ORGANISM: Rattus rattus

<400> SEQUENCE: 80

Arg Ser Met Arg Leu Ser Phe Arg Ala Arg Gly Tyr Gly Phe Arg Asp
1               5                   10                  15

Pro Gly Leu Gln Leu Arg Arg
            20

<210> SEQ ID NO 81
<211> LENGTH: 23
<212> TYPE: PRT
<213> ORGANISM: Bos taurus

<400> SEQUENCE: 81

Arg Ser Met Arg Leu Ser Phe Arg Ala Arg Gly Tyr Gly Phe Arg Gly
1               5                   10                  15

Pro Gly Leu Gln Leu Arg Arg
            20

<210> SEQ ID NO 82
<211> LENGTH: 23
<212> TYPE: PRT
<213> ORGANISM: Sus scrofa

<400> SEQUENCE: 82

Arg Ser Met Arg Leu Ser Phe Arg Ala Pro Ala Tyr Gly Phe Arg Gly
1               5                   10                  15

Pro Gly Leu Gln Leu Arg Arg
            20

<210> SEQ ID NO 83
<211> LENGTH: 23
<212> TYPE: PRT
<213> ORGANISM: Equus caballus

<400> SEQUENCE: 83

Arg Ser Met Lys Leu Ser Phe Arg Ala Arg Ala Tyr Gly Phe Arg Gly
1               5                   10                  15

Pro Gly Leu Gln Leu Arg Arg
            20

<210> SEQ ID NO 84
<211> LENGTH: 23
<212> TYPE: PRT
<213> ORGANISM: Pan troglodytes

<400> SEQUENCE: 84

Ser Ser Met Lys Leu Ser Phe Arg Ala Arg Ala Tyr Gly Phe Arg Gly
1               5                   10                  15

Pro Gly Pro Gln Leu Arg Arg
            20

<210> SEQ ID NO 85

```
<211> LENGTH: 23
<212> TYPE: PRT
<213> ORGANISM: Homo sapiens

<400> SEQUENCE: 85

Ser Ser Met Lys Leu Ser Phe Arg Ala Arg Ala Tyr Gly Phe Arg Gly
1               5                   10                  15

Pro Gly Pro Gln Leu Arg Arg
            20

<210> SEQ ID NO 86
<211> LENGTH: 23
<212> TYPE: PRT
<213> ORGANISM: Artificial Sequence
<220> FEATURE:
<223> OTHER INFORMATION: synthetic peptide

<400> SEQUENCE: 86

Ser Ser Met Lys Leu Ser Phe Arg Ala Arg Ala Tyr Ser Phe Arg Gly
1               5                   10                  15

Pro Gly Pro Gln Leu Arg Arg
            20

<210> SEQ ID NO 87
<211> LENGTH: 23
<212> TYPE: PRT
<213> ORGANISM: Artificial Sequence
<220> FEATURE:
<223> OTHER INFORMATION: synthetic peptide

<400> SEQUENCE: 87

Ser Ser Met Lys Leu Ser Phe Arg Ala Arg Ala Tyr Gly Phe Arg Gly
1               5                   10                  15

Pro Gly Leu Gln Leu Arg Arg
            20

<210> SEQ ID NO 88
<211> LENGTH: 23
<212> TYPE: PRT
<213> ORGANISM: Artificial Sequence
<220> FEATURE:
<223> OTHER INFORMATION: synthetic peptide

<400> SEQUENCE: 88

Ser Ser Met Lys Leu Ser Phe Arg Ala Arg Ala Tyr Gly Phe Arg Gly
1               5                   10                  15

Pro Gly Pro Gln Leu Arg Gln
            20

<210> SEQ ID NO 89
<211> LENGTH: 151
<212> TYPE: PRT
<213> ORGANISM: Homo sapiens

<400> SEQUENCE: 89

Met Ser Ser Phe Ser Thr Thr Thr Val Ser Phe Leu Leu Leu Leu Ala
1               5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
        35                  40                  45

Glu Lys Met Pro Leu Glu Asp Glu Val Val Pro Pro Gln Val Leu Ser
    50                  55                  60
```

```
Asp Pro Asn Glu Glu Ala Gly Ala Ala Leu Ser Pro Leu Pro Glu Val
 65                  70                  75                  80

Pro Pro Trp Thr Gly Glu Val Ser Pro Ala Gln Arg Asp Gly Gly Ala
                 85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
        115                 120                 125

Ser Cys Phe Gly Gly Arg Met Asp Arg Ile Gly Ala Gln Ser Gly Leu
    130                 135                 140

Gly Cys Asn Ser Phe Arg Tyr
145                 150

<210> SEQ ID NO 90
<211> LENGTH: 134
<212> TYPE: PRT
<213> ORGANISM: Homo sapiens

<400> SEQUENCE: 90

Met Asp Pro Gln Thr Ala Pro Ser Arg Ala Leu Leu Leu Leu Leu Phe
  1               5                  10                  15

Leu His Leu Ala Phe Leu Gly Gly Arg Ser His Pro Leu Gly Ser Pro
                 20                  25                  30

Gly Ser Ala Ser Asp Leu Glu Thr Ser Gly Leu Gln Glu Gln Arg Asn
             35                  40                  45

His Leu Gln Gly Lys Leu Ser Glu Leu Gln Val Glu Gln Thr Ser Leu
 50                  55                  60

Glu Pro Leu Gln Glu Ser Pro Arg Pro Thr Gly Val Trp Lys Ser Arg
 65                  70                  75                  80

Glu Val Ala Thr Glu Gly Ile Arg Gly His Arg Lys Met Val Leu Tyr
                 85                  90                  95

Thr Leu Arg Ala Pro Arg Ser Pro Lys Met Val Gln Ser Gly Cys
            100                 105                 110

Phe Gly Arg Lys Met Asp Arg Ile Ser Ser Ser Gly Leu Gly Cys
        115                 120                 125

Lys Val Leu Arg Arg His
    130

<210> SEQ ID NO 91
<211> LENGTH: 126
<212> TYPE: PRT
<213> ORGANISM: Homo sapiens

<400> SEQUENCE: 91

Met His Leu Ser Gln Leu Leu Ala Cys Ala Leu Leu Leu Thr Leu Leu
  1               5                  10                  15

Ser Leu Arg Pro Ser Glu Ala Lys Pro Gly Ala Pro Lys Val Pro
                 20                  25                  30

Arg Thr Pro Pro Ala Glu Glu Leu Ala Glu Pro Gln Ala Ala Gly Gly
             35                  40                  45

Gly Gln Lys Lys Gly Asp Lys Ala Pro Gly Gly Gly Ala Asn Leu
 50                  55                  60

Lys Gly Asp Arg Ser Arg Leu Leu Arg Asp Leu Arg Val Asp Thr Lys
 65                  70                  75                  80

Ser Arg Ala Ala Trp Ala Arg Leu Leu Gln Glu His Pro Asn Ala Arg
                 85                  90                  95

Lys Tyr Lys Gly Ala Asn Lys Lys Gly Leu Ser Lys Gly Cys Phe Gly
```

```
                    100                 105                 110
Leu Lys Leu Asp Arg Ile Gly Ser Met Ser Gly Leu Gly Cys
        115                 120                 125

<210> SEQ ID NO 92
<211> LENGTH: 65
<212> TYPE: PRT
<213> ORGANISM: Artificial Sequence
<220> FEATURE:
<223> OTHER INFORMATION: synthetic peptide

<400> SEQUENCE: 92

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Gly
            20                  25                  30

Gly Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Glu Thr
    50                  55                  60

Phe
65

<210> SEQ ID NO 93
<211> LENGTH: 7
<212> TYPE: PRT
<213> ORGANISM: Artificial Sequence
<220> FEATURE:
<223> OTHER INFORMATION: synthetic peptide

<400> SEQUENCE: 93

Pro Ser Ser Gly Ala Pro Ser
1               5

<210> SEQ ID NO 94
<211> LENGTH: 9
<212> TYPE: PRT
<213> ORGANISM: Artificial Sequence
<220> FEATURE:
<223> OTHER INFORMATION: synthetic peptide

<400> SEQUENCE: 94

His Ser Glu Gly Thr Phe Thr Ser Asp
1               5

<210> SEQ ID NO 95
<211> LENGTH: 32
<212> TYPE: PRT
<213> ORGANISM: Artificial Sequence
<220> FEATURE:
<223> OTHER INFORMATION: synthetic peptide

<400> SEQUENCE: 95

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 96
<211> LENGTH: 70
<212> TYPE: PRT
<213> ORGANISM: Artificial Sequence
<220> FEATURE:
<223> OTHER INFORMATION: synthetic peptide
<220> FEATURE:
```

```
<221> NAME/KEY: MOD_RES
<222> LOCATION: (31)..(32)
<223> OTHER INFORMATION: bAla bAla

<400> SEQUENCE: 96

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Phe Leu Phe His Tyr Ser Lys Thr Gln Lys Leu Gly Lys Ser Asn Val
        35                  40                  45

Val Glu Glu Leu Gln Ser Pro Phe Ala Ser Gln Ser Arg Gly Tyr Phe
    50                  55                  60

Leu Phe Arg Pro Arg Asn
65                  70

<210> SEQ ID NO 97
<211> LENGTH: 57
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(32)
<223> OTHER INFORMATION: bAla bAla

<400> SEQUENCE: 97

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Phe Arg Val Asp Glu Glu Phe Gln Ser Pro Phe Ala Ser Gln Ser Arg
        35                  40                  45

Gly Tyr Phe Leu Phe Arg Pro Arg Asn
    50                  55

<210> SEQ ID NO 98
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(32)
<223> OTHER INFORMATION: bAla bAla

<400> SEQUENCE: 98

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Gly Tyr Phe Leu Phe Arg Pro Arg Asn
        35                  40

<210> SEQ ID NO 99
<211> LENGTH: 32
<212> TYPE: PRT
<213> ORGANISM: Homo sapiens

<400> SEQUENCE: 99

Ser Pro Lys Met Val Gln Gly Ser Gly Cys Phe Gly Arg Lys Met Asp
1               5                   10                  15
```

Arg Ile Ser Ser Ser Gly Leu Gly Cys Lys Val Leu Arg Arg His
            20                  25                  30

<210> SEQ ID NO 100
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 100

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Lys Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 101
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 101

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Leu Pro Arg Thr Asn Thr Gly Ser Asn Thr
    50                  55                  60

Tyr
65

<210> SEQ ID NO 102
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 102

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

-continued

```
                    20                  25                  30
Xaa Lys Cys Asn Thr Ala Thr Cys Val Leu Gly Arg Leu Ser Gln Glu
            35                  40                  45

Leu His Arg Leu Gln Thr Tyr Pro Pro Thr Asn Thr Gly Ser Asn Thr
    50                  55                  60

Tyr
65

<210> SEQ ID NO 103
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 103

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
            35                  40                  45

Leu His Arg Leu Gln Thr Tyr Pro Arg Thr Asn Val Gly Ser Asn Thr
    50                  55                  60

Tyr
65

<210> SEQ ID NO 104
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 104

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
            35                  40                  45

Leu His Arg Leu Gln Thr Leu Pro Pro Thr Asn Val Gly Ser Asn Thr
    50                  55                  60

Tyr
65

<210> SEQ ID NO 105
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
```

<400> SEQUENCE: 105

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Asn Phe
        35                  40                  45

Leu His Arg Leu Gln Thr Tyr Pro Arg Thr Asn Thr Gly Ser Asn Thr
    50                  55                  60

Tyr
65

<210> SEQ ID NO 106
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 106

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Ala Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 107
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 107

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Ala Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 108
<211> LENGTH: 65
<212> TYPE: PRT

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 108

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Ala Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 109
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 109

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Cys Ala Asn Leu Ser Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 110
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 110

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Cys Ser Asn Ala Ser Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60
```

Tyr
65

<210> SEQ ID NO 111
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 111

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Cys Ser Asn Leu Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 112
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 112

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Cys Ser Asn Leu Ser Ala Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 113
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 113

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

```
Xaa Lys Cys Asn Thr Ala Thr Cys Val Leu Gly Arg Leu Ser Gln Glu
        35                  40                  45

Leu His Lys Leu Gln Thr Tyr Pro Arg Thr Asn Thr Gly Ser Asn Thr
 50                  55                  60

Tyr
65

<210> SEQ ID NO 114
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 114

Tyr Ala Glu Gly Thr Phe Ile Ser Asp Tyr Ser Ile Ala Met Asp Lys
 1               5                  10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Gly Thr
 50                  55                  60

Pro
65

<210> SEQ ID NO 115
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 115

Tyr Ala Glu Gly Thr Phe Ile Ser Asp Tyr Ser Ile Ala Met Asp Lys
 1               5                  10                  15

Ile Arg Gln Gln Asp Phe Val Asn Trp Leu Leu Ala Gln Lys Xaa Xaa
                20                  25                  30

Xaa Cys Ser Ala Leu Ser Thr Cys Val Leu Gly Arg Leu Ser Gln Glu
        35                  40                  45

Leu His Arg Leu Gln Thr Tyr Pro Arg Thr Asn Thr Gly Ser Asn Thr
 50                  55                  60

Tyr
65

<210> SEQ ID NO 116
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
```

<400> SEQUENCE: 116

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Leu Leu Gln Gln Leu Gln Lys Leu
        35                  40                  45

Leu Gln Lys Leu Lys Gln Tyr Pro Arg Thr Asn Thr Gly Ser Asn Thr
    50                  55                  60

Tyr
65

<210> SEQ ID NO 117
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 117

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Ser Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 118
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 118

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Val Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 119
<211> LENGTH: 62
<212> TYPE: PRT
<213> ORGANISM: Artificial Sequence

```
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 119

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Tyr Pro Arg Thr Asn Thr Gly Ser Asn Thr Tyr
    50                  55                  60

<210> SEQ ID NO 120
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Lys(For)
<220> FEATURE:
<221> NAME/KEY: MOD_RES
<222> LOCATION: (51)..(51)
<223> OTHER INFORMATION: Lys(For)

<400> SEQUENCE: 120

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Lys Leu Ser Gln Glu
        35                  40                  45

Leu His Lys Leu Gln Thr Tyr Pro Arg Thr Asn Thr Gly Ser Asn Thr
    50                  55                  60

Tyr
65

<210> SEQ ID NO 121
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (51)..(51)
<223> OTHER INFORMATION: Lys(PEG5000)

<400> SEQUENCE: 121

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30
```

```
                    20                  25                  30
Xaa Ala Cys Asn Thr Ala Thr Cys Val Leu Gly Arg Leu Ser Gln Glu
                35                  40                  45
Leu His Lys Leu Gln Thr Tyr Pro Arg Thr Asn Thr Gly Ser Asn Thr
         50                  55                  60
Tyr
 65

<210> SEQ ID NO 122
<211> LENGTH: 68
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 122

Tyr Ala Glu Gly Thr Phe Ile Ser Asp Tyr Ser Ile Ala Met Asp Lys
 1               5                  10                  15
Ile Arg Gln Gln Asp Phe Val Asn Trp Leu Leu Ala Gln Lys Xaa Xaa
                20                  25                  30
Xaa Lys Cys Asn Thr Ala Thr Cys Val Leu Gly Arg Leu Ser Gln Glu
                35                  40                  45
Leu His Arg Leu Gln Thr Leu Gln Thr Tyr Pro Arg Thr Asn Thr Gly
         50                  55                  60
Ser Asn Thr Tyr
 65

<210> SEQ ID NO 123
<211> LENGTH: 69
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 123

Tyr Ala Glu Gly Thr Phe Ile Ser Asp Tyr Ser Ile Ala Met Asp Lys
 1               5                  10                  15
Ile Arg Gln Gln Asp Phe Val Asn Trp Leu Leu Ala Gln Lys Xaa Xaa
                20                  25                  30
Xaa Lys Cys Asn Thr Ala Thr Cys Val Leu Gly Arg Leu Ser Gln Glu
                35                  40                  45
Leu His Arg Leu Gln Thr Leu Leu Gln Thr Tyr Pro Arg Thr Asn Thr
         50                  55                  60
Gly Ser Asn Thr Tyr
 65

<210> SEQ ID NO 124
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
```

<400> SEQUENCE: 124

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Lys Leu Ser Gln Glu
        35                  40                  45

Leu His Lys Leu Gln Thr Tyr Pro Arg Thr Asn Thr Gly Ser Asn Thr
    50                  55                  60

Tyr
65

<210> SEQ ID NO 125
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 125

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ser Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 126
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 126

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Ala Thr Gln Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 127
<211> LENGTH: 65
<212> TYPE: PRT

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 127

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Ala Thr Gln Arg Leu Ser Gln Glu
        35                  40                  45

Leu His Arg Leu Gln Thr Tyr Pro Arg Thr Asn Val Gly Ser Asn Thr
    50                  55                  60

Tyr
65

<210> SEQ ID NO 128
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 128

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ser Thr Cys Ala Thr Gln Arg Leu Ala Asn Glu
        35                  40                  45

Leu Val Arg Leu Gln Thr Tyr Pro Arg Thr Asn Val Gly Ser Asn Thr
    50                  55                  60

Tyr
65

<210> SEQ ID NO 129
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (39)..(39)
<223> OTHER INFORMATION: Xaa is homoserine

<400> SEQUENCE: 129

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Xaa Cys Val Leu Gly Arg Leu Ser Gln Glu
        35                  40                  45
```

Leu His Arg Leu Gln Thr Tyr Pro Arg Thr Asn Thr Gly Ser Asn Thr
    50                  55                  60

Tyr
65

<210> SEQ ID NO 130
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (39)..(39)
<223> OTHER INFORMATION: Ahb

<400> SEQUENCE: 130

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Xaa Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 131
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (39)..(39)
<223> OTHER INFORMATION: Ahp

<400> SEQUENCE: 131

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Xaa Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 132
<211> LENGTH: 65
<212> TYPE: PRT
<213> ORGANISM: Artificial Sequence
<220> FEATURE:
<223> OTHER INFORMATION: synthetic peptide

```
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (39)..(39)
<223> OTHER INFORMATION: Thr(OPO3H2)

<400> SEQUENCE: 132

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 133
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Orn
<220> FEATURE:
<221> NAME/KEY: MOD_RES
<222> LOCATION: (51)..(51)
<223> OTHER INFORMATION: Orn

<400> SEQUENCE: 133

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Xaa Leu Ser Gln Glu
        35                  40                  45

Leu His Xaa Leu Gln Thr Tyr Pro Arg Thr Asn Thr Gly Ser Asn Thr
    50                  55                  60

Tyr
65

<210> SEQ ID NO 134
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Cit
<220> FEATURE:
<221> NAME/KEY: MOD_RES
```

<222> LOCATION: (51)..(51)
<223> OTHER INFORMATION: Cit

<400> SEQUENCE: 134

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Xaa Leu Ser Gln Glu
        35                  40                  45

Leu His Xaa Leu Gln Thr Tyr Pro Arg Thr Asn Thr Gly Ser Asn Thr
    50                  55                  60

Tyr
65
```

<210> SEQ ID NO 135
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Homolysine
<220> FEATURE:
<221> NAME/KEY: MOD_RES
<222> LOCATION: (51)..(51)
<223> OTHER INFORMATION: Homolysine

<400> SEQUENCE: 135

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Xaa Leu Ser Gln Glu
        35                  40                  45

Leu His Xaa Leu Gln Thr Tyr Pro Arg Thr Asn Thr Gly Ser Asn Thr
    50                  55                  60

Tyr
65
```

<210> SEQ ID NO 136
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 136

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Met Leu Gly Arg Tyr Thr Gln Asp
        35                  40                  45
```

```
Phe His Arg Leu Gln Thr Tyr Pro Arg Thr Asn Thr Gly Ser Asn Thr
 50                  55                  60

Tyr
 65

<210> SEQ ID NO 137
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 137

Tyr Ala Glu Gly Thr Phe Ile Ser Asp Tyr Ser Ile Ala Met Asp Lys
 1               5                  10                  15

Ile Arg Gln Gln Asp Phe Val Asn Trp Leu Leu Ala Gln Lys Xaa Xaa
                 20                  25                  30

Xaa Asp Ser Asn Leu Ser Thr Lys Val Leu Gly Arg Leu Ser Gln Glu
         35                  40                  45

Leu His Arg Leu Gln Thr Tyr Pro Arg Thr Asn Thr Gly Ser Asn Thr
 50                  55                  60

Tyr
 65

<210> SEQ ID NO 138
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 138

Tyr Ala Glu Gly Thr Phe Ile Ser Asp Tyr Ser Ile Ala Met Asp Lys
 1               5                  10                  15

Ile Arg Gln Gln Asp Phe Val Asn Trp Leu Leu Ala Gln Lys Xaa Xaa
                 20                  25                  30

Xaa Lys Asp Asn Thr Ala Thr Lys Val Leu Gly Arg Leu Ser Gln Glu
         35                  40                  45

Leu His Arg Leu Gln Thr Tyr Pro Arg Thr Asn Thr Gly Ser Asn Thr
 50                  55                  60

Tyr
 65

<210> SEQ ID NO 139
<211> LENGTH: 64
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 139

Tyr Ala Glu Gly Thr Phe Ile Ser Asp Tyr Ser Ile Ala Met Asp Lys
 1               5                  10                  15
```

-continued

```
Ile Arg Gln Gln Asp Phe Val Asn Trp Leu Leu Ala Gln Lys Xaa Xaa
            20                  25                  30

Xaa Cys Asn Thr Ala Thr Cys Val Leu Gly Arg Leu Ser Gln Glu Leu
            35                  40                  45

His Arg Leu Gln Thr Tyr Pro Arg Thr Asn Thr Gly Ser Asn Thr Tyr
    50                  55                  60

<210> SEQ ID NO 140
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (65)..(65)
<223> OTHER INFORMATION: Tyr(9Anc)

<400> SEQUENCE: 140

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
            35                  40                  45

Leu His Arg Leu Gln Thr Tyr Pro Arg Thr Asn Thr Gly Ser Asn Thr
    50                  55                  60

Tyr
65

<210> SEQ ID NO 141
<211> LENGTH: 66
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (66)..(66)
<223> OTHER INFORMATION: L-octylglycine

<400> SEQUENCE: 141

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
            35                  40                  45

Leu His Arg Leu Gln Thr Tyr Pro Arg Thr Asn Thr Gly Ser Asn Thr
    50                  55                  60

Tyr Xaa
65

<210> SEQ ID NO 142
<211> LENGTH: 65
<212> TYPE: PRT
```

```
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Homoarginine
<220> FEATURE:
<221> NAME/KEY: MOD_RES
<222> LOCATION: (51)..(51)
<223> OTHER INFORMATION: Homoarginine

<400> SEQUENCE: 142

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Xaa Leu Ser Gln Glu
        35                  40                  45

Leu His Xaa Leu Gln Thr Tyr Pro Arg Thr Asn Thr Gly Ser Asn Thr
    50                  55                  60

Tyr
65

<210> SEQ ID NO 143
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 143

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Phe Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 144
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (51)..(51)
<223> OTHER INFORMATION: Cit

<400> SEQUENCE: 144
```

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Xaa Leu Gln Thr Tyr Pro Arg Thr Asn Thr Gly Ser Asn Thr
    50                  55                  60

Tyr
65

<210> SEQ ID NO 145
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (51)..(51)
<223> OTHER INFORMATION: Orn

<400> SEQUENCE: 145

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Xaa Leu Gln Thr Tyr Pro Arg Thr Asn Thr Gly Ser Asn Thr
    50                  55                  60

Tyr
65

<210> SEQ ID NO 146
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 146

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Ile Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 147
<211> LENGTH: 65

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (44)..(44)
<223> OTHER INFORMATION: Cit

<400> SEQUENCE: 147

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Xaa Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 148
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent
<220> FEATURE:
<221> NAME/KEY: MOD_RES
<222> LOCATION: (65)..(65)
<223> OTHER INFORMATION: Tyr(4ABU)

<400> SEQUENCE: 148

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 149
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 149

Tyr Ala Glu Gly Thr Phe Ile Ser Asp Tyr Ser Ile Ala Met Asp Lys
1               5                   10                  15
```

Ile Arg Gln Gln Asp Phe Val Asn Trp Leu Leu Ala Gln Lys Xaa Xaa
                20                  25                  30

Xaa Lys Cys Asn Thr Ser Thr Cys Ala Thr Gln Arg Leu Ala Asn Glu
            35                  40                  45

Leu Val Arg Leu Gln Thr Tyr Pro Arg Thr Asn Val Gly Ser Glu Ala
        50                  55                  60

Phe
65

<210> SEQ ID NO 150
<211> LENGTH: 64
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 150

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
            35                  40                  45

Leu His Arg Leu Gln Thr Tyr Pro Thr Asn Val Gly Ser Glu Ala Phe
        50                  55                  60

<210> SEQ ID NO 151
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 151

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Arg Ser
            35                  40                  45

Leu His Arg Leu Gln Thr Tyr Pro Arg Thr Asn Thr Gly Ser Asn Thr
        50                  55                  60

Tyr
65

<210> SEQ ID NO 152
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 152

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Thr His Arg Leu Ser Gln Glu
            35                  40                  45

Leu His Arg Leu Gln Thr Tyr Pro Arg Thr Asn Thr Gly Ser Asn Thr
        50                  55                  60

Tyr
65

<210> SEQ ID NO 153
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 153

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ala Asp Phe
            35                  40                  45

Leu His Arg Leu Gln Thr Tyr Pro Arg Thr Asn Thr Gly Ser Asn Thr
        50                  55                  60

Tyr
65

<210> SEQ ID NO 154
<211> LENGTH: 63
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 154

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Cys Asn Thr Ala Thr Cys Val Leu Gly Arg Leu Ser Gln Glu Leu
            35                  40                  45

His Arg Leu Gln Thr Tyr Pro Arg Thr Asn Thr Gly Ser Asn Thr
        50                  55                  60

<210> SEQ ID NO 155
<211> LENGTH: 66
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
```

```
<222> LOCATION: (31)..(33)
<223> OTHER INFORMATION: Gly-Gly-Gly, bAla-bAla or absent

<400> SEQUENCE: 155

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Asn Phe Val Pro Arg Thr Asn Thr Gly Ser Asn
    50                  55                  60

Thr Tyr
65

<210> SEQ ID NO 156
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 156

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Glu Thr
    50                  55                  60

Phe
65

<210> SEQ ID NO 157
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 157

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Ala Cys Asp Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 158
```

```
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 158

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Lys Ala
    50                  55                  60

Phe
65

<210> SEQ ID NO 159
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 159

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asp Thr Ala Thr Cys Val Thr His Arg Leu Ala Gly Leu
        35                  40                  45

Leu Ser Arg Ser Gln Thr Tyr Pro Arg Thr Asn Thr Gly Ser Asn Thr
    50                  55                  60

Tyr
65

<210> SEQ ID NO 160
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 160

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Asp Ala
        35                  40                  45

Leu His Arg Leu Gln Thr Tyr Pro Arg Thr Asn Thr Gly Ser Asn Thr
```

Tyr
65

<210> SEQ ID NO 161
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 161

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Ala Phe
        35                  40                  45

Leu His Arg Leu Gln Thr Tyr Pro Arg Thr Asn Thr Gly Ser Asn Thr
    50                  55                  60

Tyr
65

<210> SEQ ID NO 162
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 162

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Ser Cys Asn Thr Ala Thr Cys Val Leu Gly Arg Leu Ala Asp Phe
        35                  40                  45

Leu His Arg Leu Gln Thr Tyr Pro Arg Thr Asn Thr Gly Ser Asn Thr
    50                  55                  60

Tyr
65

<210> SEQ ID NO 163
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 163

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
            35                  40                  45

Leu His Arg Leu Gln Thr Met Pro Arg Thr Asn Thr Gly Ser Asn Thr
        50                  55                  60

Tyr
65

<210> SEQ ID NO 164
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 164

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ser Gln Glu
            35                  40                  45

Leu His Arg Leu Gln Thr Val Pro Arg Thr Asn Thr Gly Ser Asn Thr
        50                  55                  60

Tyr
65

<210> SEQ ID NO 165
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 165

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Asn Glu Tyr
            35                  40                  45

Leu His Arg Leu Gln Thr Tyr Pro Arg Thr Asn Thr Gly Ser Asn Thr
        50                  55                  60

Tyr
65

<210> SEQ ID NO 166
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)

<223> OTHER INFORMATION: Gly-Gly-Gly, bAla-bAla or absent

<400> SEQUENCE: 166

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Ser Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 167
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 167

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Thr Glu Phe
        35                  40                  45

Leu His Arg Leu Gln Thr Tyr Pro Arg Thr Asn Thr Gly Ser Asn Thr
    50                  55                  60

Tyr
65

<210> SEQ ID NO 168
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 168

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Glu Phe
        35                  40                  45

Leu His Arg Leu Gln Thr Tyr Pro Arg Thr Asn Thr Gly Ser Asn Thr
    50                  55                  60

Tyr
65

<210> SEQ ID NO 169
<211> LENGTH: 65

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 169

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Thr Asp Tyr
        35                  40                  45

Leu His Arg Leu Gln Thr Tyr Pro Arg Thr Asn Thr Gly Ser Asn Thr
    50                  55                  60

Tyr
65

<210> SEQ ID NO 170
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 170

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Gln Phe
        35                  40                  45

Leu His Arg Leu Gln Thr Tyr Pro Arg Thr Asn Thr Gly Ser Asn Thr
    50                  55                  60

Tyr
65

<210> SEQ ID NO 171
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 171

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Asp Phe
        35                  40                  45

Leu His Arg Phe Gln Thr Phe Pro Arg Thr Asn Thr Gly Ser Asn Thr
    50                  55                  60
```

Tyr
65

<210> SEQ ID NO 172
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 172

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Asp Phe
        35                  40                  45

Leu His Arg Phe His Thr Phe Pro Arg Thr Asn Thr Gly Ser Asn Thr
    50                  55                  60

Tyr
65

<210> SEQ ID NO 173
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 173

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ala Asp Phe
        35                  40                  45

Leu His Arg Phe Gln Thr Phe Pro Arg Thr Asn Thr Gly Ser Gly Thr
    50                  55                  60

Pro
65

<210> SEQ ID NO 174
<211> LENGTH: 64
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 174

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa

```
                20                  25                  30
Xaa Cys Asn Thr Ala Thr Cys Val Leu Gly Arg Leu Ala Asp Phe Leu
        35                  40                  45

His Arg Leu Gln Thr Tyr Pro Arg Thr Asn Thr Gly Ser Asn Thr Tyr
50                  55                  60

<210> SEQ ID NO 175
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 175

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asp Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 176
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 176

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Phe Asp Phe
        35                  40                  45

Leu His Arg Leu Gln Thr Tyr Pro Arg Thr Asn Thr Gly Ser Asn Thr
    50                  55                  60

Tyr
65

<210> SEQ ID NO 177
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 177
```

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Lys Cys Asn Thr Ala Thr Cys Val Leu Gly Arg Leu Ala Ala Ala
            35                  40                  45

Leu His Arg Leu Gln Thr Tyr Pro Arg Thr Asn Thr Gly Ser Asn Thr
        50                  55                  60

Tyr
65

<210> SEQ ID NO 178
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 178

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Thr Cys Asp Thr Ala Thr Cys Val Leu Gly Arg Leu Ser Gln Glu
            35                  40                  45

Leu His Arg Leu Gln Thr Tyr Pro Arg Thr Asn Thr Gly Ser Asn Thr
        50                  55                  60

Tyr
65

<210> SEQ ID NO 179
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 179

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
                20                  25                  30

Xaa Cys Ser Asn Leu Ser Thr Cys Ala Thr Gln Arg Leu Ala Asn Glu
            35                  40                  45

Leu Val Arg Leu Gln Thr Tyr Pro Arg Thr Asn Val Gly Ser Asn Thr
        50                  55                  60

Tyr
65

<210> SEQ ID NO 180
<211> LENGTH: 65
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 180

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Ala Thr Gln Arg Leu Ala Asn Glu
        35                  40                  45

Leu Val Arg Leu Gln Thr Tyr Pro Arg Thr Asn Val Gly Ser Asn Thr
    50                  55                  60

Tyr
65

<210> SEQ ID NO 181
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 181

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Cys Ser Asn Leu Ser Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 182
<211> LENGTH: 65
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(33)
<223> OTHER INFORMATION: Gly-Gly-Gly, bAla-bAla or absent

<400> SEQUENCE: 182

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Xaa
            20                  25                  30

Xaa Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65
```

```
<210> SEQ ID NO 183
<211> LENGTH: 19
<212> TYPE: PRT
<213> ORGANISM: Artificial Sequence
<220> FEATURE:
<223> OTHER INFORMATION: synthetic peptide

<400> SEQUENCE: 183

Leu Phe Ile Glu Trp Leu Lys Asn Gly Gly Pro Ser Ser Gly Ala Pro
1               5                   10                  15

Pro Pro Ser

<210> SEQ ID NO 184
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Val, Abu, Homoserine, cycloprpyl Ala,
      cycloHexyl Ala, Ala(NMe), Aib or cyclprop Gly

<400> SEQUENCE: 184

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 185
<211> LENGTH: 39
<212> TYPE: PRT
<213> ORGANISM: Artificial Sequence
<220> FEATURE:
<223> OTHER INFORMATION: synthetic peptide

<400> SEQUENCE: 185

Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys Pro Ser
            20                  25                  30

Ser Gly Ala Pro Pro Pro Ser
        35

<210> SEQ ID NO 186
<211> LENGTH: 39
<212> TYPE: PRT
<213> ORGANISM: Artificial Sequence
<220> FEATURE:
<223> OTHER INFORMATION: synthetic peptide

<400> SEQUENCE: 186

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 187
<211> LENGTH: 39
```

```
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-glucitol

<400> SEQUENCE: 187

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 188
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-pyroglutamyl

<400> SEQUENCE: 188

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 189
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-9-fluorenylmethoxycarbonyl

<400> SEQUENCE: 189

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 190
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-palmitate

<400> SEQUENCE: 190
```

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 191
<211> LENGTH: 39
<212> TYPE: PRT
<213> ORGANISM: Artificial Sequence
<220> FEATURE:
<223> OTHER INFORMATION: synthetic peptide

<400> SEQUENCE: 191

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 192
<211> LENGTH: 39
<212> TYPE: PRT
<213> ORGANISM: Artificial Sequence
<220> FEATURE:
<223> OTHER INFORMATION: synthetic peptide

<400> SEQUENCE: 192

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 193
<211> LENGTH: 51
<212> TYPE: PRT
<213> ORGANISM: Artificial Sequence
<220> FEATURE:
<223> OTHER INFORMATION: synthetic peptide

<400> SEQUENCE: 193

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 194
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-glucitol

<400> SEQUENCE: 194

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 195
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-pyroglutamyl

<400> SEQUENCE: 195

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 196
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-9-fluorenylmethoxycarbonyl

<400> SEQUENCE: 196

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 197
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-palmitate

<400> SEQUENCE: 197

-continued

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 198
<211> LENGTH: 51
<212> TYPE: PRT
<213> ORGANISM: Artificial Sequence
<220> FEATURE:
<223> OTHER INFORMATION: synthetic peptide

<400> SEQUENCE: 198

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 199
<211> LENGTH: 51
<212> TYPE: PRT
<213> ORGANISM: Artificial Sequence
<220> FEATURE:
<223> OTHER INFORMATION: synthetic peptide

<400> SEQUENCE: 199

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 200
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 200

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

```
<210> SEQ ID NO 201
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Sar

<400> SEQUENCE: 201

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 202
<211> LENGTH: 52
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 202

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Gly
            20                  25                  30

Lys Lys Asn Asp Trp Lys His Asn Ile Thr Gln Pro Ser Ser Gly Ala
        35                  40                  45

Pro Pro Pro Ser
    50

<210> SEQ ID NO 203
<211> LENGTH: 52
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Sar

<400> SEQUENCE: 203

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Gly
            20                  25                  30

Lys Lys Asn Asp Trp Lys His Asn Ile Thr Gln Pro Ser Ser Gly Ala
        35                  40                  45

Pro Pro Pro Ser
    50

<210> SEQ ID NO 204
<211> LENGTH: 14
<212> TYPE: PRT
<213> ORGANISM: Artificial Sequence
```

<220> FEATURE:
<223> OTHER INFORMATION: synthetic peptide

<400> SEQUENCE: 204

Tyr Ala Glu Gly Thr Phe Ile Ser Asp Tyr Ser Ile Tyr Met
1               5                   10

<210> SEQ ID NO 205
<211> LENGTH: 14
<212> TYPE: PRT
<213> ORGANISM: Artificial Sequence
<220> FEATURE:
<223> OTHER INFORMATION: synthetic peptide

<400> SEQUENCE: 205

Ala Ala Glu Gly Thr Phe Ile Ser Asp Tyr Ser Ile Ala Met
1               5                   10

<210> SEQ ID NO 206
<211> LENGTH: 14
<212> TYPE: PRT
<213> ORGANISM: Artificial Sequence
<220> FEATURE:
<223> OTHER INFORMATION: synthetic peptide

<400> SEQUENCE: 206

Tyr Ala Ala Gly Thr Phe Ile Ser Asp Tyr Ser Ile Ala Met
1               5                   10

<210> SEQ ID NO 207
<211> LENGTH: 14
<212> TYPE: PRT
<213> ORGANISM: Artificial Sequence
<220> FEATURE:
<223> OTHER INFORMATION: synthetic peptide

<400> SEQUENCE: 207

Tyr Ala Glu Ala Thr Phe Ile Ser Asp Tyr Ser Ile Ala Met
1               5                   10

<210> SEQ ID NO 208
<211> LENGTH: 14
<212> TYPE: PRT
<213> ORGANISM: Artificial Sequence
<220> FEATURE:
<223> OTHER INFORMATION: synthetic peptide

<400> SEQUENCE: 208

Tyr Ala Glu Gly Ala Phe Ile Ser Asp Tyr Ser Ile Ala Met
1               5                   10

<210> SEQ ID NO 209
<211> LENGTH: 14
<212> TYPE: PRT
<213> ORGANISM: Artificial Sequence
<220> FEATURE:
<223> OTHER INFORMATION: synthetic peptide

<400> SEQUENCE: 209

Tyr Ala Glu Gly Thr Ala Ile Ser Asp Tyr Ser Ile Ala Met
1               5                   10

<210> SEQ ID NO 210
<211> LENGTH: 14
<212> TYPE: PRT
<213> ORGANISM: Artificial Sequence
<220> FEATURE:
<223> OTHER INFORMATION: synthetic peptide

```
<400> SEQUENCE: 210

Tyr Ala Glu Gly Thr Phe Ala Ser Asp Tyr Ser Ile Ala Met
1               5                   10

<210> SEQ ID NO 211
<211> LENGTH: 14
<212> TYPE: PRT
<213> ORGANISM: Artificial Sequence
<220> FEATURE:
<223> OTHER INFORMATION: synthetic peptide

<400> SEQUENCE: 211

Tyr Ala Glu Gly Thr Phe Ile Ala Asp Tyr Ser Ile Ala Met
1               5                   10

<210> SEQ ID NO 212
<211> LENGTH: 14
<212> TYPE: PRT
<213> ORGANISM: Artificial Sequence
<220> FEATURE:
<223> OTHER INFORMATION: synthetic peptide

<400> SEQUENCE: 212

Tyr Ala Glu Gly Thr Phe Ile Ser Ala Tyr Ser Ile Ala Met
1               5                   10

<210> SEQ ID NO 213
<211> LENGTH: 14
<212> TYPE: PRT
<213> ORGANISM: Artificial Sequence
<220> FEATURE:
<223> OTHER INFORMATION: synthetic peptide

<400> SEQUENCE: 213

Tyr Ala Glu Gly Thr Phe Ile Ser Asp Ala Ser Ile Ala Met
1               5                   10

<210> SEQ ID NO 214
<211> LENGTH: 14
<212> TYPE: PRT
<213> ORGANISM: Artificial Sequence
<220> FEATURE:
<223> OTHER INFORMATION: synthetic peptide

<400> SEQUENCE: 214

Tyr Ala Glu Gly Thr Phe Ile Ser Asp Tyr Ala Ile Ala Met
1               5                   10

<210> SEQ ID NO 215
<211> LENGTH: 14
<212> TYPE: PRT
<213> ORGANISM: Artificial Sequence
<220> FEATURE:
<223> OTHER INFORMATION: synthetic peptide

<400> SEQUENCE: 215

Tyr Ala Glu Gly Thr Phe Ile Ser Asp Tyr Ser Ala Ala Met
1               5                   10

<210> SEQ ID NO 216
<211> LENGTH: 14
<212> TYPE: PRT
<213> ORGANISM: Artificial Sequence
<220> FEATURE:
<223> OTHER INFORMATION: synthetic peptide

<400> SEQUENCE: 216
```

Tyr Ala Glu Gly Thr Phe Ile Ser Asp Tyr Ser Ile Ala Ala
1               5                   10

<210> SEQ ID NO 217
<211> LENGTH: 14
<212> TYPE: PRT
<213> ORGANISM: Artificial Sequence
<220> FEATURE:
<223> OTHER INFORMATION: synthetic peptide

<400> SEQUENCE: 217

Tyr Ser Glu Gly Thr Phe Ile Ser Asp Tyr Ser Ile Ala Met
1               5                   10

<210> SEQ ID NO 218
<211> LENGTH: 14
<212> TYPE: PRT
<213> ORGANISM: Artificial Sequence
<220> FEATURE:
<223> OTHER INFORMATION: synthetic peptide

<400> SEQUENCE: 218

Tyr Gly Glu Gly Thr Phe Ile Ser Asp Tyr Ser Ile Ala Met
1               5                   10

<210> SEQ ID NO 219
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-glucitol

<400> SEQUENCE: 219

Tyr Ala Glu Gly Thr Phe Ile Ser Asp Tyr Ser Ile Ala Met
1               5                   10

<210> SEQ ID NO 220
<211> LENGTH: 9
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-pyroglutamyl

<400> SEQUENCE: 220

Tyr Ala Glu Gly Thr Phe Ile Ser Asp
1               5

<210> SEQ ID NO 221
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-9-fluorenylmethoxycarbonyl

<400> SEQUENCE: 221

Tyr Ala Glu Gly Thr Phe Ile Ser Asp Tyr Ser Ile Ala Met
1               5                   10

```
<210> SEQ ID NO 222
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr1-palmitate

<400> SEQUENCE: 222

Tyr Ala Glu Gly Thr Phe Ile Ser Asp Tyr Ser Ile Ala Met
1               5                   10

<210> SEQ ID NO 223
<211> LENGTH: 14
<212> TYPE: PRT
<213> ORGANISM: Artificial Sequence
<220> FEATURE:
<223> OTHER INFORMATION: synthetic peptide

<400> SEQUENCE: 223

Tyr Ser Glu Gly Thr Phe Ile Ser Asp Tyr Ser Ile Ala Met
1               5                   10

<210> SEQ ID NO 224
<211> LENGTH: 14
<212> TYPE: PRT
<213> ORGANISM: Artificial Sequence
<220> FEATURE:
<223> OTHER INFORMATION: synthetic peptide

<400> SEQUENCE: 224

Tyr Gly Glu Gly Thr Phe Ile Ser Asp Tyr Ser Ile Ala Met
1               5                   10

<210> SEQ ID NO 225
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 225

Tyr Xaa Ala Glu Gly Thr Phe Ile Ser Asp Tyr Ser Ile Ala Met
1               5                   10                  15

<210> SEQ ID NO 226
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Sar

<400> SEQUENCE: 226

Tyr Xaa Ala Glu Gly Thr Phe Ile Ser Asp Tyr Ser Ile Ala Met
1               5                   10                  15

<210> SEQ ID NO 227
```

```
<211> LENGTH: 11
<212> TYPE: PRT
<213> ORGANISM: Artificial Sequence
<220> FEATURE:
<223> OTHER INFORMATION: synthetic peptide

<400> SEQUENCE: 227

Tyr Ala Glu Gly Thr Phe Ile Ser Asp Tyr Ser
1               5                   10

<210> SEQ ID NO 228
<211> LENGTH: 12
<212> TYPE: PRT
<213> ORGANISM: Artificial Sequence
<220> FEATURE:
<223> OTHER INFORMATION: synthetic peptide

<400> SEQUENCE: 228

Tyr Ala Glu Gly Thr Phe Ile Ser Asp Tyr Ser Ile
1               5                   10

<210> SEQ ID NO 229
<211> LENGTH: 13
<212> TYPE: PRT
<213> ORGANISM: Artificial Sequence
<220> FEATURE:
<223> OTHER INFORMATION: synthetic peptide

<400> SEQUENCE: 229

Tyr Ala Glu Gly Thr Phe Ile Ser Asp Tyr Ser Ile Ala
1               5                   10

<210> SEQ ID NO 230
<211> LENGTH: 4
<212> TYPE: PRT
<213> ORGANISM: Artificial Sequence
<220> FEATURE:
<223> OTHER INFORMATION: synthetic peptide

<400> SEQUENCE: 230

Glu Lys Glu Lys
1

<210> SEQ ID NO 231
<211> LENGTH: 4
<212> TYPE: PRT
<213> ORGANISM: Artificial Sequence
<220> FEATURE:
<223> OTHER INFORMATION: synthetic peptide

<400> SEQUENCE: 231

Ala Ala Ala Ala
1

<210> SEQ ID NO 232
<211> LENGTH: 12
<212> TYPE: PRT
<213> ORGANISM: Artificial Sequence
<220> FEATURE:
<223> OTHER INFORMATION: synthetic peptide

<400> SEQUENCE: 232

Glu Lys Glu Glu Lys Glu Lys Glu Glu Lys Glu Lys
1               5                   10

<210> SEQ ID NO 233
<211> LENGTH: 12
<212> TYPE: PRT
```

```
<213> ORGANISM: Artificial Sequence
<220> FEATURE:
<223> OTHER INFORMATION: synthetic peptide

<400> SEQUENCE: 233

Gln Gln Asp Phe Val Asn Trp Leu Leu Ala Gln Lys
1               5                   10

<210> SEQ ID NO 234
<211> LENGTH: 12
<212> TYPE: PRT
<213> ORGANISM: Artificial Sequence
<220> FEATURE:
<223> OTHER INFORMATION: synthetic peptide

<400> SEQUENCE: 234

Gln Gln Asp Phe Val Asn Trp Leu Leu Ala Gln Arg
1               5                   10

<210> SEQ ID NO 235
<211> LENGTH: 8
<212> TYPE: PRT
<213> ORGANISM: Artificial Sequence
<220> FEATURE:
<223> OTHER INFORMATION: synthetic peptide

<400> SEQUENCE: 235

Pro Ser Ser Gly Ala Pro Pro Pro
1               5

<210> SEQ ID NO 236
<211> LENGTH: 7
<212> TYPE: PRT
<213> ORGANISM: Artificial Sequence
<220> FEATURE:
<223> OTHER INFORMATION: synthetic peptide

<400> SEQUENCE: 236

Pro Ser Ser Gly Ala Pro Pro
1               5

<210> SEQ ID NO 237
<211> LENGTH: 6
<212> TYPE: PRT
<213> ORGANISM: Artificial Sequence
<220> FEATURE:
<223> OTHER INFORMATION: synthetic peptide

<400> SEQUENCE: 237

Pro Ser Ser Gly Ala Pro
1               5

<210> SEQ ID NO 238
<211> LENGTH: 5
<212> TYPE: PRT
<213> ORGANISM: Artificial Sequence
<220> FEATURE:
<223> OTHER INFORMATION: synthetic peptide

<400> SEQUENCE: 238

Pro Ser Ser Gly Ala
1               5

<210> SEQ ID NO 239
<211> LENGTH: 4
<212> TYPE: PRT
<213> ORGANISM: Artificial Sequence
<220> FEATURE:
```

```
<223> OTHER INFORMATION: synthetic peptide

<400> SEQUENCE: 239

Pro Ser Ser Gly
1

<210> SEQ ID NO 240
<211> LENGTH: 14
<212> TYPE: PRT
<213> ORGANISM: Artificial Sequence
<220> FEATURE:
<223> OTHER INFORMATION: synthetic peptide

<400> SEQUENCE: 240

Lys Asn Gly Gly Lys Pro Ser Ser Gly Ala Pro Pro Pro Ser
1               5                   10

<210> SEQ ID NO 241
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: pSer

<400> SEQUENCE: 241

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 242
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: (N-MeGlu)

<400> SEQUENCE: 242

Tyr Ala Glu Glu Glu Gly Thr Phe Ile Ser Asp Tyr Ser Ile Ala Met
1               5                   10                  15

Asp Lys Ile His Gln Gln Asp Phe Val Asn Trp Leu Leu Ala Gln Lys
            20                  25                  30

Pro Ser Ser Gly Ala Pro Pro Pro Ser
        35                  40

<210> SEQ ID NO 243
<211> LENGTH: 39
<212> TYPE: PRT
<213> ORGANISM: Artificial Sequence
<220> FEATURE:
<223> OTHER INFORMATION: synthetic peptide

<400> SEQUENCE: 243

Tyr Pro Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
```

```
                  20                  25                  30

Ser Gly Ala Pro Pro Ser
        35

<210> SEQ ID NO 244
<211> LENGTH: 39
<212> TYPE: PRT
<213> ORGANISM: Artificial Sequence
<220> FEATURE:
<223> OTHER INFORMATION: synthetic peptide

<400> SEQUENCE: 244

Tyr Val Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 245
<211> LENGTH: 39
<212> TYPE: PRT
<213> ORGANISM: Artificial Sequence
<220> FEATURE:
<223> OTHER INFORMATION: synthetic peptide

<400> SEQUENCE: 245

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 246
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: pSer

<400> SEQUENCE: 246

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 247
<211> LENGTH: 52
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (3)..(3)
<223> OTHER INFORMATION: (N-MeGlu)
```

```
<400> SEQUENCE: 247

Tyr Ala Glu Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Gly
            20                  25                  30

Lys Lys Asn Asp Trp Lys His Asn Ile Thr Gln Pro Ser Ser Gly Ala
        35                  40                  45

Pro Pro Pro Ser
    50

<210> SEQ ID NO 248
<211> LENGTH: 51
<212> TYPE: PRT
<213> ORGANISM: Artificial Sequence
<220> FEATURE:
<223> OTHER INFORMATION: synthetic peptide

<400> SEQUENCE: 248

Tyr Pro Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 249
<211> LENGTH: 51
<212> TYPE: PRT
<213> ORGANISM: Artificial Sequence
<220> FEATURE:
<223> OTHER INFORMATION: synthetic peptide

<400> SEQUENCE: 249

Tyr Val Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 250
<211> LENGTH: 51
<212> TYPE: PRT
<213> ORGANISM: Artificial Sequence
<220> FEATURE:
<223> OTHER INFORMATION: synthetic peptide

<400> SEQUENCE: 250

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50
```

<210> SEQ ID NO 251
<211> LENGTH: 39
<212> TYPE: PRT
<213> ORGANISM: Artificial Sequence
<220> FEATURE:
<223> OTHER INFORMATION: synthetic peptide

<400> SEQUENCE: 251

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 252
<211> LENGTH: 51
<212> TYPE: PRT
<213> ORGANISM: Artificial Sequence
<220> FEATURE:
<223> OTHER INFORMATION: synthetic peptide

<400> SEQUENCE: 252

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 253
<211> LENGTH: 26
<212> TYPE: PRT
<213> ORGANISM: Homo sapiens

<400> SEQUENCE: 253

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu
            20                  25

<210> SEQ ID NO 254
<211> LENGTH: 39
<212> TYPE: PRT
<213> ORGANISM: Homo sapiens

<400> SEQUENCE: 254

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn
        35

<210> SEQ ID NO 255
<211> LENGTH: 26
<212> TYPE: PRT
<213> ORGANISM: Mus musculus

<400> SEQUENCE: 255

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu
            20                  25

<210> SEQ ID NO 256
<211> LENGTH: 30
<212> TYPE: PRT
<213> ORGANISM: Mus musculus

<400> SEQUENCE: 256

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg
            20                  25                  30

<210> SEQ ID NO 257
<211> LENGTH: 39
<212> TYPE: PRT
<213> ORGANISM: Mus musculus

<400> SEQUENCE: 257

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn
        35

<210> SEQ ID NO 258
<211> LENGTH: 26
<212> TYPE: PRT
<213> ORGANISM: Rattus rattus

<400> SEQUENCE: 258

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu
            20                  25

<210> SEQ ID NO 259
<211> LENGTH: 30
<212> TYPE: PRT
<213> ORGANISM: Rattus rattus

<400> SEQUENCE: 259

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 260
<211> LENGTH: 39
<212> TYPE: PRT
<213> ORGANISM: Rattus rattus

<400> SEQUENCE: 260

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30
```

```
Lys Asn Asp Trp Lys His Asn
            35

<210> SEQ ID NO 261
<211> LENGTH: 26
<212> TYPE: PRT
<213> ORGANISM: Sus scrofa

<400> SEQUENCE: 261

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu
            20                  25

<210> SEQ ID NO 262
<211> LENGTH: 30
<212> TYPE: PRT
<213> ORGANISM: Sus scrofa

<400> SEQUENCE: 262

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 263
<211> LENGTH: 39
<212> TYPE: PRT
<213> ORGANISM: Sus scrofa

<400> SEQUENCE: 263

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn
            35

<210> SEQ ID NO 264
<211> LENGTH: 26
<212> TYPE: PRT
<213> ORGANISM: Bos taurus

<400> SEQUENCE: 264

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu
            20                  25

<210> SEQ ID NO 265
<211> LENGTH: 30
<212> TYPE: PRT
<213> ORGANISM: Bos taurus

<400> SEQUENCE: 265

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 266
<211> LENGTH: 39
<212> TYPE: PRT
```

-continued

<213> ORGANISM: Bos taurus

<400> SEQUENCE: 266

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn
        35

<210> SEQ ID NO 267
<211> LENGTH: 51
<212> TYPE: PRT
<213> ORGANISM: Homo sapiens

<400> SEQUENCE: 267

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Pro Ser Gly Ala Pro
        35                  40                  45

Pro Pro Ser
    50

<210> SEQ ID NO 268
<211> LENGTH: 51
<212> TYPE: PRT
<213> ORGANISM: Mus musculus

<400> SEQUENCE: 268

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Ile Thr Gln Pro Ser Ser Gly Ala Pro
        35                  40                  45

Pro Pro Ser
    50

<210> SEQ ID NO 269
<211> LENGTH: 39
<212> TYPE: PRT
<213> ORGANISM: Mus musculus

<400> SEQUENCE: 269

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Pro Ser
            20                  25                  30

Ser Gly Ala Pro Pro Pro Ser
        35

<210> SEQ ID NO 270
<211> LENGTH: 51
<212> TYPE: PRT
<213> ORGANISM: Rattus rattus

<400> SEQUENCE: 270

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln Pro Ser Ser Gly Ala Pro
        35                  40                  45

Pro Pro Ser
    50

<210> SEQ ID NO 271
<211> LENGTH: 39
<212> TYPE: PRT
<213> ORGANISM: Rattus rattus

<400> SEQUENCE: 271

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 272
<211> LENGTH: 51
<212> TYPE: PRT
<213> ORGANISM: Sus scrofa

<400> SEQUENCE: 272

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Ile Thr Gln Pro Ser Ser Gly Ala Pro
        35                  40                  45

Pro Pro Ser
    50

<210> SEQ ID NO 273
<211> LENGTH: 39
<212> TYPE: PRT
<213> ORGANISM: Sus scrofa

<400> SEQUENCE: 273

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 274
<211> LENGTH: 51
<212> TYPE: PRT
<213> ORGANISM: Bos taurus

<400> SEQUENCE: 274

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln Pro Pro Ser Gly Ala Pro
        35                  40                  45

Pro Pro Ser
    50

<210> SEQ ID NO 275
<211> LENGTH: 39
<212> TYPE: PRT
<213> ORGANISM: Bos taurus

<400> SEQUENCE: 275

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Pro
            20                  25                  30

Ser Gly Ala Pro Pro Pro Ser
        35

<210> SEQ ID NO 276
<211> LENGTH: 39
<212> TYPE: PRT
<213> ORGANISM: Homo sapiens

<400> SEQUENCE: 276

Tyr Ala Glu Gly Thr Phe Ile Ser Asp Tyr Ser Ile Ala Met Asp Lys
1               5                   10                  15

Ile His Gln Gln Asp Phe Val Asn Trp Leu Lys Asn Gly Gly Pro Ser
            20                  25                  30

Ser Gly Ala Pro Pro Pro Ser
        35

<210> SEQ ID NO 277
<211> LENGTH: 39
<212> TYPE: PRT
<213> ORGANISM: Mus musculus

<400> SEQUENCE: 277

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Lys Asn Gly Gly Pro Ser
            20                  25                  30

Ser Gly Ala Pro Pro Pro Ser
        35

<210> SEQ ID NO 278
<211> LENGTH: 39
<212> TYPE: PRT
<213> ORGANISM: Rattus rattus

<400> SEQUENCE: 278

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Lys Asn Gly Gly Pro Ser
            20                  25                  30

Ser Gly Ala Pro Pro Pro Ser
        35

<210> SEQ ID NO 279
<211> LENGTH: 39
<212> TYPE: PRT
<213> ORGANISM: Sus scrofa

<400> SEQUENCE: 279

```
Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Lys Asn Gly Gly Pro Ser
            20                  25                  30

Ser Gly Ala Pro Pro Ser
            35

<210> SEQ ID NO 280
<211> LENGTH: 39
<212> TYPE: PRT
<213> ORGANISM: Bos taurus

<400> SEQUENCE: 280

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Lys Asn Gly Gly Pro Pro
            20                  25                  30

Ser Gly Ala Pro Pro Ser
            35

<210> SEQ ID NO 281
<211> LENGTH: 48
<212> TYPE: PRT
<213> ORGANISM: Homo sapiens

<400> SEQUENCE: 281

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Pro Pro Ser Gly Ala Pro Pro Pro Ser
            35                  40                  45

<210> SEQ ID NO 282
<211> LENGTH: 48
<212> TYPE: PRT
<213> ORGANISM: Mus musculus

<400> SEQUENCE: 282

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Gly Lys
            20                  25                  30

Lys Ser Asp Trp Lys His Asn Pro Ser Ser Gly Ala Pro Pro Pro Ser
            35                  40                  45

<210> SEQ ID NO 283
<211> LENGTH: 48
<212> TYPE: PRT
<213> ORGANISM: Rattus rattus

<400> SEQUENCE: 283

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Pro Ser Ser Gly Ala Pro Pro Pro Ser
            35                  40                  45

<210> SEQ ID NO 284
<211> LENGTH: 48
```

```
<212> TYPE: PRT
<213> ORGANISM: Sus scrofa

<400> SEQUENCE: 284

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn Pro Ser Ser Gly Ala Pro Pro Pro Ser
        35                  40                  45

<210> SEQ ID NO 285
<211> LENGTH: 48
<212> TYPE: PRT
<213> ORGANISM: Bos taurus

<400> SEQUENCE: 285

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Pro Pro Ser Gly Ala Pro Pro Pro Ser
        35                  40                  45

<210> SEQ ID NO 286
<211> LENGTH: 39
<212> TYPE: PRT
<213> ORGANISM: Artificial Sequence
<220> FEATURE:
<223> OTHER INFORMATION: synthetic peptide

<400> SEQUENCE: 286

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 287
<211> LENGTH: 28
<212> TYPE: PRT
<213> ORGANISM: Artificial Sequence
<220> FEATURE:
<223> OTHER INFORMATION: synthetic peptide

<400> SEQUENCE: 287

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 288
<211> LENGTH: 28
<212> TYPE: PRT
<213> ORGANISM: Artificial Sequence
<220> FEATURE:
<223> OTHER INFORMATION: synthetic peptide

<400> SEQUENCE: 288

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn
            20                  25
```

-continued

```
                20                  25

<210> SEQ ID NO 289
<211> LENGTH: 8
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Tyr(SO3)

<400> SEQUENCE: 289

Asp Tyr Met Gly Trp Met Asp Phe
1               5

<210> SEQ ID NO 290
<211> LENGTH: 51
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation

<400> SEQUENCE: 290

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 291
<211> LENGTH: 42
<212> TYPE: PRT
<213> ORGANISM: Artificial Sequence
<220> FEATURE:
<223> OTHER INFORMATION: synthetic peptide

<400> SEQUENCE: 291

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 292
<211> LENGTH: 30
<212> TYPE: PRT
<213> ORGANISM: Artificial Sequence
<220> FEATURE:
<223> OTHER INFORMATION: synthetic peptide

<400> SEQUENCE: 292

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30
```

```
<210> SEQ ID NO 293
<211> LENGTH: 30
<212> TYPE: PRT
<213> ORGANISM: Artificial Sequence
<220> FEATURE:
<223> OTHER INFORMATION: synthetic peptide

<400> SEQUENCE: 293

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 294
<211> LENGTH: 30
<212> TYPE: PRT
<213> ORGANISM: Homo sapiens

<400> SEQUENCE: 294

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 295
<211> LENGTH: 30
<212> TYPE: PRT
<213> ORGANISM: Homo sapiens

<400> SEQUENCE: 295

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 296
<211> LENGTH: 30
<212> TYPE: PRT
<213> ORGANISM: Homo sapiens

<400> SEQUENCE: 296

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 297
<211> LENGTH: 30
<212> TYPE: PRT
<213> ORGANISM: Homo sapiens

<400> SEQUENCE: 297

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 298
<211> LENGTH: 42
<212> TYPE: PRT
<213> ORGANISM: Artificial Sequence
<220> FEATURE:
<223> OTHER INFORMATION: synthetic peptide
<220> FEATURE:
```

```
<221> NAME/KEY: MOD_RES
<222> LOCATION: (1)..(1)
<223> OTHER INFORMATION: Acetylation

<400> SEQUENCE: 298
```

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40

```
<210> SEQ ID NO 299
<211> LENGTH: 39
<212> TYPE: PRT
<213> ORGANISM: Artificial Sequence
<220> FEATURE:
<223> OTHER INFORMATION: synthetic peptide

<400> SEQUENCE: 299
```

Tyr Gly Glu Gly Thr Phe Ile Ser Asp Tyr Ser Ile Ala Met Asp Lys
1               5                   10                  15

Ile His Gln Gln Asp Phe Val Asn Trp Leu Lys Asn Gly Gly Pro Ser
            20                  25                  30

Ser Gly Ala Pro Pro Pro Ser
            35

```
<210> SEQ ID NO 300
<211> LENGTH: 42
<212> TYPE: PRT
<213> ORGANISM: Gallus gallus

<400> SEQUENCE: 300
```

Tyr Ser Glu Ala Thr Leu Ala Ser Asp Tyr Ser Arg Thr Met Asp Asn
1               5                   10                  15

Met Leu Lys Lys Asn Phe Val Glu Trp Leu Leu Ala Arg Arg Glu Lys
            20                  25                  30

Lys Ser Asp Asn Val Ile Glu Pro Tyr Lys
            35                  40

```
<210> SEQ ID NO 301
<211> LENGTH: 42
<212> TYPE: PRT
<213> ORGANISM: Xenopus tropicalis

<400> SEQUENCE: 301
```

Tyr Ser Glu Ala Ile Leu Ala Ser Asp Tyr Ser Arg Ser Val Asp Asn
1               5                   10                  15

Met Leu Lys Lys Asn Phe Val Asp Trp Leu Leu Ala Arg Arg Glu Lys
            20                  25                  30

Lys Ser Glu Asn Thr Ser Glu Ala Thr Lys
            35                  40

```
<210> SEQ ID NO 302
<211> LENGTH: 35
<212> TYPE: PRT
<213> ORGANISM: Brachydanio rerio

<400> SEQUENCE: 302
```

Tyr Ala Glu Ser Thr Ile Ala Ser Asp Ile Ser Lys Ile Val Asp Ser
1               5                   10                  15

Met Val Gln Lys Asn Phe Val Asn Phe Leu Leu Asn Gln Arg Glu Lys

```
                20                  25                  30

Lys Ser Glu
         35

<210> SEQ ID NO 303
<211> LENGTH: 42
<212> TYPE: PRT
<213> ORGANISM: Monkey

<400> SEQUENCE: 303

Tyr Ala Glu Gly Thr Phe Ile Asn Asp Tyr Ser Ile Ala Met Asp Lys
1               5                   10                  15

Ile His Gln Gln His Phe Val His Trp Leu Leu Pro Pro Lys Gly Lys
                20                  25                  30

Asn Asn Asp Trp Lys His Asp Leu Pro Gln
         35                  40

<210> SEQ ID NO 304
<211> LENGTH: 42
<212> TYPE: PRT
<213> ORGANISM: Didelphis virginiana

<400> SEQUENCE: 304

Tyr Ala Glu Gly Thr Phe Ile Ser Asp Tyr Ser Ile Thr Met Asp Lys
1               5                   10                  15

Ile Met Gln Gln Asp Phe Val Asn Trp Leu Leu Ser Gln Lys Gly Lys
                20                  25                  30

Lys Asn Ser Trp Arg His Asn Ile Thr Glu
         35                  40

<210> SEQ ID NO 305
<211> LENGTH: 42
<212> TYPE: PRT
<213> ORGANISM: Cricetus sp.

<400> SEQUENCE: 305

Tyr Ala Glu Gly Thr Phe Ile Ser Asp Tyr Ser Ile Ala Leu Asp Lys
1               5                   10                  15

Ile Arg Gln Gln Asp Phe Val Asn Trp Leu Leu Ala Trp Lys Gly Lys
                20                  25                  30

Lys Asn Asp Trp Lys His Asn Ile Thr Gln
         35                  40

<210> SEQ ID NO 306
<211> LENGTH: 42
<212> TYPE: PRT
<213> ORGANISM: Artificial Sequence
<220> FEATURE:
<223> OTHER INFORMATION: synthetic peptide

<400> SEQUENCE: 306

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
                20                  25                  30

Lys Ser Asp Trp Lys His Asn Ile Thr Gln
         35                  40

<210> SEQ ID NO 307
<211> LENGTH: 42
<212> TYPE: PRT
<213> ORGANISM: Homo sapiens
```

<400> SEQUENCE: 307

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Lys Gly Lys
            20                  25                  30

Lys Asn Asp Trp Lys His Asn Ile Thr Gln
        35                  40

<210> SEQ ID NO 308
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation
<220> FEATURE:
<221> NAME/KEY: MOD_RES
<222> LOCATION: (37)..(37)
<223> OTHER INFORMATION: Lys(Palm)

<400> SEQUENCE: 308

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 309
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation

<400> SEQUENCE: 309

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 310
<211> LENGTH: 42
<212> TYPE: PRT
<213> ORGANISM: Artificial Sequence
<220> FEATURE:
<223> OTHER INFORMATION: synthetic peptide

<400> SEQUENCE: 310

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

```
<210> SEQ ID NO 311
<211> LENGTH: 30
<212> TYPE: PRT
<213> ORGANISM: Homo sapiens

<400> SEQUENCE: 311

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: synthetic peptide

<400> SEQUENCE: 312

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 313
<211> LENGTH: 30
<212> TYPE: PRT
<213> ORGANISM: Artificial Sequence
<220> FEATURE:
<223> OTHER INFORMATION: synthetic peptide

<400> SEQUENCE: 313

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 314
<211> LENGTH: 30
<212> TYPE: PRT
<213> ORGANISM: Homo sapiens

<400> SEQUENCE: 314

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: synthetic peptide

<400> SEQUENCE: 315

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 316
<211> LENGTH: 30
```

```
<212> TYPE: PRT
<213> ORGANISM: Artificial Sequence
<220> FEATURE:
<223> OTHER INFORMATION: synthetic peptide

<400> SEQUENCE: 316

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: synthetic peptide

<400> SEQUENCE: 317

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 318
<211> LENGTH: 39
<212> TYPE: PRT
<213> ORGANISM: Artificial Sequence
<220> FEATURE:
<223> OTHER INFORMATION: synthetic peptide

<400> SEQUENCE: 318

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 319
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation

<400> SEQUENCE: 319

Tyr Ala Glu Gly Thr Phe Ile Ser Asp Ala Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 320
<211> LENGTH: 39
<212> TYPE: PRT
<213> ORGANISM: Artificial Sequence
<220> FEATURE:
<223> OTHER INFORMATION: synthetic peptide

<400> SEQUENCE: 320
```

```
Tyr Ala Glu Gly Thr Phe Ile Ser Asp Ala Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 321
<211> LENGTH: 39
<212> TYPE: PRT
<213> ORGANISM: Artificial Sequence
<220> FEATURE:
<223> OTHER INFORMATION: synthetic peptide

<400> SEQUENCE: 321

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 322
<211> LENGTH: 39
<212> TYPE: PRT
<213> ORGANISM: Artificial Sequence
<220> FEATURE:
<223> OTHER INFORMATION: synthetic peptide

<400> SEQUENCE: 322

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 323
<211> LENGTH: 39
<212> TYPE: PRT
<213> ORGANISM: Artificial Sequence
<220> FEATURE:
<223> OTHER INFORMATION: synthetic peptide

<400> SEQUENCE: 323

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 324
<211> LENGTH: 39
<212> TYPE: PRT
<213> ORGANISM: Artificial Sequence
<220> FEATURE:
<223> OTHER INFORMATION: synthetic peptide

<400> SEQUENCE: 324

Tyr Ala Pro Gly Thr Phe Ile Ser Asp Tyr Ser Ile Ala Met Asp Lys
1               5                   10                  15
```

Ile His Gln Gln Asp Phe Val Asn Trp Leu Ala Gln Lys Pro Ser
            20                  25                  30

Ser Gly Ala Pro Pro Ser
        35

<210> SEQ ID NO 325
<211> LENGTH: 39
<212> TYPE: PRT
<213> ORGANISM: Artificial Sequence
<220> FEATURE:
<223> OTHER INFORMATION: synthetic peptide

<400> SEQUENCE: 325

Tyr Ala Glu Gly Thr Phe Ile Ser Asp Tyr Ser Ile Ala Met Asp Lys
1               5                   10                  15

Ile His Gln Gln Asp Phe Val Asn Trp Leu Lys Asn Gly Gly Pro Ser
            20                  25                  30

Ser Gly Ala Pro Pro Ser
        35

<210> SEQ ID NO 326
<211> LENGTH: 39
<212> TYPE: PRT
<213> ORGANISM: Artificial Sequence
<220> FEATURE:
<223> OTHER INFORMATION: synthetic peptide

<400> SEQUENCE: 326

Tyr Gly Glu Gly Thr Phe Ile Ser Asp Tyr Ser Ile Ala Met Asp Lys
1               5                   10                  15

Ile His Gln Gln Asp Phe Val Asn Trp Leu Lys Asn Gly Gly Pro Ser
            20                  25                  30

Ser Gly Ala Pro Pro Ser
        35

<210> SEQ ID NO 327
<211> LENGTH: 39
<212> TYPE: PRT
<213> ORGANISM: Artificial Sequence
<220> FEATURE:
<223> OTHER INFORMATION: synthetic peptide

<400> SEQUENCE: 327

Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys Pro Ser
            20                  25                  30

Ser Gly Ala Pro Pro Ser
        35

<210> SEQ ID NO 328
<211> LENGTH: 39
<212> TYPE: PRT
<213> ORGANISM: Artificial Sequence
<220> FEATURE:
<223> OTHER INFORMATION: synthetic peptide

<400> SEQUENCE: 328

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Lys Pro Ser
            20                  25                  30

Ser Gly Ala Pro Pro Ser

<210> SEQ ID NO 329
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Gly(Oct)

<400> SEQUENCE: 329

Gly Tyr Ala Glu Gly Thr Phe Ile Ser Asp Tyr Ser Ile Ala Leu Asp
1               5                   10                  15

Lys Ile Lys Gln Gln Glu Phe Val Asn Trp Leu Leu Ala Gln Lys Pro
            20                  25                  30

Ser Ser Gly Ala Pro Pro Ser
        35                  40

<210> SEQ ID NO 330
<211> LENGTH: 40
<212> TYPE: PRT
<213> ORGANISM: Artificial Sequence
<220> FEATURE:
<223> OTHER INFORMATION: synthetic peptide

<400> SEQUENCE: 330

Gly Tyr Ala Glu Gly Thr Phe Ile Ser Asp Tyr Ser Ile Ala Leu Asp
1               5                   10                  15

Lys Ile Lys Gln Gln Glu Phe Val Asn Trp Leu Leu Ala Gln Lys Pro
            20                  25                  30

Ser Ser Gly Ala Pro Pro Ser
        35                  40

<210> SEQ ID NO 331
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Asn(Octanoyl)

<400> SEQUENCE: 331

Asn Gly Tyr Ala Glu Gly Thr Phe Ile Ser Asp Tyr Ser Ile Ala Met
1               5                   10                  15

Asp Lys Ile His Gln Gln Asp Phe Val Asn Trp Leu Leu Ala Gln Lys
            20                  25                  30

Pro Ser Ser Gly Ala Pro Pro Ser
        35                  40

<210> SEQ ID NO 332
<211> LENGTH: 39
<212> TYPE: PRT
<213> ORGANISM: Artificial Sequence
<220> FEATURE:
<223> OTHER INFORMATION: synthetic peptide

<400> SEQUENCE: 332

Tyr Ala Glu Gly Thr Phe Ile Ser Asp Tyr Ser Ile Tyr Met Asp Lys
1               5                   10                  15

```
Ile His Gln Gln Asp Phe Val Asn Trp Leu Leu Ala Gln Lys Pro Ser
            20                  25                  30

Ser Gly Ala Pro Pro Ser
            35
```

<210> SEQ ID NO 333
<211> LENGTH: 39
<212> TYPE: PRT
<213> ORGANISM: Artificial Sequence
<220> FEATURE:
<223> OTHER INFORMATION: synthetic peptide

<400> SEQUENCE: 333

```
Tyr Ala Glu Gly Thr Phe Ile Ser Asp Tyr Ser Ile Ala Met Lys Asp
1               5                   10                  15

Ile His Gln Gln Asp Phe Val Asn Trp Leu Leu Ala Gln Lys Pro Ser
            20                  25                  30

Ser Gly Ala Pro Pro Ser
            35
```

<210> SEQ ID NO 334
<211> LENGTH: 39
<212> TYPE: PRT
<213> ORGANISM: Artificial Sequence
<220> FEATURE:
<223> OTHER INFORMATION: synthetic peptide

<400> SEQUENCE: 334

```
Tyr Ala Glu Gly Thr Phe Ile Ser Asp Tyr Ser Ile Ala Met Ala Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35
```

<210> SEQ ID NO 335
<211> LENGTH: 42
<212> TYPE: PRT
<213> ORGANISM: Homo sapiens

<400> SEQUENCE: 335

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40
```

<210> SEQ ID NO 336
<211> LENGTH: 40
<212> TYPE: PRT
<213> ORGANISM: Homo sapiens

<400> SEQUENCE: 336

```
Glu Gly Thr Phe Ile Ser Asp Tyr Ser Ile Ala Met Asp Lys Ile His
1               5                   10                  15

Gln Gln Asp Phe Val Asn Trp Leu Leu Ala Gln Lys Gly Lys Lys Asn
            20                  25                  30

Asp Trp Lys His Asn Ile Thr Gln
            35                  40
```

<210> SEQ ID NO 337

```
<211> LENGTH: 42
<212> TYPE: PRT
<213> ORGANISM: Bos taurus

<400> SEQUENCE: 337

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln
        35                  40

<210> SEQ ID NO 338
<211> LENGTH: 42
<212> TYPE: PRT
<213> ORGANISM: Rattus rattus

<400> SEQUENCE: 338

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Asn Asp Trp Lys His Asn Leu Thr Gln
        35                  40

<210> SEQ ID NO 339
<211> LENGTH: 42
<212> TYPE: PRT
<213> ORGANISM: Mus musculus

<400> SEQUENCE: 339

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Arg Gly Lys
            20                  25                  30

Lys Ser Asp Trp Lys His Asn Ile Thr Gln
        35                  40

<210> SEQ ID NO 340
<211> LENGTH: 42
<212> TYPE: PRT
<213> ORGANISM: Didelphis virginiana

<400> SEQUENCE: 340

Tyr Ala Glu Gly Thr Phe Ile Ser Asp Tyr Ser Ile Thr Met Asp Lys
1               5                   10                  15

Ile Met Gln Gln Asp Phe Val Asn Trp Leu Leu Ser Gln Lys Gly Lys
            20                  25                  30

Lys Asn Ser Trp Arg His Asn Ile Thr Glu
        35                  40

<210> SEQ ID NO 341
<211> LENGTH: 42
<212> TYPE: PRT
<213> ORGANISM: Sus scrofa

<400> SEQUENCE: 341

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30
```

```
Lys Ser Asp Trp Lys His Asn Ile Thr Gln
        35                  40

<210> SEQ ID NO 342
<211> LENGTH: 39
<212> TYPE: PRT
<213> ORGANISM: Sus scrofa

<400> SEQUENCE: 342

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Lys His Asn
        35

<210> SEQ ID NO 343
<211> LENGTH: 30
<212> TYPE: PRT
<213> ORGANISM: Sus scrofa

<400> SEQUENCE: 343

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 344
<211> LENGTH: 56
<212> TYPE: PRT
<213> ORGANISM: Canis familiaris

<400> SEQUENCE: 344

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Gln
            20                  25                  30

Glu Pro Pro Arg Arg Met Arg Leu Ser Ser Ala Pro Gly Tyr Pro Arg
        35                  40                  45

Glu Ala Lys Pro Ile Lys Phe Lys
    50                  55

<210> SEQ ID NO 345
<211> LENGTH: 42
<212> TYPE: PRT
<213> ORGANISM: Gallus gallus

<400> SEQUENCE: 345

Tyr Ser Glu Ala Thr Leu Ala Ser Asp Tyr Ser Arg Thr Met Asp Asn
1               5                   10                  15

Met Leu Lys Lys Asn Phe Val Glu Trp Leu Leu Ala Arg Arg Glu Lys
            20                  25                  30

Lys Ser Asp Asn Val Ile Glu Pro Tyr Lys
        35                  40

<210> SEQ ID NO 346
<211> LENGTH: 41
<212> TYPE: PRT
<213> ORGANISM: Xenopus sp.

<400> SEQUENCE: 346

Tyr Ser Glu Ala Ile Leu Ala Ser Asp Tyr Ser Arg Ser Val Asp Asn
```

```
                1               5                  10                 15
Met Leu Lys Lys Asn Phe Val Asp Trp Leu Leu Ala Arg Arg Glu Lys
            20                  25                 30

Lys Ser Glu Asn Thr Ser Glu Ala Thr
            35                  40

<210> SEQ ID NO 347
<211> LENGTH: 35
<212> TYPE: PRT
<213> ORGANISM: Brachydanio rerio

<400> SEQUENCE: 347

Tyr Ala Glu Ser Thr Ile Ala Ser Asp Ile Ser Lys Ile Val Asp Ser
1               5                  10                 15

Met Val Gln Lys Asn Phe Val Asn Phe Leu Leu Asn Gln Arg Glu Lys
            20                  25                 30

Lys Ser Glu
        35

<210> SEQ ID NO 348
<211> LENGTH: 41
<212> TYPE: PRT
<213> ORGANISM: Xenopus sp.

<400> SEQUENCE: 348

Tyr Ser Glu Ala Ile Leu Ala Ser Asp Tyr Ser Arg Ser Val Asp Asn
1               5                  10                 15

Met Leu Lys Lys Asn Phe Val Asp Trp Leu Leu Ala Arg Arg Glu Lys
            20                  25                 30

Lys Ser Glu Asn Thr Ser Glu Ala Thr
            35                  40

<210> SEQ ID NO 349
<211> LENGTH: 39
<212> TYPE: PRT
<213> ORGANISM: Artificial Sequence
<220> FEATURE:
<223> OTHER INFORMATION: synthetic peptide

<400> SEQUENCE: 349

Tyr Ser Glu Ala Ile Leu Ala Ser Asp Tyr Ser Arg Ser Val Asp Asn
1               5                  10                 15

Met Leu Gln Gln Asn Phe Val Asp Trp Leu Leu Ala Gln Lys Pro Ser
            20                  25                 30

Ser Gly Ala Pro Pro Pro Ser
        35

<210> SEQ ID NO 350
<211> LENGTH: 39
<212> TYPE: PRT
<213> ORGANISM: Artificial Sequence
<220> FEATURE:
<223> OTHER INFORMATION: synthetic peptide

<400> SEQUENCE: 350

Tyr Ser Asp Ala Ile Leu Ala Ser Asp Tyr Ser Arg Ser Val Asp Asn
1               5                  10                 15

Met Leu Gln Gln Asn Phe Val Asp Trp Leu Leu Ala Gln Lys Pro Ser
            20                  25                 30

Ser Gly Ala Pro Pro Pro Ser
        35
```

<210> SEQ ID NO 351
<211> LENGTH: 42
<212> TYPE: PRT
<213> ORGANISM: Gallus gallus

<400> SEQUENCE: 351

Tyr Ser Glu Ala Thr Leu Ala Ser Asp Tyr Ser Arg Thr Met Asp Asn
1               5                   10                  15

Met Leu Lys Lys Asn Phe Val Glu Trp Leu Leu Ala Arg Arg Glu Lys
            20                  25                  30

Lys Ser Asp Asn Val Ile Glu Pro Tyr Lys
        35                  40

<210> SEQ ID NO 352
<211> LENGTH: 39
<212> TYPE: PRT
<213> ORGANISM: Artificial Sequence
<220> FEATURE:
<223> OTHER INFORMATION: synthetic peptide

<400> SEQUENCE: 352

Tyr Ala Glu Gly Thr Phe Ile Ser Asp Tyr Ser Arg Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 353
<211> LENGTH: 39
<212> TYPE: PRT
<213> ORGANISM: Artificial Sequence
<220> FEATURE:
<223> OTHER INFORMATION: synthetic peptide

<400> SEQUENCE: 353

Tyr Ala Glu Gly Thr Phe Ile Ser Asp Tyr Ser Arg Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 354
<211> LENGTH: 39
<212> TYPE: PRT
<213> ORGANISM: Artificial Sequence
<220> FEATURE:
<223> OTHER INFORMATION: synthetic peptide

<400> SEQUENCE: 354

Tyr Ala Glu Gly Thr Phe Ile Ser Asp Tyr Ser Ile Thr Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 355
<211> LENGTH: 39
<212> TYPE: PRT
<213> ORGANISM: Artificial Sequence
<220> FEATURE:

<223> OTHER INFORMATION: synthetic peptide

<400> SEQUENCE: 355

Tyr Ser Glu Gly Thr Phe Ile Ser Asp Tyr Ser Arg Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 356
<211> LENGTH: 39
<212> TYPE: PRT
<213> ORGANISM: Artificial Sequence
<220> FEATURE:
<223> OTHER INFORMATION: synthetic peptide

<400> SEQUENCE: 356

Tyr Ser Glu Gly Thr Phe Ile Ser Asp Tyr Ser Ile Thr Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 357
<211> LENGTH: 35
<212> TYPE: PRT
<213> ORGANISM: Brachydanio rerio

<400> SEQUENCE: 357

Tyr Ala Glu Ser Thr Ile Ala Ser Asp Ile Ser Lys Ile Val Asp Ser
1               5                   10                  15

Met Val Gln Lys Asn Phe Val Asn Phe Leu Leu Asn Gln Arg Glu Lys
            20                  25                  30

Lys Ser Glu
        35

<210> SEQ ID NO 358
<211> LENGTH: 39
<212> TYPE: PRT
<213> ORGANISM: Artificial Sequence
<220> FEATURE:
<223> OTHER INFORMATION: synthetic peptide

<400> SEQUENCE: 358

Tyr Ala Glu Gly Thr Phe Ile Ser Asp Tyr Ser Lys Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 359
<211> LENGTH: 39
<212> TYPE: PRT
<213> ORGANISM: Artificial Sequence
<220> FEATURE:
<223> OTHER INFORMATION: synthetic peptide

<400> SEQUENCE: 359

Tyr Ala Glu Gly Thr Phe Ile Ser Asp Tyr Ser Lys Ala Leu Asp Glu
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 360
<211> LENGTH: 39
<212> TYPE: PRT
<213> ORGANISM: Artificial Sequence
<220> FEATURE:
<223> OTHER INFORMATION: synthetic peptide

<400> SEQUENCE: 360

Tyr Val Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 361
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 361

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 362
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 362

Tyr Xaa Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 363
<211> LENGTH: 39
<212> TYPE: PRT
<213> ORGANISM: Artificial Sequence
<220> FEATURE:
<223> OTHER INFORMATION: synthetic peptide
<220> FEATURE:

```
<221> NAME/KEY: MOD_RES
<222> LOCATION: (2)..(2)
<223> OTHER INFORMATION: Abu

<400> SEQUENCE: 363

Tyr Xaa Glu Gly Thr Phe Ile Ser Asp Tyr Ser Ile Ala Leu Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
            35

<210> SEQ ID NO 364
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Abu

<400> SEQUENCE: 364

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 365
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Homoserine

<400> SEQUENCE: 365

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 366
<211> LENGTH: 39
<212> TYPE: PRT
<213> ORGANISM: Artificial Sequence
<220> FEATURE:
<223> OTHER INFORMATION: synthetic peptide

<400> SEQUENCE: 366

Tyr Pro Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35
```

```
<210> SEQ ID NO 367
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: cyclopropyl Ala

<400> SEQUENCE: 367

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 368
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: cyclohexyl Ala

<400> SEQUENCE: 368

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 369
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Ala(NMe)

<400> SEQUENCE: 369

Tyr Ala Glu Gly Thr Phe Ile Ser Glu Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 370
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Ala(NMe)
```

<400> SEQUENCE: 370

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 371
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: Aib

<400> SEQUENCE: 371

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 372
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: cycloprp-Gly

<400> SEQUENCE: 372

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 373
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (2)..(2)
<223> OTHER INFORMATION: bAla

<400> SEQUENCE: 373

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 374
<211> LENGTH: 39
<212> TYPE: PRT
<213> ORGANISM: Artificial Sequence
<220> FEATURE:
<223> OTHER INFORMATION: synthetic peptide

<400> SEQUENCE: 374

Tyr Ser Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 375
<211> LENGTH: 39
<212> TYPE: PRT
<213> ORGANISM: Artificial Sequence
<220> FEATURE:
<223> OTHER INFORMATION: synthetic peptide

<400> SEQUENCE: 375

Tyr Ala Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 376
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 376

Gly Tyr Ala Asp Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 377
<211> LENGTH: 37
<212> TYPE: PRT
<213> ORGANISM: Artificial Sequence
<220> FEATURE:
<223> OTHER INFORMATION: synthetic peptide

<400> SEQUENCE: 377

Tyr Ala Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 378
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(31)
<223> OTHER INFORMATION: bAla

<400> SEQUENCE: 378

Tyr Ser Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Pro
            20                  25                  30

Ser Ser Gly Ala Pro Pro Pro Ser
        35                  40

<210> SEQ ID NO 379
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 379

Gly Tyr Ser Asp Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 380
<211> LENGTH: 37
<212> TYPE: PRT
<213> ORGANISM: Artificial Sequence
<220> FEATURE:
<223> OTHER INFORMATION: synthetic peptide

<400> SEQUENCE: 380

Tyr Ser Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 381
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Isocap-Tyr

<400> SEQUENCE: 381

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35
```

<210> SEQ ID NO 382
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Isobuoco-Tyr

<400> SEQUENCE: 382

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35
```

<210> SEQ ID NO 383
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr(NMe)

<400> SEQUENCE: 383

```
Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Lys Pro Ser
            20                  25                  30

Ser Gly Ala Pro Pro Pro Ser
            35
```

<210> SEQ ID NO 384
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Tyr(NMe)

<400> SEQUENCE: 384

```
Tyr Ala Glu Gly Thr Phe Ile Ser Glu Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35
```

<210> SEQ ID NO 385

```
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanido-Tyr

<400> SEQUENCE: 385

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Ser
            20                  25                  30

Ser Gly Ala Pro Pro Pro Ser
        35

<210> SEQ ID NO 386
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Guanido-Tyr

<400> SEQUENCE: 386

Tyr Ser Asp Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Ser
            20                  25                  30

Ser Gly Ala Pro Pro Pro Ser
        35

<210> SEQ ID NO 387
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: MeSO2-Tyr

<400> SEQUENCE: 387

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 388
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Phenyl SO2-Tyr

<400> SEQUENCE: 388
```

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 389
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Benzyl SO2-Tyr

<400> SEQUENCE: 389

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
            35

<210> SEQ ID NO 390
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: 4-hydroxy Phen Prop-Ala

<400> SEQUENCE: 390

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
            35

<210> SEQ ID NO 391
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 391

Gly Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
            35                  40
```

```
<210> SEQ ID NO 392
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 392

Gly Tyr Ala Glu Gly Thr Phe Ile Ser Asp Tyr Ser Ile Ala Met Asp
1               5                   10                  15

Lys Ile Arg Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 393
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 393

Gly Tyr Ala Glu Gly Thr Phe Ile Ser Asp Tyr Ser Ile Ala Leu Asp
1               5                   10                  15

Lys Ile Arg Gln Gln Glu Phe Val Asn Trp Leu Leu Ala Gln His Pro
            20                  25                  30

Ser Ser Gly Ala Pro Pro Pro Ser
        35                  40

<210> SEQ ID NO 394
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine

<400> SEQUENCE: 394

Gly Tyr Ala Glu Gly Thr Phe Ile Ser Asp Tyr Ser Ile Ala Met Asp
1               5                   10                  15

Lys Ile Arg Gln Gln Glu Phe Val Asn Trp Leu Leu Ala Gln His Pro
            20                  25                  30

Ser Ser Gly Ala Pro Pro Pro Ser
        35                  40

<210> SEQ ID NO 395
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine
```

-continued

<400> SEQUENCE: 395

Gly Tyr Ala Pro Gly Thr Phe Ile Ser Asp Tyr Ser Ile Ala Leu Asp
1               5                   10                  15

Lys Ile Arg Gln Gln Glu Phe Val Asn Trp Leu Leu Ala Gln His Pro
            20                  25                  30

Ser Ser Gly Ala Pro Pro Ser
        35                  40

<210> SEQ ID NO 396
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (34)..(34)
<223> OTHER INFORMATION: Octylglycine

<400> SEQUENCE: 396

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 397
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (34)..(34)
<223> OTHER INFORMATION: Octylglycine

<400> SEQUENCE: 397

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 398
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (34)..(34)
<223> OTHER INFORMATION: Octylglycine

<400> SEQUENCE: 398

Tyr Ser Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 399
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (14)..(14)
<223> OTHER INFORMATION: Octylglycine

<400> SEQUENCE: 399

Tyr Ala Glu Gly Thr Phe Ile Ser Asp Tyr Ser Ile Ala Gly Asp Lys
1               5                   10                  15

Ile His Gln Gln Asp Phe Val Asn Trp Leu Leu Ala Gln Lys
            20                  25                  30

<210> SEQ ID NO 400
<211> LENGTH: 30
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (14)..(14)
<223> OTHER INFORMATION: Lys(Oct)

<400> SEQUENCE: 400

Tyr Ala Glu Gly Thr Phe Ile Ser Asp Tyr Ser Ile Ala Lys Asp Lys
1               5                   10                  15

Ile His Gln Gln Asp Phe Val Asn Trp Leu Leu Ala Gln Lys
            20                  25                  30

<210> SEQ ID NO 401
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (40)..(40)
<223> OTHER INFORMATION: Octylglycine

<400> SEQUENCE: 401

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser Gly
        35                  40

<210> SEQ ID NO 402
<211> LENGTH: 41
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(32)
<223> OTHER INFORMATION: bAla bAla

<400> SEQUENCE: 402

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Ala
            20                  25                  30

Pro Ser Ser Gly Ala Pro Pro Ser
        35                  40

<210> SEQ ID NO 403
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Octylglycine
<220> FEATURE:
<221> NAME/KEY: MOD_RES
<222> LOCATION: (32)..(33)
<223> OTHER INFORMATION: bAla bAla

<400> SEQUENCE: 403

Gly Tyr Ala Pro Gly Thr Phe Ile Ser Asp Tyr Ser Ile Ala Leu Asp
1               5                   10                  15

Lys Ile His Gln Gln Asp Phe Val Asn Trp Leu Leu Ala Gln Lys Ala
            20                  25                  30

Ala Pro Ser Ser Gly Ala Pro Pro Ser
        35                  40

<210> SEQ ID NO 404
<211> LENGTH: 38
<212> TYPE: PRT
<213> ORGANISM: Artificial Sequence
<220> FEATURE:
<223> OTHER INFORMATION: synthetic peptide

<400> SEQUENCE: 404

Tyr Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
        35

<210> SEQ ID NO 405
<211> LENGTH: 37
<212> TYPE: PRT
<213> ORGANISM: Artificial Sequence
<220> FEATURE:
<223> OTHER INFORMATION: synthetic peptide

<400> SEQUENCE: 405

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 406
<211> LENGTH: 37
<212> TYPE: PRT
<213> ORGANISM: Artificial Sequence
<220> FEATURE:
<223> OTHER INFORMATION: synthetic peptide

<400> SEQUENCE: 406

Tyr Ser Asp Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
            35

<210> SEQ ID NO 407
<211> LENGTH: 37
<212> TYPE: PRT
<213> ORGANISM: Artificial Sequence
<220> FEATURE:
<223> OTHER INFORMATION: synthetic peptide

<400> SEQUENCE: 407

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
            35

<210> SEQ ID NO 408
<211> LENGTH: 37
<212> TYPE: PRT
<213> ORGANISM: Artificial Sequence
<220> FEATURE:
<223> OTHER INFORMATION: synthetic peptide

<400> SEQUENCE: 408

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Thr Ser
            20                  25                  30

Pro Arg Pro Pro Ser
            35

<210> SEQ ID NO 409
<211> LENGTH: 38
<212> TYPE: PRT
<213> ORGANISM: Artificial Sequence
<220> FEATURE:
<223> OTHER INFORMATION: synthetic peptide

<400> SEQUENCE: 409

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Thr Ser
            20                  25                  30

Pro Arg Pro Pro Ser Ser
            35

<210> SEQ ID NO 410
<211> LENGTH: 32
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (31)..(31)
<223> OTHER INFORMATION: Ado
<220> FEATURE:
<221> NAME/KEY: MOD_RES

```
<222> LOCATION: (32)..(32)
<223> OTHER INFORMATION: Aun

<400> SEQUENCE: 410

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Xaa
            20                  25                  30

<210> SEQ ID NO 411
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (37)..(37)
<223> OTHER INFORMATION: Lys(biotin)

<400> SEQUENCE: 411

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 412
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MOD_RES
<222> LOCATION: (16)..(16)
<223> OTHER INFORMATION: Lys(biotin)

<400> SEQUENCE: 412

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 413
<211> LENGTH: 30
<212> TYPE: PRT
<213> ORGANISM: Sus scrofa

<400> SEQUENCE: 413

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys
            20                  25                  30

<210> SEQ ID NO 414
<211> LENGTH: 39
<212> TYPE: PRT
<213> ORGANISM: Homo sapiens

<400> SEQUENCE: 414

Tyr Ala Glu Gly Thr Phe Ile Ser Asp Tyr Ser Ile Ala Met Asp Lys
```

```
                1               5                  10                  15
Ile His Gln Gln Asp Phe Val Asn Trp Leu Leu Ala Gln Lys Pro Ser
            20                  25                  30

Ser Gly Ala Pro Pro Ser
            35

<210> SEQ ID NO 415
<211> LENGTH: 39
<212> TYPE: PRT
<213> ORGANISM: Homo sapiens

<400> SEQUENCE: 415

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 416
<211> LENGTH: 39
<212> TYPE: PRT
<213> ORGANISM: Homo sapiens

<400> SEQUENCE: 416

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 417
<211> LENGTH: 39
<212> TYPE: PRT
<213> ORGANISM: Homo sapiens

<400> SEQUENCE: 417

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 418
<211> LENGTH: 39
<212> TYPE: PRT
<213> ORGANISM: Homo sapiens

<400> SEQUENCE: 418

Tyr Ala Pro Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
            35

<210> SEQ ID NO 419
<211> LENGTH: 39
<212> TYPE: PRT
```

<213> ORGANISM: Homo sapiens

<400> SEQUENCE: 419

Tyr Ala Glu Gly Thr Phe Ile Ser Asp Tyr Ser Ile Ala Met Asp Lys
1               5                   10                  15

Ile His Gln Gln Asp Phe Val Asn Trp Leu Lys Asn Gly Gly Pro Ser
            20                  25                  30

Ser Gly Ala Pro Pro Ser
        35

<210> SEQ ID NO 420
<211> LENGTH: 42
<212> TYPE: PRT
<213> ORGANISM: Bos taurus

<400> SEQUENCE: 420

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Gly Lys
            20                  25                  30

Lys Ser Asp Trp Ile His Asn Ile Thr Gln
        35                  40

<210> SEQ ID NO 421
<211> LENGTH: 7
<212> TYPE: PRT
<213> ORGANISM: Artificial
<220> FEATURE:
<223> OTHER INFORMATION: synthetic 421

<400> SEQUENCE: 421

Pro Lys Lys Ile Arg Tyr Ser
1               5

<210> SEQ ID NO 422
<211> LENGTH: 7
<212> TYPE: PRT
<213> ORGANISM: Artificial
<220> FEATURE:
<223> OTHER INFORMATION: synthetic 422

<400> SEQUENCE: 422

Pro Ala Lys Ile Arg Tyr Ser
1               5

<210> SEQ ID NO 423
<211> LENGTH: 38
<212> TYPE: PRT
<213> ORGANISM: mus musculus
<220> FEATURE:
<221> NAME/KEY: MOD_RES
<222> LOCATION: (38)..(38)
<223> OTHER INFORMATION: AMIDATION

<400> SEQUENCE: 423

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 424
<211> LENGTH: 24

```
<212> TYPE: PRT
<213> ORGANISM: Homo sapiens

<400> SEQUENCE: 424

Trp Ser Pro Gly Ala Arg Asn Gln Gly Gly Gly Ala Arg Ala Leu Leu
1               5                   10                  15

Leu Leu Leu Ala Glu Arg Phe Pro
            20

<210> SEQ ID NO 425
<211> LENGTH: 18
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: AMIDATION

<400> SEQUENCE: 425

Thr Gln Ser Gln Arg Glu Arg Ala Glu Gln Asn Arg Ile Ile Phe Asp
1               5                   10                  15

Ser Val

<210> SEQ ID NO 426
<211> LENGTH: 40
<212> TYPE: PRT
<213> ORGANISM: Homo sapiens
<220> FEATURE:
<221> NAME/KEY: MOD_RES
<222> LOCATION: (40)..(40)
<223> OTHER INFORMATION: AMIDATION

<400> SEQUENCE: 426

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 427
<211> LENGTH: 20
<212> TYPE: PRT
<213> ORGANISM: Homo sapiens

<400> SEQUENCE: 427

Ser Phe His Tyr Leu Arg Ser Arg Asp Ala Ser Ser Gly Glu Glu Glu
1               5                   10                  15

Glu Gly Lys Glu
            20

<210> SEQ ID NO 428
<211> LENGTH: 13
<212> TYPE: PRT
<213> ORGANISM: Homo sapiens

<400> SEQUENCE: 428

Ala Gln Ala Ala Ala Asn Ala His Leu Met Ala Gln Ile
1               5                   10

<210> SEQ ID NO 429
<211> LENGTH: 21
<212> TYPE: PRT
<213> ORGANISM: Homo sapiens
```

```
<400> SEQUENCE: 429

Asp Asn Pro Ser Leu Ser Ile Asp Leu Thr Phe His Leu Leu Arg Thr
 1               5                  10                  15

Leu Leu Glu Leu Ala
            20

<210> SEQ ID NO 430
<211> LENGTH: 26
<212> TYPE: PRT
<213> ORGANISM: Homo sapiens

<400> SEQUENCE: 430

Thr Lys Phe Thr Leu Ser Leu Asp Val Pro Thr Asn Ile Met Asn Leu
 1               5                  10                  15

Leu Phe Asn Ile Ala Lys Ala Lys Asn Leu
            20                  25

<210> SEQ ID NO 431
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 431

Phe Thr Leu Ser Leu Asp Val Pro Thr Asn Ile Met Asn Leu Leu Phe
 1               5                  10                  15

Asn Ile Ala Lys Ala Lys Asn Leu Arg Ala Gln Ala Ala Ala Asn Ala
            20                  25                  30

His Leu Met Ala Gln Ile
            35

<210> SEQ ID NO 432
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 432

Phe Leu Phe His Tyr Ser Lys Thr Gln Lys Leu Gly Lys Ser Asn Val
 1               5                  10                  15

Val Glu Glu Leu Gln Ser Pro Phe Ala Ser Gln Ser Arg Gly Tyr Phe
            20                  25                  30

Leu Phe Arg Pro Arg Asn
            35

<210> SEQ ID NO 433
<211> LENGTH: 30
<212> TYPE: PRT
<213> ORGANISM: Artificial
<220> FEATURE:
<223> OTHER INFORMATION: synthetic

<400> SEQUENCE: 433

Tyr Ala Glu Gly Thr Phe Ile Ser Asp Tyr Ser Ile Ala Leu Asp Lys
 1               5                  10                  15

Ile Ala Gln Gln Glu Phe Val Asn Trp Leu Leu Ala Gln Arg
            20                  25                  30
```

```
<210> SEQ ID NO 434
<211> LENGTH: 30
<212> TYPE: PRT
<213> ORGANISM: Artificial
<220> FEATURE:
<223> OTHER INFORMATION: synthetiC

<400> SEQUENCE: 434

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Arg
            20                  25                  30

<210> SEQ ID NO 435
<211> LENGTH: 30
<212> TYPE: PRT
<213> ORGANISM: Artificial
<220> FEATURE:
<223> OTHER INFORMATION: synthetic

<400> SEQUENCE: 435

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Arg
            20                  25                  30

<210> SEQ ID NO 436
<211> LENGTH: 30
<212> TYPE: PRT
<213> ORGANISM: Artificial
<220> FEATURE:
<223> OTHER INFORMATION: synthetic

<400> SEQUENCE: 436

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln His
            20                  25                  30

<210> SEQ ID NO 437
<211> LENGTH: 30
<212> TYPE: PRT
<213> ORGANISM: Artificial
<220> FEATURE:
<223> OTHER INFORMATION: synthetic

<400> SEQUENCE: 437

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His
            20                  25                  30

<210> SEQ ID NO 438
<211> LENGTH: 30
<212> TYPE: PRT
<213> ORGANISM: Artificial
<220> FEATURE:
<223> OTHER INFORMATION: synthetic

<400> SEQUENCE: 438

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln His
            20                  25                  30
```

```
<210> SEQ ID NO 439
<211> LENGTH: 30
<212> TYPE: PRT
<213> ORGANISM: Artificial
<220> FEATURE:
<223> OTHER INFORMATION: synthetic

<400> SEQUENCE: 439

Tyr Ala Glu Gly Thr Phe Ile Ser Asp Tyr Ser Ile Ala Met Asp Lys
1               5                   10                  15

Ile His Gln Val Lys Phe Val Asn Trp Leu Leu Ala Gln Lys
            20                  25                  30

<210> SEQ ID NO 440
<211> LENGTH: 30
<212> TYPE: PRT
<213> ORGANISM: Artificial
<220> FEATURE:
<223> OTHER INFORMATION: synthetic

<400> SEQUENCE: 440

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys
            20                  25                  30

<210> SEQ ID NO 441
<211> LENGTH: 30
<212> TYPE: PRT
<213> ORGANISM: Artificial
<220> FEATURE:
<223> OTHER INFORMATION: synthetic

<400> SEQUENCE: 441

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Lys
            20                  25                  30

<210> SEQ ID NO 442
<211> LENGTH: 30
<212> TYPE: PRT
<213> ORGANISM: Artificial
<220> FEATURE:
<223> OTHER INFORMATION: synthetic

<400> SEQUENCE: 442

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys
            20                  25                  30

<210> SEQ ID NO 443
<211> LENGTH: 30
<212> TYPE: PRT
<213> ORGANISM: Artificial
<220> FEATURE:
<223> OTHER INFORMATION: syntheitc

<400> SEQUENCE: 443

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His
            20                  25                  30
```

```
<210> SEQ ID NO 444
<211> LENGTH: 30
<212> TYPE: PRT
<213> ORGANISM: Artificial
<220> FEATURE:
<223> OTHER INFORMATION: synthetic

<400> SEQUENCE: 444

Tyr Ala Glu Gly Thr Phe Thr Ala Asp Tyr Ser Lys Ala Leu Asp Lys
1               5                   10                  15

Ile His Gln Gln Asp Phe Val Asn Trp Leu Leu Ala Gln Lys
            20                  25                  30

<210> SEQ ID NO 445
<211> LENGTH: 30
<212> TYPE: PRT
<213> ORGANISM: Artificial
<220> FEATURE:
<223> OTHER INFORMATION: synthetic

<400> SEQUENCE: 445

Tyr Ala Glu Gly Thr Phe Thr Ser Asp Tyr Ser Lys Ala Leu Asp Lys
1               5                   10                  15

Ile His Gln Gln Asp Phe Val Asn Trp Leu Leu Ala Gln Lys
            20                  25                  30

<210> SEQ ID NO 446
<211> LENGTH: 30
<212> TYPE: PRT
<213> ORGANISM: Artificial
<220> FEATURE:
<223> OTHER INFORMATION: synthetic

<400> SEQUENCE: 446

Tyr Ala Glu Gly Thr Phe Ile Ser Asp Tyr Ser Lys Ala Met Asp Lys
1               5                   10                  15

Ile Arg Gln Gln Glu Phe Val Asn Trp Leu Leu Ala Gln Lys
            20                  25                  30

<210> SEQ ID NO 447
<211> LENGTH: 30
<212> TYPE: PRT
<213> ORGANISM: Artificial
<220> FEATURE:
<223> OTHER INFORMATION: synthetic

<400> SEQUENCE: 447

Tyr Ala Glu Gly Thr Phe Ile Ser Asp Tyr Ser Ile Ala Leu Glu Lys
1               5                   10                  15

Ile Arg Gln Gln Lys Phe Val Asn Trp Leu Leu Ala Gln Lys
            20                  25                  30

<210> SEQ ID NO 448
<211> LENGTH: 30
<212> TYPE: PRT
<213> ORGANISM: Artificial
<220> FEATURE:
<223> OTHER INFORMATION: synthetic

<400> SEQUENCE: 448

Tyr Ala Glu Gly Thr Phe Ile Ser Asp Tyr Ser Ile Ala Leu Asp Lys
1               5                   10                  15

Ile Arg Gln Gln Asp Phe Val Glu Trp Leu Leu Ala Gln Lys
            20                  25                  30
```

```
<210> SEQ ID NO 449
<211> LENGTH: 30
<212> TYPE: PRT
<213> ORGANISM: Artificial
<220> FEATURE:
<223> OTHER INFORMATION: synthetic

<400> SEQUENCE: 449

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys
            20                  25                  30

<210> SEQ ID NO 450
<211> LENGTH: 30
<212> TYPE: PRT
<213> ORGANISM: Artificial
<220> FEATURE:
<223> OTHER INFORMATION: synthetic

<400> SEQUENCE: 450

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys
            20                  25                  30

<210> SEQ ID NO 451
<211> LENGTH: 30
<212> TYPE: PRT
<213> ORGANISM: Artificial
<220> FEATURE:
<223> OTHER INFORMATION: synthetic

<400> SEQUENCE: 451

Tyr Ala Glu Gly Thr Phe Ile Ser Asp Tyr Ser Ile Ala Met Asp Lys
1               5                   10                  15

Ile His Gln Gln Leu Phe Ile Glu Trp Leu Lys Asn Gly Gly
            20                  25                  30

<210> SEQ ID NO 452
<211> LENGTH: 30
<212> TYPE: PRT
<213> ORGANISM: Artificial
<220> FEATURE:
<223> OTHER INFORMATION: synthetic

<400> SEQUENCE: 452

Tyr Ala Glu Gly Thr Phe Ile Ser Asp Tyr Ser Ile Ala Met Asp Lys
1               5                   10                  15

Ile Arg Gln Gln Glu Phe Val Asn Trp Leu Leu Ala Gln Lys
            20                  25                  30

<210> SEQ ID NO 453
<211> LENGTH: 30
<212> TYPE: PRT
<213> ORGANISM: Artificial
<220> FEATURE:
<223> OTHER INFORMATION: synthetic

<400> SEQUENCE: 453

Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys
            20                  25                  30
```

```
<210> SEQ ID NO 454
<211> LENGTH: 34
<212> TYPE: PRT
<213> ORGANISM: Artificial
<220> FEATURE:
<223> OTHER INFORMATION: synthetic

<400> SEQUENCE: 454

Ile Lys Pro Glu His Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 455
<211> LENGTH: 39
<212> TYPE: PRT
<213> ORGANISM: Artificial
<220> FEATURE:
<223> OTHER INFORMATION: synthetic

<400> SEQUENCE: 455

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 456
<211> LENGTH: 28
<212> TYPE: PRT
<213> ORGANISM: Homo sapiens

<400> SEQUENCE: 456

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 457
<211> LENGTH: 66
<212> TYPE: PRT
<213> ORGANISM: Artificial
<220> FEATURE:
<223> OTHER INFORMATION: SYNTHETIc
<220> FEATURE:
<221> NAME/KEY: MISC_FEATURE
<222> LOCATION: (31)..(31)
<223> OTHER INFORMATION: Linker

<400> SEQUENCE: 457

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Lys
            20                  25                  30

Cys Asn Thr Ala Asp Thr His Arg Cys Val Leu Gly Arg Leu Ser Gln
        35                  40                  45

Glu Leu His Arg Leu Gln Thr Tyr Pro Arg Thr Asn Thr Gly Ser Asn
    50                  55                  60

Thr Tyr
65
```

```
<210> SEQ ID NO 458
<211> LENGTH: 63
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Linker
<220> FEATURE:
<221> NAME/KEY: MISC_FEATURE
<222> LOCATION: (37)..(37)
<223> OTHER INFORMATION: dAh

<400> SEQUENCE: 458

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Xaa Lys
            20                  25                  30

Cys Asn Thr Ala Xaa Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 459
<211> LENGTH: 69
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is bAla bAla

<400> SEQUENCE: 459

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Phe
            20                  25                  30

Leu Phe His Tyr Ser Lys Thr Gln Lys Leu Gly Lys Ser Asn Val Val
        35                  40                  45

Glu Glu Leu Gln Ser Pro Phe Ala Ser Gln Ser Arg Gly Tyr Phe Leu
    50                  55                  60

Phe Arg Pro Arg Asn
65

<210> SEQ ID NO 460
<211> LENGTH: 56
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: beta-Ala-beta-Ala

<400> SEQUENCE: 460

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Phe
            20                  25                  30

Arg Val Asp Glu Glu Phe Gln Ser Pro Phe Ala Ser Gln Ser Arg Gly
```

```
Tyr Phe Leu Phe Arg Pro Arg Asn
    50                  55

<210> SEQ ID NO 461
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: beta-Ala-beta-Ala

<400> SEQUENCE: 461

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Gly
            20                  25                  30

Tyr Phe Leu Phe Arg Pro Arg Asn
            35                  40

<210> SEQ ID NO 462
<211> LENGTH: 63
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: beta-Ala-beta-Ala

<400> SEQUENCE: 462

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Ser
            20                  25                  30

Pro Lys Met Val Gln Gly Ser Gly Cys Phe Gly Arg Lys Met Asp Arg
            35                  40                  45

Ile Ser Ser Ser Ser Gly Leu Gly Cys Lys Val Leu Arg Arg His
    50                  55                  60

<210> SEQ ID NO 463
<211> LENGTH: 63
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: beta-Ala-beta-Ala

<400> SEQUENCE: 463

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Ser
            20                  25                  30

Pro Lys Met Val Gln Gly Ser Gly Cys Phe Gly Arg Lys Met Asp Arg
            35                  40                  45

Ile Ser Ser Ser Ser Gly Leu Gly Cys Lys Val Leu Arg Arg His
    50                  55                  60
```

```
<210> SEQ ID NO 464
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: beta-ALa

<400> SEQUENCE: 464

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Xaa Pro
            20                  25                  30

Ser Ser Gly Ala Pro Pro Ser
        35                  40

<210> SEQ ID NO 465
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is any DPPIV resistant modification or
      substitution
<220> FEATURE:
<221> NAME/KEY: MISC_FEATURE
<222> LOCATION: (2)..(2)
<223> OTHER INFORMATION: Xaa is any DPPIV resistant modification or
      substitution including dAla
<220> FEATURE:
<221> NAME/KEY: MISC_FEATURE
<222> LOCATION: (3)..(3)
<223> OTHER INFORMATION: Xaa is any DPPIV resistant modification or
      substitution
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
<223> OTHER INFORMATION: Xaa is Phe or Ala
<220> FEATURE:
<221> NAME/KEY: MISC_FEATURE
<222> LOCATION: (7)..(7)
<223> OTHER INFORMATION: Xaa is Ile or Ala
<220> FEATURE:
<221> NAME/KEY: MISC_FEATURE
<222> LOCATION: (8)..(8)
<223> OTHER INFORMATION: Xaa is Ser or Ala
<220> FEATURE:
<221> NAME/KEY: MISC_FEATURE
<222> LOCATION: (9)..(9)
<223> OTHER INFORMATION: Xaa is Asp or Ala
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Ser or Ala
<220> FEATURE:
<221> NAME/KEY: MISC_FEATURE
<222> LOCATION: (12)..(12)
```

```
<223> OTHER INFORMATION: Xaa is Ile, Ala, Ser, or Lys
<220> FEATURE:
<221> NAME/KEY: MISC_FEATURE
<222> LOCATION: (13)..(13)
<223> OTHER INFORMATION: Xaa is Ala, Tyr, Gln, or Asp
<220> FEATURE:
<221> NAME/KEY: MISC_FEATURE
<222> LOCATION: (14)..(14)
<223> OTHER INFORMATION: Xaa is Met, Ala, or Leu

<400> SEQUENCE: 465

Xaa Xaa Xaa Xaa Xaa Xaa Xaa Xaa Xaa Xaa Xaa Xaa Xaa Xaa
1               5                   10

<210> SEQ ID NO 466
<211> LENGTH: 4
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is any naturally-occurring amino acid,
      non-proteinogenic amino acid, D-amino acid or is absent
<220> FEATURE:
<221> NAME/KEY: MISC_FEATURE
<222> LOCATION: (2)..(2)
<223> OTHER INFORMATION: Xaa is any naturally-occurring amino acid,
      non-proteinogenic amino acid, D-amino acid or is absent
<220> FEATURE:
<221> NAME/KEY: MISC_FEATURE
<222> LOCATION: (3)..(3)
<223> OTHER INFORMATION: Xaa is any naturally-occurring amino acid,
      non-proteinogenic amino acid, D-amino acid or is absent
<220> FEATURE:
<221> NAME/KEY: MISC_FEATURE
<222> LOCATION: (4)..(4)
<223> OTHER INFORMATION: Xaa is any naturally-occurring amino acid,
      non-proteinogenic amino acid, D-amino acid or is absent

<400> SEQUENCE: 466

Xaa Xaa Xaa Xaa
1

<210> SEQ ID NO 467
<211> LENGTH: 12
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Q or a conservative amino acid
      substitution thereof
<220> FEATURE:
<221> NAME/KEY: MISC_FEATURE
<222> LOCATION: (2)..(2)
<223> OTHER INFORMATION: Xaa is Q or a conservative amino acid
      substitution thereof
<220> FEATURE:
<221> NAME/KEY: MISC_FEATURE
<222> LOCATION: (3)..(3)
<223> OTHER INFORMATION: Xaa is D or a conservative amino acid
      substitution thereof
<220> FEATURE:
<221> NAME/KEY: MISC_FEATURE
<222> LOCATION: (4)..(4)
<223> OTHER INFORMATION: Xaa is F, Y or a conservative amino acid
      substitution thereof
<220> FEATURE:
<221> NAME/KEY: MISC_FEATURE
<222> LOCATION: (5)..(5)
<223> OTHER INFORMATION: Xaa is V, I, A or a conservative amino acid
      substitution thereof
```

```
<220> FEATURE:
<221> NAME/KEY: MISC_FEATURE
<222> LOCATION: (6)..(6)
<223> OTHER INFORMATION: Xaa is N, Q or a conservative amino acid
      substitution thereof
<220> FEATURE:
<221> NAME/KEY: MISC_FEATURE
<222> LOCATION: (7)..(7)
<223> OTHER INFORMATION: Xaa is W, F, Y, napthylalanine or a
      conservative amino acid substitution thereof
<220> FEATURE:
<221> NAME/KEY: MISC_FEATURE
<222> LOCATION: (8)..(8)
<223> OTHER INFORMATION: Xaa is L, A or a conservative amino acid
      substitution thereof
<220> FEATURE:
<221> NAME/KEY: MISC_FEATURE
<222> LOCATION: (9)..(9)
<223> OTHER INFORMATION: Xaa is L, K, R, V, A, I or a conservative amino
      acid substitution thereof or is absent
<220> FEATURE:
<221> NAME/KEY: MISC_FEATURE
<222> LOCATION: (10)..(10)
<223> OTHER INFORMATION: Xaa is A, N, D, K, R, E or a conservative amino
      acid substitution thereof or is absent
<220> FEATURE:
<221> NAME/KEY: MISC_FEATURE
<222> LOCATION: (11)..(11)
<223> OTHER INFORMATION: Xaa is Q, G or a conservative amino acid
      substitution thereof or is absent
<220> FEATURE:
<221> NAME/KEY: MISC_FEATURE
<222> LOCATION: (12)..(12)
<223> OTHER INFORMATION: Xaa is K, G, R, G, P, R or a conservative amino
      acid substitution thereof or is absent

<400> SEQUENCE: 467

Xaa Xaa Xaa Xaa Xaa Xaa Xaa Xaa Xaa Xaa Xaa Xaa
1               5                   10

<210> SEQ ID NO 468
<211> LENGTH: 9
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Pro, homoproline, 3Hyp, 4Hyp,
      thioproline, N-alkylglycine, N-alkylpentylglycine, N-alkylalanine,
      Gly or Ser
<220> FEATURE:
<221> NAME/KEY: MISC_FEATURE
<222> LOCATION: (2)..(2)
<223> OTHER INFORMATION: Xaa is Ser, Pro, His, homoproline, 3Hyp, 4Hyp,
      thioproline, N-alkylglycine, N-alkylpentylglycine or
      N-alkylalanine
<220> FEATURE:
<221> NAME/KEY: MISC_FEATURE
<222> LOCATION: (3)..(3)
<223> OTHER INFORMATION: Xaa is Ser, Arg, Thr, Trp, Lys
<220> FEATURE:
<221> NAME/KEY: MISC_FEATURE
<222> LOCATION: (4)..(4)
<223> OTHER INFORMATION: Xaa is Gly or Ser
<220> FEATURE:
<221> NAME/KEY: MISC_FEATURE
<222> LOCATION: (5)..(5)
<223> OTHER INFORMATION: Xaa is Ala, Arg, Asp, Glu, Lys, Gly
<220> FEATURE:
<221> NAME/KEY: MISC_FEATURE
<222> LOCATION: (6)..(6)
<223> OTHER INFORMATION: Xaa is Pro, homoproline, 3Hyp, 4Hyp,
      thioproline, N-alkylglycine, N-alkylpentylglycine or
      N-alkylalanine, A, or absent
<220> FEATURE:
<221> NAME/KEY: MISC_FEATURE
```

```
<222> LOCATION: (7)..(7)
<223> OTHER INFORMATION: Xaa is Pro, homoproline, 3Hyp, 4Hyp,
      thioproline, N-alkylglycine, N-alkylpentylglycine or
      N-alkylalanine, A, or absent
<220> FEATURE:
<221> NAME/KEY: MISC_FEATURE
<222> LOCATION: (8)..(8)
<223> OTHER INFORMATION: Xaa is Pro, homoproline, 3Hyp, 4Hyp,
      thioproline, N-alkylglycine, N-alkylpentylglycine or
      N-alkylalanine, Ala, Arg, Lys, His, or is absent
<220> FEATURE:
<221> NAME/KEY: MISC_FEATURE
<222> LOCATION: (9)..(9)
<223> OTHER INFORMATION: Xaa is Ser, Thr, Tyr, Leu, Ala, Lys, His, Pro,
      Lys, Arg, Gly, or absent

<400> SEQUENCE: 468

Xaa Xaa Xaa Xaa Xaa Xaa Xaa Xaa Xaa
1               5

<210> SEQ ID NO 469
<211> LENGTH: 39
<212> TYPE: PRT
<213> ORGANISM: Artificial
<220> FEATURE:
<223> OTHER INFORMATION: synthetic

<400> SEQUENCE: 469

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 470
<211> LENGTH: 39
<212> TYPE: PRT
<213> ORGANISM: Artificial
<220> FEATURE:
<223> OTHER INFORMATION: synthetic

<400> SEQUENCE: 470

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Arg Pro Ser
            20                  25                  30

Ser Gly Ala Pro Pro Pro Ser
        35

<210> SEQ ID NO 471
<211> LENGTH: 39
<212> TYPE: PRT
<213> ORGANISM: Artificial
<220> FEATURE:
<223> OTHER INFORMATION: synthetic

<400> SEQUENCE: 471

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 472
```

```
<211> LENGTH: 39
<212> TYPE: PRT
<213> ORGANISM: Artificial
<220> FEATURE:
<223> OTHER INFORMATION: synthetic

<400> SEQUENCE: 472

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 473
<211> LENGTH: 39
<212> TYPE: PRT
<213> ORGANISM: Artificial
<220> FEATURE:
<223> OTHER INFORMATION: synthetic

<400> SEQUENCE: 473

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 474
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is absent
<220> FEATURE:
<221> NAME/KEY: MISC_FEATURE
<222> LOCATION: (2)..(2)
<223> OTHER INFORMATION: Xaa is absent
<220> FEATURE:
<221> NAME/KEY: MISC_FEATURE
<222> LOCATION: (3)..(3)
<223> OTHER INFORMATION: Xaa is Glu, D-Glu, L-Pro, (N-Me)Glu, Pro,
      D-amino acid, Lys, Ser, 4-amino butyric amino acid, Aib, D-Ala,
      Sarcosine, Pro, or an N-methylated amino acid
<220> FEATURE:
<221> NAME/KEY: MISC_FEATURE
<222> LOCATION: (4)..(4)
<223> OTHER INFORMATION: Xaa is Gly or Ala
<220> FEATURE:
<221> NAME/KEY: MISC_FEATURE
<222> LOCATION: (5)..(5)
<223> OTHER INFORMATION: Xaa is Thr or Ser
<220> FEATURE:
<221> NAME/KEY: MISC_FEATURE
<222> LOCATION: (6)..(6)
<223> OTHER INFORMATION: Xaa is Phe or Ala
<220> FEATURE:
<221> NAME/KEY: MISC_FEATURE
<222> LOCATION: (7)..(7)
<223> OTHER INFORMATION: Xaa is Ile or Ala
<220> FEATURE:
<221> NAME/KEY: MISC_FEATURE
<222> LOCATION: (8)..(8)
<223> OTHER INFORMATION: Xaa is Ser or Ala
<220> FEATURE:
<221> NAME/KEY: MISC_FEATURE
<222> LOCATION: (9)..(9)
```

```
<223> OTHER INFORMATION: Xaa is Asp or Ala
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Ser or Ala
<220> FEATURE:
<221> NAME/KEY: MISC_FEATURE
<222> LOCATION: (12)..(12)
<223> OTHER INFORMATION: Xaa is Ile, Ala, Ser, or Lys
<220> FEATURE:
<221> NAME/KEY: MISC_FEATURE
<222> LOCATION: (13)..(13)
<223> OTHER INFORMATION: Xaa is Ala, Tyr, Gln or Asp
<220> FEATURE:
<221> NAME/KEY: MISC_FEATURE
<222> LOCATION: (14)..(14)
<223> OTHER INFORMATION: Xaa is Met, Ala, or Leu

<400> SEQUENCE: 474

Xaa Xaa Xaa Xaa Xaa Xaa Xaa Xaa Xaa Xaa Xaa Xaa Xaa Xaa
1               5                   10

<210> SEQ ID NO 475
<211> LENGTH: 39
<212> TYPE: PRT
<213> ORGANISM: Artificial
<220> FEATURE:
<223> OTHER INFORMATION: synthetic

<400> SEQUENCE: 475

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 476
<211> LENGTH: 51
<212> TYPE: PRT
<213> ORGANISM: Artificial
<220> FEATURE:
<223> OTHER INFORMATION: synthetic

<400> SEQUENCE: 476

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln Pro Ser Ser Gly Ala Pro
        35                  40                  45

Pro Pro Ser
    50

<210> SEQ ID NO 477
<211> LENGTH: 15
<212> TYPE: PRT
<213> ORGANISM: Artificial
<220> FEATURE:
<223> OTHER INFORMATION: synthetic

<400> SEQUENCE: 477

Tyr Ala Glu Gly Thr Phe Ile Ser Asp Tyr Ser Ile Ala Met Asp
1               5                   10                  15
```

<210> SEQ ID NO 478
<211> LENGTH: 12
<212> TYPE: PRT
<213> ORGANISM: Artificial
<220> FEATURE:
<223> OTHER INFORMATION: synthetic

<400> SEQUENCE: 478

Gly Thr Phe Ile Ser Asp Tyr Ser Ile Ala Met Asp
1               5                   10

<210> SEQ ID NO 479
<211> LENGTH: 42
<212> TYPE: PRT
<213> ORGANISM: Artificial
<220> FEATURE:
<223> OTHER INFORMATION: synthetic

<400> SEQUENCE: 479

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 480
<211> LENGTH: 63
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is a minPEG 8-mer linker

<400> SEQUENCE: 480

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

Cys Asn Thr Ala Thr Cys Val Leu Gly Arg Leu Ser Gln Glu Leu His
        35                  40                  45

Arg Leu Gln Thr Tyr Pro Arg Thr Asn Thr Gly Ser Asn Thr Tyr
    50                  55                  60

<210> SEQ ID NO 481
<211> LENGTH: 63
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 481

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

Cys Asn Thr Ala Thr Cys Val Leu Gly Arg Leu Ser Gln Glu Leu His

-continued

```
                35                  40                  45
Arg Leu Gln Thr Tyr Pro Arg Thr Asn Thr Gly Ser Asn Thr Tyr
    50                  55                  60

<210> SEQ ID NO 482
<211> LENGTH: 65
<212> TYPE: PRT
<213> ORGANISM: Artificial
<220> FEATURE:
<223> OTHER INFORMATION: synthetic

<400> SEQUENCE: 482

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Gly
            20                  25                  30

Gly Lys Cys Asn Thr Ala Thr Cys Val Leu Gly Arg Leu Ser Gln Glu
        35                  40                  45

Leu His Arg Leu Gln Thr Tyr Pro Arg Thr Asn Thr Gly Ser Asn Thr
    50                  55                  60

Tyr
65

<210> SEQ ID NO 483
<211> LENGTH: 32
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 483

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Lys
            20                  25                  30

<210> SEQ ID NO 484
<211> LENGTH: 31
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (29)..(29)
<223> OTHER INFORMATION: Xaa is beta-Ala-beta-Ala

<400> SEQUENCE: 484

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Lys Cys
            20                  25                  30

<210> SEQ ID NO 485
<211> LENGTH: 32
<212> TYPE: PRT
<213> ORGANISM: rat

<400> SEQUENCE: 485

Asn Ser Lys Met Ala His Ser Ser Ser Cys Phe Gly Gln Lys Ile Asp
1               5                   10                  15
```

```
Arg Ile Gly Ala Val Ser Arg Leu Gly Cys Asp Gly Leu Arg Leu Phe
            20                  25                  30

<210> SEQ ID NO 486
<211> LENGTH: 32
<212> TYPE: PRT
<213> ORGANISM: Homo sapiens

<400> SEQUENCE: 486

Ser Pro Lys Met Val Gln Gly Ser Gly Cys Phe Gly Arg Lys Met Asp
1               5                   10                  15

Arg Ile Ser Ser Ser Gly Leu Gly Cys Lys Val Leu Arg Arg His
            20                  25                  30

<210> SEQ ID NO 487
<211> LENGTH: 22
<212> TYPE: PRT
<213> ORGANISM: porcine

<400> SEQUENCE: 487

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 488
<211> LENGTH: 8
<212> TYPE: PRT
<213> ORGANISM: porcine
<220> FEATURE:
<221> NAME/KEY: MOD_RES
<222> LOCATION: (8)..(8)
<223> OTHER INFORMATION: AMIDATION

<400> SEQUENCE: 488

Tyr Phe Leu Phe Arg Pro Arg Asn
1               5

<210> SEQ ID NO 489
<211> LENGTH: 23
<212> TYPE: PRT
<213> ORGANISM: rat
<220> FEATURE:
<221> NAME/KEY: MOD_RES
<222> LOCATION: (23)..(23)
<223> OTHER INFORMATION: AMIDATION

<400> SEQUENCE: 489

Tyr Lys Val Asn Glu Tyr Gln Gly Pro Val Ala Pro Ser Gly Gly Phe
1               5                   10                  15

Phe Leu Phe Arg Pro Arg Asn
            20

<210> SEQ ID NO 490
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 490

Gly Tyr Phe Leu Phe Arg Pro Arg Asn
1               5
```

```
<210> SEQ ID NO 491
<211> LENGTH: 25
<212> TYPE: PRT
<213> ORGANISM: Homo sapiens
<220> FEATURE:
<221> NAME/KEY: MOD_RES
<222> LOCATION: (25)..(25)
<223> OTHER INFORMATION: AMIDATION

<400> SEQUENCE: 491

Phe Arg Val Asp Glu Glu Phe Gln Ser Pro Phe Ala Ser Gln Ser Arg
1               5                   10                  15

Gly Tyr Phe Leu Phe Arg Pro Arg Asn
            20                  25

<210> SEQ ID NO 492
<211> LENGTH: 33
<212> TYPE: PRT
<213> ORGANISM: Homo sapiens

<400> SEQUENCE: 492

Ile Leu Gln Arg Gly Ser Gly Thr Ala Ala Val Asp Phe Thr Lys Lys
1               5                   10                  15

Asp His Thr Ala Thr Trp Gly Arg Pro Phe Phe Leu Phe Arg Pro Arg
            20                  25                  30

Asn

<210> SEQ ID NO 493
<211> LENGTH: 36
<212> TYPE: PRT
<213> ORGANISM: Homo sapiens

<400> SEQUENCE: 493

Leu Val Gln Pro Arg Gly Ser Arg Asn Gly Pro Gly Pro Trp Gln Gly
1               5                   10                  15

Gly Arg Arg Lys Phe Arg Arg Gln Arg Pro Arg Leu Ser His Lys Gly
            20                  25                  30

Pro Met Pro Phe
        35

<210> SEQ ID NO 494
<211> LENGTH: 14
<212> TYPE: PRT
<213> ORGANISM: Homo sapiens

<400> SEQUENCE: 494

Pro Glu Arg Pro Arg Leu Ser His Lys Gly Pro Met Pro Phe
1               5                   10

<210> SEQ ID NO 495
<211> LENGTH: 31
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: AMIDATION

<400> SEQUENCE: 495

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30
```

```
<210> SEQ ID NO 496
<211> LENGTH: 20
<212> TYPE: PRT
<213> ORGANISM: Homo sapiens
<220> FEATURE:
<221> NAME/KEY: MOD_RES
<222> LOCATION: (20)..(20)
<223> OTHER INFORMATION: AMIDATION

<400> SEQUENCE: 496

Thr Pro Asp Ile Asn Pro Ala Trp Tyr Ala Ser Arg Gly Ile Arg Pro
1               5                   10                  15

Val Gly Arg Phe
            20

<210> SEQ ID NO 497
<211> LENGTH: 34
<212> TYPE: PRT
<213> ORGANISM: Homo sapiens
<220> FEATURE:
<221> NAME/KEY: MOD_RES
<222> LOCATION: (34)..(34)
<223> OTHER INFORMATION: AMIDATION

<400> SEQUENCE: 497

Gln Leu Gly Pro Gln Gly Pro Pro His Leu Val Ala Asp Pro Ser Lys
1               5                   10                  15

Lys Gln Gly Pro Trp Leu Glu Glu Glu Glu Ala Tyr Gly Trp Met
            20                  25                  30

Asp Phe

<210> SEQ ID NO 498
<211> LENGTH: 18
<212> TYPE: PRT
<213> ORGANISM: Homo sapiens
<220> FEATURE:
<221> NAME/KEY: MOD_RES
<222> LOCATION: (18)..(18)
<223> OTHER INFORMATION: AMIDATION
<220> FEATURE:
<221> NAME/KEY: MOD_RES
<222> LOCATION: (1)..(1)
<223> OTHER INFORMATION: pyroGlutamine

<400> SEQUENCE: 498

Pro Glu Gly Pro Trp Leu Glu Glu Glu Glu Ala Tyr Gly Trp Met
1               5                   10                  15

Asp Phe

<210> SEQ ID NO 499
<211> LENGTH: 5
<212> TYPE: PRT
<213> ORGANISM: Homo sapiens
<220> FEATURE:
<221> NAME/KEY: MOD_RES
<222> LOCATION: (5)..(5)
<223> OTHER INFORMATION: AMIDATION
<220> FEATURE:
<221> NAME/KEY: MOD_RES
<222> LOCATION: (1)..(1)
<223> OTHER INFORMATION: bAla

<400> SEQUENCE: 499

Ala Trp Met Asp Phe
1               5

<210> SEQ ID NO 500
```

```
<211> LENGTH: 33
<212> TYPE: PRT
<213> ORGANISM: Homo sapiens
<220> FEATURE:
<221> NAME/KEY: MOD_RES
<222> LOCATION: (33)..(33)
<223> OTHER INFORMATION: AMIDATION

<400> SEQUENCE: 500

Lys Ala Pro Ser Gly Arg Met Ser Ile Val Lys Asn Leu Gln Asn Leu
1               5                   10                  15

Asp Pro Ser His Arg Ile Ser Asp Arg Asp Tyr Met Gly Trp Met Asp
            20                  25                  30

Phe

<210> SEQ ID NO 501
<211> LENGTH: 29
<212> TYPE: PRT
<213> ORGANISM: Homo sapiens

<400> SEQUENCE: 501

Gln Glu Gly Ala Pro Pro Gln Gln Ser Ala Arg Arg Asp Arg Met Pro
1               5                   10                  15

Cys Arg Asn Phe Phe Trp Lys Thr Phe Ser Ser Cys Lys
            20                  25

<210> SEQ ID NO 502
<211> LENGTH: 17
<212> TYPE: PRT
<213> ORGANISM: Homo sapiens

<400> SEQUENCE: 502

Asp Arg Met Pro Cys Arg Asn Phe Phe Trp Lys Thr Phe Ser Ser Cys
1               5                   10                  15

Lys

<210> SEQ ID NO 503
<211> LENGTH: 28
<212> TYPE: PRT
<213> ORGANISM: Homo sapiens

<400> SEQUENCE: 503

Ser Ala Asn Ser Asn Pro Ala Met Ala Pro Arg Glu Arg Lys Ala Gly
1               5                   10                  15

Cys Lys Asn Phe Phe Trp Lys Thr Phe Thr Ser Cys
            20                  25

<210> SEQ ID NO 504
<211> LENGTH: 14
<212> TYPE: PRT
<213> ORGANISM: Homo sapiens

<400> SEQUENCE: 504

Ala Gly Cys Lys Asn Phe Phe Trp Lys Thr Phe Thr Ser Cys
1               5                   10

<210> SEQ ID NO 505
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION
```

-continued

```
<400> SEQUENCE: 505

Val Pro Leu Pro Ala Gly Gly Thr Val Leu Thr Lys Met Tyr Pro
1               5                   10                  15

Arg Gly Asn His Trp Ala Val Gly His Leu Met
            20                  25

<210> SEQ ID NO 506
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 506

Gly Asn His Trp Ala Val Gly His Leu Met
1               5                   10

<210> SEQ ID NO 507
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 507

Leu Ser Trp Asp Leu Pro Glu Pro Arg Ser Arg Ala Ser Lys Ile Arg
1               5                   10                  15

Val His Ser Arg Gly Asn Leu Trp Ala Thr Gly His Phe Met
            20                  25                  30

<210> SEQ ID NO 508
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 508

Gly Asn Leu Trp Ala Thr Gly His Phe Met
1               5                   10

<210> SEQ ID NO 509
<211> LENGTH: 9
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: AMIDATION

<400> SEQUENCE: 509

Pro Phe Phe Leu Phe Arg Pro Arg Asn
1               5

<210> SEQ ID NO 510
<211> LENGTH: 21
<212> TYPE: PRT
<213> ORGANISM: Homo sapiens

<400> SEQUENCE: 510

Lys Ile Pro Tyr Ile Leu Lys Arg Gln Leu Tyr Glu Asn Lys Pro Arg
```

```
                1               5                   10                  15

Arg Pro Tyr Ile Leu
                20

<210> SEQ ID NO 511
<211> LENGTH: 13
<212> TYPE: PRT
<213> ORGANISM: Homo sapiens

<400> SEQUENCE: 511

Gln Leu Tyr Glu Asn Lys Pro Arg Pro Tyr Ile Leu
1               5                   10

<210> SEQ ID NO 512
<211> LENGTH: 54
<212> TYPE: PRT
<213> ORGANISM: Homo sapiens
<220> FEATURE:
<221> NAME/KEY: MOD_RES
<222> LOCATION: (54)..(54)
<223> OTHER INFORMATION: AMIDATION

<400> SEQUENCE: 512

Gly Thr Ser Leu Ser Pro Pro Glu Ser Ser Gly Ser Pro Gln Gln
1               5                   10                  15

Pro Gly Leu Ser Ala Pro His Ser Arg Gln Ile Pro Ala Pro Gln Gly
            20                  25                  30

Ala Val Leu Val Gln Arg Glu Lys Asp Leu Pro Asn Tyr Asn Trp Asn
        35                  40                  45

Ser Phe Gly Leu Arg Phe
    50

<210> SEQ ID NO 513
<211> LENGTH: 16
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: AMIDATION

<400> SEQUENCE: 513

Glu Lys Asp Leu Pro Asn Tyr Asn Trp Asn Ser Phe Gly Leu Arg Phe
1               5                   10                  15

<210> SEQ ID NO 514
<211> LENGTH: 31
<212> TYPE: PRT
<213> ORGANISM: Homo sapiens
<220> FEATURE:
<221> NAME/KEY: MOD_RES
<222> LOCATION: (31)..(31)
<223> OTHER INFORMATION: AMIDATION

<400> SEQUENCE: 514

Ser Ala Gly Ala Thr Ala Asn Leu Pro Leu Arg Ser Gly Arg Asn Met
1               5                   10                  15

Glu Val Ser Leu Val Arg Arg Val Pro Asn Leu Pro Gln Arg Phe
            20                  25                  30

<210> SEQ ID NO 515
<211> LENGTH: 8
<212> TYPE: PRT
<213> ORGANISM: Homo sapiens
<220> FEATURE:
<221> NAME/KEY: MOD_RES
```

```
<222> LOCATION: (8)..(8)
<223> OTHER INFORMATION: AMIDATION

<400> SEQUENCE: 515

Val Pro Asn Leu Pro Gln Arg Phe
1               5

<210> SEQ ID NO 516
<211> LENGTH: 32
<212> TYPE: PRT
<213> ORGANISM: Homo sapiens

<400> SEQUENCE: 516

Tyr Gly Gly Phe Leu Arg Arg Ile Arg Pro Lys Leu Lys Trp Asp Asn
1               5                   10                  15

Gln Lys Arg Tyr Gly Gly Phe Leu Arg Arg Gln Phe Lys Val Val Thr
            20                  25                  30

<210> SEQ ID NO 517
<211> LENGTH: 13
<212> TYPE: PRT
<213> ORGANISM: Homo sapiens

<400> SEQUENCE: 517

Tyr Gly Gly Phe Leu Arg Arg Gln Phe Lys Val Val Thr
1               5                   10

<210> SEQ ID NO 518
<211> LENGTH: 14
<212> TYPE: PRT
<213> ORGANISM: Homo sapiens
<220> FEATURE:
<221> NAME/KEY: MISC_FEATURE
<223> OTHER INFORMATION: C-term amide

<400> SEQUENCE: 518

Ser Leu Arg His Tyr Leu Asn Leu Val Thr Arg Gln Arg Tyr
1               5                   10

<210> SEQ ID NO 519
<211> LENGTH: 38
<212> TYPE: PRT
<213> ORGANISM: Homo sapiens

<400> SEQUENCE: 519

Cys Ser Cys Ser Ser Leu Met Asp Lys Glu Cys Val Tyr Phe Cys His
1               5                   10                  15

Leu Asp Ile Ile Trp Val Asn Thr Pro Glu His Val Val Pro Tyr Gly
            20                  25                  30

Leu Gly Ser Pro Arg Ser
        35

<210> SEQ ID NO 520
<211> LENGTH: 21
<212> TYPE: PRT
<213> ORGANISM: Homo sapiens

<400> SEQUENCE: 520

Cys Ser Cys Ser Ser Leu Met Asp Lys Glu Cys Val Tyr Phe Cys His
1               5                   10                  15

Leu Asp Ile Ile Trp
            20

<210> SEQ ID NO 521
```

```
<211> LENGTH: 37
<212> TYPE: PRT
<213> ORGANISM: Homo sapiens

<400> SEQUENCE: 521

Cys Ser Cys Ser Ser Trp Leu Asp Lys Glu Cys Val Tyr Phe Cys His
1               5                   10                  15

Leu Asp Ile Ile Trp Val Asn Thr Pro Glu Gln Thr Ala Pro Tyr Gly
            20                  25                  30

Leu Gly Asn Pro Pro
            35

<210> SEQ ID NO 522
<211> LENGTH: 21
<212> TYPE: PRT
<213> ORGANISM: Homo sapiens

<400> SEQUENCE: 522

Cys Ser Cys Ser Ser Trp Leu Asp Lys Glu Cys Val Tyr Phe Cys His
1               5                   10                  15

Leu Asp Ile Ile Trp
            20

<210> SEQ ID NO 523
<211> LENGTH: 41
<212> TYPE: PRT
<213> ORGANISM: Homo sapiens
<220> FEATURE:
<221> NAME/KEY: MOD_RES
<222> LOCATION: (41)..(41)
<223> OTHER INFORMATION: AMIDATION

<400> SEQUENCE: 523

Cys Thr Cys Phe Thr Tyr Lys Asp Lys Glu Cys Val Tyr Tyr Cys His
1               5                   10                  15

Leu Asp Ile Ile Trp Ile Asn Thr Pro Glu Gln Thr Val Pro Tyr Gly
            20                  25                  30

Leu Ser Asn Tyr Arg Gly Ser Phe Arg
            35                  40

<210> SEQ ID NO 524
<211> LENGTH: 21
<212> TYPE: PRT
<213> ORGANISM: Homo sapiens

<400> SEQUENCE: 524

Cys Thr Cys Phe Thr Tyr Lys Asp Lys Glu Cys Val Tyr Tyr Cys His
1               5                   10                  15

Leu Asp Ile Ile Trp
            20

<210> SEQ ID NO 525
<211> LENGTH: 27
<212> TYPE: PRT
<213> ORGANISM: Homo sapiens

<400> SEQUENCE: 525

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro
            20                  25

<210> SEQ ID NO 526
```

```
<211> LENGTH: 10
<212> TYPE: PRT
<213> ORGANISM: Homo sapiens

<400> SEQUENCE: 526

Gly Ser Ser Phe Leu Ser Pro Glu His Gln
1               5                   10

<210> SEQ ID NO 527
<211> LENGTH: 37
<212> TYPE: PRT
<213> ORGANISM: Homo sapiens

<400> SEQUENCE: 527

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 528
<211> LENGTH: 29
<212> TYPE: PRT
<213> ORGANISM: Homo sapiens

<400> SEQUENCE: 528

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 529
<211> LENGTH: 42
<212> TYPE: PRT
<213> ORGANISM: Homo sapiens

<400> SEQUENCE: 529

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 530
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 530

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys
            20                  25                  30

<210> SEQ ID NO 531
<211> LENGTH: 30
<212> TYPE: PRT
<213> ORGANISM: Homo sapiens
```

<400> SEQUENCE: 531

Trp Tyr Lys His Val Ala Ser Pro Arg Tyr His Thr Val Gly Arg Ala
1               5                   10                  15

Ala Gly Leu Leu Met Gly Leu Arg Arg Ser Pro Tyr Leu Trp
            20                  25                  30

<210> SEQ ID NO 532
<211> LENGTH: 23
<212> TYPE: PRT
<213> ORGANISM: Homo sapiens

<400> SEQUENCE: 532

Trp Tyr Lys His Val Ala Ser Pro Arg Tyr His Thr Val Gly Arg Ala
1               5                   10                  15

Ala Gly Leu Leu Met Gly Leu
            20

<210> SEQ ID NO 533
<211> LENGTH: 38
<212> TYPE: PRT
<213> ORGANISM: Homo sapiens
<220> FEATURE:
<221> NAME/KEY: MOD_RES
<222> LOCATION: (38)..(38)
<223> OTHER INFORMATION: AMIDATION

<400> SEQUENCE: 533

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 534
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 534

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu
            20                  25

<210> SEQ ID NO 535
<211> LENGTH: 42
<212> TYPE: PRT
<213> ORGANISM: Homo sapiens

<400> SEQUENCE: 535

His Ala Asp Gly Val Phe Thr Ser Asp Phe Ser Lys Leu Leu Gly Gln
1               5                   10                  15

Leu Ser Ala Lys Lys Tyr Leu Glu Ser Leu Met Gly Lys Arg Val Ser
            20                  25                  30

Ser Asn Ile Ser Glu Asp Pro Val Pro Val
            35                  40

-continued

```
<210> SEQ ID NO 536
<211> LENGTH: 27
<212> TYPE: PRT
<213> ORGANISM: Homo sapiens
<220> FEATURE:
<221> NAME/KEY: MOD_RES
<222> LOCATION: (27)..(27)
<223> OTHER INFORMATION: AMIDATION

<400> SEQUENCE: 536

His Ala Asp Gly Val Phe Thr Ser Asp Phe Ser Lys Leu Leu Gly Gln
1               5                   10                  15

Leu Ser Ala Lys Lys Tyr Leu Glu Ser Leu Met
            20                  25

<210> SEQ ID NO 537
<211> LENGTH: 44
<212> TYPE: PRT
<213> ORGANISM: Homo sapiens
<220> FEATURE:
<221> NAME/KEY: MOD_RES
<222> LOCATION: (44)..(44)
<223> OTHER INFORMATION: AMIDATION

<400> SEQUENCE: 537

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 538
<211> LENGTH: 28
<212> TYPE: PRT
<213> ORGANISM: Homo sapiens

<400> SEQUENCE: 538

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser
            20                  25

<210> SEQ ID NO 539
<211> LENGTH: 84
<212> TYPE: PRT
<213> ORGANISM: Homo sapiens

<400> SEQUENCE: 539

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu Gly Ala Pro Leu Ala Pro Arg Asp Ala Gly Ser
        35                  40                  45

Gln Arg Pro Arg Lys Lys Glu Asp Asn Val Leu Val Glu Ser His Glu
    50                  55                  60

Lys Ser Leu Gly Glu Ala Asp Lys Ala Asp Val Asn Val Leu Thr Lys
65                  70                  75                  80

Ala Lys Ser Gln

<210> SEQ ID NO 540
<211> LENGTH: 37
```

```
<212> TYPE: PRT
<213> ORGANISM: Homo sapiens

<400> SEQUENCE: 540

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe Val Ala Leu
            35

<210> SEQ ID NO 541
<211> LENGTH: 34
<212> TYPE: PRT
<213> ORGANISM: Homo sapiens

<400> SEQUENCE: 541

Ser Val Ser Glu Ile Gln Leu Met His Asn Leu Gly Lys His Leu Asn
1               5                   10                  15

Ser Met Glu Arg Val Glu Trp Leu Arg Lys Lys Leu Gln Asp Val His
            20                  25                  30

Asn Phe

<210> SEQ ID NO 542
<211> LENGTH: 93
<212> TYPE: PRT
<213> ORGANISM: Homo sapiens
<220> FEATURE:
<221> NAME/KEY: MOD_RES
<222> LOCATION: (93)..(93)
<223> OTHER INFORMATION: AMIDATION

<400> SEQUENCE: 542

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile Arg Ala Thr Ser Glu Val Ser Pro Asn Ser Lys Pro
        35                  40                  45

Ser Pro Asn Thr Lys Asn His Pro Val Arg Gly Ser Asp Asp Glu Gly
    50                  55                  60

Arg Tyr Leu Thr Gln Glu Thr Asn Lys Val Glu Thr Tyr Lys Glu Gln
65                  70                  75                  80

Pro Leu Lys Thr Pro Gly Lys Lys Lys Gly Lys Pro
            85                  90

<210> SEQ ID NO 543
<211> LENGTH: 36
<212> TYPE: PRT
<213> ORGANISM: Homo sapiens

<400> SEQUENCE: 543

Ala Val Ser Glu His Gln Leu Leu His Asp Lys Gly Lys Ser Ile Gln
1               5                   10                  15

Asp Leu Arg Arg Arg Phe Phe Leu His His Leu Ile Ala Glu Ile His
            20                  25                  30

Thr Ala Glu Ile
        35

<210> SEQ ID NO 544
<211> LENGTH: 26
```

```
<212> TYPE: PRT
<213> ORGANISM: Homo sapiens

<400> SEQUENCE: 544

Tyr Val Met Gly His Phe Arg Trp Asp Arg Phe Gly Arg Arg Asn Ser
1               5                   10                  15

Ser Ser Ser Gly Ser Ser Gly Ala Gly Gln
            20                  25

<210> SEQ ID NO 545
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 545

Tyr Val Met Gly His Phe Arg Trp Asp Arg Phe
1               5                   10

<210> SEQ ID NO 546
<211> LENGTH: 39
<212> TYPE: PRT
<213> ORGANISM: Homo sapiens

<400> SEQUENCE: 546

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
            35

<210> SEQ ID NO 547
<211> LENGTH: 13
<212> TYPE: PRT
<213> ORGANISM: Homo sapiens
<220> FEATURE:
<221> NAME/KEY: MOD_RES
<222> LOCATION: (13)..(13)
<223> OTHER INFORMATION: AMIDATION

<400> SEQUENCE: 547

Ser Tyr Ser Met Glu His Phe Arg Trp Gly Lys Pro Val
1               5                   10

<210> SEQ ID NO 548
<211> LENGTH: 31
<212> TYPE: PRT
<213> ORGANISM: Homo sapiens

<400> SEQUENCE: 548

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30

<210> SEQ ID NO 549
<211> LENGTH: 27
<212> TYPE: PRT
<213> ORGANISM: Homo sapiens

<400> SEQUENCE: 549
```

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr
            20                  25

<210> SEQ ID NO 550
<211> LENGTH: 16
<212> TYPE: PRT
<213> ORGANISM: Homo sapiens

<400> SEQUENCE: 550

Tyr Gly Gly Phe Met Thr Ser Glu Lys Ser Gln Thr Pro Leu Val Thr
1               5                   10                  15

<210> SEQ ID NO 551
<211> LENGTH: 6
<212> TYPE: PRT
<213> ORGANISM: Homo sapiens

<400> SEQUENCE: 551

Met Val Pro Ile Gln Lys
1               5

<210> SEQ ID NO 552
<211> LENGTH: 6
<212> TYPE: PRT
<213> ORGANISM: Homo sapiens

<400> SEQUENCE: 552

Val Gln Asp Asp Thr Lys
1               5

<210> SEQ ID NO 553
<211> LENGTH: 4
<212> TYPE: PRT
<213> ORGANISM: Homo sapiens

<400> SEQUENCE: 553

Thr Leu Ile Lys
1

<210> SEQ ID NO 554
<211> LENGTH: 5
<212> TYPE: PRT
<213> ORGANISM: Homo sapiens

<400> SEQUENCE: 554

Thr Ile Val Thr Arg
1               5

<210> SEQ ID NO 555
<211> LENGTH: 13
<212> TYPE: PRT
<213> ORGANISM: Homo sapiens

<400> SEQUENCE: 555

Ile Asn Asp Ile Ser His Thr Gln Ser Val Ser Ser Lys
1               5                   10

<210> SEQ ID NO 556
<211> LENGTH: 18
<212> TYPE: PRT
<213> ORGANISM: Homo sapiens

<400> SEQUENCE: 556

Val Thr Gly Leu Asp Phe Ile Pro Gly Leu His Pro Ile Leu Thr Leu
1               5                   10                  15

Ser Lys

<210> SEQ ID NO 557
<211> LENGTH: 13
<212> TYPE: PRT
<213> ORGANISM: Homo sapiens

<400> SEQUENCE: 557

Asn Val Ile Gln Ile Ser Asn Asp Leu Glu Asn Leu Arg
1               5                   10

<210> SEQ ID NO 558
<211> LENGTH: 10
<212> TYPE: PRT
<213> ORGANISM: Homo sapiens

<400> SEQUENCE: 558

Asp Leu Leu His Val Leu Ala Phe Ser Lys
1               5                   10

<210> SEQ ID NO 559
<211> LENGTH: 34
<212> TYPE: PRT
<213> ORGANISM: Homo sapiens

<400> SEQUENCE: 559

Ser Cys His Leu Pro Trp Ala Ser Gly Leu Glu Thr Leu Asp Ser Leu
1               5                   10                  15

Gly Gly Val Leu Glu Ala Ser Gly Tyr Ser Thr Glu Val Val Ala Leu
            20                  25                  30

Ser Arg

<210> SEQ ID NO 560
<211> LENGTH: 18
<212> TYPE: PRT
<213> ORGANISM: Homo sapiens

<400> SEQUENCE: 560

Leu Gln Gly Ser Leu Gln Asp Met Leu Trp Gln Leu Asp Leu Ser Pro
1               5                   10                  15

Gly Cys

<210> SEQ ID NO 561
<211> LENGTH: 9
<212> TYPE: PRT
<213> ORGANISM: Artificial
<220> FEATURE:
<223> OTHER INFORMATION: genus
<220> FEATURE:
<221> NAME/KEY: MISC_FEATURE
<222> LOCATION: (1)..(1)
<223> OTHER INFORMATION: Xaa can be contiguous mouse or human leptin
      sequence
<220> FEATURE:
<221> NAME/KEY: MISC_FEATURE
<222> LOCATION: (4)..(4)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa is any amino acid

```
<220> FEATURE:
<221> NAME/KEY: MISC_FEATURE
<222> LOCATION: (9)..(9)
<223> OTHER INFORMATION: Xaa can be contigous mouse or human leptin
      sequence

<400> SEQUENCE: 561

Xaa Ser Cys Xaa Leu Pro Xaa Xaa Xaa
1               5

<210> SEQ ID NO 562
<211> LENGTH: 7
<212> TYPE: PRT
<213> ORGANISM: Mus musculus

<400> SEQUENCE: 562

Ser Cys Ser Leu Pro Gln Thr
1               5

<210> SEQ ID NO 563
<211> LENGTH: 7
<212> TYPE: PRT
<213> ORGANISM: Homo sapiens

<400> SEQUENCE: 563

Ser Cys His Leu Pro Trp Ala
1               5

<210> SEQ ID NO 564
<211> LENGTH: 52
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (6)..(6)
<223> OTHER INFORMATION: Xaa is Trp or Gln
<220> FEATURE:
<221> NAME/KEY: MISC_FEATURE
<222> LOCATION: (36)..(36)
<223> OTHER INFORMATION: Xaa is Gln or Glu
<220> FEATURE:
<221> NAME/KEY: MISC_FEATURE
<222> LOCATION: (40)..(40)
<223> OTHER INFORMATION: Xaa is Gln or Glu
<220> FEATURE:
<221> NAME/KEY: MISC_FEATURE
<222> LOCATION: (42)..(42)
<223> OTHER INFORMATION: Xaa is Ile, Leu, Met or methionine sulfoxide
<220> FEATURE:
<221> NAME/KEY: MISC_FEATURE
<222> LOCATION: (44)..(44)
<223> OTHER INFORMATION: Xaa is Trp or Gln
<220> FEATURE:
<221> NAME/KEY: MISC_FEATURE
<222> LOCATION: (45)..(45)
<223> OTHER INFORMATION: Xaa is Gln or Glu

<400> SEQUENCE: 564

Ser Cys His Leu Pro Xaa Ala Ser Gly Leu Glu Thr Leu Asp Ser Leu
1               5                   10                  15

Gly Gly Val Leu Glu Ala Ser Gly Tyr Ser Thr Glu Val Val Ala Leu
            20                  25                  30

Ser Arg Leu Xaa Gly Ser Leu Xaa Asp Xaa Leu Xaa Xaa Leu Asp Leu
                35                  40                  45

Ser Pro Gly Cys
    50
```

```
<210> SEQ ID NO 565
<211> LENGTH: 146
<212> TYPE: PRT
<213> ORGANISM: Mus musculus
<220> FEATURE:
<221> NAME/KEY: MISC_FEATURE
<222> LOCATION: (28)..(28)
<223> OTHER INFORMATION: Xaa is Gln or absent

<400> SEQUENCE: 565

Val Pro Ile Gln Lys Val Gln Asp Asp Thr Lys Thr Leu Ile Lys Thr
1               5                   10                  15

Ile Val Thr Arg Ile Asn Asp Ile Ser His Thr Xaa Ser Val Ser Ser
                20                  25                  30

Lys Gln Lys Val Thr Gly Leu Asp Phe Ile Pro Gly Leu His Pro Ile
            35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Gln Ala Ser Gly Leu Glu Thr Leu Glu Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Gln Gln Leu Asp Leu Ser Pro
    130                 135                 140

Gly Cys
145

<210> SEQ ID NO 566
<211> LENGTH: 146
<212> TYPE: PRT
<213> ORGANISM: porcine

<400> SEQUENCE: 566

Val Pro Ile Trp Arg Val Gln Asp Asp Thr Lys Thr Leu Ile Lys Thr
1               5                   10                  15

Ile Val Thr Arg Ile Ser Asp Ile Ser His Met Gln Ser Val Ser Ser
                20                  25                  30

Lys Gln Arg Val Thr Gly Leu Asp Phe Ile Pro Gly Leu His Pro Val
            35                  40                  45

Leu Ser Leu Ser Lys Met Asp Gln Thr Leu Ala Ile Tyr Gln Gln Ile
    50                  55                  60

Leu Thr Ser Leu Pro Ser Arg Asn Val Ile Gln Ile Ser Asn Asp Leu
65                  70                  75                  80

Glu Asn Leu Arg Asp Leu Leu His Leu Leu Ala Ser Ser Lys Ser Cys
                85                  90                  95

Pro Leu Pro Gln Ala Arg Ala Leu Glu Thr Leu Glu Ser Leu Gly Gly
            100                 105                 110

Val Leu Glu Ala Ser Leu Tyr Ser Thr Glu Val Val Ala Leu Ser Arg
        115                 120                 125

Leu Gln Gly Ala Leu Gln Asp Met Leu Arg Gln Leu Asp Leu Ser Pro
    130                 135                 140

Gly Cys
145
```

```
<210> SEQ ID NO 567
<211> LENGTH: 146
<212> TYPE: PRT
<213> ORGANISM: bovine
<220> FEATURE:
<221> NAME/KEY: MISC_FEATURE
<222> LOCATION: (28)..(28)
<223> OTHER INFORMATION: Xaa is Gln or absent

<400> SEQUENCE: 567

Val Pro Ile Cys Lys Val Gln Asp Asp Thr Lys Thr Leu Ile Lys Thr
1               5                   10                  15

Ile Val Thr Arg Ile Asn Asp Ile Ser His Thr Xaa Ser Val Ser Ser
            20                  25                  30

Lys Gln Arg Val Thr Gly Leu Asp Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Thr Ser Leu Pro Ser Arg Asn Val Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 568
<211> LENGTH: 146
<212> TYPE: PRT
<213> ORGANISM: Homo sapiens
<220> FEATURE:
<221> NAME/KEY: MISC_FEATURE
<222> LOCATION: (27)..(27)
<223> OTHER INFORMATION: Xaa is Thr or Ala
<220> FEATURE:
<221> NAME/KEY: MISC_FEATURE
<222> LOCATION: (28)..(28)
<223> OTHER INFORMATION: Xaa is Gln or absent

<400> SEQUENCE: 568

Val Pro Ile Gln Lys Val Gln Asp Asp Thr Lys Thr Leu Ile Lys Thr
1               5                   10                  15

Ile Val Thr Arg Ile Asn Asp Ile Ser His Xaa Xaa Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125
```

```
Leu Gln Gly Ser Leu Gln Asp Met Leu Trp Gln Leu Asp Leu Ser Pro
        130                 135                 140

Gly Cys
145

<210> SEQ ID NO 569
<211> LENGTH: 146
<212> TYPE: PRT
<213> ORGANISM: rhesus

<400> SEQUENCE: 569

Val Pro Ile Gln Lys Val Gln Ser Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Phe Ile Pro Gly Leu His Pro Val
        35                  40                  45

Leu Thr Leu Ser Gln Met Asp Gln Thr Leu Ala Ile Tyr Gln Gln Ile
    50                  55                  60

Leu Ile Asn Leu Pro Ser Arg Asn Val Ile Gln Ile Ser Asn Asp Leu
65                  70                  75                  80

Glu Asn Leu Arg Asp Leu Leu His Leu Leu Ala Phe Ser Lys Ser Cys
                85                  90                  95

His Leu Pro Leu Ala Ser Gly Leu Glu Thr Leu Glu Ser Leu Gly Asp
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 570
<211> LENGTH: 146
<212> TYPE: PRT
<213> ORGANISM: Rattus norvegicus

<400> SEQUENCE: 570

Val Pro Ile His Lys Val Gln Asp Asp Thr Lys Thr Leu Ile Lys Thr
1               5                   10                  15

Ile Val Thr Arg Ile Asn Asp Ile Ser His Thr Gln Ser Val Ser Ala
            20                  25                  30

Arg Gln Arg Val Thr Gly Leu Asp Phe Ile Pro Gly Leu His Pro Ile
        35                  40                  45

Leu Ser Leu Ser Lys Met Asp Gln Thr Leu Ala Val Tyr Gln Gln Ile
    50                  55                  60

Leu Thr Ser Leu Pro Ser Gln Asn Val Leu Gln Ile Ala His Asp Leu
65                  70                  75                  80

Glu Asn Leu Arg Asp Leu Leu His Leu Leu Ala Phe Ser Lys Ser Cys
                85                  90                  95

Ser Leu Pro Gln Thr Arg Gly Leu Gln Lys Pro Glu Ser Leu Asp Gly
            100                 105                 110

Val Leu Glu Ala Ser Leu Tyr Ser Thr Glu Val Val Ala Leu Ser Arg
        115                 120                 125

Leu Gln Gly Ser Leu Gln Asp Ile Leu Gln Gln Leu Asp Leu Ser Pro
    130                 135                 140
```

Glu Cys
145

<210> SEQ ID NO 571
<211> LENGTH: 146
<212> TYPE: PRT
<213> ORGANISM: Artificial
<220> FEATURE:
<223> OTHER INFORMATION: leptin genus
<220> FEATURE:
<221> NAME/KEY: MISC_FEATURE
<222> LOCATION: (22)..(22)
<223> OTHER INFORMATION: Xaa is Asn, Asp or Glu
<220> FEATURE:
<221> NAME/KEY: MISC_FEATURE
<222> LOCATION: (27)..(27)
<223> OTHER INFORMATION: Xaa is Thr or Ala
<220> FEATURE:
<221> NAME/KEY: MISC_FEATURE
<222> LOCATION: (28)..(28)
<223> OTHER INFORMATION: Xaa is Gln, Glu, or absent
<220> FEATURE:
<221> NAME/KEY: MISC_FEATURE
<222> LOCATION: (54)..(54)
<223> OTHER INFORMATION: Xaa is Met or Ala
<220> FEATURE:
<221> NAME/KEY: MISC_FEATURE
<222> LOCATION: (68)..(68)
<223> OTHER INFORMATION: Xaa is Met or Leu
<220> FEATURE:
<221> NAME/KEY: MISC_FEATURE
<222> LOCATION: (72)..(72)
<223> OTHER INFORMATION: Xaa is Asn, Asp or Glu
<220> FEATURE:
<221> NAME/KEY: MISC_FEATURE
<222> LOCATION: (77)..(77)
<223> OTHER INFORMATION: Xaa is Ser or Ala
<220> FEATURE:
<221> NAME/KEY: MISC_FEATURE
<222> LOCATION: (118)..(118)
<223> OTHER INFORMATION: Xaa is Gly or Leu

<400> SEQUENCE: 571

Val Pro Ile Gln Lys Val Gln Asp Asp Thr Lys Thr Leu Ile Lys Thr
1               5                   10                  15

Ile Val Thr Arg Ile Xaa Asp Ile Ser His Xaa Xaa Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Xaa Asp Gln Thr Leu Ala Val Tyr Gln Gln Ile
    50                  55                  60

Leu Thr Ser Xaa Pro Ser Arg Xaa Val Ile Gln Ile Xaa Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 572
<211> LENGTH: 146
<212> TYPE: PRT
<213> ORGANISM: Artificial -continued

```
<220> FEATURE:
<223> OTHER INFORMATION: leptin genus
<220> FEATURE:
<221> NAME/KEY: MISC_FEATURE
<222> LOCATION: (27)..(27)
<223> OTHER INFORMATION: Xaa is Thr or Ala
<220> FEATURE:
<221> NAME/KEY: MISC_FEATURE
<222> LOCATION: (77)..(77)
<223> OTHER INFORMATION: Xaa is Ser or Ala
<220> FEATURE:
<221> NAME/KEY: MISC_FEATURE
<222> LOCATION: (118)..(118)
<223> OTHER INFORMATION: Xaa is Gly or Leu

<400> SEQUENCE: 572

Val Pro Ile Gln Lys Val Gln Asp Asp Thr Lys Thr Leu Ile Lys Thr
1               5                   10                  15

Ile Val Thr Arg Ile Asn Asp Ile Ser His Xaa Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Xaa Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Xaa Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 573
<211> LENGTH: 105
<212> TYPE: PRT
<213> ORGANISM: Artificial
<220> FEATURE:
<223> OTHER INFORMATION: leptin genus
<220> FEATURE:
<221> NAME/KEY: MISC_FEATURE
<222> LOCATION: (13)..(13)
<223> OTHER INFORMATION: Xaa is Ile, Leu, Met or methionine sulfoxide
<220> FEATURE:
<221> NAME/KEY: MISC_FEATURE
<222> LOCATION: (15)..(15)
<223> OTHER INFORMATION: Xaa is Gln or Glu
<220> FEATURE:
<221> NAME/KEY: MISC_FEATURE
<222> LOCATION: (21)..(21)
<223> OTHER INFORMATION: Xaa is Gln or Glu
<220> FEATURE:
<221> NAME/KEY: MISC_FEATURE
<222> LOCATION: (22)..(22)
<223> OTHER INFORMATION: Xaa is Gln or Glu
<220> FEATURE:
<221> NAME/KEY: MISC_FEATURE
<222> LOCATION: (27)..(27)
<223> OTHER INFORMATION: Xaa is Ile, Leu, Met or methionine sulfoxide
<220> FEATURE:
<221> NAME/KEY: MISC_FEATURE
<222> LOCATION: (31)..(31)
<223> OTHER INFORMATION: Xaa is Asn, Asp or Gln
<220> FEATURE:
<221> NAME/KEY: MISC_FEATURE
```

```
<222> LOCATION: (34)..(34)
<223> OTHER INFORMATION: Xaa is Gln or Glun
<220> FEATURE:
<221> NAME/KEY: MISC_FEATURE
<222> LOCATION: (37)..(37)
<223> OTHER INFORMATION: Xaa is Asn, Asp or Gln
<220> FEATURE:
<221> NAME/KEY: MISC_FEATURE
<222> LOCATION: (41)..(41)
<223> OTHER INFORMATION: Xaa is Asn, Asp or Gln
<220> FEATURE:
<221> NAME/KEY: MISC_FEATURE
<222> LOCATION: (59)..(59)
<223> OTHER INFORMATION: Xaa is Trp or Gln
<220> FEATURE:
<221> NAME/KEY: MISC_FEATURE
<222> LOCATION: (89)..(89)
<223> OTHER INFORMATION: Xaa is Gln or Glu
<220> FEATURE:
<221> NAME/KEY: MISC_FEATURE
<222> LOCATION: (93)..(93)
<223> OTHER INFORMATION: Xaa is Gln or Glu
<220> FEATURE:
<221> NAME/KEY: MISC_FEATURE
<222> LOCATION: (95)..(95)
<223> OTHER INFORMATION: Xaa is Ile, Leu, Met or methionine sulfoxide
<220> FEATURE:
<221> NAME/KEY: MISC_FEATURE
<222> LOCATION: (97)..(97)
<223> OTHER INFORMATION: Xaa is Trp or Gln
<220> FEATURE:
<221> NAME/KEY: MISC_FEATURE
<222> LOCATION: (98)..(98)
<223> OTHER INFORMATION: Xaa is Gln or Glu

<400> SEQUENCE: 573

Ile Pro Gly Leu His Pro Ile Leu Thr Leu Ser Lys Xaa Asp Xaa Thr
1               5                   10                  15

Leu Ala Val Tyr Xaa Xaa Ile Leu Thr Ser Xaa Pro Ser Arg Xaa Val
            20                  25                  30

Ile Xaa Ile Ser Xaa Asp Leu Glu Xaa Leu Arg Asp Leu Leu His Val
        35                  40                  45

Leu Ala Phe Ser Lys Ser Cys His Leu Pro Xaa Ala Ser Gly Leu Glu
    50                  55                  60

Thr Leu Asp Ser Leu Gly Gly Val Leu Glu Ala Ser Gly Tyr Ser Thr
65                  70                  75                  80

Glu Val Val Ala Leu Ser Arg Leu Xaa Gly Ser Leu Xaa Asp Xaa Leu
                85                  90                  95

Xaa Xaa Leu Asp Leu Ser Pro Gly Cys
            100                 105

<210> SEQ ID NO 574
<211> LENGTH: 36
<212> TYPE: PRT
<213> ORGANISM: Artificial
<220> FEATURE:
<223> OTHER INFORMATION: PPF genus
<220> FEATURE:
<221> NAME/KEY: MISC_FEATURE
<222> LOCATION: (1)..(1)
<223> OTHER INFORMATION: Xaa is Tyr or absent
<220> FEATURE:
<221> NAME/KEY: MISC_FEATURE
<222> LOCATION: (2)..(2)
<223> OTHER INFORMATION: Xaa is Ile, Pro, or absent
<220> FEATURE:
<221> NAME/KEY: MISC_FEATURE
<222> LOCATION: (3)..(3)
<223> OTHER INFORMATION: Xaa is Ile, Bolton-Hunter-modified Lys, Lys,
      Val, or Pro
<220> FEATURE:
<221> NAME/KEY: MISC_FEATURE
```

```
<222> LOCATION: (4)..(4)
<223> OTHER INFORMATION: Xaa is Lys, Bolton-Hunter-modified Lys, Ala,
      Ser, or Arg
<220> FEATURE:
<221> NAME/KEY: MISC_FEATURE
<222> LOCATION: (7)..(7)
<223> OTHER INFORMATION: Xaa is Ala, Gly, or His
<220> FEATURE:
<221> NAME/KEY: MISC_FEATURE
<222> LOCATION: (9)..(9)
<223> OTHER INFORMATION: Xaa is Gly or Ala
<220> FEATURE:
<221> NAME/KEY: MISC_FEATURE
<222> LOCATION: (12)..(12)
<223> OTHER INFORMATION: Xaa is Ala or Pro
<220> FEATURE:
<221> NAME/KEY: MISC_FEATURE
<222> LOCATION: (13)..(13)
<223> OTHER INFORMATION: Xaa is Ser or Pro
<220> FEATURE:
<221> NAME/KEY: MISC_FEATURE
<222> LOCATION: (14)..(14)
<223> OTHER INFORMATION: Xaa is Pro, Ala, or Ser
<220> FEATURE:
<221> NAME/KEY: MISC_FEATURE
<222> LOCATION: (16)..(16)
<223> OTHER INFORMATION: Xaa is Glu or Asp
<220> FEATURE:
<221> NAME/KEY: MISC_FEATURE
<222> LOCATION: (17)..(17)
<223> OTHER INFORMATION: Xaa is Leu or Ile
<220> FEATURE:
<221> NAME/KEY: MISC_FEATURE
<222> LOCATION: (18)..(18)
<223> OTHER INFORMATION: Xaa is Asn or Ala
<220> FEATURE:
<221> NAME/KEY: MISC_FEATURE
<222> LOCATION: (19)..(19)
<223> OTHER INFORMATION: Xaa is Arg, Lys, Bolton-Hunter-modified Lys,
      Gln, or N(Me)Ala
<220> FEATURE:
<221> NAME/KEY: MISC_FEATURE
<222> LOCATION: (21)..(21)
<223> OTHER INFORMATION: Xaa is Tyr, Ala, Phe, Lys or Bolton-Hunter-
      modified Lys
<220> FEATURE:
<221> NAME/KEY: MISC_FEATURE
<222> LOCATION: (22)..(22)
<223> OTHER INFORMATION: Xaa is Ala or Ser
<220> FEATURE:
<221> NAME/KEY: MISC_FEATURE
<222> LOCATION: (23)..(23)
<223> OTHER INFORMATION: Xaa is Ser, Ala, or Asp
<220> FEATURE:
<221> NAME/KEY: MISC_FEATURE
<222> LOCATION: (25)..(25)
<223> OTHER INFORMATION: Xaa is Arg, Lys or Bolton-Hunter-modified Lys
<220> FEATURE:
<221> NAME/KEY: MISC_FEATURE
<222> LOCATION: (26)..(26)
<223> OTHER INFORMATION: Xaa is His, Ala, or Arg
<220> FEATURE:
<221> NAME/KEY: MISC_FEATURE
<222> LOCATION: (28)..(28)
<223> OTHER INFORMATION: Xaa is Leu or Ile
<220> FEATURE:
<221> NAME/KEY: MISC_FEATURE
<222> LOCATION: (30)..(30)
<223> OTHER INFORMATION: Xaa is Leu or Met
<220> FEATURE:
<221> NAME/KEY: MISC_FEATURE
<222> LOCATION: (31)..(31)
<223> OTHER INFORMATION: Xaa is Val, Ile, or Leu
<220> FEATURE:
<221> NAME/KEY: MISC_FEATURE
<222> LOCATION: (35)..(35)
<223> OTHER INFORMATION: Xaa is Lys, Bolton-Hunter-modified Lys, or Arg
<220> FEATURE:
<221> NAME/KEY: MISC_FEATURE
<222> LOCATION: (36)..(36)
```

<223> OTHER INFORMATION: Xaa is Tyr, Trp, or Phe

<400> SEQUENCE: 574

Xaa Xaa Xaa Xaa Pro Glu Xaa Pro Xaa Glu Asp Xaa Xaa Glu Xaa
1               5                   10                  15

Xaa Xaa Xaa Tyr Xaa Xaa Xaa Leu Xaa Xaa Tyr Xaa Asn Xaa Xaa Thr
            20                  25                  30

Arg Gln Xaa Xaa
        35

<210> SEQ ID NO 575
<211> LENGTH: 36
<212> TYPE: PRT
<213> ORGANISM: Artificial
<220> FEATURE:
<223> OTHER INFORMATION: PPF genus
<220> FEATURE:
<221> NAME/KEY: MISC_FEATURE
<222> LOCATION: (1)..(1)
<223> OTHER INFORMATION: Xaa is Tyr or absent
<220> FEATURE:
<221> NAME/KEY: MISC_FEATURE
<222> LOCATION: (2)..(2)
<223> OTHER INFORMATION: Xaa is Ile, Pro, or absent
<220> FEATURE:
<221> NAME/KEY: MISC_FEATURE
<222> LOCATION: (4)..(4)
<223> OTHER INFORMATION: Xaa is Lys, Bolton-Hunter-modified Lys, Ala,
      Ser, or Arg
<220> FEATURE:
<221> NAME/KEY: MISC_FEATURE
<222> LOCATION: (6)..(6)
<223> OTHER INFORMATION: Xaa is Glu, Gln, Ala, Asn, Asp, or Val
<220> FEATURE:
<221> NAME/KEY: MISC_FEATURE
<222> LOCATION: (9)..(9)
<223> OTHER INFORMATION: Xaa is Gly or Ala
<220> FEATURE:
<221> NAME/KEY: MISC_FEATURE
<222> LOCATION: (10)..(10)
<223> OTHER INFORMATION: Xaa is Glu, Ala, Asp, Asn, Gln, Gly, Pro, or
      Aib
<220> FEATURE:
<221> NAME/KEY: MISC_FEATURE
<222> LOCATION: (11)..(11)
<223> OTHER INFORMATION: Xaa is Glu, Ala, Asp, Asn, Gln, Gly, Pro, or
      Aib
<220> FEATURE:
<221> NAME/KEY: MISC_FEATURE
<222> LOCATION: (12)..(12)
<223> OTHER INFORMATION: Xaa is Ala or Pro
<220> FEATURE:
<221> NAME/KEY: MISC_FEATURE
<222> LOCATION: (13)..(13)
<223> OTHER INFORMATION: Xaa is Ser or Pro
<220> FEATURE:
<221> NAME/KEY: MISC_FEATURE
<222> LOCATION: (14)..(14)
<223> OTHER INFORMATION: Xaa is Pro, Ala, or Ser
<220> FEATURE:
<221> NAME/KEY: MISC_FEATURE
<222> LOCATION: (15)..(15)
<223> OTHER INFORMATION: Xaa is Glu, Ala, Asp, Asn, Gln, Gly, Pro, or
      Aib
<220> FEATURE:
<221> NAME/KEY: MISC_FEATURE
<222> LOCATION: (16)..(16)
<223> OTHER INFORMATION: Xaa is Glu or Asp
<220> FEATURE:
<221> NAME/KEY: MISC_FEATURE
<222> LOCATION: (17)..(17)
<223> OTHER INFORMATION: Xaa is Leu or Ile
<220> FEATURE:
<221> NAME/KEY: MISC_FEATURE
<222> LOCATION: (19)..(19)
<223> OTHER INFORMATION: Xaa is Arg, Lys, BH-modified Lys, Gln, or

```
                N(Me)Ala
<220> FEATURE:
<221> NAME/KEY: MISC_FEATURE
<222> LOCATION: (21)..(21)
<223> OTHER INFORMATION: Xaa is Tyr, Ala, Phe, Lys, or BH-modified Lys
<220> FEATURE:
<221> NAME/KEY: MISC_FEATURE
<222> LOCATION: (22)..(22)
<223> OTHER INFORMATION: Xaa is Ala or Ser
<220> FEATURE:
<221> NAME/KEY: MISC_FEATURE
<222> LOCATION: (23)..(23)
<223> OTHER INFORMATION: Xaa is Ser, Ala, or Asp
<220> FEATURE:
<221> NAME/KEY: MISC_FEATURE
<222> LOCATION: (25)..(25)
<223> OTHER INFORMATION: Xaa is Arg, Lys or Bolton-Hunter-modified Lys
<220> FEATURE:
<221> NAME/KEY: MISC_FEATURE
<222> LOCATION: (26)..(26)
<223> OTHER INFORMATION: Xaa is His, Ala, or Arg
<220> FEATURE:
<221> NAME/KEY: MISC_FEATURE
<222> LOCATION: (27)..(27)
<223> OTHER INFORMATION: Xaa is Tyr or Phe
<220> FEATURE:
<221> NAME/KEY: MISC_FEATURE
<222> LOCATION: (28)..(28)
<223> OTHER INFORMATION: Xaa is Leu or Ile
<220> FEATURE:
<221> NAME/KEY: MISC_FEATURE
<222> LOCATION: (29)..(29)
<223> OTHER INFORMATION: Xaa is Asn or Gln
<220> FEATURE:
<221> NAME/KEY: MISC_FEATURE
<222> LOCATION: (30)..(30)
<223> OTHER INFORMATION: Xaa is Leu or Met
<220> FEATURE:
<221> NAME/KEY: MISC_FEATURE
<222> LOCATION: (31)..(31)
<223> OTHER INFORMATION: Xaa is Val, Ile, or Leu

<400> SEQUENCE: 575

Xaa Xaa Pro Xaa Pro Xaa His Pro Xaa Xaa Xaa Xaa Xaa Xaa Xaa Xaa
1               5                   10                  15

Xaa Ala Xaa Tyr Xaa Xaa Xaa Leu Xaa Xaa Xaa Xaa Xaa Xaa Xaa Thr
            20                  25                  30

Arg Gln Arg Tyr
        35

<210> SEQ ID NO 576
<211> LENGTH: 34
<212> TYPE: PRT
<213> ORGANISM: Artificial
<220> FEATURE:
<223> OTHER INFORMATION: PPY-NPY chimera

<400> SEQUENCE: 576

Pro Lys Pro Glu His Pro Gly Glu Asp Ala Ser Pro Glu Glu Leu Ala
1               5                   10                  15

Arg Tyr Tyr Ala Ser Leu Arg Ala Tyr Ile Asn Leu Ile Thr Arg Gln
            20                  25                  30

Arg Tyr

<210> SEQ ID NO 577
<211> LENGTH: 36
<212> TYPE: PRT
<213> ORGANISM: Homo sapiens

<400> SEQUENCE: 577

Tyr Pro Ser Lys Pro Asp Asn Pro Gly Glu Asp Ala Pro Ala Glu Asp
```

```
                1               5                  10                  15
Met Ala Arg Tyr Tyr Ser Ala Leu Arg His Tyr Ile Asn Leu Ile Thr
                    20                  25                  30

Arg Gln Arg Tyr
            35

<210> SEQ ID NO 578
<211> LENGTH: 14
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is absent
<220> FEATURE:
<221> NAME/KEY: MISC_FEATURE
<222> LOCATION: (2)..(2)
<223> OTHER INFORMATION: Xaa is absent
<220> FEATURE:
<221> NAME/KEY: MISC_FEATURE
<222> LOCATION: (3)..(3)
<223> OTHER INFORMATION: Xaa is amino acid substitution or modification
      providing DPP-IV resistance
<220> FEATURE:
<221> NAME/KEY: MISC_FEATURE
<222> LOCATION: (4)..(4)
<223> OTHER INFORMATION: Xaa is amino acid substitution or modification
      providing DPP-IV resistance
<220> FEATURE:
<221> NAME/KEY: MISC_FEATURE
<222> LOCATION: (5)..(5)
<223> OTHER INFORMATION: Xaa is amino acid substitution or modification
      providing DPP-IV resistance
<220> FEATURE:
<221> NAME/KEY: MISC_FEATURE
<222> LOCATION: (6)..(6)
<223> OTHER INFORMATION: Xaa is Phe or Ala
<220> FEATURE:
<221> NAME/KEY: MISC_FEATURE
<222> LOCATION: (7)..(7)
<223> OTHER INFORMATION: Xaa is Ile or Ala
<220> FEATURE:
<221> NAME/KEY: MISC_FEATURE
<222> LOCATION: (8)..(8)
<223> OTHER INFORMATION: Xaa is Ser or Ala
<220> FEATURE:
<221> NAME/KEY: MISC_FEATURE
<222> LOCATION: (9)..(9)
<223> OTHER INFORMATION: Xaa is Asp or Ala
<220> FEATURE:
<221> NAME/KEY: MISC_FEATURE
<222> LOCATION: (10)..(10)
<223> OTHER INFORMATION: Xaa is Tyr or Ala
<220> FEATURE:
<221> NAME/KEY: MISC_FEATURE
<222> LOCATION: (11)..(11)
<223> OTHER INFORMATION: Xaa is Ser or Ala
<220> FEATURE:
<221> NAME/KEY: MISC_FEATURE
<222> LOCATION: (12)..(12)
<223> OTHER INFORMATION: Xaa is Ile, Ala, Ser, or Lys
<220> FEATURE:
<221> NAME/KEY: MISC_FEATURE
<222> LOCATION: (13)..(13)
<223> OTHER INFORMATION: Xaa is Ala, Tyr, Gln, or Asp
<220> FEATURE:
<221> NAME/KEY: MISC_FEATURE
<222> LOCATION: (14)..(14)
<223> OTHER INFORMATION: Xaa is Met, Ala, or Leu

<400> SEQUENCE: 578

Xaa Xaa Xaa Xaa Xaa Xaa Xaa Xaa Xaa Xaa Xaa Xaa Xaa Xaa
1               5                   10
```

<210> SEQ ID NO 579
<211> LENGTH: 39
<212> TYPE: PRT
<213> ORGANISM: Artificial
<220> FEATURE:
<223> OTHER INFORMATION: synthetic

<400> SEQUENCE: 579

Tyr Ala Glu Gly Thr Phe Ile Ser Asp Tyr Ser Ile Ala Met Asp Lys
1               5                   10                  15

Ile Lys Gln Gln Asp Phe Val Asn Trp Leu Leu Ala Gln Lys Pro Ser
            20                  25                  30

Ser Gly Ala Pro Pro Pro Ser
        35

<210> SEQ ID NO 580
<211> LENGTH: 39
<212> TYPE: PRT
<213> ORGANISM: Artificial
<220> FEATURE:
<223> OTHER INFORMATION: synthetic

<400> SEQUENCE: 580

Tyr Ala Glu Gly Thr Phe Ile Ser Asp Tyr Ser Ile Ala Met Asp Lys
1               5                   10                  15

Ile Ala Gln Gln Asp Phe Val Asn Trp Leu Leu Ala Gln Lys Pro Ser
            20                  25                  30

Ser Gly Ala Pro Pro Pro Ser
        35

<210> SEQ ID NO 581
<211> LENGTH: 39
<212> TYPE: PRT
<213> ORGANISM: Artificial
<220> FEATURE:
<223> OTHER INFORMATION: synthetic

<400> SEQUENCE: 581

Tyr Ala Glu Gly Thr Phe Ile Ser Glu Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 582
<211> LENGTH: 39
<212> TYPE: PRT
<213> ORGANISM: Artificial
<220> FEATURE:
<223> OTHER INFORMATION: synthetic

<400> SEQUENCE: 582

Tyr Ala Glu Gly Thr Phe Ile Ser Asp Tyr Ser Ile Ala Met Asp Lys
1               5                   10                  15

Ile His Gln Gln Glu Phe Val Asn Trp Leu Leu Ala Gln Lys Pro Ser
            20                  25                  30

Ser Gly Ala Pro Pro Pro Ser
        35

<210> SEQ ID NO 583
<211> LENGTH: 39
<212> TYPE: PRT

```
<213> ORGANISM: Artificial
<220> FEATURE:
<223> OTHER INFORMATION: synthetic

<400> SEQUENCE: 583

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Leu Ala Gln Lys Pro Ser
            20                  25                  30

Ser Gly Ala Pro Pro Pro Ser
        35

<210> SEQ ID NO 584
<211> LENGTH: 39
<212> TYPE: PRT
<213> ORGANISM: Artificial
<220> FEATURE:
<223> OTHER INFORMATION: synthetic

<400> SEQUENCE: 584

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Ala Pro Ser
            20                  25                  30

Ser Gly Ala Pro Pro Pro Ser
        35

<210> SEQ ID NO 585
<211> LENGTH: 39
<212> TYPE: PRT
<213> ORGANISM: Artificial
<220> FEATURE:
<223> OTHER INFORMATION: synthetic

<400> SEQUENCE: 585

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Arg Pro Ser
            20                  25                  30

Ser Gly Ala Pro Pro Pro Ser
        35

<210> SEQ ID NO 586
<211> LENGTH: 39
<212> TYPE: PRT
<213> ORGANISM: Artificial
<220> FEATURE:
<223> OTHER INFORMATION: synthetic

<400> SEQUENCE: 586

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln His Pro Ser
            20                  25                  30

Ser Gly Ala Pro Pro Pro Ser
        35

<210> SEQ ID NO 587
<211> LENGTH: 40
<212> TYPE: PRT
<213> ORGANISM: Artificial
<220> FEATURE:
<223> OTHER INFORMATION: synthetic
<220> FEATURE:
```

```
<221> NAME/KEY: MOD_RES
<222> LOCATION: (31)..(31)
<223> OTHER INFORMATION: beta-Ala-beta-Ala

<400> SEQUENCE: 587
```

Tyr Ala Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Xaa Pro
            20                  25                  30

Ser Ser Gly Ala Pro Pro Ser
        35                  40

```
<210> SEQ ID NO 588
<211> LENGTH: 39
<212> TYPE: PRT
<213> ORGANISM: Artificial
<220> FEATURE:
<223> OTHER INFORMATION: synthetic

<400> SEQUENCE: 588
```

Tyr Ala Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

```
<210> SEQ ID NO 589
<211> LENGTH: 42
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (31)..(31)
<223> OTHER INFORMATION: 8-amino 3,6-dioxaoctanoyl

<400> SEQUENCE: 589
```

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
            20                  25                  30

Ser Ser Gly Ala Pro Pro Ser Asn His
        35                  40

```
<210> SEQ ID NO 590
<211> LENGTH: 37
<212> TYPE: PRT
<213> ORGANISM: Artificial
<220> FEATURE:
<223> OTHER INFORMATION: synthetic

<400> SEQUENCE: 590
```

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ser Gly
            20                  25                  30

Ala Pro Pro Pro Ser
        35

```
<210> SEQ ID NO 591
<211> LENGTH: 39
<212> TYPE: PRT
```

```
<213> ORGANISM: Artificial
<220> FEATURE:
<223> OTHER INFORMATION: synthetic
<220> FEATURE:
<221> NAME/KEY: MOD_RES
<222> LOCATION: (16)..(16)
<223> OTHER INFORMATION: octyl-Gly

<400> SEQUENCE: 591

Tyr Ala Glu Gly Thr Phe Ile Ser Asp Tyr Ser Ile Ala Met Asp Xaa
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 592
<211> LENGTH: 39
<212> TYPE: PRT
<213> ORGANISM: Artificial
<220> FEATURE:
<223> OTHER INFORMATION: synthetic

<400> SEQUENCE: 592

Tyr Ala Glu Gly Thr Phe Ile Ser Asp Tyr Ser Ile Thr Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 593
<211> LENGTH: 39
<212> TYPE: PRT
<213> ORGANISM: Artificial
<220> FEATURE:
<223> OTHER INFORMATION: synthetic

<400> SEQUENCE: 593

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ser Gln Lys Pro Ser
            20                  25                  30

Ser Gly Ala Pro Pro Pro Ser
        35

<210> SEQ ID NO 594
<211> LENGTH: 39
<212> TYPE: PRT
<213> ORGANISM: Artificial
<220> FEATURE:
<223> OTHER INFORMATION: synthetic

<400> SEQUENCE: 594

Tyr Ala Glu Gly Thr Phe Ile Ser Asp Tyr Ser Ile Ala Met Asp Lys
1               5                   10                  15

Ile His Gln Gln Leu Phe Ile Glu Trp Leu Lys Asn Gly Gly Pro Ser
            20                  25                  30

Ser Gly Ala Pro Pro Pro Ser
        35

<210> SEQ ID NO 595
<211> LENGTH: 37
<212> TYPE: PRT
```

```
<213> ORGANISM: Artificial
<220> FEATURE:
<223> OTHER INFORMATION: synthetic

<400> SEQUENCE: 595

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 596
<211> LENGTH: 37
<212> TYPE: PRT
<213> ORGANISM: Artificial
<220> FEATURE:
<223> OTHER INFORMATION: synthetic

<400> SEQUENCE: 596

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Lys Glu Ile Ile Ser
        35

<210> SEQ ID NO 597
<211> LENGTH: 39
<212> TYPE: PRT
<213> ORGANISM: Artificial
<220> FEATURE:
<223> OTHER INFORMATION: synthetic

<400> SEQUENCE: 597

Tyr Ala Glu Gly Thr Phe Ile Ser Asp Tyr Ser Ile Ala Met Asp Lys
1               5                   10                  15

Ile His Gln Val Lys Phe Val Asn Trp Leu Leu Ala Gln Lys Pro Ser
            20                  25                  30

Ser Gly Ala Pro Pro Pro Ser
        35

<210> SEQ ID NO 598
<211> LENGTH: 37
<212> TYPE: PRT
<213> ORGANISM: Artificial
<220> FEATURE:
<223> OTHER INFORMATION: synthetic

<400> SEQUENCE: 598

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Thr Ser
            20                  25                  30

Pro Arg Pro Pro Ser
        35

<210> SEQ ID NO 599
<211> LENGTH: 39
<212> TYPE: PRT
<213> ORGANISM: Artificial
<220> FEATURE:
<223> OTHER INFORMATION: synthetic
<220> FEATURE:
```

```
<221> NAME/KEY: MOD_RES
<222> LOCATION: (34)..(34)
<223> OTHER INFORMATION: octyl-Gly

<400> SEQUENCE: 599

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Xaa Ala Pro Pro Pro Ser
        35

<210> SEQ ID NO 600
<211> LENGTH: 39
<212> TYPE: PRT
<213> ORGANISM: Artificial
<220> FEATURE:
<223> OTHER INFORMATION: synthetic

<400> SEQUENCE: 600

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Arg Pro Ser
            20                  25                  30

Ser Gly Ala Pro Pro Pro Ser
        35

<210> SEQ ID NO 601
<211> LENGTH: 39
<212> TYPE: PRT
<213> ORGANISM: Artificial
<220> FEATURE:
<223> OTHER INFORMATION: synthetic

<400> SEQUENCE: 601

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Arg Pro Ser
            20                  25                  30

Ser Gly Ala Pro Pro Pro Ser
        35

<210> SEQ ID NO 602
<211> LENGTH: 39
<212> TYPE: PRT
<213> ORGANISM: Artificial
<220> FEATURE:
<223> OTHER INFORMATION: synthetic

<400> SEQUENCE: 602

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Arg Pro Ser
            20                  25                  30

Ser Gly Ala Pro Pro Pro Ser
        35

<210> SEQ ID NO 603
<211> LENGTH: 39
<212> TYPE: PRT
<213> ORGANISM: Artificial
<220> FEATURE:
<223> OTHER INFORMATION: synthetic
```

-continued

<400> SEQUENCE: 603

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Ser
            20                  25                  30

Ser Gly Ala Pro Pro Ser
        35

<210> SEQ ID NO 604
<211> LENGTH: 39
<212> TYPE: PRT
<213> ORGANISM: Artificial
<220> FEATURE:
<223> OTHER INFORMATION: synthetic

<400> SEQUENCE: 604

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Lys Pro Ser
            20                  25                  30

Ser Gly Ala Pro Pro Ser
        35

<210> SEQ ID NO 605
<211> LENGTH: 39
<212> TYPE: PRT
<213> ORGANISM: Artificial
<220> FEATURE:
<223> OTHER INFORMATION: synthetic

<400> SEQUENCE: 605

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Ser
        35

<210> SEQ ID NO 606
<211> LENGTH: 39
<212> TYPE: PRT
<213> ORGANISM: Artificial
<220> FEATURE:
<223> OTHER INFORMATION: synthetic

<400> SEQUENCE: 606

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His Pro Ser
            20                  25                  30

Ser Gly Ala Pro Pro Ser
        35

<210> SEQ ID NO 607
<211> LENGTH: 39
<212> TYPE: PRT
<213> ORGANISM: Artificial
<220> FEATURE:
<223> OTHER INFORMATION: synthetic

<400> SEQUENCE: 607

Tyr Ala Glu Gly Thr Phe Thr Ala Asp Tyr Ser Lys Ala Leu Asp Lys
1               5                   10                  15

```
Ile His Gln Gln Asp Phe Val Asn Trp Leu Leu Ala Gln Lys Pro Ser
            20                  25                  30

Ser Gly Ala Pro Pro Ser
            35

<210> SEQ ID NO 608
<211> LENGTH: 39
<212> TYPE: PRT
<213> ORGANISM: Artificial
<220> FEATURE:
<223> OTHER INFORMATION: synthetic

<400> SEQUENCE: 608

Tyr Ala Glu Gly Thr Phe Ile Ser Asp Tyr Ser Ile Ala Met Asp Lys
1               5                   10                  15

Ile Arg Gln Gln Glu Phe Val Asn Trp Leu Leu Ala Gln Lys Pro Ser
            20                  25                  30

Ser Gly Ala Pro Pro Ser
            35

<210> SEQ ID NO 609
<211> LENGTH: 39
<212> TYPE: PRT
<213> ORGANISM: Artificial
<220> FEATURE:
<223> OTHER INFORMATION: synthetic

<400> SEQUENCE: 609

Tyr Ala Glu Gly Thr Phe Ile Ser Asp Tyr Ser Ile Ala Leu Asp Lys
1               5                   10                  15

Ile Arg Gln Gln Asp Phe Val Glu Trp Leu Leu Ala Gln Lys Pro Ser
            20                  25                  30

Ser Gly Ala Pro Pro Ser
            35

<210> SEQ ID NO 610
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: octyl-Gly
<220> FEATURE:
<221> NAME/KEY: MOD_RES
<222> LOCATION: (32)..(32)
<223> OTHER INFORMATION: beta-Ala-beta-Ala

<400> SEQUENCE: 610

Xaa Tyr Ala Glu Gly Thr Phe Ile Ser Asp Tyr Ser Ile Ala Leu Asp
1               5                   10                  15

Lys Ile His Gln Gln Asp Phe Val Asn Trp Leu Leu Ala Gln Lys Xaa
            20                  25                  30

Pro Ser Ser Gly Ala Pro Pro Ser
            35                  40

<210> SEQ ID NO 611
<211> LENGTH: 39
<212> TYPE: PRT
<213> ORGANISM: Artificial
<220> FEATURE:
<223> OTHER INFORMATION: synthetic
<220> FEATURE:
```

```
<221> NAME/KEY: MOD_RES
<222> LOCATION: (14)..(14)
<223> OTHER INFORMATION: octyl-Gly

<400> SEQUENCE: 611

Tyr Ala Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 612
<211> LENGTH: 35
<212> TYPE: PRT
<213> ORGANISM: Artificial
<220> FEATURE:
<223> OTHER INFORMATION: synthetic

<400> SEQUENCE: 612

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Thr Ser
            20                  25                  30

Pro Pro Pro
        35

<210> SEQ ID NO 613
<211> LENGTH: 39
<212> TYPE: PRT
<213> ORGANISM: Artificial
<220> FEATURE:
<223> OTHER INFORMATION: synthetic

<400> SEQUENCE: 613

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Leu Ile Lys Leu Ile Lys Ser
        35

<210> SEQ ID NO 614
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (30)..(30)
<223> OTHER INFORMATION: Lysine linked via N-epsilon to Pro in tail

<400> SEQUENCE: 614

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Xaa Pro Ser
            20                  25                  30

Ser Gly Ala Pro Pro Pro Ser
        35

<210> SEQ ID NO 615
<211> LENGTH: 37
<212> TYPE: PRT
```

```
<213> ORGANISM: Artificial
<220> FEATURE:
<223> OTHER INFORMATION: synthetic

<400> SEQUENCE: 615

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Lys
            20                  25                  30

Lys Ile Arg Tyr Ser
            35

<210> SEQ ID NO 616
<211> LENGTH: 37
<212> TYPE: PRT
<213> ORGANISM: Artificial
<220> FEATURE:
<223> OTHER INFORMATION: synthetic

<400> SEQUENCE: 616

Tyr Ala Glu Gly Thr Phe Ile Ser Asp Tyr Ser Ile Ala Leu Asp Lys
1               5                   10                  15

Ile Arg Gln Gln Asp Phe Val Glu Trp Leu Leu Ala Gln Lys Pro Lys
            20                  25                  30

Lys Ile Arg Tyr Ser
            35

<210> SEQ ID NO 617
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: octyl-Gly
<220> FEATURE:
<221> NAME/KEY: MOD_RES
<222> LOCATION: (32)..(32)
<223> OTHER INFORMATION: beta-Ala-beta-Ala

<400> SEQUENCE: 617

Xaa Tyr Ala Pro Gly Thr Phe Ile Ser Asp Tyr Ser Ile Ala Leu Asp
1               5                   10                  15

Lys Ile His Gln Gln Asp Phe Val Asn Trp Leu Leu Ala Gln Lys Xaa
            20                  25                  30

Pro Ser Ser Gly Ala Pro Pro Pro Ser
            35                  40

<210> SEQ ID NO 618
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: octyl-Gly

<400> SEQUENCE: 618

Xaa Tyr Ala Pro Gly Thr Phe Ile Ser Asp Tyr Ser Ile Ala Leu Asp
1               5                   10                  15

Lys Ile Arg Gln Gln Glu Phe Val Asn Trp Leu Leu Ala Gln His Pro
            20                  25                  30
```

```
Ser Ser Gly Ala Pro Pro Ser
        35                  40

<210> SEQ ID NO 619
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (14)..(14)
<223> OTHER INFORMATION: octyl-Lys

<400> SEQUENCE: 619

Tyr Ala Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 620
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 620

Xaa Tyr Ala Glu Gly Thr Phe Ile Ser Asp Tyr Ser Ile Ala Met Asp
1               5                   10                  15

Lys Ile Arg Gln Gln Glu Phe Val Asn Trp Leu Leu Ala Gln His Pro
            20                  25                  30

Lys Lys Ile Arg Tyr Ser
        35

<210> SEQ ID NO 621
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Octyl-Gly

<400> SEQUENCE: 621

Xaa Tyr Ala Glu Gly Thr Phe Ile Ser Asp Tyr Ser Ile Ala Met Asp
1               5                   10                  15

Lys Ile Arg Gln Gln Glu Phe Val Asn Trp Leu Leu Ala Gln His Pro
            20                  25                  30

Ser Ser Gly Ala Pro Pro Ser
        35                  40

<210> SEQ ID NO 622
<211> LENGTH: 40
<212> TYPE: PRT
<213> ORGANISM: Artificial
<220> FEATURE:
<223> OTHER INFORMATION: synthetic
```

```
<220> FEATURE:
<221> NAME/KEY: MISC_FEATURE
<222> LOCATION: (1)..(1)
<223> OTHER INFORMATION: Xaa is octyl-Gly

<400> SEQUENCE: 622

Xaa Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 623
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Gly

<400> SEQUENCE: 623

Xaa Tyr Ala Glu Gly Thr Phe Ile Ser Asp Tyr Ser Ile Ala Met Asp
1               5                   10                  15

Lys Ile Arg Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 624
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Gly

<400> SEQUENCE: 624

Xaa Tyr Ala Glu Gly Thr Phe Ile Ser Asp Tyr Ser Ile Ala Leu Asp
1               5                   10                  15

Lys Ile Arg Gln Gln Glu Phe Val Asn Trp Leu Leu Ala Gln His Pro
            20                  25                  30

Ser Ser Gly Ala Pro Pro Pro Ser
        35                  40

<210> SEQ ID NO 625
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 625

Xaa Tyr Ala Glu Gly Thr Phe Ile Ser Asp Tyr Ser Ile Ala Leu Asp
1               5                   10                  15

Lys Ile Ala Gln Gln Glu Phe Val Asn Trp Leu Leu Ala Gln Lys Pro
```

```
                20                  25                  30

Ser Ser Gly Ala Pro Pro Ser
        35                  40

<210> SEQ ID NO 626
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(34)
<223> OTHER INFORMATION: Xaa is octyl-Gly

<400> SEQUENCE: 626

Tyr Ala Glu Gly Thr Phe Ile Ser Asp Tyr Ser Ile Ala Leu Asp Lys
1               5                  10                  15

Ile His Gln Gln Asp Phe Val Asn Trp Leu Leu Ala Gln Lys Pro Ser
                20                  25                  30

Ser Xaa Ala Pro Pro Pro Ser
        35

<210> SEQ ID NO 627
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(34)
<223> OTHER INFORMATION: Xaa is octyl-Gly

<400> SEQUENCE: 627

Tyr Ala Glu Gly Thr Phe Ile Ser Asp Tyr Ser Ile Ala Leu Asp Lys
1               5                  10                  15

Ile Arg Gln Gln Glu Phe Val Asn Trp Leu Leu Ala Gln Lys Pro Ser
                20                  25                  30

Ser Xaa Ala Pro Pro Pro Ser
        35

<210> SEQ ID NO 628
<211> LENGTH: 37
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: Xaa is octyl-Gly

<400> SEQUENCE: 628

Tyr Ala Glu Gly Thr Phe Ile Ser Asp Tyr Ser Ile Ala Xaa Asp Lys
1               5                  10                  15

Ile His Gln Gln Asp Phe Val Asn Trp Leu Leu Ala Gln Lys Pro Lys
                20                  25                  30

Lys Ile Arg Tyr Ser
        35

<210> SEQ ID NO 629
<211> LENGTH: 40
<212> TYPE: PRT
<213> ORGANISM: Artificial
<220> FEATURE:
```

```
<223> OTHER INFORMATION: synthetic
<220> FEATURE:
<221> NAME/KEY: MISC_FEATURE
<222> LOCATION: (14)..(14)
<223> OTHER INFORMATION: Xaa is octyl-Gly
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 629

Tyr Ala Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Xaa Pro
            20                  25                  30

Ser Ser Gly Ala Pro Pro Pro Ser
        35                  40

<210> SEQ ID NO 630
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: Xaa is octyl-Gly

<400> SEQUENCE: 630

Tyr Ala Glu Gly Thr Phe Ile Ser Asp Tyr Ser Ile Ala Xaa Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Pro Ser
        35

<210> SEQ ID NO 631
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (40)..(40)
<223> OTHER INFORMATION: Xaa is octyl-Gly

<400> SEQUENCE: 631

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser Xaa
        35                  40

<210> SEQ ID NO 632
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: epsilon-NH-octanoyl
<220> FEATURE:
<221> NAME/KEY: MISC_FEATURE
```

```
<222> LOCATION: (41)..(41)
<223> OTHER INFORMATION: octyl-GLy

<400> SEQUENCE: 632

Lys Tyr Ala Glu Gly Thr Phe Ile Ser Tyr Asp Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser Xaa
        35                  40

<210> SEQ ID NO 633
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: epsilon-NH-octanoyl

<400> SEQUENCE: 633

Lys Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 634
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: (EPSILON-NH-(2-(2-
      (2METHOXYETOXY)ETHOXY)ACETOYL))
<220> FEATURE:
<221> NAME/KEY: MISC_FEATURE
<222> LOCATION: (41)..(41)
<223> OTHER INFORMATION: Xaa is ocytl-Gly

<400> SEQUENCE: 634

Lys Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser Xaa
        35                  40

<210> SEQ ID NO 635
<211> LENGTH: 37
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(34)
<223> OTHER INFORMATION: (EPSILON-NH-(PALMITOYL))

<400> SEQUENCE: 635

Tyr Ala Glu Gly Thr Phe Ile Ser Asp Tyr Ser Ile Ala Lys Asp Lys
```

```
                1               5                  10                 15
Ile His Gln Gln Asp Phe Val Asn Trp Leu Leu Ala Gln Lys Pro Lys
                20                 25                 30

Lys Lys Arg Tyr Ser
            35

<210> SEQ ID NO 636
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: (EPSILON-NH-(2-(2-
      (2METHOXYETOXY)ETHOXY)ACETOYL))

<400> SEQUENCE: 636

Lys Tyr Ala Glu Gly Thr Phe Ile Ser Asp Tyr Ser Ile Ala Met Asp
1               5                  10                 15

Lys Ile His Gln Gln Asp Phe Val Asn Trp Leu Leu Ala Gln Lys Pro
                20                 25                 30

Ser Ser Gly Ala Pro Pro Pro Ser
            35                  40

<210> SEQ ID NO 637
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 637

Tyr Ala Glu Gly Thr Phe Ile Ser Asp Tyr Ser Ile Ala Met Asp Lys
1               5                  10                 15

Ile His Gln Gln Asp Phe Val Asn Trp Leu Leu Ala Gln Lys Xaa Pro
                20                 25                 30

Ser Ser Gly Ala Pro Pro Pro Ser
            35                  40

<210> SEQ ID NO 638
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Gly
<220> FEATURE:
<221> NAME/KEY: MISC_FEATURE
<222> LOCATION: (32)..(32)
<223> OTHER INFORMATION: Xaa is beta-Ala-beta-Ala

<400> SEQUENCE: 638

Xaa Tyr Ala Glu Gly Thr Phe Ile Ser Asp Tyr Ser Ile Ala Met Asp
1               5                  10                 15

Lys Ile His Gln Gln Asp Phe Val Asn Trp Leu Leu Ala Gln Lys Xaa
                20                 25                 30

Pro Ser Ser Gly Ala Pro Pro Pro Ser
```

35          40

<210> SEQ ID NO 639
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 639

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
            20                  25                  30

Ser Ser Gly Ala Pro Pro Pro Ser
        35                  40

<210> SEQ ID NO 640
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 640

Tyr Ala Glu Gly Thr Phe Ile Ser Asp Tyr Ser Ile Ala Met Asp Lys
1               5                   10                  15

Ile Arg Gln Gln Glu Phe Val Asn Trp Leu Leu Ala Gln Lys Xaa Pro
            20                  25                  30

Ser Ser Gly Ala Pro Pro Pro Ser
        35                  40

<210> SEQ ID NO 641
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 641

Tyr Ala Glu Gly Thr Phe Ile Ser Asp Tyr Ser Ile Ala Met Asp Lys
1               5                   10                  15

Ile Arg Gln Gln Asp Phe Val Glu Trp Leu Leu Ala Gln Lys Xaa Pro
            20                  25                  30

Ser Ser Gly Ala Pro Pro Pro Ser
        35                  40

<210> SEQ ID NO 642
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE

```
<222> LOCATION: (1)..(1)
<223> OTHER INFORMATION: octyl-Gly
<220> FEATURE:
<221> NAME/KEY: MISC_FEATURE
<222> LOCATION: (32)..(32)
<223> OTHER INFORMATION: Xaa is beta-Ala-beta-Ala

<400> SEQUENCE: 642

Xaa Tyr Ala Glu Gly Thr Phe Ile Ser Asp Tyr Ser Ile Ala Met Asp
1               5                   10                  15

Lys Ile Arg Gln Gln Glu Phe Val Asn Trp Leu Leu Ala Gln His Xaa
            20                  25                  30

Pro Ser Ser Gly Ala Pro Pro Pro Ser
        35                  40

<210> SEQ ID NO 643
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 643

Tyr Ala Glu Gly Thr Phe Ile Ser Asp Tyr Ser Ile Ala Met Asp Lys
1               5                   10                  15

Ile Ala Gln Gln Glu Phe Val Asn Trp Leu Leu Ala Gln Lys Xaa Pro
            20                  25                  30

Ser Ser Gly Ala Pro Pro Pro Ser
        35                  40

<210> SEQ ID NO 644
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is Aca

<400> SEQUENCE: 644

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
            20                  25                  30

Ser Ser Gly Ala Pro Pro Pro Ser
        35                  40

<210> SEQ ID NO 645
<211> LENGTH: 39
<212> TYPE: PRT
<213> ORGANISM: Artificial
<220> FEATURE:
<223> OTHER INFORMATION: synhtetic
<220> FEATURE:
<221> NAME/KEY: MISC_FEATURE
<222> LOCATION: (6)..(6)
<223> OTHER INFORMATION: Xaa is D-Nal2

<400> SEQUENCE: 645

Tyr Ala Glu Gly Thr Xaa Ile Ser Asp Tyr Ser Ile Ala Met Asp Lys
1               5                   10                  15
```

-continued

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 646
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (10)..(10)
<223> OTHER INFORMATION: Xaa is D-Nal2

<400> SEQUENCE: 646

Tyr Ala Glu Gly Thr Phe Ile Ser Asp Xaa Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 647
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: Xaa is D-Nal2

<400> SEQUENCE: 647

Tyr Ala Glu Gly Thr Phe Ile Ser Asp Tyr Ser Ile Ala Xaa Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 648
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (22)..(22)
<223> OTHER INFORMATION: Xaa is D-Nal2

<400> SEQUENCE: 648

Tyr Ala Glu Gly Thr Phe Ile Ser Asp Tyr Ser Ile Ala Met Asp Lys
1               5                   10                  15

Ile His Gln Gln Asp Xaa Val Asn Trp Leu Leu Ala Gln Lys Pro Ser
            20                  25                  30

Ser Gly Ala Pro Pro Ser
        35

<210> SEQ ID NO 649
<211> LENGTH: 39
<212> TYPE: PRT

-continued

```
<213> ORGANISM: Artificial
<220> FEATURE:
<223> OTHER INFORMATION: synthetic
<220> FEATURE:
<221> NAME/KEY: MISC_FEATURE
<222> LOCATION: (25)..(25)
<223> OTHER INFORMATION: Xaa is D-Nal2

<400> SEQUENCE: 649

Tyr Ala Glu Gly Thr Phe Ile Ser Asp Tyr Ser Ile Ala Met Asp Lys
1               5                   10                  15

Ile His Gln Gln Asp Phe Val Asn Xaa Leu Leu Ala Gln Lys Pro Ser
            20                  25                  30

Ser Gly Ala Pro Pro Ser
        35

<210> SEQ ID NO 650
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: (EPSILON-NH-(AUN-AUN-(2-(2METHOXYETHOXY)-
      ACETOYL)))

<400> SEQUENCE: 650

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 651
<211> LENGTH: 39
<212> TYPE: PRT
<213> ORGANISM: Artificial
<220> FEATURE:
<223> OTHER INFORMATION: synthetic

<400> SEQUENCE: 651

Tyr Ala Glu Gly Thr Phe Ile Ser Asp Tyr Ser Ile Ala Met Asp Lys
1               5                   10                  15

Ile Arg Gln Gln Asp Phe Val Asn Trp Leu Glu Ala Gln Glu Pro Ser
            20                  25                  30

Ser Gly Ala Pro Pro Ser
        35

<210> SEQ ID NO 652
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is a linker

<400> SEQUENCE: 652

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
```

```
                    20                  25                  30

Ser Ser Gly Ala Pro Pro Ser
        35                  40

<210> SEQ ID NO 653
<211> LENGTH: 38
<212> TYPE: PRT
<213> ORGANISM: Artificial
<220> FEATURE:
<223> OTHER INFORMATION: synthetic

<400> SEQUENCE: 653

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Arg Pro Ser
                20                  25                  30

Ser Gly Ala Pro Pro
        35

<210> SEQ ID NO 654
<211> LENGTH: 39
<212> TYPE: PRT
<213> ORGANISM: Artificial
<220> FEATURE:
<223> OTHER INFORMATION: synthetic

<400> SEQUENCE: 654

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His Pro Ser
                20                  25                  30

Ser Gly Ala Pro Pro Ser
        35

<210> SEQ ID NO 655
<211> LENGTH: 39
<212> TYPE: PRT
<213> ORGANISM: Artificial
<220> FEATURE:
<223> OTHER INFORMATION: synthetic

<400> SEQUENCE: 655

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln His Pro Ser
                20                  25                  30

Ser Gly Ala Pro Pro Ser
        35

<210> SEQ ID NO 656
<211> LENGTH: 39
<212> TYPE: PRT
<213> ORGANISM: Artificial
<220> FEATURE:
<223> OTHER INFORMATION: synthetic

<400> SEQUENCE: 656

Tyr Ala Glu Gly Thr Phe Thr Ser Asp Tyr Ser Lys Ala Leu Asp Lys
1               5                   10                  15

Ile His Gln Gln Asp Phe Val Asn Trp Leu Leu Ala Gln Lys Pro Ser
                20                  25                  30

Ser Gly Ala Pro Pro Ser
        35
```

```
<210> SEQ ID NO 657
<211> LENGTH: 39
<212> TYPE: PRT
<213> ORGANISM: Artificial
<220> FEATURE:
<223> OTHER INFORMATION: synthetic

<400> SEQUENCE: 657

Tyr Ala Glu Gly Thr Phe Ile Ser Asp Tyr Ser Lys Ala Met Asp Lys
1               5                   10                  15

Ile Arg Gln Gln Glu Phe Val Asn Trp Leu Leu Ala Gln Lys Pro Ser
            20                  25                  30

Ser Gly Ala Pro Pro Pro Ser
        35

<210> SEQ ID NO 658
<211> LENGTH: 39
<212> TYPE: PRT
<213> ORGANISM: Artificial
<220> FEATURE:
<223> OTHER INFORMATION: synthetic

<400> SEQUENCE: 658

Tyr Ala Glu Gly Thr Phe Ile Ser Asp Tyr Ser Ile Ala Leu Glu Lys
1               5                   10                  15

Ile Arg Gln Gln Lys Phe Val Asn Trp Leu Leu Ala Gln Lys Pro Ser
            20                  25                  30

Ser Gly Ala Pro Pro Pro Ser
        35

<210> SEQ ID NO 659
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala

<400> SEQUENCE: 659

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Xaa Pro
            20                  25                  30

Ser Ser Gly Ala Pro Pro Pro Ser
        35                  40

<210> SEQ ID NO 660
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-ALa

<400> SEQUENCE: 660

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Xaa Pro
```

-continued

```
                20                  25                  30
Ser Ser Gly Ala Pro Pro Ser
        35                  40
```

<210> SEQ ID NO 661
<211> LENGTH: 39
<212> TYPE: PRT
<213> ORGANISM: Artificial
<220> FEATURE:
<223> OTHER INFORMATION: synthetic

<400> SEQUENCE: 661

```
Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys Pro Ser
                20                  25                  30

Ser Gly Ala Pro Pro Ser
        35
```

<210> SEQ ID NO 662
<211> LENGTH: 39
<212> TYPE: PRT
<213> ORGANISM: Artificial
<220> FEATURE:
<223> OTHER INFORMATION: synthetic

<400> SEQUENCE: 662

```
Tyr Ala Glu Gly Thr Phe Ile Ser Asp Tyr Ser Ile Ala Met Asp Lys
1               5                   10                  15

Ile Leu Gln Gln Asp Phe Val Asn Trp Leu Ser Ala Gln Gln Pro Ser
                20                  25                  30

Ser Gly Ala Pro Pro Ser
        35
```

<210> SEQ ID NO 663
<211> LENGTH: 38
<212> TYPE: PRT
<213> ORGANISM: Artificial
<220> FEATURE:
<223> OTHER INFORMATION: synthetic

<400> SEQUENCE: 663

```
Leu Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
                20                  25                  30

Lys Lys Ile Arg Tyr Ser
        35
```

<210> SEQ ID NO 664
<211> LENGTH: 38
<212> TYPE: PRT
<213> ORGANISM: Artificial
<220> FEATURE:
<223> OTHER INFORMATION: synthetic

<400> SEQUENCE: 664

```
Leu Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
                20                  25                  30

Lys Lys Ile Arg Tyr Ser
        35
```

<210> SEQ ID NO 665
<211> LENGTH: 38
<212> TYPE: PRT
<213> ORGANISM: Artificial
<220> FEATURE:
<223> OTHER INFORMATION: synthetic

<400> SEQUENCE: 665

Ile Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Pro
            20                  25                  30

Lys Lys Ile Arg Tyr Ser
        35

<210> SEQ ID NO 666
<211> LENGTH: 38
<212> TYPE: PRT
<213> ORGANISM: Artificial
<220> FEATURE:
<223> OTHER INFORMATION: synthetic

<400> SEQUENCE: 666

Leu Tyr Ala Glu Gly Thr Phe Ile Ser Asp Tyr Ser Ile Ala Leu Asp
1               5                   10                  15

Lys Ile Ala Gln Gln Glu Phe Val Asn Trp Leu Leu Ala Gln Lys Pro
            20                  25                  30

Lys Lys Ile Arg Tyr Ser
        35

<210> SEQ ID NO 667
<211> LENGTH: 38
<212> TYPE: PRT
<213> ORGANISM: Artificial
<220> FEATURE:
<223> OTHER INFORMATION: synthetic

<400> SEQUENCE: 667

Leu Tyr Ala Glu Gly Thr Phe Ile Ser Asp Tyr Ser Ile Ala Leu Asp
1               5                   10                  15

Lys Ile Ala Gln Gln Glu Phe Val Asn Trp Leu Leu Ala Gln Lys Pro
            20                  25                  30

Lys Lys Ile Arg Tyr Ser
        35

<210> SEQ ID NO 668
<211> LENGTH: 38
<212> TYPE: PRT
<213> ORGANISM: Artificial
<220> FEATURE:
<223> OTHER INFORMATION: synthetic

<400> SEQUENCE: 668

Leu Tyr Ala Glu Gly Thr Phe Ile Ser Asp Tyr Ser Ile Ala Leu Asp
1               5                   10                  15

Lys Ile Ala Gln Gln Glu Phe Val Asn Trp Leu Leu Ala Gln Lys Pro
            20                  25                  30

Lys Lys Ile Arg Tyr Ser
        35

<210> SEQ ID NO 669
<211> LENGTH: 37

```
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-methyl

<400> SEQUENCE: 669

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 670
<211> LENGTH: 37
<212> TYPE: PRT
<213> ORGANISM: Artificial
<220> FEATURE:
<223> OTHER INFORMATION: synthetic

<400> SEQUENCE: 670

His Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 671
<211> LENGTH: 37
<212> TYPE: PRT
<213> ORGANISM: Artificial
<220> FEATURE:
<223> OTHER INFORMATION: synthetic

<400> SEQUENCE: 671

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 672
<211> LENGTH: 37
<212> TYPE: PRT
<213> ORGANISM: Artificial
<220> FEATURE:
<223> OTHER INFORMATION: synthetic

<400> SEQUENCE: 672

His Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 673
<211> LENGTH: 37
```

```
<212> TYPE: PRT
<213> ORGANISM: Artificial
<220> FEATURE:
<223> OTHER INFORMATION: synthetic

<400> SEQUENCE: 673

His Gly Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Lys
            20                  25                  30

Lys Ile Arg Tyr Ser
        35

<210> SEQ ID NO 674
<211> LENGTH: 37
<212> TYPE: PRT
<213> ORGANISM: Artificial
<220> FEATURE:
<223> OTHER INFORMATION: synthetic

<400> SEQUENCE: 674

His Gly Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Lys
            20                  25                  30

Lys Ile Arg Tyr Ser
        35

<210> SEQ ID NO 675
<211> LENGTH: 37
<212> TYPE: PRT
<213> ORGANISM: Artificial
<220> FEATURE:
<223> OTHER INFORMATION: synthetic

<400> SEQUENCE: 675

His Gly Glu Gly Thr Leu Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 676
<211> LENGTH: 37
<212> TYPE: PRT
<213> ORGANISM: Artificial
<220> FEATURE:
<223> OTHER INFORMATION: syntheitc
<220> FEATURE:
<221> NAME/KEY: MISC_FEATURE
<222> LOCATION: (2)..(2)
<223> OTHER INFORMATION: Xaa is Aib

<400> SEQUENCE: 676

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 677
<211> LENGTH: 37
```

```
<212> TYPE: PRT
<213> ORGANISM: Artificial
<220> FEATURE:
<223> OTHER INFORMATION: synthetic

<400> SEQUENCE: 677

Tyr Ala Glu Gly Thr Phe Ile Ser Asp Tyr Ser Ile Ala Leu Asp Lys
1               5                   10                  15
Ile His Gln Gln Asp Phe Val Asn Trp Leu Leu Ala Gln Lys Pro Lys
            20                  25                  30
Lys Ile Arg Tyr Ser
        35

<210> SEQ ID NO 678
<211> LENGTH: 37
<212> TYPE: PRT
<213> ORGANISM: Artificial
<220> FEATURE:
<223> OTHER INFORMATION: synthetic

<400> SEQUENCE: 678

Tyr Ala Glu Gly Thr Phe Ile Ser Asp Tyr Ser Ile Ala Met Asp Lys
1               5                   10                  15
Ile His Gln Gln Asp Phe Val Asn Trp Leu Leu Ala Gln Lys Pro Lys
            20                  25                  30
Lys Ile Arg Tyr Ser
        35

<210> SEQ ID NO 679
<211> LENGTH: 37
<212> TYPE: PRT
<213> ORGANISM: Artificial
<220> FEATURE:
<223> OTHER INFORMATION: synthetic

<400> SEQUENCE: 679

Tyr Ala Glu Gly Thr Phe Ile Ser Asp Tyr Ser Ile Ala Met Asp Lys
1               5                   10                  15
Ile His Gln Gln Asp Phe Val Asn Trp Leu Leu Ala Gln Lys Pro Lys
            20                  25                  30
Lys Ile Arg Tyr Ser
        35

<210> SEQ ID NO 680
<211> LENGTH: 37
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: GUANIDO-

<400> SEQUENCE: 680

Tyr Ala Glu Gly Thr Phe Ile Ser Asp Tyr Ser Ile Ala Met Asp Lys
1               5                   10                  15
Ile His Gln Gln Asp Phe Val Asn Trp Leu Leu Ala Gln Lys Pro Lys
            20                  25                  30
Lys Ile Arg Tyr Ser
        35

<210> SEQ ID NO 681
<211> LENGTH: 37
```

```
<212> TYPE: PRT
<213> ORGANISM: Artificial
<220> FEATURE:
<223> OTHER INFORMATION: synthetic
<220> FEATURE:
<221> NAME/KEY: MOD_RES
<222> LOCATION: (1)..(1)
<223> OTHER INFORMATION: GUANIDO-

<400> SEQUENCE: 681

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Lys
            20                  25                  30

Lys Ile Arg Tyr Ser
        35

<210> SEQ ID NO 682
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 682

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
            20                  25                  30

Lys Lys Ile Arg Tyr Ser
        35

<210> SEQ ID NO 683
<211> LENGTH: 37
<212> TYPE: PRT
<213> ORGANISM: Artificial
<220> FEATURE:
<223> OTHER INFORMATION: synthetic

<400> SEQUENCE: 683

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Lys
            20                  25                  30

Lys Ile Arg Tyr Ser
        35

<210> SEQ ID NO 684
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: octyl-Gly

<400> SEQUENCE: 684

Xaa Tyr Ala Glu Gly Thr Phe Ile Ser Asp Tyr Ser Ile Ala Leu Asp
1               5                   10                  15

Lys Ile Ala Gln Gln Glu Phe Val Asn Trp Leu Leu Ala Gln Lys Pro
```

```
                  20                  25                  30

Lys Lys Ile Arg Tyr Ser
        35

<210> SEQ ID NO 685
<211> LENGTH: 38
<212> TYPE: PRT
<213> ORGANISM: Artificial
<220> FEATURE:
<223> OTHER INFORMATION: syntheitc
<220> FEATURE:
<221> NAME/KEY: MISC_FEATURE
<222> LOCATION: (1)..(1)
<223> OTHER INFORMATION: Xaa is octyl-Gly

<400> SEQUENCE: 685

Xaa Tyr Ala Glu Gly Thr Phe Ile Ser Asp Tyr Ser Ile Ala Met Asp
1               5                  10                  15

Lys Ile Arg Gln Gln Glu Phe Val Asn Trp Leu Leu Ala Gln Lys Pro
            20                  25                  30

Lys Lys Ile Arg Tyr Ser
        35

<210> SEQ ID NO 686
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Gly

<400> SEQUENCE: 686

Xaa Tyr Ala Glu Gly Thr Phe Ile Ser Asp Tyr Ser Ile Ala Leu Asp
1               5                  10                  15

Lys Ile Ala Gln Gln Glu Phe Val Asn Trp Leu Leu Ala Gln Lys Pro
            20                  25                  30

Lys Lys Ile Arg Tyr Ser
        35

<210> SEQ ID NO 687
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Gly

<400> SEQUENCE: 687

Xaa Tyr Ala Glu Gly Thr Phe Ile Ser Asp Tyr Ser Ile Ala Leu Asp
1               5                  10                  15

Lys Ile Ala Gln Gln Asp Phe Val Glu Trp Leu Leu Ala Gln Lys Pro
            20                  25                  30

Lys Lys Ile Arg Tyr Ser
        35

<210> SEQ ID NO 688
<211> LENGTH: 37
<212> TYPE: PRT
<213> ORGANISM: Artificial
<220> FEATURE:
```

<223> OTHER INFORMATION: synthetic
<220> FEATURE:
<221> NAME/KEY: MISC_FEATURE
<222> LOCATION: (1)..(1)
<223> OTHER INFORMATION: guanido-

<400> SEQUENCE: 688

Tyr Ala Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Lys
            20                  25                  30

Lys Ile Arg Tyr Ser
        35

<210> SEQ ID NO 689
<211> LENGTH: 37
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: guanido-

<400> SEQUENCE: 689

Tyr Ala Glu Gly Thr Phe Ile Ser Asp Tyr Ser Ile Ala Leu Asp Lys
1               5                   10                  15

Ile Ala Gln Gln Asp Phe Val Glu Trp Leu Leu Ala Gln Lys Pro Lys
            20                  25                  30

Lys Ile Arg Tyr Ser
        35

<210> SEQ ID NO 690
<211> LENGTH: 37
<212> TYPE: PRT
<213> ORGANISM: Artificial
<220> FEATURE:
<223> OTHER INFORMATION: synthetic

<400> SEQUENCE: 690

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Lys Glu Ile Ile Ser
        35

<210> SEQ ID NO 691
<211> LENGTH: 37
<212> TYPE: PRT
<213> ORGANISM: Artificial
<220> FEATURE:
<223> OTHER INFORMATION: syntheitc

<400> SEQUENCE: 691

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Lys Glu Ile Ile His
        35

<210> SEQ ID NO 692

```
<211> LENGTH: 37
<212> TYPE: PRT
<213> ORGANISM: Artificial
<220> FEATURE:
<223> OTHER INFORMATION: syntheitc

<400> SEQUENCE: 692

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Lys Glu Ile Ile Ser
        35

<210> SEQ ID NO 693
<211> LENGTH: 37
<212> TYPE: PRT
<213> ORGANISM: Artificial
<220> FEATURE:
<223> OTHER INFORMATION: synthetic

<400> SEQUENCE: 693

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Gly Lys Gly Lys Ser
        35

<210> SEQ ID NO 694
<211> LENGTH: 39
<212> TYPE: PRT
<213> ORGANISM: Artificial
<220> FEATURE:
<223> OTHER INFORMATION: synthetic

<400> SEQUENCE: 694

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Phe
            20                  25                  30

Val Leu Trp Lys Gly Ile Gln
        35

<210> SEQ ID NO 695
<211> LENGTH: 37
<212> TYPE: PRT
<213> ORGANISM: Artificial
<220> FEATURE:
<223> OTHER INFORMATION: synthetic

<400> SEQUENCE: 695

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Ala Lys
            20                  25                  30

Lys Ile Arg Tyr Ser
        35

<210> SEQ ID NO 696
<211> LENGTH: 37
<212> TYPE: PRT
<213> ORGANISM: Artificial
<220> FEATURE:
```

<223> OTHER INFORMATION: synthetic

<400> SEQUENCE: 696

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ala
            20                  25                  30

Lys Ile Arg Tyr Ser
        35

<210> SEQ ID NO 697
<211> LENGTH: 37
<212> TYPE: PRT
<213> ORGANISM: Artificial
<220> FEATURE:
<223> OTHER INFORMATION: synthetic

<400> SEQUENCE: 697

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Ala Ile Arg Tyr Ser
        35

<210> SEQ ID NO 698
<211> LENGTH: 37
<212> TYPE: PRT
<213> ORGANISM: Artificial
<220> FEATURE:
<223> OTHER INFORMATION: synthetic

<400> SEQUENCE: 698

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Ala Tyr Ser
        35

<210> SEQ ID NO 699
<211> LENGTH: 37
<212> TYPE: PRT
<213> ORGANISM: Artificial
<220> FEATURE:
<223> OTHER INFORMATION: synthetic

<400> SEQUENCE: 699

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Ala Ser
        35

<210> SEQ ID NO 700
<211> LENGTH: 37
<212> TYPE: PRT
<213> ORGANISM: Artificial
<220> FEATURE:
<223> OTHER INFORMATION: synthetic

<400> SEQUENCE: 700

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ala
        35

<210> SEQ ID NO 701
<211> LENGTH: 38
<212> TYPE: PRT
<213> ORGANISM: Artificial
<220> FEATURE:
<223> OTHER INFORMATION: synthetic

<400> SEQUENCE: 701

Tyr Ala Glu Gly Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Pro
            20                  25                  30

Lys Lys Ile Arg Tyr Ser
        35

<210> SEQ ID NO 702
<211> LENGTH: 39
<212> TYPE: PRT
<213> ORGANISM: Artificial
<220> FEATURE:
<223> OTHER INFORMATION: synthetic

<400> SEQUENCE: 702

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Pro Lys Lys Ile Arg Tyr Ser
        35

<210> SEQ ID NO 703
<211> LENGTH: 37
<212> TYPE: PRT
<213> ORGANISM: Artificial
<220> FEATURE:
<223> OTHER INFORMATION: synthetic

<400> SEQUENCE: 703

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Ser Ala Arg Pro Ser
        35

<210> SEQ ID NO 704
<211> LENGTH: 37
<212> TYPE: PRT
<213> ORGANISM: Artificial
<220> FEATURE:
<223> OTHER INFORMATION: synthetic

<400> SEQUENCE: 704

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys

```
                    20                  25                  30

Lys Leu Lys Pro Ser
        35

<210> SEQ ID NO 705
<211> LENGTH: 37
<212> TYPE: PRT
<213> ORGANISM: Artificial
<220> FEATURE:
<223> OTHER INFORMATION: synthetic

<400> SEQUENCE: 705

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Asn
                20                  25                  30

Lys Ile Arg Tyr Ser
        35

<210> SEQ ID NO 706
<211> LENGTH: 37
<212> TYPE: PRT
<213> ORGANISM: Artificial
<220> FEATURE:
<223> OTHER INFORMATION: synthetic

<400> SEQUENCE: 706

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
                20                  25                  30

Asn Ile Arg Tyr Ser
        35

<210> SEQ ID NO 707
<211> LENGTH: 37
<212> TYPE: PRT
<213> ORGANISM: Artificial
<220> FEATURE:
<223> OTHER INFORMATION: synthetic

<400> SEQUENCE: 707

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Gln
                20                  25                  30

Lys Ile Arg Tyr Ser
        35

<210> SEQ ID NO 708
<211> LENGTH: 37
<212> TYPE: PRT
<213> ORGANISM: Artificial
<220> FEATURE:
<223> OTHER INFORMATION: synthetic

<400> SEQUENCE: 708

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
                20                  25                  30

Gln Ile Arg Tyr Ser
        35
```

```
<210> SEQ ID NO 709
<211> LENGTH: 37
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(43)
<223> OTHER INFORMATION: Xaa is octyl-Gly

<400> SEQUENCE: 709

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Xaa Arg Tyr Ser
        35

<210> SEQ ID NO 710
<211> LENGTH: 38
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (38)..(38)
<223> OTHER INFORMATION: Xaa is octyl-Gly

<400> SEQUENCE: 710

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser Xaa
        35

<210> SEQ ID NO 711
<211> LENGTH: 37
<212> TYPE: PRT
<213> ORGANISM: Artificial
<220> FEATURE:
<223> OTHER INFORMATION: synthetic

<400> SEQUENCE: 711

Tyr Ala Glu Gly Thr Phe Ile Ser Asp Tyr Ser Ile Ala Met Asp Lys
1               5                   10                  15

Ile His Gln Gln Asp Phe Val Glu Trp Leu Leu Ala Gln Lys Pro Lys
            20                  25                  30

Lys Ile Arg Tyr Ser
        35

<210> SEQ ID NO 712
<211> LENGTH: 37
<212> TYPE: PRT
<213> ORGANISM: Artificial
<220> FEATURE:
<223> OTHER INFORMATION: synthetic

<400> SEQUENCE: 712

Tyr Ala Glu Gly Thr Phe Ile Ser Asp Tyr Ser Ile Ala Met Asp Lys
1               5                   10                  15

Ile His Gln Gln Asp Phe Val Pro Trp Leu Leu Ala Gln Lys Pro Lys
```

-continued

```
                20                  25                  30
Lys Ile Arg Tyr Ser
        35

<210> SEQ ID NO 713
<211> LENGTH: 37
<212> TYPE: PRT
<213> ORGANISM: Artificial
<220> FEATURE:
<223> OTHER INFORMATION: synthetic

<400> SEQUENCE: 713

Tyr Ala Glu Gly Thr Phe Ile Ser Asp Tyr Ser Ile Ala Met Asp Lys
1               5                   10                  15

Ile His Gln Gln Asp Phe Val Asn Glu Leu Leu Ala Gln Lys Pro Lys
            20                  25                  30

Lys Ile Arg Tyr Ser
        35

<210> SEQ ID NO 714
<211> LENGTH: 37
<212> TYPE: PRT
<213> ORGANISM: Artificial
<220> FEATURE:
<223> OTHER INFORMATION: synthetic

<400> SEQUENCE: 714

Tyr Ala Glu Gly Thr Phe Ile Ser Asp Tyr Ser Ile Ala Met Asp Lys
1               5                   10                  15

Ile His Gln Gln Asp Phe Val Asn Pro Leu Leu Ala Gln Lys Pro Lys
            20                  25                  30

Lys Ile Arg Tyr Ser
        35

<210> SEQ ID NO 715
<211> LENGTH: 37
<212> TYPE: PRT
<213> ORGANISM: Artificial
<220> FEATURE:
<223> OTHER INFORMATION: synthetic

<400> SEQUENCE: 715

Tyr Ala Glu Gly Thr Phe Ile Ser Asp Tyr Ser Ile Ala Met Asp Lys
1               5                   10                  15

Ile His Gln Gln Asp Phe Val Asn Trp Leu Glu Ala Gln Lys Pro Lys
            20                  25                  30

Lys Ile Arg Tyr Ser
        35

<210> SEQ ID NO 716
<211> LENGTH: 37
<212> TYPE: PRT
<213> ORGANISM: Artificial
<220> FEATURE:
<223> OTHER INFORMATION: synthetic

<400> SEQUENCE: 716

Tyr Ala Glu Gly Thr Phe Ile Ser Asp Tyr Ser Ile Ala Met Asp Lys
1               5                   10                  15

Ile His Gln Gln Asp Phe Val Asn Trp Leu Pro Ala Gln Lys Pro Lys
            20                  25                  30

Lys Ile Arg Tyr Ser
        35
```

<210> SEQ ID NO 717
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is Ado
<220> FEATURE:
<221> NAME/KEY: MISC_FEATURE
<222> LOCATION: (2)..(2)
<223> OTHER INFORMATION: Xaa is Ado

<400> SEQUENCE: 717

Xaa Xaa Tyr Ala Glu Gly Thr Phe Ile Ser Asp Tyr Ser Ile Ala Met
1               5                   10                  15

Asp Lys Ile His Gln Gln Asp Phe Val Asn Trp Leu Leu Ala Gln Lys
            20                  25                  30

Pro Ser Ser Gly Ala Pro Pro Pro Ser
        35                  40

<210> SEQ ID NO 718
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (16)..(16)
<223> OTHER INFORMATION: -(EPSILON-NH-(ADO-ADO-ADO-(2-(2-METHOXYETOXY)-
      ACETOYL))) linker

<400> SEQUENCE: 718

Tyr Ala Glu Gly Thr Phe Ile Ser Tyr Asp Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 719
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is ((2-(2-METHOXYETHOXY)-ACETOYL)-ADO-ADO)-

<400> SEQUENCE: 719

Xaa Tyr Ala Glu Gly Thr Phe Ile Ser Tyr Asp Ser Ile Ala Met Asp
1               5                   10                  15

Lys Ile His Gln Gln Asp Phe Val Asn Trp Leu Leu Ala Gln Lys Pro
            20                  25                  30

Ser Ser Gly Ala Pro Pro Pro Ser
        35                  40

<210> SEQ ID NO 720
<211> LENGTH: 41
<212> TYPE: PRT
<213> ORGANISM: Artificial

```
<220> FEATURE:
<223> OTHER INFORMATION: synthetic
<220> FEATURE:
<221> NAME/KEY: MISC_FEATURE
<222> LOCATION: (40)..(40)
<223> OTHER INFORMATION: Xaa is Ado
<220> FEATURE:
<221> NAME/KEY: MISC_FEATURE
<222> LOCATION: (41)..(41)
<223> OTHER INFORMATION: Xaa is Ado

<400> SEQUENCE: 720

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser Xaa Xaa
        35                  40

<210> SEQ ID NO 721
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (14)..(14)
<223> OTHER INFORMATION: (EPSILON-NH-(ADO-(2-(2-METHOXYETHOXY)-
      ACETYOL))) linker

<400> SEQUENCE: 721

Tyr Ala Glu Gly Thr Phe Ile Ser Asp Tyr Ser Ile Ala Lys Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 722
<211> LENGTH: 39
<212> TYPE: PRT
<213> ORGANISM: Artificial
<220> FEATURE:
<223> OTHER INFORMATION: synthetic

<400> SEQUENCE: 722

Tyr Ala Glu Gly Thr Phe Ile Ser Asp Tyr Ser Ile Ala Met Asp Lys
1               5                   10                  15

Ile His Gln Gln Asp Phe Val Asn Gln Leu Leu Ala Gln Lys Pro Ser
            20                  25                  30

Ser Gly Ala Pro Pro Pro Ser
        35

<210> SEQ ID NO 723
<211> LENGTH: 37
<212> TYPE: PRT
<213> ORGANISM: Artificial
<220> FEATURE:
<223> OTHER INFORMATION: synthetic

<400> SEQUENCE: 723

Tyr Ala Glu Gly Thr Phe Ile Ser Asp Tyr Ser Ile Ala Met Asp Lys
1               5                   10                  15

Ile His Gln Gln Asp Phe Val Asn Gln Leu Leu Ala Gln Lys Pro Lys
            20                  25                  30
```

```
Lys Ile Arg Tyr Ser
        35

<210> SEQ ID NO 724
<211> LENGTH: 39
<212> TYPE: PRT
<213> ORGANISM: Artificial
<220> FEATURE:
<223> OTHER INFORMATION: synthetic

<400> SEQUENCE: 724

Tyr Ala Glu Gly Thr Phe Ile Ser Asp Tyr Ser Ile Ala Met Asp Lys
1               5                   10                  15

Ile His Gln Gln Asp Phe Val Gln Trp Leu Leu Ala Gln Lys Pro Ser
            20                  25                  30

Ser Gly Ala Pro Pro Pro Ser
        35

<210> SEQ ID NO 725
<211> LENGTH: 37
<212> TYPE: PRT
<213> ORGANISM: Artificial
<220> FEATURE:
<223> OTHER INFORMATION: synthetic

<400> SEQUENCE: 725

Tyr Ala Glu Gly Thr Phe Ile Ser Asp Tyr Ser Ile Ala Met Asp Lys
1               5                   10                  15

Ile His Gln Gln Asp Phe Val Gln Trp Leu Leu Ala Gln Lys Pro Lys
            20                  25                  30

Lys Ile Arg Tyr Ser
        35

<210> SEQ ID NO 726
<211> LENGTH: 39
<212> TYPE: PRT
<213> ORGANISM: Artificial
<220> FEATURE:
<223> OTHER INFORMATION: synthetic

<400> SEQUENCE: 726

Tyr Ala Glu Gly Thr Phe Ile Ser Asp Tyr Ser Ile Ala Met Asp Lys
1               5                   10                  15

Ile His Gln Gln Asp Phe Val Asn Asn Leu Leu Ala Gln Lys Pro Ser
            20                  25                  30

Ser Gly Ala Pro Pro Pro Ser
        35

<210> SEQ ID NO 727
<211> LENGTH: 39
<212> TYPE: PRT
<213> ORGANISM: Artificial
<220> FEATURE:
<223> OTHER INFORMATION: synthetic

<400> SEQUENCE: 727

Tyr Ala Glu Gly Thr Phe Ile Ser Asp Tyr Ser Ile Ala Met Asp Lys
1               5                   10                  15

Ile His Gln Gln Asp Phe Val Asn Trp Leu Asn Ala Gln Lys Pro Ser
            20                  25                  30

Ser Gly Ala Pro Pro Pro Ser
        35
```

<210> SEQ ID NO 728
<211> LENGTH: 39
<212> TYPE: PRT
<213> ORGANISM: Artificial
<220> FEATURE:
<223> OTHER INFORMATION: synthetic

<400> SEQUENCE: 728

Tyr Ala Glu Gly Thr Phe Ile Ser Asp Tyr Ser Ile Ala Met Asp Lys
1               5                   10                  15

Ile His Gln Gln Asp Phe Val Asn Trp Leu Ser Ala Gln Lys Pro Ser
            20                  25                  30

Ser Gly Ala Pro Pro Pro Ser
            35

<210> SEQ ID NO 729
<211> LENGTH: 39
<212> TYPE: PRT
<213> ORGANISM: Artificial
<220> FEATURE:
<223> OTHER INFORMATION: synthetic

<400> SEQUENCE: 729

Tyr Ala Glu Gly Thr Phe Ile Ser Asp Tyr Ser Ile Ala Met Asp Lys
1               5                   10                  15

Ile His Gln Gln Asp Phe Val Asn Trp Leu Gln Ala Gly Lys Pro Ser
            20                  25                  30

Ser Gly Ala Pro Pro Pro Ser
            35

<210> SEQ ID NO 730
<211> LENGTH: 39
<212> TYPE: PRT
<213> ORGANISM: Artificial
<220> FEATURE:
<223> OTHER INFORMATION: synthetic

<400> SEQUENCE: 730

Tyr Ala Glu Gly Thr Phe Ile Ser Asp Tyr Ser Ile Ala Met Asp Lys
1               5                   10                  15

Ile His Gln Gln Asp Phe Val Asn Trp Asn Leu Ala Gln Lys Pro Ser
            20                  25                  30

Ser Gly Ala Pro Pro Pro Ser
            35

<210> SEQ ID NO 731
<211> LENGTH: 39
<212> TYPE: PRT
<213> ORGANISM: Artificial
<220> FEATURE:
<223> OTHER INFORMATION: synthetic

<400> SEQUENCE: 731

Tyr Ala Glu Gly Thr Phe Ile Ser Asp Tyr Ser Ile Ala Met Asp Lys
1               5                   10                  15

Ile His Gln Gln Asp Phe Val Asn Trp Ser Leu Ala Gln Lys Pro Ser
            20                  25                  30

Ser Gly Ala Pro Pro Pro Ser
            35

<210> SEQ ID NO 732
<211> LENGTH: 39
<212> TYPE: PRT

<213> ORGANISM: Artificial
<220> FEATURE:
<223> OTHER INFORMATION: synthetic

<400> SEQUENCE: 732

Tyr Ala Glu Gly Thr Phe Ile Ser Asp Tyr Ser Ile Ala Met Asp Lys
1               5                   10                  15

Ile His Gln Gln Asp Phe Val Asn Trp Gln Leu Ala Gln Lys Pro Ser
            20                  25                  30

Ser Gly Ala Pro Pro Pro Ser
        35

<210> SEQ ID NO 733
<211> LENGTH: 39
<212> TYPE: PRT
<213> ORGANISM: Artificial
<220> FEATURE:
<223> OTHER INFORMATION: synthetic

<400> SEQUENCE: 733

Tyr Ala Glu Gly Thr Phe Ile Ser Asp Tyr Ser Ile Ala Met Asp Lys
1               5                   10                  15

Ile His Gln Gln Asp Phe Val Glu Trp Leu Lys Ala Gly Lys Pro Ser
            20                  25                  30

Ser Gly Ala Pro Pro Pro Ser
        35

<210> SEQ ID NO 734
<211> LENGTH: 39
<212> TYPE: PRT
<213> ORGANISM: Artificial
<220> FEATURE:
<223> OTHER INFORMATION: synthetic

<400> SEQUENCE: 734

Tyr Ala Glu Gly Thr Phe Ile Ser Asp Tyr Ser Ile Ala Met Asp Lys
1               5                   10                  15

Ile His Gln Gln Asp Phe Val Asn Asn Leu Asn Ala Gln Lys Pro Ser
            20                  25                  30

Ser Gly Ala Pro Pro Pro Ser
        35

<210> SEQ ID NO 735
<211> LENGTH: 39
<212> TYPE: PRT
<213> ORGANISM: Artificial
<220> FEATURE:
<223> OTHER INFORMATION: synthetic

<400> SEQUENCE: 735

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Asn Pro Pro Pro Ser
        35

<210> SEQ ID NO 736
<211> LENGTH: 39
<212> TYPE: PRT
<213> ORGANISM: Artificial
<220> FEATURE:
<223> OTHER INFORMATION: synthetic

```
<400> SEQUENCE: 736

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Asn Pro Pro Ser
        35

<210> SEQ ID NO 737
<211> LENGTH: 39
<212> TYPE: PRT
<213> ORGANISM: Artificial
<220> FEATURE:
<223> OTHER INFORMATION: synthetic

<400> SEQUENCE: 737

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Asn Pro Ser
        35

<210> SEQ ID NO 738
<211> LENGTH: 39
<212> TYPE: PRT
<213> ORGANISM: Artificial
<220> FEATURE:
<223> OTHER INFORMATION: synthetic

<400> SEQUENCE: 738

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Asn Ser
        35

<210> SEQ ID NO 739
<211> LENGTH: 42
<212> TYPE: PRT
<213> ORGANISM: Artificial
<220> FEATURE:
<223> OTHER INFORMATION: synthetic

<400> SEQUENCE: 739

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 740
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-Acetyl
```

```
<400> SEQUENCE: 740

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 741
<211> LENGTH: 39
<212> TYPE: PRT
<213> ORGANISM: Artificial
<220> FEATURE:
<223> OTHER INFORMATION: synthetic

<400> SEQUENCE: 741

Tyr Ala Glu Gly Thr Phe Ile Ser Asp Tyr Ser Ile Ala Met Asp Lys
1               5                   10                  15

Ile His Gln Gln Asp Phe Val Asn Phe Leu Leu Ala Gln Lys Pro Ser
            20                  25                  30

Ser Gly Ala Pro Pro Ser
        35

<210> SEQ ID NO 742
<211> LENGTH: 39
<212> TYPE: PRT
<213> ORGANISM: Artificial
<220> FEATURE:
<223> OTHER INFORMATION: synthetic

<400> SEQUENCE: 742

Tyr Ala Glu Gly Thr Phe Ile Ser Glu Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 743
<211> LENGTH: 39
<212> TYPE: PRT
<213> ORGANISM: Artificial
<220> FEATURE:
<223> OTHER INFORMATION: synthetic

<400> SEQUENCE: 743

Tyr Ala Glu Gly Thr Phe Ile Ser Asp Tyr Ser Ile Ala Met Asp Lys
1               5                   10                  15

Ile His Gln Gln Glu Phe Val Asn Trp Leu Val Lys Gly Arg Pro Ser
            20                  25                  30

Ser Gly Ala Pro Pro Ser
        35

<210> SEQ ID NO 744
<211> LENGTH: 39
<212> TYPE: PRT
<213> ORGANISM: Artificial
<220> FEATURE:
<223> OTHER INFORMATION: synhthetic

<400> SEQUENCE: 744

Tyr Ala Glu Gly Thr Phe Ile Ser Asp Tyr Ser Ile Ala Met Glu Glu
1               5                   10                  15
```

Glu Ala Gln Gln Asp Phe Val Asn Trp Leu Leu Ala Gln Lys Pro Ser
            20                  25                  30

Ser Gly Ala Pro Pro Ser
        35

<210> SEQ ID NO 745
<211> LENGTH: 39
<212> TYPE: PRT
<213> ORGANISM: Artificial
<220> FEATURE:
<223> OTHER INFORMATION: synthetic

<400> SEQUENCE: 745

Tyr Ala Glu Gly Thr Phe Ile Ser Asp Tyr Ser Ile Ala Met Glu Gly
1               5                   10                  15

Gln Ala Gln Gln Glu Phe Val Asn Trp Leu Val Lys Gly Arg Pro Ser
            20                  25                  30

Ser Gly Ala Pro Pro Ser
        35

<210> SEQ ID NO 746
<211> LENGTH: 39
<212> TYPE: PRT
<213> ORGANISM: Artificial
<220> FEATURE:
<223> OTHER INFORMATION: synthetic

<400> SEQUENCE: 746

Tyr Ala Glu Gly Thr Phe Ile Ser Glu Tyr Ser Ile Ala Met Glu Lys
1               5                   10                  15

Ile Ala Gln Gln Glu Phe Val Asn Trp Leu Leu Ala Gln Lys Pro Ser
            20                  25                  30

Ser Gly Ala Pro Pro Ser
        35

<210> SEQ ID NO 747
<211> LENGTH: 39
<212> TYPE: PRT
<213> ORGANISM: Artificial
<220> FEATURE:
<223> OTHER INFORMATION: synthetic

<400> SEQUENCE: 747

Tyr Ala Glu Gly Thr Phe Ile Ser Asp Tyr Ser Ile Ala Met Asp Lys
1               5                   10                  15

Ile His Gln Val Lys Phe Val Asn Trp Leu Leu Ala Gln Lys Pro Ser
            20                  25                  30

Ser Gly Ala Pro Pro Ser
        35

<210> SEQ ID NO 748
<211> LENGTH: 39
<212> TYPE: PRT
<213> ORGANISM: Artificial
<220> FEATURE:
<223> OTHER INFORMATION: synthetic

<400> SEQUENCE: 748

Tyr Ala Glu Gly Thr Phe Ile Ser Asp Tyr Ser Ile Ala Met Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Ser
        35

<210> SEQ ID NO 749
<211> LENGTH: 39
<212> TYPE: PRT
<213> ORGANISM: Artificial
<220> FEATURE:
<223> OTHER INFORMATION: synthetic

<400> SEQUENCE: 749

Tyr Ala Glu Gly Thr Phe Thr Ser Asp Tyr Ser Lys Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 750
<211> LENGTH: 39
<212> TYPE: PRT
<213> ORGANISM: Artificial
<220> FEATURE:
<223> OTHER INFORMATION: synthetic

<400> SEQUENCE: 750

Tyr Ala Glu Gly Thr Phe Thr Ser Asp Tyr Ser Lys Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 751
<211> LENGTH: 39
<212> TYPE: PRT
<213> ORGANISM: Artificial
<220> FEATURE:
<223> OTHER INFORMATION: synthetic

<400> SEQUENCE: 751

Tyr Ala Glu Gly Thr Phe Ile Ser Asp Tyr Ser Ile Ala Leu Glu Lys
1               5                   10                  15

Ile Arg Gln Gln Lys Phe Val Asn Trp Leu Leu Ala Gln Lys Pro Ser
            20                  25                  30

Ser Gly Ala Pro Pro Ser
        35

<210> SEQ ID NO 752
<211> LENGTH: 39
<212> TYPE: PRT
<213> ORGANISM: Artificial
<220> FEATURE:
<223> OTHER INFORMATION: synthetic

<400> SEQUENCE: 752

Tyr Ala Glu Gly Thr Phe Ile Ser Asp Tyr Ser Ile Ala Leu Asp Lys
1               5                   10                  15

Ile Arg Gln Gln Lys Phe Val Asn Trp Leu Leu Ala Gln Lys Pro Ser
            20                  25                  30

Ser Gly Ala Pro Pro Ser
        35

```
<210> SEQ ID NO 753
<211> LENGTH: 39
<212> TYPE: PRT
<213> ORGANISM: Artificial
<220> FEATURE:
<223> OTHER INFORMATION: synthetic

<400> SEQUENCE: 753

Tyr Ala Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His Pro Ser
            20                  25                  30

Ser Gly Ala Pro Pro Pro Ser
        35

<210> SEQ ID NO 754
<211> LENGTH: 39
<212> TYPE: PRT
<213> ORGANISM: Artificial
<220> FEATURE:
<223> OTHER INFORMATION: synthetic

<400> SEQUENCE: 754

Tyr Ala Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln His Pro Ser
            20                  25                  30

Ser Gly Ala Pro Pro Pro Ser
        35

<210> SEQ ID NO 755
<211> LENGTH: 39
<212> TYPE: PRT
<213> ORGANISM: Artificial
<220> FEATURE:
<223> OTHER INFORMATION: synthetic

<400> SEQUENCE: 755

Tyr Ala Glu Ala Ile Leu Ala Ser Asp Tyr Ser Arg Ser Val Asp Asn
1               5                   10                  15

Met Leu Gln Gln Asn Phe Val Asp Trp Leu Leu Ala Gln Lys Pro Ser
            20                  25                  30

Ser Gly Ala Pro Pro Pro Ser
        35

<210> SEQ ID NO 756
<211> LENGTH: 39
<212> TYPE: PRT
<213> ORGANISM: Artificial
<220> FEATURE:
<223> OTHER INFORMATION: synthetic

<400> SEQUENCE: 756

Tyr Ala Glu Gly Ile Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 757
<211> LENGTH: 39
<212> TYPE: PRT
<213> ORGANISM: Artificial
```

```
<220> FEATURE:
<223> OTHER INFORMATION: synthetic

<400> SEQUENCE: 757

Tyr Ala Glu Gly Thr Phe Ile Ser Asp Tyr Ser Ile Ser Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 758
<211> LENGTH: 39
<212> TYPE: PRT
<213> ORGANISM: Artificial
<220> FEATURE:
<223> OTHER INFORMATION: synthetic

<400> SEQUENCE: 758

Tyr Ala Glu Gly Thr Phe Ile Ser Asp Tyr Ser Ile Ala Met Asp Lys
1               5                   10                  15

Met His Gln Gln Asp Phe Val Asn Trp Leu Leu Ala Gln Lys Pro Ser
            20                  25                  30

Ser Gly Ala Pro Pro Pro Ser
        35

<210> SEQ ID NO 759
<211> LENGTH: 39
<212> TYPE: PRT
<213> ORGANISM: Artificial
<220> FEATURE:
<223> OTHER INFORMATION: synthetic

<400> SEQUENCE: 759

Tyr Ala Glu Gly Thr Phe Ile Ser Asp Tyr Ser Ile Ala Met Asp Lys
1               5                   10                  15

Ile His Gln Gln Asp Phe Val Asp Trp Leu Leu Ala Gln Lys Pro Ser
            20                  25                  30

Ser Gly Ala Pro Pro Pro Ser
        35

<210> SEQ ID NO 760
<211> LENGTH: 39
<212> TYPE: PRT
<213> ORGANISM: Artificial
<220> FEATURE:
<223> OTHER INFORMATION: synthetic

<400> SEQUENCE: 760

Tyr Ala Glu Ala Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 761
<211> LENGTH: 39
<212> TYPE: PRT
<213> ORGANISM: Artificial
<220> FEATURE:
<223> OTHER INFORMATION: synthetic

<400> SEQUENCE: 761
```

```
Tyr Ala Glu Gly Thr Leu Ile Ser Asp Tyr Ser Ile Ala Met Asp Lys
1               5                  10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 762
<211> LENGTH: 39
<212> TYPE: PRT
<213> ORGANISM: Artificial
<220> FEATURE:
<223> OTHER INFORMATION: synthetic

<400> SEQUENCE: 762

Tyr Ala Glu Gly Thr Phe Ala Ser Asp Tyr Ser Ile Ala Met Asp Lys
1               5                  10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 763
<211> LENGTH: 39
<212> TYPE: PRT
<213> ORGANISM: Artificial
<220> FEATURE:
<223> OTHER INFORMATION: synthetic

<400> SEQUENCE: 763

Tyr Ala Glu Gly Thr Phe Ile Ser Asp Tyr Ser Arg Ala Met Asp Lys
1               5                  10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 764
<211> LENGTH: 39
<212> TYPE: PRT
<213> ORGANISM: Artificial
<220> FEATURE:
<223> OTHER INFORMATION: synthetic 764

<400> SEQUENCE: 764

Tyr Ala Glu Gly Thr Phe Ile Ser Asp Tyr Ser Ile Thr Met Asp Lys
1               5                  10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 765
<211> LENGTH: 39
<212> TYPE: PRT
<213> ORGANISM: Artificial
<220> FEATURE:
<223> OTHER INFORMATION: synthetic

<400> SEQUENCE: 765

Tyr Ala Glu Gly Thr Phe Ile Ser Asp Tyr Ser Ile Ala Met Asp Asn
1               5                  10                  15
```

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 766
<211> LENGTH: 39
<212> TYPE: PRT
<213> ORGANISM: Artificial
<220> FEATURE:
<223> OTHER INFORMATION: synthetic

<400> SEQUENCE: 766

Tyr Ala Glu Gly Thr Phe Ile Ser Asp Tyr Ser Ile Ala Met Asp Lys
1               5                   10                  15

Ile Leu Gln Gln Asp Phe Val Asn Trp Leu Leu Ala Gln Lys Pro Ser
            20                  25                  30

Ser Gly Ala Pro Pro Pro Ser
        35

<210> SEQ ID NO 767
<211> LENGTH: 39
<212> TYPE: PRT
<213> ORGANISM: Artificial
<220> FEATURE:
<223> OTHER INFORMATION: syunthetic

<400> SEQUENCE: 767

Tyr Ala Glu Ala Thr Leu Ala Ser Asp Tyr Ser Arg Thr Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 768
<211> LENGTH: 39
<212> TYPE: PRT
<213> ORGANISM: Artificial
<220> FEATURE:
<223> OTHER INFORMATION: synthetic 768

<400> SEQUENCE: 768

Tyr Ala Glu Ser Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 769
<211> LENGTH: 39
<212> TYPE: PRT
<213> ORGANISM: Artificial
<220> FEATURE:
<223> OTHER INFORMATION: synthetic

<400> SEQUENCE: 769

Tyr Ala Glu Gly Thr Ile Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser

<210> SEQ ID NO 770
<211> LENGTH: 39
<212> TYPE: PRT
<213> ORGANISM: Artificial
<220> FEATURE:
<223> OTHER INFORMATION: synthetic

<400> SEQUENCE: 770

Tyr Ala Glu Gly Thr Phe Ile Ser Asp Ile Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 771
<211> LENGTH: 39
<212> TYPE: PRT
<213> ORGANISM: Artificial
<220> FEATURE:
<223> OTHER INFORMATION: synthetic

<400> SEQUENCE: 771

Tyr Ala Glu Gly Thr Phe Ile Ser Asp Tyr Ser Lys Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 772
<211> LENGTH: 39
<212> TYPE: PRT
<213> ORGANISM: Artificial
<220> FEATURE:
<223> OTHER INFORMATION: synthetic

<400> SEQUENCE: 772

Tyr Ala Glu Gly Thr Phe Ile Ser Asp Tyr Ser Ile Ile Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 773
<211> LENGTH: 39
<212> TYPE: PRT
<213> ORGANISM: Artificial
<220> FEATURE:
<223> OTHER INFORMATION: synthetic

<400> SEQUENCE: 773

Tyr Ala Glu Gly Thr Phe Ile Ser Asp Tyr Ser Ile Ala Val Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 774

```
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is d-Norvaline

<400> SEQUENCE: 774

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 775
<211> LENGTH: 39
<212> TYPE: PRT
<213> ORGANISM: Artificial
<220> FEATURE:
<223> OTHER INFORMATION: synthetic

<400> SEQUENCE: 775

Tyr Ser Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 776
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is d-Homoserine

<400> SEQUENCE: 776

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 777
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is d-CYCLOPROPYL Alanine

<400> SEQUENCE: 777

Tyr Xaa Glu Gly Thr Phe Ile Ser Asp Tyr Ser Ile Ala Met Asp Lys
1               5                   10                  15
```

```
Ile His Gln Gln Asp Phe Val Asn Trp Leu Leu Ala Gln Lys Pro Ser
            20                  25                  30

Ser Gly Ala Pro Pro Ser
        35

<210> SEQ ID NO 778
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: Xaa is d-CYCLOHEXYL Alanine

<400> SEQUENCE: 778

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 779
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-methyl

<400> SEQUENCE: 779

Tyr Ala Glu Gly Thr Phe Ile Ser Glu Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 780
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: N-methyl

<400> SEQUENCE: 780

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 781
<211> LENGTH: 39
<212> TYPE: PRT
<213> ORGANISM: Artificial
```

```
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: SUCCINOYL

<400> SEQUENCE: 781

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 782
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: SUCCINIMIDO

<400> SEQUENCE: 782

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 783
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: GUANIDO

<400> SEQUENCE: 783

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 784
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: GUANIDO

<400> SEQUENCE: 784

Tyr Ala Glu Gly Thr Phe Ile Ser Asp Tyr Ser Ile Ala Leu Asp Lys
1               5                   10                  15
```

-continued

Ile Arg Gln Gln Glu Phe Val Asn Trp Leu Leu Ala Gln Lys Pro Ser
            20                  25                  30

Ser Gly Ala Pro Pro Ser
        35

<210> SEQ ID NO 785
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: MeSO2

<400> SEQUENCE: 785

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 786
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: PHENYL SO2

<400> SEQUENCE: 786

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 787
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: BENZYL SO2

<400> SEQUENCE: 787

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Ser
        35

<210> SEQ ID NO 788
<211> LENGTH: 39
<212> TYPE: PRT

```
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is 4-HYDROXYPHENPROP

<400> SEQUENCE: 788

Xaa Ala Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 789
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Glycine

<400> SEQUENCE: 789

Xaa Tyr Ala Pro Gly Thr Phe Ile Ser Asp Tyr Ser Ile Ala Leu Asp
 1               5                  10                  15

Lys Ile Arg Gln Gln Glu Phe Val Asn Trp Leu Leu Ala Gln His Pro
            20                  25                  30

Ser Ser Gly Ala Pro Pro Pro Ser
        35                  40

<210> SEQ ID NO 790
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(34)
<223> OTHER INFORMATION: Xaa is octyl-Glycine

<400> SEQUENCE: 790

Tyr Ala Glu Gly Thr Phe Ile Ser Asp Tyr Ser Ile Ala Leu Asp Lys
 1               5                  10                  15

Ile His Gln Gln Asp Phe Val Asn Trp Leu Leu Ala Gln Lys Pro Ser
            20                  25                  30

Ser Xaa Ala Pro Pro Pro Ser
        35

<210> SEQ ID NO 791
<211> LENGTH: 39
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (34)..(34)
<223> OTHER INFORMATION: octyl-Glycine

<400> SEQUENCE: 791

Tyr Ala Glu Gly Thr Phe Ile Ser Asp Tyr Ser Ile Ala Leu Asp Lys
```

```
                 1               5                  10                  15
Ile Arg Gln Gln Glu Phe Val Asn Trp Leu Leu Ala Gln Lys Pro Ser
                20                  25                  30

Ser Xaa Ala Pro Pro Ser
        35
```

<210> SEQ ID NO 792
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 792

```
Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Xaa Pro
                20                  25                  30

Ser Ser Gly Ala Pro Pro Ser
        35                  40
```

<210> SEQ ID NO 793
<211> LENGTH: 41
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: Xaa is octyl-Glycine
<220> FEATURE:
<221> NAME/KEY: MISC_FEATURE
<222> LOCATION: (32)..(32)
<223> OTHER INFORMATION: Xaa is beta-Ala-beta-Ala

<400> SEQUENCE: 793

```
Xaa Tyr Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Xaa
                20                  25                  30

Pro Ser Ser Gly Ala Pro Pro Ser
        35                  40
```

<210> SEQ ID NO 794
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 794

```
Tyr Ala Glu Gly Thr Phe Ile Ser Asp Tyr Ser Ile Ala Met Asp Lys
1               5                   10                  15

Ile Arg Gln Gln Glu Phe Val Asn Trp Leu Leu Ala Gln Lys Xaa Pro
                20                  25                  30

Ser Ser Gly Ala Pro Pro Ser
        35                  40
```

<210> SEQ ID NO 795
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 795

Tyr Ala Glu Gly Thr Phe Ile Ser Asp Tyr Ser Ile Ala Met Asp Lys
1               5                   10                  15

Ile Arg Gln Gln Asp Phe Val Glu Trp Leu Leu Ala Gln Lys Xaa Pro
            20                  25                  30

Ser Ser Gly Ala Pro Pro Ser
        35                  40

<210> SEQ ID NO 796
<211> LENGTH: 41
<212> TYPE: PRT
<213> ORGANISM: Artificial
<220> FEATURE:
<223> OTHER INFORMATION: synthetic 796
<220> FEATURE:
<221> NAME/KEY: MISC_FEATURE
<222> LOCATION: (1)..(1)
<223> OTHER INFORMATION: Xaa is octyl-GLy
<220> FEATURE:
<221> NAME/KEY: MISC_FEATURE
<222> LOCATION: (32)..(32)
<223> OTHER INFORMATION: Xaa is beta-Ala-beta-Ala

<400> SEQUENCE: 796

Xaa Tyr Ala Glu Gly Thr Phe Ile Ser Asp Tyr Ser Ile Ala Met Asp
1               5                   10                  15

Lys Ile Arg Gln Gln Glu Phe Val Asn Trp Leu Leu Ala Gln His Xaa
            20                  25                  30

Pro Ser Ser Gly Ala Pro Pro Ser
        35                  40

<210> SEQ ID NO 797
<211> LENGTH: 40
<212> TYPE: PRT
<213> ORGANISM: Artificial
<220> FEATURE:
<223> OTHER INFORMATION: synthetic
<220> FEATURE:
<221> NAME/KEY: MISC_FEATURE
<222> LOCATION: (31)..(31)
<223> OTHER INFORMATION: Xaa is beta-Ala-beta-Ala

<400> SEQUENCE: 797

Tyr Ala Glu Gly Thr Phe Ile Ser Asp Tyr Ser Ile Ala Met Asp Lys
1               5                   10                  15

Ile Ala Gln Gln Glu Phe Val Asn Trp Leu Leu Ala Gln Lys Xaa Pro
            20                  25                  30

Ser Ser Gly Ala Pro Pro Ser
        35                  40

<210> SEQ ID NO 798
<211> LENGTH: 38
<212> TYPE: PRT
<213> ORGANISM: Artificial
<220> FEATURE:

<223> OTHER INFORMATION: synthetic

<400> SEQUENCE: 798

Tyr Ala Glu Gly Thr Phe Ile Ser Asp Tyr Ser Ile Ala Met Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
        35

<210> SEQ ID NO 799
<211> LENGTH: 38
<212> TYPE: PRT
<213> ORGANISM: Artificial
<220> FEATURE:
<223> OTHER INFORMATION: synthetic

<400> SEQUENCE: 799

Tyr Ala Glu Gly Thr Phe Ile Ser Asp Tyr Ser Ile Ala Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
        35

<210> SEQ ID NO 800
<211> LENGTH: 38
<212> TYPE: PRT
<213> ORGANISM: Artificial
<220> FEATURE:
<223> OTHER INFORMATION: synthetic

<400> SEQUENCE: 800

Tyr Ala Glu Gly Thr Phe Ile Ser Asp Tyr Ser Ile Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
        35

<210> SEQ ID NO 801
<211> LENGTH: 38
<212> TYPE: PRT
<213> ORGANISM: Artificial
<220> FEATURE:
<223> OTHER INFORMATION: synthetic

<400> SEQUENCE: 801

Tyr Ala Glu Gly Thr Phe Ile Ser Asp Tyr Ser Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Pro Ser
        35

<210> SEQ ID NO 802
<211> LENGTH: 38
<212> TYPE: PRT
<213> ORGANISM: Artificial
<220> FEATURE:
<223> OTHER INFORMATION: synthetic

<400> SEQUENCE: 802

Tyr Ala Glu Gly Thr Phe Ile Ser Asp Tyr Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 803
<211> LENGTH: 38
<212> TYPE: PRT
<213> ORGANISM: Artificial
<220> FEATURE:
<223> OTHER INFORMATION: synthetic

<400> SEQUENCE: 803

Tyr Ala Glu Gly Thr Phe Ile Ser Asp Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 804
<211> LENGTH: 38
<212> TYPE: PRT
<213> ORGANISM: Artificial
<220> FEATURE:
<223> OTHER INFORMATION: synthetic

<400> SEQUENCE: 804

Tyr Ala Glu Gly Thr Phe Ile Ser Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 805
<211> LENGTH: 38
<212> TYPE: PRT
<213> ORGANISM: Artificial
<220> FEATURE:
<223> OTHER INFORMATION: synthetic

<400> SEQUENCE: 805

Tyr Ala Glu Gly Thr Phe Ile Asp Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 806
<211> LENGTH: 38
<212> TYPE: PRT
<213> ORGANISM: Artificial
<220> FEATURE:
<223> OTHER INFORMATION: synthetic

<400> SEQUENCE: 806

Tyr Ala Glu Gly Thr Phe Ser Asp Tyr Ser Ile Ala Met Asp Lys Ile
1               5                   10                  15

His Gln Gln Asp Phe Val Asn Trp Leu Leu Ala Gln Lys Pro Ser Ser

```
                20                  25                  30

Gly Ala Pro Pro Pro Ser
        35

<210> SEQ ID NO 807
<211> LENGTH: 38
<212> TYPE: PRT
<213> ORGANISM: Artificial
<220> FEATURE:
<223> OTHER INFORMATION: synthetic

<400> SEQUENCE: 807

Tyr Ala Glu Gly Thr Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 808
<211> LENGTH: 38
<212> TYPE: PRT
<213> ORGANISM: Artificial
<220> FEATURE:
<223> OTHER INFORMATION: synthetic

<400> SEQUENCE: 808

Tyr Ala Glu Gly Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 809
<211> LENGTH: 38
<212> TYPE: PRT
<213> ORGANISM: Artificial
<220> FEATURE:
<223> OTHER INFORMATION: synthetic 809

<400> SEQUENCE: 809

Tyr Ala Glu Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35

<210> SEQ ID NO 810
<211> LENGTH: 38
<212> TYPE: PRT
<213> ORGANISM: Artificial
<220> FEATURE:
<223> OTHER INFORMATION: synthetic

<400> SEQUENCE: 810

Tyr Ala Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
                20                  25                  30

Gly Ala Pro Pro Pro Ser
        35
```

<210> SEQ ID NO 811
<211> LENGTH: 38
<212> TYPE: PRT
<213> ORGANISM: Artificial
<220> FEATURE:
<223> OTHER INFORMATION: synthetic

<400> SEQUENCE: 811

Ala Glu Gly Thr Phe Ile Ser Asp Tyr Ser Ile Ala Met Asp Lys Ile
1               5                   10                  15

His Gln Gln Asp Phe Val Asn Trp Leu Leu Ala Gln Lys Pro Ser Ser
            20                  25                  30

Gly Ala Pro Pro Ser
        35

<210> SEQ ID NO 812
<211> LENGTH: 39
<212> TYPE: PRT
<213> ORGANISM: Artificial
<220> FEATURE:
<223> OTHER INFORMATION: synhtetic
<220> FEATURE:
<221> NAME/KEY: MISC_FEATURE
<222> LOCATION: (15)..(16)
<223> OTHER INFORMATION: cyclo D-K

<400> SEQUENCE: 812

Tyr Ala Glu Gly Thr Phe Ile Ser Asp Tyr Ser Ile Ala Met Xaa Xaa
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 813
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-alanine

<400> SEQUENCE: 813

Ala Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 814
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-alanine

<400> SEQUENCE: 814

Tyr Xaa Glu Gly Thr Phe Ile Ser Asp Ala Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 815
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 815

Tyr Xaa Glu Gly Thr Phe Ile Ser Asp Tyr Ser Ile Ala Met Asp Lys
1               5                   10                  15

Ile His Gln Gln Asp Ala Val Asn Trp Leu Leu Ala Gln Lys Pro Ser
            20                  25                  30

Ser Gly Ala Pro Pro Pro Ser
        35

<210> SEQ ID NO 816
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 816

Tyr Xaa Glu Gly Thr Phe Ile Ser Asp Tyr Ser Ile Ala Met Asp Lys
1               5                   10                  15

Ile His Gln Gln Asp Phe Ala Asn Trp Leu Leu Ala Gln Lys Pro Ser
            20                  25                  30

Ser Gly Ala Pro Pro Pro Ser
        35

<210> SEQ ID NO 817
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 817

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Ala Ala Gln Lys Pro Ser
            20                  25                  30

Ser Gly Ala Pro Pro Pro Ser
        35

<210> SEQ ID NO 818

```
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 818

Tyr Xaa Ala Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 819
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 819

Tyr Xaa Glu Gly Ala Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 820
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 820

Tyr Xaa Glu Gly Thr Ala Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 821
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 821
```

```
Tyr Xaa Glu Gly Thr Phe Ile Ala Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 822
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 822

Tyr Xaa Glu Gly Thr Phe Ile Ser Ala Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 823
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 823

Tyr Xaa Glu Gly Thr Phe Ile Ser Asp Tyr Ala Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 824
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 824

Tyr Xaa Glu Gly Thr Phe Ile Ser Asp Tyr Ser Ala Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35
```

<210> SEQ ID NO 825
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 825

Tyr Xaa Glu Gly Thr Phe Ile Ser Asp Tyr Ser Ile Ala Ala Asp Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 826
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 826

Tyr Xaa Glu Gly Thr Phe Ile Ser Asp Tyr Ser Ile Ala Met Ala Lys
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 827
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 827

Tyr Xaa Glu Gly Thr Phe Ile Ser Asp Tyr Ser Ile Ala Met Asp Ala
1               5                   10                  15

Ile His Gln Gln Asp Phe Val Asn Trp Leu Leu Ala Gln Lys Pro Ser
            20                  25                  30

Ser Gly Ala Pro Pro Pro Ser
        35

<210> SEQ ID NO 828
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 828

Tyr Xaa Glu Gly Thr Phe Ile Ser Asp Tyr Ser Ile Ala Met Asp Lys
1               5                   10                  15

Ala His Gln Gln Asp Phe Val Asn Trp Leu Leu Ala Gln Lys Pro Ser
            20                  25                  30

Ser Gly Ala Pro Pro Pro Ser
        35

<210> SEQ ID NO 829
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 829

Tyr Xaa Glu Gly Thr Phe Ile Ser Asp Tyr Ser Ile Ala Met Asp Lys
1               5                   10                  15

Ile His Ala Gln Asp Phe Val Asn Trp Leu Leu Ala Gln Lys Pro Ser
            20                  25                  30

Ser Gly Ala Pro Pro Pro Ser
        35

<210> SEQ ID NO 830
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 830

Tyr Xaa Glu Gly Thr Phe Ile Ser Asp Tyr Ser Ile Ala Met Asp Lys
1               5                   10                  15

Ile His Gln Ala Asp Phe Val Asn Trp Leu Leu Ala Gln Lys Pro Ser
            20                  25                  30

Ser Gly Ala Pro Pro Pro Ser
        35

<210> SEQ ID NO 831
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 831

Tyr Xaa Glu Gly Thr Phe Ile Ser Asp Tyr Ser Ile Ala Met Asp Lys
1               5                   10                  15

Ile His Gln Gln Ala Phe Val Asn Trp Leu Leu Ala Gln Lys Pro Ser
            20                  25                  30

Ser Gly Ala Pro Pro Pro Ser
        35

```
<210> SEQ ID NO 832
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 832

Tyr Xaa Glu Gly Thr Phe Ile Ser Asp Tyr Ser Ile Ala Met Asp Lys
1               5                   10                  15

Ile His Gln Gln Asp Phe Val Ala Trp Leu Leu Ala Gln Lys Pro Ser
            20                  25                  30

Ser Gly Ala Pro Pro Pro Ser
        35

<210> SEQ ID NO 833
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 833

Tyr Xaa Glu Gly Thr Phe Ile Ser Asp Tyr Ser Ile Ala Met Asp Lys
1               5                   10                  15

Ile His Gln Gln Asp Phe Val Asn Ala Leu Leu Ala Gln Lys Pro Ser
            20                  25                  30

Ser Gly Ala Pro Pro Pro Ser
        35

<210> SEQ ID NO 834
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..()
<223> OTHER INFORMATION: Xaa is D-Alanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 834

Tyr Xaa Glu Gly Thr Phe Ile Ser Asp Tyr Ser Ile Ala Met Asp Lys
1               5                   10                  15

Ile His Gln Gln Asp Phe Val Asn Trp Ala Leu Ala Gln Lys Pro Ser
            20                  25                  30

Ser Gly Ala Pro Pro Pro Ser
        35

<210> SEQ ID NO 835
<211> LENGTH: 39
<212> TYPE: PRT
<213> ORGANISM: Artificial Sequence
<220> FEATURE:
<223> OTHER INFORMATION: synthetic peptide
```

```
<220> FEATURE:
<221> NAME/KEY: MISC_FEATURE
<222> LOCATION: (2)..(2)
<223> OTHER INFORMATION: D-Alanine

<400> SEQUENCE: 835

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Ala Lys Pro Ser
            20                  25                  30

Ser Gly Ala Pro Pro Pro Ser
        35

<210> SEQ ID NO 836
<211> LENGTH: 8
<212> TYPE: PRT
<213> ORGANISM: Artificial Sequence
<220> FEATURE:
<223> OTHER INFORMATION: synthetic peptide

<400> SEQUENCE: 836

Pro Lys Lys Ile Pro Pro Pro Ser
1               5

<210> SEQ ID NO 837
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 837

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Pro Pro Pro Ser
        35

<210> SEQ ID NO 838
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 838

His Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 839
<211> LENGTH: 37
<212> TYPE: PRT
<213> ORGANISM: Artificial Sequence
```

```
<220> FEATURE:
<223> OTHER INFORMATION: synthetic peptide

<400> SEQUENCE: 839

His Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 840
<211> LENGTH: 37
<212> TYPE: PRT
<213> ORGANISM: Artificial Sequence
<220> FEATURE:
<223> OTHER INFORMATION: synthetic peptide

<400> SEQUENCE: 840

His Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 841
<211> LENGTH: 37
<212> TYPE: PRT
<213> ORGANISM: Artificial Sequence
<220> FEATURE:
<223> OTHER INFORMATION: synthetic peptide

<400> SEQUENCE: 841

His Gly Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Lys
            20                  25                  30

Lys Ile Arg Tyr Ser
        35

<210> SEQ ID NO 842
<211> LENGTH: 37
<212> TYPE: PRT
<213> ORGANISM: Artificial Sequence
<220> FEATURE:
<223> OTHER INFORMATION: synthetic peptide

<400> SEQUENCE: 842

His Gly Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln Lys Pro Lys
            20                  25                  30

Lys Ile Arg Tyr Ser
        35

<210> SEQ ID NO 843
<211> LENGTH: 37
<212> TYPE: PRT
<213> ORGANISM: Artificial Sequence
<220> FEATURE:
<223> OTHER INFORMATION: synthetic peptide

<400> SEQUENCE: 843
```

```
His Gly Glu Gly Thr Leu Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35

<210> SEQ ID NO 844
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 844

Tyr Xaa Glu Gly Thr Phe Ile Ser Asp Tyr Ser Ile Ala Met Asp Lys
1               5                   10                  15

Ile His Gln Gln Asp Phe Val Asn Gln Leu Leu Ala Gln Lys Pro Lys
            20                  25                  30

Lys Ile Arg Tyr Ser
        35

<210> SEQ ID NO 845
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 845

Tyr Xaa Glu Gly Thr Phe Ile Ser Asp Tyr Ser Ile Ala Met Asp Lys
1               5                   10                  15

Ile His Gln Gln Asp Phe Val Gln Trp Leu Leu Ala Gln Lys Pro Lys
            20                  25                  30

Lys Ile Arg Tyr Ser
        35

<210> SEQ ID NO 846
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is Aib

<400> SEQUENCE: 846

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Lys Ile Arg Tyr Ser
        35
```

```
<210> SEQ ID NO 847
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 847

Tyr Xaa Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Pro Lys
            20                  25                  30

Lys Ala Arg Tyr Ser
        35

<210> SEQ ID NO 848
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 848

Tyr Xaa Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Pro Lys
            20                  25                  30

Lys Gln Arg Tyr Ser
        35

<210> SEQ ID NO 849
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 849

Tyr Xaa Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Pro Lys
            20                  25                  30

Lys Ile Gln Tyr Ser
        35

<210> SEQ ID NO 850
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine
```

<400> SEQUENCE: 850

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Arg Tyr Ser
        35

<210> SEQ ID NO 851
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: D-Alanine

<400> SEQUENCE: 851

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Asn
            20                  25                  30

Lys Ile Arg Tyr Ser
        35

<210> SEQ ID NO 852
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 852

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Asn Ile Arg Tyr Ser
        35

<210> SEQ ID NO 853
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 853

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Gln
            20                  25                  30

Gln Ile Arg Tyr Ser
        35

<210> SEQ ID NO 854
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 854

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Gln
            20                  25                  30

Lys Ile Arg Tyr Ser
        35

<210> SEQ ID NO 855
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 855

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Gln Ile Arg Tyr Ser
        35

<210> SEQ ID NO 856
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 856

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Ser Ile Arg Tyr Ser
        35

<210> SEQ ID NO 857
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 857

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Lys Ile Arg Tyr Ser
        35

<210> SEQ ID NO 858
<211> LENGTH: 37
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 858

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Gln
            20                  25                  30

Lys Ile Gln Tyr Ser
        35

<210> SEQ ID NO 859
<211> LENGTH: 38
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 859

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Lys
            20                  25                  30

Gly Lys Ile Arg Tyr Ser
        35

<210> SEQ ID NO 860
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 860

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Asn Ser
        35

```
<210> SEQ ID NO 861
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 861

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Gln Ser
        35

<210> SEQ ID NO 862
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 862

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Gln Ser Lys
        35                  40

<210> SEQ ID NO 863
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 863

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Pro Ser Lys
        35                  40

<210> SEQ ID NO 864
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
```

<223> OTHER INFORMATION: Xaa is D-Alanine

<400> SEQUENCE: 864

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Lys Gln Lys Pro Ser
            20                  25                  30

Ser Gly Ala Pro Pro Pro Ser
        35

<210> SEQ ID NO 865
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 865

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Lys Pro Pro Pro Ser
        35

<210> SEQ ID NO 866
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 866

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Lys Pro Pro Ser
        35

<210> SEQ ID NO 867
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 867

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Lys Pro Ser

35

<210> SEQ ID NO 868
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 868

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Lys Ser
        35

<210> SEQ ID NO 869
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 869

Tyr Xaa Glu Gly Thr Phe Ile Ser Asp Tyr Ser Ile Ala Leu Asp Lys
1               5                   10                  15

Ile Ala Gln Gln Glu Phe Val Asn Trp Leu Leu Ala Gln Lys Pro Ser
            20                  25                  30

Ser Gly Ala Pro Pro Lys Ser Lys
        35                  40

<210> SEQ ID NO 870
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 870

Tyr Xaa Glu Gly Thr Phe Ile Ser Asp Tyr Ser Ile Ala Met Glu Lys
1               5                   10                  15

Ile Arg Gln Gln Glu Phe Val Asn Trp Leu Leu Ala Gln Lys Pro Ser
            20                  25                  30

Ser Gly Ala Pro Pro Pro Ser
        35

<210> SEQ ID NO 871
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE

```
<222> LOCATION: (2)..(2)
<223> OTHER INFORMATION: Xaa is D-Alanine

<400> SEQUENCE: 871

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30

Ser Gly Ala Pro Pro Asn Ser
        35

<210> SEQ ID NO 872
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 872

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30

Ser Gly Ala Arg Pro Pro Ser
        35

<210> SEQ ID NO 873
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 873

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30

Ser Gly Ala Lys Pro Pro Ser
        35

<210> SEQ ID NO 874
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 874

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30
```

Ser Gly Ala Pro Lys Pro Ser
        35

<210> SEQ ID NO 875
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 875

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30

Ser Gly Ala Pro Asp Pro Ser
        35

<210> SEQ ID NO 876
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 876

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gln Lys Pro Ser
            20                  25                  30

Ser Gly Ala Pro Pro Lys Ser Lys
        35                  40

<210> SEQ ID NO 877
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 877

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Lys Gln Lys Pro Ser
            20                  25                  30

Ser Gly Ala Pro Pro Pro Ser
        35

<210> SEQ ID NO 878
<211> LENGTH: 39
<212> TYPE: PRT
<213> ORGANISM: Artificial Sequence
<220> FEATURE:
<223> OTHER INFORMATION: synthetic peptide
<220> FEATURE:

```
<221> NAME/KEY: MISC_FEATURE
<222> LOCATION: (2)..(2)
<223> OTHER INFORMATION: Xaa is D-Alanine

<400> SEQUENCE: 878

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Lys Gln Lys Pro Ser
            20                  25                  30

Ser Gly Ala Pro Pro Lys Ser
        35

<210> SEQ ID NO 879
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 879

Tyr Xaa Glu Gly Thr Phe Ile Ser Asp Tyr Ser Ile Ala Leu Glu Lys
1               5                   10                  15

Ile Arg Gln Gln Glu Phe Val Asn Trp Leu Leu Ala Gly Lys Pro Ser
            20                  25                  30

Ser Gly Ala Pro Pro Asn Ser Lys
        35                  40

<210> SEQ ID NO 880
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 880

Tyr Xaa Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gly Lys Pro Ser
            20                  25                  30

Ser Gly Ala Pro Pro Gln Ser
        35

<210> SEQ ID NO 881
<211> LENGTH: 9
<212> TYPE: PRT
<213> ORGANISM: Artificial Sequence
<220> FEATURE:
<223> OTHER INFORMATION: synthetic peptide

<400> SEQUENCE: 881

Pro Ser Ser Gly Ala Pro Pro Asn Ser
1               5

<210> SEQ ID NO 882
<211> LENGTH: 39
<212> TYPE: PRT
<213> ORGANISM: Artificial Sequence
<220> FEATURE:
```

<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 882

Tyr Xaa Glu Gly Thr Phe Ile Ser Asp Tyr Ser Ile Ala Met Asp Lys
1               5                   10                  15

Ile His Gln Gln Asp Phe Val Asn Gln Leu Leu Ala Gln Lys Pro Ser
            20                  25                  30

Ser Gly Ala Pro Pro Pro Ser
        35

<210> SEQ ID NO 883
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 883

Tyr Xaa Glu Gly Thr Phe Ile Ser Asp Tyr Ser Ile Ala Met Asp Lys
1               5                   10                  15

Ile His Gln Gln Asp Phe Val Gln Trp Leu Leu Ala Gln Lys Pro Ser
            20                  25                  30

Ser Gly Ala Pro Pro Pro Ser
        35

<210> SEQ ID NO 884
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 884

Tyr Xaa Glu Gly Thr Phe Ile Ser Asp Tyr Ser Ile Ala Met Asp Lys
1               5                   10                  15

Ile His Gln Gln Asp Phe Val Asn Asn Leu Leu Ala Gln Lys Pro Ser
            20                  25                  30

Ser Gly Ala Pro Pro Pro Ser
        35

<210> SEQ ID NO 885
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..()
<223> OTHER INFORMATION: Xaa is D-Alanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 885

Tyr Xaa Glu Gly Thr Phe Ile Ser Asp Tyr Ser Ile Ala Met Asp Lys
1               5                   10                  15

Ile His Gln Gln Asp Phe Val Asn Ser Leu Leu Ala Gln Lys Pro Ser
            20                  25                  30

Ser Gly Ala Pro Pro Pro Ser
        35

<210> SEQ ID NO 886
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 886

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Asn Ala Gln Lys Pro Ser
            20                  25                  30

Ser Gly Ala Pro Pro Pro Ser
        35

<210> SEQ ID NO 887
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 887

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Ser Ala Gln Lys Pro Ser
            20                  25                  30

Ser Gly Ala Pro Pro Pro Ser
        35

<210> SEQ ID NO 888
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 888

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Gln Ala Gln Lys Pro Ser
            20                  25                  30

Ser Gly Ala Pro Pro Pro Ser
        35

```
<210> SEQ ID NO 889
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 889

Tyr Xaa Glu Gly Thr Phe Ile Ser Asp Tyr Ser Ile Ala Met Asp Lys
1               5                   10                  15

Ile His Gln Gln Asp Phe Val Asn Trp Asn Leu Ala Gln Lys Pro Ser
            20                  25                  30

Ser Gly Ala Pro Pro Pro Ser
        35

<210> SEQ ID NO 890
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 890

Tyr Xaa Glu Gly Thr Phe Ile Ser Asp Tyr Ser Ile Ala Met Asp Lys
1               5                   10                  15

Ile His Gln Gln Asp Phe Val Asn Trp Ser Leu Ala Gln Lys Pro Ser
            20                  25                  30

Ser Gly Ala Pro Pro Pro Ser
        35

<210> SEQ ID NO 891
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 891

Tyr Xaa Glu Gly Thr Phe Ile Ser Asp Tyr Ser Ile Ala Met Asp Lys
1               5                   10                  15

Ile His Gln Gln Asp Phe Val Asn Trp Gln Leu Ala Gln Lys Pro Ser
            20                  25                  30

Ser Gly Ala Pro Pro Pro Ser
        35

<210> SEQ ID NO 892
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine
```

<400> SEQUENCE: 892

Tyr Xaa Glu Gly Thr Phe Ile Ser Asp Tyr Ser Ile Ala Met Asp Lys
1               5                   10                  15

Ile His Gln Gln Asp Phe Val Glu Trp Leu Lys Ala Gln Lys Pro Ser
            20                  25                  30

Ser Gly Ala Pro Pro Pro Ser
            35

<210> SEQ ID NO 893
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 893

Tyr Xaa Glu Gly Thr Phe Ile Ser Asp Tyr Ser Ile Ala Met Asp Lys
1               5                   10                  15

Ile His Gln Gln Asp Phe Val Asn Asn Leu Asn Ala Gln Lys Pro Ser
            20                  25                  30

Ser Gly Ala Pro Pro Pro Ser
            35

<210> SEQ ID NO 894
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 894

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Lys Gln Lys Pro Ser
            20                  25                  30

Ser Gly Ala Pro Pro Pro Ser
            35

<210> SEQ ID NO 895
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 895

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu His Gln Lys Pro Ser
            20                  25                  30

Ser Gly Ala Pro Pro Pro Ser
            35

<210> SEQ ID NO 896
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 896

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Gly Gln Lys Pro Ser
            20                  25                  30

Ser Gly Ala Pro Pro Pro Ser
        35

<210> SEQ ID NO 897
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 897

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly His Pro Pro Pro Ser
        35

<210> SEQ ID NO 898
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 898

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Asn Pro Pro Pro Ser
        35

<210> SEQ ID NO 899
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

```
<400> SEQUENCE: 899

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Gln Pro Pro Ser
        35

<210> SEQ ID NO 900
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 900

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Asn Pro Pro Ser
        35

<210> SEQ ID NO 901
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 901

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Asn Pro Ser
        35

<210> SEQ ID NO 902
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 902

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Asn Ser
        35
```

<210> SEQ ID NO 903
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 903

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Gln Ser
        35

<210> SEQ ID NO 904
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 904

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Asp Ser
        35

<210> SEQ ID NO 905
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..()
<223> OTHER INFORMATION: Xaa is D-Alanine
<220> FEATURE:
<221> NAME/KEY: misc_feature
<222> LOCATION: (2)..(2)
<223> OTHER INFORMATION: Xaa can be any naturally occurring amino acid

<400> SEQUENCE: 905

Tyr Xaa Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Asn Ser
        35

<210> SEQ ID NO 906
<211> LENGTH: 39
<212> TYPE: PRT
<213> ORGANISM: Artificial Sequence
<220> FEATURE:

<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 906

Tyr Xaa Glu Gly Thr Phe Ile Ser Asp Tyr Ser Ile Ala Leu Asp Lys
1               5                   10                  15

Ile His Gln Gln Asp Phe Val Asn Trp Leu Leu Ala Gln Lys Pro Ser
            20                  25                  30

Ser Gly Ala Pro Pro Gln Ser
        35

<210> SEQ ID NO 907
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 907

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Gln Pro Pro Gln Ser Lys
        35                  40

<210> SEQ ID NO 908
<211> LENGTH: 40
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 908

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Gln Ser Lys
        35                  40

<210> SEQ ID NO 909
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 909

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Gly Pro Ser
        35

<210> SEQ ID NO 910
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 910

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Lys Pro Pro Pro Ser
        35

<210> SEQ ID NO 911
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 911

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Pro Lys Ser
        35

<210> SEQ ID NO 912
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 912

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Lys Pro Pro Lys Ser
        35

<210> SEQ ID NO 913
<211> LENGTH: 39
<212> TYPE: PRT
<213> ORGANISM: Artificial Sequence

```
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 913

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Gln Pro Pro Ser
        35

<210> SEQ ID NO 914
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 914

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Pro Ser
            20                  25                  30

Ser Gly Ala Pro Gly Gly Ser
        35

<210> SEQ ID NO 915
<211> LENGTH: 42
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 915

Tyr Xaa Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Pro Ser Ser Gly Ala Pro Pro Ser
        35                  40

<210> SEQ ID NO 916
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 916

Tyr Xaa Glu Gly Thr Phe Ile Ser Asp Tyr Ser Ile Ala Leu Asp Lys
1               5                   10                  15
```

Ile Arg Gln Gln Glu Phe Val Asn Trp Leu Leu Ala Gln His Pro Ser
            20                  25                  30

Ser Gly Ala Pro Pro Gln Ser
        35

<210> SEQ ID NO 917
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 917

Tyr Xaa Glu Gly Thr Phe Ile Ser Asp Tyr Ser Ile Ala Leu Asp Lys
1               5                   10                  15

Ile Arg Gln Gln Lys Phe Val Asn Trp Leu Leu Ala Gln Lys Pro Ser
            20                  25                  30

Ser Gly Ala Pro Pro Gln Ser
        35

<210> SEQ ID NO 918
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 918

Tyr Xaa Glu Gly Thr Phe Ile Ser Asp Tyr Ser Ile Ala Leu Asp Lys
1               5                   10                  15

Ile Arg Gln Gln Lys Phe Val Asn Trp Leu Leu Ala Gln Lys Pro Ser
            20                  25                  30

Ser Gly Ala Pro Pro Asn Ser
        35

<210> SEQ ID NO 919
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 919

Tyr Xaa Glu Gly Thr Phe Ile Ser Asp Tyr Ser Ile Ala Leu Asp Lys
1               5                   10                  15

Ile Arg Gln Gln Glu Phe Val Asn Trp Leu Leu Ala Gln His Pro Ser
            20                  25                  30

Ser Gly Ala Pro Pro Asn Ser
        35

<210> SEQ ID NO 920
<211> LENGTH: 39
<212> TYPE: PRT

```
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 920

Tyr Xaa Glu Gly Thr Phe Ile Ser Asp Tyr Ser Ile Ala Leu Asp Lys
 1               5                  10                  15

Ile Arg Gln Gln Glu Phe Val Asn Trp Leu Leu Ala Gln Lys Pro Ser
            20                  25                  30

Ser Gly Ala Pro Pro Lys Ser
        35

<210> SEQ ID NO 921
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 921

Tyr Xaa Glu Gly Thr Phe Ile Ser Asp Tyr Ser Ile Ala Leu Asp Lys
 1               5                  10                  15

Ile Lys Gln Gln Glu Phe Val Asn Trp Leu Leu Ala Gln Lys Pro Ser
            20                  25                  30

Ser Gly Ala Pro Pro Lys Ser
        35

<210> SEQ ID NO 922
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 922

Tyr Xaa Glu Gly Thr Phe Ile Ser Asp Tyr Ser Ile Ala Leu Asp Lys
 1               5                  10                  15

Ile His Gln Gln Glu Phe Val Asn Trp Leu Leu Ala Gln Lys Pro Ser
            20                  25                  30

Ser Gly Gln Pro Pro Gln Ser
        35

<210> SEQ ID NO 923
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine
<220> FEATURE:
<221> NAME/KEY: misc_feature
<222> LOCATION: (2)..(2)
<223> OTHER INFORMATION: Xaa can be any naturally occurring amino acid
```

<400> SEQUENCE: 923

Tyr Xaa Glu Gly Thr Phe Ile Ser Asp Tyr Ser Ile Ala Leu Asp Lys
1               5                   10                  15

Ile Lys Gln Gln Glu Phe Val Asn Trp Leu Leu Ala Gln Lys Pro Ser
            20                  25                  30

Ser Gly Ala Pro Pro Asn Ser
        35

<210> SEQ ID NO 924
<211> LENGTH: 39
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (2)..(2)
<223> OTHER INFORMATION: Xaa is D-Alanine

<400> SEQUENCE: 924

Tyr Xaa Glu Gly Thr Phe Ile Ser Asp Tyr Ser Ile Ala Met Asp Lys
1               5                   10                  15

Ile Lys Gln Gln Asp Glu Val Asn Trp Leu Leu Ala Gln Lys Pro Ser
            20                  25                  30

Ser Gly Ala Pro Pro Pro Ser
        35

<210> SEQ ID NO 925
<211> LENGTH: 10
<212> TYPE: PRT
<213> ORGANISM: Artificial Sequence
<220> FEATURE:
<223> OTHER INFORMATION: synthetic peptide

<400> SEQUENCE: 925

Pro Ser Ser Gly Gln Pro Pro Gln Ser Lys
1               5                   10

<210> SEQ ID NO 926
<211> LENGTH: 10
<212> TYPE: PRT
<213> ORGANISM: Artificial Sequence
<220> FEATURE:
<223> OTHER INFORMATION: synthetic peptide

<400> SEQUENCE: 926

Pro Ser Ser Gly Ala Pro Pro Gln Ser Lys
1               5                   10

<210> SEQ ID NO 927
<211> LENGTH: 10
<212> TYPE: PRT
<213> ORGANISM: Artificial Sequence
<220> FEATURE:
<223> OTHER INFORMATION: synthetic peptide

<400> SEQUENCE: 927

Pro Ser Ser Gly Ala Pro Pro Lys Ser Lys
1               5                   10

<210> SEQ ID NO 928
<211> LENGTH: 9
<212> TYPE: PRT
<213> ORGANISM: Artificial Sequence
<220> FEATURE:

```
<223> OTHER INFORMATION: synthetic peptide

<400> SEQUENCE: 928

Pro Ser Ser Gly Ala Pro Pro Lys Ser
1               5

<210> SEQ ID NO 929
<211> LENGTH: 9
<212> TYPE: PRT
<213> ORGANISM: Artificial Sequence
<220> FEATURE:
<223> OTHER INFORMATION: synthetic peptide

<400> SEQUENCE: 929

Pro Ser Ser Gly Ala Arg Pro Pro Ser
1               5

<210> SEQ ID NO 930
<211> LENGTH: 9
<212> TYPE: PRT
<213> ORGANISM: Artificial Sequence
<220> FEATURE:
<223> OTHER INFORMATION: synthetic peptide

<400> SEQUENCE: 930

Pro Ser Ser Gly Ala Lys Pro Pro Ser
1               5

<210> SEQ ID NO 931
<211> LENGTH: 9
<212> TYPE: PRT
<213> ORGANISM: Artificial Sequence
<220> FEATURE:
<223> OTHER INFORMATION: synthetic peptide

<400> SEQUENCE: 931

Pro Ser Ser Gly Ala Pro Lys Pro Ser
1               5

<210> SEQ ID NO 932
<211> LENGTH: 9
<212> TYPE: PRT
<213> ORGANISM: Artificial Sequence
<220> FEATURE:
<223> OTHER INFORMATION: synthetic peptide

<400> SEQUENCE: 932

Pro Ser Ser Gly Ala Pro Asp Pro Ser
1               5

<210> SEQ ID NO 933
<211> LENGTH: 8
<212> TYPE: PRT
<213> ORGANISM: Artificial Sequence
<220> FEATURE:
<223> OTHER INFORMATION: synthetic peptide

<400> SEQUENCE: 933

Pro Lys Gly Lys Ile Arg Tyr Ser
1               5
```

GIP ANALOG AND HYBRID POLYPEPTIDES WITH SELECTABLE PROPERTIES

RELATED APPLICATIONS

The present application is a continuation-in-part of and claims priority to commonly-owned U.S. patent application Ser. No. 11/507,081 filed Aug. 17, 2006, now abandoned and claims priority to United States provisional applications: U.S. Provisional Application No. 60/652,662 filed Feb. 11, 2005; U.S. Provisional Application No. 60/653,433 filed Feb. 15, 2005; U.S. Provisional Application No. 60/651,647 filed Feb. 11, 2005; U.S. Provisional Application No. 60/707,244 filed Aug. 11, 2005; U.S. Provisional Application No. 60/707,369 filed Aug. 11, 2005; U.S. Provisional Application No. 60/709,320 filed Aug. 17, 2005; U.S. Provisional Application No. 60/709,316 filed Aug. 17, 2005; and PCT/US2006/005020 filed 10 Feb. 2006, each of which are hereby incorporated by reference in their entirety. Also incorporated herein by reference is PCT application entitled "GIP ANALOG AND HYBRID POLYPEPTIDES WITH SELECTABLE PROPERTIES" filed with the USPTO RO on even date herewith PCT/US07/18415. Incorporated herein by reference is Sequence Listing file "0601CIP2 Seq Listing 2-25-08_ST25.txt" dated Feb. 25, 2008 and submitted herewith via EFS.

FIELD OF THE INVENTION

The present invention relates to peptide chemistry and pharmaceuticals, and more particularly to novel gastric inhibitory peptide ("GIP") analog and GIP-containing hybrid polypeptides with selectable properties. It further relates to the use of these and other GIP compounds either alone or in adjunct with other compounds such as glucagon-like peptide 1 ("GLP1"), exendin-4, or amylin polypeptides, to treat metabolic disorders and conditions.

BACKGROUND OF THE INVENTION

Incretin peptides are hormones and peptide mimetics that cause an increase in the amount of insulin released when glucose levels are normal or particularly when they are elevated. These incretin peptides have other actions beyond the initial incretin action defined by insulin secretion. For instance, they may also have actions to reduce glucagon production and delay gastric emptying. In addition, they may have actions to improve insulin sensitivity, and they may increase islet cell neogenesis—the formation of new islets.

The concept of the incretin effect developed from the observation that insulin responses to oral glucose exceeded those measured after intravenous administration of equivalent amounts of glucose. It was concluded that gut-derived factors, or incretins, influenced postprandial insulin release. Nutrient entry into the stomach and proximal gastrointestinal tract causes release of incretin hormones, which then stimulate insulin secretion. This insulinotropism, or ability to stimulate insulin secretion, can be quantified by comparing insulin or C-peptide responses to oral vs. intravenous glucose loads. In this way, it has been shown that the incretin effect is responsible for about 50% to 70% of the insulin response to oral glucose in healthy individuals.

Although many postprandial hormones have incretin-like activity, predominant incretin peptides include glucose-dependent insulinotropic polypeptide, also known as gastric inhibitory polypeptide (GIP), glucagon-like peptide-1 (GLP-1), and exendin peptides (which are non-endogenous incretin mimetics). GIP and GLP-1 both belong to the glucagon peptide superfamily and thus share amino acid sequence homology. GIP and GLP-1 are secreted by specialized cells in the gastrointestinal tract and have receptors located on islet cells as well as other tissues. As incretins, both are secreted from the intestine in response to ingestion of nutrients, which results in enhanced insulin secretion. The insulinotropic effect of GIP and GLP-1 is dependent on elevations in ambient glucose. Both are rapidly inactivated by the ubiquitous enzyme dipeptidyl peptidase IV (DPP-IV).

Native human GIP is a single 42-amino acid peptide synthesized in and secreted by specialized enteroendocrine K-cells. These cells are concentrated primarily in the duodenum and proximal jejunum, although they also can be found throughout the intestine. The main stimulant for GIP secretion is ingestion of carbohydrate- and lipid-rich meals. Following ingestion, circulating plasma GIP levels increase 10- to 20-fold. The half-life of intact GIP is estimated to be approximately 7.3 minutes in healthy subjects and 5.2 minutes in diabetic subjects.

The physiologic effects of GIP have been elucidated using GIP receptor antagonists, GIP peptide antagonists, and GIP receptor knockout mice, in addition to GIP infusion protocols. Blocking GIP binding to its receptor results in attenuated glucose-dependent insulin secretion following oral glucose load in rats and mice. Similarly, administration of GIP antagonists or GIP antisera markedly reduces the postprandial insulin release in rats. GIP receptor knockout mice demonstrate normal fasting glucose levels but mild glucose intolerance following oral glucose loads. Interestingly, they also exhibit resistance to diet-induced obesity following months of high-fat feeding. Additionally, in the leptin-deficient ob/ob mouse, the GIP receptor knockout genotype appears to decrease the extent of obesity that develops.

GIP infusion has consistently demonstrated stimulation of insulin secretion in isolated rat islets, isolated perfused rat pancreas, dogs, and humans. During stepwise euglycemic, mild hyperglycemic (54 mg/dL above basal), and moderate hyperglycemic (143 mg/dL above basal) clamps, it has been demonstrated that GIP infusion results in insulin secretion only in the presence of elevated glucose concentrations. Furthermore, it has been demonstrated that GIP is not glucagonotropic in normal humans during either euglycemic or hyperglycemic conditions. Thus, the effect of endogenously released GIP appears to be an important mechanism of postprandial insulin secretion and does not appear to play a role in the fasting state.

GIP has many non-incretin effects as well. Unlike other insulin secretagogues, GIP stimulates beta-cell proliferation and cell survival in INS-1 islet cell-line studies. Furthermore, animal studies have suggested a role for GIP in lipid metabolism by stimulating lipoprotein lipase activity, inducing fatty acid incorporation into adipose tissue and stimulating fatty acid synthesis. However, in humans, there is no clear evidence for an effect of GIP on lipid metabolism. GIP also appears to stimulate glucagon secretion from the isolated perfused rat pancreas, although human studies have not demonstrated any significant influence on glucagon secretion. Furthermore, unlike GLP-1, GIP appears to act by accelerating emptying of the stomach rather than by inhibiting gastrointestinal motility.

The GIP-receptor, a member of the G-protein-coupled receptor family has a high specificity for GIP and does not bind other peptides of the glucagon family. For this reason, GLP-1/GIP chimeric peptides show nearly no affinity for the GIP-receptor. From such studies it has been concluded that the GIP(1-30) sequence of the GIP(1-42) is sufficient for recognizing the receptor. GIP(6-30)-amide contains the high affinity binding region of GIP(1-42) but exhibits antagonist activity.

Despite potent glucoregulatory actions through glucose-dependant stimulation of insulin secretion, the insulinotropic effect of GIP is significantly reduced in diabetic subjects compared to normal individuals (16-18). Consequently, clinical use of GIP has not been significantly advanced. Further, there remains a need to develop additional diabetic treatment modalities as well as treatments for metabolic diseases, conditions, and disorders. Accordingly, it is an object of the present invention to provide GIP analog and GIP-containing hybrid polypeptides and methods for their use to treat or prevent metabolic diseases, conditions, and disorders.

The issued patents, applications, and references that are cited herein are hereby incorporated by reference to the same extent as if each was specifically and individually indicated to be incorporated by reference and as though fully set forth herein.

SUMMARY OF THE INVENTION

Provided are methods for treating or preventing metabolic diseases and disorders including those which can be alleviated by control of plasma glucose levels, insulin levels, and/or insulin secretion, such as diabetes and diabetes-related conditions, and conditions and disorders including, but not limited to, hypertension, dyslipidemia, cardiovascular disease, eating disorders, insulin-resistance, obesity, and diabetes mellitus of any kind, including type 1, type 2, and gestational diabetes. The methods comprise administering a therapeutically or prophylactically effective amount of a GIP or GIP analog, fragment or derivative thereof, or a GIP hybrid or derivatives thereof as described herein, alone (monotherapy) or in combination with another agent or therapy (adjunct therapy), for example a glucose lowering agent (e.g., antidiabetic) or agents or methods that inhibit or reduce gastric emptying (examples of such agents are presented herein), to a subject in need thereof. By providing a GIP bioactivity as part of a GIP hybrid having one or more other hormonal bio-activities, e.g., pramlintide, exendin, BNP, compounds with one or more selectable functions will have the additional benefit of a property of a GIP bio-activity such as lowering plasma glucose, increasing insulin secretion, without the side effects associated with other incretin molecules. For example, a GIP-sCT hybrid compound of the invention can have a selectable property of a salmon calcitonin, such as decreasing bone loss and bone resorption or reducing cartilage turnover (chondroprotection), and a property of a GIP, such as plasma glucose lowering (concomitant with an anti-catabolic aspect as described herein) and/or inhibiting bone resorption and maintaining or increasing bone density. A GIP hybrid with such selectable properties can enhance treatment of osteoporosis or conditions of high cartilage turnover, particularly in those who can also benefit from glycemic control, such as subjects with diabetes or under going critical care.

In one embodiment are provided novel GIP analogs having one or more enhanced properties. The GIP analogs have increased resistance to DPP-IV or to other proteases, such as those found in human plasma and/or on kidney brush border membranes, which increases in vivo half-life. In a further embodiment the GIP analogs have at least one substitution, modification, insertion or deletion in amino acids 4-30. These changes can provide enhanced properties such as increased GIP receptor binding, increased receptor selectivity, and/or increased resistance to degradation by chemical and/or proteolytic means. In another embodiment the GIP analog further has least 50% sequence identity to native GIP(1-30), native GIP(1-14), native GIP(19-30) or native GIP(1-42) over the entire length of each molecule, and at least one biological property of a GIP. In certain embodiments, novel GIP analog polypeptides include unnatural amino acids, such as a D amino acid. In a further embodiment a GIP analog or hybrid is modified to have reduced renal clearance, such as by fatty acyl derivatization.

In another embodiment are provided novel GIP-containing hybrid polypeptides with selectable properties. The hybrid polypeptides exhibit at least one hormonal activity. In one embodiment the GIP-hybrid polypeptides comprise at least two biologically active ("bio-active") peptide hormone modules covalently linked together, wherein at least one of the bio-active peptide hormone modules comprises a GIP polypeptide. The other bio-active peptide hormone module can be: (a) a native component peptide hormone, (b) an analog or derivative of a native component peptide hormone that retains hormonal activity, (c) a fragment of a native component peptide hormone that retains hormonal activity, (d) a fragment of analogs or derivatives of a native component peptide hormone that retains hormonal activity, (e) a structural motif of a native component peptide hormone that imparts a desired chemical stability, conformational stability, metabolic stability, bioavailability, organ/tissue targeting, receptor interaction, protease inhibition, plasma protein binding, and/or other pharmacokinetic characteristic to the hybrid polypeptide; or (f) a structural motif of analogs or derivatives of a native component peptide hormone that imparts a desired chemical stability, conformational stability, metabolic stability, bioavailability, organ/tissue targeting, receptor interaction, protease inhibition, plasma protein binding, and/or other pharmacokinetic characteristic to the hybrid polypeptide. The structural motifs of (e) and (f) will collectively be referred to herein as "peptidic enhancers". An example of a peptidic enhancer is a Trp cage sequence, particularly one derived from exendin-4.

In a further embodiment a GIP-hybrid polypeptide comprises at least two bio-active peptide hormone modules covalently linked together, wherein at least one of the bio-active peptide hormone modules is comprised of a GIP polypeptide, and the second exhibits at least one hormonal activity of a component peptide hormone. The bio-active peptide hormone modules are independently selected from: component peptide hormones, fragments of component peptide hormones that exhibit at least one hormonal activity of the component peptide hormones, analogs and derivatives of component peptide hormones that exhibit at least one hormonal activity of the component peptide hormones, and fragments of analogs and derivatives of component peptide hormones that exhibit at least one hormonal activity of the component peptide hormones.

In one embodiment the GIP-hybrid polypeptides comprise a novel GIP analog polypeptide of the invention covalently linked to at least one additional bio-active peptide hormone module. In a further embodiment the bio-active peptide hormone module is a peptidic enhancer. In one embodiment the GIP hybrid polypeptide of the invention will exhibit at least 50% sequence identity to a native GIP(1-30), native GIP(1-14), native GIP(19-30) or native GIP(1-42) over the entire length of the GIP portion. In certain embodiments the GIP portion can comprise a novel GIP analog further comprising a peptidic enhancer, such as a trp-cage motif. Accordingly, a GIP hybrid can comprise a GIP portion that is a GIP analog, fragment or derivative thereof with a peptidic enhancer, such as a trp-cage motif, and having enhanced properties, that is linked covalently to an additional bio-active peptide hormone module, such as another hormone or growth factor or fragment thereof.

Component peptide hormones for use in a GIP-hybrid polypeptide include: amylin, adrenomedullin (ADM), calcitonin (CT), calcitonin gene related peptide (CGRP), intermedin, cholecystokinin ("CCK"), leptin, peptide YY (PYY), glucagon-like peptide-1 (GLP-1), glucagon-like peptide 2 (GLP-2), oxyntomodulin (OXM), natriuretic peptides (e.g. ANP, BNP, CNP or urodilatin), urocortin family peptide, e.g., Ucn-2 and Ucn-3, neuromedin family peptide, e.g. neuromedin U25 or splice variants, exendin-3 and exendin-4.

In other GIP hybrid embodiments the GIP portion is combined with a gastrin/CCK receptor ligand; an amylin receptor ligand; a calcitonin receptor ligand; a CGRP receptor ligand, a PYY receptor ligand, an EGF receptor ligand; a Glucagon-like peptide 1 receptor ligand; a Glucagon-like peptide 2 receptor ligand; a gastric inhibitory polypeptide (GIP) receptor ligand; a keratinocyte growth factor (KGF) receptor 1 ligand; a dipeptidyl peptidase IV inhibitor; a REG protein receptor ligand; a Growth Hormone receptor ligand; a Prolactin (PRL) receptor ligand; an Insulin-like Growth Factor (IGF) receptor ligand; PTH-related protein (PTHrP) receptor ligand; hepatocyte growth factor (HGF) receptor ligand; a bone morphogenetic protein (BMP) receptor ligand, a transforming growth factor (TGF receptor ligand; a laminin receptor ligand; a vasoactive intestinal peptide (VIP) receptor ligand; a fibroblast growth factor (FGF) receptor ligand; a nerve growth factor (NGF) receptor ligand; an islet neogenesis associated protein (INGAP) receptor ligand; an Activin-A receptor ligand; a vascular endothelial growth factor (VEGF) receptor ligand; an erythropoietin (EPO) receptor ligand; a pituitary adenylate cyclase activating polypeptide (PACAP) receptor ligand; a granulocyte colony stimulating factor (G-CSF) receptor ligand; a granulocyte-macrophage colony stimulating factor (GM-CSF); a platelet-derived growth factor (PDGF) receptor ligand, a cannabinoid CB1 receptor antagonist, and a secretin receptor ligand.

In one embodiment desirable GIP hybrid polypeptides include an N-terminal GIP or novel GIP analog fragment in combination with a C-terminal polypeptide or fragment thereof having a glucose lowering activity (e.g., antidiabetics, exendin) or the ability to inhibit or reduce gastric emptying. Such desirable GIP hybrids include an N-terminal GIP fragment or novel GIP analog or derivative fragment in combination with a C-terminal exendin, GLP1, pramlintide, amylin, CCK, gastrin, PYY, secretin, GRP, neuromedins, urocortin, calcitonin, or salmon calcitonin, a natriuretic peptide (e.g., ANP, BNP, CNP, urodilatin) or analog (e.g. amylin-sCT-amylin chimera), derivative or fragment thereof. In other embodiments desirable GIP hybrids include a C-terminal GIP or novel GIP analog fragment in combination with an N-terminal polypeptide or fragment thereof having a glucose lowering activity (e.g., antidiabetics, exendin) or the ability to inhibit or reduce gastric emptying. In such embodiments, the chimeric polypeptides can include a C-terminal GIP, a novel GIP analog, or fragment thereof, in combination with a N-terminal exendin, GLP1, pramlintide, amylin, CCK, gastrin, PYY, secretin, GRP, neuromedins, urocortin, calcitonin, or salmon calcitonin, a natriuretic peptide or analog, derivative or fragment thereof.

In other embodiments the peptidic enhancer is a tail or terminal extension derived from a second hormone, such as exendin, human GLP-1, or frog GLP-1, or is empirically determined. In one embodiment the peptidic enhancer is a heterologous C-terminal tail or terminal extension to the GIP portion. As with the other GIP hybrids described herein, in one embodiment of the peptidic-enhancer containing hybrid, the GIP portion can be native GIP, an active fragment thereof, or their analogs or derivatives. In another aspect the GIP portion of the hybrid comprises at least one modification, substitution, deletion or addition that provides one or more enhanced properties, e.g. increased resistance to proteolytic digestion (thus prolonging half-life), fatty acyl derivatization that reduces renal clearance. In one embodiment the tail comprises a Trp-cage motif sequence. In another embodiment the GIP analog polypeptide portion includes unnatural amino acids, such as a D amino acid, e.g. that inhibits to reduces the rate of proteolysis by DPP-IV.

The present invention also provides for the treatment and prevention of metabolic diseases and disorders, particularly those which can be alleviated by control of plasma glucose levels, insulin levels, and/or insulin secretion, such as diabetes and diabetes-related conditions. Such conditions and disorders include, but are not limited to, hypertension, dyslipidemia, cardiovascular disease, eating disorders, insulin-resistance, obesity, and diabetes mellitus of any kind, including type 1, type 2, and gestational diabetes, diabetes complications (e.g. neuropathy (treating with a GIP hybrid containing an exendin family hormone module for example), neuropathic pain (treating with GIP hybrids comprising an amylin family hormone module for example), retinopathy, nephropathy, conditions of insufficient pancreatic beta cell mass (based on, e.g., islet neogenesis actions of exendin-4 and GLP-1). Accordingly, provided are methods for treating or preventing such conditions, wherein the method comprises administering a therapeutically or prophylactically effective amount of a GIP or an analog or derivative thereof, including a novel GIP analog of the invention, or a GIP-hybrid of the invention, including one having a peptidic enhancer, to a subject in need thereof. In one embodiment the polypeptides of the invention can be provided as monotherapy. In another embodiment for treating diabetes or conditions associated with elevated glucose levels, the GIP compound can be administered in adjunct therapy with a glucose lowering agents (e.g., antidiabetics) or agents or methods that inhibit or reduce gastric emptying. Examples of such agents are presented herein. For example, in one embodiment is provided an adjunct therapy method for reducing blood glucose levels of a subject, e.g., one having type 1, type 2 or gestational diabetes mellitus, comprising administering to the subject a therapeutically effective amount of an exendin or an exendin agonist, such as wherein said exendin agonist is a peptide, in adjunct therapy with a GIP or novel GIP analog of the invention, or an effective amount of a GIP-exendin hybrid.

Compounds of the invention, alone or in combination with a glucose lowering agent (e.g., antidiabetics) or with agents or methods that inhibit or reduce gastric emptying, can also be useful for potentiating, inducing, enhancing or restoring glucose responsivity in pancreatic islets or cells. These actions may also be used to treat or prevent conditions associated with metabolic disorders such as those described above and in U.S. Patent Application No. US20040228846, incorporated herein by reference in its entirety.

In another aspect methods for treating or preventing obesity are provided, wherein the method comprises administering a therapeutically or prophylactically effective amount of a GIP or an analog or derivative thereof, including a novel GIP analog of the invention, or a GIP-hybrid of the invention, including those having a peptidic enhancer, to a subject in need thereof. In one embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from this method. Compounds of the invention can also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, *Am. Fam. Phys.* 63:2185, 2001). Where conditions are associated with elevated glucose or hyperglycemia, the method comprises administering a therapeutically or prophylactically effective amount of a GIP compound, alone or in combination with a glucose lowering agent (e.g., antidiabetic) or agent or method that inhibits or reduces gastric emptying.

In yet another aspect, GIP compounds, particularly GIP hybrids of the invention, can be used in methods of reducing food intake, reducing appetite, inducing satiety, reducing nutrient availability, reducing caloric efficiency, causing weight loss, affecting body composition, altering body energy content or energy expenditure, and improving lipid profile (including reducing LDL cholesterol and triglyceride levels and/or changing HDL cholesterol levels) wherein the methods comprise administering to a subject an effective amount of a GIP compound, particularly a GIP hybrid compound, of the invention. In one embodiment, the methods of the invention are used to treat or prevent conditions or disorders which can be alleviated by reducing nutrient availability in a subject in need thereof, comprising administering to said subject a therapeutically or prophylactically effective amount of a GIP compound of the invention. Conditions and disorders include, but are not limited to, hypertension, dyslipidemia, cardiovascular disease, eating disorders, insulin-resistance, obesity, and diabetes mellitus of any kind, including type 1, type 2, and gestational diabetes, diabetes complications (neuropathy (based on, e.g., neurotrophic actions of exendin-4), neuropathic pain (based on, e.g., amylin action), retinopathy, nephropathy, conditions of insufficient pancreatic beta cell mass (based on, e.g., islet neogenesis actions of exendin-4 and GLP-1). Where conditions are associated with elevated glucose or hyperglycemia, the method comprises administering a therapeutically or prophylactically effective amount of a GIP compound, alone or in combination with a glucose lowering agent (e.g., antidiabetic) or agent or method that inhibits or reduces gastric emptying.

In addition to the amelioration of hypertension in subjects in need thereof as a result of reduced food intake, weight loss, and/or treating obesity, compounds of the invention may be used to treat or prevent hypotension and conditions associated therewith.

In another aspect GIP analogs and hybrids are useful for decreasing or inhibiting bone resorption and maintaining or increasing bone density. When combined with an appropriate second hormonal module, GIP hybrids are useful to treat these conditions as well as decreasing plasma calcium, and/or inducing an analgesic effect, particularly to treat bone disorders such as osteopenia and osteoporosis, and treating painful neuropathy. In one embodiment such hybrids contain an exendin, GLP1, amylin and/or sCT portion. For example, a GIP-sCT or GIP-amylin/sCT hybrid compound of the invention can have a selectable property of a salmon calcitonin or amylin/sCT/Amylin chimera, such as decreasing bone loss and bone resorption or reducing cartilage turnover (chondroprotection), and a property of a GIP, such as plasma glucose lowering (concomitant with an anabolic aspect as described herein) and/or inhibiting bone resorption and maintaining or increasing bone density. A GIP hybrid with such selectable properties can enhance treatment of osteoporosis or conditions of high cartilage turnover, particularly in those who can also benefit from glycemic control, such as subjects with diabetes or under going critical care.

GIP compounds, particularly GIP analogs, extended half-life GIP hybrids (e.g. DPP-IV cleavage resistant (such as a D-Ala2, N-Acetyl or N-pyroglutamyl analogs) optionally further comprising a peptidic enhancer such as a heterologous C-terminal tail, and GIP hybrids comprising other hormone modules known to provide beneficial cardiovascular effects, are useful to treat cardiovascular disease and related conditions. As demonstrated herein GIP compounds increase cardiac contractility (dp/dt), decrease blood pressure (for example by acute vasodilatation), decrease systolic pressure, decrease diastolic pressure, and can provide a direct beneficial action on cardiac cells. GIP compounds also improve cardiac function via metabolic actions, e.g. glucose lowering, insulin secretion, beta cell proliferation. However, by also providing direct effects on cardiovascular system, the GIP compounds are surprisingly even more beneficial.

Compounds of the invention can also be useful in the treatment or prevention of any number of gastrointestinal disorders that are associated with excess gastric secretion, excess intestinal electrolytes and water secretion as well as decreased absorption, e.g., infectious (e.g., viral or bacterial) diarrhea, inflammatory diarrhea, short bowel syndrome, or the diarrhea which typically occurs following surgical procedure, e.g., ileostomy (see e.g., Harrison's principles of Internal Medicine, McGraw Hill Inc., New York, 12th ed.). Examples of infectious diarrhea include, without limitation, acute viral diarrhea, acute bacterial diarrhea (e.g., *salmonella, campylobacter,* and *clostridium*) or diarrhea due to protozoal infections, or travelers' diarrhea (e.g., Norwalk virus or rotavirus). Examples of inflammatory diarrhea include, without limitation, malabsorption syndrome, tropical spue, chronic pancreatitis, Crohn's disease, diarrhea, and irritable bowel syndrome. GIP and GIP compounds of the invention can be used to treat or prevent an emergency or life-threatening situation involving a gastrointestinal disorder, e.g., after surgery or due to cholera. Furthermore, the compounds can be used to treat intestinal dysfunction in patients with Acquired Immune Deficiency Syndrome (AIDS), especially during cachexia. The compounds may also be useful for inhibiting small intestinal fluid and electrolyte secretion, and augmenting nutrient transport, as well as increasing cell proliferation in the gastrointestinal tract, regulating lipolysis in, e.g., adipose tissue and regulating blood flow in a mammal. GIP compounds of the invention may also be useful for treating or preventing the above conditions by their gastrointestinal protective activity (e.g., inhibition of gastric secretion). Accordingly, a GIP compound of the invention may be used to treat gastrointestinal or mucosal damage. Exemplary types of damage include, but are not limited to, inflammatory bowel disease, bowel atrophy, conditions characterized by loss of bowel mucosa or bowel mucosal function, and other conditions of the gastrointestinal tract, including those which may be brought about by exposure to cytotoxic agents, radiation, toxicity, infection and/or injury. Moreover, these compounds of the invention may be combined with analgesics, anti-inflammatory agents, growth hormone, heparin, or any other therapies that may be used to treat inflammatory bowel disease or other conditions listed above.

In another embodiment GIP compounds can be useful for treating or preventing gastritis, pancreatitis, Barrett's esophagus, Gastroesophageal Reflux Disease (GERD) and conditions associated therewith. Such conditions can include, but are not limited to, heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), and pulmonary aspiration. GIP compounds can have antisecretory properties, such as inhibition of gastric acids, inhibition of bile acids, and inhibition of pancreatic enzymes. Moreover, GIP compounds can also have gastroprotective effects. Accordingly, GIP compounds of the invention may be particularly useful in the treatment or prevention of gastritis, pancreatitis, Barrett's esophagus, and/or GERD and related or associated conditions.

The present invention also relates to pharmaceutical compositions comprising a therapeutically or prophylactically effective amount of at least one novel GIP analog or GIP hybrid polypeptide of the invention, or a pharmaceutically acceptable salt thereof, together with pharmaceutically acceptable diluents, preservatives, solubilizers, emulsifiers, adjuvants and/or carriers useful in the delivery of the GIP compound.

These and other aspects of the invention will be more clearly understood with reference to the following embodiments and detailed description.

BRIEF DESCRIPTION OF THE DRAWINGS

FIG. 1A shows an NMR-derived ensemble structure of exendin-4 in 30% aqueous trifluoroethanol. The Trp-cage can be seen folding back towards the central region of exendin. FIG. 1B shows a CPK view of the "Trp-cage" motif (residues 21-38) of a representative structure from the solution-state NMR structure ensemble of exendin-4.

FIG. 2 presents sequences and receptor binding and glucose lowering (oral glucose tolerance test (OGTT) in non-diabetic NIH/Swiss mice) activities of reference sequences and novel GIP analog sequences of the invention.

In FIG. 3A, bars represent mean±sd, n=6-10. Peptide was injected IP at t=−5 into overnight-fasted NIH/Swiss mice. Gavage (1.5 g/kg) was given at t=0, Sample was taken at t=30 min. Blood glucose was measured with a OneTouch® Ultra® (LifeScan, Inc., a Johnson & Johnson Company, Milpitas, Calif.) * p<0.05 vs. vehicle control; ANOVA, Dunnett's test. In FIG. 3B, points represent mean±sem, n=8-15. Peptide was injected IP at t=0 immediately following baseline sample into 2-hour fasted NIH/Swiss mice. Samples were taken at t=60, 120, and 180 minutes. Blood glucose was measured with a OneTouch® Ultra® (LifeScan, Inc., a Johnson & Johnson Company, Milpitas, Calif.). *p<0.05 vs. vehicle control; ANOVA, Dunnett's test. Compound No. G is (D-Ala2)GIP(1-30)-PSS-GAPPPS (SEQ ID NO: 1) amide form: sequence Y(D-Ala)EGTFISDYSIAMDKIHQQDFVNWLLAQKPSSGAPPPS-NH2 (SEQ ID NO: 186).

FIGS. 5A to 5D present examples of GIP phybrids comprising GIP and amylin/calcitonin-like analog peptides. The compounds would have both GIP activity (e.g., glucose lowering) and reduction of gastric emptying.

FIG. 6 depicts the structures of various chemical groups mentioned herein.

FIG. 7 depicts the structures of various chemical Fmoc derivatives mentioned herein.

FIGS. 8A and 8B depict glucose lowering effect of novel GIP analogs. The figures demonstrate that a D-alanine substitution at position 2 in the analogs herein improves glucose lowering ability. Points represent mean±sem. Peptide was injected IP at t=0 immediately following baseline sample into 2-hour fasted NIH/Swiss mice. Samples were taken at t=60, 120, 180 and 240 minutes. Blood glucose was measured with a OneTouch® Ultra® (LifeScan, Inc., a Johnson & Johnson Company, Milpitas, Calif.). *p<0.05 vs. vehicle control; ANOVA, Dunnett's test.

FIGS. 12.15 to 12.65 depict further exemplary analogs and reference peptides of the invention. It is intended that the various modifications and variants shown are to be used in the present invention, and may be combined as discussed herein. For example, the terms exendin tail or exendin trp-cage motif includes any of the exendin tail variants depicted, which are useful as shield sequences (peptidic enhancers). Of further interest are the frog GLP1 C-terminal extensions as shown in the figures, which are yet another example of a shield sequence that can be used in place of an exendin tail.

19D) and diastolic pressure (FIG. 19E) as determined by telemetry in conscious rats to administration of GIP compounds. Mean arterial pressure is presented as % of predose values measured over the 30 minutes prior to drug administration. FIG. 19C reflects the inotropic response to GIP compounds. The rate of change of blood pressure (dP/dt) is indicative of cardiac contractility.

FIG. 22 provides an alignment of mammalian and non-mammalian GIP. Positions Y1, E3, D9, S11, D15, F22, V23, L26, L27 and K32 are conserved across all species.

FIG. 24 depicts further linkers useful in the invention.

FIG. 27 presents an exemplary pH versus solubility profile and a pH versus stability profile of a GIP analog.

DETAILED DESCRIPTION OF THE INVENTION

Figure 1:
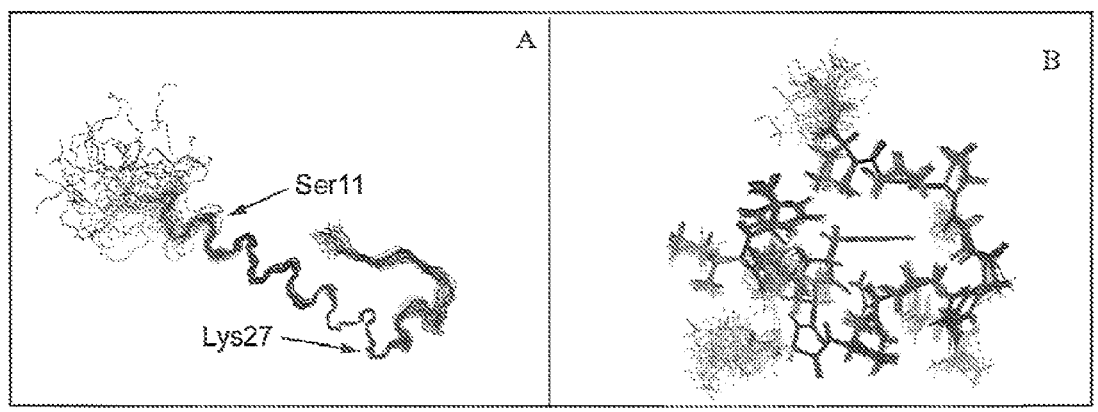
FIGS. 1A and 1B present views of the exendin-4 Trp-cage.

Gastric inhibitory polypeptide (GIP) and glucagon-like peptide 1 (GLP-1) are gut peptide hormones that exert potent glucoregulatory action through their glucose-dependant stimulation of insulin secretion. Consequently, these incretin hormones have attracted great interest as potential anti-diabetic agents with reduced risk for hypoglycemia. Whereas GLP-1, GLP-1 analogs and mimetics have been shown to be efficacious in controlling glucose levels in type 2 diabetic patients, the insulinotropic effect of GIP is reportedly significantly reduced in diabetic subjects, compared to normal individuals (16-18). The preservation of insulinotropic action of GLP-1 but not of GIP in the same diabetic subjects suggests that GIP signal transduction is impaired in type 2 diabetes. Reduced GIP receptor expression in pancreatic beta cells has been proposed to contribute to overall reduced incretin effects in diabetic subjects (19). Despite the reduced insulinotropic response to GIP in subjects with type 2 diabetes, it is possible that administration of elevated pharmacological doses of GIP or analogues could have therapeutic utility. Of note, GIP lacks the gastrointestinal effects of GLP-1 (20) that has limited the latter peptide's therapeutic window, thus permitting the possibility of higher dosing regimens (21).

One of the major hurdles in the therapeutic development of these incretin hormones is their short duration of action due to enzymatic degradation in vivo. The enzyme dipeptidyl peptidase IV (DPP-IV) plays a key role in the N-terminal cleavage of the peptides in vivo, and more recently, neutral endopeptidase 24.11 (NEP) has also be implicated in their degradation (22-26). Several studies have reported greater in vivo efficacy of DPP-IV resistant GIP analogues in rodent diabetic models (27-28).

Provided herein are novel GIP analogs and GIP-containing hybrid polypeptides, or derivatives thereof, which have enhanced or novel properties, including enhanced DPP-IV resistance, dual hormonal activity, and improved plasma half-life. Also provided are methods for treating or preventing metabolic diseases and disorders including those which can be alleviated by control of plasma glucose levels, insulin levels, and/or insulin secretion, such as diabetes and diabetes-related conditions, and conditions and disorders including, but not limited to, hypertension, dyslipidemia, cardiovascular disease, eating disorders, insulin-resistance, obesity, and diabetes mellitus of any kind, including type 1, type 2, and gestational diabetes. The methods comprise administering a therapeutically or prophylactically effective amount of a GIP or GIP analog, fragment or derivative thereof or a novel GIP analog or GIP hybrid or derivatives thereof as described herein, alone (monotherapy) or in combination with another agent or therapy (adjunct therapy), for example a glucose lowering agent (e.g., antidiabetic) or agents or methods that inhibit or reduce gastric emptying (examples of such agents are presented herein), to a subject in need thereof.

In addition to novel GIP analogs and derivatives, the present invention relates to novel, GIP-containing selectable hybrid polypeptides useful as agents for the treatment and prevention of metabolic diseases and disorders which can be alleviated by control of plasma glucose levels, insulin levels, and/or insulin secretion, such as diabetes and diabetes-related conditions. Such conditions and disorders include, but are not limited to, hypertension, dyslipidemia, cardiovascular disease, eating disorders, insulin-resistance, obesity, and diabetes mellitus of any kind, including type 1, type 2, and gestational diabetes.

In one aspect, the invention involves the modular assembly of physiologically, metabolically, and/or pharmacokinetically active peptidic modules that may be selectable based on "bio-activities", e.g., therapeutic efficacy, scope of function, duration of action, physicochemical properties, and/or other pharmacokinetic properties.

Without intending to be limited by theory, the present invention relates at least in part to a "toolbox" approach, wherein bio-active peptide hormone modules are linked in binary, tertiary or higher order combinations to create novel, efficacious therapeutic agents with selectable properties. The "bio-active peptide hormone modules" may be peptide hormones, peptide fragments with hormonal activity, or structural motifs of peptide hormones that impart chemical, metabolic, and/or other pharmacokinetic stability. The peptide hormones can include native peptide hormones, as well as peptide hormone analogs and derivatives, as known in the art and described herein.

In one aspect of the invention, it has been found that the combination of certain physicochemical characteristics of two or more peptide hormones into a single modality can facilitate intervention at several points in a dysfunctional metabolic circuit. As such, in one aspect of the invention, rationally-designed hybrid polypeptides are provided that integrate selectable bio-activities into a single polypeptide agent. In one embodiment, the selectable hybrid polypeptides of the invention may involve the use of chemically stable linkers to covalently attach the bio-active modules. In another embodiment, the selectable hybrid polypeptides of the invention may involve the use of cleavable linkers, which themselves may be or form part of a bio-active module.

Again, without intending to be limited by theory, design of the hybrid polypeptides of the present invention may generally involve: (1) the identification, selection and pairing of bio-active peptide hormone modules for desired efficacy and therapeutic use, and (2) the covalent linking of the bio-active modules (e.g. native peptide hormones, peptide hormone analogs or derivatives with hormonal activity, peptide hormone fragments with hormonal activity, stabilizing motifs, etc.) either directly or via a linker without loss of bio-activity of the component modules. In certain embodiments, module selection criteria may include, but not be limited to: (a) desired in vivo efficacy for desired therapeutic or prophylactic indication, such as an additive or a synergistic effect; (b) optional synergism or dual action of the linked modules for multiple therapeutic or prophylactic indications; and/or (c) a desired chemical stability, conformational stability, metabolic stability, bioavailability, organ/tissue targeting, receptor interaction, protease inhibition, plasma protein binding, and/or other pharmacokinetic characteristic.

GIP, GIP Analogs and Novel GIP Analogs. (The section headings are used herein for organizational purposes only, and are not to be construed as in any way limiting the subject matter described.) Reference sequences include human GIP, truncated GIP, human GLP-1, exendin-4, an exemplary Trp-cage, and exemplary "shield" sequences (e.g. a short and a long "exendin tail"):

| SEQ ID NO: | Description | Sequence |
|---|---|---|
| 2 | GIP(1-42) acid | YAEGTFISDYSIAMDKIHQQDFVNWLLAQKGKKNDWKHNITQ-OH |
| 293 | GIP(1-30) | YAEGTFISDYSIAMDKIHQQDFVNWLLAQK-NH2 |
| 4 | GLP-1 | HAEGTFTSDVSSYLEGQAAKEFIAWLVKGR-NH2 |
| 5 | Exendin-4 | HGEGTFTSDLSKQMEEEAVRLFIEWLKNGGPSSGAPPPS-NH2 |
| 6 | Ex-4 tail/long | .........................KNGGPSSGAPPPS |
| 1 | Ex-4 tail/short | ..............................PSSGAPPPS |
| 7 | Trp-cage | ....................FIEWLKNGGPSSGAPPPS |
| 421 | frog GLP-1 "tail" | PKKIRYS |

Useful in the therapies disclosed herein and in the novel GIP hybrids disclosed herein, are native GIP peptide hormones, and functional peptide analogs and derivatives-thereof. Certain exemplary native peptides, peptide analogs and derivatives are described herein, however it should be recognized that any known GIP peptide that exhibits hormonal activity known in the art may be used either as a component of a novel GIP analog or hybrid herein or in the novel adjunct therapies disclosed herein. In one embodiment, the GIP peptide analogs and derivatives have at least one hormonal activity of a native GIP peptide. In certain embodiments, the GIP peptide analogs are agonists of a receptor that a native GIP peptide is capable of specifically binding. Exemplary GIP peptide analogs and derivatives include those described in the references herein, which are hereby incorporated by reference. While the present application describes GIP polypeptide compounds as GIP analogs, novel GIP analogs, and novel GIP hybrids for use in the methods and therapies described herein, it is further intended that any suitable GIP agonist can be administered in place of a GIP compound, such agonists include agonist antibodies and antibody fragments and derivatives, and small molecule GIP receptor agonists. Accordingly, when a GIP compound or polypeptide is indicated for use in a particular therapeutic method, in another embodiment it is intended that a GIP agonist be used, particularly an agonist antibody or fragment or derivative thereof.

In serum, GIP is degraded by dipeptidyl peptidase IV (DPP-IV). The resulting short biological half-life (about 2 minutes in vivo) limits the therapeutic use of GIP.

The following references relate to various GIP analogs that are useful to provide as components for the novel GIP analogs and GIP hybrids of the present invention and find use in the novel therapies of the present invention based on their function on various target organs.

German Patent Application 19921537 discloses a method for extending the survival of insulin producing beta-cells by stimulation of their proliferation and prevention of their programmed cell death. The specific goal is to increase the endogenous insulin content and insulin response to elevated blood glucose levels. An important component of this invention is the activation of protein kinase B/Akt in insulin producing beta-cells in response to the administration of effectors such as GLP-1, GIP, Exendin-4 or GLP-1 receptor agonists or GIP-receptor agonists.

European Patent Application 0479210 discloses GIP analogs of the formula GIP(1-13)-X-GIP(15-30)-Y, wherein X is an amino acid residue other than Met, and Y is selected from homoserine (inclusive homoserine-lactone) (referred to as "Hse"), homoserine amide (Hse-NH2), H-Gly-Lys-Lys-Asn-Asp-Trp-Lys-His-Asn-Ile-Thr-Gln-Hse (SEQ ID NO: 8) or H-Gly-Lys-Lys-Asn-Asp-Trp-Lys-His-Asn-Ile-Thr-Gln-Hse-NH2 (SEQ ID NO: 9).

United States Patent Application 20030232761 by Hinke et al, published Dec. 18, 2003, reports C-terminal truncated fragments and N-terminal modified analogs of GIP as well as various GIP analogs with a reduced peptide bond or alterations of the amino acids close to the dipeptidyl peptidase IV (DPP-IV)-specific cleavage site providing DPP-IV-resistance and prolonged half-life. Also reported are analogs with different linkers between potential receptor binding sites of GIP.

WO98/24464 discloses an antagonist of glucose-dependent insulinotropic polypeptide (GIP) consisting essentially of a 24 amino acid polypeptide corresponding to positions 7-30 of the sequence of GIP, a method of treating non-insulin dependent diabetes mellitus and a method of improving glucose tolerance in a non-insulin dependent diabetes mellitus patient.

WO 00/58360 and EP1171465 disclose peptides, which stimulate the release of insulin. This disclosure provides a process of N terminally-modifying GIP and the use of the peptide analogues for treatment of diabetes. The specific peptide analog, which is disclosed in this invention, comprises at least 15 amino acid residues from the N terminal end of GIP (1-42). In another embodiment, Tyr1-glucitol GIP (1-42) is disclosed.

WO 00/20592 discloses GIP or anti-idiotypic antibodies of GIP or fragments thereof as GIP-analogs for maintaining or increasing bone density or bone formation.

Kuhn-Wache et al. (2000) discloses analogs of GIP with increased dipeptidyl peptidase IV resistance (Kuhn-Wache et al, in Langner & Ansorge, Cellular peptidases in Immune Functions and Diseases 2. Kluwer Academic/Plenum Publishers, 187-195.)

O'Harte et al. and Gault et al. have reported GIP(1-30) analogs-Tyr1-glucitol-GIP and (Pro3)GIP-displaying DPP-IV resistance and enhanced bioactivity. (O'Harte et al., NH2-terminally modified gastric inhibitory polypeptide exhibits amino-peptidase resistance and enhanced antihyperglycemic activity, Diabetes 48, 758-765 (1999)); and see Gault et al. "Characterization of the cellular and metabolic effects of a novel enzyme-resistant antagonist of Glucose-dependent insulinotropic polypeptide." Biochemical and Biophysical Research Communications 290, 1420-1426 (2002)).

Specific active GIP and GIP analogs known in the art include:

being biologically active. This includes modification by fatty acid addition at an epsilon amino group of at least one lysine residue, either present in or introduced into the molecule. Particular modifications include Tyr1-glucitol of a GIP, for example Tyr1-Glucitol GIP(1-42) or Tyr1-glucitol GIP(1-30). GIP analogs of interest include those comprising a substitution or modification selected from the group comprising D-amino acid substitutions in 1, 2 and/or 3 positions and/or N-terminal glycation, alkylation, acetylation or acylation, or other N-terminal modifications described herein. Of further interest are analogs wherein the amino acid in the 2 or 3 position is substituted by lysine, serine, 4-amino butyric amino acid, Aib, D-alanine, Sarcosine or proline. Further exemplary substitutions in the 1, 2, or 3 position, and more particularly in the 2 position of GIP are dAla, Val, dnorVal, dSer, Abu, dAbu, homo-Ser, d-homoSer, dPro, cyclopropyl Ala, d-cyclopropyl Ala, cycloHexyl Ala, d-cyclohexyl Ala, A(NMe), Aib, and cyclpropGly.

In one embodiment, a GIP analog or hybrid has a serine at position 2 in order to reduce DPP-IV cleavage, while retain-

| SEQ ID No: | Description | Sequence |
|---|---|---|
| 2 | hGIP(1-42) | YAEGTFISDYSIAMDKIHQQDFVNWLLAQKGKKNDWKHNITQ |
| 3 | hGIP(1-30) | YAEGTFISDYSIAMDKIHQQDFVNWLLAQK |
| 10 | Mouse | YAEGTFISDYSIAMDKIRQQDFVNWLLAQRGKKSDWKHNITQ |
| 11 | Rat | YAEGTFISDYSIAMDKIRQQDFVNWLLAQKGKKNDWKHNLTQ |
| 12 | Pig | YAEGTFISDYSIAMDKIRQQDFVNWLLAQKGKKSDWKHNITQ |
| 13 | Bovine | YAEGTFISDYSIAMDKIRQQDFVNWLLAQKGKKSDWIHNITQ |
| 14 | GIP(1-14) | YAEGTFISDYSIAM |
| 15 | GIP(19-30) | QQDFVNWLLAQK |
| 16 | GIP(3-42) antagonist | EGTFISDYSIAMDKIHQQDFVNWLLAQKGKKNDWKHNITQ |

Of particular interest are analogs modified at or near the dipeptidyl peptidase IV (DPP-IV) specific cleavage site, which improve DPP-IV-resistance and consequently prolong half-life. Amino acid alterations include modifications of the first 3 or 4 residues of GIP and/or the bond between residues 2 and 3, which is cleaved by DPP-IV. Modifications and substitutions include N-terminal modifications, L-amino acids, D-amino acids, proteinogenic and non-proteinogenic amino acids. Proteinogenic amino acids are defined as natural protein-derived alpha-amino acids. Non-proteinogenic amino acids are defined as all other amino acids, which are not building blocks of common natural proteins.

Of further interest are novel GIP analogs having one or more modifications as described herein and that exhibit at least 50%, at least 60%, at least 65%, at least 70%, at least 75%, at least 80%, at least 85%, at least 90%, at least 95% or at least 98% sequence identity to a native GIP(1-30), native GIP(1-26), native GIP(1-14), native GIP(1-39), native GIP (19-30), native GIP(19-26), native GIP(19-39), native GIP (19-42) or native GIP(1-42) over the entire length of the GIP portion.

Of particular interest are those GIP compounds comprising at least 11, 12, 13, 14 or 15 amino acid residues from the N-terminal end of a GIP, e.g., GIP(1-42)-, having a least one amino acid substitution or modification at position 1-3 and ing receptor binding and activation. Thus, specifically contemplated herein is a Ser2 analog of each of the GIP analogs and hybrids disclosed herein. By way of example, the analog of 0601GIP3794 having a serine substitution for the dAla at position 2 is specifically contemplated.

Further exemplary GIP analog compounds have a modification at the N-terminus, retaining their GIP Receptor binding, in which the N-terminus modification includes H, isocap, isoBuOCO, octylglycine, Y(NMe) and succinoyl. Further exemplary GIP compounds include those with fatty acid modifications or combinations of modifications as described herein, while retaining their GIP Receptor binding and receptor activation activity, For example, an N-terminus modification can be combined with a substitution or modification at positions 1, 2 or 3 (which imparts resistance to DPP-IV as described herein) or with a fatty acyl derivative modification (which can reduce renal clearance). In another example, a substitution or modification at positions 1, 2 or 3 is combined with a fatty acyl derivative. For example an N-terminus octylglycine is combined with a d-amino acid at 1, 2, or, particularly a D-Ala at position 2. In one embodiment a fatty acyl substitution is a octylglycine for lysine at position 16 or methionine at position 14. In other embodiments the methionine at position 14 is deleted, and which, for example, can be further combined with a octylglycine for lysine at position 16 or 30. Another substitution is acylation of the lysine at position 16 or 30, for example with an octyl or palmitoyl group. Other embodiments include a fatty acyl substitution where an octylglycine is substituted for lysine at position 16 or 30 or for methionine at position 14. To eliminate or reduce oxidation, the methionine at position 14 is deleted or substituted, for example with a leucine or other small hydrophobic amino acid, and/or the tryptophan at position 25 is deleted or substituted, for example with a phenylalanine.

In one embodiment are analogs having at least one or two amino acid deletions in amino acids 1-30 of GIP, those having one or two deletions in amino acids 4 to 30, and those having one or more deletions in amino acids 4-15, and those having one amino acid deletion in amino acids 1-30, 4-30 or 4-15 of a GIP. Of course it is intended that such a modification can be combined with at least one other change as described herein, such as a change that imparts DPP-IV resistance, reduces or eliminates oxidation, reduces renal clearance, improves receptor binding, or improves receptor activation.

Further exemplary substitutions are those derived from GIP of other (non-human) species, for example the methionine 14 replaced by leucine, the D at position 9 or 21 replaced by E, the histidine 18 replaced by alanine, arginine or lysine, the lysine at position 30 replaced by alanine, arginine or histidine, the alanine at position 13 replaced by leucine, and the alanine at position 28 replaced by serine.

In one embodiment the GIP analogs have one or more of the following modifications: dAla2 to Abu, Ala, Gly, or Ser; Met14 to Leu; His18 to Ala, Arg, or Lys; Asp21 to Glu; Lys30 to Arg or His; and/or an N-terminus as Gly(Oct).

Further exemplary GIP modifications and combinations are shown in the following compounds:

| SEQ ID NO: | Sequence |
| --- | --- |
| 3 | YAEGTFISDYSIAMDKIHQQDFVNWLLAQK |
| 433 | YaEGTFISDYSIALDKIAQQEFVNWLLAQR |
| 434 | YaEGTFISDYSIALDKIRQQEFVNWLLAQR |
| 435 | YaEGTFISDYSIALDKIKQQEFVNWLLAQR |
| 436 | YaEGTFISDYSIALDKIAQQEFVNWLLAQH |
| 437 | YaEGTFISDYSIALDKIRQQEFVNWLLAQH |
| 438 | YaEGTFISDYSIALDKIKQQEFVNWLLAQH |
| 439 | YaEGTFISDYSIAMDKIHQVKFVNWLLAQK |
| 440 | YaEGTFISDYSIALDKIRQQEFVNWLLAQK |
| 441 | YaEGTFISDYSIALDKIKQQEFVNWLLAQK |
| 442 | YaEGTFISDYSIALDKIAQQEFVNWLLAQK |
| 443 | YaEGTFISDYSIALDKIRQQEFVNWLLAQH |
| 444 | YaEGTFTADYSKALDKIHQQDFVNWLLAQK |
| 445 | YaEGTFTSDYSKALDKIHQQDFVNWLLAQK |
| 446 | YaEGTFISDYSKAMDKIRQQEFVNWLLAQK |
| 447 | YaEGTFISDYSIALEKIRQQKFVNWLLAQK |
| 448 | YaEGTFISDYSIALDKIRQQDFVEWLLAQK |
| 449 | YaEGTFISDYSIALDKIRQQEFVNWLLAQK |
| 450 | YaEGTFISDYSIALDKIRQQEFVNWLLAQK |
| 451 | YaEGTFISDYSIAMDKIHQQLFIEWLKNGG |
| 452 | YaEGTFISDYSIAMDKIRQQEFVNWLLAQK |
| 453 | YaEGTFISDYSIAMDKIHQQDFVNFLLAQK |
| 17 | YAEGTFISDYSIAMDKIHQQDFVNFLLAQK |

Accordingly, it is intended that the modifications described herein can be combined with at least one other change as described herein, such as a change that imparts DPP-IV resistance, reduces or eliminates oxidation, reduces renal clearance, improves receptor binding, or improves receptor activation. For example, intended are specific analogs that have one or more replacements or modifications as described herein, such as a GIP D-Ala2 or L-Ala2 analog that also has a Phe for Trp replacement at position 25.

GIP Hybrid Polypeptides.

Bio-Active Peptide Hormone Modules. As discussed herein the GIP hybrid polypeptides of the present invention (also referred to as "phybrids"), generally comprise at least two bio-active peptide hormone modules covalently linked together, with a GIP peptide as one of the modules. The bio-active peptide hormone modules may be: (a) native component peptide hormones, (b) analogs or derivatives of native component peptide hormones that retain hormonal activity, (c) fragments of native component peptide hormones that retain hormonal activity, (d) fragments of analogs or derivatives of native component peptide hormones that retain hormonal activity, (e) structural motifs of native component peptide hormones that impart a desired chemical stability, conformational stability, metabolic stability, bioavailability, organ/tissue targeting, receptor interaction, protease inhibition, plasma protein binding, and/or other pharmacokinetic characteristic to the hybrid polypeptide; or (f) structural motifs of analogs or derivatives of native component peptide hormones that impart a desired chemical stability, conformational stability, metabolic stability, bioavailability, organ/tissue targeting, receptor interaction, protease inhibition, plasma protein binding, and/or other pharmacokinetic characteristic to the hybrid polypeptide. The structural motifs of (e) and (f) will collectively be referred to herein as "peptidic enhancers". An example of a peptidic enhancer is a Trp cage sequence, particularly one derived from exendin-4, such as the Ex-4 short or long tails.

Exemplary bio-active peptide hormone modules include native peptide hormones selected from: amylin, ADM, CT, CGRP, intermedin, CCK(1-33), CCK-8, leptin, PYY(1-36), PYY(3-36), an PYY-NPY chimera, GLP-1(1-37), GLP-1(7-37), GLP-1(7-36), GLP-2, OXM, exendin-3, exendin-4, catestatin family peptides, natriuretic peptide hormones, urocortin family peptides, e.g., Ucn-2 and Ucn-3, neuromedin family peptides, e.g. neuromedin U25 or splice variants, and ANP, BNP, CNP or urodilatin.

Other exemplary bio-active peptide hormone modules include analogs and derivatives of a component peptide hormone selected from: amylin, ADM, CT, CGRP, intermedin, CCK, leptin, PYY(1-36), PYY(3-36), PYY-NPY chimera, GLP-1(1-37), GLP-1(7-37), GLP-1(7-36), GLP-2, OXM, a catestatin family peptide, a natriuretic peptide hormone, a urocortin family peptide, e.g., Ucn-2 and Ucn-3, a neuromedin family peptide, e.g. neuromedin U25 or splice variants, exendin-3, and exendin-4, wherein the analog or derivative exhibits at least one hormonal activity of the component peptide hormone. The analog may comprise one or more insertions, deletions, or substitutions of the amino acid sequence of the component peptide hormone, and the derivative may comprise one or more chemical modifications of an amino acid residue of an analog or component peptide hormone, as described more fully herein and known in the art.

More specifically, analogs and derivatives may be selected from any described above and/or known in the art. Particularly exemplary analogs and derivatives that exhibit at least one hormonal activity useful as bio-active peptide hormone modules of the invention include the following:

```
Amylin:  ²Ala-h-amylin, ²,⁷Ala-h-amylin, ²⁸Pro-h-amylin, ²⁵,²⁸Pro-h-amylin,

²⁵,²⁸,²⁹Pro-h-amylin, ²⁵Pro, ²⁶Val, ²⁸,²⁹Pro-h-amylin, ¹⁸Arg,

²⁵,²⁸Pro-h-amylin, ¹⁸Arg, ²⁵,²⁸,²⁹Pro-h-amylin, ²⁵Pro, ²⁶Val,

²⁸,²⁹Pro-h-amylin, ¹⁸Arg, ²³Leu, ²⁵,²⁸,²⁹Pro-h-amylin, ¹⁸Arg²³Leu,

²⁵,²⁸Pro-h-amylin, and 2,7-Cyclo-[²Asp, ⁷Lys]-h-amylin

CT:      ¹⁴Glu-sCT, ¹⁸Arg-sCT, ¹¹,¹⁸Arg-sCT, ¹⁴Glu, ¹⁸Arg-sCT, ¹⁴Glu,

¹¹,¹⁸Arg-Sct

CGRP:    ³⁶D-Ser-CGRP, ³⁶D-Thr-CGRP, ³⁶D-Asp-CGRP, ³⁶D-Asn-CGRP,

³⁶Ser-CGRP, ³⁶Hse-CGRP, ³⁶Asp-CGRP, ³⁶Thr-CGRP, ³⁶Asn-CGRP

AFP-6:   TQAQLLRVGCGNLSTCQVQNLSHRLWQLMGPAGRQDSAPVDPSSPHSY,   (SEQ ID NO: 18)

TQAQLLRVGCDTATCQVQNLSHRLWQLMGPAGRQDSAPVDPSSPHSY,    (SEQ ID NO: 19)

TQAQLLRVGMVLGTMQVQNLSHRLWQLMGPAGRQDSAPVDPSSPHSY,    (SEQ ID NO: 20)

TQAQLLRVGCVLGTCQVQNLSHRLWQLMGPAGRQDSAPVEPSSPHSY,    (SEQ ID NO: 21)

TQAQLLRVGCVLGTCQVQNLSHRLWQLMGPAGRQESAPVEPSSPHSY,    (SEQ ID NO: 22)

CCK:     DY(OSO₃H)MGWMDF,                                   (SEQ ID NO: 23)

DYMGWMDF,                                          (SEQ ID NO: 24)

MGWMDF,                                            (SEQ ID NO: 25)

GWMDF,                                             (SEQ ID NO: 26)

WMDF,                                              (SEQ ID NO: 27)

KDY(OSO₃H)MGWMDF,                                  (SEQ ID NO: 28)

KDYMGWMDF,                                         (SEQ ID NO: 29)

KMGWMDF,                                           (SEQ ID NO: 30)

KGWMDF,                                            (SEQ ID NO: 31)

KWMDF                                              (SEQ ID NO: 32)

Leptin:  ⁴³Asp-leptin, ⁴³Glu-leptin, ⁴⁸Ala-leptin, ⁴⁹Glu-leptin, ⁴⁹Des-AAleptin, ⁷⁵Ala-leptin, ⁸⁹Leu-leptin, ⁹³Asp-leptin, ⁹³Glu-leptin, ⁹⁸Ala-leptin, ¹³⁹Leu-leptin, PYY:     ³Leu-PYY, ³Val-PYY, ⁴Arg-PYY, ⁴Gln-PYY, ⁴Asn-PYY, ²⁵Lys-PYY, ³⁴Pro-PYY, ³⁴His-PYY, ¹,³⁶Tyr-PYY, ¹³Pro¹⁴Ala-PYY, ³¹Leu³⁴Pro-PYY, des-AA-4-PYY GLP-1    ⁹Gln-GLP-1(7-37), D-⁹Gln-GLP-1(7-37), ¹⁶Thr-¹⁸Lys-GLP-1(7-37), ¹⁸Lys-GLP-1(7-37), ⁸Gly-GLP-1(7-36), ⁹Gln-GLP-1(7-37), D-⁹Gln- GLP-1(7-37), acetyl-⁹Lys-GLP-1(7-37), ⁹Thr-GLP-1(7-37), D-⁹Thr-GLP-1(7-37), ⁹Asn-GLP-1(7-37), D-⁹Asn-GLP-1(7-37), ²²Ser²³Arg²⁴Arg²⁶Gln-GLP-1(7-37), ¹⁶Thr¹⁸Lys-GLP-1(7-37), ¹⁸Lys-GLP-1(7-37), ²³Arg-GLP-1(7-37), ²⁴Arg-GLP-1(7-37)
```

| | |
|---|---|
| GIP | Y-dAla$^2$-GIP |
| Exendin | $^{14}$Leu, $^{25}$Phe-exendin-4, $^{14}$Leu, $^{25}$Phe-exendin-4, $^5$Ala, $^{14}$Leu, $^{25}$Phe-exendin-4, and $^{14}$Leu, $^{22}$Ala, $^{25}$Phe-exendin-4. |

As known in the art, such peptide compounds may preferably be amidated, but within the context of the present invention, may optionally be in the acid form unless otherwise specified.

Still other exemplary bioactive peptide hormone modules include fragments of a component peptide hormone selected from: amylin, ADM, CT, CGRP, intermedin, CCK, leptin, PYY(1-36), PYY(3-36), GLP-1(1-37), GLP-1(7-37), GLP-1(7-36), GLP-2, OXM, a natriuretic peptide, a urocortin family peptide, e.g., Ucn-2 and Ucn-3, a neuromedin family peptide, e.g. neuromedin U25 or splice variant, exendin-3, and exendin-4, wherein the fragment exhibits at least one hormonal activity of the component peptide hormone.

Yet other exemplary bioactive peptide hormone modules include fragments of analogs or derivatives of a component peptide hormone selected from: amylin, ADM, CT, CGRP, intermedin, CCK, leptin, PYY(1-36), PYY(3-36), the specific PYY-NPY chimera sequences disclosed herein, GLP-1 (1-37), GLP-1(7-37), GLP-1(7-36), GLP-2, human catestatin, OXM, ANP, BNP, CNP, urodilatin, Ucn-2 and Ucn-3, neuromedin U25 or splice variant, neuromedin S, exendin-3 and exendin-4, wherein the fragment exhibits at least one hormonal activity of the component peptide hormone. Again, the analog may comprise one or more insertions, deletions, or substitutions of the amino acid sequence of the component peptide hormone, and the derivative may comprise one or more chemical modifications of an amino acid residue of an analog or component peptide hormone, as described more fully herein and known in the art.

Certain exemplary fragments that exhibit at least one hormonal activity include the following. However, it should be understood that combinations of the above-described analogs and derivatives taken with fragments known in the art, including the exemplary fragments described herein, are contemplated.

| | |
|---|---|
| Amylin: | amylin(1-36), amylin(1-35), amylin(1-20), amylin(1-18), amylin(1-17), amylin (1-16), amylin(1-15), amylin(1-7) |
| CT: | CT(8-32), CT(8-27), CT(8-26), CT(8-10), CT(18-26), CT(18-27) |
| AFP-6: | AFP-6(18-27) |
| CCK: | CCK-8, CCK-5, CCK-4 |
| Leptin: | leptin (22-167), leptin(56-73) |
| PYY: | PYY(1-35), PYY(1-30), PYY(1-25), PYY(1-15), PYY(1-10), PYY(2-36), PYY(3-36), PYY(4-36), PYY(5-36) |
| GLP-1 | GLP-1(7-37), GLP-1(7-36), GLP-1(7-35) |
| GIP | GIP(1-14), GIP(1-30) or longer, GIP(1-39) or longer |
| Exendin | exendin-4(1-27), exendin-4(1-28), exendin-4(1-29), exendin-4(1-30) or longer |

Again, as known in the art, such peptide compounds may preferably be amidated, but within the context of the present invention, may optionally be in the acid form unless otherwise specified. Further, the above exemplary fragments may be combined with any of the analogs or derivatives discussed herein or known in the art. For example, exemplary analog fragments may include $^5$Ala, $^{14}$Leu, $^{25}$Phe-exendin-4(1-28), $^{14}$Leu, $^{25}$Phe-exendin-4(1-27), $^5$Ala, $^{14}$Leu, $^{25}$Phe-exendin-4 (1-28), $^{14}$Leu, $^{25}$Phe-exendin-4(1-27), or any other combinations of the disclosed fragments, analogs, and derivatives. Further embodiments include NN2211 and ZP-10.

Yet other exemplary bio-active peptide modules include "peptidic enhancer", i.e., structural motifs of component peptide hormones (including analogs and derivatives thereof) that impart a desired chemical stability, conformational stability, metabolic stability, bioavailability, organ/tissue targeting, receptor interaction, protease inhibition, plasma protein binding, and/or other pharmacokinetic characteristic to the hybrid polypeptide. Exemplary peptidic enhancers include the following.

| | |
|---|---|
| Amylin Family | amylin(32-37), amylin(33-37), amylin(34-37), amylin(35-37), amylin(36-37), amylin(37), ADM(47-52), ADM(48-52), ADM(49-52), ADM(50-52), ADM(51-52), ADM(52), CT(27-32), CT(27-32), CT(28-32), CT(29-32), CT(30-32), CT(31-32), CT(32), CGRP(32-37), CGRP(33-37), CGRP(34-37), CGRP(35-37), CGRP(36-37), CGRP(37), intermedin (42-47), intermedin (43-47), intermedin (44-47), intermedin (45-47), intermedin (46-47), intermedin (47) |
| PYY | PYY(25-36), PYY(26-36), PYY(27-36), PYY(28-36), PYY(29-36), PYY(30-36), PYY(31-36), PYY(32-36), PYY(25-35), PYY(26-35), PYY(27-35), PYY(28-35), PYY(29-35), PYY(30-35), PYY(31-35), PYY(32-35); PPY-NPY chimera Ile, Lys, Pro, Glu, His, Pro, Gly, Glu, Asp, Ala, Ser, Pro, Glu, Glu, Leu, Ala, Arg, Tyr, Tyr, Ala, Ser, Leu, Arg, Ala, Tyr, Ile, Asn, Leu, Ile, Thr, Arg, Gln, Arg, Tyr (SEQ ID No. 454) |
| GLP-1 and 2 | frog GLP-1(29-37); frog GLP-1(30-37); frog GLP-2(24-31), frog GLP-2(25-31) |
| GIP | GIP(31-42), GIP(32-42), GIP(33-42), GIP(34-42), GIP(35-42), GIP(36-42), GIP(37-42), GIP(38-42), GIP(39-42), GIP(40-42), GIP(41-42), GIP(42) |
| Exendin-4 | exendin-4(31-39), exendin-4(32-39), exendin-4(33-39), exendin-4(34-39), exendin-4(35-39), exendin-4(36-39), exendin-4(37-39), exendin-4(38-39), exendin-4(39) |

Again, it should be understood that combinations of the above-described GIP analogs and derivatives taken together with the bio-active peptide modules described herein are contemplated. For example, the last six amino acid residues of amylin family peptide hormone analogs and derivatives known in the art and/or described above are also contemplated as exemplary bio-active peptide modules. For example, as further discussed herein, the peptidic enhancer Ex-4 short tail, which is an exemplary Trp-Cage sequence, or analog thereof, is added to the C-terminus of any GIP analog, and in further embodiments the peptidic enhancer is attached using a linker.

In one aspect, the novel GIP hybrid include a GIP portion exhibiting at least 50%, at least 60%, at least 65%, at least 70%, at least 75%, at least 80%, at least 85%, at least 90%, at least 95% or at least 98% sequence identity to a native GIP (1-30), native GIP(1-26), native GIP(1-14), native GIP(1-39), native GIP(19-30), native GIP(19-26), native GIP(19-39), native GIP(19-42) or native GIP(1-42) over the entire length of that GIP portion.

Accordingly, in certain embodiments the GIP portion of a GIP hybrid can comprise a trp-cage motif. Such desirable GIP hybrids include an N-terminal GIP or novel GIP analog fragment in combination with a C-terminal polypeptide or fragment thereof having a glucose lowering activity (e.g., antidiabetics, exendin) or the ability to inhibit or reduce gastric emptying. Such desirable GIP hybrids include an N-terminal GIP fragment or novel GIP analog fragment in combination with a C-terminal exendin, GLP1, pramlintide, amylin, CCK, gastrin, PYY, secretin, GRP, neuromedins, urocortin, calcitonin, or salmon calcitonin, or fragment thereof. In other embodiments desirable GIP hybrids include a C-terminal GIP or novel GIP analog fragment in combination with an N-terminal polypeptide or fragment thereof having a glucose lowering activity (e.g., antidiabetics, exendin) or the ability to inhibit or reduce gastric emptying. In such embodiments, the chimeric polypeptides can include a C-terminal GIP, a novel GIP analog (in which case a Trp-cage forming sequence is present), or fragment thereof, in combination with a N-terminal exendin, GLP1, pramlintide, amylin, CCK, gastrin, PYY, secretin, GRP, neuromedins, urocortin, calcitonin, or salmon calcitonin, or fragment thereof.

In other embodiments the GIP or novel GIP analog is combined with a gastrin/CCK receptor ligand; an amylin receptor ligand; a calcitonin receptor ligand; an CGRP receptor ligand, a PYY receptor ligand, an EGF receptor ligand; a Glucagon-like peptide 1 receptor ligand; a Glucagon-like peptide 2 receptor ligand; a gastric inhibitory polypeptide (GIP) receptor ligand; a keratinocyte growth factor (KGF) receptor 1 ligand; a dipeptidyl peptidase IV inhibitor; a REG protein receptor ligand; a Growth Hormone receptor ligand; a Prolactin (PRL) receptor ligand; an Insulin-like Growth Factor (IGF) receptor ligand; PTH-related protein (PTHrP) receptor ligand; hepatocyte growth factor (HGF) receptor ligand; a bone morphogenetic protein (BMP) receptor ligand, a transforming growth factor (TGF receptor ligand; a laminin receptor ligand; a vasoactive intestinal peptide (VIP) receptor ligand; a fibroblast growth factor (FGF) receptor ligand; a nerve growth factor (NGF) receptor ligand; an islet neogenesis associated protein (INGAP) receptor ligand; an Activin-A receptor ligand; a vascular endothelial growth factor (VEGF) receptor ligand; an erythropoietin (EPO) receptor ligand; a pituitary adenylate cyclase activating polypeptide (PACAP) receptor ligand; a granulocyte colony stimulating factor (G-CSF) receptor ligand; a granulocyte-macrophage colony stimulating factor (GM-CSF); a platelet-derived growth factor (PDGF) receptor ligand, and a secretin receptor ligand.

The polypeptides of the present invention will preferably retain, at least in part, a biological activity of native human GIP, e.g., the polypeptides of the present invention will generally be GIP agonists or antagonists. In one embodiment, the polypeptides of the present invention will exhibit biological activity in the treatment and prevention of metabolic conditions and disorders. Further, the novel GIP analog polypeptides of the invention may include internal linker compounds, may include chemical modifications at internal amino acid residues, or may be chemically modified at the N-terminal or C-terminal residue. In yet another embodiment, the polypeptides of the invention include only natural L amino acid residues and/or modified natural L amino acid residues. Alternatively, in another embodiment, the polypeptides of the invention do not include unnatural amino acid residues.

In exemplary GIP hybrid embodiments, the GIP portion comprises a GIP N-terminal region modified or substituted to provide DPP-IV resistance superior to that of native GIP.

Exemplary Peptide Component Families.

Native peptide hormones are known in the art, as are their analogs and derivatives. For reference, the sequences of several native peptide hormones are provided herein.

Exemplary Peptide Hormones

| Seq ID | Description | Sequence |
|---|---|---|
| 33 | Rat Amylin | KCNTATCATQRLANFLVRSSNNLGPVLPPTNVGSNTY |
| 34 | h-Amylin | KCNTATCATQRLANFLVHSSNNFGAILSSTNVGSNTY |
| 35 | h-ADM | YRQSMNNFQGLRSFGCRFGTCTVQKLAHQIYQFTDKDKDN VAPRSKISPQGY |
| 36 | s-CT | CSNLSTCVLGKLSQELHKLQTYPRTNTGSGTP |
| 37 | h-CT | CGNLSTCMLGTYTQDFNKFHTFPQTAIGVGAP |
| 38 | h-CGRP α | ACDTATCVTHRLAGLLSRSGGVVKNNFVPTNVGSKAF |
| 39 | h-CGRP β | ACNTATCVTHRLAGLLSRSGGMVKSNFVPTNVGSKAF |
| 40 | h-AFP-6 (1-47) | TQAQLLRVGCVLGTCQVQNLSHRLWQLMGPAGRQDSAPV DPSSPHSY |
| 41 | h-AFP-6 (8-47) | VGCVLGTCQVQNLSHRLWQLMGPAGRQDSAPVDPSSPHSY |

-continued

| Seq ID | Description | Sequence |
|---|---|---|
| 42 | Mouse AFP-6 (1-47) | PHAQLLRVGCVLGTCQVQNLSHRLWQLVRPAGRRDSAPVDPSSPHSY |
| 43 | Mouse AFP-6 (8-47) | VGCVLGTCQVQNLSHRLWQLVRPAGRRDSAPVDPSSPHSY |
| 289 | CCK-8 - sulfated | DY(SO$_3$)MGWMDF |
| 45 | h-Leptin | MHWGTLCGFLWLWPYLFYVQAVPIQKVQDDTKTLIKTIVTRINDISHTQSVSSKQKVTGLDFIPGLHPILTLSKMDQTLAVYQQILTSMPSRNVIQISNDLENLRDLLHVLAFSKSCHLPWASGLETLDSLGGVLEASGYSTEVVALSRLQGSLQDMLWQLDLSPGC |
| 46 | h-PYY | YPIKPEAPGEDASPEELNRYYASLRHYLNLVTRQRY |
| 47 | h-PYY (3-36) | IKPEAPGEDASPEELNRYYASLRHYLNLVTRQRY |
| 48 | hGLP-1 (1-37) | HDEFERHAEGTFTSDVSSTLEGQAALEFIAWLVKGRG |
| 49 | Frog GLP-1 | HAEGTYTNDVTEYLEEKAAKEFIEWLIKGKPKKIRYS-OH; |
| 50 | Frog GLP-1 | HAEGTFTSDVTQQLDEKAAKEFIDWLINGGPSKEIIS-OH |
| 51 | h-GLP-1 (7-36) | HAEGTFTSDVSSYLEGQAALEFIAWLVKGR |
| 52 | h-GLP-2 | HADGSFSDEMNTILDNLAARDFINWLIETKITD |
| 53 | Frog GLP-2 | HAEGTFTNDMTNYLEEKAAKEFVGWLIKGRP-OH |
| 54 | OXM | HSQGTFTSDYSKYLDSRRAQDFVQWLMNTKRNRNNIA |
| 55 | Exendin-3 | HSDGTFTSDLSKQMEEEAVRLFIEWLKNGGPSSGAPPPS |
| 5 | Exendin-4 | HGEGTFTSDLSKQMEEEAVRLFIEWLKNGGPSSGAPPPS |
| 423 | Urocortin II (Mouse) | VILSLDVPIGLLRILLEQARYKAARNQAATNAQILAHV-NH2 |
| 424 | WP-24 (Urocortin) | WSPGARNQGGGARALLLLLAERFP-OH |
| 425 | TV-18 (Urocortin) | TQSQRERAEQNRIIFDSV-NH2 |
| 426 | Human Urocortin | DNPSLSIDLTFHLLRTLLELARTQSQRERAEQNRIIFDSV-NH2 |
| 427 | SE-20 (Urocortin-111/Stresseopin) | SFHYLRSRDASSGEEEEGKE-OH |
| 428 | AI-13 (Urocortin-III/Stresscopin) | AQAAANAHLMAQI-OH |
| 429 | DA-21 (Urocortin) | DNPSLSIDLTFHLLRTLLELA-OH |
| 430 | TL-26 (Urocortin-III/Stresscopin) | TKFTLSLDVPTNIMNLLFNIAKAKNL-OH |
| 431 | Human Urocortin III | FTLSLDVPTNIMNLLFNIAKAKNLRAQAAANAHLMAQI-NH2 |
| 432 | FN-38 (SLM14) | FLFHYSKTQKLGKSNVVEELQSPFASQSRGYFLFRPRN-NH2 |
| 456 | alpha-Atrial Natriuretic Polypeptide (1-28) human, porcine, bovine | SLRRSSCFGGRMDRIGAQSGLGCNSFRY-OH |
| 485 | Brain natriuretic peptide, Rat; BNP, Rat | c(NSKMAHSSSCFGQKIDRIGAVSRLGCDGLRLF)-OH |
| 486 | Brain Natriuretic Peptide (BNP) (human) | SPKMVQGSGCFGRKMDRISSSSGLGCKVLRRH-OH |
| 487 | C-TYPE Natriuretic peptide, Porcine; Cnp, Porcine | GLSKGCFGLKLDRIGSMSGLGC-OH |
| 488 | Neuromedin U-8 (porcine) | YFLFRPRN-NH2 |
| 489 | Neuromedin U (rat) | YKVNEYQGPVAPSGGFFLFRPRN-NH2 |

| Seq ID | Description | Sequence |
|---|---|---|
| 490 | Neuromedin U-9 | GYFLFRPRN-NH2 |
| 491 | Neuromedin (U25), human | FRVDEEFQSPFASQSRGYFLFRPRN-NH2 |

These peptides are generally C-terminally amidated when expressed physiologically, but need not be for the purposes of the instant invention. In other words, the C-terminus of these peptides, as well as the GIP hybrid polypeptides of the present invention, may have a free —OH or —NH2 group. These peptides may also have other post-translational modifications. One skilled in the art will appreciate that the hybrid polypeptides of the present invention may also be constructed with an N-terminal methionine residue.

Exemplary peptide modules for use in the invention further include, N-terminally extendable peptide modules (and their analogs and fragments) including Apelin, which exists in 2 forms, Apelin 36 and 13, both active at the AJP receptor (LVQPRGSRNGPGPWQGGRRKFRRQR-PRLSHKGPMPF-OH (SEQ ID NO: 493) and pERPRLSH-KGPMPF-OH (SEQ ID NO:494)); Prolactin Releasing peptide, which exists in 2 forms, PRP31 and PRP20, equally active at GPR10 (SRTHRHSMEIRTPDINPAWYASRGIR-PVGRF-NH2 (SEQ ID NO: 495) and TPDINPAWYASR-GIRPVGRF-NH2 (SEQ ID NO: 496)); Gastrin, which exists as big gastrin and mini-gastrin, the bulk of activity however residing in resides in pentagastrin (QLGPQGPPHL-VADPSKKQGPWLEEEEEAYGWMDF-NH2 (SEQ ID NO: 497); pEGPWLEEEEEAYGWMDF-NH2 (SEQ ID NO: 498); beta-AWMDF-NH2 (SEQ ID NO: 499)); CCK, which exists as CCK33 or CCK8 (central vs. peripheral; KAPSGRMSIVKNLQNLDPSHRISDRDYMGWMDF-NH2 (SEQ ID NO: 500); DYMGWMDF-NH2) (SEQ ID NO: 55); Cortistatin, which exists as cortistatin 17 or 29 (QEGAP-PQQSARRDRMPCRNFFWKTFSSCK-OH (SEQ ID NO: 501) and DRMPCRNFFWKTFSSCK-OH (SEQ ID NO: 502)); somatostatin, which exists as somatostatin 14 or 28 (SANSNPAMAPRERKAGCKNFFWKTFTSC-OH (SEQ ID NO: 503); AGCKNFFWKTFTSC-OH (SEQ ID NO: 504)); GRP for which a C-terminal 10 amino acid sequence possesses most of the activity (VPLPAGGGTVLTK-MYPRGNHWAVGHLM-NH2 (SEQ ID NO: 505); GNH-WAVGHLM-NH2 (SEQ ID NO: 506)); Neuromedin B for which a C-terminal 10 amino acid region possesses most of the activity (LSWDLPEPRSRASKIRVHSRGNLWAT-GHFM-NH2 (SEQ ID NO: 507); GNLWATGHFM-NH2 (SEQ ID NO: 508)); Neuromedin S for which a C-terminal 9 amino acid region possesses most of the activity (ILQRGS-GTAAVDFTKKDHTATWGRPFFLFRPRN-NH2 (SEQ ID NO: 492); PFFLFRPRN-NH2 (SEQ ID NO: 509)); Neuromedin U for which a C-terminal 9 amino acid region possesses most of the activity (FRVDEEFQSPFASQSRGY-FLFRPRN-NH2 (SEQ ID NO: 491); GYFLFRPRN-NH2 (SEQ ID NO: 490)); Neurotensin, which exists as long and short forms (KIPYILKRQLYENKPRRPYIL-OH (SEQ ID NO: 510); QLYENKPRRPYIL-OH) (SEQ ID NO: 511); Kiss-1 whose activity lies mainly in its C-terminus (GTSL-SPPPESSGSPQQPGLSAPHSRQIPAPQ-GAVLVQREKDLPNYNWNSFGLRF-NH2 (SEQ ID NO: 512); EKDLPNYNWNSFGLRF-NH2 (SEQ ID NO: 513)); RF-amide-3, whose C-terminal fragments possess activity (SAGATANLPLRSGRNMEVSLVRRVPNLPQRF-NH2 (SEQ ID NO: 514); VPNLPQRF-NH2 (SEQ ID NO: 515)); Dynorphin, which exists as big dynorphin (A) of dynorphin B (rimorphin) (YGGFLRRIRPKLKWDNQKRYGGFLR-RQFKVVT-OH (SEQ ID NO: 516) and YGGFLR-RQFKVVT-OH (SEQ ID NO: 517)); PYY whose C-terminal fragments are active at Y2 receptor (YPIKPEAPGE-DASPEELNRYYASLRHYLNLVTRQRY-NH2 (SEQ ID NO: 46); SLRHYLNLVTRQRY-NH2 (SEQ ID NO: 518)); AFP-6 whose 7-47 region retains activity (TQAQLL-RVGCVLGTCQVQNLSHRLWQLMG-PAGRQDSAPVDPSSPHSY-NH2 (SEQ ID NO: 40); VGCVLGTCQVQNLSHRLWQLMGPAGRQD-SAPVDPSSPHSY-NH2 (SEQ ID NO: 41)); the amylin family including adrenomedullin, calcitonin and CGRP; Oxytocin whose C-terminal amide is generally needed for activity and can tolerate N-terminal extensions.

Exemplary peptide modules for use in the invention further include, C-Terminally extendable peptide modules including, Endothelin I, II and III: ETI (CSCSSLMDKECVYFCHL-DIIWVNTPEHVVPYGLGSPRS-OH (SEQ ID NO: 519); CSCSSLMDKECVYFCHLDIIW-OH (SEQ ID NO: 529)), ETII (CSCSSWLDKECVYFCHLDIIWVNT-PEQTAPYGLGNPP-OH (SEQ ID NO: 521); CSCSSWLD-KECVYFCHLDIIW-OH (SEQ ID NO: 522)) and ETIII (CTCFTYKDKECVYYCHLDIIWIN-TPEQTVPYGLSNYRGSFR-NH2 (SEQ ID NO: 523); CTCFTYKDKECVYYCHLDIIW-OH (SEQ ID NO: 524)); ghrelin whose activity lies mainly in its first 10 residues (GSSFLSPEHQRVQQRKESKKPPAKLQP-OH (SEQ ID NO: 525); GSSFLSPEHQ-OH (SEQ ID NO: 526)); glucagons, including oxyntomodulin which is a C-terminally extended glucagon with glucagons-like activity (HSQGT-FTSDYSKYLDSRRAQDFVQWLMNTKRNRNNIA-OH (SEQ ID NO: 527); HSQGTFTSDYSKYLDSRRAQD-FVQWLMNT-OH (SEQ ID NO: 528)); GLP-1/GLP-2 whose activities are retained with or without a C-terminal amide; GIP, which circulates in 2 forms, GIP1-42 and GIP1-30, both fully active at GIP Receptor (YAEGTFISDYSIAM-DKIHQQDFVNWLLAQKGKKNDWKHNITQ-OH (SEQ ID NO: 529); YAEGTFISDYSIAMDKIHQQDFVNWL-LAQK-NH2 (SEQ ID NO: 530)); neuropeptide W, which exists as NPW23 and NPW30, equally active at GPR7 and 8 (WYKHVASPRYHTVGRAAGLLMGLRRSPYLW-OH (SEQ ID NO: 531); WYKHVASPRYHTVGRAAGLLMGL-OH (SEQ ID NO: 532)); PACAP which exists in 2 forms, PACAP27 and 38 (HSDGIFTDSYSRYRKQMAVKKY-LAAVLGKRYKQRVKNK-NH2 (SEQ ID NO: 533); HSDGIFTDSYSRYRKQMAVKKYLAAVL-NH2 (SEQ ID NO: 534)); PHI and PHV (HADGVFTSDFSKLLGQL-SAKKYLESLMGKRVSSNISEDPVPV-OH (SEQ ID NO: 535); HADGVFTSDFSKLLGQLSAKKYLESLM-NH2 (SEQ ID NO: 536)); GRF, which exists in 2 forms GRF29 and GRF40 (YADAIFTNSYRKVLGQLSARKLLQDIM-SRQQGESNQERGARARL-NH2 (SEQ ID NO: 537); YADAIFTNSYRKVLGQLSARKLLQDIMS-OH (SEQ ID NO:538)); PTH 1-34 and 1-37 forms which possess activity of full length PTH 1-84 (SVSEIQLMHNLGKHLNS- MERVEWLRKKLQDVHNFVALGAPLA-PRDAGSQRPRKKEDNVLVESHE KSLGEADKADVNV-LTKAKSQ (SEQ ID NO: 539); SVSEIQLMHNLGKHLNSMERVEWL-RKKKLQDVHNFVAL-OH (SEQ ID NO: 540); SVSEIQLM-HNLGKHLNSMERVEWLRKKLQDVHNF-OH (SEQ ID NO: 541)) PTH-RP for which 1-36 possesses activity of full length 1-86 (AVSEHQLLHDKGKSIQDLRRRFFLHHLI-AEIHTAEIRATSEVSPNSKPSPNTKN-HPVRFGSDDEGRY LTQETNKVETYKEQPLKT-PGKKKKGKP-NH2 (SEQ ID NO: 542); AVSEHQLLHDKGKSIQDLRRRFFLHHLIAEIHTAEI-OH (SEQ ID NO:543)) gamma-MSH for which the shorter gamma-MSH1 and the longer gamma-MSH3 have similar activities (YVMGHFRWDRFGRRNSSSSGSSGAGQ-OH (SEQ ID NO: 544); YVMGHFRWDRF-NH2 (SEQ ID NO: 545)); MSH for which alpha-MSH is an active portion of ACTH (SYSMEHFRWGKPVGKKRRPVKVYPN-GAEDESAEAFPLEF-OH (SEQ ID NO: 546); SYSMEH-FRWGKPV-NH2 (SEQ ID NO: 547)); and endorphins for which the A, delta, and γ endorphin are active subpeptides of the larger β endorphin (YGGFMTSEKSQTPLVTLFKNAI-IKNAYKKGE-OH (SEQ ID NO: 548); YGGFMTSEKSQT-PLVTLFKNAIIKNAY-OH (SEQ ID NO:549); YGGFMT-SEKSQTPLVTL-OH (SEQ ID NO: 373); YGGFMTSEKSQTPLVT-OH (SEQ ID NO: 550)).

For example, the melanocortins are peptides from the pro-opiomelanocortin gene, including alpha-melanocyte-stimulating hormone (alpha-MSH) and adrenocorticotrophic hormone (ACTH), and five melanocortin receptors are known, MC1-5R. MC4R appears to play a role in energy balance and obesity. See, for example, Anderson et al., Expert Opin. Ther. Patents 11:1583-1592 (2001), Speake et al., Expert Opin. Ther. Patents 12:1631-1638 (2002), Bednarek et al., Expert Opin. Ther. Patents 14:327-336 (2004).

It is also intended that in addition to comprising a GIP hybrid, in other embodiments the hormones described herein can be used in adjunct therapy, co-administered with, a GIP analog of the invention.

The Amylin Family. As discussed herein component peptide hormones useful in the present invention with a GIP or a novel GIP analog include amylin family peptide hormones including amylin, adrenomedullin ("ADM"), calcitonin ("CT"), calcitonin gene related peptide ("CGRP"), intermedin (also known as "AFP-6") and related peptides. Native amylin family peptide hormones are known in art, as are functional peptide analogs and derivatives. Certain exemplary native peptides, peptide analogs and derivatives are described herein, however it should be recognized that any known amylin family peptides that exhibit hormonal activity known in the art may be used in conjunction with the present invention. Any amylin analog or derivative known in the art may be used in conjunction with the present invention.

Another family of peptide hormones implicated in metabolic diseases and disorders is the amylin family of peptide hormones, including amylin, calcitonin, calcitonin gene related peptide, adrenomedullin, and intermedin (also known as "AFP-6"). Amylin is a 37-amino acid peptide hormone. It was isolated, purified and chemically characterized as the major component of amyloid deposits in the islets of pancreases of human Type 2 diabetics (Cooper et al., Proc. Natl. Acad. Sci., USA, 84:8628-8632 (1987)). The amylin molecule has two post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the N-terminal position, a typical sequence for amidation by protein amidating enzyme, PAM (Cooper et al., Biochem. Biophys. Acta, 1014: 247-258 (1989)). By "adrenomedullin" or "ADM" is meant the human peptide hormone and species variants thereof. More particularly, ADM is generated from a 185 amino acid preprohormone through consecutive enzymatic cleavage and amidation. This process culminates in the liberation of a 52 amino acid bioactive peptide. By "calcitonin" or "CT" is meant the human peptide hormone and species variants thereof, including salmon calcitonin ("sCT"). More particularly, CT is a 32 amino acid peptide cleaved from a larger prohormone. It contains a single disulfide bond, which causes the amino terminus to assume the shape of a ring. Alternative splicing of the calcitonin pre-mRNA can yield a mRNA encoding calcitonin gene-related peptide; that peptide appears to function in the nervous and vascular systems. The calcitonin receptor has been cloned and shown to be a member of the seven-transmembrane, G protein-coupled receptor family. By "calcitonin gene related peptide" or "CGRP" is meant the human peptide hormone and species variants thereof, in any physiological form. By "intermedin" or "AFP-6" is meant the human peptide hormone and species variants thereof, in any physiological form.

Amylin is believed to regulate gastric emptying, and suppress glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intra-hypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT(1-32) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT(1-32) is to combat acute hypercalcemia in emergency situations and/or protect the skeleton during periods of "calcium stress" such as growth, pregnancy, and lactation. (Reviewed in Becker, JCEM, 89(4): 1512-1525 (2004) and Sexton, Current Medicinal Chemistry 6: 1067-1093 (1999)). Consistent with this is recent data from the calcitonin gene knockout mouse, which removes both the calcitonin and the CGRP-I peptides, that revealed that the mouse had normal levels of basal calcium-related values, but an increased calcemic response (Kurihara H, et al., Hypertens Res. 2003 February; 26 Suppl:S105-8).

CT has an effect on plasma calcium levels and inhibits osteoclast function and is widely used for the treatment of osteoporosis. Therapeutically, salmon CT (sCT) appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptide discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake. (Wimalawansa, Amylin, calcitonin gene-related peptide, calcitonin and ADM: a peptide superfamily. Crit. Rev Neurobiol. 1997; 11(2-3):167-239). An important role of CGRP is to control blood flow to various organs by its potent vasodilatory actions, as evidenced by a decrease of mean arterial pressure following intravenous administration of α-CGRP. The vasodilatory actions are also supported by recent analysis of homozygous knockout CGRP mice, which demonstrated elevated peripheral vascular resistance and high blood pressure caused by increased peripheral sympathetic activity (Kurihara H, et al., Targeted disruption of ADM and αCGRP genes reveals their distinct biological roles. Hypertens Res. 2003 February; 26 Suppl:S105-8). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor are also potentially treatable. (Wimalawansa, 1997). Recent therapeutic uses include the use of CGRP antagonists for the treatment of migraine headaches.

Adrenomedullin (ADM) is almost ubiquitously expressed with many more tissues containing the peptide than not. A published review of ADM, (Hinson, J. P. et al., Endocrine Reviews (2000) 21(2): 138-167) details its effects on the cardiovascular system, cellular growth, the central nervous system and the endocrine system, with a range of biological actions including vasodilation, cell growth, regulation of hormone secretion, and natriuresis. Studies in rat, cat, sheep, and man confirm that intravenous infusion of ADM results in potent and sustained hypotension, and is comparable to that of CGRP. However, the hypotensive effect of ADM on mean arterial pressure in the anesthetized rat is not inhibited by the CGRP antagonist CGRP8-37 suggesting that this effect is not mediated via CGRP receptors. Acute or chronic administration of human ADM in rats, anesthetized, conscious or hypertensive, results in a significant decrease in total peripheral resistance accompanied by a fall in blood pressure, with a concomitant rise in heart rate, cardiac output and stroke volume.

ADM has also been proposed as an important factor in embryogenesis and differentiation and as an apoptosis survival factor for rat endothelial cells. This is supported by recent mouse ADM knockout studies, in which mice homozygous for loss of the ADM gene demonstrated defective vascular formation during embryogenesis and thus died mid-gestation. It was reported that ADM+/−heterozygous mice had high blood pressure along with susceptibility to tissue injury (Kurihara H, et al., Hypertens Res. 2003 February; 26 Suppl:S105-8).

ADM affects such endocrine organs as the pituitary, the adrenal gland, reproductive organs and the pancreas. The peptide appears to have a role in inhibiting ACTH release from the pituitary. In the adrenal gland, it appears to affect the secretory activity of the adrenal cortex in both rat and human and it increases adrenal blood flow, acting as a vasodilator in the adrenal vascular bed in intact rats. ADM has been shown to be present throughout the female reproductive tract and plasma levels are elevated in normal pregnancy. Studies in a rat model of preeclampsia show that ADM can reverse hypertension and decrease pup mortality when given to rats during late gestation. Because it did not have a similar effect in animals in early gestation or non-pregnant rats in the preeclampsia model, this suggests that ADM may play an important regulatory role in the utero-placental cardiovascular system. In the pancreas, ADM most likely plays an inhibitory role since it attenuated and delayed insulin response to an oral glucose challenge, resulting in initial elevated glucose levels. ADM can also affect renal function. A bolus administered peripherally can significantly lower mean arterial pressure and raise renal blood flow, glomerular filtration rate and urine flow. In some cases, there is also an increase in Na+ excretion.

ADM also has other peripheral effects on bone and on the lung. For bone, studies have supported a role beyond the cardiovascular system and fluid homeostasis and have demonstrated that ADM acts on fetal and adult rodent osteoblasts to increase cell growth comparable to those of known osteoblast growth factors such as transforming growth factor-alpha. This is important clinically as one of the major challenges in osteoporosis research is to develop a therapy that increases bone mass via osteoblastic stimulation. In the lung, ADM not only causes pulmonary vasodilation, but also inhibits bronchoconstriction induced by histamine or acetylcholine. Recent studies using aerosolized ADM to treat pulmonary hypertension in a rat model indicate that inhalation treatment of this condition is effective, as evidenced by the fact that mean pulmonary arterial pressure and total pulmonary resistance were markedly lower in rats treated with ADM than in those given saline. This result was achieved without an alteration in systemic arterial pressure or heart rate (Nagaya N et al., Am J Physiol Heart Circ Physiol. 2003; 285:H2125-31).

In healthy volunteers, i.v. infusion of ADM has been shown to reduce arterial pressure and to stimulate heart rate, cardiac output, plasma levels of cAMP, prolactin, norepinephrine and rennin. In these patients, there was little or no increase in urine volume or sodium excretion observed. In patients with heart failure or chronic renal failure, i.v. ADM had similar effects to those seen in normal subjects, and also induced diuresis and natriuresis, depending on the dose administered (Nicholls, M G et al. Peptides. 2001; 22:1745-1752) Experimental ADM treatment has also been shown to be beneficial in arterial and pulmonary hypertension, septic shock and ischemia/reperfusion injury (Beltowski J., Pol J. Pharmacol. 2004; 56:5-27). Other indications for ADM treatment include: peripheral vascular disease, subarachnoid hemorrhage, hypertension, preeclamptic toxemia of pregnancy and preterm labor, and osteoporosis.

Expression of AFP-6 (i.e., intermedin) is primarily in the pituitary and gastrointestinal tract. A specific receptor for AFP-6 has not been reported; however, binding studies indicate that AFP-6 binds to all the known receptors of the Amylin Family. AFP-6 has been shown to increase cAMP production in SK-N-MC and L6 cells expressing endogenous CGRP receptors and competes with labeled CGRP for binding to its receptors in these cells. In published in vivo studies, AFP-6 administration led to blood pressure reduction in both normal and spontaneously hypertensive rats, most likely via interactions with the CRLR/RAMP receptors. In vivo administration in mice led to a suppression of gastric emptying and food intake. (Roh et al. J Biol. Chem. 2004 Feb. 20; 279(8):7264-74.)

It has been reported that the biological actions of amylin family peptide hormones are generally mediated via binding to two closely related type II G protein-coupled receptors (GPCRs), the calcitonin receptor (CTR) and the calcitonin receptor like receptor (CRLR). Cloning and functional studies have shown that CGRP, ADM, and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, ADM, and amylin. The RAMP family comprises three members (RAMP1, -2, and -3), which share less then 30% sequence identity, but have a common topological organization. Co-expression of CRLR and RAMP1 leads to the formation of a receptor for CGRP. Co-expression of CRLR and RAMP2 leads to the formation of a receptor for ADM. Co-expression of CRLR and RAMP3 leads to the formation of a receptor for ADM and CGRP. Co-expression of hCTR2 and RAMP1 leads to the formation of a receptor for amylin and CGRP. Co-expression of hCTR2 and RAMP3 leads to the formation of a receptor for amylin.

Thus a GIP hybrid comprising an amylin family hormone module can provide the functions and uses associated with the amylin family module, e.g. amylin, amylin/sCT/amylin, ADM, CGRP, as discussed, in addition to a GIP function.

In one embodiment, the amylin analogs and derivatives have at least one hormonal activity of native amylin. In certain embodiments, the amylin analogs are agonists of a receptor which native amylin is capable of specifically binding. Exemplary amylin analogs and derivatives include those described in US 2003/0026812 A1, which is hereby incorporated by reference.

Exemplary amylin analogs include:

$^{25,28,29}$Pro-h-amylin (pramlintide)
des-$^{1}$Lys-h-amylin
$^{25}$Pro, $^{26}$Val, $^{28,29}$Pro-h-amylin
$^{18}$Arg, $^{25,28}$Pro-h-amylin
des-$^{1}$Lys, $^{18}$Arg, $^{25,28}$Pro-h-amylin
$^{18}$Arg, $^{25,28,29}$Pro-h-amylin
des-$^{1}$Lys, $^{18}$Arg, $^{25,28,29}$Pro-h-amylin
des-$^{1}$, Lys$^{25,28,29}$Pro-h-amylin
$^{25}$Pro, $^{26}$Val, $^{28,29}$Pro-h-amylin
$^{28}$Pro-h-amylin, 2,7-Cyclo-[$^{2}$Asp, $^{7}$Lys]-h-amylin
$^{2-37}$h-amylin
$^{1}$Ala-h-amylin
$^{2}$Ala-h-amylin
$^{2,7}$Ala-h-amylin
$^{1}$Ser-h-amylin
$^{29}$Pro-h-amylin
$^{25,28}$Pro-h-amylin
des-$^{1}$Lys, $^{25,28}$Pro-h-amylin
$^{23}$Leu, $^{25}$Pro, $^{26}$Val, $^{28,29}$Pro-h-amylin
$^{23}$Leu$^{25}$Pro$^{26}$Val$^{28}$Pro-h-amylin
des-$^{1}$Lys, $^{23}$Leu, $^{25}$Pro, $^{26}$Val, $^{28}$Pro-h-amylin
$^{18}$Arg, $^{23}$Leu, $^{25}$Pro, $^{26}$Val, $^{28}$Pro-h-amylin
$^{18}$Arg, $^{23}$Leu, $^{25,28,29}$Pro-h-amylin
$^{18}$Arg$^{23}$Leu, $^{25,28}$Pro-h-amylin
$^{17}$Ile, $^{23}$Leu, $^{25,28,29}$Pro-h-amylin
$^{17}$Ile, $^{25,28,29}$Pro-h-amylin
des-$^{1}$Lys, $^{17}$Ile, $^{23}$Leu, $^{25,28,29}$Pro-h-amylin
$^{17}$Ile, $^{18}$Arg, $^{23}$Leu-h-amylin
$^{17}$Ile, $^{18}$Arg, $^{23}$Leu, $^{26}$Val, $^{29}$Pro-h-amylin
$^{17}$Ile, $^{18}$Arg, $^{23}$Leu, $^{25}$Pro, $^{26}$Val, $^{28,29}$Pro-h-amylin,
$^{13}$Thr, $^{21}$His, $^{23}$Leu, $^{26}$Ala, $^{28}$Leu, $^{29}$Pro, $^{31}$Asp-h-amylin
$^{13}$Thr, $^{21}$His, $^{23}$Leu, $^{26}$Ala, $^{29}$Pro, $^{31}$Asp-h-amylin
des-$^{1}$Lys, $^{13}$Thr, $^{21}$His, $^{23}$Leu, $^{26}$Ala, $^{28}$Pro, $^{31}$Asp-h-amylin
$^{13}$Thr, $^{18}$Arg, $^{21}$His, $^{23}$Leu, $^{26}$Ala, $^{29}$Pro, $^{31}$Asp-h-amylin
$^{13}$Thr, $^{18}$Arg, $^{21}$His, $^{23}$Leu, $^{28,29}$Pro, $^{31}$Asp-h-amylin
$^{13}$Thr, $^{18}$Arg, $^{21}$His, $^{23}$Leu, $^{25}$Pro, $^{26}$Ala, $^{28,29}$Pro, $^{31}$Asp-h-amylin As known in the art, such amylin analogs are preferably amidated, but within the context of the present invention, may optionally be in the acid form unless otherwise specified.

Any ADM analog or derivative known in the art may be used in conjunction with the present invention. In one embodiment, the ADM analogs and derivatives have at least one hormonal activity of native ADM. In certain embodiments, the ADM analogs are agonists of a receptor which native ADM is capable of specifically binding.

Any CT analog or derivative known in the art may be used in conjunction with the present invention. In one embodiment, the CT analogs and derivatives have at least one hormonal activity of native CT. In certain embodiments, the CT analogs are agonists of a receptor which native CT is capable of specifically binding. Exemplary CT analogs and derivatives include those described in U.S. Pat. Nos. 4,652,627; 4,606,856; 4,604,238; 4,597,900; 4,537,716; 4,497,731; 4,495,097; 4,444,981; 4,414,149; 4,401,593; and 4,397,780, which are hereby incorporated by reference.

Exemplary CT analogs include:

$^{8}$Gly-CT
$^{22}$Leu-CT
$^{2}$Gly, $^{3}$Ser, $^{8}$Gly, $^{22}$des-Tyr-CT
$^{14}$Glu-sCT,
$^{18}$Arg-sCT,
$^{11,18}$Arg-sCT,
$^{14}$Glu, $^{18}$Arg-sCT,
$^{14}$Glu, $^{11,18}$Arg-sCT As known in the art, such CT analogs are preferably amidated, but within the context of the present invention, may optionally be in the acid form unless otherwise specified.

Any CGRP analog or derivative known in the art may be used in conjunction with the present invention. In one embodiment, the CGRP analogs and derivatives have at least one hormonal activity of native CGRP. In certain embodiments, the CGRP analogs are agonists of a receptor which native CGRP is capable of specifically binding. Exemplary CGRP analogs and derivatives include those described in U.S. Pat. Nos. 4,697,002; and 4,687,839, which are hereby incorporated by reference.

Exemplary CGRP analogs include:

$^{36}$D-Ser-CGRP
$^{36}$D-Thr-CGRP
$^{36}$D-Asp-CGRP
$^{36}$D-Asn-CGRP
$^{36}$Ser-CGRP
$^{36}$Hse-CGRP
$^{36}$Asp-CGRP
$^{36}$Thr-CGRP
$^{36}$Asn-CGRP

Any AFP-6 analog or derivative known in the art may be used in conjunction with the present invention. In one embodiment, the AFP-6 analogs and derivatives have at least one hormonal activity of native AFP-6. In certain embodiments, the AFP-6 analogs are agonists of a receptor which native AFP-6 is capable of specifically binding. Exemplary AFP-6 analogs and derivatives include those described in WO 2003/022304, which is hereby incorporated by reference.

Exemplary AFP-6 analogs include:

| SEQ ID No: | Sequence |
|---|---|
| 18 | TQAQLLRVGCGNLSTCQVQNLSHRLWQLMGPAGRQDSAPVDPSSPHSY |
| 19 | TQAQLLRVGCDTATCQVQNLSHRLWQLMGPAGRQDSAPVDPSSPHSY |
| 20 | TQAQLLRVGMVLGTMQVQNLSHRLWQLMGPAGRQDSAPVDPSSPHSY |
| 21 | TQAQLLRVGCVLGTCQVQNLSHRLWQLMGPAGRQDSAPVEPSSPHSY |
| 22 | TQAQLLRVGCVLGTCQVQNLSHRLWQLMGPAGRQESAPVEPSSPHSY |
| 56 | TQAQLLRVGCVLGTCQVQNLSHRLWQL----RQDSAPVDPSSPHSY |
| 57 | TQAQLLRVGCVLGTCQVQNLSHRLWQL----DSAPVDPSSPHSY |
| 58 | RVGCVLGTCQVQNLSHRLWQLMGPAGRQDSAPVDPSSPHSY |
| 59 | VGCVLGTCQVQNLSHRLWQLMGPAGRQDSAPVEPSSPHSY |
| 60 | VGCVLGTCQVQNLSHRLWQL----RQDSAPVEPSSPHSY |
| 61 | GCVLGTCQVQNLSHRLWQLMGPAGRQDSAPVDPSSPHSY |
| 62 | GCNTATCQVQNLSHRLWQL----RQDSAPVDPSSPHSY |
| 63 | GCNTATCQVQNLSHRLWQL----RQDSAPVEPSSPHSY |
| 64 | GCSNLSTCQVQNLSHRLWQL----RQDSAPVEPSSPHSY |
| 65 | GCGNLSTCQVQNLSHRLWQL----RQDSAPVEPSSPHSY |
| 66 | GCVLGTCQVQNLSHRLWQL----RQESAPVEPSSPHSY |
| 67 | CVLGTCQVQNLSHRLWQLMGPAGRQDSAPVDPSSPHSY |
| 68 | QVQNLSHRLWQLMGPAGRQDSAPVDPSSPHSY |
| 69 | VQNLSHRLWQLMGPAGRQDSAPVDPSSPHSY |
| 70 | VQNLSHRL----QLMGPAGRQDSAPVDPSSPHSY |
| 71 | GTMQVQNLSHRLWQL----RQDSAPVEPSSPHSY |

As known in the art, such AFP-6 analogs are preferably amidated, but within the context of the present invention, may optionally be in the acid form unless otherwise specified.

The CCK Family. CCKs, including hCCK (cholecystokinin) and species variants, and various analogs thereof are known in the art. Generally, CCK has a 33-amino acid sequence first identified in humans, and includes a 8-amino acid in vivo C-terminal fragment ("CCK-8") that has been reportedly demonstrated in pig, rat, chicken, chinchilla, dog and humans. Other species variants include a 39-amino acid sequence found in pig, dog and guinea pig, and a 58-amino acid found in cat, dog and humans, and a 47-amino acid sequences homologous to both CCK and gastrin. The C-terminal tyrosine-sulfated octapeptide sequence (CCK-8) is relatively conserved across species, and may be the minimum sequence for biological activity in the periphery of rodents. Thus, the term CCK-33 will generally refer to human CCK (1-33), while CCK-8 (CCK(26-33)) will refer to the C-terminal octapeptide generically in both the sulfated and unsulfated unless otherwise specified. Further, pentagastrin or CCK-5 will refer to the C-terminal peptide CCK(29-33), and the CCK-4 will refer to the C-terminal tetrapeptide CCK(30-33).

CCK was reportedly identified in 1928 from preparations of intestinal extracts by its ability to stimulate gallbladder contraction. Other biological actions of CCK have since been reported, including stimulation of pancreatic secretion, delayed gastric emptying, stimulation of intestinal motility and stimulation of insulin secretion. See Lieverse et al., Ann. N.Y. Acad. Sci. 713: 268-272 (1994). The actions of CCK, also reportedly include effects on cardiovascular function, respiratory function, neurotoxicity and seizures, cancer cell proliferation, analgesia, sleep, sexual and reproductive behaviors, memory, anxiety and dopamine-mediated behaviors. Crawley and Corwin, Peptides 15: 731-755 (1994). Other reported effects of CCK include stimulation of pancreatic growth, stimulation of gallbladder contraction, inhibition of gastric acid secretion, pancreatic polypeptide release and a contractile component of peristalsis. Additional reported effects of CCK include vasodilation. Walsh, "Gastrointestinal Hormones," In Physiology of the Gastrointestinal Tract (3d ed. 1994; Raven Press, New York).

It has been reported that injections of combinations of glucagon, CCK and bombesin potentiated the inhibition of intake of condensed milk test meals in nondeprived rats over the inhibitions observed with individual compounds. Hinton et al., Brain Res. Bull. 17:615-619 (1986). It has also been reported that glucagon and CCK synergistically inhibit sham feeding in rats. LeSauter and Geary, Am. J. Physiol. 253: R217-225 (1987); Smith and Gibbs, Annals N.Y. Acad. Sci. 713:236-241 (1994). It has also been suggested that estradiol and CCK can have a synergistic effect on satiety. Dulawa et al., Peptides 15:913-918 (1994); Smith and Gibbs, supra. It has also been proposed that signals arising from the small intestine in response to nutrients therein may interact synergistically with CCK to reduce food intake. Cox, Behav. Brain Res. 38:35-44 (1990). Additionally, it has been reported that CCK induces satiety in several species. For example, it has been reported that feeding depression was caused by CCK injected intraperitoneally in rats, intraarterially in pigs, intravenously in cats and pigs, into the cerebral ventricles in monkeys, rats, dogs and sheep, and intravenously in obese and non-obese humans. See Lieverse et al., supra. Studies from several laboratories have reportedly confirmed the behavioral specificity of low doses of CCK on inhibition in feeding, by comparing responding for food to responding for nonfood reinforcers in both monkeys and rats and by showing that CCK elicits the sequence of behaviors normally observed after meal ingestion (i.e., the postprandial satiety sequence). Additionally, comparison of behavior after CCK to behavior after food ingestion, alone or in combination with CCK has reportedly revealed behavioral similarities between CCK and food ingestion. Crawley and Corwin, supra. It has also been reported that CCK in physiological plasma concentrations inhibits food intake and increases satiety in both lean and obese humans. See Lieverse et al., supra.

CCK was characterized in 1966 as a 33-amino acid peptide. Crawley and Corwin, supra. Species-specific molecular variants of the amino acid sequence of CCK have been identified. The 33-amino acid sequence and a truncated peptide, its 8-amino acid C-terminal sequence (CCK-8) have been reportedly identified in pig, rat, chicken, chinchilla, dog and humans. A 39-amino acid sequence was reportedly found in pig, dog and guinea pig. A 58-amino acid sequence was reported to have been found in cat, dog and humans. Frog and turtle reportedly show 47-amino acid sequences homologous to both CCK and gastrin. Very fresh human intestine has been reported to contain small amounts of an even larger molecule, termed CCK-83. In the rat, a principal intermediate form has been reportedly identified, and is termed CCK-22. Walsh, "Gastrointestinal Hormones," In Physiology of the Gastrointestinal Tract (3d ed. 1994; Raven Press, New York). A non-sulfated CCK-8 and a tetrapeptide (termed CCK-4 (CCK (30-33)) have been reported in rat brain. The C-terminal pentapeptide (termed CCK-4 (CCK(29-33)) conserves the structural homology of CCK, and also homology with the neuropeptide, gastrin. The C-terminal sulfated octapeptide sequence, CCK-8, is reportedly relatively conserved across species. Cloning and sequence analysis of a cDNA encoding preprocholecystokinin from rat thyroid carcinoma, porcine brain, and porcine intestine reportedly revealed 345 nucleotides coding for a precursor to CCK, which is 115 amino acids and contains all of the CCK sequences previously reported to have been isolated. Crawley and Corwin, supra.

CCK is said to be distributed throughout the central nervous system and in endocrine cells and enteric nerves of the upper small intestine. CCK agonists include CCK itself (also referred to as CCK-33), CCK-8 (CCK(26-33)), non-sulfated CCK-8, pentagastrin (CCK-5 or CCK(29-33)), and the tetrapeptide, CCK-4 (CCK(30-33)). At the pancreatic CCK receptor, CCK-8 reportedly displaced binding with a 1000-5000 greater potency than unsulfated CCK-8 or CCK-4, and CCK-8 has been reported to be approximately 1000-fold more potent than unsulfated CCK-8 or CCK-4 in stimulating pancreatic amylase secretion. Crawley and Corwin, supra. In homogenates from the cerebral cortex, CCK receptor binding was said to be displaced by unsulfated CCK-8 and by CCK-4 at concentrations that were equimolar, 10-fold or 100-fold greater than sulfated CCK-8. Id. Receptors for CCK have been reportedly identified in a variety of tissues, and two primary subtypes have been described: type A receptors and type B receptors. Type A receptors have been reported in peripheral tissues including pancreas, gallbladder, pyloric sphincter and afferent vagal fibers, and in discrete areas of the brain. The type A receptor subtype (CCKA) has been reported to be selective for the sulfated octapeptide. The Type B receptor subtype (CCKB) has been identified throughout the brain and in the stomach, and reportedly does not require sulfation or all eight amino acids. See Reidelberger, J. Nutr. 124 (8 Suppl.) 1327S-1333S (1994); Crawley and Corwin, supra.

Various in vivo and in vitro screening methods for CCK analogs are known in the art. Examples include in vivo assays involving the contraction of the dog or guinea pig gallbladder after rapid intravenous injection of the compound to be tested for CCK-like activity, and in vitro assays using strips of rabbit gallbladder. See Walsh, "Gastrointestinal Hormones", In Physiology of the Gastrointestinal Tract (3d ed. 1994; Raven Press, New York).

Certain exemplary CCK and CCK analogs with CCK activity include:

| SEQ ID NO: | Sequence |
|---|---|
| 72 | DY(SO$_3$H)MGWMDF |
| 24 | DYMGWMDF |
| 25 | MGWMDF |
| 26 | GWMDF |

| SEQ ID NO: | Sequence |
|---|---|
| 27 | WMDF |
| 73 | KDY(SO$_3$H)MGWMDF |
| 29 | KDYMGWMDF |
| 30 | KMGWMDF |
| 31 | KGWMDF |
| 32 | KWMDF |

As known in the art, such CCK peptides are preferably amidated, but within the context of the present invention, may optionally be in the acid form unless otherwise specified.

The Leptin Family. Component peptide hormones useful in the present invention also include leptin family peptide hormones. Native leptin family peptide hormones are known in art, as are functional peptide analogs and derivatives. Certain exemplary native peptides, peptide analogs and derivatives are described herein, however it should be recognized that any known leptin family peptides that exhibit hormonal activity known in the art may be used in conjunction with the present invention.

Thus a GIP hybrid comprising a leptin family hormone module can provide the functions and uses associated with the leptin family module, e.g. leptin, leptin fragment, as discussed, in addition to a GIP function.

Any leptin analog or derivative known in the art may be used in conjunction with the present invention. In one embodiment, the leptin analogs and derivatives have at least one hormonal activity of native leptin. In certain embodiments, the leptin analogs are agonists of a receptor which native leptin is capable of specifically binding. Preferred leptin analogs and derivatives include those described in, e.g., WO 2004/039832, WO 98/55139, WO 98/12224, and WO 97/02004, all of which are hereby incorporated by reference.

In one embodiment leptin peptides include MVPIQK (SEQ ID NO: 551), VQDDTK (SEQ ID NO: 552), TLIK (SEQ ID NO: 553), TIVTR (SEQ ID NO: 554), INDISHTQSVSSK (SEQ ID NO: 555), VTGLDFIPGLHPILTLSK (SEQ ID NO: 556), NVIQISNDLENLR (SEQ ID NO: 557), DLLHVLAFSK (SEQ ID NO: 558), SCHLPWASGLETLDSLGGVLEASGYSTEVVALSR (SEQ ID NO: 559) and LQGSLQDMLWQLDLSPGC (SEQ ID NO: 560) as disclosed in WO97046585.

In one embodiment a leptin peptide may have an amino acid sequence Xaan-Ser-Cys-Xaa1-Leu-Pro-Xaa2-Xaa3-Xaan (SEQ ID NO: 561), wherein Xaan may be zero residues in length, or may be a contiguous stretch of peptide residues derived from full length human or mouse leptin sequences, a stretch of between 1 and 7 at either the C-terminus or N-terminus, or wherein the leptin peptide is a total of 15 amino acids or less in length. In another embodiment, Xaa1, Xaa2 or Xaa3 may be any amino acid substitution. In yet another embodiment, Xaa1, Xaa2 or Xaa3 may be any conservative amino acid substitution of the respective residues in full length mouse or human leptin. In a further embodiment, Xaa1 may be selected from the group consisting of His or Ser, and Xaa2 or Xaa3 is any amino acid substitution. In another embodiment, Xaa2 may be selected from the group consisting of Trp or Gln, and Xaa1 or Xaa3 is any amino acid substitution. In yet another embodiment, Xaa3 may be selected from the group consisting of Ala or Thr, and Xaa1 or Xaa2 is any amino acid substitution. In another embodiment Xaa1 is selected from the group consisting of His or Ser. Xaa2 is selected from the group consisting of Trp or Gln, and Xaa3 is selected from the group consisting of Ala or Thr. See WO04039832.

In one embodiment leptin peptide comprises the C-terminal amino acid residues 116-122 of native full length human or mouse leptin (corresponding to positions 95-101 of their mature forms) and D-isoforms, fragments, derivatives, analogs and homologs thereof, which possess the ability to modulate body mass homeostasis in test animals upon i.p. (intraperitoneal) administration. Specific mouse D-substituted peptides of sequence SCSLPQT include [D-Ser-1]-, [D-Cys-2]-, [D-Ser-3]-, [D-Leu-4]-, [D-Pro-5]-, [D-Gln-6]-[D-Thr-7]-SCSLPQT and all [D] SCSLPQT. Specific human D-substituted peptides of SCHLPWA include [D-Ser-1]-, [D-Cys-2]-, [D-His-3]-, [D-Leu-4]-, [D-Pro-5]-, [D-Trp-6]-, [D-Ala-7]-SCHLPWA and all [D]-SCHLPWA. In addition the SCHLPWA and SCSLPQT peptides may contain D-substituted amino acids for any two, three, four, five or six positions. Also disclosed are leptin related peptides comprising N-terminal amino acids 21-35, 31-45, 41-55 and 51-65 of native leptin and fragments, derivatives, analogs and homologs thereof. Additional leptin peptides of the invention comprise amino acids sequences 61-75, 71-85, 81-95, 91-105, 106-120, 116-130, 126-140, 136-150, 146-160, and 156-167 of mouse and/or human full length leptin. See WO04039832.

In one embodiment the leptin is of the sequence Ser Cys His Leu Pro Xaa Ala Ser Gly Leu Glu Thr Leu Asp Ser Leu Gly Gly Val Leu Glu Ala Ser Gly Tyr Ser Thr Glu Val Val Ala Leu Ser Arg Leu Xaa Gly Ser Leu Xaa Asp Xaa Leu Xaa Xaa Leu Asp Leu Ser Pro Gly Cys (SEQ ID NO: 564) wherein: Xaa at position 6 is Trp or Gln; Xaa at position 36 is Gln or Glu; Xaa at position 40 is Gln or Glu; Xaa at position 42 is Ile, Leu, Met or methionine sulfoxide; Xaa at position 44 is Trp or Gln; and Xaa at position 45 is Gln or Glu. In another embodiment are leptin of the above are where Xaa at position 6 is Trp; Xaa at position 36 is Gln; Xaa at position 40 is Gln; Xaa at position 42 is Met; Xaa at position 44 is Trp; and Xaa at position 45 is Gln. See U.S. Pat. No. 5,521,283.

In one embodiment leptins are native sequences, including Murine leptin: Val Pro Ile Gln Lys Val Gln Asp Asp Thr Lys Thr Leu Ile Lys Thr Ile Val Thr Arg Ile Asn Asp Ile Ser His Thr Xaa Ser Val Ser Ser Lys Gln Lys Val Thr Gly Leu Asp Phe Ile Pro Gly Leu His Pro Ile Leu Thr Leu Ser Lys Met Asp Gln Thr Leu Ala Val Tyr Gln Gln Ile Leu Thr Ser Met Pro Ser Arg Asn Val Ile Gln Ile Ser Asn Asp Leu Glu Asn Leu Arg Asp Leu Leu His Val Leu Ala Phe Ser Lys Ser Cys His Leu Pro Gln Ala Ser Gly Leu Glu Thr Leu Glu Ser Leu Gly Gly Val Leu Glu Ala Ser Gly Tyr Ser Thr Glu Val Val Ala Leu Ser Arg Leu Gln Gly Ser Leu Gln Asp Met Leu Gln Gln Leu Asp Leu Ser Pro Gly Cys (SEQ ID NO:565), wherein: Xaa at position 28 is Gln or absent;

Porcine leptin: Val Pro Ile Trp Arg Val Gln Asp Asp Thr Lys Thr Leu Ile Lys Thr Ile Val Thr Arg Ile Ser Asp Ile Ser His Met Gln Ser Val Ser Ser Lys Gln Arg Val Thr Gly Leu Asp Phe Ile Pro Gly Leu His Pro Val Leu Ser Leu Ser Lys Met Asp Gln Thr Leu Ala Ile Tyr Gln Gln Ile Leu Thr Ser Leu Pro Ser Arg Asn Val Ile Gln Ile Ser Asn Asp Leu Glu Asn Leu Arg Asp Leu Leu His Leu Leu Ala Ser Ser Lys Ser Cys Pro Leu Pro Gln Ala Arg Ala Leu Glu Thr Leu Glu Ser Leu Gly Gly Val Leu Glu Ala Ser Leu Tyr Ser Thr Glu Val Val Ala Leu Ser Arg Leu Gln Gly Ala Leu Gln Asp Met Leu Arg Gln Leu Asp Leu Ser Pro Gly Cys (SEQ ID NO: 566);

Bovine leptin: Val Pro Ile Cys Lys Val Gln Asp Asp Thr Lys Thr Leu Ile Lys Thr Ile Val Thr Arg Ile Asn Asp Ile Ser His Thr Xaa Ser Val Ser Ser Lys Gln Arg Val Thr Gly Leu Asp Phe Ile Pro Gly Leu His Pro Leu Leu Ser Leu Ser Lys Met Asp Gln Thr Leu Ala Ile Tyr Gln Gln Ile Leu Thr Ser Leu Pro Ser Arg Asn Val Val Gln Ile Ser Asn Asp Leu Glu Asn Leu Arg Asp Leu Leu His Leu Leu Ala Ala Ser Lys Ser Cys Pro Leu Pro Gln Val Arg Ala Leu Glu Ser Leu Glu Ser Leu Gly Val Val Leu Glu Ala Ser Leu Tyr Ser Thr Glu Val Val Ala Leu Ser Arg Leu Gln Gly Ser Leu Gln Asp Met Leu Arg Gln Leu Asp Leu Ser Pro Gly Cys (SEQ ID NO:567) wherein Xaa at position 28 is Gln or absent;

Human leptin: Val Pro Ile Gln Lys Val Gln Asp Asp Thr Lys Thr Leu Ile Lys Thr Ile Val Thr Arg Ile Asn Asp Ile Ser His Xaa Xaa Ser Val Ser Ser Lys Gln Lys Val Thr Gly Leu Asp Phe Ile Pro Gly Leu His Pro Ile Leu Thr Leu Ser Lys Met Asp Gln Thr Leu Ala Val Tyr Gln Gln Ile Leu Thr Ser Met Pro Ser Arg Asn Val Ile Gln Ile Ser Asn Asp Leu Glu Asn Leu Arg Asp Leu Leu His Val Leu Ala Phe Ser Lys Ser Cys His Leu Pro Trp Ala Ser Gly Leu Glu Thr Leu Asp Ser Leu Gly Gly Val Leu Glu Ala Ser Gly Tyr Ser Thr Glu Val Val Ala Leu Ser Arg Leu Gln Gly Ser Leu Gln Asp Met Leu Trp Gln Leu Asp Leu Ser Pro Gly Cys (SEQ ID NO:568) wherein: Xaa at position 27 is Thr or Ala; and Xaa at position 28 is Gln or absent; Rhesus Leptin: Val Pro Ile Gln Lys Val Gln Ser Asp Thr Lys Thr Leu Ile Lys Thr Ile Val Thr Arg Ile Asn Asp Ile Ser His Thr Gln Ser Val Ser Ser Lys Gln Arg Val Thr Gly Leu Asp Phe Ile Pro Gly Leu His Pro Val Leu Thr Leu Ser Gln Met Asp Gln Thr Leu Ala Ile Tyr Gln Gln Ile Leu Ile Asn Leu Pro Ser Arg Asn Val Ile Gln Ile Ser Asn Asp Leu Glu Asn Leu Arg Asp Leu Leu His Leu Leu Ala Phe Ser Lys Ser Cys His Leu Pro Leu Ala Ser Gly Leu Glu Thr Leu Glu Ser Leu Gly Asp Val Leu Glu Ala Ser Leu Tyr Ser Thr Glu Val Val Ala Leu Ser Arg Leu Gln Gly Ser Leu Gln Asp Met Leu Trp Gln Leu Asp Leu Ser Pro Gly Cys (SEQ ID NO: 569); and Rat leptin: Val Pro Ile His Lys Val Gln Asp Asp Thr Lys Thr Leu Ile Lys Thr Ile Val Thr Arg Ile Asn Asp Ile Ser His Thr Gln Ser Val Ser Ala Arg Gln Arg Val Thr Gly Leu Asp Phe Ile Pro Gly Leu His Pro Ile Leu Ser Leu Ser Lys Met Asp Gln Thr Leu Ala Val Tyr Gln Gln Ile Leu Thr Ser Leu Pro Ser Gln Asn Val Leu Gln Ile Ala His Asp Leu Glu Asn Leu Arg Asp Leu Leu His Leu Leu Ala Phe Ser Lys Ser Cys Ser Leu Pro Gln Thr Arg Gly Leu Gln Lys Pro Glu Ser Leu Asp Gly Val Leu Glu Ala Ser Leu Tyr Ser Thr Glu Val Val Ala Leu Ser Arg Leu Gln Gly Ser Leu Gln Asp Ile Leu Gln Gln Leu Asp Leu Ser Pro Glu Cys (SEQ ID NO:570).

In another embodiment leptin peptide components are of the sequence:
Val Pro Ile Gln Lys Val Gln Asp Asp Thr Lys Thr Leu Ile Lys Thr Ile Val Thr Arg Ile Xaa Asp Ile Ser His Xaa Xaa Ser Val Ser Ser Lys Gln Lys Val Thr Gly Leu Asp Phe Ile Pro Gly Leu His Pro Ile Leu Thr Leu Ser Lys Xaa Asp Gln Thr Leu Ala Val Tyr Gln Gln Ile Leu Thr Ser Xaa Pro Ser Arg Xaa Val Ile Gln Ile Xaa Asn Asp Leu Glu Asn Leu Arg Asp Leu Leu His Val Leu Ala Phe Ser Lys Ser Cys His Leu Pro Trp Ala Ser Gly Leu Glu Thr Leu Asp Ser Leu Gly Gly Val Leu Glu Ala Ser Xaa Tyr Ser Thr Glu Val Val Ala Leu Ser Arg Leu Gln Gly Ser Leu Gln Asp Met Leu Trp Gln Leu Asp Leu Ser Pro Gly Cys (SEQ ID NO:571), wherein: Xaa at position 22 is Asn, Asp or Glu; Xaa at position 27 is Thr or Ala; Xaa at position 28 is Gln, Glu, or absent; Xaa at position 54 s Met or Ala; Xaa at position 68 s Met or Leu; Xaa at position 72 Asn, Asp or Glu; Xaa at position 77 is Ser or Ala; Xaa at position 118 is Gly or Leu; said protein having at least one substitution selected from the group consisting of: His at position 97 is replaced with Ser or Pro; Trp at position 100 is replaced with Gln, Ala or Leu; Ala at position 101 is replaced with Thr or Val; Ser at position 102 is replaced with Arg; Gly at position 103 is replaced with Ala; Glu at position 105 is replaced with Gln; Thr at position 106 is replaced with Lys or Ser; Leu at position 107 is replaced with Pro; Asp at position 108 is replaced with Glu; or Gly at position 111 is replaced with Asp.

In another embodiment leptin are of the sequence: Val Pro Ile Gln Lys Val Gln Asp Asp Thr Lys Thr Leu Ile Lys Thr Ile Val Thr Arg Ile Asn Asp Ile Ser His Xaa Gln Ser Val Ser Ser Lys Gln Lys Val Thr Gly Leu Asp Phe Ile Pro Gly Leu His Pro Ile Leu Thr Leu Ser Lys Met Asp Gln Thr Leu Ala Val Tyr Gln Gln Ile Leu Thr Ser Met Pro Ser Arg Asn Val Ile Gln Ile Xaa Asn Asp Leu Glu Asn Leu Arg Asp Leu Leu His Val Leu Ala Phe Ser Lys Ser Cys His Leu Pro Trp Ala Ser Gly Leu Glu Thr Leu Asp Ser Leu Gly Gly Val Leu Glu Ala Ser Xaa Tyr Ser Thr Glu Val Val Ala Leu Ser Arg Leu Gln Gly Ser Leu Gln Asp Met Leu Trp Gln Leu Asp Leu Ser Pro Gly Cys (SEQ ID NO:572), wherein: Xaa at position 27 is Thr or Ala; Xaa at position 77 is Ser or Ala; Xaa at position 118 is Gly or Leu; said protein having at least one substitution, preferably having one to five substitutions and, most preferably, one to two substitutions selected from the group consisting of: His at position 97 is replaced with Ser; Trp at position 100 is replaced with Gln; Ala at position 101 is replaced with Thr; Glu at position 105 is replaced with Gln; Thr at position 106 is replaced with Lys; Leu at position 107 is replaced with Pro; Asp at position 108 is replaced with Glu; or Gly at position 111 is replaced with Asp. In further embodiments of the above sequence Xaa at position 27 is Thr; Xaa at position 77 is Ser; Xaa at position 118 is Gly; and the amino acid residues at positions 97, 100, 101, 105, 106, 107, 108, and 111 are as in the following table:

|  | 97 | 100 | 101 | 105 | 106 | 107 | 108 | 111 |
|---|---|---|---|---|---|---|---|---|
| native human | His | Trp | Ala | Glu | Thr | Leu | Asp | Gly |
|  | Ser | Trp | Ala | Glu | Thr | Leu | Asp | Gly |
|  | His | Gln | Ala | Glu | Thr | Leu | Asp | Gly |
|  | His | Trp | Thr | Glu | Thr | Leu | Asp | Gly |
|  | His | Trp | Ala | Gln | Thr | Leu | Asp | Gly |
|  | His | Trp | Ala | Glu | Lys | Leu | Asp | Gly |
|  | His | Trp | Ala | Glu | Thr | Pro | Asp | Gly |
|  | His | Trp | Ala | Glu | Thr | Leu | Glu | Gly |
|  | His | Trp | Ala | Glu | Thr | Leu | Asp | Asp |
|  | Ser | Gln | Ala | Glu | Thr | Leu | Asp | Gly |
|  | Ser | Trp | Thr | Glu | Thr | Leu | Asp | Gly |
|  | Ser | Trp | Ala | Gln | Thr | Leu | Asp | Gly |
|  | Ser | Trp | Ala | Glu | Lys | Leu | Asp | Gly |
|  | Ser | Trp | Ala | Glu | Thr | Pro | Asp | Gly |
|  | Ser | Trp | Ala | Glu | Thr | Leu | Glu | Gly |
|  | Ser | Trp | Ala | Glu | Thr | Leu | Asp | Asp |
|  | His | Gln | Thr | Glu | Thr | Leu | Asp | Gly |
|  | His | Gln | Ala | Gln | Thr | Leu | Asp | Gly |
|  | His | Gln | Ala | Glu | Lys | Leu | Asp | Gly |
|  | His | Gln | Ala | Glu | Thr | Pro | Asp | Gly |
|  | His | Gln | Ala | Glu | Thr | Leu | Glu | Gly |
|  | His | Gln | Ala | Glu | Thr | Leu | Asp | Asp |
|  | His | Trp | Thr | Gln | Thr | Leu | Asp | Gly |
|  | His | Trp | Thr | Glu | Lys | Leu | Asp | Gly |
|  | His | Trp | Thr | Glu | Thr | Pro | Asp | Gly |
|  | His | Trp | Thr | Glu | Thr | Leu | Glu | Gly |
|  | His | Trp | Thr | Glu | Thr | Leu | Asp | Asp |
|  | His | Trp | Ala | Gln | Lys | Leu | Asp | Gly |
|  | His | Trp | Ala | Gln | Thr | Pro | Asp | Gly |
|  | His | Trp | Ala | Gln | Thr | Leu | Glu | Gly |
|  | His | Trp | Ala | Gln | Thr | Leu | Asp | Asp |
|  | His | Trp | Ala | Glu | Lys | Pro | Asp | Gly |
|  | His | Trp | Ala | Glu | Lys | Leu | Glu | Gly |
|  | His | Trp | Ala | Glu | Lys | Leu | Asp | Asp |
|  | His | Trp | Ala | Glu | Thr | Pro | Glu | Gly |
|  | His | Trp | Ala | Glu | Thr | Pro | Asp | Asp |
|  | His | Trp | Ala | Glu | Thr | Leu | Glu | Asp |
|  | Ser | Gln | Thr | Glu | Thr | Leu | Asp | Gly |
|  | Ser | Gln | Ala | Gln | Thr | Leu | Asp | Gly |

| 97 | 100 | 101 | 105 | 106 | 107 | 108 | 111 |
|---|---|---|---|---|---|---|---|
| Ser | Gln | Ala | Glu | Lys | Leu | Asp | Gly |
| Ser | Gln | Ala | Glu | Thr | Pro | Asp | Gly |
| Ser | Gln | Ala | Glu | Thr | Leu | Glu | Gly |
| Ser | Gln | Ala | Glu | Thr | Leu | Asp | Asp |
| Ser | Trp | Thr | Gln | Thr | Leu | Asp | Gly |
| Ser | Trp | Thr | Glu | Lys | Leu | Asp | Gly |
| Ser | Trp | Thr | Glu | Thr | Pro | Asp | Gly |
| Ser | Trp | Thr | Glu | Thr | Leu | Glu | Gly |
| Ser | Trp | Thr | Glu | Thr | Leu | Asp | Asp |
| Ser | Trp | Ala | Gln | Lys | Leu | Asp | Gly |
| Ser | Trp | Ala | Gln | Thr | Pro | Asp | Gly |
| Ser | Trp | Ala | Gln | Thr | Leu | Glu | Gly |
| Ser | Trp | Ala | Gln | Thr | Leu | Asp | Asp |
| Ser | Trp | Ala | Glu | Lys | Pro | Asp | Gly |
| Ser | Trp | Ala | Glu | Lys | Leu | Glu | Gly |
| Ser | Trp | Ala | Glu | Lys | Leu | Asp | Asp |
| Ser | Trp | Ala | Glu | Thr | Pro | Glu | Gly |
| Ser | Trp | Ala | Glu | Thr | Pro | Asp | Asp |
| Ser | Trp | Ala | Glu | Thr | Leu | Glu | Asp |
| His | Gln | Thr | Gln | Thr | Leu | Asp | Gly |
| His | Gln | Thr | Glu | Lys | Leu | Asp | Gly |
| His | Gln | Thr | Glu | Thr | Pro | Asp | Gly |
| His | Gln | Thr | Glu | Thr | Leu | Glu | Gly |
| His | Gln | Thr | Glu | Thr | Leu | Asp | Asp |
| His | Gln | Ala | Gln | Lys | Leu | Asp | Gly |
| His | Gln | Ala | Gln | Thr | Pro | Asp | Gly |
| His | Gln | Ala | Gln | Thr | Leu | Glu | Gly |
| His | Gln | Ala | Gln | Thr | Leu | Asp | Asp |
| His | Gln | Ala | Glu | Lys | Pro | Asp | Gly |
| His | Gln | Ala | Glu | Lys | Leu | Glu | Gly |
| His | Gln | Ala | Glu | Lys | Leu | Asp | Asp |
| His | Gln | Ala | Glu | Thr | Pro | Glu | Gly |
| His | Gln | Ala | Glu | Thr | Pro | Asp | Asp |
| His | Gln | Ala | Glu | Thr | Leu | Glu | Asp |
| His | Trp | Thr | Gln | Lys | Leu | Asp | Gly |
| His | Trp | Thr | Gln | Thr | Pro | Asp | Gly |
| His | Trp | Thr | Gln | Thr | Leu | Glu | Gly |
| His | Trp | Thr | Gln | Thr | Leu | Asp | Asp |
| His | Trp | Thr | Glu | Lys | Pro | Asp | Gly |
| His | Trp | Thr | Glu | Lys | Leu | Glu | Gly |
| His | Trp | Thr | Glu | Lys | Leu | Asp | Asp |
| His | Trp | Thr | Glu | Thr | Pro | Glu | Gly |
| His | Trp | Thr | Glu | Thr | Pro | Asp | Asp |
| His | Trp | Thr | Glu | Thr | Leu | Glu | Asp |
| His | Trp | Ala | Gln | Lys | Pro | Asp | Gly |
| His | Trp | Ala | Gln | Lys | Leu | Glu | Gly |
| His | Trp | Ala | Gln | Lys | Leu | Asp | Asp |
| His | Trp | Ala | Gln | Thr | Pro | Glu | Gly |
| His | Trp | Ala | Gln | Thr | Pro | Asp | Asp |
| His | Trp | Ala | Gln | Thr | Leu | Glu | Asp |
| His | Trp | Ala | Glu | Lys | Pro | Glu | Gly |
| His | Trp | Ala | Glu | Lys | Pro | Asp | Asp |
| His | Trp | Ala | Glu | Lys | Leu | Asp | Asp |
| His | Trp | Ala | Glu | Thr | Pro | Glu | Asp |
| Ser | Gln | Thr | Gln | Thr | Leu | Asp | Gly |
| Ser | Gln | Thr | Glu | Lys | Leu | Asp | Gly |
| Ser | Gln | Thr | Glu | Thr | Pro | Asp | Gly |
| Ser | Gln | Thr | Glu | Thr | Leu | Glu | Gly |
| Ser | Gln | Thr | Glu | Thr | Leu | Asp | Asp |
| Ser | Gln | Ala | Gln | Lys | Leu | Asp | Gly |
| Ser | Gln | Ala | Gln | Thr | Pro | Asp | Gly |
| Ser | Gln | Ala | Gln | Thr | Leu | Glu | Gly |
| Ser | Gln | Ala | Gln | Thr | Leu | Asp | Asp |
| Ser | Gln | Ala | Glu | Lys | Pro | Asp | Gly |
| Ser | Gln | Ala | Glu | Lys | Leu | Glu | Gly |
| Ser | Gln | Ala | Glu | Lys | Leu | Asp | Asp |
| Ser | Gln | Ala | Glu | Thr | Pro | Glu | Gly |
| Ser | Gln | Ala | Glu | Thr | Pro | Asp | Asp |
| Ser | Gln | Ala | Glu | Thr | Leu | Glu | Asp |
| Ser | Trp | Thr | Gln | Lys | Leu | Asp | Gly |
| Ser | Trp | Thr | Gln | Thr | Pro | Asp | Gly |
| Ser | Trp | Thr | Gln | Thr | Leu | Glu | Gly |
| Ser | Trp | Thr | Gln | Thr | Leu | Asp | Asp |
| Ser | Trp | Thr | Glu | Lys | Pro | Asp | Gly |
| Ser | Trp | Thr | Glu | Lys | Leu | Glu | Gly |
| Ser | Trp | Thr | Glu | Lys | Leu | Asp | Asp |
| Ser | Trp | Thr | Glu | Thr | Pro | Glu | Gly |
| Ser | Trp | Thr | Glu | Thr | Pro | Asp | Asp |
| Ser | Trp | Ala | Gln | Lys | Pro | Asp | Gly |
| Ser | Trp | Ala | Gln | Lys | Leu | Glu | Gly |
| Ser | Trp | Ala | Gln | Lys | Leu | Asp | Asp |
| Ser | Trp | Ala | Gln | Thr | Pro | Glu | Gly |
| Ser | Trp | Ala | Gln | Thr | Pro | Asp | Asp |
| Ser | Trp | Ala | Gln | Thr | Leu | Glu | Asp |
| Ser | Trp | Ala | Glu | Lys | Pro | Glu | Gly |
| Ser | Trp | Ala | Glu | Lys | Pro | Asp | Asp |
| Ser | Trp | Ala | Glu | Lys | Leu | Glu | Asp |
| Ser | Trp | Ala | Glu | Thr | Pro | Glu | Asp |
| His | Gln | Thr | Gln | Lys | Leu | Asp | Gly |
| His | Gln | Thr | Gln | Thr | Pro | Asp | Gly |
| His | Gln | Thr | Gln | Thr | Leu | Glu | Gly |
| His | Gln | Thr | Gln | Thr | Leu | Asp | Asp |
| His | Gln | Thr | Glu | Lys | Pro | Asp | Gly |
| His | Gln | Thr | Glu | Lys | Leu | Glu | Gly |
| His | Gln | Thr | Glu | Lys | Leu | Asp | Asp |
| His | Gln | Thr | Glu | Thr | Pro | Glu | Gly |
| His | Gln | Thr | Glu | Thr | Pro | Asp | Asp |
| His | Gln | Thr | Glu | Thr | Leu | Glu | Asp |
| His | Gln | Ala | Gln | Lys | Pro | Asp | Gly |
| His | Gln | Ala | Gln | Lys | Leu | Glu | Gly |
| His | Gln | Ala | Gln | Lys | Leu | Asp | Asp |
| His | Gln | Ala | Gln | Thr | Pro | Glu | Gly |
| His | Gln | Ala | Gln | Thr | Pro | Asp | Asp |
| His | Gln | Ala | Gln | Thr | Leu | Glu | Asp |

In one embodiment the leptin is of the sequence: Ile Pro Gly Leu His Pro Ile Leu Thr Leu Ser Lys Xaa Asp Xaa Thr Leu Ala Val Tyr Xaa Xaa Ile Leu Thr Ser Xaa Pro Ser Arg Xaa Val Ile Xaa Ile Ser Xaa Asp Leu Glu Xaa Leu Arg Asp Leu Leu His Val Leu Ala Phe Ser Lys Ser Cys His Leu Pro Xaa Ala Ser Gly Leu Glu Thr Leu Asp Ser Leu Gly Gly Val Leu Glu Ala Ser Gly Tyr Ser Thr Glu Val Val Ala Leu Ser Arg Leu Xaa Gly Ser Leu Xaa Asp Xaa Leu Xaa Xaa Leu Asp Leu Ser Pro Gly Cys (SEQ ID NO:573), wherein: Xaa at position 13 is Ile, Leu, Met or methionine sulfoxide; Xaa at position 15 is Gln or Glu; Xaa at position 21 is Gln or Glu; Xaa at position 22 is Gln or Glu; Xaa at position 27 is Ile, Leu, Met or methionine sulfoxide; Xaa at position 31 is Asn, Asp or Gln; Xaa at position 34 is Gln or Glu; Xaa at position 37 is Asn, Asp or Gln; Xaa at position 41 is Asn, Asp or Gln; Xaa at position 59 is Trp or Gln; Xaa at position 89 is Gln or Glu; Xaa at position 93 is Gln or Glu; Xaa at position 95 is Ile, Leu, Met or methionine sulfoxide; Xaa at position 97 is Trp or Gln; and Xaa at position 98 is Gln or Glu. In another embodiment the leptin of the above formula has Xaa at position 13 is Met; Xaa at position 15 is Gln; Xaa at position 21 is Gln; Xaa at position 22 is Gln; Xaa at position 27 is Met; Xaa at position 31 is Asn; Xaa at position 34 is Gln; Xaa at position 37 is Asn; Xaa at position 41 is Asn; Xaa at position 59 is Trp; Xaa at position 89 is Gln; Xaa at position 93 is Gln; Xaa at position 95 is Met; Xaa at position 97 is Trp; and Xaa at position 98 is Gln. See U.S. Pat. No. 5,532,336.

Exemplary leptin analogs include those where the amino acid at position 43 is substituted with Asp or Glu; position 48 is substituted Ala; position 49 is substituted with Glu, or absent; position 75 is substituted with Ala; position 89 is substituted with Leu; position 93 is substituted with Asp or Glu; position 98 is substituted with Ala; position 117 is substituted with Ser, position 139 is substituted with Leu, position 167 is substituted with Ser, and any combination thereof.

Certain exemplary leptin and leptin analogs with leptin activity include:

$^{43}$Asp-leptin
$^{43}$Glu-leptin
$^{48}$Ala-leptin
$^{49}$Glu-leptin
$^{49}$Des-AA-leptin
$^{75}$Ala-leptin
$^{89}$Leu-leptin
$^{93}$Asp-leptin
$^{93}$Glu-leptin
$^{98}$Ala-leptin
$^{117}$Ser-leptin
$^{139}$Leu-leptin
$^{167}$Ser-leptin
$^{43}$Asp, $^{49}$Glu-leptin
$^{43}$Asp, $^{75}$Ala-leptin
$^{89}$Leu, $^{117}$Ser-leptin
$^{93}$Glu, $^{167}$Ser-leptin The PPF or PYY Family. Component peptide hormones useful in the present invention also include Pancreatic Polypeptide Family (PPF) peptide hormones, including PYY and chimeras of PPY-NPY. Native PPF peptide hormones are known in art, as are functional peptide analogs and derivatives. Certain exemplary native peptides, peptide analogs and derivatives are described herein, however it should be recognized that any known PYY family peptides that exhibit hormonal activity known in the art may be used in conjunction with the present invention.

Yet another family of peptide hormones implicated in metabolic diseases and disorders is the pancreatic polypeptide family ("PPF"). Pancreatic polypeptide ("PP") was discovered as a contaminant of insulin extracts and was named by its organ of origin rather than functional importance (Kimmel et al., Endocrinology 83: 1323-30 (1968)). PP is a 36-amino acid peptide containing distinctive structural motifs. A related peptide was subsequently discovered in extracts of intestine and named Peptide YY ("PYY") because of the N- and C-terminal tyrosines (Tatemoto, Proc. Natl. Acad. Sci. USA 79: 2514-8 (1982)). A third related peptide was later found in extracts of brain and named Neuropeptide Y ("NPY") (Tatemoto, Proc. Natl. Acad. Sci. USA 79: 5485-9 (1982); Tatemoto et al., Nature 296: 659-60 (1982)).

These three related peptides have been reported to exert various biological effects. Effects of PP include inhibition of pancreatic secretion and relaxation of the gallbladder. Centrally administered PP produces modest increases in feeding that may be mediated by receptors localized to the hypothalamus and brainstem (reviewed in Gehlert, Proc. Soc. Exp. Biol. Med. 218: 7-22 (1998)).

Release of PYY occurs following a meal. An alternate molecular form of PYY is PYY(3-36) (Eberlein et al., Peptides 10: 797-803 (1989); Grandt et al., Regul. Pept. 51: 151-9 (1994)). This fragment constitutes approximately 40% of total PYY-like immunoreactivity in human and canine intestinal extracts and about 36% of total plasma PYY immunoreactivity in a fasting state to slightly over 50% following a meal. It is apparently a dipeptidyl peptidase-IV (DPP4) cleavage product of PYY. PYY(3-36) is reportedly a selective ligand at the Y2 and Y5 receptors, which appear pharmacologically unique in preferring N-terminally truncated (i.e., C-terminal fragments of) NPY analogs. Peripheral administration of PYY reportedly reduces gastric acid secretion, gastric motility, exocrine pancreatic secretion (Yoshinaga et al., Am. J. Physiol. 263: G695-701 (1992); Guan et al., Endocrinology 128: 911-6 (1991); Pappas et al., Gastroenterology 91: 1386-9 (1986)), gallbladder contraction and intestinal motility (Savage et al., Gut 28: 166-70 (1987)). The effects of central injection of PYY on gastric emptying, gastric motility and gastric acid secretion, as seen after direct injection in or around the hindbrain/brainstem (Chen and Rogers, Am. J. Physiol. 269: R787-92 (1995); Chen et al., Regul. Pept. 61: 95-98 (1996); Yang and Tache, Am. J. Physiol. 268: G943-8 (1995); Chen et al., Neurogastroenterol. Motil. 9: 109-16 (1997)), may differ from those effects observed after peripheral injection. For example, centrally administered PYY had some effects opposite to those described herein for peripherally injected PYY(3-36) in that gastric acid secretion was stimulated, not inhibited. Gastric motility was suppressed only in conjunction with TRH stimulation, but not when administered alone, and was indeed stimulatory at higher doses through presumed interaction with PP receptors. PYY has been shown to stimulate food and water intake after central administration (Morley et al., Brain Res. 341: 200-3 (1985); Corp et al., Am. J. Physiol. 259: R317-23 (1990)).

Any PPF analog or derivative known in the art may be used in conjunction with a GIP component in the present invention. In one embodiment, the PPF analogs and derivatives have at least one hormonal activity of a native PPF polypeptide. In certain embodiments, the PPF analogs are agonists of a receptor which native PPF polypeptide is capable of specifically binding. Exemplary PPF analogs and derivatives include those described in WO 03/026591 and WO 03/057235, which are herein incorporated by reference in their entirety.

In one embodiment, preferred PPF analogs and derivatives that exhibit at least one PPF hormonal activity generally comprise at least two PYY motifs including a polyproline motif and C-terminal tail motif. Such analogs are generally described in U.S. Provisional Application No. 60/543,406 filed Feb. 11, 2004, published as US 2006/013547A1 on Jun. 22, 2006, which are herein incorporated by reference. Other preferred PPF analogs are disclosed in PCT/US2005/004351, entitled "Pancreatic Polypeptide Family Motifs and Polypeptides Comprising the Same", published as WO2005/077094 on Aug. 25, 2005, the contents of which are hereby incorporated by reference. Other preferred PPF analogs are disclosed in PCT/US2005/045471, entitled "Pancreatic Polypeptide Family Motifs, Polypeptides and Methods Comprising the Same", published as WO2006/066024 on Jun. 22, 2006, the contents of which are hereby incorporated by reference. By way of background, research has suggested that the differences in Y receptor binding affinities are correlated with secondary and tertiary structural differences. See, e.g., Keire et al, *Biochemistry* 2000, 39, 9935-9942. Native porcine PYY has been characterized as including two C-terminal helical segments from residues 17 to 22 and 25 to 33 separated by a kink at residues 23, 24, and 25, a turn centered around residues 12-14, and the N-terminus folded near residues 30 and 31. Further, full-length porcine PYY has been characterized as including the PP fold, stabilized by hydrophobic interactions among residues in the N- and C-termini. See id.

A "PYY motif" is generally a structural component, primary, secondary, or tertiary, of a native PP family polypeptide that is critical to biological activity, i.e., biological activity is substantially decreased in the absence or disturbance of the motif. Preferred PYY motifs include the N-terminal polyproline type II motif of a native PP family polypeptide, the type II β-turn motif of native PP family polypeptide, the α-helical motif at the C-terminal end of native PP family polypeptide, and the C-terminal tail motif of native PP family polypeptide. More particularly, in the N-terminal polyproline region, amino acids corresponding to residues 5 and 8 of a native PP family polypeptide are generally conserved as a proline. The type III β-turn motif will generally include amino acids corresponding to residues 12-14 of a native PP family polypeptide. The α-helical motif can generally extend from amino acids corresponding to approximately residue 14 of a native PP family polypeptide to any point up to and including the C-terminal end, so long as the α-helical motif includes a sufficient number of amino acid residues such that an α-helical turn is formed in solution. The α-helical motif can also include amino acid substitutions, insertions and deletions to the native PP family sequence, so long as the α-helical turn is still formed in solution. The C-terminal tail motif generally includes amino acids corresponding to approximately the last 10 residues of a native PP family polypeptide, more preferably the last 7, 6, or 5 residues of a native PP family polypeptide, and more preferably amino acid residues 32-35.

Preferred PYY analogs include those with internal deletions, insertions, and substitutions in areas of the PYY molecule not corresponding to the polyproline motif and/or the C-terminal tail motif. For instance, internal deletions at positions 4, 6, 7, 9, or 10 are envisioned.

In another embodiment of particular interest, the component hormone is a PPF polypeptide containing at least two PPF motifs including at least the N-terminal polyproline PPF motif and the C-terminal tail PPF motif. As used herein, "motif" refers to an amino acid sequence that is characteristic of a specific biochemical function or defines an independently folded domain. Additional PPF motifs can correspond to a motif of any of the PP family polypeptides, including PP, PYY and NPY, for example the type II beta-turn region motif of PYY, or the α-helical motif at the C-terminal end of PYY.

In yet another embodiment the PPF family component module is a PPF chimeric polypeptide comprising a fragment of a PP, PYY or NPY polypeptide covalently linked to at least one additional fragment of a second PP, PYY or NPY polypeptide, wherein each PP, PYY or NPY fragment includes a PPF motif. Alternatively, the PPF chimeric can comprise a fragment of a PP family polypeptide linked to one, two, three, or four polypeptides segments, wherein at least one of the linked polypeptide segments is a fragment of a second PP family polypeptide. In certain embodiments, PPF polypeptides do not include an N-terminal PP fragment with a C-terminal NPY fragment. PPF chimeric polypeptide component module will exhibit at least 50% sequence identity to a native PYY(3-36) over the entire length of the PYY(3-36). In some embodiments, such PPF chimeric polypeptide can exhibit at least 60%, at least 70%, at least 80%, at least 90%, at least 92%, at least 94% or at least 97% sequence identity to a native PYY(3-36) over the entire length of the PYY(3-36). Such PPF chimeric polypeptides can exhibit at least 50%, at least 60%, at least 70%, at least 80%, at least 90%, at least 92%, at least 94% or at least 97% sequence identity to a native PP. In yet another embodiment, such PPF chimeric polypeptide can exhibit at least 50%, at least 60%, at least 70%, at least 80%, at least 90%, at least 92%, at least 94% or at least 97% sequence identity to a native NPY. In some embodiments, the PPF chimeric polypeptides can include at least the N-terminal polyproline PPF motif and the C-terminal tail PPF motif. These PPF chimeras as well as other PYY and PP analogs, are described in US 2006/013547A1 published Jun. 22, 2006. In one embodiment, any of the PPF family peptides, if not contained as a hybrid component, can be provided as a second agent, e.g. as a second anti-obesity agent, with a hybrid as described herein.

Again, the PPF chimeric polypeptide will generally retain, at least in part, a biological activity of native human PP, PYY, or NPY. In some embodiments, the PPF chimeric polypeptide exhibits a biological activity in the treatment and prevention of metabolic conditions and disorders.

The polypeptide fragments of the PPF chimeras can be covalently linked together in any manner known in the art, including but not limited to direct amide bonds or chemical linker groups. Chemical linker groups may include peptide mimetics which induce or stabilize polypeptide conformation. PPF chimeric polypeptides include PYY-PP, PYY-NPY, PP-PYY, PP-NPY, NPY-PP, or NPY-PYY chimeras.

The PPF chimera can be at least 21, 22, 23, 24, 25, 26, 27, 28, 29, 30, 31, 32, 33, or 34 amino acids in length. In some embodiments, the PYY analog polypeptides include only natural L amino acid residues and/or modified natural L amino acid residues. In some embodiments, the PYY analog polypeptides do not include unnatural amino acid residues.

In some embodiments, the PPF chimeric polypeptides include: hPP(1-7)-pNPY, hPP(1-17)-pNPY, hPP(19-23)-pNPY, hPP(19-23)-Pro$^{34}$pNPY, hPP(19-23)-His$^{34}$pNPY, rPP(19-23)-pNPY, rPP(19-23)-Pro$^{34}$pNPY, rPP(19-23)-His$^{34}$pNPY, hPP(1-17)-His$^{34}$pNPY, pNPY(1-7)-hPP, pNPY(1-7, 19-23)-hPP, cPP(1-7)-pNPY(19-23)-hPP, cPP(1-7)-NPY(19-23)-His$^{34}$hPP, hPP(1-17)-His$^{34}$pNPY, hPP(19-23)-pNPY, hPP(19-23)-Pro$^{34}$pNPY, pNPY(1-7)-hPP, pNPY(19-23)-hPP, pNPY(19-23)-Gln$^{34}$hPP, pNPY(19-23)-His$^{34}$hPP, pNPY(19-23)-Phe$^6$Gln$^{34}$hPP, pNPY(19-23)-Phe$^6$His$^{34}$hPP, pNPY(1-7,19-23)-hPP, pNPY(1-7,19-23)-Gln$^{34}$hPP, cPP(20-23)-Pro$^{34}$-pNPY, cPP(21-23)-Pro$^{34}$-pNPY, cPP(22-23)-Pro$^{34}$-pNPY, cPP(1-7)-Pro$^{34}$-pNPY, cPP(20-23)-Pro$^{34}$-pNPY, cPP(1-7, 20-23)-Pro$^{34}$-pNPY, cPP(1-7)-pNPY(19-23)-hPP, cPP(1-7)-pNPY(19-23)-His$^{34}$hPP, cPP(1-7)-gPP(19-23)-hPP, cPP(1-7)-pNPY(19-23)-Ala$^{31}$Aib$^{32}$Gln$^{34}$-hPP, cPP(1-7)-pNPY(19-23)-Ala$^{31}$Aib$^{32}$His$^{34}$-hPP, hPP(1-7)-Ala$^{31}$Aib$^{32}$-pNPY, hPP(1-17)-Ala$^{31}$Aib$^{32}$-pNPY, pNPY(1-7)-Ala$^{31}$Aib$^{32}$Gln$^{34}$-hPP, or pNPY(1-7, 19-23)-Ala$^{31}$Aib$^{32}$Gln$^{34}$-hPP.

In some embodiments, the PPF chimeric polypeptides can comprise fragments of PP family analog polypeptides. For instance, the PPF chimeric polypeptides may comprise PPF analog polypeptides described herein, as well as PP analog polypeptides, and NPY analog polypeptides.

PYY analog polypeptide for use in the GIP hybrids of the invention, or administered as a second agent with a GIP hybrid, are those having a potency in one of the assays described herein (including food intake, gastric emptying, pancreatic secretion, body composition or weight reduction assays) which is equal to or greater than the potency of NPY, PYY, or PYY(3-36) in that same assay. In some embodiments, the PPY analog polypeptide for use in a GIP hybrid component may be useful in the treatment of metabolic diseases, such as, for example, obesity, insulin resistance syndrome (Syndrome X) or diabetes mellitus. In some embodiments, the PYY analog polypeptide for use in a GIP hybrid may exhibit improved ease of manufacture, stability, and/or ease of formulation, as compared to PP, NPY, PYY, or PYY (3-36).

In some embodiments, the PPF chimeric polypeptide component portion retains at least about 25%, or from about 30%, about 40%, about 50%, about 60%, about 70%, about 80%, about 90%, about 95%, about 98%, or about 99% percent of the biological activity of native human PYY with regard to the reduction of nutrient availability, the reduction of food intake, the effect of body weight gain, and/or the treatment and prevention of metabolic conditions and disorders. In another embodiment, the PPF chimeric polypeptide for use in a GIP hybrid exhibits improved PYY agonist activity. In some embodiments, the PPF chimeric polypeptides exhibits at least about 110%, about 125%, about 130%, about 140%, about 150%, about 200%, or more of the biological activity of native human PYY with regard to the reduction of nutrient availability the reduction of food intake, the effect of body weight gain, and/or the treatment and prevention of metabolic conditions and disorders.

More particularly, in one aspect, the PPF chimeric polypeptides comprise a fragment of PP linked to a fragment of PYY. In one embodiment, the PPF chimeric polypeptides comprise an N-terminal fragment of PP or a PP analog polypeptide linked at its C-terminal end to a C-terminal fragment of PYY or a PYY analog polypeptide. In another embodiment, the PPF chimeric polypeptides comprise an N-terminal fragment of PYY, PYY(3-36), or a PYY analog polypeptide linked at its C-terminal end to a C-terminal fragment of PP or a PP analog polypeptide.

In some embodiments, the PPF chimeric polypeptides comprise a fragment of PYY linked to a fragment of NPY. In one embodiment, the PPF chimeric polypeptides comprise an N-terminal fragment of PYY, PYY(3-36), or a PYY analog polypeptide linked at its C-terminal end to a C-terminal fragment of NPY or a NPY analog polypeptide. In another embodiment, the PPF chimeric polypeptides comprise an N-terminal fragment of NPY or a NPY analog polypeptide linked at its C-terminal end to a C-terminal fragment of PYY or a PYY analog polypeptide.

In some embodiments, the PPF chimeric polypeptides comprise a fragment of PP linked to a fragment of NPY. In one embodiment, the PPF chimeric polypeptides comprise an N-terminal fragment of PP or a PP analog polypeptide linked at its C-terminal end to a C-terminal fragment of NPY or a NPY analog polypeptide. In another embodiment, the PPF chimeric polypeptides comprise an N-terminal fragment of NPY or a NPY analog polypeptide linked at its C-terminal end to a C-terminal fragment of PP or a PP analog polypeptide.

In some embodiments, a fragment of PP, a PP analog polypeptide, PYY, PYY(3-36), a PYY analog polypeptide, NPY, or an NPY analog polypeptide is a fragment comprising anywhere from 4 to 20 amino acid residues of the PP, PP analog polypeptide, PYY, PYY(3-36), PYY analog polypeptide, NPY, or NPY analog polypeptide. In some embodiments, the length of fragment is selected so as to obtain a final PPF chimeric polypeptide of at least 34 amino acids in length.

The PPF chimeric polypeptides when used in a GIP hybrid may also comprise further modifications including, but are not limited to, substitution, deletion, and insertion to the amino acid sequence of such PPF chimeric polypeptides and any combination thereof. In some embodiments, the PPF chimeric polypeptides include one or more modifications of a "non-essential" amino acid residue. A "non-essential" amino acid residue is a residue that can be altered, i.e., deleted or substituted, in the native human amino acid sequence without abolishing or substantially reducing the activity interest.

Derivatives of the PPF chimeric polypeptides are also useful in a GIP hybrid. Such derivatives include PPF chimeric polypeptides conjugated to one or more water soluble polymer molecules, such as polyethylene glycol ("PEG") or fatty acid chains of various lengths (e.g., stearyl, palmitoyl, octanoyl, oleoyl etc.), or by the addition of polyamino acids, such as poly-his, poly-arg, poly-lys, and poly-ala. Modifications to the PPF chimeric polypeptides can also include small molecule substituents, such as short alkyls and constrained alkyls (e.g., branched, cyclic, fused, adamantyl), and aromatic groups. In some embodiments, the water soluble polymer molecules will have a molecular weight ranging from about 500 to about 20,000 Daltons.

Such polymer-conjugations and small molecule substituent modifications may occur singularly at the N- or C-terminus or at the side chains of amino acid residues, which are not involved in formation of the hybrid, within the sequence of the PPF chimeric polypeptides. Alternatively, there may be multiple sites of derivatization along the PPF chimeric polypeptide. Substitution of one or more amino acids with lysine, aspartic acid, glutamic acid, or cysteine may provide additional sites for derivatization. See, e.g., U.S. Pat. Nos. 5,824,784 and 5,824,778. In some embodiments, the PPF chimeric polypeptides may be conjugated to one, two, or three polymer molecules.

In some embodiments, the water soluble polymer molecules are linked to an amino, carboxyl, or thiol group, and may be linked by N or C terminus, or at the side chains of lysine, aspartic acid, glutamic acid, or cysteine. Alternatively, the water soluble polymer molecules may be linked with diamine and dicarboxylic groups. In some embodiments, the PPF chimeric polypeptides are conjugated to one, two, or three PEG molecules through an epsilon amino group on a lysine amino acid.

PPF chimeric polypeptides also include PPF chimeric polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the PPF chimeric polypeptides. In one embodiment, the C-terminus of these peptides may have a free —OH or —NH$_2$ group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group. In some embodiments, cyclization can be through the formation of disulfide bridges. Alternatively, there may be multiple sites of chemical alteration along the PYY analog polypeptide.

In some embodiments, the PPF chimeric polypeptides include those having an amino acid sequence of SEQ ID NOs. 238-347 of US2006/013547A1.

Exemplary PPF chimeric polypeptides include polypeptides of the Formula (VI):

(SEQ ID NO: 574)
Xaa$_1$ Xaa$_2$ Xaa$_3$ Xaa$_4$ Pro Glu Xaa$_7$ Pro Xaa$_9$ Glu

Asp Xaa$_{12}$ Xaa$_{13}$ Xaa$_{14}$ Glu Xaa$_{16}$ Xaa$_{17}$ Xaa$_{18}$ Xaa$_{19}$

Tyr Xaa$_{21}$ Xaa$_{22}$ Xaa$_{23}$ Leu Xaa$_{25}$ Xaa$_{26}$ Tyr Xaa$_{28}$

Asn Xaa$_{30}$ Xaa$_{31}$ Thr Arg Gln Xaa$_{35}$ Xaa$_{36}$ wherein:
Xaa$_1$ is Tyr or absent;
Xaa$_2$ is Ile, Pro, or absent;
Xaa$_3$ is Ile, BH-modified Lys, Lys, Val, or Pro;
Xaa$_4$ is Lys, BH-modified Lys, Ala, Ser, or Arg;
Xaa$_7$ is Ala, Gly, or His;
Xaa$_9$ is Gly or Ala;
Xaa$_{12}$ is Ala or Pro;
Xaa$_{13}$ is Ser or Pro;
Xaa$_{14}$ is Pro, Ala, or Ser;
Xaa$_{16}$ is Glu or Asp;
Xaa$_{17}$ is Leu or Ile;
Xaa$_{18}$ is Asn or Ala;
Xaa$_{19}$ is Arg, Lys, BH-modified Lys, Gln, or N(Me)Ala;
Xaa$_{21}$ is Tyr, Ala, Phe, Lys or BH-modified Lys;

$Xaa_{22}$ is Ala or Ser;
$Xaa_{23}$ is Ser, Ala, or Asp;
$Xaa_{25}$ is Arg, Lys or BH-modified Lys;
$Xaa_{26}$ is His, Ala, or Arg;
$Xaa_{28}$ is Leu or Ile;
$Xaa_{30}$ is Leu or Met;
$Xaa_{31}$ is Val, Ile, or Leu;
$Xaa_{35}$ is Lys, BH-modified Lys, or Arg; and
$Xaa_{36}$ is Tyr, Trp, or Phe.

In one embodiment the PPF polypeptide of Formula VI can be a native PPF polypeptide, PYY(2-36), Val3hPYY(3-36), Lys25hPYY(3-36), Lys25Ile28hPYY(3-36), Lys25Ile31hPYY(3-36), Lys25Leu31hPYY(3-36), Lys25Phe36hPYY(3-36), Ile28hPYY(3-36), Ile31hPYY(3-36), Leu31hPYY(3-36), Phe36hPYY(3-36), Leu31Phe36hPYY(3-36), or Pro13Ala14hPYY.

As will be recognized by one of skill in the art, the polypeptides of Formula VI may be in the free acid form, or may be C-terminally amidated.

In some embodiments, the PPF polypeptide may comprise an N-terminal fragment consisting essentially of the first 17 amino acid residues of native human PYY (Tyr Pro Ile Lys Pro Glu Ala Pro Gly Glu Asp Ala Ser Pro Glu Glu Leu Asn Arg Tyr Tyr Ala Ser Leu Arg His Tyr Leu Asn Leu Val Thr Arg Gln Arg Tyr) (SEQ ID NO:46) linked to a C-terminal fragment consisting essentially of amino acid residues 18-36 of native human NPY (Tyr Pro Ser Lys Pro Asp Asn Pro Gly Glu Asp Ala Pro Ala Glu Asp Met Ala Arg Tyr Tyr Ser Ala Leu Arg His Tyr Ile Asn Leu Ile Thr Arg Gln Arg Tyr) (SEQ ID NO:577), wherein one or more amino acid residues at the N-terminus of the PYY fragment may be deleted or absent, and wherein one, two, three, four, five, six, seven, eight, nine or ten amino acid substitutions may be made in each of the PYY and NPY fragments. In some embodiments, an N-terminal fragment consisting essentially of the first 17 amino acids of the PPF polypeptide may exhibit at least 50%, at least 60%, at least 70%, at least 80%, at least 90%, at least 92%, at least 94% or at least 97% sequence identity to the first 17 amino acids of a native PYY. In some embodiments, a C-terminal fragment of the PPF polypeptide consisting essentially of amino acid residues 18-36 may exhibit at least 50%, at least 60%, at least 70%, at least 80%, at least 90%, at least 92%, at least 94% or at least 97% sequence identity to amino acids 18-36 of a native NPY. In some embodiments, amino acids in the N-terminal fragment of PYY (e.g., prolines at position 5 and 8, glutamates at positions 6, 10 and 15, or aspartate at position 11), and/or amino acids in the C-terminal fragment of NPY (e.g., tyrosines at positions 20 and 27, leucine at position 24, asparagine at position 29, threonine at position 32, arginine at position 33, or glutamine at position 34) are not substituted. In some embodiments, the PPF polypeptides include those having an amino acid sequence of SEQ ID Nos. 266, 267, 274, 282, 320, and 436 to 480 of US2006/013547A1. In some embodiments, the PPF polypeptides further comprise an N-terminal cap. Examples of these PPF polypeptides include SEQ ID NOs: 282, 320, 437, 441, 444, 445-447, 452, 454-459, 461-464, 466, 468-470 and 472-480 of US2006/013547A1.

Other PPF polypeptides include polypeptides of the Formula (VII):

```
                                              (SEQ ID NO: 575)
Xaa1 Xaa2 Pro Xaa4 Pro Xaa6 His Pro Xaa9 Xaa10

Xaa11 Xaa12 Xaa13 Xaa14 Xaa15 Xaa16 Xaa17 Ala

Xaa19 Tyr Xaa21 Xaa22 Xaa23 Leu Xaa25 Xaa26

Xaa27 Xaa28 Xaa29 Xaa30 Xaa31 Thr Arg Gln Arg Tyr,
``` wherein:
$Xaa_1$ is Tyr or absent;
$Xaa_2$ is Ile, Pro, or absent;
$Xaa_4$ is Lys, BH-modified Lys, Ala, Ser, or Arg;
$Xaa_6$ is Glu, Gln, Ala, Asn, Asp, or Val;
$Xaa_9$ is Gly or Ala;
$Xaa_{10}$ is Glu, Ala, Asp, Asn, Gln, Gly, Pro, or Aib;
$Xaa_{11}$ is Glu, Ala, Asp, Asn, Gln, Gly, Pro, or Aib;
$Xaa_{12}$ is Ala or Pro;
$Xaa_{13}$ is Ser or Pro;
$Xaa_{14}$ is Pro, Ala, or Ser;
$Xaa_{15}$ is Glu, Ala, Asp, Asn, Gln, Gly, Pro, or Aib;
$Xaa_{16}$ is Glu or Asp;
$Xaa_{17}$ is Leu or Ile;
$Xaa_{19}$ is Arg, Lys, BH-modified Lys, Gln, or N(Me)Ala;
$Xaa_{21}$ is Tyr, Ala, Phe, Lys, or BH-modified Lys;
$Xaa_{22}$ is Ala or Ser;
$Xaa_{23}$ is Ser, Ala, or Asp;
$Xaa_{25}$ is Arg, Lys or BH-modified Lys;
$Xaa_{26}$ is His, Ala, or Arg;
$Xaa_{27}$ is Tyr, or Phe;
$Xaa_{28}$ is Leu or Ile;
$Xaa_{29}$ is Asn, or Gln;
$Xaa_{30}$ is Leu or Met; and
$Xaa_{31}$ is Val, Ile, or Leu.

As will be recognized by one of skill in the art, the polypeptides of Formula VII may be in the free acid form, or may be C-terminally amidated, depending on the linkage to the GIP or other peptide family component in a GIP hybrid.

In some embodiments, the PPF polypeptide may comprise an N-terminal fragment consisting essentially of the first 17 amino acid residues of native human PYY (SEQ ID NO: 2 of US2006/013547A1) linked to a C-terminal fragment consisting essentially of amino acid residues 18-36 of native human NPY (SEQ ID NO: 4 of US 2006/013547A1), wherein one or more amino acid residues at the N-terminus of the PYY fragment may be deleted or absent, and wherein one, two, three, four, five, six, seven, eight, nine or ten amino acid substitutions may be made in each of the PYY and NPY fragments. In some embodiments, an N-terminal fragment consisting essentially of the first 17 amino acids of the PPF polypeptide may exhibit at least 50%, at least 60%, at least 70%, at least 80%, at least 90%, at least 92%, at least 94% or at least 97% sequence identity to the first 17 amino acids of a native PYY. In some embodiments, a C-terminal fragment of the PPF polypeptide consisting essentially of amino acid residues 18-36 may exhibit at least 50%, at least 60%, at least 70%, at least 80%, at least 90%, at least 92%, at least 94% or at least 97% sequence identity to amino acids 18-36 of a native NPY. In some embodiments, amino acids in the N-terminal fragment of PYY (e.g., prolines at positions 3, 5 and 8, or histidine 7), and/or amino acids in the C-terminal fragment of NPY (e.g., alanine at position 18, tyrosines at positions 20 and 36, leucine at position 24, threonine at position 32, arginine at position 33, glutamine at position 34, or arginine at position 35) are not substituted. In some embodiments, the PPF polypeptides include those having an amino acid sequence of a PYY-NPY chimera such as SEQ ID Nos. 266, 437, 438, 439, 442, 462, 469, 470, 471 and 472 of US 2006/013547A1, or a PYY-NPY chimera compound with the amino acid sequence Ile, Lys, Pro, Glu, His, Pro, Gly, Glu, Asp, Ala, Ser, Pro, Glu, Glu, Leu, Ala, Arg, Tyr, Tyr, Ala, Ser, Leu, Arg, Ala, Tyr, Ile, Asn, Leu, Ile, Thr, Arg, Gln, Arg, Tyr-NH2 (SEQ ID No. 456). In some embodiments, the PPF polypeptides further comprise an N-terminal cap. Examples of these PPF polypeptides include SEQ ID NOs: 437, 462, 469, 470 and 472 of US 2006/013547A1. For example sequence 438 of US2006/013547A1 is Pro Lys Pro Glu His Pro Gly Glu Asp Ala Ser Pro Glu Glu Leu Ala Arg Tyr Tyr Ala Ser Leu Arg Ala Tyr Ile Asn Leu Ile Thr Arg Gln Arg Tyr (SEQ ID NO:576). In one embodiment, a hybrid of the present invention includes as one component the sequence 438 of US2006/013547A1 or a PYY-NPY chimera with the amino acid sequence Ile, Lys, Pro, Glu, His, Pro, Gly, Glu, Asp, Ala, Ser, Pro, Glu, Glu, Leu, Ala, Arg, Tyr, Tyr, Ala, Ser, Leu, Arg, Ala, Tyr, Ile, Asn, Leu, Ile, Thr, Arg, Gln, Arg, Tyr (SEQ ID No. 456), particularly in GIP hybrids useful to treat obesity, reduce weight, reduce or redistribute fat, and reduce caloric intake. Such a GIP hybrid can also further contain an amylinomimetic component or a leptin component or both.

The GIP hybrids containing a PPF polypeptide or PPF chimera component find use in methods including, altering body composition of a subject, comprising administering to the subject the hybrid wherein the hybrid alters the fat to lean ratio, thereby altering and improving body composition. In one embodiment the PPF polypeptide can comprise an amino acid sequence selected from the group consisting of a PYY-NPY chimera compound with the amino acid sequence Ile, Lys, Pro, Glu, His, Pro, Gly, Glu, Asp, Ala, Ser, Pro, Glu, Glu, Leu, Ala, Arg, Tyr, Tyr, Ala, Ser, Leu, Arg, Ala, Tyr, Ile, Asn, Leu, Ile, Thr, Arg, Gln, Arg, Tyr (SEQ ID No. 456), and of the following sequences from US2006/013547A1: SEQ ID NOs: 266, 267, 274, 282, 320, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479 and 480. In one embodiment body fat is reduced and lean body mass is maintained or increased. In one embodiment the body fat and lean body mass are measured as percent body fat and percent lean body mass, respectively. In one further embodiment body weight is reduced. In another embodiment body weight is maintained or increased. The compounds can be administered peripherally. The PPF polypeptide or PPF chimera or PPF-containing GIP hybrid can be used in a method that further comprises administering to the subject at least one other agent selected from the group consisting of an amylin, amylin agonist or amylin analog agonist, salmon calcitonin, a cholecystokinin (CCK) or CCK agonist, a leptin (OB protein) or leptin agonist, an exendin or exendin analog agonist, a GLP-1, GLP-1 agonist or GLP-1 analog agonist, a CCK or CCK agonist, calcitonin, a calcitonin agonist, a small molecule cannabinoid CB1 receptor antagonist, rimonabant, an 11 beta-hydroxysteroid dehydrogenase-1 inhibitor, sibutramine, and phentermine. In one embodiment the subject is overweight or obese. In yet another embodiment the GIP hybrids containing a PPF polypeptide or PPF chimera component, find use in methods including a method for preferentially lowering plasma triglyceride levels in a subject, comprising administering to the subject an amount of the compound effective to lower plasma triglyceride levels, wherein cholesterol levels are lowered to a lesser extent. In a further embodiment triglyceride levels are lowered and cholesterol levels are not lowered. In a further embodiment triglyceride levels are lowered and LDL cholesterol levels are not lowered. In a further embodiment triglyceride levels are lowered and LDL cholesterol levels are lowered to a lesser extent. In yet a further embodiment amylase levels are also lowered. In yet another embodiment the GIP hybrids containing a PPF polypeptide or PPF chimera find use in methods including a method for reducing body fat or body fat gain in a subject while maintaining or increasing lean body mass, comprising administering to the subject an amount of the compound effective to reduce body fat or body fat gain while maintaining or increasing lean body mass. In another embodiment the GIP hybrid containing a PPF polypeptide or PPF chimera find use in methods including a method of reducing visceral body fat in a subject, comprising administering to the subject an amount of the compound effective to reduce visceral body fat and preserve or increase lean body mass. In another embodiment the GIP hybrid containing a PPF polypeptide or PPF chimera find use in methods including a method to alter fat distribution in the subject. In one aspect, the alteration results from an increased metabolism of visceral or ectopic fat, or both in the subject. In another embodiment the GIP hybrid containing a PPF polypeptide or PPF chimera find use in methods including a method of increasing fatty acid β-oxidation while preserving or increasing lean body mass in a subject comprising administering to the subject an amount of the compound effective to increase fatty acid β-oxidation while preserving or increasing lean body mass. In another embodiment the GIP hybrid containing a PPF polypeptide or PPF chimera find use in methods including a method of treating nonalcoholic steatohepatitis or lipodystrophy in a subject comprising administering to the subject an amount of a compound effective to treat nonalcoholic steatohepatitis or lipodystrophy. GIP hybrids of particular interest in the above uses can contain a PPF chimera as described herein in further combination with a component from the leptin family or the amylin family, such as an amylin-sCT-amylin hybrid, or both. A GIP/PPF-chimera/leptin hybrid or a GIP/PPF-chimera/amylin-sCT-amylin hybrid will provide an effect superior to either parent compound alone. In yet further embodiments a GIP/PPF-chimera/leptin hybrid is administered with an amylinomimetic such as an amylin-sCT-amylin chimera, and alternatively a GIP/PPF-chimera/amylin-sCT-amylin hybrid is administered with a leptin.

Incretins and Incretin Mimetics. Component peptide hormones useful in the present invention also include GLP-1 peptide hormones. Native GLP-1 peptide hormones, including GLP-1(1-37), GLP-1(7-37), and GLP-1(7-36)amide, are known in art, as are functional peptide analogs and derivatives. As used herein, GLP-1 refers to all native forms of GLP-1 peptide hormones. Certain exemplary native peptides, peptide analogs and derivatives are described herein, however it should be recognized that any known GLP-1 peptides that exhibit hormonal activity known in the art may be used in conjunction with the present invention.

Central to many metabolic diseases and disorders is the regulation of insulin levels and blood glucose levels. Insulin secretion is modulated in part by secretagogue hormones, termed as incretins, which are produced by enteroendocrine cells. The incretin hormone, glucagon-like peptide-1 ("GLP-1") is a peptide hormone secreted by intestinal cells that has been shown in multiple studies to produce an enhancing effect on insulin secretion. GLP-1 is processed from proglucagon in the gut and enhances nutrient-induced insulin release (Krcymann B., et al., Lancet, 2:1300-1303 (1987)). Various truncated forms of GLP-1, are known to stimulate insulin secretion (insulinotropic action) and cAMP formation (see, e.g., Mojsov, S., Int. J. Pep. Pro. Res., 40:333-343 (1992)). A relationship between various in vitro laboratory experiments and mammalian, especially human, insulinotropic responses to exogenous administration of GLP-1, GLP-1 (7-36) amide, and GLP-1(7-37) acid has been established (see, e.g., Nauck, M. A., et al., Diabetologia, 36:741-744 (1993); Gutniak, M., et al., New Eng. J. of Med., 326(20):

1316-1322 (1992); Nauck, M. A., et al., J. Clin. Invest., 91:301-307 (1993); and Thorens, B., et al., Diabetes, 42:1219-1225 (1993)).

GLP-1(7-36) amide exerts a pronounced antidiabetogenic effect in insulin-dependent diabetics by stimulating insulin sensitivity and by enhancing glucose-induced insulin release at physiological concentrations (Gutniak M., et al., New Eng. J. Med., 326:1316-1322 (1992)). When administered to non-insulin dependent diabetics, GLP-1(7-36) amide stimulates insulin release, lowers glucagon secretion, inhibits gastric emptying and enhances glucose utilization (Nauck, 1993; Gutniak, 1992; Nauck, 1993). However, the use of GLP-1 type molecules for prolonged therapy of diabetes has been complicated because the serum half-life of such peptides is quite short.

More particularly, GLP-1 is a 30-amino acid peptide derived from proglucagon, a 160-amino acid prohormone. Actions of different prohormone convertases in the pancreas and intestine result in the production of glucagon and other ill-defined peptides, whereas cleavage of proglucagon results in the production of GLP-1 and GLP-2 as well as two other peptides. The amino acid sequence of GLP-1 is 100% homologous in all mammals studied so far, implying a critical physiological role. GLP-1 (7-37) acid is C-terminally truncated and amidated to form GLP-1 (7-36) NH2. The biological effects and metabolic turnover of the free acid GLP-1 (7-37) OH, and the amide, GLP-1 (7-36) NH2, are indistinguishable. By convention, the numbering of the amino acids is based on the processed GLP-1 (1-37) OH from proglucagon. The biologically active GLP-1 is the result of further processing: GLP-1 (7-36) NH2. Thus the first amino acid of GLP-1 (7-37) OH or GLP-1 (7-36)NH2 is 7His.

In the gastrointestinal tract, GLP-1 is produced by L-cells of intestinal, colonic and rectal mucosa, in response to stimulation by intraluminal glucose. The plasma half-life of active GLP-1 is <5 minutes, and its metabolic clearance rate is around 12-13 minutes (Holst, Gastroenterology 107(6):1848-55 (1994)). The major protease involved in the metabolism of GLP-1 is dipeptidyl peptidase (DPP) IV (CD26) which cleaves the N-terminal His-Ala dipeptide, thus producing metabolites, GLP-1 (9-37) OH or GLP-1 (9-36) NH2 which are variously described as inactive, weak agonist or antagonists of GLP-1 receptor. The GLP-1 receptor (GLP-1R) is a G protein coupled receptor of 463 amino acid and is localized in pancreatic beta cells, in the lungs, and to a lesser extent in the brain, adipose tissue and kidneys. The stimulation of GLP-1R by GLP-1 (7-37) OH or GLP-1 (7-36)NH2 results in adenylate cyclase activation, cAMP synthesis, membrane depolarization, rise in intracellular calcium and increase in glucose-induced insulin secretion (Holz et al., J. Biol. Chem. 270(30): 17749-57 (1995)).

GLP-1 is a potent insulin secretagogue that is secreted from the intestinal mucosa in response to food intake. The profound incretin effect of GLP-1 is underscored by the fact that GLP-1R knockout mice are glucose-intolerant. The incretin response of i.v. infused GLP-1 is preserved in diabetic subjects, though the incretin response to oral glucose in these patients is compromised. GLP-1 administration by infusion or sc injections controls fasting glucose levels in diabetic patients, and maintains the glucose threshold for insulin secretion (Gutniak et al., N. Engl. J. Med. 326:1316-22 (1992); Nauck et al., Diabet. Med. 13:(9 Suppl 5):S39-S43 (1996); Nauck et al., J. Clin. Endocrinol. Metab. 76:912-917 (1993)). GLP-1 has shown tremendous potential as a therapeutic agent capable of augmenting insulin secretion in a physiological manner, while avoiding hypoglycemia associated with sulfonylurea drugs.

Other important effects of GLP-1 on glucose homeostasis are suppression of glucagon secretion and inhibition of gastric motility. GLP-1 inhibitory actions on pancreatic alpha cell secretion of glucagon leads to decreases in hepatic glucose production via reduction in gluconeogenesis and glycogenolysis. This antiglucagon effect of GLP-1 is preserved in diabetic patients.

The so-called ileal brake effect of GLP-1, in which gastric motility and gastric secretion are inhibited, is effected via vagal efferent receptors or by direct action on intestinal smooth muscle. Reduction of gastric acid secretion by GLP-1 contributes to a lag phase in nutrient availability, thus obviating the need for rapid insulin response. In summary, the gastrointestinal effects of GLP-1 contribute significantly to delayed glucose and fatty acid absorption and modulate insulin secretion and glucose homeostasis.

GLP-1 has also been shown to induce beta cell specific genes, such as GLUT-1 transporter, insulin (via the interaction of PDX-1 with insulin gene promoter), and hexokinase-1. Thus GLP-1 could potentially reverse glucose intolerance normally associated with aging, as demonstrated by rodent experiments. In addition, GLP-1 may contribute to beta cell neogenesis and increase beta cell mass, in addition to restoring beta cell function during states of beta cell insufficiency.

Central effects of GLP-1 include increases in satiety coupled with decreases in food intake, effected via the action of hypothalamic GLP-1R. A 48 hour continuous SC infusion of GLP-1 in type II diabetic subjects, decreased hunger and food intake and increased satiety. These anorectic effects were absent in GLP-1R knock out mice.

Thus a GIP hybrid comprising an incretin family hormone module can provide the functions and uses associated with the incretin family module, e.g. exendin-4, GLP1, GLP2, as discussed, in addition to having a GIP function.

Any GLP-1 peptide analog or derivative known in the art may be used in conjunction with the present invention. In one embodiment, the GLP-1 peptide analogs and derivatives have at least one hormonal activity of a native GLP-1 peptide. In certain embodiments, the GLP-1 peptide analogs are agonists of a receptor which a native GLP-1 peptide is capable of specifically binding. Exemplary GLP-1 peptide analogs and derivatives include those described in, e.g., WO 91/11457, which is hereby incorporated by reference.

GLP-1 analogs known in the art include:

$^9$Gln-GLP-1 (7-37)
D-$^9$Gln-GLP-1 (7-37)
$^{16}$Thr-$^{18}$Lys-GLP-1 (7-37)
$^{18}$Lys-GLP-1 (7-37)
$^8$Gly-GLP-1 (7-36)
$^9$Gln-GLP-1 (7-37)
D-$^9$Gln-GLP-1 (7-37)
acetyl-$^9$Lys-GLP-1 (7-37)
$^9$Thr-GLP-1 (7-37)
D-$^9$Thr-GLP-1 (7-37)
$^9$Asn-GLP-1 (7-37)
D-$^9$Asn-GLP-1 (7-37)
$^{22}$Ser$^{23}$Arg$^{24}$Arg$^{26}$Gln-GLP-1 (7-37)
$^{16}$Thr$^{18}$Lys-GLP-1 (7-37)
$^{18}$Lys-GLP-1 (7-37)
$^{23}$Arg-GLP-1 (7-37)
$^{24}$Arg-GLP-1 (7-37)

As known in the art, such GLP-1 analogs may preferably be amidated, but within the context of the present invention, may optionally be in the acid form unless otherwise specified.

Other GLP-1 analogs and derivatives are disclosed in U.S. Pat. No. 5,545,618 which is incorporated herein by reference.

A exemplary group of GLP-1 analogs and derivatives include those disclosed in U.S. Pat. No. 6,747,006, which is herein incorporated by reference in its entirety. The use in the present invention of a molecule described in U.S. Pat. No. 5,188,666, which is expressly incorporated by reference, is also contemplated. Another group of molecules for use in the present invention includes compounds described in U.S. Pat. No. 5,512,549, which is expressly incorporated herein by reference. Another exemplary group of GLP-1 compounds for use in the present invention is disclosed in WO 91/11457, which is herein incorporated by reference.

In another embodiment useful with GIP or novel GIP analogs are GLP1 analogs with Trp-Cage tails (e.g. exendin C-terminal sequence with or without the tryptophan (or similar residue) (which can be optionally provided as described, e.g. by the presence of a tryptophan advantageously located in the hormone that is either naturally occurring, added as a substitution or as part of a linker.). These include:

```
                                            (SEQ ID NO: 74)
GLP1(7-26)Gly8Ex-4(21-39):
HGEGTFTSDVSSYLEGQAAKLFIEWLKNGG PSSGAPPPS-NH2;

(SEQ ID NO: 75)
GLP1(7-33)(G8, E30, K33)[Ex-4(28-39)]:
HGEGTFTSDVSSYLEGQAAKEFIEWLKNGGPSSGAPPPS-NH2;

(SEQ ID NO: 76)
GLP1(7-33)(G8, K33)[EX4(28-39)]:
HGEGTFTSDVSSYLEGQAAKEFIAWLKNGGPSSGAPPPS-NH2;

(SEQ ID NO: 77)
GLP1(7-33)G8[Ex-4(28-39)]:
HGEGTFTSDVSSYLEGQAAKEFIAWLVNGGPSSGAPPPS-NH2;
and (SEQ ID NO: 78)
GLP1(7-35)G8[Ex-4(30-39)]:
HGEGTFTSDVSSYLEGQAAKEFIAWLVKGGPSSGAPPPS-NH2.
```

Component peptide hormones useful in the GIP hybrids of the present invention also include GLP-2 peptide hormones. Native GLP-2 peptide hormones, e.g., rat GLP-2 and its homologous including ox GLP-2, porcine GLP-2, degu GLP-2, bovine GLP-2, guinea pig GLP-2, hamster GLP-2, human GLP-2, rainbow trout GLP-2, and chicken GLP-2, are known in art, as are functional peptide analogs and derivatives. Certain exemplary native peptides, peptide analogs and derivatives are described herein, however it should be recognized that any known GLP-2 peptides that exhibit hormonal activity known in the art may be used in conjunction with the present invention.

Any GLP-2 peptide analog or derivative known in the art may be used in conjunction with the present invention. In one embodiment, the GLP-2 peptide analogs and derivatives have at least one hormonal activity of a native GLP-2 peptide. In certain embodiments, the GLP-2 peptide analogs are agonists of a receptor which a native GLP-2 peptide is capable of specifically binding. Exemplary GLP-2 peptide analogs and derivatives include those described in, e.g., U.S. Ser. No. 08/669,791 and PCT Application PCT/CA97/00252, both of which are hereby incorporated by reference. Specific GLP-2 analogs known in the art include: rat or human GLP-2 altered at position 2 to confer DPP-IV resistance by substituting a Gly for an Ala.

Component peptide hormones useful in the present invention also include oxyntomodulin (OXM) peptide hormones. Native OXM peptide hormones are known in art, as are functional peptide analogs and derivatives. Certain exemplary native peptides, peptide analogs and derivatives are described herein, however it should be recognized that any known OXM peptides that exhibit hormonal activity known in the art may be used in conjunction with the present invention.

Any OXM peptide analog or derivative known in the art may be used in conjunction with the present invention. In one embodiment, the OXM peptide analogs and derivatives have at least one hormonal activity of a native OXM peptide. In certain embodiments, the OXM peptide analogs are agonists of a receptor which a native OXM peptide is capable of specifically binding.

Component peptide hormones useful in the present invention also include exendin peptide hormones. Native exendin peptide hormones are known in art, as are functional peptide analogs and derivatives. Certain exemplary native peptides, peptide analogs and derivatives are described herein, however it should be recognized that any known exendin peptides that exhibit hormonal activity known in the art may be used in conjunction with the present invention.

Exendins are another family of peptides implicated in insulin secretion. Exendins are found in the saliva of the Gila-monster, a lizard endogenous to Arizona, and the Mexican Beaded Lizard. Exendin-3 is present in the saliva of *Heloderma horridum*, and exendin-4 is present in the saliva of *Heloderma suspectum* (Eng, J., et al., J. Biol. Chem., 265: 20259-62, 1990; Eng., J., et al., J. Biol. Chem., 267:7402-05 (1992)). The exendins have some sequence similarity to several members of the glucagon-like peptide family, with the highest identity, 53%, being to GLP-1 (Goke, et al., J. Biol. Chem., 268:19650-55 (1993)).

Exendin-4 binds the GLP-1 receptors on insulin-secreting TC1 cells, at dispersed acinar cells from guinea pig pancreas, and at parietal cells from stomach; the peptide also stimulates somatostatin release and inhibits gastrin release in isolated stomachs (Goke, et al., J. Biol. Chem., 268:19650-55 (1993); Schepp, et al., Eur. J. Pharmacol., 69:183-91 (1994); Eissele, et al., Life Sci., 55:629-34 (1994)). Exendin-3 and exendin-4 were found to bind the GLP-1 receptors on, to stimulating cAMP production in, and amylase release from, pancreatic acinar cells (Malhotra, R., et al., Relulatory Peptides, 41:149-56 (1992); Raufman, et al., J. Biol. Chem., 267:21432-37 (1992); Singh, et al., Regul. Pept., 53:47-59 (1994)). The use of the insulinotropic activities of exendin-3 and exendin-4 for the treatment of diabetes mellitus and the prevention of hyperglycemia has been proposed (Eng, U.S. Pat. No. 5,424,286).

Truncated exendin peptides such as exendin[9-39], a carboxyamidated molecule, and fragments 3-39 through 9-39 have been reported to be potent and selective antagonists of GLP-1 (Goke, et al., J. Biol. Chem., 268:19650-55 (1993); Raufman, J. P., et al., J. Biol. Chem., 266:2897-902 (1991); Schepp, W., et al., Eur. J. Pharm., 269:183-91 (1994); Montrose-Rafizadeh, et al., Diabetes, 45(Suppl. 2):152A (1996)). Exendin[9-39] blocks endogenous GLP-1 in vivo, resulting in reduced insulin secretion (Wang, et al., J. Clin. Invest., 95:417-21 (1995); D'Alessio, et al., J. Clin. Invest., 97:133-38 (1996)). The receptor apparently responsible for the insulinotropic effect of GLP-1 has been cloned from rat pancreatic islet cells (Thorens, B., Proc. Natl. Acad. Sci. USA 89:8641-8645 (1992)). Exendins and exendin[9-39] bind to the cloned GLP-1 receptor (rat pancreatic-cell GLP-1 receptor: Fehmann H C, et al., Peptides, 15 (3): 453-6 (1994); human GLP-1 receptor: Thorens B, et al., Diabetes, 42 (11): 1678-82 (1993)). In cells transfected with the cloned GLP-1 receptor, exendin-4 is an agonist, i.e., it increases cAMP, while exendin [9-39] is an antagonist, i.e., it blocks the stimulatory actions of exendin-4 and GLP-1. Id.

More particularly, exendin-4 is a 39 amino acid C-terminal amidated peptide found in the saliva of the Gila Monster (*Heloderma suspectum*), with a 53% amino acid sequence identity to the GLP-1 peptide sequence. See, e.g., Eng, J., et al. "Isolation and Characterization of Exendin-4, and Exendin-3 Analogue from *Heloderma suspectum* Venom," J. Bio. Chem., 267:11, p. 7402-7405 (1992), Young, A. A., et al., "Glucose-Lowering and Insulin-Sensitizing Actions of Exendin-4," Diabetes, Vol. 48, p. 1026-1034, May, 1999. In terms of its activity, exendin-4 is a highly specific agonist for the GLP-1 receptor, and, like GLP-1, is able to stimulate insulin secretion. Therefore, like GLP-1, exendin-4 is regarded as an insulinotropic peptide.

However, unlike GLP-1, exendin-4 has a relatively long half-life in humans, because of its resistance to the dipeptidyl peptidase IV which rapidly degrades the GLP-1 sequence in vivo. Furthermore, it has been shown that, as compared to GLP-1, exendin-4 has a stronger capability to stimulate insulin secretion, and that a lower concentration of exendin-4 may be used to obtain such stimulating activity. See, e.g., U.S. Pat. No. 5,424,286, herein incorporated by reference. Therefore exendin-4 peptides or derivatives thereof (for examples of such derivatives, see, e.g., U.S. Pat. No. 6,528,486, herein incorporated by reference, and its corresponding international application WO 01/04156) have a greater potential utility for the treatment of conditions involving the dysregulation of insulin levels (e.g., conditions such as diabetes) than either insulin or GLP-1. Thus a GIP hybrid comprising an exendin family hormone module can provide the functions and uses associated with the exendin family module, e.g. exendin-4, exendin tail, as discussed, in addition to having a GIP function.

Any exendin peptide analog or derivative known in the art may be used in conjunction with the present invention. In one embodiment, the exendin peptide analogs and derivatives have at least one hormonal activity of a native exendin peptide. In certain embodiments, the exendin peptide analogs are agonists of a receptor which a native exendin peptide is capable of specifically binding.

Exemplary exendin analogs include:

---
$^{14}$Leu, $^{25}$Phe-exendin-4
$^{5}$Ala, $^{14}$Leu, $^{25}$Phe-exendin-4
$^{14}$Leu, $^{22}$Ala, $^{25}$Phe-exendin-4
---

As known in the art, such exendin analogs are preferably amidated, but within the context of the present invention, may optionally be in the acid form unless otherwise specified.

Additional exemplary exendin analogs and derivatives are described in PCT Application Ser. No. PCT/US98/16387 filed Aug. 6, 1998, entitled "Novel Exendin Agonist Compounds," which claims the benefit of U.S. patent application Ser. No. 60/055,404, filed Aug. 8, 1997, both of which are herein incorporated by reference. Other exendin analogs and derivatives are described in PCT Application Ser. No. PCT/US98/24210, filed Nov. 13, 1998, entitled "Novel Exendin Agonist Compounds," which claims the benefit of U.S. Provisional Application No. 60/065,442 filed Nov. 14, 1997, both of which are herein incorporated by reference. Still other exendin analogs and derivatives are described in PCT Application Ser. No. PCT/US98/24273, filed Nov. 13, 1998, entitled "Novel Exendin Agonist Compounds," which claims the benefit of U.S. Provisional Application No. 60/066,029 filed Nov. 14, 1997, both of which are herein incorporated by reference. Still other exendin analogs and derivatives are described in PCT Application Ser. No. PCT/US97/14199, filed Aug. 8, 1997, entitled "Methods for Regulating Gastrointestinal Activity," which is a continuation-in-part of U.S. patent application Ser. No. 08/694,954 filed Aug. 8, 1996, both of which are hereby incorporated by reference. Still other exendin analogs and derivatives are described in PCT Application Ser. No. PCT/US98/00449, filed Jan. 7, 1998, entitled "Use of Exendins and Agonists Thereof for the Reduction of Food Intake," which claims priority to U.S. Provisional Application No. 60/034,905 filed Jan. 7, 1997, both of which are hereby incorporated by reference. Yet other exendin analogs and derivatives are described in US 2004/0209803 A1, filed Dec. 19, 2003, entitled "Compositions for the Treatment and Prevention of Neuropathy," which is hereby incorporated by reference.

Catestatin Family. The catestatin fragment of chromogranin A is an endogenous inhibitor of nicotinic cholinergic transmission, functioning in negative feedback control of catecholamine secretion. We explored naturally occurring polymorphisms in the amino acid sequence of catestatin. Three human variants were identified: Gly364Ser, Pro370Leu, and Arg374Gln.

Sequence variants in human catestatin (human chromogranin A352-372) and interspecies homologies in humans and other mammals are shown below. Amino acids at positions variant in human catestatin are shown in bold type. The typical dibasic proteolytic cleavage site at the carboxy-terminal side of catestatin is given in brackets, [RR]. For human chromogranin A, this [RR] site is Arg373Arg374. In further embodiments, variants absent either or both arginines are included. GIP hybrids containing catestatin family members, analogs, derivatives or fragments thereof, find use in the treatment methods of the invention. For example, such hybrids will find use in treating cardiovascular diseases and conditions as discussed herein, including hypertension and congestive heart failure and related conditions. Combined with an active GIP hormone module, the compounds will find use in the critical care conditions described herein. Catestatin species variants include:

| | | (SEQ ID NO: 79) |
|---|---|---|
| Mouse | RSMRLSFRTRGYGFRDPGLQL[RR] | CGA364-384 |
| | | (SEQ ID NO: 80) |
| Rat | RSMRLSFRARGYGFRDPGLQL[RR] | CGA367-387 |
| | | (SEQ ID NO: 81) |
| Cow | RSMRLSFRARGYGFRGPGLQL[RR] | CGA344-364 |
| | | (SEQ ID NO: 82) |
| Pig | RSMRLSFRAPAYGFRGPGLQL[RR] | CGA343-363 |
| | | (SEQ ID NO: 83) |
| Horse | RSMKLSFRARAYGFRGPGLQL[RR] | CGA343-363 |
| | | (SEQ ID NO: 84) |
| Chimp | SSMKLSFRARAYGFRGPGPQL[RR] | CGA354-374 |
| Human: | | |
| | | (SEQ ID NO: 85) |
| Wild-type | SSMKLSFRARAYGFRGPGPQL[RR] | CGA352-372 |
| | | (SEQ ID NO: 86) |
| Variant | SSMKLSFRARAYSFRGPGPQL[RR] | |
| | | (SEQ ID NO: 87) |
| Variant | SSMKLSFRARAYGFRGPGLQL[RR] | |
| | | (SEQ ID NO: 88) |
| Variant | SSMKLSFRARAYGFRGPGPQL[RQ] | |

Natriuretic Peptides. Natriuretic peptides are a family of hormones that consist of atrial natriuretic peptide (ANP), brain natriuretic peptide (BNP), and C-type natriuretic peptide (CNP). They are synthesized and stored as 3 distinct precursor prohormones, which are the 126 amino acid ANP, 108 amino acid BNP, and 104 amino acid CNP. They are each encoded by separate genes and have distinct sites of synthesis and mechanisms of regulation. Parental natriuretic peptide sequences include:

| SEQ ID No: | Description | Sequence |
|---|---|---|
| 89 | 151 amino acid human ANP prepro- hormone | MSSFSTTTVSFLLLLAFQLLGQTRANPMYNAVS NADLMDFKNLLDHLEEKMPLEDEVVPPQVLSD PNEEAGAALSPLPEVPPWTGEVSPAQRDGGALG RGPWDSSDRSALLKSKLRALLTAPRSLRRSSCFG GRMDRIGAQSGLGCNSFRY |
| 90 | 134 amino acid human BNP prepro- hormone | MDPQTAPSRALLLLLFLHLAFLGGRSHPLGSPGS ASDLETSGLQEQRNHLQGKLSELQVEQTSLEPL QESPRPTGVWKSREVATEGIRGHRKMVLYTLRA PRSPKMVQGSGCFGRKMDRISSSSGLGCKVLRR H |
| 91 | 126 amino acid human CNP preproCNP | MHLSQLLACALLLTLLSLRPSEAKPGAPPKVPRT PPAEELAEPQAAGGGQKGDKAPGGGGANLKG DRSRLLRDLRVDTKSRAAWARLLQEHPNARKY KGANKKGLSKGCFGLKLDRIGSMSGLGC |

The main site of synthesis of the ANP prohormone is the atrial myocyte where it is synthesized as a 151-amino acid preprohormone. Removal of a 25-amino acid signal peptide from its N terminal end occurs in the endoplasmic reticulum, leaving a 126-amino acid ANP prohormone (ProANP), the main storage form of ANP within the heart. The prohormone consists of 4 biologically active peptide segments: amino acids 1-30 (ProANF 1-30, also known as long acting Na stimulator), 31-67 (ProANF 31-67, also known as vessel dilator), 79-98 (ProANF 79-98, also known as potassium excreter), and 99-126 (ANF, also known as atrial natriuretic factor).

BNP was originally isolated from porcine brain but in humans it is synthesized and secreted from the left ventricle. Sequence analysis reveals that preproBNP consists of 134 residues and is cleaved to a 108-amino acid ProBNP. Cleavage of a 32-amino acid sequence from the C-terminal end of ProBNP results in human BNP (77-108), which is the physiologically active form in plasma.

CNP is the third member of the natriuretic peptide system and is primarily found in human vascular endothelial cells, kidney, and porcine brain. High concentrations of CNP are also found in human hypothalamus and midbrain. In humans, preproCNP is a 126-amino acid precursor processed into proCNP by cleavage of 23 residues from its N-terminal end. This 23-amino acid sequence serves as a signal peptide. The terminal 22 (105-126) amino acids are cleaved from proCNP to yield a biologically active form of CNP.

Urodilatin is a kidney-derived member of the natriuretic peptide family and is formed from the same ANP prohormone and consists of amino acids 95-126. Except for the 4 amino acid N terminal extension, it is identical to ANF (99-126). Urodilatin appears to be an important regulator of sodium and water handling in the kidney, as well as a mediator of sodium excretion in patients with congestive heart failure (CHF).

Natriuretic peptides exert their biologic effects by binding to high-affinity receptors on the surface of target cells. Three subtypes of NPRs—NPR-A, NPR-B, and NPRC—have been isolated. Consequently, in one embodiment is provided a method to screen hybrids for natriuretic receptor binding and/or activation. Natriuretic peptides including prohormone variants can impart numerous natriuretic peptide hormone activities to hybrids of the invention. In other embodiments of interest are natriuretic antagonist hybrids. Natriuresis is the excretion of an excessively large amount of sodium into the urine. Natriuresis is similar to diuresis (the excretion of an unusually large quantity of urine), except that in natriuresis the urine is exceptionally salty. Natriuresis occurs with some diuretics and diseases (as of the adrenal) and can lead to the salt-losing syndrome characterized by dehydration, vomiting, low blood pressure, and the risk of sudden death. Exogenous administration of the 4 independent circulating peptides of the ANP prohormone (1-30, 31-67, 79-98, and 99-126) produce in vivo vasodilation, diuresis, suppression of the renin-angiotensin-aldosterone system and enhanced natriuresis and/or kaliuresis. ProANF 1-30, ProANF 31-67 and ANF 99-126 each have natriuretic, blood pressure lowering and diuretic properties with ProANF 31-67 and ANF 99-126 having the greatest impact on blood pressure. There are varying effects of the ANP peptides on potassium homeostasis: ProANF 79-98 stimulates potassium excretion, whereas ProANF 31-67 spares potassium loss by inhibiting Na/K ATPase in the medullary collecting duct cells. Specific to ANF 99-126 is a dose-dependent inhibition of angiotensin II-mediated aldosterone secretion, whereas proANF 31-67 has the property of inducing natriuresis through generation of prostaglandin.

BNP produces similar biologic effects as ANF in normal humans. Infusions of BNP in normal men produced a 2-fold increase in sodium excretion, 50% reduction in plasma renin, angiotensin II and aldosterone secretion as well as a reduction in plasma volume.

CNP induces cardiovascular effects similar to the other natriuretic peptides but does not appear to mediate any renal effects. When CNP is infused in anesthetized dogs at equivalent doses of ANF, plasma cGMP rose with a concomitant reduction in mean arterial pressure, right atrial pressure and cardiac output, but glomerular filtration rate, renal blood flow and sodium excretion decreased.

Natriuretic peptides can provide therapeutic benefit in heart failure. Congestive heart failure (CHF) is associated with increases in vasopressin, endothelin, and with activation of the renin-angiotensin-aldosterone system, and sympathetic nervous systems, mediating vasoconstriction, sodium and water retention, and negative vascular and cardiac remodeling. These effects occur despite the elevated levels of the natriuretic peptides in patients with heart failure. In one embodiment of the invention are hybrids that provide increased or therapeutic serum levels of natriuretic peptide activity for treatment or prevention of cardiac related diseases and conditions, including CHF. Although ANF infusion in normal individuals can result in a sustained increase in sodium excretion and urine flow rates, in the heart failure patient a marked beneficial reduction in renal response can be obtained. BNP infusion markedly increases sodium excretion in patients with heart failure and exerts significant beneficial hemodynamic effects. As compared with ANP, the diuretic and natriuretic effects of BNP are significantly greater. BNP is cleared more slowly than ANP and exerts other effects including suppressing aldosterone secretion and increasing serum levels of ANP. BNP peptides can also provide a beneficial decrease in pulmonary capillary wedge pressure, systemic vascular resistance, right atrial pressure and systolic blood pressure, with an increase in cardiac index in patients hospitalized for symptomatic CHF. In patients with decompensated heart failure, natriuretic peptide hybrids can provide a beneficial decrease in pulmonary capillary wedge pressure and an improved dyspnea score. (Dyspnea is an unpleasant sensation of difficulty in breathing, typically associated with early stages of cardiac heart failure.) The hybrids containing one, two or three natriuretic hormone functions provide methods of administration of pharmaceutically active compositions that are useful for both the prophylactic and therapeutic treatment of CHF patients, preferably CHF patients that are decompensated, patients with chronic CHF, and patients with hypertension. The natriuretic portion(s) of a hybrid is sufficient to provide a therapeutically effective amount of a natriurertic peptide to such patient when administered in a therapeutically effective dose over a therapeutically effective period.

As discussed herein any of the family of therapeutically effective natriuretic peptides or their analogs can be used as a component of a GIP hybrid. Useful natriuretic peptides include, for example, atrial natriuretic peptide (ANP), brain natriuretic peptide (BNP or B-type natriuretic peptide) and C-type natriuretic peptide (CNP). Sequences of useful forms of natriuretic peptides are disclosed in U.S. Patent Publication 20010027181, which is incorporated herein by reference. Examples of ANPs include human ANP (Kangawa et al., BBRC 118:131 (1984)) or that from various species, including pig and rat ANP (Kangawa et al., BBRC 121:585 (1984)). Such ANPs comprise 28 amino acids. Such ANPs may be administered as a peptide having a ring structure of ANP (formation of a disulfide bond based on Cys), and a C-terminal portion succeeding the ring structure. An example of such a peptide is a peptide having amino acid residues at the 7-position to the 28-position of ANP is provided in U.S. Patent Application Publication No. 20010027181. Another example is frog ANP. Specific examples of BNPs that can be used in the methods of the invention include human BNP (hBNP). Human BNP comprises 32 amino acids and involves the formation of a disulfide bond (Sudoh et al., BBRC 159: 1420 (1989)) and U.S. Pat. Nos. 5,114,923, 5,674,710, 5,674, 710, and 5,948,761, each of which is incorporated by reference. Various BNP's of origin other than human, including as pig BNP and rat BNP, are also known, and can be used. A further example is chicken BNP. Examples of CNPs that can be used in the methods of the invention include pig CNP. Pig CNP comprises 22 amino acids and involves the formation of a disulfide bond, like the above-described ANP and BNP (Sudoh et al., BBRC 168:863 (1990)) (human and rat have the same amino acid sequence), chicken CNP (Arimura et al., BBRC 174:142 (1991)). Frog CNP (Yoshihara et al., BBRC 173:591 (1990) can also be used. As discussed herein, one skilled in the art can apply modifications, such as a deletion, substitution, addition or insertion, and/or chemical modification to amino acid residues in the amino acid sequence of a known natriuretic peptide as desired, by known methods. The resulting compound has the activity of acting on a receptor of the starting ANP, BNP or CNP. Analogs having this activity, therefore, are included in the hybrids for use in accordance with the methods of the present invention.

In another embodiment, the hybrids containing one or more natriuretic functions can be used in treating hypertension. In one embodiment a natriuretic hybrid will have no deleterious effect on heart rate and is not associated with arrhythmias. In one embodiment the hybrid will comprise at least one, two or three natriuretic peptide functions, for example, both ANP and BNP activity. One or more natriuretic hormone functions can be combined with any other hormone function or peptidic enhancer, as described herein. In another embodiment the natriuretic portion(s) is a more stable analog having an extended in vivo half-life when compared with that of a native natriuretic peptide. Analogs that prevent undesirable cleavage by endogenous enzymes such as NEP are also envisioned. The natriuretic containing hybrids are also further directed to hypertension reduction, diuresis inducement, natriuresis inducement, vascular conduct dilatation or relaxation, natriuretic peptide receptors (such as NPR-A) binding, renin secretion suppression from the kidney, aldostrerone secretion suppression from the adrenal gland, treatment of cardiovascular diseases and disorders, reducing, stopping or reversing cardiac remodeling in congestive heart failure, treatment of renal diseases and disorders; treatment or prevention of ischemic stroke, and treatment of asthma. Hybrids can be administered to patients that would benefit from inducing natriuresis, diuresis and vasodilatation. Hybrids can be administered alone or in combination with one or more of the following types of compounds: ACE inhibitors, beta-blockers, diuretics, spironolactone, digoxin, anticoagulation and antiplatelet agents, and angiotensin receptor blockers. Additional diseases or conditions include renal disorders and diseases, asthma, hypertension and pulmonary hypertension. Hybrids are also useful to treat inflammatory-related diseases, erectile dysfunction and hypercholesterolemia.

Peptide Module Selection Considerations Spacers and Linking Groups.

The GIP hybrid polypeptides of the present invention generally comprise at least two bio-active peptide hormone modules of the invention, wherein at least one of the bio-active peptide hormone modules, typically a GIP module, exhibits at least one hormonal activity. Within the context of the present invention, at least one of the bio-active peptide hormone modules will be comprised from a GIP peptide hormone, analog, derivative, fragment, or peptidic enhancer. The bio-active peptide hormone module that exhibits the at least one hormonal activity may be located at the N-terminal end of the hybrid polypeptide, the C-terminal end of the hybrid polypeptide, or in the event that the hybrid polypeptide comprises more than two bio-active peptide hormone modules, may be located in the internal portion of the hybrid polypeptide.

In certain embodiments, it may be preferable to locate the bio-active peptide hormone module exhibiting the at least one hormonal activity such that the C-terminal end of the bio-active peptide hormone module is amidated. Amidation of the C-terminal end of the bio-active peptide hormone module may be accomplished by locating the module at the C-terminal end of the hybrid peptide, or by configuring the module in the C-terminal-to-N-terminal direction at the N-terminal end of the hybrid polypeptide. In both configurations, the C-terminal end of the bio-active peptide hormone module is available for amidation. Specific component peptide hormones where C-terminal amidation may preferably include amylin family peptide hormones, CCK, PYY, hGLP-1(7-36) and hGLP-2. Specific component peptide hormones where C-terminal amidation is not necessarily exemplary (stated otherwise, where elongation at the C-terminal end of the module is easily tolerated) include exendin-4, exendin-4(1-28), GIP, GLP-1(7-37), frog GLP-1(7-36), and frog GLP-2. However, if these component peptide hormones are located at the C-terminal end of the hybrid polypeptide, they may still be optionally amidated, and in fact may preferably be optionally amidated.

The bio-active peptide hormone modules may be covalently linked in any manner known in the art. Stable linkages may be used, or cleavable linkage may be used. In one embodiment, the carboxy of a first module may be directly linked to the amino of a second module. In another embodiment, linking groups may be used to attached modules. Further, if desired, spacers or turn inducers known in the art may be employed to stabilize the linkage. By way of example, where amidation of the C-terminal end of the N-terminally located bio-active peptide hormone module is not desired, the module may be attached to a second module directly, or using any appropriate linking group known in the art, such as, an alkyl; PEG; amino acid, e.g., Lys, Glu, beta-Ala; polyaminoacids, e.g., poly-his, poly-arg, poly-lys, poly-ala, Gly-Lys-Arg (GKR) etc.; bifunctional linker (see, e.g., Pierce catalog, Rockford, Ill.); aminocaproyl ("Aca"), beta-alanyl, 8-amino-3,6-dioxaoctanoyl, or other cleavable and non-cleavable linker known in the art. Specifically described herein, as if each were explicitly drawn, are embodiments of specific hybrids in which the linker in each exemplified linker-containing hybrid is replaced by a Gly linker, particularly embodiments where the Gly linker is Gly-Gly-Gly. As an example, for exemplified YAEGTFISDYSIAMD-KIRQQDFVNWLLAQK-Linker-KCNTATCV-LGRLSQELHRLQTYPRTNTGSETF (SEQ ID NO: 92) (see tables herein) its Gly linker species analog is also specifically intended and disclosed: this species is YAEGTFIS-DYSIAMDKIRQQDFVNWLLAQK-Gly-Gly-Gly-KCN-TATCVLGRLSQELHRLQTYPRTNTGSETF (SEQ ID NO: 92). In one embodiment a linker or spacer is 1 to 30 residues long, in another embodiment 2 to 30 residues, and in yet another 3-30 residues long, and any integer length from 2 to 30 inclusive; each integer unit is contemplated, e.g. 2, 3, 4, 5, 6, 7, etc. In one embodiment a Gly linker is used, and in a particular embodiment a three residue linker Gly-Gly-Gly.

In one embodiment the linker is an K(N-epsilon) linker, as used for example in 0601GIP4619:

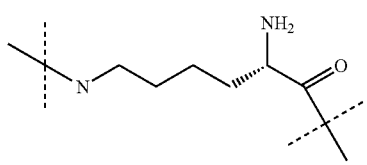

In one embodiment as discussed herein the GIP is attached to the second bio-active hormone module in a C-terminus to C-terminus orientation. The C-terminus of a GIP is linked to the C-terminus of a second bio-active hormone module, optionally with a linker. Orthogonal chemistries can be used to ligate functionalized peptide modules, optionally with linkers as described herein. For example, native chemical ligation chemistries can be used. As shown below, where R is a good leaving group, a hybrid can be generated with a Cys-Lys linkage:

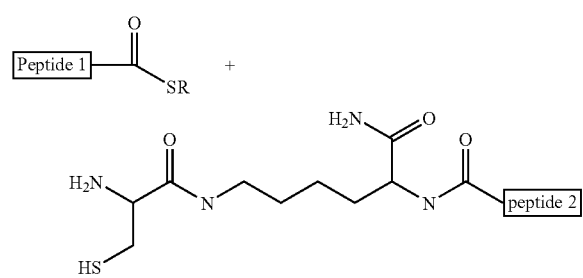

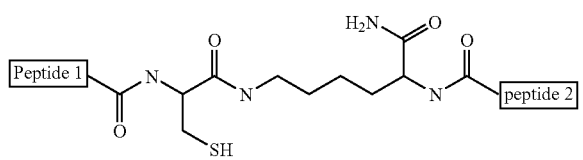

In a further example the hybrid can be prepared using functionalized modules:

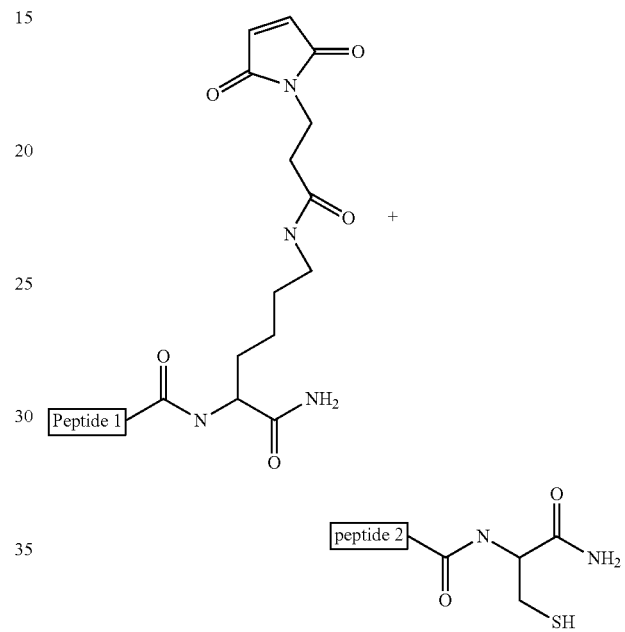

to generate:

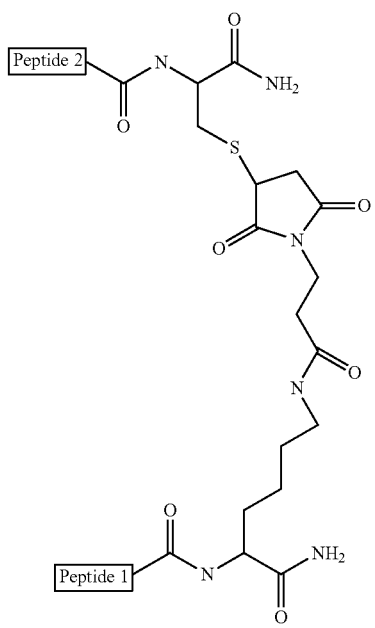

Using a similar approach, a hybrid having a lysine linker can be created:

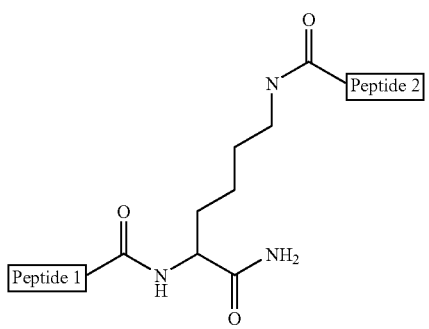

Additional linkers are shown in FIG. 24. The linkers are particularly useful for N-terminal to N-terminal linking, however either or both ends of these linkers can be readily adapted to react to the C-terminus of a GIP compound. The C-terminus of a GIP compound is the preferred terminal for linking a GIP analog or derivative to another peptide component of a GIP-containing hybrid, because as shown herein, linking a peptide module to the N-terminus of GIP resulted in lack of receptor activation, unless the module was cleaved off in vivo. Such N-terminal extensions are known that act to extend plasma half life of the GIP compound and prevent or reduce receptor activation until removed by a serum or membrane protease.

Of particular interest are GIP-exendin family hybrids that are linked C-terminus to C-terminus, keeping their respective receptor activation N-termini unhindered. The receptor activation regions of both molecules are present in such hybrids, for example using any of the GIP and the exendin and GLP1 family peptides and analogs, active fragments and derivatives herein. For example a dAla(2)-GIP(1-30) analog can be linked to exendin-4, in a tail to tail manner, via suitable linking chemistry.

Further, as will be recognized by those of skill in the art, the peptides of the invention may be C-terminally amidated, or may exist as a free acid. In an exemplary embodiment the peptides of the invention are C-terminally amidated. Where amidation of the C-terminal end of N-terminally located bio-active peptide hormone module is desired, the module may again be attached to a second module using any appropriate linking group known in the art. More specifically, in the event that a bio-active peptide hormone module exhibiting at least one hormonal activity has been configured in the C-terminal-to-N-terminal orientation, resulting in an amino to amino linkage, exemplary linking groups include dicarboxylic acids, alkyls, PEGs, and amino acids such as Lys, Cys, and Glu.

As mentioned above, the hybrid polypeptides may also preferably include spacer to further stabilize the linkage of the bio-active peptide hormone modules. Any spacer or turn inducer known in the art may be used. By way of example, referred beta-turn mimetics include mimic A and mimic B illustrated herein, also Ala-Aib and Ala-Pro dipeptides. Their IUPAC names are Mimic A: N-(3S,6S,9S)-2-oxo-3-amino-1-azabicyclo[4.3.0]-nonane-9-carboxylic acid. Mimic B: N-(3S,6S,9R)-2-oxo-3-amino-7-thia-1-azabicyclo[4.3.0]-nonane-9-carboxylic acid.

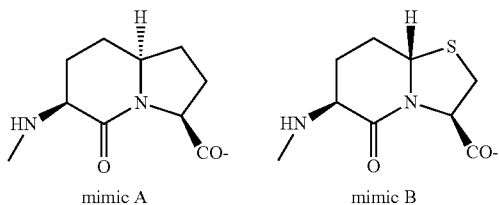

mimic A      mimic B

By agonist is meant a compound which elicits a biological activity of native human hormone. In a exemplary embodiment, the terms refer to a compound which elicits a biological effect in glucose lowering or other activity of native human GIP. Novel GIP analogs for example have activity in a glucose lowering assay, gastric secretion inhibition assay, dP/dt assay, blood pressure assay, insulin secretion assay, bone density assay, or plasma stability assay, preferably similar to or better than native human GIP and/or which binds specifically in a GIP receptor assay or in a competitive binding assay with labeled GIP. In one embodiment, the agonists will bind in such assays with an affinity of greater than 1 µM, and more preferably with an affinity of greater than 1-5 nM. In another embodiment the agonist (or antagonist as the case may be) IC50 will be less than or about 100 micromolar, less than or about 50 micromolar, less than about 20 micromolar, and less than or about 10 micromolar. Such agonists may comprise a polypeptide having a GIP sequence with a Trp-cage motif (e.g. exendin tail PSSGAPS (SEQ ID NO: 93) or variant) or frog GLP-1 tail or analog or derivative of the tail.

By "amino acid" and "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid, thioproline, sarcosine and citrulline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., J. Med. Chem. 41: 2481-91, 1998.

By "Ahx" is meant 6-amino hexanoic acid. As used herein: "5 Apa" means 5 amino-pentanoyl, "12 Ado" means 12-amino dodecanoyl, "PEG(8)" mean 3,6,-dioxyoctanoyl, and "PEG(13)" means 1-amino-4,7,10-trioxa-13-tridecan-amine succinimoyl. In addition are the following abbreviations: "ACN" or "CH3CN" refers to acetonitrile. "Boc", "tBoc" or "Tboc" refers to t-butoxy carbonyl. "DCU" refers to N,N'-dicyclohexylcarbodiimide. "Fmoc" refers to fluorenylmethoxycarbonyl. "HBTU" refers to 2-(1H-benzotriazol-1-yl)-1,1,3,3,-tetramethyluronium hexafluorophosphate. "HOBt" refers to 1-hydroxybenzotriazole monohydrate. "HomoP" or "HPro" refers to homoproline. "MeAla" or "Nme" refers to N-methylalanine. "Naph" refers to naphthylalanine. "pG" or "pGly" refers to pentylglycine. "tBuG" refers to tertiary-butylglycine. "ThioP" or "tPro" refers to thioproline. "3Hyp" refers to 3-hydroxyproline. "4Hyp" refers to 4-hydroxyproline. "NAG" refers to N-alkylglycine. "NAPG" refers to N-alkylpentylglycine. "Norval" refers to norvaline. "Norleu" refers to norleucine. "OctGly" refers to octyl-glycine in which the glycine amino acid side group H is replaced with an eight carbon saturated aliphatic chain.

Further Exemplary Combinations and Specific Embodiments.

Exemplary combinations of bio-active peptide hormone modules to form the GIP hybrid polypeptides of the invention include combinations of two or more bio-active peptide hormone modules selected from: native peptide hormones, analogs and derivatives of peptide hormones that exhibit at least one hormonal activity, fragments of native peptide hormones that exhibit at least one hormonal activity, fragments of analogs and derivatives of peptides hormones that exhibit at least one hormonal activity, and peptidic enhancers, with the proviso that at least one module exhibit at least one hormonal activity.

The hybrid polypeptides of the invention will include at least two bio-active peptide hormone modules, wherein at least one module is comprised from a GIP peptide hormone, analog, derivative, fragment or peptidic enhancer. In one embodiment, at least two of the component peptide hormones are from different peptide hormone families, e.g., the amylin family, CCK, the leptin family, PPF, the proglucagon family, the natriuretic peptide family, and the exendin family. For example, a GIP hybrid can comprise a GIP portion, with or without a tail sequence, combined with a bio-active module that comprises two or more hormone modules (a non-GIP hormone hybrid) such as an exendin-amylin/sCT hybrid or a hormone chimera such as an amylin-sCT chimera.

In certain embodiments, the hybrid polypeptides of the invention may comprise two or more modules that exhibit at least one hormonal activity. For instance, the hybrid polypeptide may comprise a fragment of a first peptide hormone or analog that exhibits at least one hormonal activity covalently linked to a fragment of at least one additional peptide hormone analog. The additional fragment(s) may optionally exhibit at least one hormonal activity. The first peptide hormone may be the same or different from the additional peptide hormone(s), with the proviso that at least one of the additional peptide hormones are different from the first peptide hormone, and the first hormonal activity may be the same or different from the optional additional hormonal activity.

In other embodiments, the hybrid polypeptides of the invention may comprise one or more modules that exhibit at least one hormonal activity in combination with one or more peptidic enhancer modules. For instance, a fragment of a first peptide hormone that exhibits a at least one hormonal activity may be covalently linked to a peptidic enhancer, or a fragment of a first peptide hormone that exhibits at least one hormonal activity may be covalently linked to a second peptide hormone that exhibits at least one hormonal activity, which is in turn linked to a peptidic enhancer. Alternatively, a peptidic enhancer may be located between two peptide hormone modules as a stabilizing spacer. Again, the first peptide hormone may be the same or different from the second peptide hormone, and the first hormonal activity may be the same or different from the second hormonal activity.

In another embodiment, the hybrid polypeptides of the invention may comprise two, three, four, or more bio-active peptide hormone modules. Exemplary combinations include a module with a hormonal activity in combination with one, two, or three peptidic enhancers; two modules with a hormonal activity in combination with one or two peptidic enhancers; three modules with a hormonal activity in combination with one peptidic enhancer, etc.

The component peptide hormones are preferably selected from amylin, adrenomedullin, calcitonin, calcitonin gene related peptide, intermedin, cholecystokinin, leptin peptide YY, glucagon-like peptide-1, glucagon-like peptide 2, oxyntomodulin, ANP, BNP, CNP, urodilatin, GIP, GLP1 or exendin-4.

More particularly, exemplary module combinations include those involving combinations of at least GIP and amylin (and/or sCT), BNP, CGRP, CT, CCK, leptin, PYY, GLP1, and exendin-4.

In exemplary embodiments, a first module comprising a GIP peptide is linked to a second bio-active peptide hormone module comprising an amylin peptide that exhibits at least one hormonal activity. In another embodiment, the second module is further linked to a third bio-active peptide hormone module comprising a calcitonin peptide that exhibits at least one hormonal activity. In yet another embodiment, the third module may be further linked to a fourth bio-active peptide hormone module comprising a peptidic enhancer selected from amylin peptides. In one embodiment, the first module may be located at the C-terminal end of the hybrid polypeptide. Alternatively, the first module may be located at the N-terminal end of the hybrid polypeptide. In certain embodiments, spacers or linkers such as betaAla or Gly may be inserted if desired to link the modules.

Exemplary exendin-4 peptides include: exendin-4, exendin-4(1-27), exendin-4(1-28), $^{14}$Leu, $^{25}$Phe-exendin-4(1-28), and $^{5}$Ala, $^{14}$Leu, $^{25}$Phe-exendin-4(1-28). Also useful are exendin(7-15) and its Ser2 analog, HSEGTFTSD (SEQ ID NO. 94). Exemplary amylin peptides that exhibit at least one hormonal activity include amylin, amylin fragments such as amylin(1-17), amylin (1-16), amylin(1-15), and amylin(1-7), and amylin analogs such as pramlintide, $^{2}$Ala-h-amylin, $^{27}$Ala-h-amylin, and fragments thereof. Exemplary calcitonin peptides that exhibit at least one hormonal activity sCT, sCT fragments such as sCT(8-10), sCT(8-27), and, and calcitonin analogs such as $^{11,18}$Arg-sCT, $^{18}$Arg-sCT, $^{14}$Glu, $^{18}$Arg-sCT, $^{14}$Glu, $^{11,18}$Arg-sCT, and fragments thereof. Exemplary amylin peptidic enhancers include amylin(32-37), amylin(33-37), and amylin(34-37), and analogs thereof. Amylin/sCT combinations useful in connection with the present invention include those disclosed in PCT/US2005/004631 Amylin Family Agonist which is herein incorporated by reference. An amylin/sCT chimera particularly useful for creating hybrids of the invention with GIP is an amylin-sCT-amylin chimera, for example hAmylin(1-7)-$^{11,18}$Arg-sCT(8-27)-Amylin(33-37), which has the sequence KCNTATCVLGRLSQELHR-LQTYPRTNTGSNTY (SEQ ID NO: 95), and is preferably in its C-terminal amide form and analogs and derivatives thereof (described herein and in PCT/US2005/004631).

In one aspect, module combinations include those involving a first module comprising GIP, a fragment of GIP that exhibits at least one hormonal activity, a GIP analog or derivative that exhibits at least one hormonal activity, or a fragment of an GIP analog that exhibits at least one hormonal activity in combination with a second module comprising CCK, a fragment of CCK that exhibits at least one hormonal activity, a CCK analog or derivative that exhibits at least one hormonal activity, or a fragment of a CCK analog that exhibits at least one hormonal activity. Exemplary CCK compounds include: CCK-8, and CCK-8(Phe(CH₂SO₃)). In one embodiment, the first module is located at the C-terminal end of the hybrid polypeptide and the second module is located at the N-terminal end of the hybrid polypeptide. Alternatively, the first module may be located at the N-terminal end of the hybrid polypeptide and second located at the C-terminal end of the hybrid polypeptide. In certain embodiments, spacers or linkers such as beta-Ala or Gly may be inserted if desired to attach the modules.

In one aspect, exemplary module combinations include those involving a first module comprising GIP, a fragment of GIP that exhibits at least one hormonal activity, a GIP analog or derivative that exhibits at least one hormonal activity, or a fragment of an GIP analog that exhibits at least one hormonal activity in combination a second module comprising amylin, a fragment of amylin that exhibits at least one hormonal activity, an amylin analog or derivative that exhibits at least one hormonal activity, or a fragment of an amylin analog that exhibits at least one hormonal activity. The amylin module can be an Amylin/sCT chimera as disclosed herein. In one embodiment, the first module is located at the C-terminal end of the hybrid polypeptide and the peptidic enhancer is located at the N-terminal end of the hybrid polypeptide. Alternatively, the first module may be located at the N-terminal end of the hybrid polypeptide and second located at the C-terminal end of the hybrid polypeptide. In certain embodiments, spacers or linkers such as betaAla or Gly may be inserted if desired to attach the modules.

Yet other exemplary module combinations include those involving combinations of GIP, amylin and calcitonin as tertiary and tetra-hybrid molecules. Exemplary combinations include GIP/amylin/calcitonin; GIP/amylin/calcitonin/amylin; amylin/calcitonin/GIP; and amylin/calcitonin/amylin/GIP combinations, with and without spacers or linking groups. Each module may independently be a peptidic enhancer or may exhibit a hormonal activity, depending on the desired properties of the hybrid polypeptide.

In another embodiment, one of the bio-active peptide hormone module(s) that exhibits at least one hormonal activity is GLP-1 or an analog or fragment thereof, and a second bio-active peptide hormone module comprises GIP. In yet another such hybrid, the hybrid polypeptide comprises a third bio-active peptide hormone module. Exemplary third bio-active peptide hormone modules include amylin (including analogs, derivatives and fragments thereof) and amylin-sCT chimeras, PYY (including analogs, derivatives and fragments thereof) and CCK (including analogs, derivatives and fragments thereof).

Exemplary compounds of GIP-Neuromedin peptide hybrids include

```
                                              (SEQ ID NO: 96)
YaGIP(1-30)-beta-Ala-beta-Ala-FN-38:
YAEGTFISDYSIAMDKIHQQDFVNWLLAQK-beta-Ala-beta-
Ala-FLFHYSKTQKLGKSNVVEELQSPFASQSRGYFLFRPRN-NH2;

(SEQ ID NO: 97)
YaGIP(1-30)-beta-Ala-beta-Ala-Neuromedin(U25):
YAEGTFISDYSIAMDKIHQQDFVNWLLAQK-beta-
Ala-beta-Ala-FRVDEEFQSPFASQSRGYFLFRPRN-NH2;
and (SEQ ID NO: 98)
YaGIP(1-30)-beta-Ala-beta-Ala-Neuromedin(U-9):
YAEGTFISDYSIAMDKIHQQDFVNWLLAQK-beta-
Ala-beta-Ala-GYFLFRPRN-NH2.
```

The beta-Ala-beta-Ala spacer is optional, and can be replaced with Gly-Gly-Gly, a mini-PEG group, or other linker known in the art, particularly those described herein.

Exemplary compounds of GIP and a natriuretic peptide include GIP-hBNP peptide hybrids, including YaGIP(1-30)-beta-Ala-beta-Ala-hBNP where hBNP is SPKMVQGSGCF-GRKMDRISSSSGLGCKVLRRH (SEQ ID NO: 99) and YaGIP(1-30)-exendin(31-39)-beta-Ala-beta-Ala-hBNP, where hBNP is SPKMVQGSGCFGRKMDRISSSS-GLGCKVLRRH (SEQ ID NO: 99). The beta-Ala-beta-Ala spacer is optional, and can be replaced with Gly-Gly-Gly, a mini-PEG group, or other linker known in the art, particularly those described herein.

Embodiments include:

| SEQ ID NO.: | Sequence |
|---|---|
| 100 | YAEGTFISDYSIAMDKIRQQDFVNWLLAQK-Linker-KCNTATCVLGKLSQELHRLQTYPRTNTGSNTY |
| 101 | YAEGTFISDYSIAMDKIRQQDFVNWLLAQK-Linker-KCNTATCVLGRLSQELHRLQTLPRTNTGSNTY |
| 102 | YAEGTFISDYSIAMDKIRQQDFVNWLLAQK-Linker-KCNTATCVLGRLSQELHRLQTYPPTNTGSNTY |
| 103 | YAEGTFISDYSIAMDKIRQQDFVNWLLAQK-Linker-KCNTATCVLGRLSQELHRLQTYPRTNVGSNTY |
| 104 | YAEGTFISDYSIAMDKIRQQDFVNWLLAQK-Linker-KCNTATCVLGRLSQELHRLQTLPPTNVGSNTY |
| 105 | YAEGTFISDYSIAMDKIRQQDFVNWLLAQK-Linker-KCNTATCVLGRLANFLHRLQTYPRTNTGSNTY |
| 106 | YAEGTFISDYSIAMDKIRQQDFVNWLLAQK-Linker-ACNTATCVLGRLSQELHRLQTYPRTNTGSNTY |
| 107 | YAEGTFISDYSIAMDKIRQQDFVNWLLAQK-Linker-KCNAATCVLGRLSQELHRLQTYPRTNTGSNTY |
| 108 | YAEGTFISDYSIAMDKIRQQDFVNWLLAQK-Linker-KCNTAACVLGRLSQELHRLQTYPRTNTGSNTY |

-continued

| SEQ ID NO.: | Sequence |
|---|---|
| 109 | YAEGTFISDYSIAMDKIRQQDFVNWLLAQK-Linker-CANLSTCVLGRLSQELHRLQTYPRTNTGSNTY |
| 110 | YAEGTFISDYSIAMDKIRQQDFVNWLLAQK-Linker-CSNASTCVLGRLSQELHRLQTYPRTNTGSNTY |
| 111 | YAEGTFISDYSIAMDKIRQQDFVNWLLAQK-Linker-CSNLATCVLGRLSQELHRLQTYPRTNTGSNTY |
| 112 | YAEGTFISDYSIAMDKIRQQDFVNWLLAQK-Linker-CSNLSACVLGRLSQELHRLQTYPRTNTGSNTY |
| 113 | YAEGTFISDYSIAMDKIRQQDFVNWLLAQK-Linker-KCNTATCVLGRLSQELHKLQTYPRTNTGSNTY |
| 114 | YAEGTFISDYSIAMDKIRQQDFVNWLLAQK-Linker-KCNTATCVLGRLSQELHRLQTYPRTNTGSGTP |
| 115 | YAEGTFISDYSIAMDKIRQQDFVNWLLAQK-Linker-CSALSTCVLGRLSQELHRLQTYPRTNTGSNTY |
| 116 | YAEGTFISDYSIAMDKIRQQDFVNWLLAQK-Linker-KCNTATCLLQQLQKLLQKLKQYPRTNTGSNTY |
| 117 | YAEGTFISDYSIAMDKIRQQDFVNWLLAQK-Linker-KCNTASCVLGRLSQELHRLQTYPRTNTGSNTY |
| 118 | YAEGTFISDYSIAMDKIRQQDFVNWLLAQK-Linker-KCNTAVCVLGRLSQELHRLQTYPRTNTGSNTY |
| 119 | YAEGTFISDYSIAMDKIRQQDFVNWLLAQK-Linker-KCNTATCVLGRLSQELHRYPRTNTGSNTY |
| 120 | YAEGTFISDYSIAMDKIRQQDFVNWLLAQK-Linker-KCNTATCVLGK(For)LSQELHK(For)LQTYPRTNTGSNTY |
| 457 | YAEGTFISDYSIAMDKIRQQDFVNWLLAQK-Linker-KCNTA(d-Thr)CVLGRLSQELHRLQTYPRTNTGSNTY |
| 458 | YAEGTFISDYSIAMDKIRQQDFVNWLLAQK-Linker-KCNTA(dAh)CVLGRLSQELHRLQTYPRTNTGSNTY |
| 121 | YAEGTFISDYSIAMDKIRQQDFVNWLLAQK-Linker-ACNTATCVLGRLSQELHK(PEG5000)LQTYPRTNTGSNTY |
| 122 | YAEGTFISDYSIAMDKIRQQDFVNWLLAQK-Linker-KCNTATCVLGRLSQELHRLQTLQTYPRTNTGSNTY |
| 123 | YAEGTFISDYSIAMDKIRQQDFVNWLLAQK-Linker-KCNTATCVLGRLSQELHRLQTLLQTYPRTNTGSNTY |
| 124 | YAEGTFISDYSIAMDKIRQQDFVNWLLAQK-Linker-KCNTATCVLGKLSQELHKLQTYPRTNTGSNTY |
| 125 | YAEGTFISDYSIAMDKIRQQDFVNWLLAQK-Linker-KCNTSTCVLGRLSQELHRLQTYPRTNTGSNTY |
| 126 | YAEGTFISDYSIAMDKIRQQDFVNWLLAQK-Linker-KCNTATCATQRLSQELHRLQTYPRTNTGSNTY |
| 127 | YAEGTFISDYSIAMDKIRQQDFVNWLLAQK-Linker-KCNTATCATQRLSQELHRLQTYPRTNVGSNTY |
| 128 | YAEGTFISDYSIAMDKIRQQDFVNWLLAQK-Linker-KCNTSTCATQRLANELVRLQTYPRTNVGSNTY |
| 129 | YAEGTFISDYSIAMDKIRQQDFVNWLLAQK-Linker-KCNTA(Hse)CVLGRLSQELHRLQTYPRTNTGSNTY |
| 130 | YAEGTFISDYSIAMDKIRQQDFVNWLLAQK-Linker-KCNTA(Ahb)CVLGRLSQELHRLQTYPRTNTGSNTY |
| 131 | YAEGTFISDYSIAMDKIRQQDFVNWLLAQK-Linker-KCNTA(Ahp)CVLGRLSQELHRLQTYPRTNTGSNTY |

| SEQ ID NO.: | Sequence |
|---|---|
| 132 | YAEGTFISDYSIAMDKIRQQDFVNWLLAQK-Linker-KCNTAT(OPO3H2)CVLGRLSQELHRLQTYPRTNTGSNTY |
| 133 | YAEGTFISDYSIAMDKIRQQDFVNWLLAQK-Linker-KCNTATCVLG(Orn)LSQELH(Orn)LQTYPRTNTGSNTY |
| 134 | YAEGTFISDYSIAMDKIRQQDFVNWLLAQK-Linker-KCNTATCVLG(Cit)LSQELH(Cit)LQTYPRTNTGSNTY |
| 135 | YAEGTFISDYSIAMDKIRQQDFVNWLLAQK-Linker-KCNTATCVLG(homoK)LSQELH(homoK)LQTYPRTNTGSNTY |
| 136 | YAEGTFISDYSIAMDKIRQQDFVNWLLAQK-Linker-KCNTATCMLGRYTQDFHRLQTYPRTNTGSNTY |
| 137 | YAEGTFISDYSIAMDKIRQQDFVNWLLAQK-Linker-DSNLSTKVLGRLSQELHRLQTYPRTNTGSNTY |
| 138 | YAEGTFISDYSIAMDKIRQQDFVNWLLAQK-Linker-KDNTATKVLGRLSQELHRLQTYPRTNTGSNTY |
| 139 | YAEGTFISDYSIAMDKIRQQDFVNWLLAQK-Linker-CNTATCVLGRLSQELHRLQTYPRTNTGSNTY |
| 140 | YAEGTFISDYSIAMDKIRQQDFVNWLLAQK-Linker-KCNTATCVLGRLSQELHRLQTYPRTNTGSNTY(9Anc) |
| 141 | YAEGTFISDYSIAMDKIRQQDFVNWLLAQK-Linker-KCNTATCVLGRLSQELHRLQTYPRTNTGSNTY(L-octylglycine) |
| 142 | YAEGTFISDYSIAMDKIRQQDFVNWLLAQK-Linker-KCNTATCVLG(homoR)LSQELH(homoR)LQTYPRTNTGSNTY |
| 143 | YAEGTFISDYSIAMDKIRQQDFVNWLLAQK-Linker-FCNTATCVLGRLSQELHRLQTYPRTNTGSNTY |
| 144 | YAEGTFISDYSIAMDKIRQQDFVNWLLAQK-Linker-KCNTATCVLGRLSQELH(Cit)LQTYPRTNTGSNTY |
| 145 | YAEGTFISDYSIAMDKIRQQDFVNWLLAQK-Linker-KCNTATCVLGRLSQELH(Orn)LQTYPRTNTGSNTY |
| 146 | YAEGTFISDYSIAMDKIRQQDFVNWLLAQK-Linker-ICNTATCVLGRLSQELHRLQTYPRTNTGSNTY |
| 147 | YAEGTFISDYSIAMDKIRQQDFVNWLLAQK-Linker-KCNTATCVLG(Cit)LSQELHRLQTYPRTNTGSNTY |
| 148 | YAEGTFISDYSIAMDKIRQQDFVNWLLAQK-Linker-KCNTATCVLGRLSQELHRLQTYPRTNTGSNTY(4ABU) |
| 149 | YAEGTFISDYSIAMDKIRQQDFVNWLLAQK-Linker-KCNTSTCATQRLANELVRLQTYPRTNVGSEAF |
| 150 | YAEGTFISDYSIAMDKIRQQDFVNWLLAQK-Linker-KCNTATCVLGRLSQELHRLQTYPTNVGSEAF |
| 151 | YAEGTFISDYSIAMDKIRQQDFVNWLLAQK-Linker-KCNTATCVLGRLSRSLHRLQTYPRTNTGSNTY |
| 152 | YAEGTFISDYSIAMDKIRQQDFVNWLLAQK-Linker-KCNTATCVTHRLSQELHRLQTYPRTNTGSNTY |
| 153 | YAEGTFISDYSIAMDKIRQQDFVNWLLAQK-Linker-KCNTATCVLGRLADFLHRLQTYPRTNTGSNTY |
| 154 | YAEGTFISDYSIAMDKIRQQDFVNWLLAQK-Linker-CNTATCVLGRLSQELHRLQTYPRTNTGSNT |
| 155 | YAEGTFISDYSIAMDKIRQQDFVNWLLAQK-Linker-KCNTATCVLGRLSQELHRLQNFVPRTNTGSNTY |
| 156 | YAEGTFISDYSIAMDKIRQQDFVNWLLAQK-Linker-KCNTATCVLGRLSQELHRLQTYPRTNTGSETF |

| SEQ ID NO.: | Sequence |
|---|---|
| 157 | YAEGTFISDYSIAMDKIRQQDFVNWLLAQK-Linker-ACDTATCVLGRLSQELHRLQTYPRTNTGSNTY |
| 158 | YAEGTFISDYSIAMDKIRQQDFVNWLLAQK-Linker-KCNTATCVLGRLSQELHRLQTYPRTNTGSKAF |
| 159 | YAEGTFISDYSIAMDKIRQQDFVNWLLAQK-Linker-KCDTATCVTHRLAGLLSRSQTYPRTNTGSNTY |
| 160 | YAEGTFISDYSIAMDKIRQQDFVNWLLAQK-Linker-KCNTATCVLGRLADALHRLQTYPRTNTGSNTY |
| 161 | YAEGTFISDYSIAMDKIRQQDFVNWLLAQK-Linker-KCNTATCVLGRLAAFLHRLQTYPRTNTGSNTY |
| 162 | YAEGTFISDYSIAMDKIRQQDFVNWLLAQK-Linker-SCNTATCVLGRLADFLHRLQTYPRTNTGSNTY |
| 163 | YAEGTFISDYSIAMDKIRQQDFVNWLLAQK-Linker-KCNTATCVLGRLSQELHRLQTMPRTNTGSNTY |
| 164 | YAEGTFISDYSIAMDKIRQQDFVNWLLAQK-Linker-KCNTATCVLGRLSQELHRLQTVPRTNTGSNTY |
| 165 | YAEGTFISDYSIAMDKIRQQDFVNWLLAQK-Linker-KCNTATCVLGRLNEYLHRLQTYPRTNTGSNTY |
| 166 | YAEGTFISDYSIAMDKIRQQDFVNWLLAQK-Linker-SCNTATCVLGRLSQELHRLQTYPRTNTGSNTY |
| 167 | YAEGTFISDYSIAMDKIRQQDFVNWLLAQK-Linker-KCNTATCVLGRLTEFLHRLQTYPRTNTGSNTY |
| 168 | YAEGTFISDYSIAMDKIRQQDFVNWLLAQK-Linker-KCNTATCVLGRLAEFLHRLQTYPRTNTGSNTY |
| 169 | YAEGTFISDYSIAMDKIRQQDFVNWLLAQK-Linker-KCNTATCVLGRLTDYLHRLQTYPRTNTGSNTY |
| 170 | YAEGTFISDYSIAMDKIRQQDFVNWLLAQK-Linker-KCNTATCVLGRLAQFLHRLQTYPRTNTGSNTY |
| 171 | YAEGTFISDYSIAMDKIRQQDFVNWLLAQK-Linker-KCNTATCVLGRLADFLHRFQTFPRTNTGSNTY |
| 172 | YAEGTFISDYSIAMDKIRQQDFVNWLLAQK-Linker-KCNTATCVLGRLADFLHRFHTFPRTNTGSNTY |
| 173 | YAEGTFISDYSIAMDKIRQQDFVNWLLAQK-Linker-KCNTATCVLGRLADFLHRFQTFPRTNTGSGTP |
| 174 | YAEGTFISDYSIAMDKIRQQDFVNWLLAQK-Linker-CNTATCVLGRLADFLHRLQTYPRTNTGSNTY |
| 175 | YAEGTFISDYSIAMDKIRQQDFVNWLLAQK-Linker-KCDTATCVLGRLSQELHRLQTYPRTNTGSNTY |
| 176 | YAEGTFISDYSIAMDKIRQQDFVNWLLAQK-Linker-KCNTATCVLGRLFDFLHRLQTYPRTNTGSNTY |
| 177 | YAEGTFISDYSIAMDKIRQQDFVNWLLAQK-Linker-KCNTATCVLGRLAAALHRLQTYPRTNTGSNTY |
| 178 | YAEGTFISDYSIAMDKIRQQDFVNWLLAQK-Linker-TCDTATCVLGRLSQELHRLQTYPRTNTGSNTY |
| 179 | YAEGTFISDYSIAMDKIRQQDFVNWLLAQK-Linker-CSNLSTCATQRLANELVRLQTYPRTNVGSNTY |
| 180 | YAEGTFISDYSIAMDKIRQQDFVNWLLAQK-Linker-KCNTATCATQRLANELVRLQTYPRTNVGSNTY |
| 181 | YAEGTFISDYSIAMDKIRQQDFVNWLLAQK-Linker-CSNLSTCVLGRLSQELHRLQTYPRTNTGSNTY |

| SEQ ID NO.: | Sequence |
|---|---|
| 182 | YAEGTFISDYSIAMDKIRQQDFVNWLLAQK-Linker-KCNTATCVLGRLSQELHRLQTYPRTNTGSNTY |
| | GIP(1-30)-(12 Ado)-hAmylin(1-7)-$^{11,18}$Arg-sCt(8-27)-hAmylin(33-37) |
| | GIP(1-30)-(12 Ado)-$^{1}$des-Lys-hAmylin(1-7)-$^{11,18}$Arg-sct(8-27)-hAmylin(33-37) |
| | GIP(1-30)-(3,6-dioxaoctanoyl)-hAmylin(1-7)-$^{11,18}$Arg-sCt(8-27)-hAmylin(33-37) |
| | GIP(1-30)-(3,6-dioxaoctanoyl)-$^{1}$des-Lys-hAmylin(1-7), $^{11,18}$Arg-sCt(8-27)-hAmylin(33-37) |
| | GIP(1-30)-(5 Apa)-hAmylin(1 -7)-$^{11,18}$Arg-sCt(8-27)-hAmylin(33-37) |
| | GIP(1-30)-(5 Apa)-$^{1}$des-Lys-hAmylin(1-7)-$^{11,18}$Arg-sCt(8-27)-Amylin(33-37) |
| | GIP(1-30)-betaAla-betaAla-hAmylin(1-7)-$^{11,18}$Arg-sCt(8-27)-Amylin(33-37) |
| | GIP(1-30)-betaAla-betaAla-$^{1}$desLys-Amylin(1-7)-$^{11,18}$Arg-sCt(27)-hAmylin(33-37) |
| | GIP(1-30)-(4,7,10-trioxa-13-tridecanamine succinimidyl)-hAmylin(1-7) $^{11,18}$Arg-sCt(8-27)-hAmylin(33-37) |
| | GIP(1-30)-(4,7,10-trioxa-13-tridecanamine succinimidyl)-$^{1}$des-Lys-hAmylin(1-7)-$^{11,18}$Arg sCt(8-27)-hAmylin(33-37) |
| | GIP(1-30)-(Gly-Gly-Gly)-hAmylin(1-7)-$^{11,18}$Arg-sCt(8-27)-Hamylin(33-37) |
| | GIP(1-30)-(Gly-Gly-Gly)-$^{1}$des-Lys-hAmylin(1-7)-$^{11,18}$Arg-sCt(27)-hAmylin(33-37) |
| | GIP(1-30)-(4,7,10-trioxa-13-tridecanamine succinimidyl)-hAmylin(1-7) $^{11,18}$Arg-sCt(8-27)-hAmylin(33-37) |
| | GIP(1-30)-(4,7,10-trioxa-13-tridecanamine succinimidyl)-$^{1}$des-Lys-hAmylin(1-7)-$^{11,18}$Arg sCt(8-27)-hAmylin(33-37) |

Further exemplary GIP hybrids include GIP and neuromedin hybrids, for example dAla2-GIP(1-30)-beta-Ala-beta-Ala-FN-38:
(SEQ ID No. 459)
YaEGTFISDYSIAMDKIHQQDFVNWLLAQK-beta-Ala-beta-Ala-FLFHYSKTQKLGKSNVVEELQSPFASQSRGYFLFRPRN-NH2;

dAla2-GIP(1-30)-beta-Ala-beta-Ala-Neuromedin(U25):
(SEQ ID No. 460)
YaEGTFISDYSIAMDKIHQQDFVNWLLAQK-beta-Ala-beta-Ala-FRVDEEFQSPFASQSRGYFLFRPRN-NH2;
and dAla2-GIP(1-30)-beta-Ala-beta-Ala-Neuromedin(U-9):
(SEQ ID No. 461)
YaEGTFISDYSIAMDKIHQQDFVNWLLAQK-beta-Ala-beta-Ala-GYFLFRPRN-NH2.

The beta-Ala-beta-Ala spacer is optional, and can be replaced with Gly-Gly-Gly, a mini-PEG group, or other linker known in the art, particularly those described herein.

Exemplary GIP and natriuretic peptide hybrids include GIP-hBNP peptide hybrids, including (SEQ ID No.462)
dAla2-GIP(1-30)-beta-Ala-beta-Ala-hBNP:
YaEGTFISDYSIAMDKIHQQDFVNWLLAQK-beta-Ala-beta-Ala-SPKMVQGSGCFGRKMDRISSSSGLGCKVLRRH;

and (SEQ ID No. 463)
dAla2-GIP(1-30)-beta-Ala-beta-Ala-hBNP:
YaEGTFISDYSIAMDKIHQQDFVNWLLAQK-beta-Ala-beta-Ala-SPKMVQGSGCFGRKMDRISSSSGLGCKVLRRH.

As has been discussed throughout, in any of the embodiments herein, including the above hybrids, additional changes as discussed can be included. For example, in any of the embodiments herein, including the above hybrids, positions 1 (including the N-terminus), 2 or 3 can be modified to impart DPP-IV resistance. For example, specifically exemplified herein are each of the D-Ala2 analogs of each embodiment herein as well as of the above species.

GIP and Peptidic Enhancer Hybrid

In one hybrid embodiment GIP is C-terminally extended by a peptidic enhancer, e.g., a tail or C-terminal portion of another hormone, such as exendin or GLP-1, which provide analogs that have enhanced in vivo efficacy. Exendin-4 (FIG. 1) is a potent incretin mimetic that shares a 53% homology with GLP-1, and mirrors many of the key biological actions of GLP-1. Unlike GLP-1, exendin-4 is much more resistant to proteolytic cleavage to DPP-IV peptidase and NEP. This confers greater enhanced pharmacokinetics and improved in vivo efficacy in humans compared to GLP-1. Circular dichroism (CD) and NMR studies of Exendin-4 in aqueous media and in media containing organic cosolvents reveal that the C-terminal segment containing the sequence LFIEWLKNGGPSSGAPPPS (SEQ ID NO: 183) (residues 21-39) forms a unique hydrophobic Trp-cage cluster resulting from interactions of Pro37 with Phe22 and Pro38 with Trp25 (29-31). This Trp-cage cluster motif is the first example of a protein-like tertiary structure displayed by a peptide, and could be responsible for imparting greater metabolic stability by masking protease-sensitive sites in the molecule in vivo (32).

Accordingly, in one aspect, exemplary module combinations include those involving a first module comprising GIP, a fragment of GIP that exhibits at least one hormonal activity, a GIP analog or derivative that exhibits at least one hormonal activity, or a fragment of an GIP analog that exhibits at least one hormonal activity in combination with a peptidic enhancer. Useful peptidic enhancers are the exendin-4 and frog GLP tails, as described herein, as well as PYY(25-36), PYY(30-36) and PYY(31-36). In one embodiment, the first module is located at the C-terminal end of the hybrid polypeptide and the peptidic enhancer is located at the N-terminal end of the hybrid polypeptide. Alternatively, the first module may be located at the N-terminal end of the hybrid polypeptide and the peptidic enhancer may be located at the C-terminal end of the hybrid polypeptide. In certain embodiments, spacers or linkers such as betaAla or Gly may be inserted if desired to attach the modules.

A particular compound of interest is YaEGTFISDYSIAM-DKIHQQDFVNWLLAQKPSSGAPPPS-NH2 (Compound 0601GIP3794; which has a D-Ala at position 2, and is in amide form). Exemplary compounds having a modification at position 2 (i.e. residue 2) or positions 2 and 3 (e.g. Ser at 2 with Asp at 3), and their GIP Receptor binding and receptor activation activities include Y-Residue2-EGTFISDYSIAM-DKIHQQDFVNWLLAQKPSSGAPPPS-NH2 where Residues 2 and/or 3 are shown in the table (and see FIG. 12):

| Cmpd# | Residue 2 or Residues 2 + 3 | GIP RBA | GIPR Cyclase |
|---|---|---|---|
| 0601GIP3794 | dAla | 3.8 | 38 |
| 0601GIP4189 | V | 12 | >1000 |
| 0601GIP4145 | dnorV | 83 | 10000 |
| 0601GIP4146 | dSer | 20 | 171 |
| 0601GIP4147 | Abu | 7.4 | 126 |
| 0601GIP4148 | dAbu | 34 | 248 |
| 0601GIP4186 | homo-Ser | 20 | >1000 |
| 0601GIP4195 | d-homoSer | 52 | 10000 |
| 0601GIP4164 | dPro | 501 | 10000 |
| 0601GIP4187 | cyclopropyl Ala | 67 | >1000 |
| 0601GIP4188 | d-cyclopropyl Ala | 214 | 10000 |
| 0601GIP4181 | cycloHexyl Ala | 35.3151 (% Inh 10 nM) | 10000 |
| 0601GIP4182 | d-cyclohexyl Ala | 37.42591 (% Inh 10 nM) | 10000 |
| 0601GIP4237 | A(NMe) | 28 | 10000 |
| 0601GIP4324 | Aib | 104.7129 (% Inh 10 nM) | 13.4 |
| CC | cyclpropGly | | |
| 0601GIP4458 | betaAla | 51.122 (% Inh 10 nM) | |
| 0601GIP4215 | Ser + Asp | 4.5 | 57.6 |
| 0601GIP4389 | Asp | 66.554 (% Inh 10 nM) | 128 |
| 0601GIP4703 | dGlu | 71.4 (% Inh 10 nM) | |

Further exemplary compounds having a modification at the N-terminus and their GIP Receptor binding and receptor activation activity, include N-Terminus-YaEGTFISDYSIAMD-KIHQQDFVNWLLAQKPSSGAPPPS-NH2 (SEQ ID No. 186) where the N-terminus modification is shown in the table (and see FIG. 12):

| Cmpd# | N-Terminus | GIP RBA | Cyclase |
|---|---|---|---|
| 0601GIP3794 | H | 3.8 | 38 |
| 0601GIP4196 | Isocap | 11 | 10000 |
| 0601GIP4180 | isoBuOCO | 88.0407 (% Inh 10 nM) | 386 |
| 0601GIP4178 | Octylglycine | 1.5 | 96 |
| 0601GIP4238 | Y(NMe) | 4.2 | 144 |
| 0601GIP4291 | Succinoyl | 179 | 10000 |

Further exemplary compounds with various linkers or fatty acid modifications, or combinations of modifications, as described herein and their GIP Receptor binding and receptor activation activity, are shown in the table (and see FIG. 12). Note that Ocg and OctG both designate octylglycine. DNal indicates D-2-Naphthylalanine amino acid.

| Cmpd # | Sequence | GIP RBA | Cyclase |
|---|---|---|---|
| 0601GIP3794 | YaEGTFISDYSIAMDKIHQQDFVNWLLAQKPSSGAPPPS-NH2 (SEQ ID No. 186) | 3.8 | 38 |
| 0601GIP4290 | YaEGTFISDYSIALDKIRQQEFVNWLLAQK-bAla-PSSGAPPPS-NH2 (SEQ ID No. 464) | 0.35 | 14 |
| 0601GIP4178 | OctG-YAEGTFISDYSIAMDKIHQQDFVNWLLAQKPSSGAPPPS-NH2 (SEQ ID No. 391) | 1.5 RIN, 0.170 IC50 in HEK-GIPR | 36.2 |
| 0601GIP4293 | octG-YAEGTFISDYSIAMDKIRQQDFVNWLLAQKPSSGAPPPS-NH2 (SEQ ID No. 392) | 0.12 | 20 |
| 0601GIP4292 | octG-YAEGTFISDYSIALDKIRQQEFVNWLLAQHPSSGAPPPS-NH2 (SEQ ID No. 393) | 0.17 | 3.46 |

| Cmpd # | Sequence | GIP RBA | Cyclase |
|---|---|---|---|
| 0601GIP4806 | OctG-YAEGTFISDYSIAMDKIRQQEFVNWLLAQHPKKIRYS-NH2 (SEQ ID No. 620) | 101.3 (% Inh 10 nM) | |
| 0601GIP4670 | OctG-YAEGTFISDYSIAMDKIRQQEFVNWLLAQHPSSGAPPPS-NH2 (SEQ ID No. 621) | 96.9324 (% Inh, 10 nM) | |
| 0601GIP4635 | OctG-YaEGTFISDYSIAMDKIHQQDFVNWLLAQKPSSGAPPPS-NH2 (SEQ ID No. 622) | 87.7032 (% Inh, 10 nM) | |
| 0601GIP4636 | OctG-YaEGTFISDYSIAMDKIRQQDFVNWLLAQKPSSGAPPPS-NH2 (SEQ ID No. 623) | 92.8656 (% Inh, 10 nM) | |
| 0601GIP4637 | OctG-YaEGTFISDYSIALDKIRQQEFVNWLLAQHPSSGAPPPS-NH2 (SEQ ID No. 624) | 95.7634 (% Inh, 10 nM) | |
| 0601GIP4543 | OctG-YAPGTFISDYSIALDKIRQQEFVNWLLAQHPSSGAPPPS-NH2 (SEQ ID No. 395) | 85.4306 (% Inh, 10 nM) | |
| 0601GIP | OctG-YaPGTFISDYSIALDKIRQQEFVNWLLAQHPSSGAPPPS-NH2 (SEQ ID No. 618) | 81.7225 (% Inh, 10 nM) | |
| 0601GIP4712 | OctG-YaEGTFISDYSIALDKIAQQEFVNWLLAQKPSSGAPPPS-NH2 (SEQ ID No. 625) | 94.7 (% Inh, 10 nM) | |
| 0601GIP4194 | YaEGTFISDYSIAMD(OctG)IHQQDFVNWLLAQKPSSGAPPPS-NH2 (SEQ ID No. 591) | 68 | 933 |
| 0601GIP4252 | YaEGTFISDYSIAMDKIHQQDFVNWLLAQKPSS(OctG)APPPS-NH2 (SEQ ID No. 599) | 5.6 | 154 |
| 0601GIP4548 | YAEGTFISDYSIAMDKIHQQDFVNWLLAQKPSS(OctG)APPPS-NH2 (SEQ ID No. 396) | 93.9341 (% Inh, 10 nM) | |
| 0601GIP4549 | YSEGTFISDYSIAMDKIHQQDFVNWLLAQKPSS(OctG)APPPS-NH2 (SEQ ID No. 397) | 87.5173 (% Inh, 10 nM) | |
| 0601GIP4550 | YSDGTFISDYSIAMDKIHQQDFVNWLLAQKPSS(OctG)APPPS-NH2 (SEQ ID No. 398) | 78.9341 (% Inh, 10 nM) | |
| 0601GIP4606 | YaEGTFISDYSIALDKIHQQDFVNWLLAQKPSS(OctG)APPPS-NH2 (SEQ ID No. 626) | 79.8162 (% Inh, 10 nM) | |
| 0601GIP4607 | YaEGTFISDYSIALDKIRQQEFVNWLLAQKPSS(OctG)APPPS-NH2 (SEQ ID No. 627) | 84.6962 (% Inh, 10 nM) | |
| 0601GIP4325 | YAEGTFISDYSIA(Ocg)DKIHQQDFVNWLLAQK-NH2 (SEQ ID No. 399) | 106.9993 (% Inh, 10 nM) | 219 |
| 0601GIP4326 | YaEGTFISDYSIA(OctG)DKIHQQDFVNWLLAQKPSSGAPPPS)-NH2 (SEQ ID No. 611) | 97.448 (% Inh, 10 nM) | 53 |

-continued

| Cmpd # | Sequence | GIP RBA | Cyclase |
|---|---|---|---|
| 0601GIP4671 | YaEGTFISDYSIA(OctG)DKIHQQDFVNWLL AQKPKKIRYS-NH2 (SEQ ID No. 628) | 97.4262 (% Inh, 10 nM) | |
| 0601GIP4693 | YaEGTFISDYSIA(OctG)DKIHQQDFVNWLL AQK(beta-A)(beta-A)PSSGAPPPS-NH2 (SEQ ID No. 629) | 91.6712 (% Inh, 10 nM) | |
| 0601GIP4755 | YaEGTFISDYSIA(OctG)DKIAQQEFVNWLL AQKPSSGAPPPS-NH2 (SEQ ID No. 630) | 96.3 (% Inh, 10 nM) | |
| 0601GIP4547 | YaEGTFISDYSIA(K(Oct))DKIHQQDFVNWL LAQKPSSGAPPPS-NH2 (SEQ ID No. 619) | 41.3078 (% Inh 10 nM) | |
| 0601GIP4461 | YAEGTFISDYSIAMDKIHQQDFVNWLLAQ KPSSGAPPPS(OctG)-NH2 (SEQ ID No. 401) | 95.785 (% Inh 10 nM) | |
| 0601GIP4581 | YaEGTFISDYSIAMDKIHQQDFVNWLLAQ KPSSGAPPPS(OctG)-NH2 (SEQ ID No. 631) | 97.512 (% Inh 10 nM) | |
| 0601GIP4583 | K(epsilon-NH-Octanoyl)- YaEGTFISYDSIAMDKIHQQDFVNWLLAQ KPSSGAPPPS(OctG)-NH2 (SEQ ID No. 632) | 85.4997 (% Inh 10 nM) | |
| 0601GIP4585 | K(epsilon-NH-Octanoyl)- YaEGTFISDYSIAMDKIHQQDFVNWLLAQ KPSSGAPPPS-NH2 (SEQ ID No. 633) | 85.1781 (% Inh 10 nM) | |
| 0601GIP4584 | K(epsilon-NH-(2-(2- (2methoxyetoxy)ethoxy)acetyl))- YaEGTFISDYSIAMDKIHQQDFVNWLLAQ KPSSGAPPPS(OctG)-NH2 (SEQ ID NO. 634) | 26.5178 (% Inh 10 nM) | |
| 0601GIP4833 | YaEGTFISDYSIAKDKIHQQDFVNWLLAQK PKKK(epsilon-NH-(palmitoyl))RYS-NH2 (SEQ ID No. 635) | | |
| 0601GIP4586 | K(epsilon-NH-(2-(2- (2methoxyetoxy)ethoxy)acetyl))- YaEGTFISDYSIAMDKIHQQDFVNWLLAQ KPSSGAPPPS-NH2 (SEQ ID NO. 636) | 19.2602 (% Inh 10 nM) | |
| 0601GIP4647 | YaEGTFISDYSIAMDKIHQQDFVNWLLAQ K(beta-A)(beta-A)PSSGAPPPS-NH2 (SEQ ID No. 637) | 76.6236 (% Inh, 10 nM) | |
| 0601GIP4179 | YaEGTFISDYSIALDKIHQQDFVNWLLAQK (beta-A)(beta-A)PSSGAPPPS-NH2 (SEQ ID NO. 587) | 3.3 RIN, 0.700 IC50 in HEK-GIPR | 55.9 |
| 0601GIP4649 | OctG- YaEGTFISDYSIAMDKIHQQDFVNWLLAQ K(beta-A)(beta-A)PSSGAPPPS-NH2 (SEQ ID No. 638) | 87.3376 (% Inh, 10 nM) | |
| 0601GIP4642 | YAEGTFISDYSIAMDKIHQQDFVNWLLAQ K(beta-A)(beta-A)PSSGAPPPS-NH2 (SEQ ID No. 639) | 82.0796 (% Inh, 10 nM) | |
| 0601GIP4643 | YaEGTFISDYSIAMDKIRQQEFVNWLLAQK (beta-A)(beta-A)PSSGAPPPS-NH2 (SEQ ID 640) | 84.7142 (% Inh, 10 nM) | |
| 0601GIP4644 | YaEGTFISDYSIAMDKIRQQDFVEWLLAQK (beta-A)(beta-A)PSSGAPPPS-NH2 (SEQ ID No. 641) | 70.8009 (% Inh, 10 nM) | |

-continued

| Cmpd # | Sequence | GIP RBA | Cyclase |
| --- | --- | --- | --- |
| 0601GIP4645 | OctG-YaEGTFISDYSIAMDKIRQQEFVNWLLAQH(beta-A)(beta-A)PSSGAPPPS-NH2 (SEQ ID No. 642) | 82.1831 (% Inh, 10 nM) | |
| 0601GIP4646 | YaEGTFISDYSIAMDKIAQQEFVNWLLAQK(beta-A)(beta-A)PSSGAPPPS-NH2 (SEQ ID NO. 643) | 82.1763 (% Inh, 10 nM) | |
| 0601GIP4294 | octG-YaEGTFISDYSIALDKIHQQDFVNWLLAQK(beta-A)(beta-A)PSSGAPPPS-NH2 (SEQ ID No. 610) | 0.92 | 282 |
| 0601GIP4542 | OctG-YaPGTFISDYSIALDKIHQQDFVNWLLAQK(beta-A)(beta-A)PSSGAPPPS-NH2 (SEQ ID No. 617) | 19.1733 (% Inh, 10 nM) | |
| 0601GIP4541 | OctG-YAPGTFISDYSIALDKIHQQDFVNWLLAQK(beta-A)(beta-A)PSSGAPPPS-NH2 (SEQ ID No. 403) | 14.3806 (% Inh, 10 nM) | |
| 0601GIP4191 | YaEGTFISDYSIAMDKIHQQDFVNWLLAQK-8-amino 3,6-dioxaoctanoyl-PSSGAPPPS-NH2 (SEQ ID NO: 589) | 10 | 81 |
| 0601GIP4756 | YaEGTFISDYSIAMDKIHQQDFVNWLLAQK(Aca)PSSGAPPPS-NH2 (SEQ ID NO. 644) | 60.5 (% Inh, 10 nM) | |
| 0601GIP4562 | YaEGT(D-Nal2]ISDYSIAMDKIHQQDFVNWLLAQKPSSGAPPPS-NH2 (SEQ ID No. 645) | | |
| 0601GIP4572 | YaEGTFISD(D-Nal2)SIAMDKIHQQDFVNWLLAQKPSSGAPPPS-NH2 (SEQ ID NO. 646) | 33.6497 (% Inh, 10 nM) | |
| 0601GIP4573 | YaEGTFISDYSIA(D-Nal2)DKIHQQDFVNWLLAQKPSSGAPPPS-NH2 (SEQ ID NO. 647) | 57.9293 (% Inh, 10 nM) | |
| 0601GIP4595 | YaEGTFISDYSIAMDKIHQQD(D-Nal2)VNWLLAQKPSSGAPPPS-NH2 (SEQ ID No. 648) | | |
| 0601GIP4605 | YaEGTFISDYSIAMDKIHQQDFVN(D-Nal2)LLAQKPSSGAPPPS-NH2 (SEQ ID No. 649) | 9.4012 (% Inh, 10 nM) | |
| 0601GIP4609 | YaEGTFISDYSIAMDK-(epsilon-NH-(Aun-Aun-(2-(2methoxyethoxy)-acetoyl)))-IHQQDFVNWLLAQKPSSGAPPPS-NH2 (SEQ ID NO. 650) | | |

Alternative representations of some of the above compounds are as follows:
0601GIP4584 (SEQ ID No. 634)
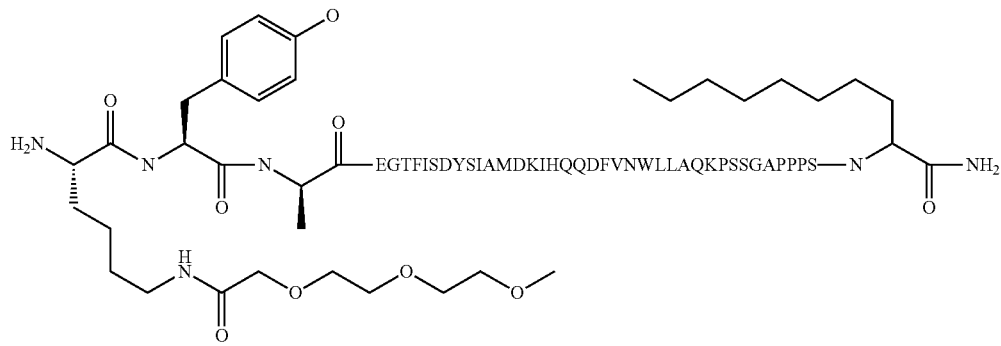
Lys(s-NH-(2-(2-(2-methoxyethoxy)ethoxy)acetoyl I)-[dAla2] GIP(1-30)-Exendin-4-(31-39)-Octylgly
0601GIP4833 (SEQ ID No. 635)
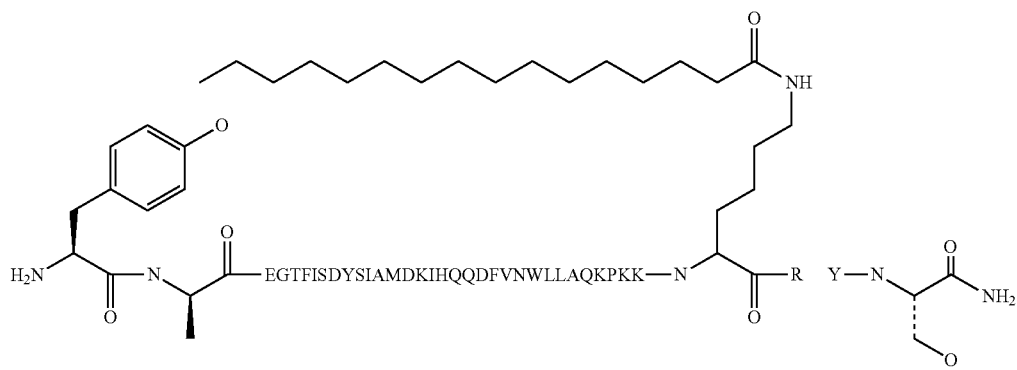
[dAla²]-GIP-(1-30)-(Lys34(z-NH-(palmitoyl)))-fGLP-1 v2-(31-37)
Molecular Weight = 4658.53
0601GIP4586 (SEQ ID No. 636)
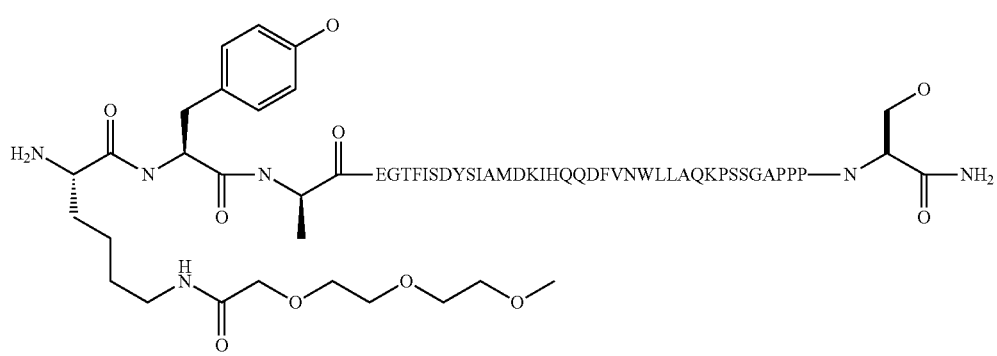
Lys(s-NH-(2-(2-(2-methoxyethoxy)ethoxy)acetoyl I)-[dAla2] GIP(1-30)-Exendin-4-(31-39)
Molecular Weight = 4598.21
Exact Mass = 4593
Molecular Formula = C209H315N51O64S 0601GIP4609 (SEQ ID No. 650)

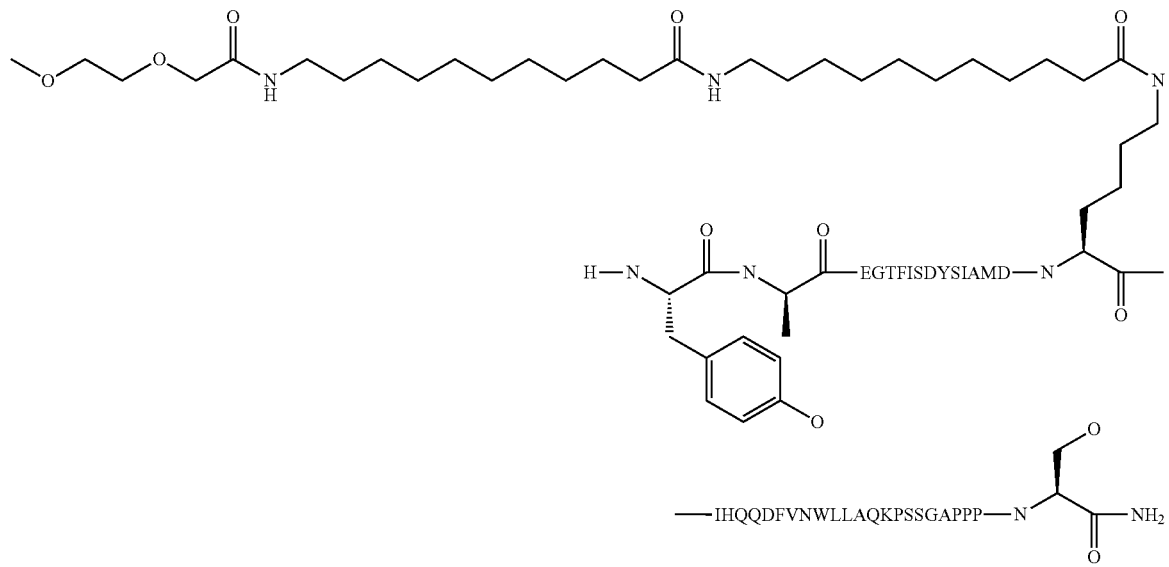

In other embodiments GIP compounds incorporate one or more modifications or derivatizations. For example, 0601GIP4294 contains both an octylglycyl N-terminus modification and a beta-Ala linker. Further exemplary compounds include:

| | | |
|---|---|---|
| 0601GIP4399 | N-octylglycine-YADGTFISDYSIAMDKIHQQDFVNWLLAQKPSSGAPPPS-NH2 (SEQ ID NO. 376) | 104.3139 (% Inh 10 nM) |
| 0601GIP4390 | YADGTFISDYSIAMDKIHQQDFVNWLLAQKPKKIRYS-NH2 (SEQ ID NO. 377) | 90.281 (% Inh 10 nM) |
| 0601GIP4395 | YSDGTFISDYSIAMDKIHQQDFVNWLLAQK(beta-A)PSSGAPPPS-NH2 (SEQ ID NO. 378) | 74.626 (% Inh 10 nM) |
| 0601GIP4387 | N-octylglycine-YSDGTFISDYSIAMDKIHQQDFVNWLLAQKPSSGAPPPS-NH2 (SEQ ID No. 379) | 97.011 (% Inh 10 nM) |
| 0601GIP4386 | YSDGTFISDYSIAMDKIHQQDFVNWLLAQKPKKIRYS-NH2 (SEQ ID No. 406) (SEQ ID No. 380) | |

Further exemplary compounds depict incorporation of modifications from other (non-human) species, or combinations of modifications as described herein, and their GIP Receptor binding and receptor activation activity, are shown in the table (changes from Compound 0601GIP3794 are highlighted in bold italic; and see also FIG. 12).

| Cmpd# | Sequence | GIP RBA | Cyclase |
|---|---|---|---|
| 0601GIP3794 | YaEGTFISDYSIAMDKIHQQDFVNWLLAQKPSSGAPPPS-NH2 (SEQ ID No. 186) | 3.8 | 38 |
| 0601GIP4190 | YaEGTFISDYSIA*L*DKIHQQDFVNWLLAQKPSSGAPPPS-NH2 (SEQ ID NO: 588) | 2.4 | 31 |
| 0601GIP4151 | YaEGTFIS*E*YSIAMDKIHQQDFVNWLLAQKPSSGAPPPS-NH2 (SEQ ID NO: 581) | 20 | 10000 |

| Cmpd# | Sequence | GIP RBA | Cyclase |
|---|---|---|---|
| 0601GIP4152 | YaEGTFISDYSIAMDKIHQQEFVNWLLAQKPSSGAPPPS-NH2 (SEQ ID NO: 582) | 2.3 | 22 |
| 0601GIP4150 | YaEGTFISDYSIAMDKIAQQDFVNWLLAQKPSSGAPPPS-NH2 (SEQ ID NO: 580) | 1.6 | 14 |
| 0601GIP4153 | YaEGTFISDYSIAMDKIRQQDFVNWLLAQKPSSGAPPPS-NH2 (SEQ ID NO: 583) | 0.53 | 11.4 |
| 0601GIP4149 | YaEGTFISDYSIAMDKIKQQDFVNWLLAQKPSSGAPPPS-NH2 (SE ID NO: 579) | 1.5 | 36 |
| 0601GIP4165 | YaEGTFISDYSIAMDKIHQQDFVNWLLAQAPSSGAPPPS-NH2 (SEQ ID NO: 584) | 21 | 40 |
| 0601GIP4176 | YaEGTFISDYSIAMDKIHQQDFVNWLLAQRPSSGAPPPS-NH2 (SEQ ID NO: 585) | 4.8 | 28 |
| 0601GIP4177 | YaEGTFISDYSIAMDKIHQQDFVNWLLAQHPSSGAPPPS-NH2 (SEQ ID NO: 586) | 2.9 | 11 |
| 0601GIP4213 | YaEGTFISDYSITMDKIHQQDFVNWLLAQKPSSGAPPPS-NH2 (SEQ ID NO. 592) | | 44 |
| 0601GIP4214 | YaEGTFISDYSIAMDKIHQQDFVNWLLSQKPSSGAPPPS-NH2 (SEQ ID No. 593) | | 145 |
| 0601GIP4694 | YaEGTFISDYSIAMDKIRQQDFVNWLEAQEPSSGAPPPS-NH2 (SEQ ID No. 651) | 8.1 (% Inh, 10 nM) | 305 |

In one embodiment the GIP hybrids or GIP portions thereof have one or more of the following modifications (for reference only to formula N-terminus-YaEGTFISDYSIAM-DKIHQQDFVNWLLAQK-Linker-PSSGAPPPS-NH2) (SEQ ID No. 652): dAla2 to Abu, Ala, Gly, or Ser; Met14 to Leu; His18 to Ala, Arg, or Lys; Asp21 to Glu; Lys30 to Arg or His; an N-terminus as Gly(Oct); and/or a bAla-bAla or Gly-Gly-Gly linker. In a further embodiment one or more of such changes are made to compound 0601GIP3794.

In one embodiment the GIP analogs or GIP portions of hybrids do not have a substitution, modification and/or substitution at any one or more of the following positions: Tyr1, Ty10, Val23, Leu27 and/or Phe22. As demonstrated in the following table, substitution by alanine at one or more of these positions in 0601GIP3794 result in an analog having less than 25% inhibition of receptor binding (at 10 nM peptide concentration). In yet another embodiment, the GIP analogs and hybrids do not contain an alanine substitution at one or more of Tyr1, Ty10, Val23, Leu27 and/or Phe22.

| | | | |
|---|---|---|---|
| 0601GIP4958 | AaEGTFISDYSIAMDKIHQQDFVNWLLAQKPSSGAPPPS-NH2 (SEQ ID No: 813) | 9.4 (% Inh 10 nM) | |
| 0601GIP4964 | YaEGTFISDASIAMDKIHQQDFVNWLLAQKPSSGAPPPS-NH2 (SEQ ID No: 814) | 15.7 (% Inh 10 nM) | |
| 0601GIP4940 | YaEGTFISDYSIAMDKIHQQDAVNWLLAQKPSSGAPPPS-NH2 (SEQ ID No: 815) | 21.9 (% Inh 10 nM) | |
| 0601GIP4941 | YaEGTFISDYSIAMDKIHQQDFANWLLAQKPSSGAPPPS-NH2 (SEQ ID No: 816) | -2.5' (% Inh 10 nM) | |
| 0601GIP4945 | YaEGTFISDYSIAMDKIHQQDFVNWLAAQKPSSGAPPPS-NH2 (SEQ ID No: 817) | 26.6 (% Inh 10 nM) | |

In yet a further embodiment, a GIP analog or hybrid can have an alanine substitution at one or more of the positions as compared to 0601GIP3794 and retain receptor binding as indicated in the following table. The data also indicate that these positions of GIP are tolerant to substitution and modification, as described herein.

| | | | |
|---|---|---|---|
| 0601GIP4959 | YaAGTFISDYSIAMDKIHQQDFVNWLLAQKPSSGAPPPS-NH2 (SEQ ID No: 818) | 72.2 (% Inh 10 nM) | |

```
0601GIP4960  YaEGAFISDYSIAMDKIHQQDFVNWLLAQKPSSGAPPPS-    55.9 (% Inh
             NH2 (SEQ ID No: 819)                         10 nM)

0601GIP4961  YaEGTAISDYSIAMDKIHQQDFVNWLLAQKPSSGAPPPS-    47 (% Inh
             NH2 (SEQ ID No: 820)                         10 nM)

0601GIP4962  YaEGTFIADYSIAMDKIHQQDFVNWLLAQKPSSGAPPPS-    72 (% Inh
             NH2 (SEQ ID No: 821)                         10 nM)

0601GIP4963  YaEGTFISAYSIAMDKIHQQDFVNWLLAQKPSSGAPPPS-    82.1 (% Inh
             NH2 (SEQ ID No: 822)                         10 nM)

0601GIP4967  YaEGTFISDYAIAMDKIHQQDFVNWLLAQKPSSGAPPPS-    90.2 (% Inh
             NH2 (SEQ ID No: 823)                         10 nM)

0601GIP4968  YaEGTFISDYSAAMDKIHQQDFVNWLLAQKPSSGAPPPS-    82 (% Inh
             NH2 (SEQ ID No: 824)                         10 nM)

0601GIP4969  YaEGTFISDYSIAADKIHQQDFVNWLLAQKPSSGAPPPS-    62.9 (% Inh
             NH2 (SEQ ID No: 825)                         10 nM)

0601GIP4970  YaEGTFISDYSIAMAKIHQQDFVNWLLAQKPSSGAPPPS-    86.7 (% Inh
             NH2 (SEQ ID No: 826)                         10 nM)

0601GIP4935  YaEGTFISDYSIAMDAIHQQDFVNWLLAQKPSSGAPPPS-    61.4 (% Inh
             NH2 (SEQ ID No: 827)                         10 nM)

0601GIP4936  YaEGTFISDYSIAMDKAHQQDFVNWLLAQKPSSGAPPPS-    84.6 (% Inh
             NH2 (SEQ ID No: 828)                         10 nM)

0601GIP4937  YaEGTFISDYSIAMDKIHAQDFVNWLLAQKPSSGAPPPS-    85.4 (% Inh
             NH2 (SEQ ID No: 829)                         10 nM)

0601GIP4938  YaEGTFISDYSIAMDKIHQADFVNWLLAQKPSSGAPPPS-    79.3 (% Inh
             NH2 (SEQ ID No: 830)                         10 nM)

0601GIP4939  YaEGTFISDYSIAMDKIHQQAFVNWLLAQKPSSGAPPPS-    91.9 (% Inh
             NH2 (SEQ ID No: 831)                         10 nM)

0601GIP4942  YaEGTFISDYSIAMDKIHQQDFVAWLLAQKPSSGAPPPS-    78.8 (% Inh
             NH2 (SEQ ID No: 832)                         10 nM)

0601GIP4943  YaEGTFISDYSIAMDKIHQQDFVNALLAQKPSSGAPPPS-    49 (% Inh
             NH2 (SEQ ID No: 833)                         10 nM)

0601GIP4944  YaEGTFISDYSIAMDKIHQQDFVNWALAQKPSSGAPPPS-    65.7 (% Inh
             NH2 (SEQ ID No: 834)                         10 nM)

0601GIP4946  YaEGTFISDYSIAMDKIHQQDFVNWLLAAKPSSGAPPPS-    73.9 (% Inh
             NH2 (SEQ ID No: 835)                         10 nM)
```

Further exemplary modifications (compared to 0601GIP3794) which can be used in the GIP portions of the compounds of the invention, and exemplary compounds containing them, are shown in the table (and see FIG. 12):

| Cmpd# | Sequence | GIP RBA | Cyclase |
|---|---|---|---|
| 0601GIP4263 | YaEGTFISDYSIALDKIAQQEFVNWLLAQRPSSGAPPPS-NH2 (SEQ ID No. 600) | 0.66 | 6.2 |
| 0601GIP4278 | YaEGTFISDYSIALDKIRQQEFVNWLLAQRPSSGAPPPS-NH2 (SEQ ID No. 601) | 0.24 | 3.5 |
| 0601GIP4264 | YaEGTFISDYSIALDKIKQQEFVNWLLAQRPSSGAPPPS-NH2 (SEQ ID NO. 653) | 2.1 | 14 |
| 0601GIP4279 | YaEGTFISDYSIALDKIAQQEFVNWLLAQHPSSGAPPPS-NH2 (SEQ ID NO. 602) | 2.1 | 14 |

| Cmpd# | Sequence | GIP RBA | Cyclase |
|---|---|---|---|
| OO | YaEGTFISDYSIALDKIRQQEFVNWLLAQHPSSGAPPPS-NH2 (SEQ ID No. 654) | | |
| PP | YaEGTFISDYSIALDKIKQQEFVNWLLAQHPSSGAPPPS-NH2 (SEQ ID No. 655) | | |
| 0601GIP4235 | YaEGTFISDYSIAMDKIHQVKFVNWLLAQKPSSGAPPPS-NH2 (SEQ ID No. 597) | | |
| 0601GIP4283 | YaEGTFISDYSIALDKIRQQEFVNWLLAQKPSSGAPPPS-NH2 (SEQ ID No. 603) | 0.41 | |
| 0601GIP4284 | YaEGTFISDYSIALDKIQQEFVNWLLAQKPSSGAPPPS-NH2 (SEQ ID No. 604) | 1.8 | |
| 0601GIP4285 | YaEGTFISDYSIALDKIAQQEFVNWLLAQKPSSGAPPPS-NH2 (SEQ ID No. 605) | 0.58 | |
| 0601GIP4286 | YaEGTFISDYSIALDKIRQQEFVNWLLAQHPSSGAPPPS-NH2 (SEQ ID No. 606) | 1000 | |
| 0601GIP4287 | YaEGTFTADYSKALDKIHQQDFVNWLLAQKPSSGAPPP-S-NH2 (SEQ ID NO. 607) | 27 | |
| VV | YaEGTFTSDYSKALDKIHQQDFVNWLLAQKPSSGAPPPS-NH2 (SEQ ID No. 656) | | |
| WW | YaEGTFISDYSKAMDKIRQQEFVNWLLAQKPSSGAPPPS-NH2 (SEQ ID NO. 657) | | |
| XX | YaEGTFISDYSIALEKIRQQKFVNWLLAQKPSSGAPPPS-NH2 (SEQ ID No. 658) | | |
| 0601GIP4289 | YaEGTFISDYSIALDKIRQQDFVEWLLAQKPSSGAPPPS-NH2 (SEQ ID No 609) | 0.58 | 2 |
| ZZ | YaEGTFISDYSIALDKIRQQEFVNWLLAQK-bAla-PSSGAPPPS-NH2 (SEQ ID No. 659) | | |
| AAA | YaEGTFISDYSIALDKIRQQEFVNWLAQK-bAla-PSSGAPPPS-NH2 (SEQ ID No. 660) | | |
| 0601GIP4215 | YaEGTFISDYSIAMDKIHQQLFIEWLKNGGPSSGAPPPS-NH2 (SEQ ID No. 374) | | |
| 0601GIP4288 | YaEGTFISDYSIAMDKIRQQEFVNWLLAQKPSSGAPPPS-NH2 (SEQ ID NO. 608) | | |
| AAAA | YaEGTFISDYSIAMDKIHQQDFVNFLLAQKPSSGAPPPS-NH2 (SEQ ID No. 661) | | |
| BBBB | YAEGTFISDYSIAMDKIHQQDFVNFLLAQKPSSGAPPPS-NH2 (SEQ ID No. 185) | | |
| 0601GIP4696 | YaEGTFISDYSIAMDKILQQDFVNWLSAQQPSSGAPPPS-NH2 (SEQ ID No. 662) | 17.0923 (% Inh, 10 nM) | |

Exemplary analogs also include amino acid modifications that eliminate or reduce oxidation. Such replacements include a deletion or replacement of methionine 14 with leucine and/or the tryptophan 25 with phenylalanine. Accordingly, specific exemplary analogs include a variant of each analog described herein by having one or more such replacements. As an example are compounds AAAA and BBBB which are the D-Ala2 and L-Ala2 analogs of 0601GIP3794 having a Phe for Trp replacement at position 25.

Further exemplary "tail" modifications (compare to 0601GIP3794 (SEQ ID No. 186)), for example those having a frog GLP-1 tail (PKKIRYS) (SEQ ID NO. 421) alone or in combination with other modifications and derivatizations, and exemplary compounds having them, are depicted in the table below (and see FIG. 12), along with receptor binding and activation data. Ado is 8-Amino 3,6 dioxaoctanoic acid and Aun is 11-amino undecanoic acid.

| Cmpd # | Sequence | GIP RBA | GIPR Cyclase |
|---|---|---|---|
| 0601GIP3794 | YaEGTFISDYSIAMDKIHQQDFVNWLLAQKPSSGAPPPS-NH2 (SEQ ID No. 186) | 3.8 | 38 |
| 0601GIP4216 Trp cage "Leu21-Pro38" | YaEGTFISDYSIAMDKIHQQLFIEWLKNGGPSSGAPPPS-NH2 (SEQ ID No. 594) | 12 | 122 |
| 0601GIP4233 fGLP1 tail | YaEGTFISDYSIAMDKIHQQDFVNWLLAQKPKKIRYS-NH2 (SEQ ID No. 595) | 0.1 | 31 |
| 0601GIP4234 fGLP1 tail | YaEGTFISDYSIAMDKIHQQDFVNWLLAQKPSKEIIS-NH2 (SEQ ID No. 596) | 3.4 | 83 |
| 0601GIP4236 Helospectin II tail | YaEGTFISDYSIAMDKIHQQDFVNWLLAQKTSPRPPS-NH2 (SEQ ID No. 598) | 0.62 | 29 |
| 0601GIP4798 | LYaEGTFISDYSIAMDKIHQQDFVNWLLAQKPKKIRYS-NH2 (SEQ ID No. 663) | 82.3 (% Inh 10 nM) | |
| 0601GIP4799 | LYAEGTFISDYSIAMDKIHQQDFVNWLLAQKPKKIRYS-NH2 (SEQ ID No. 664) | 91.6 (% Inh 10 nM) | |
| 0601GIP4801 | IYaEGTFISDYSIAMDKIHQQDFVNWLLAQKPKKIRYS-NH2 (SEQ ID No. 665) | 88.8 (% Inh 10 nM) | |
| 0601GIP4802 | LYaEGTFISDYSIALDKIAQQEFVNWLLAQKPKKIRYS-NH2 (SEQ ID No. 666) | 87.3 (% Inh 10 nM) | |
| 0601GIP4803 | LYAEGTFISDYSIALDKIAQQEFVNWLLAQKPKKIRYS-NH2 (SEQ ID No. 667) | 89.9 (% Inh 10 nM) | |
| 0601GIP4804 | IYaEGTFISDYSIALDKIAQQEFVNWLLAQKPKKIRYS-NH2 (SEQ ID No. 668) | 85.3 (% Inh 10 nM) | |
| 0601GIP4766 | Methyl-YaEGTFISDYSIAMDKIHQQDFVNWLLAQKPKKIRYS-NH2 (SEQ ID No. 669) | 94.5 (% Inh, 10 nM) | |
| | HaEGTFISDYSIAMDKIHQQDFVNWLLAQKPKKIRYS-NH2 (SEQ ID No. 670) | | |
| | HGEGTFISDYSIAMDKIHQQDFVNWLLAQKPKKIRYS-NH2 (SEQ ID No. 671) | | |
| | HAEGTFISDYSIAMDKIHQQDFVNWLLAQKPKKIRYS-NH2 (SEQ ID No. 672) | | |
| | HGEGTFISDYSIALDKIAQQEFVNWLLAQKPKKIRYS-NH2 (SEQ ID No. 673) | | |

| Cmpd # | Sequence | GIP RBA | GIPR Cyclase |
|---|---|---|---|
| | HGEGTFISDYSIALDKIRQQEFVNWLLAQKPKKIRYS-NH2 (SEQ ID No. 674) | | |
| | HGEGTLISDYSIAMDKIHQQDFVNWLLAQKPKKIRYS-NH2 (SEQ ID No, 675) | | |
| | YAibEGTFISDYSIAMDKIHQQDFVNWLLAQKPKKIRYS-NH2 (SEQ ID No. 676) | | |
| 0601GIP4192 | YaEGTFISDYSIAMDKIHQQDFVNWLLAQKSGAPPPS-NH2 (SEQ ID NO 590) | 7 | 135 |
| 0601GIP4807 | YaEGTFISDYSIALDKIHQQDFVNWLLAQKPKKIRYS-NH2 (SEQ ID No. 677) | 96.1 (% Inh 10 nM) | |
| 0601GIP4233 | YaEGTFISDYSIAMDKIHQQDFVNWLLAQKPKKIRYS-NH2 (SEQ ID NO. 678) | 0.1 RIN, 0.210, IC50 HEK-GIPR | 31 |
| 0601GIP4327 | YAEGTFISDYSIAMDKIHQQDFVNWLLAQKPKKIRYS-NH2 (SEQ ID NO. 405) | 96.504 (% Inh, 10 nM) | 92.6 |
| 0601GIP4762 | YAEGTFISDYSIAMDKIHQQDFVNWLLAQKPKKIRYS-OH (SEQ ID No. 679) | 79.1 (% Inh, 10 nM | |
| 0601GIP4386 | YSDGTFISDYSIAMDKIHQQDFVNWLLAQKPKKIRYS-NH2 (SEQ ID NO. 406) | IC50 = 156 nM RIN, 93.588 (% Inh 10 nM) | 56 |
| 0601GIP4698 | Guanido-YaEGTFISDYSIAMDKIHQQDFVNWLLAQKPKKIRYS-NH2 (SEQ ID No. 680) | 78.3 (% Inh 10 nM) | |
| 0601GIP4791 | Guanido-YaEGTFISDYSIALDKIRQQEFVNWLLAQKPKKIRYS-NH2 (SEQ ID No. 681) | | |
| 0601GIP4538 | YSEGTFISDYSIAMDKIHQQDFVNWLLAQKPKKIRYS-NH2 (SEQ ID No. 407) | 94.2371 (% Inh 10 nM) | |
| 0601GIP4539 | YaEGTFISDYSIALDKIRQQEFVNWLLAQKPKKIRYS-NH2 (SEQ ID No. 615) | 98.6752 (% Inh 10 nM) | |
| 0601GIP4540 | YaEGTFISDYSIALDKIRQQDFVEWLLAQKPKKIRYS-NH2 (SEQ ID No. 616) | 92.2169 (% Inh 10 nM) | |
| 0601GIP4648 | YaEGTFISDYSIAMDKIHQQDFVNWLLAQK(beta-A)(beta-A)PKKIRYS-NH2 (SEQ ID No. 682) | 85.1034 (% Inh 10 nM) | |
| 0601GIP4631 | YaEGTFISDYSIALDKIAQQEFVNWLLAQKPKKIRYS-NH2 (SEQ ID No. 683) | 79.031 (% Inh 10 nM) | |
| 0601GIP4805 | OctG-YAEGTFISDYSIALDKIAQQEFVNWLLAQKPKKIRYS-NH2 (SEQ ID No. 684) | 83.5 (% Inh 10 nM) | |

-continued

| Cmpd # | Sequence | GIP RBA | GIPR Cyclase |
|---|---|---|---|
| 0601GIP4561 | OctG-YaEGTFISDYSIAMDKIRQQEFVNWLLAQKPKKIRYS-NH2 (SEQ ID No. 685) | | |
| 0601GIP4673 | OctG-YaEGTFISDYSIALDKIAQQEFVNWLLAQKPKKIRYS-NH2 (SEQ ID No. 686) | 94.9197 (% Inh 10 nM) | |
| 0601GIP4672 | OctG-YaEGTFISDYSIALDKIAQQDFVEWLLAQKPKKIRYS-NH2 (SEQ ID No. 687) | 91.9031 (% Inh 10 nM) | |
| 0601GIP4713 | Guan-YaEGTFISDYSIALDKIAQQEFVNWLLAQKPKKIRYS-NH2 (SEQ ID No. 688) | 86.7 (% Inh 10 nM) | |
| 0601GIP4711 | Guan-YaEGTFISDYSIALDKIAQQDFVEWLLAQKPKKIRYS-NH2 (SEQ ID No. 689) | 95 (% Inh 10 nM) | |
| 0601GIP83 | YaEGTFISDYSIAMDKIHQQDFVNWLLAQKPSKEIIS-NH2 (SEQ ID No. 690) | 3.4 | |
| 0601GIP4710 | YaEGTFISDYSIAMDKIHQQDFVNWLLAQKPSKEIIH-OH (SEQ ID No. 691) | 79.2 (% Inh 10 nM) | |
| 0601GIP4765 | YaEGTFISDYSIAMDKIHQQDFVNWLLAQKPSKEIIS-OH (SEQ ID No. 692) | 67 (% Inh 10 nM) | |
| 0601GIP4236 | YaEGTFISDYSIAMDKIHQQDFVNWLLAQKTSPRPPS-NH2 (SEQ ID No. 598) | 0.62 | 29 |
| 0601GIP4328 | YAEGTFISDYSIAMDKIHQQDFVNWLLAQKTSPRPPS-NH2 (SEQ ID No. 408) | 104.7575 (% Inh, 10 nM) | 46.8 |
| 0601GIP4345 | YAEGTFISDYSIAMDKIHQQDFVNWLLAQKTSPPP-NH2 (SEQ ID No. 612) | 76.134 (% Inh, 10 nM) | 103 |
| 0601GIP4401 | YAEGTFISDYSIAMDKIHQQDFVNWLLAQKTSPRPPSS-NH2 (SEQ ID No. 409) | 102.8819 (% Inh, 10 nM) | |
| 0601GIP4346 | YaEGTFISDYSIAMDKIHQQDFVNWLLAQKPKLIKLIKS-NH2 (SEQ ID No. 613) | 91.004 (% Inh, 10 nM) | 235 |
| 0601GIP4700 | YAEGTFISDYSIAMDKIHQQDFVNWLLAQKPKGKGKS-NH2 (SEQ ID No. 693) | 86.6 (% Inh, 10 nM) | |
| 0601GIP4400 | YAEGTFISDYSIAMDKIHQQDFVNWLLAQK-Ado-Aun (SEQ ID No. 410) | 98.3705 (% Inh, 10 nM) | |
| 0601GIP4402 | YAEGTFISDYSIAMDKIHQQDFVNWLLAQ-K(N-epsilon)-PSSGAPPPS-NH2 (SEQ ID No. 614) | 103.3047 (% Inh, 10 nM) | |
| 0601GIP4619 | YaEGTFISDYSIAMDKIHQQDFVNWLLAQKGFVLWKGIQ-NH2 (SEQ ID No. 694) | 84.5725 (% Inh, 10 nM) | |

Even further exemplary "tail" modifications (compare to 0601GIP4233 which incorporates a frog GLP1 tail PKKIRYS (SEQ ID NO. 421)) which can be used alone or in combination with other modifications and derivatizations, and the exemplary GIP compounds containing them, are depicted in the following table along with various activities. Analog 0601GIP4233 is an example of a GIP analog having surprisingly high solubility (e.g., solubility greater than 5 mg/ml in 30 mM histidine buffer at pH 4 to 8) and contains a frog GLP-1 C-terminal tail. A further such tail modification that improves solubility of a GIP analog or hybrid into which it is incorporated is a chimera of the frog tail and the exendin tail: PKKIPPPS (SEQ ID NO. 836) as found in 0601GIP4951. This chimeric tail can be incorporated into other GIP analogs and hybrids as disclosed herein to improve solubility. Further modification and derivatizations as shown in the table below can also improve duration of action, e.g. as tested in a rat IVGTT assay, and plasma stability, when incorporated into a GIP analog or hybrid. In in vitro studies, the main cleavage site of an analog having the frog tail was at the Ile34-Arg35 peptide bond. Accordingly, in one embodiment is a GIP analog or hybrid having a modification, substitution or derivitization at one or both of these two positions to reduce in vitro cleavage as compared to the parent peptide. Examples of such modifications (as compared to 0601GIP4233) are shown in the table below, and are contemplated to be used with any of the other GIP analogs and hybrids shown herein.

|  |  | (% Inh 10 nm, GIP-LF Assay) | OGTT/ GL(%) | Basal Gluc. Low. 80 nmol/Kg | Solubility | Duration In The Rat IVGTT Assay |
|---|---|---|---|---|---|---|
| 0601 GIP 4233 | YaEGTFISDYSIA MDKIHQQDFVN WLLAQKPKKIR YS-NH2 (SEQ ID No. 595) | 89 (% Inh 10 nM); 0.12, 0.41, 0.21 IC50 HEK-GIPR | -22 350 nmol/ kg, -17 30 nmol/ kg | -8 to -19%, AUC240 | >5 mg/ml | <794 @ -120 min |
| 0601 GIP 4807 | YaEGTFISDYSIA LDKIHQQDFVN WLLAQKPKKIR YS-NH2 (SEQ ID No. 677) | 96.1 (% Inh 10 nM) | -27, 30 nmol/ kg | -26%, AUC240 |  | <794 @ -120 min |
| 0601 GIP 4798 | LYaEGTFISDYSI AMDKIHQQDFV NWLLAQKPKKI RYS-NH2 (SEQ ID No. 663) | 82.3 (% Inh 10 nM) | -27, 30 nmol/ kg | -8%, AUC240 |  | <3794 @ -120 min |
| 0601 GIP 4799 | LYAEGTFISDYS IAMDKIHQQDF VNWLLAQKPK KIRYS-NH2 (SEQ ID No. 664) | 91.6 (% Inh 10 nM) | -10, 30 nmol/ kg |  |  |  |
| 0601 GIP 4801 | IYaEGTFISDYSI AMDKIHQQDFV NWLLAQKPKKI RYS-NH2 (SEQ ID No. 665) | 88.8 (% Inh 10 nM) | -23, 30 nmol/ kg | -1%, AUC240 |  |  |
| 0601 GIP 4802 | LYaEGTFISDYSI ALDKIAQQEFV NWLLAQKPKKI RYS-NH2 (SEQ ID No. 666) | 87.3 (% Inh 10 nM) | -28, 30 nmol/ kg | -15%, AUC240 |  | <794 @ -120 min |
| 0601 GIP 4803 | LYAEGTFISDYS IALDKIAQQEFV NWLLAQKPKKI RYS-NH2 (SEQ ID No. 667) | 89.9 (% Inh 10 nM) | -16, 30 nmol/ kg |  |  |  |
| 0601 GIP 4804 | IYaEGTFISDYSI ALDKIAQQEFV NWLLAQKPKKI RYS-NH2 (SEQ ID No. 668) | 85.3 (% Inh 10 nM) | -15, 30 nmol/ kg |  |  |  |
| 0601 GIP 4951 | YaEGTFISDYSIA MDKIHQQDFVN WLLAQKPKKIP PPS-NH2 (SEQ ID No: 837) | 102.6 (% Inh, 10 nM) | -25, 30 nmol/ kg | -17%, AUC240 | >5 mg/ml | <794 @ -120 min |
| 0601 GIP 4838 | HaEGTFISDYSIA MDKIHQQDFVN WLLAQKPKKIR YS-NH2 (SEQ ID No: 838) | 34.3 (% Inh 10 nM) |  |  |  |  |

| | | (% Inh 10 nm, GIP-LF Assay) | OGTT/ GL(%) | Basal Gluc. Low. 80 nmol/Kg | Solubility | Duration In The Rat IVGTT Assay |
|---|---|---|---|---|---|---|
| 0601 GIP 4839 | HGEGTFISDYSI AMDKIHQQDFV NWLLAQKPKKI RYS-NH2 (SEQ ID No: 839) | 23.9 (% Inh 10 nM) | | | | |
| 0601 GIP 4840 | HAEGTFISDYSI AMDKIHQQDFV NWLLAQKPKKI RYS-NH2 (SEQ ID No: 840) | 44.1 (% Inh 10 nM) | | | | |
| 0601 GIP 4841 | HGEGTFISDYSI ALDKIAQQEFV NWLLAQKPKKI RYS-NH2 (SEQ ID No: 841) | 56.6 (% Inh 10 nM) | | | | |
| 0601 GIP 4842 | HGEGTFISDYSI ALDKIRQQEFV NWLLAQKPKKI RYS-NH2 (SEQ ID No: 842) | 40.8 (% Inh 10 nM) | | | | |
| 0601 GIP 4843 | HGEGTLISDYSI AMDKIHQQDFV NWLLAQKPKKI RYS-NH2 (SEQ ID No: 843) | 3 (% Inh 10 nM) | | | | |
| 0601 GIP 4845 | YaEGTFISDYSIA MDKIHQQDFVN QLLAQKPKKIR YS-NH2 (SEQ ID No: 844) | 69.5 (% Inh, 10 nM) | −21, 30 nmol/ kg | −14%, AUC240 | | |
| 0601 GIP 4865 | YaEGTFISDYSIA MDKIHQQDFVQ WLLAQKPKKIR YS-NH2 (SEQ ID No: 845) | 85.6 (% Inh 10 nM) | −17, 30 nmol/ kg | | | |
| 0601 GIP 4864 | Y(Aib)EGTFISD YSIAMDKIHQQ DFVNWLLAQKP KKIRYS-NH2 (SEQ ID No: 846) | 91.2 (% Inh 10 nM) | −13, 30 nmol/ kg | | | |
| 0601 GIP 4814 | YaEGTFISDYSIA MDKIHQQDFVN WLLAQKAKKIR YS-NH2 (SEQ ID No. 695) | 88 (% Inh 10 nM) | −22, 30 nmol/ kg | −16%, AUC240 | | |
| 0601 GIP 4815 | YaEGTFISDYSIA MDKIHQQDFVN WLLAQKPAKIR YS-NH2 (SEQ ID No. 696) | 89 (% Inh 10 nM) | −23, 30 nmol/ kg | −14%, AUC240 | | <794 @ −120 min |
| 0601 GIP 4816 | YaEGTFISDYSIA MDKIHQQDFVN WLLAQKPKAIR YS-NH2 (SEQ ID NO: 697) | 87.3 (% Inh 10 nM) | −19, 30 nmol/ kg | −9%, AUC240 | | <794 @ −120 min |
| 0601 GIP 4856 | YaEGTFISDYSIA MDKIHQQDFVN WLLAQKPKKA RYS-NH2 (SEQ ID No: 847) | 83.7 (% Inh 10 nM) | −29, 30 nmol/ kg | −3%, AUC240 | | <794 @ −120 min |

-continued

| | | (% Inh 10 nm, GIP-LF Assay) | OGTT/GL(%) | Basal Gluc. Low. 80 nmol/Kg | Solubility | Duration In The Rat IVGTT Assay |
|---|---|---|---|---|---|---|
| 0601 GIP 4817 | YaEGTFISDYSIA MDKIHQQDFVN WLLAQKPKKIA YS-NH2 (SEQ ID No. 698) | 80.5 (% Inh 10 nM); 0.45IC50Hek GIPR | -20, 30 nmol/ kg | -4%, AUC240 | | <794 @ -120 min |
| 0601 GIP 4818 | YaEGTFISDYSIA MDKIHQQDFVN WLLAQKPKKIR AS-NH2 (SEQ ID No. 699) | 76.1 (% Inh 10 nM) | -23, 30 nmol/ kg | -9%, AUC240 | | |
| 0601 GIP 4819 | YaEGTFISDYSIA MDKIHQQDFVN WLLAQKPKKIR YA-NH2 (SEQ ID No. 700) | 80.4 (% Inh 10 nM) | -26, 30 nmol/ kg | -15%, AUC240 | | |
| 0601 GIP 4820 | YaEGFISDYSIA MDKIHQQDFVN WLLAQKPSPKK IRYS-NH2 (SEQ ID No. 701) | 46 (% Inh 10 nM) | | | | |
| 0601 GIP 4823 | YaEGTFISDYSIA MDKIHQQDFVN WLLAQKPSPKK IRYS-NH2 (SEQ ID No. 702) | 94.1 (% Inh 10 nM) | -23, 30 nmol/ kg | -23%, AUC240 | | <794 @ -120 min |
| 0601 GIP 4821 | YaEGTFISDYSIA MDKIHQQDFVN WLLAQKPKSAR PS-NH2 (SEQ ID No. 703) | 93.5 (% Inh 10 nM) | -28, 30 nmol/ kg | -5%, AUC240 | | <794 @ -120 min |
| 0601 GIP 4822 | YaEGTFISDYSIA MDKIHQQDFVN WLLAQKPKKLK PS-NH2 (SEQ ID No. 704) | 95.4 (% Inh 10 nM) | -23, 30 nmol/ kg | -11% AUC240 | | <794 @ -120 min |
| 0601 GIP 4914 | YaEGTFISDYSIA MDKIHQQDFVN WLLAQKPKKQ RYS-NH2 (SEQ ID No: 848) | 96.3 (% Inh 10 nM) | | | | |
| 0601 GIP 4913 | YaEGTFISDYSIA MDKIHQQDFVN WLLAQKPKKIQ YS-NH2 (SEQ ID No: 849) | 92.1 (% Inh 10 nM) | | | | |
| 0601 GIP 4906 | YaEGTFISDYSIA MDKIHQQDFVN WLLAQKPSSGR YS-NH2 (SEQ ID No: 850) | | -28, 30 nmol/ kg | -15%, AUC240 | | |
| 0601 GIP 4851 | YaEGTFISDYSIA MDKIHQQDFVN WLLAQKPNKIR YS-NH2 (SEQ ID No: 851) | 87 (% Inh 10 nM) | | | | |
| 0601 GIP 4852 | YaEGTFISDYSIA MDKIHQQDFVN WLLAQKPKNIR YS-NH2 (SEQ ID No: 852) | 90 (% Inh 10 nM) | | | | |

-continued

| | | (% Inh 10 nm, GIP-LF Assay) | OGTT/ GL(%) | Basal Gluc. Low. 80 nmol/Kg | Solubility | Duration In The Rat IVGTT Assay |
|---|---|---|---|---|---|---|
| 0601 GIP 4855 | YaEGTFISDYSIA MDKIHQQDFVN WLLAQKPQQIR YS-NH2 (SEQ ID No: 853) | 78.8 (% Inh 10 nM); IC50 = 0.72 H EKGIPR | -21, 30 nmol/ kg | | | <794 @ -120 min |
| 0601 GIP 4853 | YaEGTFISDYSIA MDKIHQQDFVN WLLAQKPQKIR YS-NH2 (SEQ ID No: 854) | 91 (% Inh 10 nM) | -25, 30 nmol/ kg | -20%, AUC240 | | <794 @ -120 min |
| 0601 GIP 4854 | YaEGTFISDYSIA MDKIHQQDFVN WLLAQKPKQIR YS-NH2 (SEQ ID No: 855) | 93.5 (% Inh 10 nM) | -14, 30 nmol/ kg | | | <794 @ -120 min |
| 0601 GIP 4898 | YaEGTFISDYSIA MDKIHQQDFVN WLLAQKPKSIR YS-NH2 (SEQ ID No: 856) | | -23, 30 nmol/ kg | | | |
| 0601 GIP 4899 | YaEGTFISDYSIA MDKIHQQDFVN WLLAQKPSKIR YS-NH2 (SEQ ID No: 857) | | -26, 30 nmol/ kg | | | |
| 0601 GIP 4900 | YaEGTFISDYSIA MDKIHQQDFVN WLLAQKPQKIQ YS-NH2 (SEQ ID No: 858) | | -29, 30 nmol/ kg | | | |
| 0601 GIP 4904 | YaEGTFISDYSIA MDKIHQQDFVN WLLAQKPKGKI RYS-NH2 (SEQ ID No: 859) | | -35, 30 nmol/ kg | | | |
| 0601 GIP 4824 | YaEGTFISDYSIA MDKIHQQDFVN WLLAQKPKK(O ctG)RYS-NH2 (SEQ ID No. 709) | 92.9 (% Inh 10 nM) | -15, 30 nmol/ kg | | | |
| 0601 GIP 4825 | YaEGTFISDYSIA MDKIHQQDFVN WLLAQKPKKIR YS(OctG)-NH2 (SEQ ID No. 710) | 77.5 (% Inh 10 nM) | -22, 30 nmol/ kg | -15%, AUC240 | | |
| 0601 GIP 4806 | OctG- YAEGTFISDYSI AMDKIRQQEFV NWLLAQHPKKI RYS-NH2 (SEQ ID No. 620) | 101.3 (% Inh 10 nM) | -14, 30 nmol/ kg | -5%, AUC240 | | |
| 0601 GIP 4805 | OctG- YAEGTFISDYSI ALDKIAQQEFV NWLLAQKPKKI RYS-NH2 (SEQ ID No. 684) | 83.5 (% Inh 10 nM) | -13, 30 nmol/ kg | | | |

Accordingly, in one embodiment are GIP analogs having a potency loss of less than 25%, less than 15%, less than 10% or less than about 5%, at pH 4 to 9, at pH 5 to 7, or further at pH 6 to 7, under accelerated stability of 40 degrees C. for at least 1, at least 3 or at least 7 days. In yet a further embodiment, the GIP analog has a solubility greater than about at least 1 mg/ml, at least 2 mg/ml, at least 3 mg/ml, at least 4 mg/ml or greater than at least 5 mg/ml, at least one or more of about pH 4, 5, 6, 7, 8, or 9, and further at at least three or more of these pHs, and even further at all of these pHs. In one embodiment the GIP compound has a solubility of at least about 2.0 mg/ml in 30 mM histidine buffer at pH 6 and/or at least about 5.0 mg/ml in 30 mM histidine buffer at pH 6. In yet a further embodiment, the GIP compound retains at least about 80% activity, at least about 90% activity or at least about 95% activity in 30 mM histidine buffer at pH 6 for at least 7 days at 40 degrees C.

Further exemplary "tail" modifications (compare to 0601GIP4285 (SEQ ID No. 605) which has Leu14, Ala18 and Glu21 substitutions compared to 0601GIP3794) that increase solubility of GIP analogs, improve their duration of action and/or increase glucose lowering, as compared to 0601GIP4285, and that can be used alone or combined with other modifications and derivatizations, and the exemplary GIP compounds containing them, are depicted in the following table along with their receptor binding and activation data. For example, the N for P substitution in the tail region of 0601GIP4974 as compared to 0601GIP4285, and more specifically the modified tail region, are such modifications that can be incorporated into other GIP compounds. ("Ocg" below stands for octylglycine).

| | | (% Inh 10 nm, GIP-LF Assay) | OGTT/ GL(%) | Basal Gluc. Low. 80 nmol/kg | Solu- bility | Duration In The Rat TVGTT Assay |
|---|---|---|---|---|---|---|
| 0601 GIP 4285 | YaEGTFISDYSIALDKIAQ QEFVNWLLAQKPSSGAPP PS-NH2 (SEQ ID No. 605) | IC50 = 0.110, 0.22 HEK-GIPR) | -17 30 nmol/ kg | -2%, AUC240 | <1 mg/ ml | =794 at -120 min |
| 0601 GIP 4974 | YaEGTFISDYSIALDKIAQ QEFVNWLLAQKPSSGAPP NS-NH2 (SEQ ID No: 860) | IC50 HEK-GIPR 0.18; | -21, 30 nmol/ kg; ED50 ~0.4 nmol/ kg | -19%, AUC240 | <1 mg/ ml | >794 at -120 min |
| 0601 GIP 4992 | YaEGTFISDYSIALDKIAQ QEFVNWLLAQKPSSGAPP QS-NH2 (SEQ ID No: 861) | 85.8 (% Inh, 10 nM) | -18, 30 nmol/ kg | -17%, AUC240 | | |
| 0601 GIP 4979 | YaEGTFISDYSIALDKIAQ QEFVNWLLAQKPSSGAPP QSK-NH2 (SEQ ID No: 862) | 84.5 (% Inh, 10 nM) | -20, 30 nmol/ kg | -19%, AUC240 | <1 mg/ ml | =794 at -120 min |
| 0601 GIP 5074 | YaEGTFISDYSIALDKIAQ QEFVNWLLAQKPSSGAPP PSK-NH2 (SEQ ID No: 863) | 95.8 (% Inh, 10 nM) | -37, 30 nmol/ kg | | | |
| 0601 GIP 5083 | YaEGTFISDYSIALDKIAQ QEFVNWLLKQKPSSGAPP PS-NH2 (SEQ ID No: 864) | 98.9 (% Inh, 10 nM) | -23, 30 nmol/ kg | | | |
| 0601 GIP 5084 | YaEGTFISDYSIALDKIAQ QEFVNWLLAQKPSSGKPP PS-NH2 (SEQ ID No: 865) | 99.4 (% Inh, 10 nM) | -22, 30 nmol/ kg | | | |
| 0601 GIP 5085 | YaEGTFISDYSIALDKIAQ QEFVNWLLAQKPSSGAK PPS-NH2 (SEQ ID No: 866) | 98.1 (% Inh, 10 nM) | -26, 30 nmol/ kg | | | |
| 0601 GIP 5095 | YaEGTFISDYSIALDKIAQ QEFVNWLLAQKPSSGAP KPS-NH2 (SEQ ID No: 867) | 98.9 (% Inh, 10 nM) | -22, 30 nmol/ kg | | | |
| 0601 GIP 5096 | YaEGTFISDYSIALDKIAQ QEFVNWLLAQKPSSGAPP KS-NH2 (SEQ ID No: 868) | 98.2 (% Inh, 10 nM) | -18, 30 nmol/ kg | | | |
| 0601 GIP 5097 | YaEGTFISDYSIALDKIAQ QEFVNWLLAQKPSSGAPP KSK-NH2 (SEQ ID No: 869) | 100.9 % Inh, 10 nM) | -21, 30 nmol/ kg | | | |

Further exemplary tail modifications are described in the following table. The modifications provide increased plasma stability. In one embodiment the frog GLP-1 tail region is substituted or modified at or near the "KK" sequence to prevent or reduce proteolytic cleavage. While such modified tail region is depicted in the context of specific GIP analogs in the table below, it is intended that such a modified tail sequence that increases plasma stability of the attached GIP portion, is to be used with any GIP analog or derivative, including those disclosed herein, to provide enhanced plasma stability and longer half-life. The modified tail can be combined with one or more other GIP modifications or derivatizations as discussed herein. Further, modified-frog-tail-containing GIP compounds are particularly useful components of GIP hybrids. In a further embodiment the frog GLP1 tail and analogs and derivatives thereof that enhance stability are of particular interest as an alternative to the exendin tail as used with GIP, exendin, GLP1 or other peptide hormones, as discussed herein.

```
0601GIP4814    YaEGTFISDYSIAMDKIHQQDFVNWLLAQKAKKI      88 (% Inh
               RYS-NH2                                 10 nM)
               (SEQ ID No. 695)

0601GIP4815    YaEGTFISDYSIAMDKIHQQDFVNWLLAQKPAKI      89 (% Inh
               RYS-NH2                                 10 nM)
               (SEQ ID No. 696)

0601GIP4816    YaEGTFISDYSIAMDKIHQQDFVNWLLAQKPKAI      87.3 (% Inh
               RYS-NH2                                 10 nM)
               (SEQ ID NO. 697)

0601GIP4817    YaEGTFISDYSIAMDKIHQQDFVNWLLAQKPKKI      80.5 (% Inh
               AYS-NH2                                 10 nM)
               (SEQ ID No. 698)

0601GIP4818    YaEGTFISDYSIAMDKIHQQDFVNWLLAQKPKKI      76.1 (% Inh
               RAS-NH2                                 10 nM)
               (SEQ ID No. 699)

0601GIP4819    YaEGTFISDYSIAMDKIHQQDFVNWLLAQKPKKI      80.4 (% Inh
               RYA-NH2                                 10 nM)
               (SEQ ID No. 700)

0601GIP4820    YaEGFISDYSIAMDKIHQQDFVNWLLAQKPSPKKI     46 (% Inh
               RYS-NH2                                 10 nM)
               (SEQ ID No. 701)

0601GIP4823    YaEGTFISDYSIAMDKIHQQDFVNWLLAQKPSPK      94.1 (% Inh
               KIRYS-NH2                               10 nM)
               (SEQ ID No. 702)

0601GIP4821    YaEGTFISDYSIAMDKIHQQDFVNWLLAQKPKSA      93.5 (% Inh
               RPS-NH2                                 10 nM)
               (SEQ ID No. 703)

0601GIP4822    YaEGTFISDYSIAMDKIHQQDFVNWLLAQKPKKL      95.4 (% Inh
               KPS-NH2                                 10 nM)
               (SEQ ID No. 704)

YaEGTFISDYSIAMDKIHQQDFVNWLLAQKPNKI
               RYS-NH2
               (SEQ ID No. 705)

YaEGTFISDYSIAMDKIHQQDFVNWLLAQKPKNI
               RYS-NH2
               (SEQ ID No. 706)

YaEGTFISDYSIAMDKIHQQDFVNWLLAQKPQKI
               RYS-NH2
               (SEQ ID No. 707)

YaEGTFISDYSIAMDKIHQQDFVNWLLAQKPKQI
               RYS-NH2
               (SEQ ID No. 708)

0601GIP4824    YaEGTFISDYSIAMDKIHQQDFVNWLLAQKPKK       92.9 (% Inh
               (OctG)RYS-NH2                           10 nM)
               (SEQ ID No. 709)

0601GIP4825    YaEGTFISDYSIAMDKIHQQDFVNWLLAQKPKKI      77.5 (% Inh
               RYS(OctG)-NH2                           10 nM)
               (SEQ ID No. 710)
```

Further exemplary "tail" modifications (compare to 0601GIP4288 (SEQ ID NO. 608) which has Leu14, Glu15 and Arg18 and Glu21 substitutions compared to 0601GIP3794), that improve solubility, duration of action or glucose lowering of GIP analogs compared to human GIP or to 0601GIP4288, and that can be used alone or combined with other modifications and derivatizations disclosed herein, and the exemplary compounds containing them, are depicted in the following table along with various activities. ("Ocg" below stands for octylglycine).

| | | (% Inh 10 nm, GI P-LF Assay) | OGTT/GL(%) | Basal Gluc. Low. at Peptide Conc. of 80 nmol/Kg | Solubility | Duration In The Rat IVGTT Assay |
|---|---|---|---|---|---|---|
| 0601GIP4288 | YaEGTFISDYSIALE KIRQQEFVNWLLA QKPSSGAPPPS-NH2 (SEQ ID NO. 608) | HEK-GIPR IC50 = 0.16 | -19 350 nmol/kg, -24 30 nmol/kg ED50~0.8 nmol/kg | -9 to -22%, AUC240 | <1 mg/ml | >794 at -240 min |
| 0601GIP5040 | YaEGTFISDYSIAME KIRQQEFVNWLLA QKPSSGAPPPS-NH2 (SEQ ID No: 870) | 91.3 (% Inh 10 nM) | -24, 30 nmol/kg | -16%, AUC240 | | |
| 0601GIP4975 | YaEGTFISDYSIALE KIRQQEFVNWLLA QKPSSGAPPNS-NH2 (SEQ ID No: 871) | GIPR-HEK IC50 = 0.1 | -14 and -24, 30 nmol/kg | -3% to -14%, AUC240 | | >794 at -240 min |
| 0601GIP5070 | YaEGTFISDYSIALE KIRQQEFVNWLLA QKPSSGARPPS-NH2 (SEQ ID No: 872) | 97.3 (% Inh 10 nM) | -30, 30 nmol/kg | | | |
| 0601GIP5071 | YaEGTFISDYSIALE KIRQQEFVNWLLA QKPSSGAKPPS-NH2 (SEQ ID No: 873) | 97.8 (% Inh 10 nM) | -31, 30 nmol/kg | | | |
| 0601GIP5072 | YaEGTFISDYSIALE KIRQQEFVNWLLA QKPSSGAPKPS-NH2 (SEQ ID No: 874) | 98.8 (% Inh 10 nM) | -22, 30 nmol/kg | | | |
| 0601GIP5073 | YaEGTFISDYSIALE KIRQQEFVNWLLA QKPSSGAPDPS-NH2 (SEQ ID No: 875) | 91.1 (% Inh 10 nM) | -32, 30 nmol/kg | | | |
| 0601GIP5080 | YaEGTFISDYSIALE KIRQQEFVNWLLA QKPSSGAPPKSK-NH2 (SEQ ID No: 876) | 95.3 (% Inh 10 nM) | -32, 30 nmol/kg | | | |
| 0601GIP5081 | YaEGTFISDYSIALE KIRQQEFVNWLLK QKPSSGAPPPS-NH2 (SEQ ID No: 877) | 100 (% Inh 10 nM) | -28, 30 nmol/kg | | | |
| 0601GIP5082 | YaEGTFISDYSIALE KIRQQEFVNWLLK QKPSSGAPPKS-NH2 (SEQ ID No: 878) | 99.7 (% Inh 10 nM) | -24, 30 nmol/kg | | | |
| 0601GIP5098 | YaEGTFISDYSIALE KIRQQEFVNWLLA QKPSSGAPPNSK-NH2 (SEQ ID No: 879) | 97 (% Inh 10 nM) | -20, 30 nmol/kg | | | |
| 0601GIP4996 | YaEGTFISDYSIALD KIKQQEFVNWLLA QKPSSGAPPQS-NH2 (SEQ ID No: 880) | 88.2 (% Inh 10 nM) | -14, 30 nmol/kg | | | |

Yet even further exemplary "tail" modifications (compare to 0601GIP3794 which incorporates the exendin tail PSS-GAPPPS (SEQ ID NO. 1) that can improve solubility, duration of action and/or glucose lowering activity, and which can be used alone or in combination with other modifications and derivatizations as disclosed herein, and exemplary GIP compounds having them, are depicted in the following table. For example, in one embodiment a GIP analog or hybrid will incorporate (at its C-terminus) any one of the tail sequences, such as PSSGAPPNS (SEQ ID No: 881), in the following table, to achieve greater solubility, improved duration of action or improved glucose lowering as compared to the parent compound. In another embodiment, a GIP analog or hybrid can incorporate any one or more of the non-tail amino acid substitutions from the table below (as compared to 0601GIP3794) to improve solubility, duration of action or glucose lowering activity.

| | | (% Inh 10 nm, GIP-LF Assay) | OGTT/ GL(%) | Basal Gluc. Lowering at 80 nmol/ Kg | Solubility | Duration In The Rat IVGTT Assay |
|---|---|---|---|---|---|---|
| 0601 GIP 4844 | YaEGTFISDYSIAMDKI HQQDFVNQLLAQKPSS GAPPPS-NH2 (SEQ ID No: 882) | 27 (% Inh, 10 nM); IC5011 HEKG IPR | −4, 30 nmol/ kg | | | duration < 0601GIP3794 @ −120 min |
| 0601 GIP 4846 | YaEGTFISDYSIAMDKI HQQDFVQWLLAQKPSS GAPPPS-NH2 (SEQ ID No: 883) | 79.6 (% Inh, 10 nM) | −25, 30 nmol/ kg | −6%, AUC240 | | |
| 0601 GIP 4866 | YaEGTFISDYSIAMDKI HQQDFVNNLLAQKPSS GAPPPS-NH2 (SEQ ID No: 884) | 47.9 (% Inh, 10 nM); IC50 = 39 HEK GIPR | +7, 30 nmol/ kg | | | |
| 0601 GIP 4901 | YaEGTFISDYSIAMDKI HQQDFVNSLLAQKPSS GAPPPS-NH2 (SEQ ID No: 885) | | −10, 30 nmol/ kg | | | |
| 0601 GIP 4867 | YaEGTFISDYSIAMDKI HQQDFVNWLNAQKPS SGAPPPS-NH2 (SEQ ID No: 886) | 0.3 (% Inh, 10 nM) | | | | |
| 0601 GIP 4868 | YaEGTFISDYSIAMDKI HQQDFVNWLSAQKPSS GAPPPS-NH2 (SEQ ID No. 887) | 8.1 (% Inh, 10 nM) | | | | |
| 0601 GIP 4869 | YaEGTFISDYSIAMDKI HQQDFVNWLQAQKPS SGAPPPS-NH2 (SEQ ID No: 888) | 18.9 (% Inh, 10 nM) | | | | |
| 0601 GIP 4858 | YaEGTFISDYSIAMDKI HQQDFVNWNLAQKPS SGAPPPS-NH2 (SEQ ID No: 889) | 11.4 (% Inh, 10 nM) | | | | |
| 0601 GIP 4859 | YaEGTFISDYSIAMDKI HQQDFVNWSLAQKPSS GAPPPS-NH2 (SEQ ID No: 890) | 4.5 (% Inh, 10 nM) | | | | |
| 0601 GIP 4860 | YaEGTFISDYSIAMDKI HQQDFVNWQLAQKPS SGAPPPS-NH2 (SEQ ID No: 891) | −1.8 (% Inh, 10 nM) | | | | |
| 0601 GIP 4861 | YaEGTFISDYSIAMDKI HQQDFVEWLKAQKPSS GAPPPS-NH2 (SEQ ID No: 892) | 17.4 (% Inh, 10 nM) | | | | |

-continued

| | (% Inh 10 nM, GIP-LF Assay) | OGTT/ GL(%) | Basal Gluc. Lowering at 80 nmol/ Kg | Solubility | Duration In The Rat IVGTT Assay |
|---|---|---|---|---|---|
| 0601 GIP 4862 | YaEGTFISDYSIAMDKI HQQDFVNNLNAQKPSS GAPPPS-NH2 (SEQ ID No: 893) | −14.3 (% Inh, 10 nM) | | | |
| 0601 GIP 4902 | YaEGTFISDYSIAMDKI HQQDFVNWLLKQKPSS GAPPPS-NH2 (SEQ ID No: 894) | | −19, 30 nmol/ kg | −28, AUC240 | | |
| 0601 GIP 4909 | YaEGTFISDYSIAMDKI HQQDFVNWLLHQKPSS GAPPPS-NH2 (SEQ ID No: 895) | 55 (% Inh, 10 nM) | | | |
| 0601 GIP 4911 | YaEGTFISDYSIAMDKI HQQDFVNWLLGQKPSS GAPPPS-NH2 (SEQ ID No: 896) | 79 (% Inh, 10 nM) | | | |
| 0601 GIP 4910 | YaEGTFISDYSIAMDKI HQQDFVNWLLAQKPSS GHPPPS-NH2 (SEQ ID No: 897) | 78.8 (% Inh, 10 nM) | | | |
| 0601 GIP 4847 | YaEGTFISDYSIAMDKI HQQDFVNWLLAQKPSS GNPPPS-NH2 (SEQ ID No: 898) | 70 (% Inh, 10 nM); IC50 = 1.3 HEK GIPR | −20, 30 nmol/ kg | −1 to −15%, AUC240 | | =794 @ −120 min |
| 0601 GIP 4971 | YaEGTFISDYSIAMDKI HQQDFVNWLLAQKPSS GQPPPS-NH2 (SEQ ID No: 899) | 97.1 (% Inh, 10 nM) | −22, 30 nmol/ kg | −15, AUC240 | | |
| 0601 GIP 4848 | YaEGTFISDYSIAMDKI HQQDFVNWLLAQKPSS GANPPS-NH2 (SEQ ID No: 900) | 75 (% Inh, 10 nM); IC50 = 0.93 HE KGIPR | −22, 30 nmol/ kg | | | <794 @ −120 min |
| 0601 GIP 4849 | YaEGTFISDYSIAMDKI HQQDFVNWLLAQKPSS GAPNPS-NH2 (SEQ ID No: 901) | 66, 81.4 (% Inh, 10 nM); IC50 = 0.79 HE KGIPR | −19, 30 nmol/ kg | | | =794 @ −120 min |
| 0601 GIP 4850 | YaEGTFISDYSIAMDKI HQQDFVNWLLAQKPSS GAPPNS-NH2 (SEQ ID No: 902) | 69 (% Inh, 10 nM); IC50 = 0.64, 0.5, 0.41 HE KGIPR | −21, 30 nmol/ kg, ED50~6 nmol/ kg | −21% to 2%, AUC240 | ~1 mg/ ml | =794 @ −120 min |
| 0601 GIP 4957 | YaEGTFISDYSIAMDKI HQQDFVNWLLAQKPSS GAPPQS-NH2 (SEQ ID No: 903) | 99.4 (% Inh, 10 nM); IC50 HEK-GIPR 0.51; | −13 and −22, 30 nmol/ kg | −8%, AUC240 | | =794 @ −120 min |

| | | (% Inh 10 nm, GIP-LF Assay) | OGTT/ GL(%) | Basal Gluc. Lowering at 80 nmol/ Kg | Solubility | Duration In The Rat IVGTT Assay |
|---|---|---|---|---|---|---|
| 0601 GIP 5029 | YaEGTFISDYSIAMDKI HQQDFVNWLLAQKPSS GAPPDS-NH2 (SEQ ID No: 904) | GIPR-HEK IC50 = 2.2 | -22, 30 nmol/ kg | -1%, AUC240 | | |
| 0601 GIP 4972 | YaEGTFISDYSIALDKIH QQDFVNWLLAQKPSSG APPNS-NH2 (SEQ ID No: 905) | 101 (% Inh, 10 nM) | -17, 30 nmol/ /kg | | | |
| 0601 GIP 4973 | YaEGTFISDYSIALDKIH QQDFVNWLLAQKPSSG APPQS-NH2 (SEQ ID No: 906) | 102.3 (% Inh, 10 nM) | -19, 30 nmol/ kg | -17, AUC240 | | |
| 0601 GIP 5075 | YaEGTFISDYSIAMDKI HQQDFVNWLLAQKPSS GQPPQSK-NH2 (SEQ ID No: 907) | 83.7 (% Inh, 10 nM) | -30, 30 nmol/ kg | | | |
| 0601 GIP 5076 | YaEGTFISDYSIAMDKI HQQDFVNWLLAQKPSS GAPPQSK-NH2 (SEQ ID No: 908) | 90.9 (% Inh, 10 nM) | -30, 30 nmol/ kg | | | |
| 0601 GIP 4952 | YaEGTFISDYSIAMDKI HQQDFVNWLLAQKPSS GAPGPS-NH2 (SEQ ID No: 909) | 96.1 (% Inh, 10 nM) | -21, 30 nmol/ kg | -1, AUC240 | | |
| 0601 GIP 4948 | YaEGTFISDYSIAMDKI HQQDFVNWLLAQKPSS GKPPPS-NH2 (SEQ ID No: 910) | 93.7 (% Inh, 10 nM); GIPR-HEK IC50 = 0.42 | -32, 30 nmol/ kg | -14, AUC240 | >5 mg/ ml | <794 @ -120 min |
| 0601 GIP 4947 | YaEGTFISDYSIAMDKI HQQDFVNWLLAQKPSS GAPPKS-NH2 (SEQ ID No: 911) | 90.9 (% Inh, 10 nM), GIPR-HEK IC50 = 0.59 | -29, 30 nmol/ kg | -19, AUC240 | >5 mg/ ml | <794 @ -120 min |
| 0601 GIP 4949 | YaEGTFISDYSIAMDKI HQQDFVNWLLAQKPSS GKPPKS-NH2 (SEQ ID No: 912) | | -26, 30 nmol/ kg | -16, AUC240 | | |
| 0601 GIP 4912 | YaEGTFISDYSIAMDKI HQQDFVNWLLAQKPSS GAQPPS-NH2 (SEQ ID No: 913) | 82.7 (% Inh, 10 nM) | -23, 30 nmol/ kg | | | |
| 0601 GIP 4905 | YaEGTFISDYSIAMDKI HQQDFVNWLLAQKPSS GAPGGS-NH2 (SEQ ID No: 914) | | -29, 30 nmol/ kg | -11%, AUC240 | | |
| 0601 GIP 4903 | YaEGTFISDYSIAMDKI HQQDFVNWLLAQKGK KPSSGAPPPS-NH2 (SEQ ID No: 915) | | -27, 30 nmol/ kg | -15%, AUC240 | | |

In yet other embodiments are the modifications and the specific GIP compounds described in the following table to provide increased solubility, particularly when combined with the exendin tail modification. Modifications to the FVN-WLLA region are of particular interest to improve solubility as are changes to the exendin tail itself. In other embodiments solubility is enhanced by addition of a water soluble polymer, e.g. PEG, either to either terminal or to an internal amino acid, e.g. lysine, as shown herein.

| | | |
|---|---|---|
| 0601GIP4767 | YaEGTFISDYSIAMDKIHQQDFVEWLLAQKPKKIRYS-NH2 (SEQ ID No. (711)) | 82.4(% Inh, 10 nM) |
| 0601GIP4768 | YaEGTFISDYSIAMDKIHQQDFVPWLLAQKPKKIRYS-NH2 (SEQ ID No. 712) | 17.9(% Inh, 10 nM) |
| 0601GIP4769 | YaEGTFISDYSIAMDKIHQQDFVNELLAQKPKKIRYS-NH2 (SEQ ID No. 713) | 42.8(% Inh, 10 nM) |
| 0601GIP4770 | YaEGTFISDYSIAMDKIHQQDFVNPLLAQKPKKIRYS-NH2 (SEQ ID No. 714) | 10.8(% Inh, 10 nM) |
| 0601GIP4771 | YaEGTFISDYSIAMDKIHQQDFVNWLEAQKPKKIRYS-NH2 (SEQ ID No. 715) | 17.8(% Inh, 10 nM) |
| 0601GIP4772 | YaEGTFISDYSIAMDKIHQQDFVNWLPAQKPKKIRYS-NH2 (SEQ ID No. 716) | 0.2(% Inh, 10 nM) |
| 0601GIP4289 | YaEGTFISDYSIALDKIRQQDFVEWLLAQKPSSGAPPPS-NH2 (SEQ ID No. 609) | 0.58 |
| 0601GIP4708 | Ado-Ado-YaEGTFISDYSIAMDKIHQQDFVNWLLAQKPSSGAPPPS-NH2 (SEQ ID No. 717) | 19.2(% Inh, 10 nM) |
| 0601GIP4709 | YaEGTFISYDSIAMDK-(epsilon-NH-(Ado-Ado-Ado-(2-(2-methoxyetoxy)-acetoyl)))-IHQQDFVNWLLAQKPSSGAPPPS-NH2 (SEQ ID No. 718) | 42.9(% Inh, 10 nM) |
| 0601GIP4763 | ((2-(2-methoxyethoxy)-acetoyl)-Ado-Ado)-YaEGTFISYDSIAMDKIHQQDFVNWLLAQKPSSGAPPPS-NH2 (SEQ ID No. 719) | 14.6(% Inh, 10 nM) |
| 0601GIP4761 | YaEGTFISDYSIAMDKIHQQDFVNWLLAQKPSSGAPPPS-Ado-Ado-NH2 (SEQ ID No. 720) | 87.3(% Inh, 10 nM) |
| 0601GIP4832 | YaEGTFISDYSIAK(epsilon-NH-(Ado-(2-(2-methoxyethoxy)-acetoyol)))DKIHQQDFVNWLLAQKPSSGAPPPS-NH2 (SEQ ID No. 721) | |
| | YaEGTFISDYSIAMDKIHQQDFVNQLLAQKPSSGAPPPS-NH2 (SEQ ID No. 722) | |
| | YaEGTFISDYSIAMDKIHQQDFVNQLLAQKPKKIRYS-NH2 (SEQ ID No. 723) | |
| | YaEGTFISDYSIAMDKIHQQDFVQWLLAQKPSSGAPPPS-NH2 (SEQ ID No. 724) | |
| | YaEGTFISDYSIAMDKIHQQDFVQWLLAQKPKKIRYS-NH2 (SEQ ID No. 725) | |
| | YaEGTFISDYSIAMDKIHQQDFVNNLLAQKPSSGAPPPS-NH2 (SEQ ID No. 726) | |
| | YaEGTFISDYSIAMDKIHQQDFVNWLNAQKPSSGAPPPS-NH2 (SEQ ID No. 727) | |
| | YaEGTFISDYSIAMDKIHQQDFVNWLSAQKPSSGAPPPS-NH2 (SEQ ID No. 728) | |

```
YaEGTFISDYSIAMDKIHQQDFVNWLQAQKP
SSGAPPPS-NH2
(SEQ ID No. 729)

YaEGTFISDYSIAMDKIHQQDFVNWNLAQKP
SSGAPPPS-NH2
(SEQ ID No. 730)

YaEGTFISDYSIAMDKIHQQDFVNWSLAQKPS
SGAPPPS-NH2
(SEQ ID No. 731)

YaEGTFISDYSIAMDKIHQQDFVNWQLAQKP
SSGAPPPS-NH2
(SEQ ID No. 732)

YaEGTFISDYSIAMDKIHQQDFVEWLKAQKPS
SGAPPPS-NH2
(SEQ ID No. 733)

YaEGTFISDYSIAMDKIHQQDFVNNLNAQKPS
SGAPPPS-NH2
(SEQ ID No. 734)

YaEGTFISDYSIAMDKIHQQDFVNWLLAQKPS
SGNPPPS-NH2
(SEQ ID No. 735)

YaEGTFISDYSIAMDKIHQQDFVNWLLAQKPS
SGANPPS-NH2
(SEQ ID No. 736)

YaEGTFISDYSIAMDKIHQQDFVNWLLAQKPS
SGAPNPS-NH2
(SEQ ID No. 737)

YaEGTFISDYSIAMDKIHQQDFVNWLLAQKPS
SGAPPNS-NH2
(SEQ ID No. 738)
```

Alternative representations of some of the above compounds are as follows:

0601GIP4708 (SEQ ID No. 717)

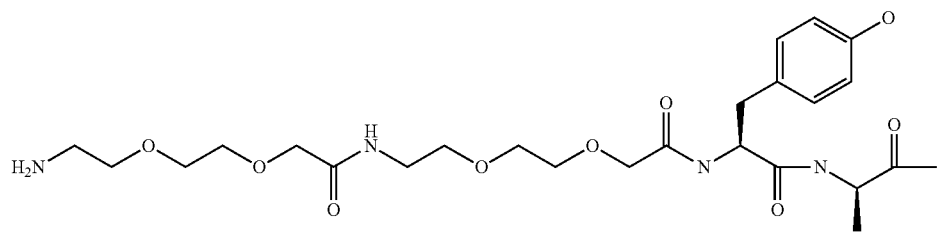

AR2734-28(N-Ado-Ado) [d Ala2] GIP-(1-30)-Exendin-4-(31-39)

Molecular Weight = 4600.18
Molecular Formula = C208H313N51O65S

0601GIP4709 (SEQ ID No. 718)

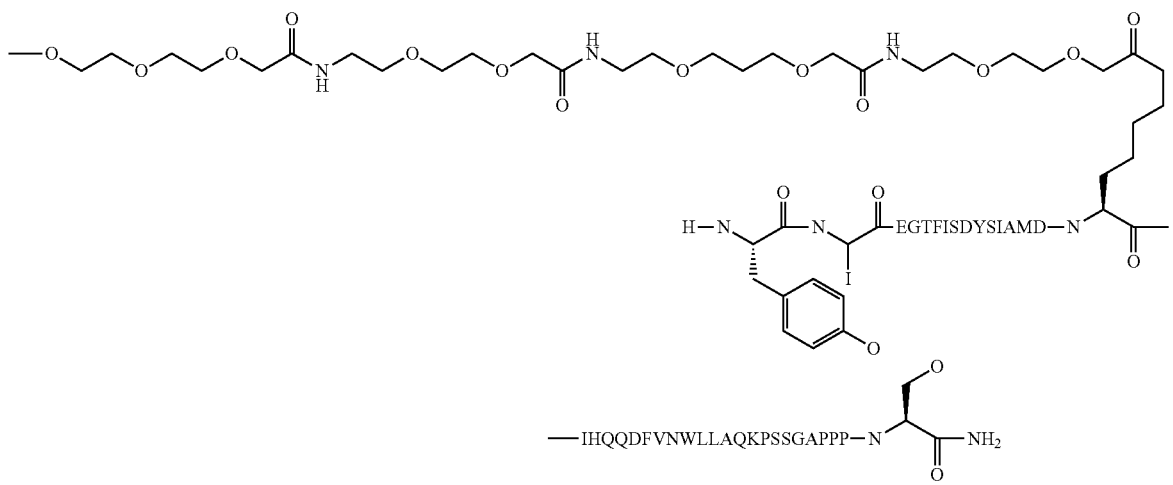

AR2734-30 Lys$^{16}$ (z-NH-(Ado-Ado-Ado-(2-(2-methoxyethoxy)-acetoyl)))-[dAla$^2$]-GIP-(1-30)-Exendin-4-(31-39)

Molecular Weight = 4919.54
Molecular Formula = C222H338N52O72S

0601GIP4763 (SEQ ID No. 719)

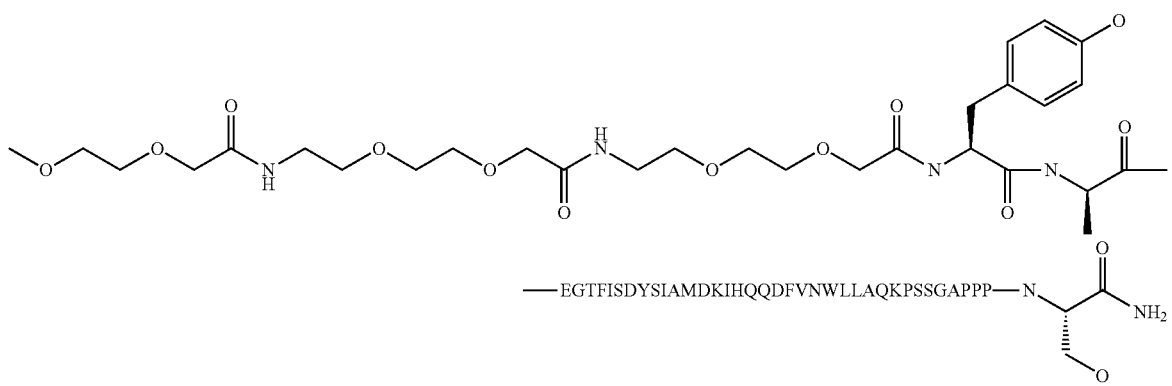

((2-(2-methoxyethoxy)-acetoyl)-Ado-Ado) [dAla2] GIP-(1-30)-Exendin-4-(31-39)

Molecular Weight = 4716.30
Molecular Formula = C213H321N51O68S

0601GIP4832 (SEQ ID No. 721)

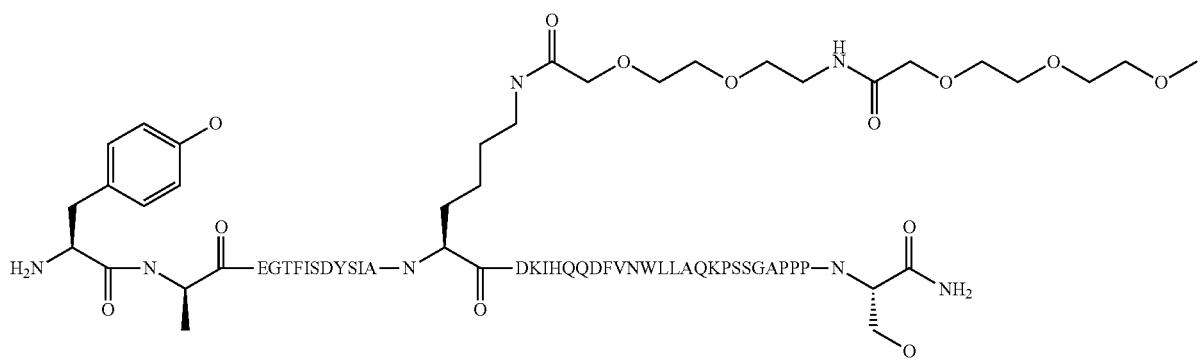

Lys$^{16}$(z-NH-(Ado-(2-(2--methoxyethoxy)-acetoyl)))-[dAla$^2$]-GIP-(1-30)-Exendin-4-(31-39)

Yet further embodiments contain modifications and specific GIP sequences described in the following table that may provide increased solubility, glucose lowering or duration of action as compared to human GIP, and in some embodiments, greater than or equal to 0601GIP3794. Modifications can be in the tail region (PSSGAPPPS) or elsewhere in the compound or both, as shown in the following table. The modified GIP sequences and modified tail sequences can be used in other GIP analogs or hybrids. Receptor binding and glucose lowering activity via OGTT are shown.

0601GIP5072, 0601GIP5073 as compared to 0601GIP4288 that provide solubility and bioactivity. In one embodiment are GIP analogs or hybrids that contain one or more or all of the modifications in analog 0601GIP4904 as compared to

```
0601GIP   YaEGTFISDYSIALDKIRQQEFVNWLLA    94 (% Inh 10 nM)   -17, 30 nmol/kg
4997      QHPSSGAPPQS-NH2
          (SEQ ID No: 916)

0601GIP   YaEGTFISDYSIALDKIRQQKFVNWLLA    84.9 (% Inh        -11, 30 nmol/kg
4998      QKPSSGAPPQS-NH2                 10 nM)
          (SEQ ID No: 917)

0601GIP   YaEGTFISDYSIALDKIRQQKFVNWLLA    87.8 (% Inh         -7, 30 nmol/kg
4995      QKPSSGAPPNS-NH2                 10 nM)
          (SEQ ID No: 918)

0601GIP   YaEGTFISDYSIALDKIRQQEFVNWLLA    101.9 (% Inh       -16, 30 nmol/kg
4994      QHPSSGAPPNS-NH2                 10 nM)
          (SEQ ID No: 919)

0601GIP   YaEGTFISDYSIALDKIRQQEFVNWLLA    100.2 (% Inh       -33, 30 nmol/kg
5078      QKPSSGAPPKS-NH2                 10 nM)
          (SEQ ID No: 920)

0601GIP   YaEGTFISDYSIALDKIKQQEFVNWLLA    98.6 (% Inh        -28, 30 nmol/kg
5079      QKPSSGAPPKS-NH2                 10 nM)
          (SEQ ID No: 921)

0601GIP   YaEGTFISDYSIALDKIHQQEFVNWLLA    81.3 (% Inh        -34, 30 nmol/kg
5077      QKPSSGQPPQS-NH2                 10 nM)
          (SEQ ID No: 922)

0601GIP   YaEGTFISDYSIALDKIKQQEFVNWLLA    91.7 (% Inh        -19, 30 nmol/kg
4993      QKPSSGAPPNS-NH2                 10 nM)
          (SEQ ID No: 923)

0601GIP   YaEGTFISDYSIAMDKIKQQDEVNWLL      4.7 (% Inh,
4950      AQKPSSGAPPPS-NH2                10 nM)
          (SEQ ID No: 924)
```

In one embodiment are GIP analogs with surprisingly high solubility, and in a further embodiment, surprisingly greater solubility than either or both 0601GIP3794 and 0601GIP4850, as measured at about pH 5 to 7, while retaining glucose lowering (e.g. OGTT or glucose lowering assay) greater than human GIP or about equal to or better than either or both 0601GIP3794 and 0601GIP4850, as shown in the following table. In one embodiment the analog has greater solubility than either or both 0601GIP3794 and 0601GIP4850 at pH 6.0 buffered with 30 mM histidine or pH 7.0 buffered with 30 mM histidine. In one embodiment are GIP analogs or hybrids that contain one or more or all of the modifications in each of analogs 0601GIP5075, 0601GIP5076, 0601GIP508, 0601GIP5081, 0601GIP5082 and 0601GIP4850 as compared to 0601GIP3794 that provide solubility and bioactivity. In one embodiment are GIP analogs or hybrids that contain one or more or all of the modifications in each of analogs 0601GIP5070, 165071, 0601GIP4233 that provide solubility and bioactivity. In one embodiment the analog has a solubility of greater than or about 5 mg/ml, and further retains glucose lowering greater than or about that of human GIP, 0601GIP3794 and/or 0601GIP4850. In one embodiment the GIP analog or hybrid is or comprises 0601GIP4904, 0601GIP5072, 0601GIP5075, 0601GIP508, 0601GIP5081, 0601GIP5082, 0601 GIP507, 0601GIP5071, 0601GIP5073, or 0601GIP5076. In another embodiment the GIP analog is or comprises 0601GIP4904, 0601GIP5072, 0601GIP5075, 0601GIP508, 0601GIP5081, 0601GIP5082, which analogs also demonstrate superior stability in solution, for example as determined by an accelerated stability study at 40 degrees C. for at least 3 days or at least 7 days. In one such embodiment are analogs 0601GIP508, 0601GIP5081, 0601GIP5082 or 0601GIP5072, or analogs or hybrids containing these sequences. (In the table herein, "794" means 0601GIP3794.)

```
                                              OGTT   GL     DOA    solubility/
                                                                   stability 0601GIP   YaEGTFISDYSIAMDKIHQQDFV     =794   =794   =794   <1 mg/ml
3794      NWLLAQKPSSGAPPPS-NH2
          (SEQ ID No: 186)

0601GIP   YaEGTFISDYSIAMDKIHQQDFV     =794   =794   =794   ~1 mg/ml
4850      NWLLAQKPSSGAPPNS-NH2
          (SEQ ID No: 902)
```

-continued

| | | OGTT | GL | DOA | solubility/stability |
|---|---|---|---|---|---|
| 0601GIP 5075 | YaEGTFISDYSIAMDKIHQQDFV NWLLAQKPSSGQPPQSK-NH2 (SEQ ID No: 907) | =794 | | <794@ -120 min | >5 mg @ pH 5-9 |
| 0601GIP 5076 | YaEGTFISDYSIAMDKIHQQDFV NWLLAQKPSSGAPPQSK-NH2 (SEQ ID No: 908) | =794 | | =794@ -120 min | 1 mg/ml |
| 0601GIP 5080 | YaEGTFISDYSIALEKIRQQEFVN WLLAQKPSSGAPPKSK-NH2 (SEQ ID No: 876) | =794 | =794 | submitted | >5 mg/ml |
| 0601GIP 5081 | YaEGTFISDYSIALEKIRQQEFVN WLLKQKPSSGAPPPS-NH2 (SEQ ID No: 877) | =794 | =794 | =794@ -120 min | >5 mg/ml |
| 0601GIP 5082 | YaEGTFISDYSIALEKIRQQEFVN WLLKQKPSSGAPPKS-NH2 (SEQ ID No: 878) | =794 | =794 | =794@ -120 min | >5 mg/ml |
| 0601GIP 5070 | YaEGTFISDYSIALEKIRQQEFVN WLLAQKPSSGARPPS-NH2 (SEQ ID No: 872) | =794 | | | 1 mg/ml |
| 0601GIP 5071 | YaEGTFISDYSIALEKIRQQEFVN WLLAQKPSSGAKPPS-NH2 (SEQ ID No: 873) | =794 | | | 1 mg/ml |
| 0601GIP 5072 | YaEGTFISDYSIALEKIRQQEFVN WLLAQKPSSGAPKPS-NH2 (SEQ ID No: 874) | =794 | | | >5 mg/ml |
| 0601GIP 5073 | YaEGTFISDYSIALEKIRQQEFVN WLLAQKPSSGAPDPS-NH2 (SEQ ID No: 875) | =794 | | | 1 mg/ml |
| 0601GIP 4904 | YaEGTFISDYSIAMDKIHQQDFV NWLLAQKPKGKIRYS-NH2 (SEQ ID No: 859) | >=794 | | <794@ -120 min | >5 mg/ml |

In a further embodiment are analogs or derivatives, or hybrids thereof, of the GIP compounds in the above table, and further in each of the tables and figures herein, having no more than 5, no more than 4, no more than 3, no more than 2 or no more than 1 substitution, modification and/or derivatization as described herein and/or that exhibits at least 50%, at least 60%, at least 65%, at least 70%, at least 75%, at least 80%, at least 85%, at least 90%, at least 95% or at least 98% sequence identity to the parent GIP analog of the above table, or other table or figure herein, over the entire length of the parent GIP compound.

FIGS. 12.15 to 12.65 depict further exemplary analogs and reference peptides of the invention. It is intended that the various modifications and variants shown are to be used in the present invention, and may be combined as discussed herein. For example, the terms exendin tail or exendin trp-cage motif includes any of the exendin tail variants depicted, which are useful as shield sequences (peptidic enhancers). Of further interest are the frog GLP1 C-terminal extensions as shown in the figures, which are yet another example of a shield sequence that can be used in place of an exendin tail. For example, in one embodiment the GIP compounds of the invention comprise a frog GLP1 "tail" sequence as a peptidic enhancer as described herein (and see FIG. 12). Of particular interest are compounds 0601GIP4179, 0601GIP4233, 0601GIP4285, 0601GIP4178, and 0601GIP4467. In other embodiment, the "S" or shield region or C-terminal tail can be any of the tails depicted herein, including for example PSS-GQPPQSK (SEQ ID No: 925), PSSGAPPQSK (SEQ ID No: 926), PSSGAPPKSK (SEQ ID No: 927), PSSGAPPPS (SEQ ID No: 1), PSSGAPPKS (SEQ ID No: 928), PSSGARPPS (SEQ ID No: 929), PSSGAKPPS (SEQ ID No: 930), PSSGAPKPS (SEQ ID No: 931), PSSGAPDPS (SEQ ID No: 932) or PKGKIRYS (SEQ ID No: 933). Further the "S" or shield region or C-terminal tail can be any of the tails found in any of the GIP analogs depicted herein including those from GIP compounds 0601GIP3794, 0601GIP485, 0601GIP5075, 0601GIP5076, 0601GIP508, 0601GIP5081, 0601GIP5082, 0601GIP507, 0601GIP5071, 0601GIP5072, 0601GIP5073 or 0601GIP4904.

In yet a further embodiment of any of the GIP modules herein, is a Serine-2, Aspartic acid3 (i.e. S2,D3), double substitution at positions 2 and 3 at the N-terminus of a GIP. Thus it is expressly intended that for each of the species and formulas depicted herein, that each S2,D3 analog is explicitly disclosed herein as if it had been written. As with the other DPP-IV resistance modifications described herein, the S2,D3 can be combined with one or two or more other modifications, for example a fatty acyl derivatization to decrease plasma (e.g. renal clearance) and/or increase duration of action, and/or with a C-terminal shield sequence, and/or with a GIP species amino acid substitution. Of course these GIP analogs can be used directly or as the GIP portion of a GIP hybrid.

Exemplary compounds (see FIG. 12 for example) showing exceptional GIP Receptor binding activity at less than about 10 nm include 0601GIP3794 at 3.8 nM, 0601GIP4283 0.41 nM, 0601GIP4284 1.8 nM, 0601GIP4285 0.58 nM, 0601GIP4288 0.28 nM, 0601GIP4289 0.58 nM, 0601GIP4290 0.35 nM, 0601GIP4147 at 7.4 nM, 0601GIP4178 1.5 nM, 0601GIP4293 0.12 nM, 0601GIP4292 0.17 nM, 0601GIP4238 4.2 nM, 0601GIP4179 3.3 nM, 0601GIP4294 0.92 nM, 0601GIP4252 5.6 nM, 0601GIP3794 3.8 nM, 0601GIP4190 2.4 nM, 0601GIP4152 2.3 nM, 0601GIP4150 1.6 nM, 0601GIP4153 0.53 nM, 0601GIP4149 1.5 nM, 0601GIP4176 4.8 nM, 0601GIP4177 2.9 nM, 0601GIP4213 7.9 nM, 0601GIP4215 4.5 nM, 0601GIP4263 0.66 nM, 0601GIP4278 0.24 nM, 0601GIP4264 0.4 nM, 0601GIP4279 2.1 nM, 0601GIP4233 0.1 nM, 0601GIP4234 3.4 nM, 0601GIP4236 0.62 nM. These compounds also display GIP Receptor activation and appropriate receptor specificity (e.g., lack of binding to GLP1-R or glucagon receptor in absence of appropriate hybrid module).

As demonstrated herein, DPP-IV resistant hybrids of the invention have increased plasma stability compared to native GIP. For example, 0601GIP3796 amide form is essentially 100% present after 5 hours in human plasma, in contrast to about 60% for GIP(1-42) acid form.

The following table further demonstrates that GIP peptides of the invention and their analogs and derivatives have in vivo activities that are directly related to desirable therapeutic effects as discussed herein. Compounds marked in bold are of particular interest, as are the modifications and/or derivatizations, which can be combined or used with other modifications or derivatives herein. These compounds find particular use in the GIP hybrids of the invention. Bolded compounds demonstrate very effective activity.

| Cmpd # | OGTT OGTT/GL (%) 350 nmol/Kg | Basal Glucose Lowering Basal Glucose Lowering at 80 nmol/Kg | IVGTT AUC Change in Insulin Pre IVGTT | IVGTT AUC Change in Insulin Post IVGTT | IVGTT >=< Compared to 0601GIP3794 | Basal Glucose Lowering in db/db |
|---|---|---|---|---|---|---|
| 0601GIP3757 | −22 | −2%, t = 120 | | | | |
| 0601GIP4044 | | −2%, AUC 180 | | | | |
| 0601GIP4045 | | no data | | | | |
| 0601GIP3794 | −21% 350 nmol/kg, −17% 10 nmol/kg, ED50 ~2 nmol/kg | −7 to −20%, AUC 240, −9%, AUC 180 | 28.8 +− 10.7 | 173.1 +− 29.4 | = | −33%, 80 nmol/kg, t = 120 |
| 0601GIP4046 | | −5%, AUC 180, −2%, AUC 240 | | | | |
| 0601GIP3793 | −26 | −2%, t = 120 | | | | |
| 0601GIP3756 | −12 | | | | | |
| 0601GIP3974 | | 8%, AUC 240, 10% (80 nmol/Kg) and 0% (100 nmol/kg), t = 120 | | | | |
| 0601GIP4429 | −8, 30 nmol/kg | | | | | |
| 0601GIP4283 | −14 | | | | | |
| 0601GIP4284 | −21 | −7%, AUC 240 | | | | |
| 0601GIP4405 | −19, 30 nmol/kg | −0%, AUC 240 | | | | |
| 0601GIP4406 | −21, 30 nmol/kg | −0%, AUC 240 | | | | |
| 0601GIP4403 | −12, 30 nmol/kg | | | | | |
| 0601GIP4404 | −15, 30 nmol/kg | | | | | |
| 0601GIP4285 | −10 350 nmol/kg, −17 30 nmol/kg | −2%, AUC 240 | 22.1 +− 10.7 | 206.2 +− 11.8 | = | |
| 0601GIP4286 | −22, 30 nmol/kg | | | | | |
| 0601GIP4313 | −5, 30 nmol/kg | | | | | |
| 0601GIP4288 | −19 | | | | | |
| 0601GIP4344 | −24, 30 nmol/kg | | | | | |
| 0601GIP4290 | −17 | | | | | |
| 0601GIP4456 | −3, 30 nmol/kg | | | | | |
| 0601GIP4457 | 4, 30 nmol/kg | | | | | |
| 0601GIP4460 | −12, 30 nmol/kg | | | | | |
| AC1540 Human | | | | | | −19% 80 nmol/kg t = 60 and 120 |
| 0601GIP3300 | | −2%, AUC 240 at 800 nmol/kg | | | | |

-continued

| Cmpd # | OGTT OGTT/GL (%) 350 nmol/Kg | Basal Glucose Lowering Basal Glucose Lowering at 80 nmol/Kg | IVGTT AUC Change in Insulin Pre IVGTT | IVGTT AUC Change in Insulin Post IVGTT | IVGTT > = < Compared to 0601GIP3794 | Basal Glucose Lowering Basal Glucose Lowering in db/db |
|---|---|---|---|---|---|---|
| 0601GIP3943 | | −8%, AUC 180 | | | | |
| chicken 0601GIP3794 | −7, 30 nmol/kg −21% 350 nmol/kg, −17% 10 nmol/kg, ED50 ~2 nmol/kg | −7 to −20%, AUC 240, −9%, AUC 180 | 28.8 +− 10.7 | 173.1 +− 29.4 | = | −33%, 80 nmol/kg, t = 120 |
| 0601GIP4190 | −14 | | | | | |
| 0601GIP4152 | −20 | | | | | |
| 0601GIP4150 | −13 | | | | | |
| 0601GIP4153 | −14 | | | | | |
| 0601GIP4149 | −16% | | | | | |
| 0601GIP4176 | −10 | | | | | |
| 0601GIP4177 | −19 | | | | | |
| 0601GIP4213 | −17 | | | | | |
| 0601GIP4263 | −17 | | | | | |
| 0601GIP4278 | −12 | | | | | |
| 0601GIP4264 | −12 | | | | | |
| 0601GIP4279 | −7 | | | | | |
| 0601GIP4306 | −20, 30 nmol/kg | −5%, AUC 240 | | | | |
| Xenopus | −3, 30 nmol/kg | | | | | |
| 0601GIP4503 | −4, 30 nmol/kg | | | | | |
| 0601GIP4504 | −2, 30 nmol/kg | | | | | |
| 0601GIP4505 | +9, 30 nmol/kg | | | | | |
| 0601GIP4506 | −14, 30 nmol/kg | | | | | |
| 0601GIP4753 | −22, 30 nmol/kg | −13%, AUC 240 | | | | |
| 0601GIP4754 | −20, 30 nmol/kg | −13%, AUC 240 | | | | |
| 0601GIP4596 | −7, 30 nmol/kg | | | | | |
| 0601GIP4465 | −16, 30 nmol/kg | | | | | |
| 0601GIP4466 | −20, 30 nmol/kg | −26%, AUC 240 | 17.3 +− 3.3 | 113.9 +− 18.9 | < | |
| 0601GIP4478 | −7, 30 nmol/kg | | | | | |
| 0601GIP4467 | −18, 30 nmol/kg | −7%, AUC 240 | | | | |
| 0601GIP4479 | −16, 30 nmol/kg | | | | | |
| 0601GIP4480 | −12, 30 nmol/kg | | | | | |
| 0601GIP4571 | −23, 30 nmol/kg | −11%, AUC 240 | | | | |
| 0601GIP4551 | −14, 30 nmol/kg | | | | | |
| 0601GIP4407 | −9, 30 nmol/kg | | | | | |
| 0601GIP4650 | −11, 30 nmol/kg | | | | | |
| 0601GIP4651 | −7, 30 nmol/kg | | | | | |
| 0601GIP4576 | −22, 30 nmol/kg | −2%, AUC 240 | | | | |
| 0601GIP4507 | −5, 30 nmol/kg | | | | | |
| 0601GIP4536 | −15, 30 nmol/kg | | | | | |
| 0601GIP4537 | −7, 30 nmol/kg | | | | | |
| 0601GIP4627 | −17, 30 nmol/kg | | | | | |
| 0601GIP4391 | −12, 30 nmol/kg | | | | | |
| 0601GIP4459 | −7, 30 nmol/kg | | | | | |
| 0601GIP4147 | −9 | | | | | |
| 0601GIP4324 BB | −23, 30 nmol/kg | −23%, AUC 240 | | | | |
| 0601GIP4458 | −14, 30 nmol/kg | | | | | |
| 0601GIP4215 | −23 | −0%, AUC 240 | | | | |
| 0601GIP4389 | −6, 30 nmol/kg | | | | | |
| 0601GIP4399 | −3, 30 nmol/kg | | | | | |
| 0601GIP4390 | 1, 30 nmol/kg | | | | | |
| 0601GIP4395 | −11, 30 nmol/kg | −0%, AUC 240 | | | | |
| 0601GIP4387 | −7, 30 nmol/kg | | | | | |
| 0601GIP4386 | −0, 30 nmol/kg | | | | | |
| 0601GIP4703 | −18, 30 nmol/kg | | | | | |
| 0601GIP4180 | −11, 30 nmol/kg | | | | | |
| 0601GIP4238 | −25 | −6%, AUC 240 | | | | |

|  |  | Basal | IVGTT | | | Basal |
|---|---|---|---|---|---|---|
| Cmpd # | OGTT OGTT/GL (%) 350 nmol/Kg | Glucose Lowering Basal Glucose Lowering at 80 nmol/Kg | AUC Change in Insulin Pre IVGTT | AUC Change in Insulin Post IVGTT | IVGTT >=< Compared to 0601GI P3794 | Glucose Lowering Basal Glucose Lowering in db/db |
| 0601GIP4392 | −20, 30 nmol/kg | −9%, AUC 240 | | | | |
| 0601GIP4577 | −27, 30 nmol/kg | −8%, AUC 240 | | | | |
| 0601GIP4790 | −24, 30 nmol/kg | | | | | |
| 0601GIP4588 | −8 to −20, 30 nmol/kg | | | | | |
| 0601GIP4331 | −25 and −16, 30 nmol/kg | −13%, AUC 240 | 17.4 +− 6.5 | 131.3 +− 15.5 | = | |
| 0601GIP4580 | −17, 30 nmol/kg | −2%, AUC 240 | | | | |
| 0601GIP4582 | −23, 30 nmol/kg | −5%, AUC 240 | | | | |
| 0601GIP4699 | −18, 30 nmol/kg | | | | | |
| 0601GIP4764 | −18, 30 nmol/kg | | | | | |
| 0601GIP4620 | −8, 30 nmol/kg | | | | | |
| 0601GIP4359 | −11, 30 nmol/kg | | | | | |
| 0601GIP4347 | −10, 30 nmol/kg | | | | | |
| 0601GIP4384 | −12, 30 nmol/kg | | | | | |
| 0601GIP4385 | −8, 30 nmol/kg | | | | | |
| 0601GIP4608 | −8, 30 nmol/kg | | | | | |
| 0601GIP4798 | −27, 30 nmol/kg | | | | | |
| 0601GIP4799 | −10, 30 nmol/kg | | | | | |
| 0601GIP4801 | −23, 30 nmol/kg | | | | | |
| 0601GIP4766 | −25, 30 nmol/kg | | | | | |
| 0601GIP4178 | −20 | −13%, AUC 240 | 18.5 +− 6.7 | 106.6 +− 23.8 | < | |
| 0601GIP4293 | −22 | −13%, AUC 240 | | | | |
| 0601GIP4292 | −24 | −10%, AUC 240 | 35.6 +− 5.4 | 183.9 +− 26.6 | = | |
| 0601GIP4806 | −14, 30 nmol/kg | | | | | |
| 0601GIP4670 | −24, 30 nmol/kg | −14%, AUC 240 | 27.3 +− 5.7 | 175.9 +− 19.0 | = | |
| 0601GIP4635 | −17, 30 nmol/kg | | | | | |
| 0601GIP4636 | −19, 30 nmol/kg | −16%, AUC 240 | | | | |
| 0601GIP4637 | −11, 30 nmol/kg | | | | | |
| 0601GIP4543 | −0, 30 nmol/kg | | | | | |
| 0601GIP4544 | −13, 30 nmol/kg | | | | | |
| 0601GIP4712 | −10, 30 nmol/kg | | | | | |
| 0601GIP4252 | −18 | −7%, AUC 240 | 11.9 +− 11.7 | 1218.1 +− 12.7 | = | |
| 0601GIP4548 | −12, 30 nmol/kg | | | | | |
| 0601GIP4549 | −13, 30 nmol/kg | | | | | |
| 0601GIP4550 | −3, 30 nmol/kg | | | | | |
| 0601GIP4606 | −18, 30 nmol/kg | −9%, AUC 240 | | | | |
| 0601GIP4607 | −4, 30 nmol/kg | | | | | |
| 0601GIP4326 | −18 and −25, 30 nmol/kg | −8%, AUC 240 | 37.6 +− 7.0 | 154.9 +− 17.3 | = | |
| 0601GIP4671 | −24, 30 nmol/kg | −14%, AUC 240 | 29.1 +− 4.5 | 243.7 +− 20.6 | = | |
| 0601GIP4693 | −17, 30 nmol/kg | | | | | |
| 0601GIP4755 | −21, 30 nmol/kg | −7%, AUC 240 | | | | |
| 0601GIP4547 | +5, 30 nmol/kg | | | | | |
| 0601GIP4461 | −20, 30 nmol/kg | +12%, AUC 240 | | | | |
| 0601GIP4581 | −20, 30 nmol/kg | −12%, AUC 240 | | | | |
| 0601GIP4585 | −15, 30 nmol/kg | −4%, AUC 240 | | | | |
| 0601GIP4586 | −15, 30 nmol/kg | −9%, AUC 240 | | | | |
| 0601GIP4179 | −23 350 nmol/kg, −24 30 nmol/kg | −17%, AUC 240 | 52.4 +− 9.6 | 206.8 +− 30.1 | = | |
| 0601GIP4649 | −14, 30 nmol/kg | | | | | |
| 0601GIP4642 | −17, 30 nmol/kg | | | | | |
| 0601GIP4645 | −24, 30 nmol/kg | | | | | |

-continued

| Cmpd # | OGTT OGTT/GL (%) 350 nmol/Kg | Basal Glucose Lowering Basal Glucose Lowering at 80 nmol/Kg | IVGTT AUC Change in Insulin Pre IVGTT | IVGTT AUC Change in Insulin Post IVGTT | IVGTT > = < Compared to 0601GIP3794 | Basal Glucose Lowering Basal Glucose Lowering in db/db |
|---|---|---|---|---|---|---|
| 0601GIP4294 | −27 | −10%, AUC 240 | | | | |
| 0601GIP4756 | −21, 30 nmol/kg | −1%, AUC 240 | | | | |
| 0601GIP4562 | −10, 30 nmol/kg | | | | | |
| 0601GIP4572 | +1, 30 nmol/kg | | | | | |
| 0601GIP4573 | +10, 30 nmol/kg | | | | | |
| 0601GIP4609 | −5, 30 nmol/kg | | | | | |
| 0601GIP3794 | −21% 350 nmol/kg, −17% 10 nmol/kg, ED50 ~2 nmol/kg | −7 to −20%, AUC 240, −9%, AUC 180 | 28.8 +− 10.7 | 173.1 +− 29.4 | = | −33%, 80 nmol/kg, t = 120 |
| 0601GIP4414 | +3, 30 nmol/kg | | | | | |
| 0601GIP4415 | +10, 30 nmol/kg | | | | | |
| 0601GIP4416 | −0, 30 nmol/kg | | | | | |
| 0601GIP4417 | +9, 30 nmol/kg | | | | | |
| 0601GIP4192 | −16 | | | | | |
| 0601GIP4807 | −27, 30 nmol/kg | | | | | |
| 0601GIP4233 | −22 350 nmol/kg, −17 30 nmol/kg | −11 to −18%, AUC 240 | 53.8 +− 14.7 | 234.5 +− 25.5 | = | |
| 0601GIP4327 | −7, 30 nmol/kg | | | | | |
| 0601GIP4386 | −0, 30 nmol/kg | | | | | |
| 0601GIP4698 | −14, 30 nmol/kg | | | | | |
| 0601GIP4538 | −9, 30 nmol/kg | | | | | |
| 0601GIP4539 | −12, 30 nmol/kg | −5%, AUC 240 | | | | |
| 0601GIP4540 | −16, 30 nmol/kg | −12%, AUC 240 | | | | |
| 0601GIP4648 | −20, 30 nmol/kg | −8%, AUC 240 | | | | |
| 0601GIP4631 | −14, 30 nmol/kg | | | | | |
| 0601GIP4805 | −13, 30 nmol/kg | | | | | |
| 0601GIP4561 | −15, 30 nmol/kg | −8%, AUC 240 | | | | |
| 0601GIP4673 | −23, 30 nmol/kg | −21%, AUC 240 | 51.9 +− 8.1 | 205.5 +− 21.0 | = | |
| 0601GIP4672 | −21, 30 nmol/kg | −9%, AUC 240 | | | | |
| 0601GIP4713 | −21, 30 nmol/kg | −12%, AUC 240 | | | | |
| 0601GIP4711 | −22, 30 nmol/kg | −11%, AUC 240 | | | | |
| 0601GIP4234 | −17 | −11%, AUC 240 | | | | |
| 0601GIP4710 | −12, 30 nmol/kg | | | | | |
| 0601GIP4765 | −12, 30 nmol/kg | | | | | |
| 0601GIP4236 | −16 | −12%, AUC 240 | | | | |
| 0601GIP4328 | −2, 30 nmol/kg | | | | | |
| 0601GIP4345 | −14 @ 30 nmol/kg, −25 @ 250 nmol/kg | −11%, AUC 240 | | | | |
| 0601GIP4401 | 1, 30 nmol/kg | | | | | |
| 0601GIP4346 | −20, 30 nmol/kg | −10%, AUC 240 | | | | |
| 0601GIP4700 | −21, 30 nmol/kg | −6%, AUC 240 | | | | |
| 0601GIP4400 | −2, 30 nmol/kg | | | | | |
| 0601GIP4402 | −8, 30 nmol/kg | | | | | |
| 0601GIP4619 | −19, 30 nmol/kg | −10%, AUC 240 | 16.6 +− 1.5 | 151.2 +− 19.0 | < | |
| 0601GIP4767 | −24, 30 nmol/kg | | | | | |
| 0601GIP4289 | −24 | −4%, AUC 240 | | | | |
| 0601GIP4708 | −14, 30 nmol/kg | | | | | |
| 0601GIP4709 | +4, 30 nmol/kg | | | | | |
| 0601GIP4761 | −17, 30 nmol/kg | | | | | |

Embodiments of the invention further include the following. The following also provides in shorthand notation a description of each species and sub-genus derivable therefrom.

In one embodiment, the novel GIP analog or a GIP hybrid comprises a polypeptide comprising the formula D-L-C-S, wherein
D comprises a dipeptidyl peptidase IV resistant GIP N-terminal region,
L comprises a linker,
C comprises a GIP C-terminal region, and
S comprises a shield region; and
wherein L is optionally present and at least one of D or C are present, and wherein when C is present then C-S comprises a Trp-cage motif, or when C is absent then L-S further comprises a Trp-cage motif, and the polypeptide has GIP receptor binding and/or activating activity. When at least one of D or C is present, the at least one present D or C has GIP receptor activation and/or binding activity. In another embodiment both D and C are present. Either or both D and C can have GIP receptor activation and/or binding activity. In one embodiment the polypeptide can specifically bind a GIP receptor. Typically this binding will be at least two-fold greater than binding to another receptor such as an incretin receptor, e.g., GLP1R. The binding can be at least 5-, 10-, 50-, or even 100-fold greater than binding to another receptor such as an incretin receptor, e.g., GLP1R. In one embodiment the novel GIP analog comprises GIP agonist activity. In one embodiment the polypeptide can specifically activate a GIP receptor. Typically this activation will be at least two-fold greater than activation of another receptor such as an incretin receptor, e.g., GLP1R. The activation can be at least 3-, 4-, 5-, 10-, 50-, or even 100-fold greater than activation of another receptor such as an incretin receptor, e.g., GLP1R.

In another embodiment the polypeptide comprises at least one desired activity of a native GIP. When a desired activity of a novel GIP hybrid is greater than that of the native form, the activity can be at least two-fold greater. In further embodiments the desired activity is at least 3-, 4-, 5-, 10-, 50-, or even 100-fold greater than the activity compared to a native GIP. The activity may be receptor binding, receptor activation, receptor antagonism, glucose lowering, inhibition or reduction of gastric secretion, or any other activity, in vitro, ex vivo or in vivo, that may be known in the art or that is provided herein.

In further embodiments the D region of a novel GIP analog or hybrid comprises an 11 N-terminal amino acid sequence of a native GIP or a 14 N-terminal amino acid sequence of native GIP. In other embodiments the D region comprises the N-terminal portion of a modified or substituted GIP, e.g. see WO 00/58360, EP 1171465 or published United States Patent Application 20030232761.

In further embodiments region C comprises C-terminal amino acids 19-26 of native GIP, C-terminal amino acids 19-30 of native GIP, C-terminal amino acids 19-39 of native GIP or C-terminal amino acids 19-42 of a native GIP. In one such embodiment region C can comprise amino acids 19-26, 19-30, 19-39 or 19-42 of human, mouse, porcine or rat GIP. In other embodiments the C region comprises the C-terminal portion of a modified or substituted GIP, e.g. see published United States Patent Application 20030232761.

In one embodiment L comprises a sequence from native GIP, including DKIH or DKIH. In a further such embodiment the D-L-C portion of a novel GIP analog comprises amino acids 1-26, 1-30, 1-39, or 1-42 of a native GIP. In one such embodiment regions D-L-C comprise amino acids 1-26, 1-30, 1-39 or 1-42 of human, mouse, porcine or rat GIP (see for example Li et al., Regulatory Peptides 121(1-3) pages 107-112 (2004)). In yet a further such embodiment the D-L-C portion of a novel GIP analog comprises amino acids 1-26, 1-30, 1-39, or 1-42 of an N-terminally modified or substituted GIP (in any of positions 1-4) that comprises DPP-IV resistance, e.g. see WO 00/58360, EP 1171465 or published United States Patent Application 20030232761.

Novel GIP compounds of the formula D-L-C-S can comprise the sequence

```
                                       (SEQ ID NO: 186)
YAEGTFISDYSIAMDKIHQQDFVNWLLAQKPSSGAPPPS, (SEQ ID NO: 187)
(Tyr1-glucitol)AEGTFISDYSIAMDKIHQQDFVNWLLAQKPSSGAP
PPS, (SEQ ID NO: 188)
(Tyr1-pyroglutamyl)AEGTFISDYSIAMDKIHQQDFVNWLLAQKPS
SGAPPPS, (SEQ ID NO: 187)
(Tyr1-glucitol)AEGTFISDYSIAMDKIHQQDFVNWLLAQKPSSGAP
PPS, (SEQ ID NO: 189)
(Tyr1-9-fluorenylmethoxycarbonyl)AEGTFISDYSIAMDKIH
QQDFVNWLLAQKPSSGAPPPS, (SEQ ID NO: 190)
(Tyr1-palmitate)AEGTFISDYSIAMDKIHQQDFVNWLLAQKPSSGA
PPPS, (SEQ ID NO: 191)
YSEGTFISDYSIAMDKIHQQDFVNWLLAQKPSSGAPPPS,
or (SEQ ID NO: 192)
YGEGTFISDYSIAMDKIHQQDFVNWLLAQKPSSGAPPPS.
```

In another embodiment novel GIP compounds comprise the sequence

```
                                       (SEQ ID NO: 193)
YAEGTFISDYSIAMDKIHQQDFVNWLLAQKGKKNDWKHNITQPSSGAPPP
S, (SEQ ID NO: 194)
(Tyr1-glucitol) AEGTFISDYSIAMDKIHQQDFVNWLLAQKGKKND
WKHNITQPSSGAPPPS, (SEQ ID NO: 195)
(Tyr1-pyroglutamyl) AEGTFISDYSIAMDKIHQQDFVNWLLAQKG
KKNDWKHNITQPSSGAPPPS, (SEQ ID NO: 194)
(Tyr1-glucitol) AEGTFISDYSIAMDKIHQQDFVNWLLAQKGKKND
WKHNITQPSSGAPPPS, (SEQ ID NO: 196)
(Tyr1-9-fluorenylmethoxycarbonyl) AEGTFISDYSIAMDKI
HQQDFVNWLLAQKGKKNDWKHNITQPSSGAPPPS, (SEQ ID NO: 197)
(Tyr1-palmitate) AEGTFISDYSIAMDKIHQQDFVNWLLAQKGKKN
DWKHNITQPSSGAPPPS, (SEQ ID NO: 198)
YSEGTFISDYSIAMDKIHQQDFVNWLLAQKGKKNDWKHNITQPSSGAPPP
S,
or (SEQ ID NO: 199)
YGEGTFISDYSIAMDKIHQQDFVNWLLAQKGKKNDWKHNITQPSSGAPPP
S.
```

Novel GIP compounds can also comprise the sequence

Y(D-Ala)EGTFISDYSIAMDKIHQQDFVNWLLAQKPSSGAPPPS, (SEQ ID No. 186)

YAbuAEGTFISDYSIAMDKIHQQDFVNWLLAQKPSSGAPPPS, (SEQ ID NO: 200)
or

YSarAEGTFISDYSIAMDKIHQQDFVNWLLAQKPSSGAPPPS. (SEQ ID NO: 201)

In yet another embodiment novel GIP compounds comprise the sequence

Y(D-Ala)EGTFISDYSIAMDKIHQQDFVNWLLAQKGKKNDWKHNITQPSSGAPPPS, (SEQ ID No. 193)

YAbuAEGTFISDYSIAMDKIHQQDFVNWLLAQKGKKNDWKHNITQPSSGAPPPS, (SEQ ID NO: 202)
or

YSarAEGTFISDYSIAMDKIHQQDFVNWLLAQKGKKNDWKHNITQPSSGAPPPS. (SEQ ID NO: 203)

In one embodiment of novel GIP analog or hybrid, D comprises the sequence X1-X2-X3-X4-X5-X6-X7-X8-X9-X10-X11-X12-X13-X14 (SEQ ID No. 465), wherein at least one of X1, X2, and X3 is an amino acid substitution or modification providing DPP-IV resistance. In a further such embodiment DPP-IV resistance is provided by a modification comprising a peptide mimetic bond between X2 and X3. Such a bond can be provided as a reduced peptide bond of the formula Ψ(CH2NH), for example as when X1-X2-X3 is Tyr1-AlaΨ(CH2NH)-Glu. In a further embodiment any bond of the novel GIP analog is a reduced peptide bond of the formula Ψ(CH2NH), particularly one that is identified as susceptible to protease or peptidase degradation. In a further embodiment the substitution or modification comprises a D-amino acid substitution in X1, X2 and/or X3 and/or glycation, alkylation, acetylation or acylation of the N-terminus. Positions X1-X14 can be independently selected. In other embodiments any or more of X12-X14 are optionally absent.

Of interest are novel GIP analogs or hybrids wherein X2 and X3 are independently Lys, Ser, 4-amino butyric amino acid, Aib, D-Ala, Sarcosine or Pro. The N-terminal modification can be selected from the group of glycation, alkylation, acetylation, alkyloxycarbonylation or arylalkoxycarbonylation.

In yet another embodiment X1 is Tyr, desamino-Tyr, D-Tyr, Ala, a D-amino acid, Tyr-glucitol, an N-methylated amino acid, and/or comprises an N-terminal glycation, alkylation, acetylation, alkyloxycarbonylation, arylalkoxycarbonylation or acylation. In a further embodiment when X1 is Tyr then the N-terminus of the tyrosine residue can be modified by alkylation, alkyloxycarbonylation, arylalkoxycarbonylation, sulphonylation, glycation, homoserine formation, pyroglutamic acid formation, acylation, methylation, t-butylation, t-butyloxycarbonylation, 4-methylbenzylation, benzyloxymethylation, benzyloxycarbonylation, 4-toluenesulphonylation, diphenylmethylation, 2-bromobenzyloxycarbonylation, 9-fluorenylmethyloxycarbonylation, acylation, formylation, acetylation, benzylation, benzoylation, phosphorylation, sulphation, glycolysation with pentoses, deoxyhexoses, glucosamines, or N-acetylglucosamines, farnesylation, biotinylation, palmitoylation, stearoylation, geranylgeranylation, glutathionylation, and modification with lipoic acid. In yet a further embodiment the N-terminus of the X1 residue can be modified by alkylation, alkyloxycarbonylation, arylalkoxycarbonylation, sulphonylation, glycation, homoserine formation, pyroglutamic acid formation, acylation, methylation, t-butylation, t-butyloxycarbonylation, 4-methylbenzylation, benzyloxymethylation, benzyloxycarbonylation, 4-toluenesulphonylation, diphenylmethylation, 2-bromobenzyloxycarbonylation, 9-fluorenylmethyloxycarbonylation, acylation, formylation, acetylation, benzylation, benzoylation, phosphorylation, sulphation, glycolysation with pentoses, deoxyhexoses, glucosamines, or N-acetylglucosamines, farnesylation, biotinylation, palmitoylation, stearoylation, geranylgeranylation, glutathionylation, and modification with lipoic acid.

In yet another embodiment X2 is Ala, AlaΨ(CH2NH), Ser, D-amino acid, Lys, 4-amino butyric amino acid, Aib, D-Ala, Sarcosine, Pro, Gly, phosphorylated Ser, Val, Leu, Ile, Thr, or an N-methylated amino acid.

In a further embodiment X2 is a conservative amino acid change from a native residue or from an X2 residue provided herein. In yet another embodiment X2 is any naturally occurring amino acid. In a still further embodiment X2 is any non-proteinogenic amino acid.

In yet another embodiment X3 is Glu, D-Glu, L-Pro, (N-Me)Glu, Pro, D-amino acid, Lys, Ser, 4-amino butyric amino acid, Aib, D-Ala, Sarcosine, Pro, or an N-methylated amino acid. In a further embodiment X3 is a conservative amino acid change from a native residue or from an X3 residue provided herein. In yet another embodiment X3 is any naturally occurring amino acid. In a still further embodiment X3 is any non-proteinogenic amino acid.

In yet another embodiment X4 is Gly or Ala. In a further embodiment X4 is a conservative amino acid change from a native residue or from an X4 residue provided herein.

In yet another embodiment X5 is Thr or Ser.

In yet another embodiment X6 is Phe or Ala. In a further embodiment X6 is a conservative amino acid change from a native residue or from an X6 residue provided herein.

In yet another embodiment X7 is Ile or Ala. In a further embodiment X7 is a conservative amino acid change from a native residue or from an X7 residue provided herein.

In yet another embodiment X8 is Ser or Ala. In a further embodiment X8 is a conservative amino acid change from a native residue or from an X8 residue provided herein.

In yet another embodiment X9 is Asp or Ala. In a further embodiment X9 is a conservative amino acid change from a native residue or from an X9 residue provided herein.

In yet another embodiment X10 is Tyr or Ala. In a further embodiment X10 is a conservative amino acid change from a native residue or from an X10 residue provided herein.

In yet another embodiment X11 is Ser or Ala. In a further embodiment X11 is a conservative amino acid change from a native residue or from an X11 residue provided herein.

In yet another embodiment X12 is Ile, Ala, Ser, or Lys. In a further embodiment X12 is a conservative amino acid change from a native residue or from an X12 residue provided herein. In yet another embodiment X12 is any naturally occurring amino acid. In a still further embodiment X12 is absent.

In yet another embodiment X13 is Ala, Tyr, Glutamine, or Asp. In a further embodiment X13 is a conservative amino acid change from a native residue or from an X13 residue provided herein. In yet another embodiment X13 is any naturally occurring amino acid. In a still further embodiment X13 is absent.

In yet another embodiment X14 is Met, Ala, or Leu. In a further embodiment X14 is a conservative amino acid change from a native residue or from an X14 residue provided herein. In yet another embodiment X14 is any naturally occurring amino acid. In a still further embodiment X14 is absent.

In certain embodiments a modified D region of a novel GIP analog and a hybrid comprises the sequence Tyr-Ala-Glu-Gly-Thr-Phe-Ile-Ser-Asp-Tyr-Ser-Ile-Tyr-Met (SEQ ID NO: 204).

In certain embodiments D comprises the sequence

```
                                     (SEQ ID NO: 205)
Ala-Ala-Glu-Gly-Thr-Phe-Ile-Ser-Asp-Tyr-Ser-Ile-
Ala-Met;

(SEQ ID NO: 206)
Tyr-Ala-Ala-Gly-Thr-Phe-Ile-Ser-Asp-Tyr-Ser-Ile-
Ala-Met;

(SEQ ID NO: 207)
Tyr-Ala-Glu-Ala-Thr-Phe-Ile-Ser-Asp-Tyr-Ser-Ile-
Ala-Met;

(SEQ ID NO: 208)
Tyr-Ala-Glu-Gly-Ala-Phe-Ile-Ser-Asp-Tyr-Ser-Ile-
Ala-Met;

(SEQ ID NO: 209)
Tyr-Ala-Glu-Gly-Thr-Ala-Ile-Ser-Asp-Tyr-Ser-Ile-
Ala-Met;

(SEQ ID NO: 210)
Tyr-Ala-Glu-Gly-Thr-Phe-Ala-Ser-Asp-Tyr-Ser-Ile-
Ala-Met;

(SEQ ID NO: 211)
Tyr-Ala-Glu-Gly-Thr-Phe-Ile-Ala-Asp-Tyr-Ser-Ile-
Ala-Met;

(SEQ ID NO: 212)
Tyr-Ala-Glu-Gly-Thr-Phe-Ile-Ser-Ala-Tyr-Ser-Ile-
Ala-Met;

(SEQ ID NO: 213)
Tyr-Ala-Glu-Gly-Thr-Phe-Ile-Ser-Asp-Ala-Ser-Ile-
Ala-Met;

(SEQ ID NO: 214)
Tyr-Ala-Glu-Gly-Thr-Phe-Ile-Ser-Asp-Tyr-Ala-Ile-
Ala-Met;

(SEQ ID NO: 215)
Tyr-Ala-Glu-Gly-Thr-Phe-Ile-Ser-Asp-Tyr-Ser-Ala-
Ala-Met;
or
                                     (SEQ ID NO: 216)
Tyr-Ala-Glu-Gly-Thr-Phe-Ile-Ser-Asp-Tyr-Ser-Ile-
Ala-Ala.
```

In still further embodiments D comprises the sequence

```
                                     (SEQ ID NO: 217)
TyrSerGluGlyThrPheIleSerAspTyrSerIleAlaMet;

(SEQ ID NO: 218)
TyrGlyGluGlyThrPheIleSerAspTyrSerIleAlaMet;
or

Tyr-DAla-GluGlyThrPheIleSerAspTyrSerIleAlaMet.
```

In further embodiments D comprises the sequence

```
                                     (SEQ ID NO: 14)
YAEGTFISDYSIAM, (SEQ ID NO: 219)
(Tyr1-glucitol)AEGTFISDYSIAM,
```

```
                                     (SEQ ID NO: 220)
(Tyr1-pyroglutamyl)AEGTFISD, (SEQ ID NO: 219)
(Tyr1-glucitol)AEGTFISDYSIAM, (SEQ ID NO: 221)
(Tyr1-9-fluorenylmethoxycarbonyl)AEGTFISDYSIAM, (SEQ ID NO: 222)
(Tyr1-palmitate)AEGTFISDYSIAM, (SEQ ID NO: 223)
YSEGTFISDYSIAM,
or
                                     (SEQ ID NO: 224)
YGEGTFISDYSIAM.
```

In yet other embodiments D comprises the sequence Y(D-Ala)EGTFISDYSIAM, YAbuAEGTFISDYSIAM (SEQ ID NO: 225), or YSarAEGTFISDYSIAM (SEQ ID NO: 226).

In a still further embodiment a novel GIP analog or hybrid region D may exhibit at least 60%, 65%, 70%, 80%, 85%, 90%, 95%, 98% or 100% sequence identity to a corresponding region of a native GIP, for example amino acids 1-11, 1-12, 1-13 or 1-14 of a native GIP, preferably a human GIP, over the entire length of each corresponding sequence. Furthermore, a region D of a novel GIP analog may also exhibit at least 50%, 60%, 65%, 70%, 80%, 85%, 90%, 95% or even 100% sequence identity to a modified or substituted GIP, e.g. see WO 00/58360, EP1171465 or published United States Patent Application 20030232761. Percent identity can be determined manually or by analysis with the AlignX module in Vector NTI (Invitrogen; Carlsbad Calif.) or the ClustalW algorithm for global alignment. Native region D GIP sequences include those derived from human, mouse, rat, porcine or bovine GIP. Native GIP sequences include human GIP(1-42) (YAEGTFISDYSIAMDKIHQQDFVNWL-LAQKGKKNDWKHNITQ; SEQ ID NO: 2), mouse GIP(1-42) (YAEGTFISDYSIAMDKIRQQDFVNWL-LAQRGKKSDWKHNITQ; SEQ ID NO: 10), rat GIP(1-42) (YAEGTFISDYSIAMDKIRQQDFVNWL-LAQKGKKNDWKHNLTQ; SEQ ID NO: 11), pig GIP(1-42)(YAEGTFISDYSIAMDKIRQQDFVNWL-LAQKGKKSDWKHNITQ; SEQ ID NO: 12), or bovine GIP (1-42) (YAEGTFISDYSIAMDKIRQQDFVNWL-LAQKGKKSDWIHNITQ; SEQ ID NO: 13). In yet other embodiments region D comprises amino acids 1-11, 1-12, 1-13 or 1-14 of human, mouse, rat, pig or bovine GIP, e.g. wherein region D comprises YAEGTFISDYS (SEQ ID NO: 227), YAEGTFISDYSI (SEQ ID NO: 228), YAEGTFIS-DYSIA (SEQ ID NO: 229) or YAEGTFISDYSIAM (SEQ ID NO: 14). In still further embodiments a region D amino acid sequence further comprises a modified or substituted amino acid in addition to any one of positions X1, X2 or X3.

In some embodiments of the novel GIP analog or hybrid L can be absent. In other embodiments L comprises
a) Aha,
b) Aha-Aha,
c) Aha-Aha-Aha,
d) Amino alkanoic acid (C5-C12),
e) Glu-Lys-Glu-Lys (SEQ ID NO: 230),
f) Ala-Ala-Ala-Ala (SEQ ID NO: 231),
g) a linker peptide comprising 12 amino acid residues selected from the group consisting of amino acid residues, D-amino acids and non-proteinogenic amino acids, h) Glu-Lys-Glu-Glu-Lys-Glu-Lys-Glu-Glu-Lys-Glu-Lys (SEQ ID NO: 232),
i) an omega-amino fatty acids (saturated and unsaturated) of omega-NH2-(CHx)n-COOH where n=10 to 34; or
j) the sequence X15-X16-X17-X18 (SEQ ID No. 466) wherein each of X15-X18 is independently any naturally-occurring amino acid, non-proteinogenic amino acid, D-amino acid or is absent.

In further embodiments X15 is D, E, or a conservative amino acid change thereof or of a native X15 residue. In further embodiments X16 is K, G, E, or a conservative amino acid change thereof or of a native X16 residue. In further embodiments X17 is I, Q, E, or a conservative amino acid change thereof or of a native X17 residue. In further embodiments X18 is H, R, A or a conservative amino acid change thereof or of a native X18 residue. In novel GIP analogs L can comprise the sequence D-K-I-H or D-K-I-R. In further embodiments L comprises a modified or substituted amino acid. In one such embodiment L comprises in a first position (e.g. X16) a (hetero)aryl (both optionally substituted) or 3-7C cycloalkyl, 1-10C (hetero)alkylene, 2-10C (hetero)alkenylene, 2-10C (hetero)alkynylene or phenyl, and in a second C-terminally adjacent position (e.g. X17) a 1-10C (hetero) alkylene, 2-10C (hetero)alkenylene, 2-10C (hetero)alkynylene, or phenyl linked via a —CO— to the next residue in the amino acid backbone. In still further embodiments a region L amino acid sequence further comprises a modified or substituted amino acid.

In one embodiment of the invention region C comprises the sequence X19-X20-X21-X22-X23-X24-X25-X26-X27-X28-X29-X30 (SEQ ID NO. 467), each position being independently selected, wherein
X19 is Q or a conservative amino acid substitution thereof,
X20 is Q or a conservative amino acid substitution thereof,
X21 is D or a conservative amino acid substitution thereof,
X22 is F, Y or a conservative amino acid substitution thereof,
X23 is V, I, A, or a conservative amino acid substitution thereof,
X24 is N, Q or a conservative amino acid substitution thereof,
X25 is W, F, Y, napthylalanine or a conservative amino acid substitution thereof,
X26 is L, A or a conservative amino acid substitution thereof,
X27 is L, K, R, V, A, I or a conservative amino acid substitution thereof, or is absent
X28 is A, N, D, K, R, E or a conservative amino acid substitution thereof, or is absent
X29 is Q, G or a conservative amino acid substitution thereof or is absent, and
X30 is K, G, R, G, P, R or a conservative amino acid substitution thereof or is absent.

In a further aspect any one, two, or three of X26 to X30 is absent in region C.

In yet another embodiment a novel GIP analog region C comprises 8 to 24 C-terminal amino acids of a GIP (beginning at a position in the GIP corresponding to position X19 (Gln) in human GIP), at least the first such 8 amino acids (e.g., comprising positions X19-X26, such as X19-27, X19-X28, X19-29), at least the first 12 such amino acids (e.g., comprising positions X19 to X30, such as X19-X31, X19-X32, X19-X33, X19-X34, X19-X35, X19-X36, X19-X37, X19-X38), at least the first 21 such amino acids (e.g. comprising positions X19 to X39, such as X19-X40, X19-X41) or at least 24 such amino acids. Notably in these embodiments X27-X30 may be independently present or absent. For example, region C can further comprise residues 31 to 39 of a GIP or a native GIP, and X27 to X30 may be optionally absent.

In a still further embodiment a novel GIP analog or hybrid region C may exhibit at least 60%, 65%, 70%, 80%, 85%, 90%, 95%, 98% or 100% sequence identity to a corresponding region of a native GIP, for example amino acids 19-30, 19-26, 19-26 or 19-42 of a native GIP over the entire length of each corresponding sequence. Furthermore, a region C of a novel GIP analog may also exhibit at least 50%, 60%, 65%, 70%, 80%, 85%, 90%, 95%, 98% or even 100% sequence identity to a modified or substituted GIP, e.g. see WO 00/58360, EP1171465 or published United States Patent Application 20030232761. Native region C GIP sequences include those derived from human, mouse, rat, porcine or bovine GIP. Native GIP sequences include human GIP(1-42) (YAEGTFISDYSIAMDKIHQQDFVNWL-LAQKGKKNDWKHNITQ; SEQ ID NO: 2), mouse GIP(1-42) (YAEGTFISDYSIAMDKIRQQDFVNWL-LAQRGKKSDWKHNITQ; SEQ ID NO: 10), rat GIP(1-42) (YAEGTFISDYSIAMDKIRQQDFVNWL-LAQKGKKNDWKHNLTQ; SEQ ID NO: 11), pig GIP(1-42) (YAEGTFISDYSIAMDKIRQQDFVNWL-LAQKGKKSDWKHNITQ; SEQ ID NO: 12), or bovine GIP (1-42) (YAEGTFISDYSIAMDKIRQQDFVNWL-LAQKGKKSDWIHNITQ; SEQ ID NO: 13). In yet other embodiments region C comprises amino acids 19-30, 19-26, 19-26 or 19-42 of human, mouse, rat, pig or bovine GIP, e.g. region C comprises GlnGlnAspPheValAsnTrpLeuLeuAlaGlnLys (SEQ ID NO: 233) or GlnGlnAspPheValAsnTrpLeuLeuAlaGlnArg (SEQ ID NO: 234). In still further embodiments a region C amino acid sequence further comprises a modified or substituted amino acid.

In one embodiment of the novel GIP analog or hybrid region S comprises the sequence X31-X32-X33-X34-X35-X36-X37-X38-X39 (SEQ ID No. 468), each independently selected, wherein
X31 is Pro, homoproline, 3Hyp, 4Hyp, thioproline, N-alkylglycine, N-alkylpentylglycine or N-alkylalanine, G, S;
X32 is Ser, Pro, His, homoproline, 3Hyp, 4Hyp, thioproline, N-alkylglycine, N-alkylpentylglycine or N-alkylalanine;
X33 is Ser, Arg, Thr, Trp, Lys;
X34 is Gly, Ser;
X35 is Ala, Arg, Asp, Glu, Lys, Gly;
X36 is Pro, homoproline, 3Hyp, 4Hyp, thioproline, N-alkylglycine, N-alkylpentylglycine or N-alkylalanine, A, absent;
X37 is Pro, homoproline, 3Hyp, 4Hyp, thioproline, N-alkylglycine, N-alkylpentylglycine or N-alkylalanine, A, absent;
X38 is Pro, homoproline, 3Hyp, 4Hyp, thioproline, N-alkylglycine, N-alkylpentylglycine or N-alkylalanine, Ala, Arg, Lys, His, or is absent; and
X39 is Ser, Thr, Tyr, Leu, Ala, Lys, His, Pro, Lys, Arg, Gly, or absent, wherein if an amino acid is absent then all subsequent positions are absent.

In a further embodiment at least one of X31-X39 contains a conservative substitution of an amino acid listed herein for the embodiments of region S. In further embodiments region S comprises ProSerSerGlyAlaProProProSer (SEQ ID NO: 1), ProSerSerGlyAlaProProPro (SEQ ID NO: 235), ProSerSerGlyAlaProPro (SEQ ID NO: 236), ProSerSerGlyAlaPro (SEQ ID NO: 237), ProSerSerGlyAla (SEQ ID NO: 238), ProSerSerGly (SEQ ID NO: 239), or ProSerSer. In yet a further embodiment region S comprises a C-terminal amide. In still a further embodiment region S comprises a sequence wherein X37 is Pro, homoproline, 3Hyp, 4Hyp, thioproline, N-alkylglycine, N-alkylpentylglycine or N-alkylalanine that is capable of interacting with a Trp or Trp-like residue in region C to form a Trp-cage. In still another embodiment region S comprises a sequence wherein X31 is Pro, homoproline, 3Hyp, 4Hyp, thioproline, N-alkylglycine, N-alkylpentylglycine or N-alkylalanine that is capable of interacting with a Trp or Trp-like residue in region C to form a Trp-cage. In yet a further embodiment region S comprises a sequence wherein X31 and X37 are both Pro, homoproline, 3Hyp, 4Hyp, thioproline, N-alkylglycine, N-alkylpentylglycine or N-alkylalanine and that is capable of interacting with a Trp or Trp-like residue in region C to form a Trp-cage. In some embodiments region S comprises a sequence of 5 to 14 amino acids, 5 to 10 amino acids, or 6 to 9 amino acids that is capable of forming a Trp cage with the region C.

In other embodiments the S region contains or alternatively comprises a frog GLP1 tail region. GIP analog 0601GIP4673 is an example of such a compound, which also has a DPPP-IV resistant N-terminus and modifications that reduce hydrophobicity to increase solubility. Accordingly, in a further embodiment, the GLP-1 frog tail containing GIP compounds and hybrids further include at least one, two or three modifications that increase solubility of the parent compound, as discussed and exemplified herein. Of particular interest are embodiments wherein the frog GLP-1 tail is PKKIRYS (SEQ ID No. 421) or an analog or derivative thereof. In one embodiment, GIP analogs and derivatives, and GIP hybrids containing such GIP compounds do not include the frog GLP-1 tails specifically exemplified in PCT/US2006/005020 of Levy et al., but would include the novel analogs and derivatives thereof disclosed herein. It is expressly intended that for each GIP analog and derivative exemplified herein, a second compound is expressly intended wherein a novel frog GLP-1 tail region as disclosed herein is substituted or added to the C-terminal region of the GIP compound as taught herein. According to this aspect, for example, the C-terminal PSSGAPPPS region of 0601GIP4645 would be replaced with PKKIRYS (SEQ ID No. 421) or a novel analog or derivative thereof to generate a new GIP compound useful either alone or as a GIP hybrid component. Such specific molecules are hereby expressly intended and described as if each was individually listed herein.

In one embodiment are GIP compounds having an analog or derivative of the PKKIRYS tail (SEQ ID No. 421) wherein any one of the positions in the tail is substituted with an alanine, e.g. PAKIRYS (SEQ ID No. 422). In one embodiment the PKKIRYS tail (SEQ ID No. 421) analog has serine-proline dipeptide is inserted between the proline and serine. In one embodiment GIP compounds have a PKKIRYS tail (SEQ ID No. 421) analog wherein any one, two or three of positions 3, 4 and 6 are substituted with serine, alanine and proline, respectively. In one embodiment the PKKIRYS tail (SEQ ID No. 421) analog has any one, two or three of positions 4, 5 and 7 substituted with lysine, leucine, and proline, respectively. In one embodiment having the PKKIRYS tail (SEQ ID No. 421) is an tail analog wherein any one or two of positions 2 and 3 are substituted with either asparagine, glutamine or both, which effectively reduces proteolytic cleavage at the 2-3 bond. In one embodiment having the PKKIRYS tail (SEQ ID No. 421) is a tail analog wherein any one or two of positions 2 and 3 are substituted or derivatized to effectively reduce proteolytic cleavage at the 2-3 bond. Such substitutions or derivatives include those known to prevent cleavage of a KK bond, and will maintain peptide function as is readily determined as taught herein. In one embodiment having the PKKIRYS tail (SEQ ID No. 421) is a tail analog wherein any one or two of positions 4 and 7 are substituted with an octylglycine, which effectively reduces proteolytic cleavage at the 2-3 bond. In yet other embodiments, a PKKIRYS tail (SEQ ID No. 421) or analog or derivative thereof is combined with a modification that increases the hydrophilicity of the GIP analog. In one such embodiment at least any one, two or three of positions N24, W25, L26 or L27 are substituted with a more hydrophilic amino acid. In one such embodiment the more hydrophilic amino acid is selected from with E, P, N, S, T, K, R or Q. In one such embodiment the N24 is substituted with E, P or Q. In one such embodiment the W25 is substituted with E, P, N or Q. In one such embodiment either or both L26 or L27 is substituted with E, P, Q, N, S, T or K. In one such embodiment the W25 is substituted with E, P, N, S, T, K or Q.

In one embodiment the novel GIP analog or hybrid is modified. The novel GIP hybrid can comprise a modification by fatty acid addition at an epsilon amino group of at least one lysine residue.

In one embodiment a novel GIP analog or hybrid is a GIP-receptor agonist. The novel GIP hybrid can potentiate cyclic AMP production. In another embodiment a novel GIP hybrid is a GIP-receptor antagonist. The applicant appreciates that GIP compounds and hybrids as disclosed herein may bind but not significantly activate the GIP receptor. Such GIP receptor antagonists are useful, for example, as in chronic administration to treat obesity-related diabetes, possibly by increasing insulin resistance (see for example, Gault et al. Diabetes (2005) 54(8):2436-3446).

In one embodiment a novel GIP analog or hybrid comprises a sequence of the formula D-L-C-S where D comprises a D-amino acid alanine at X2 and wherein D, L, C and S are as defined herein and is any of the other embodiments herein. For example, in a further such embodiment region C comprises amino acids 19-30 of a GIP, particularly a human GIP, even more particularly comprises the sequence QQDFVNWLLAQK (SEQ ID NO: 15). In a further such embodiment L is naturally occurring sequence X15-X18 from a native GIP, particularly human GIP. In a further exemplary embodiment S is a sequence comprising PSSGAPPPS (SEQ ID NO: 1), PSSGAPPP (SEQ ID NO: 235), PSSGAPP (SEQ ID NO: 236), PSSGAP (SEQ ID NO: 237), PSSGA (SEQ ID NO: 238), or PSSG (SEQ ID NO: 239). In yet another embodiment a novel GIP hybrid comprise the sequence:

```
                                         (SEQ ID No. 469)
Y(D-Ala)EGTFISDYSIAMDKIHQQDFVNWLLAQKPSSGAPPPS;

(SEQ ID No. 470)
Y(D-Ala)EGTFISDYSIAMDKIRQQDFVNWLLAQRPSSGAPPPS;

(SEQ ID No. 471)
Y(D-Ala)EGTFISDYSIAMDKIRQQDFVNWLLAQKPSSGAPPPS;

(SEQ ID No. 472)
Y(D-Ala)EGTFISDYSIAMDKIRQQDFVNWLLAQKPSSGAPPPS;
or (SEQ ID No. 473)
Y(D-Ala)EGTFISDYSIAMDKIRQQDFVNWLLAQKPSSGAPPPS.
```

In a further example, an embodiment of such a novel D-Ala2-containing GIP analog or hybrid can exhibit at least 50% sequence identity to one of the above analogs and comprises a D-Ala at position X2. In additional embodiments, the embodiment can further comprise the sequence PSSGAPPPS (SEQ ID NO: 1) or KNGGKPSSGAPPPS (SEQ ID NO: 240).

In one embodiment of a novel GIP analog or hybrid region D comprises the formula X1-X2-X3-X4-X5-X6-X7-X8-X9-X10-X11-X12-X13-X14 (SEQ ID No. 474) wherein X1 and X2 are absent. In a further embodiment region D comprises the formula X1-X2-X3-X4-X5-X6-X7-X8-X9-X10-X11-X12-X13-X14 (SEQ ID NO: 578) wherein X1 and X2 are absent and at least one of X3, X4 or X5 is an amino acid substitution or modification providing DPP-IV resistance, for example with a modification or substitution or reduced bond as defined herein. Other amino acid positions are as defined herein. Typically such embodiment of a novel GIP analog or hybrid has GIP antagonist activity.

In one embodiment D is absent. In another embodiment when D is absent, a novel GIP analog can comprise L-C-S or C-S where region L or C comprises an N-terminal modification, substitution or modification providing protease resistance, particularly DPP-IV resistance. In yet a further embodiment is X18-X19-C-S wherein one or both of X18 and X19 are absent, such that for X18-X19-X20, X19-X20-X21, and X20-X21-X22, an amino acid substitution or modification or N-terminal modification of at least one of X18, X19, X20, X21 or X22 provides DPP-IV resistance.

Additional embodiments include compounds comprising the sequence

```
                                        (SEQ ID NO. 186)
Y(DAla)EGTFISDYSIAMDKIHQQDFVNWLLAQKPSSGAPPPS, (SEQ ID NO: 241)
Y(pSer)EGTFISDYSIAMDKIHQQDFVNWLLAQKPSSGAPPPS, (SEQ ID NO: 242)
YA(N-MeGlu)EGTFISDYSIAMDKIHQQDFVNWLLAQKPSSGAPPPS, (SEQ ID NO: 243)
YPEGTFISDYSIAMDKIHQQDFVNWLLAQKPSSGAPPPS, (SEQ ID NO: 244)
YVEGTFISDYSIAMDKIHQQDFVNWLLAQKPSSGAPPPS, (SEQ ID No. 475)
(D-Tyr)AEGTFISDYSIAMDKIHQQDFVNWLLAQKPSSGAPPPS,
or
                                        (SEQ ID NO: 245)
YAPGTFISDYSIAMDKIHQQDFVNWLLAQKPSSGAPPPS.
```

Further embodiments include compounds comprising the sequence

```
                                        (SEQ ID No. 193)
Y(DAla)EGTFISDYSIAMDKIHQQDFVNWLLAQKGKKNDWKHNITQPSS
GAPPPS, (SEQ ID NO: 246)
Y(pSer)EGTFISDYSIAMDKIHQQDFVNWLLAQKGKKNDWKHNITQPSS
GAPPPS, (SEQ ID NO: 247)
YA(N-MeGlu)EGTFISDYSIAMDKIHQQDFVNWLLAQKGKKNDWKHNIT
QPSSGAPPPS, (SEQ ID NO: 248)
YPEGTFISDYSIAMDKIHQQDFVNWLLAQKGKKNDWKHNITQPSSGAPPP
S, (SEQ ID NO: 249)
YVEGTFISDYSIAMDKIHQQDFVNWLLAQKGKKNDWKHNITQPSSGAPPP
S, (SEQ ID No. 476)
(D-Tyr)AEGTFISDYSIAMDKIHQQDFVNWLLAQKGKKNDWKHNITQPS
SGAPPPS,
or
                                        (SEQ ID NO: 250)
APGTFISDYSIAMDKIHQQDFVNWLLAQKGKKNDWKHNITQPSSGAPPP
S.
```

In a further embodiment any of the GIP polypeptides comprises an N-terminal His, D-histidine, desamino-histidine, 2-amino-histidine, beta-hydroxy-histidine, homohistidine, alpha-fluoromethyl-histidine, alpha-methyl histidine. Additional embodiments include compounds comprising the sequence

```
                                        (SEQ ID NO: 251)
HGEGTFISDYSIAMDKIHQQDFVNWLLAQKPSSGAPPPS
or
                                        (SEQ ID NO: 252)
HGEGTFISDYSIAMDKIHQQDFVNWLLAQKGKKNDWKHNITQPSSGAPPP
S.
```

In one embodiment of a novel GIP analog or hybrid, region L and/or C comprises a modified or substituted amino acid. In certain embodiments the novel GIP analog comprises Cys, D-Cys, HomoCys or Penicillamine. In a further embodiment the linker L and/or region C comprises Cys, D-Cys, homoCys or penicillamine. These amino acids are inserted as a site for modification to add peg molecules, lipids or link to other SH containing molecules such as other peptides or reactive molecules. In another embodiment at least one Cys, D-Cys, HomoCys or Penicillamine is modified with a lipid or a peg molecule or a reactive group. Typically 0, 1, 2 or 3 such residues are present.

In one such embodiment region L and/or C comprises at least one Cys, D-Cys, homocys or penicillamine residue. In one such embodiment of the novel GIP analog at least one of X15 to X18 or X31 to X40 is Cys, D-Cys, homocys or penicillamine. In a further such embodiment, no more than two of X15 to X18 or X31 to X40 is Cys, D-Cys, homocys or penicillamine. In a further embodiment no more than one of X15 to X18 or X31 to X40 is Cys, D-Cys, homocys or penicillamine. In a further such embodiment at least one of X15 to X18 or X31 to X40 is Cys, D-Cys, homocys or penicillamine and at least one of said residues is modified by a lipid.

In an embodiment a novel GIP analog or hybrid comprises a pegylated amino acid. At least one PEG molecule can be attached to the polypeptide. In one such embodiment each peg molecule is attached to the compound at a D-Cys, homocys or penicillamine or Lys amino acid or to the carboxy terminal amino acid. In a further such embodiment the at least one PEG molecule is attached to an amino acid in region L and/or C. In a further embodiment a pegylated novel GIP analog has an elimination half-life of at least one hour. Further a novel GIP analog or hybrid can comprise 1, 2, or 3 peg molecules. In a further embodiment at least one of X15 to X18 or X31 to X40 is Cys, D-Cys, homocys or penicillamine and at least one of said residues is attached to a peg molecule. Furthermore at least one, two or three of X15 to X18 or X31 to X40 is Cys, D-Cys, homocys or penicillamine and at least one, two or three of said residues are attached to a peg molecule.

A GIP compound of the present invention can be modified by attaching or coupling a reactive group. A GIP compound is thereby capable of covalently binding to a blood component through the reactive group. The reactive group typically will covalently bond with an amino group, a hydroxyl group, or a thiol group on a blood component, thereby covalently linking the GIP peptide to the blood component. In one embodiment, the reactive group will react with a thiol group on a blood component. More preferably, the reactive group will react with a thiol group on blood serum albumin. The reactive group may contain any of a number of chemically reactive entities that are capable of forming a covalent bond. In one embodiment, the reactive group will be capable of reacting with a thiol group on a blood component to form a disulfide bond. Such reactive groups are found for example in U.S. Pat. No. 6,593,295. In one embodiment of particular interest, the GIP compound is reacted ex vivo with along-lived blood component such as albumin to form a composition suitable for sustained release. Other suitable long-lived components of the blood include immunoglobulin, human serum albumin, red blood cells and platelets.

Reactive groups that are capable of forming disulfide bonds with thiol groups include those having an activated disulfide bond or an S-sulfonate. Reactive groups having an activated disulfide bond can be derived by coupling a GIP peptide cysteine (or cysteine analog) with an activating group, such as 2,2'-dithiodipyridine (DTDP), 2,2'-dithiobis (5-Nitropyridine) (NPYS), 5,5'-dithiobis(2-nitrobenzoic acid) (Ellman's reagent), or 6,6'-dithiodinicotinic acid. Reactive groups containing an activated disulfide bond are herein referred to as activated disulfide bond groups. In addition, an activated disulfide bond group can be derived by acylating a lysine side chain of a GIP peptide with a mercapto-activated carboxylic acid. Another exemplary embodiment of the present invention is to utilize a reactive group that is capable of reacting with a thiol group on a blood component to form a thioether linkage. In one embodiment, such a reactive group will be derived by coupling a GIP peptide with a chemically reactive entity from a maleimido-containing group, such as gamma-maleimide-butyrylamide (GMBA), maleimide-benzoyl-succinimide (MBS), gamma-maleimido-butyryloxy succinimide ester (GMBS), and maleimidopropionic acid (MPA). These and other maleimide containing groups are herein referred to as maleimido groups. In an alternative embodiment of the present invention, the reactive group of a GIP compound will be capable of covalently bonding to a primary amine on a blood component to form an amide bond. In one embodiment, such reactive groups will be derived by coupling a GIP peptide with N-hydroxysuccinimide (NHS) or N-hydroxysulfosuccinimide (sulfo-NHS) to form an NHS or sulfo-NHS ester. These succinimidyl groups may potentially react with alpha-amine groups on the N-termini of blood component proteins, provided that such amine groups are accessible or available to the reactive group. In one embodiment, these succinimidyl groups will react with the epsilon-amine of lysine in blood component proteins, since the epsilon-amine of lysine is the only amino acid side chain that reacts significantly with NHS esters. In yet another embodiment, GIP compounds of the present invention contain reactive groups that are designed to covalently bond with thiol groups on blood components. Binding to thiol groups is exemplary over binding to amino groups, because thiol groups are less abundant in vivo than are amino groups. Fewer blood components are thereby targeted through binding to thiol groups compared to binding to amino groups, resulting in greater specificity of binding. Accordingly, the exemplary GIP compounds will contain GIP peptides modified with a maleimido group or more In one embodiment, an S-sulfonate or an activated disulfide bond group. While the GIP compounds of the present invention may bind to any of several blood components that contain a free thiol group, the GIP compounds preferably will covalently bond with the thiol group on serum albumin. Serum albumin is the most abundant blood protein, and contains a single thiol group, located at amino acid residue 34 in the protein (Cys34), which is highly conserved among species. The binding of GIP compounds to serum albumin not only provides specificity of binding, but also provides a reproducible formation of conjugates having a 1:1 binding of GIP compound to serum albumin. The reproducibility of this 1:1 ratio is desirable for use of a GIP compound as a therapeutic, since reproducible conjugates of GIP compound and serum albumin will result upon administration of the GIP compound. Furthermore, the reproducibility of 1:1 conjugates of GIP compound and serum albumin is desirable for ex vivo or in vitro approaches to form conjugates for therapy. Conjugates can be formed ex vivo by combining GIP compounds of the present invention with blood, allowing formation of the conjugates, and then administering the conjugate-containing blood to the host. Alternatively, GIP compound-serum albumin conjugates can also be formed in vitro, by combining GIP compound with recombinant serum albumin to form conjugates which can be administered. The reproducibility of 1:1 conjugates of GIP compound and serum albumin provides for reproducible conjugates from ex vivo administration or in vitro batch to batch preparation.

In another embodiment provided are GIP compounds covalently attached to one or more molecules of polyethylene glycol (peg), or a derivative thereof wherein each peg is attached at a Cys or Lys amino acid or the carboxy terminus of the peptide, resulting in pegylated GIP compound with a half-life of at least one hour, at least 4, 6, 10, 15, 20 or 24. In one embodiment a pegylated GIP compound comprises any of the novel GIP compound sequences taught herein with a peg molecule covalently attached at 1, 2 or 3 residues.

In yet further contemplated embodiments the embodiments presented above or herein are combined in any consistent combination. For example embodiments describing region D can be combined with embodiments describing region L to describe novel GIP analog embodiments having the combined changes in region D and in region L. The analogs can be further combined with a second hormone module to form a GIP hybrid.

In another embodiment, the novel GIP analog or hybrid polypeptides of the invention are at least amino acids 25 amino acids in length. In other embodiments, the polypeptides may be at least 21, 22, 23, 24, 25, 26, 27, 28, 29, 30, 31, 32, 33, and each integer up to 54 amino acids in length (e.g. GIP(1-42)+long exendin tail (27-39)). Further, in one embodiment, the polypeptides of the invention include only natural L amino acid residues and/or modified natural L amino acid residues. Alternatively, in another embodiment, the polypeptides of the invention do not include unnatural amino acid residues.

In yet another embodiment, the novel GIP analog or hybrid may exhibit at least 60%, 65%, 70%, 80%, 85%, 90%, 95% or 98% sequence identity to a native GIP(1-42), GIP(1-30), GIP(1-26), GIP(1-39), GIP(19-30), GIP(19-26), GIP(19-39), GIP(19-42), GIP(1-11), or GIP(1-14) over the entire length of each corresponding sequence. Such polypeptides of the invention may also exhibit at least 50%, 60%, 65%, 70%, 80%, 85%, 90%, 95% or 98% sequence identity to a modified or substituted GIP, e.g. see WO 00/58360, EP1171465 or published United States Patent Application 20030232761. In yet another embodiment the D-L-C region of a novel GIP analog may exhibit at least 60%, 65%, 70%, 80%, 85%, 90%, 95% or 98% sequence identity to a native GIP(1-42), GIP(1-30), GIP(1-26), GIP(1-39), GIP(19-30), GIP(19-26), GIP (19-39), GIP(19-42), GIP(1-11), or GIP(1-14) over the entire length of each corresponding sequence. Native GIP sequences include those derived from

```
human GIP(1-42)   (YAEGTFISDYSIAMDKIHQQDFVNWLLAQKG
                   KKNDWKHNITQ; SEQ ID NO: 2), human GIP(1-26)   (YAEGTFISDYSIAMDKIRQQDFVNWL;
                   SEQ ID NO: 253),
```

```
human GIP(1-30)   (YAEGTFISDYSIAMDKIHQQDFVNWLLAQK;
                  SEQ ID NO: 3),
human GIP(1-39)   (YAEGTFISDYSIAMDKIHQQDFVNWLLAQKG
                  KKNDWKHN; SEQ ID NO: 254),
mouse GIP(1-42)   (YAEGTFISDYSIAMDKIRQQDFVNWLLAQRG
                  KKSDWKHNITQ; SEQ ID NO: 10),
mouse GIP(1-26)   (YAEGTFISDYSIAMDKIRQQDFVNWL;
                  SEQ ID NO: 255),
mouse GIP(1-30)   (YAEGTFISDYSIAMDKIRQQDFVNWLLAQR;
                  SEQ ID NO: 256),
mouse GIP(1-39)   (YAEGTFISDYSIAMDKIRQQDFVNWLLAQRG
                  KKSDWKHN; SEQ ID NO: 257)),
rat GIP(1-42)     YAEGTFISDYSIAMDKIRQQDFVNWLLAQKGK
                  NDWKHNLTQ (SEQ ID NO: 11),
rat GIP(1-26)     YAEGTFISDYSIAMDKIRQQDFVNWL
                  (SEQ ID NO: 258),
rat GIP(1-30)     YAEGTFISDYSIAMDKIRQQDFVNWLLAQK
                  (SEQ ID NO: 259),
rat GIP(1-39)     YAEGTFISDYSIAMDKIRQQDFVNWLLAQKGK
                  NDWKHN (SEQ ID NO: 260),
pig GIP(1-42)     YAEGTFISDYSIAMDKIRQQDFVNWLLAQKGK
                  KSDWKHNITQ (SEQ ID NO: 12),
pig GIP(1-26)     YAEGTFISDYSIAMDKIRQQDFVNWL
                  (SEQ ID NO: 261),
pig GIP(1-30)     YAEGTFISDYSIAMDKIRQQDFVNWLLAQK
                  (SEQ ID NO: 262),
pig GIP(1-39)     YAEGTFISDYSIAMDKIRQQDFVNWLLAQKGK
                  KSDWKHN (SEQ ID NO: 263),
bovine GIP(1-42)  YAEGTFISDYSIAMDKIRQQDFVNWLLAQKGK
                  KSDWIHNITQ (SEQ ID NO: 13),
bovine GIP(1-26)  YAEGTFISDYSIAMDKIRQQDFVNWL
                  (SEQ ID NO: 264),
bovine GIP(1-30)  YAEGTFISDYSIAMDKIRQQDFVNWLLAQK
                  (SEQ ID NO: 265), or
bovine GIP(1-39)  YAEGTFISDYSIAMDKIRQQDFVNWLLAQKGK
                  KSDWIHN (SEQ ID NO: 266).
```

In yet another embodiment, the S region of a novel GIP analog or hybrid of the invention may exhibit at least 50%, 60%, 65%, 70%, 80%, 85%, 90%, 95% or 98% sequence identity to a native Trp-cage sequence, such as PSSGAPPPS (SEQ ID NO: 1).

In a further embodiment a novel GIP analog or hybrid polypeptide of the invention comprises a sequence comprising at least 60%, 65%, 70%, 80%, 85%, 90%, 95% or 98% sequence identity to a novel GIP analog sequence disclosed herein. Such novel GIP analog or hybrid sequences, which are also useful for the sequence comparison, include:

```
                                    (SEQ ID NO: 267)
YAEGTFISDYSIAMDKIHQQDFVNWLLAQKGKKNDWKHNITQPPSGAPPP
S
(human GIP(1-42) core), (SEQ ID NO: 186)
YAEGTFISDYSIAMDKIHQQDFVNWLLAQKPSSGAPPPS
(human GIP(1-30) core), (SEQ ID NO: 268)
YAEGTFISDYSIAMDKIRQQDFVNWLLAQRGKKSDWKHNITQPSSGAPPP
S
(mouse GIP(1-42) core), (SEQ ID NO: 269)
YAEGTFISDYSIAMDKIRQQDFVNWLLAQRPSSGAPPPS
(mouse GIP(1-30) core), (SEQ ID NO: 270)
YAEGTFISDYSIAMDKIRQQDFVNWLLAQKGKKNDWKHNLTQPSSGAPPP
S
(rat GIP(1-42) core), (SEQ ID NO: 271)
YAEGTFISDYSIAMDKIRQQDFVNWLLAQKPSSGAPPPS
(rat GIP(1-30) core), (SEQ ID NO: 272)
YAEGTFISDYSIAMDKIRQQDFVNWLLAQKGKKSDWKHNITQPSSGAPPP
S
(pig GIP(1-42) core), (SEQ ID NO: 273)
YAEGTFISDYSIAMDKIRQQDFVNWLLAQKPSSGAPPPS
(pig GIP(1-30) core), (SEQ ID NO: 274)
YAEGTFISDYSIAMDKIRQQDFVNWLLAQKGKKSDWIHNITQPPSGAPPP
S
(bovine GIP(1-42) core),
or (SEQ ID NO: 275)
YAEGTFISDYSIAMDKIRQQDFVNWLLAQKPPSGAPPPS
(bovine GIP(1-30) core).
```

Further novel GIP analog or hybrid sequences, which are also used in the sequence comparisons mentioned above, include:

```
                                    (SEQ ID NO: 276)
YAEGTFISDYSIAMDKIHQQDFVNWLKNGGPSSGAPPPS
(human GIP(1-26) core), (SEQ ID NO: 277)
YAEGTFISDYSIAMDKIRQQDFVNWLKNGGPSSGAPPPS
(mouse GIP(1-26) core), (SEQ ID NO: 278)
YAEGTFISDYSIAMDKIRQQDFVNWLKNGGPSSGAPPPS
(rat GIP(1-26) core), (SEQ ID NO: 279)
YAEGTFISDYSIAMDKIRQQDFVNWLKNGGPSSGAPPPS
(pig GIP(1-26) core),
or (SEQ ID NO: 280)
YAEGTFISDYSIAMDKIRQQDFVNWLKNGGPSSGAPPPS
(bovine GIP(1-26) core).
```

Further novel GIP analog or hybrid sequences, which are also used in the sequence comparisons mentioned above, include:

```
YAEGTFISDYSIAMDKIHQQDFVNWLLAQKGKKNDWKHNPPSGAPPPS
(SEQ ID NO: 281) (human GIP(1-39) core), YAEGTFISDYSIAMDKIRQQDFVNWLLAQRGKKSDWKHNPSSGAPPPS
(SEQ ID NO: 282) (mouse GIP(1-39) core), YAEGTFISDYSIAMDKIRQQDFVNWLLAQKGKKNDWKHNPSSGAPPPS
(SEQ ID NO: 283) (rat GIP(1-39) core), YAEGTFISDYSIAMDKIRQQDFVNWLLAQKGKKSDWKHNPSSGAPPPS
(SEQ ID NO: 284) (pig GIP(1-39) core), or YAEGTFISDYSIAMDKIRQQDFVNWLLAQKGKKSDWIHNPPSGAPPPS
(SEQ ID NO: 285) (bovine GIP(1-39) core).
```

Further Applicable Considerations and Intentions.

Within each of the combinations described herein, it is understood that reference to a component peptide hormone or module includes reference to analogs, derivatives, fragments, as well as peptidic enhancers related thereto.

As mentioned, the novel GIP analogs are preferably C-terminally amidated, but need not be for the purposes of the instant invention. In other words, the C-terminus of these peptides, may have a free —OH or —NH2 group. These peptides may also have other post-translational modifications. One skilled in the art will appreciate that the novel GIP analog polypeptides of the present invention may also be constructed with an N-terminal methionine residue.

In yet other embodiments envisioned are variants of each of the sequences where the GIP portion is modified by one, two or three modifications as described herein. Exemplary modifications are those at the first (including the terminal NH2), second or third N-terminal amino acid of GIP that impart DPP-IV resistance superior to that of native GIP. Of particular interest are GIP compounds as described herein having at least a D-Ala substitution at position 2.

More particularly, in one aspect, the present invention relates to novel GIP analog polypeptides including one or more amino acid sequence modifications. Such modifications include substitutions, insertions, and/or deletions, alone or in combination. In one aspect the GIP analog or hybrid polypeptide includes one or more modifications of a "non-essential" amino acid residue. In the context of the invention, a "non-essential" amino acid residue is a residue that can be altered, i.e., deleted or substituted, in the native human amino acid sequence without abolishing or substantially reducing the GIP or component peptide hormone receptor agonist activity of the GIP analog or hybrid.

Substitutions. In one embodiment, the GIP analog or hybrid polypeptides of the invention may have one or more substitutions in the amino acid sequence of native GIP, GIP (1-30), GIP(1-14), GIP(1-26), GIP(1-39), GIP(19-26), GIP (19-30), GIP(19-39) or GIP(19-42) or a region S, alone or in combination with one or more insertions or deletions. In one embodiment, the substitution does not abolish or substantially reduce the GIP agonist activity of the GIP analog polypeptide. In one aspect, the present invention relates to GIP analog polypeptides that have a single substitution, or consecutive or non-consecutive substitution of more than one amino acid residues in the amino acid sequence of native human GIP. In one embodiment, the GIP analog polypeptides of the invention include one, two, or three amino acid substitutions. In one embodiment the native GIP is human, rat, mouse, porcine or bovine.

Particularly useful substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), beta-branched side chains (e.g., threonine, valine, isoleucine) and aromatic side chains (e.g., tyrosine, phenylalanine, tryptophan, histidine). In yet other embodiments exemplary conservative substitutions are shown in the following table under the column "Exemplary Substitutions".

In still other embodiments conserved substitutions are selected from the amino acids listed in the column labeled "Preferred Substitutions."

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp; lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (l) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | phe |
| Val (V) | ile; leu; met; phe; ala; norleucine | leu |

Optionally, a novel GIP analog or hybrid will have no more than one conservative amino acid substitution as compared to the sequence against which is being compared, alternatively no more than 2, 3, 4, 5, 6, 7, 8, 9, or 10 conservative amino acid substitution as compared to the sequence against which is being compared.

In another embodiment, the GIP analog or hybrid polypeptides of the invention may include substitutions of one or more unnatural and/or non-amino acids, e.g., amino acid mimetics, into the sequence of GIP. In a exemplary embodiment, the non-amino acids inserted into the sequence of GIP may be beta-turn mimetics or linker molecules, such as —NH—X—CO—, wherein X=(CH$_2$), (where n can be 2-20) or —NH—CH$_2$CH$_2$(—O—CH$_2$CH$_2$—O—)$_m$—CH$_2$—CO— (where m=1-5). Exemplary linker molecules include aminocaproyl ("Aca"), beta-alanyl, and 8-amino-3,6-dioxaoctanoyl. beta-turn mimetics are available commercially (BioQuadrant Inc, Quebec, Canada) and have been described in literature (Hanessian et al, Tetrahedron 12789-854 (1997); Gu et al, Tetrahedron Letters 44: 5863-6 (2003); Bourguet et al., Bioorganic & Medicinal Chemistry Letters 13: 1561-4 (2003); Grieco et al., Tetrahedron Letters 43: 6297-9 (2002); Souers et al., Tetrahedron 57: 7431-48 (2001); Tsai et al, Bioorganic & Medicinal Chemistry 7: 29-38 (1999); Virgilio et al, Tetrahedron 53: 6635-44 (1997)). Exemplary beta-turn mimetics include mimic A and mimic B illustrated herein. Their IUPAC names are Mimic A: N-(3S, 6S,9S)-2-oxo-3-amino-1-azabicyclo[4.3.0]-nonane-9-carboxylic acid. Mimic B: N-(3S,6S,9R)-2-oxo-3-amino-7-thia-1-azabicyclo[4.3.0]-nonane-9-carboxylic acid.

Exemplary GIP analog or hybrid polypeptides comprising amino acid sequence beta-turn mimetic substitutions include native human GIP, wherein amino acids at positions x and x+1 are substituted with beta-turn mimetics selected from the group consisting of mimic A and mimic B, wherein x is selected from the amino acids at amino acid positions 8 to 14 of native human GIP. (In addition to mimic A and B, Ala-Aib and Ala-Pro dipeptides are good turn inducers). These linkers are particularly useful to comprise region the region "L" of the D-L-C-S novel GIP analogs of the invention.

Deletions and Truncations. In another embodiment, the GIP analog or hybrid polypeptides of the invention may have one or more amino acid residues deleted from the amino acid sequence of native GIP, or a region S, alone or in combination with one or more insertions or substitutions. In one aspect, the GIP analog or hybrid polypeptides of the invention may have one or more amino acid residues deleted from the N-terminus or C-terminus of a native GIP. In another embodiment, the GIP analog or hybrid polypeptides of the invention may have one or more amino acid residues deleted at amino acid positions 1 through 42 of a native GIP, GIP(1-14), GIP(1-26), GIP(1-30), GIP(1-39), GIP(19-26), GIP(19-30), GIP(19-39) or GIP(19-42) or a region S. Such deletions may include more than one consecutive or non-consecutive deletion. In a exemplary embodiments no more than 1, no more than 2, no more than 3, no more than 4, or no more than 5 amino acids are deleted from a native GIP, from GIP(1-30), GIP(1-14), GIP (1-26), GIP(1-39), GIP(19-30), GIP(19-26), GIP(19-39) or GIP(19-42) or from a region S as when region is exendin(31-39) or exendin(27-39) for example. In one embodiment the native GIP is human, rat, mouse, porcine or bovine.

In one embodiment the GIP compound, either analog, derivative or hybrid, when intended for use as an agonist, does not include a deletion at any one of positions 1-15, corresponding to positions YAEGTFISDYSIAMD (SEQ ID No. 477), of the C-terminal sequence of GIP. In other words, each of the corresponding 1-15 positions of GIP will be present, although they may be substituted or derivatized. In a further embodiment the agonist GIP compound does not include a deletion at any one of positions 4-15, corresponding to positions GTFISDYSIAMD (SEQ ID No. 478), of the C-terminal sequence of GIP. In other words, each of the corresponding 4-15 positions of GIP will be present, although they may be substituted or derivatized. Accordingly, in embodiments of an agonist GIP compound, each of the positions 1-15 or 4-15 will be present and occupied by the amino acid present in that position of a naturally-occurring GIP species or by a substitution or derivative thereof. In yet another embodiment of agonist GIP compounds, excluded from the various embodiments described herein are the GIP compounds that did not demonstrate adequate receptor binding activity or receptor activation activity as shown.

In one embodiment the GIP compound, either analog, derivative or hybrid, when intended for use as an agonist, does not include a deletion at any one of positions 1-15, corresponding to positions YAEGTFISDYSIAMD (SEQ ID No. 477), of the C-terminal sequence of GIP. In other words, each of the corresponding 1-15 positions of GIP will be present, although they may be substituted or derivatized. In a further embodiment the agonist GIP compound does not include a deletion at any one of positions 4-15, corresponding to positions GTFISDYSIAMD (SEQ ID No. 478), of the C-terminal sequence of GIP. In other words, each of the corresponding 4-15 positions of GIP will be present, although they may be substituted or derivatized.

Insertions. In another embodiment, the GIP analog or hybrid polypeptides of the invention may have one or more amino acid residues inserted into the amino acid sequence of native GIP from GIP(1-30), GIP(1-14), GIP(1-26), GIP(1-39), GIP(19-30), GIP(19-26), GIP(19-39) or GIP(19-42) or region S, alone or in combination with one or more deletions and/or substitutions. In one aspect, the present invention relates to GIP analog or hybrid polypeptides that have a single insertion, or consecutive or non-consecutive insertions of more than one amino acid residues into the amino acid sequence of native GIP, GIP(1-30), GIP(1-14), GIP(1-26), GIP(1-39), GIP(19-30), GIP(19-26), GIP(19-39) or GIP(19-42), or region S, for example exendin(27-39) and exendin(31-39). In one embodiment the native GIP is human, rat, mouse, porcine or bovine.

In another embodiment, the GIP analog or hybrid polypeptides of the invention may include insertions of one or more unnatural amino acids and/or non-amino acids into the sequence of GIP, GIP(1-30), GIP(1-14), GIP(1-26), GIP(1-39), GIP(19-30), GIP(19-26), GIP(19-39) or GIP(19-42), or a region S, for example exendin(27-39) and exendin(31-39). In a exemplary embodiment, the unnatural amino acids inserted into the sequence of GIP, GIP(1-30), GIP(1-14), GIP(1-26), GIP(1-39), GIP(19-30), GIP(19-26), GIP(19-39) or GIP(19-42) or region S, for example exendin(27-39) and exendin(31-39) may be beta-turn mimetics or linker molecules. In further such embodiments the native GIP can be human, rat, mouse, porcine or bovine. In some embodiments region S retains at least Proline (or proline analog) at X37 in order to interact with a Trp (or Trp analog) to favor Trp cage formation. In further exemplary embodiments a Pro is retained at position X31 to also interact with Trp at X25. In the case of N-terminally truncated exendin-4 analogs (Trp-cages), it has been established that the helix is not significantly populated unless it is capped by either a Trp25/Pro31 hydrophobic staple or the complete formation of the Trp-cage. The latter, complete Trp-cage formation, serves as a very effective helix C-cap. There is also evidence for the contribution of the half-cage structure, with the Pro at X36, X37, X38 unit undocked, in partially melted Trp-cage species.

Accordingly, while compounds are shown with optional linking groups, in one embodiment of the sequences herein, the linker is a Gly linker, for example Gly-Gly-Gly, or a betaAla linker, for example betaAla-betaAla; all of which are specifically envisioned. Linker molecules of particular interest include aminocaproyl ("Aca"), beta-alanyl, and 8-amino-3,6-dioxaoctanoyl. Further in other embodiments a beta-turn mimetic is used, which includes mimic A: N-(3S,6S,9S)-2-oxo-3-amino-1-azabicyclo[4.3.0]-nonane-9-carboxylic acid, mimic B: N-(3S,6S,9R)-2-oxo-3-amino-7-thia-1-azabicyclo [4.3.0]-nonane-9-carboxylic acid, and also Ala-Aib and Ala-Pro dipeptides.

In another embodiment, GIP analog or hybrid polypeptides of the invention may include insertions of polyamino acid sequences (e.g., poly-his, poly-arg, poly-lys, poly-ala, etc.) at either terminus of the polypeptide, known as "extensions" or "tails."

In some embodiments novel GIP analog or hybrid polypeptides comprising amino acid sequence insertions include an alanine substitution at each amino acid position along the length of native GIP, GIP(1-30), GIP(1-14), GIP(1-26), GIP (1-39), GIP(19-30), GIP(19-26), GIP(19-39) or GIP(19-42), or region S, for example exendin(27-39) and exendin(31-39).

Derivatives. The present invention also relates to derivatives of the GIP analogs and hybrid polypeptides. Such derivatives include GIP analog and hybrid polypeptides conjugated to one or more water soluble polymer molecules, such as polyethylene glycol ("PEG") or fatty acid chains of various lengths (e.g., stearyl, palmitoyl, octanoyl, etc.), or by the addition of polyamino acids, such as poly-his, poly-arg, poly-lys, and poly-ala. Modifications to the polypeptides can also include small molecule substituents, such as short alkyls and constrained alkyls (e.g., branched, cyclic, fused, adamantyl), and aromatic groups. The water soluble polymer molecules will preferably have a molecular weight ranging from about 500 to about 20,000 Daltons.

Such polymer-conjugations and small molecule substituent modifications may occur singularly at the N- or C-terminus or at the side chains of amino acid residues within the sequence of the GIP analog and hybrid polypeptides. Alternatively, there may be multiple sites of derivatization along the GIP analog and hybrid polypeptide. Substitution of one or more amino acids with lysine, aspartic acid, glutamic acid, or cysteine may provide additional sites for derivatization. See, e.g., U.S. Pat. Nos. 5,824,784 and 5,824,778. In one embodiment, the GIP analog and hybrid polypeptides may be conjugated to one, two, or three polymer molecules.

The water soluble polymer molecules are preferably linked to an amino, carboxyl, or thiol group, and may be linked by N or C termini, or at the side chains of lysine, aspartic acid, glutamic acid, or cysteine. Alternatively, the water soluble polymer molecules may be linked with diamine and dicarboxylic groups. In a exemplary embodiment, GIP analog and hybrid polypeptides of the invention are conjugated to one, two, or three PEG molecules through an epsilon amino group on a lysine amino acid.

GIP analog and hybrid polypeptide derivatives of the invention also include GIP analog and hybrid polypeptides with chemical alterations to one or more amino acid residues. Such chemical alterations include amidation, glycosylation, acylation, sulfation, phosphorylation, acetylation, and cyclization. The chemical alterations may occur singularly at the N- or C-terminus or at the side chains of amino acid residues within the sequence of the GIP analog and hybrid polypeptides. In one embodiment, the C-terminus of these peptides may have a free —OH or —NH2 group. In another embodiment, the N-terminal end may be capped with an isobutyloxycarbonyl group, an isopropyloxycarbonyl group, an n-butyloxycarbonyl group, an ethoxycarbonyl group, an isocaproyl group (isocap), an octanyl group, an octyl glycine group (G(Oct)), or an 8-aminooctanic acid group or a Fmoc group. In a exemplary embodiment, cyclization can be through the formation of disulfide bridges. Alternatively, there may be multiple sites of chemical alteration along the GIP analog and hybrid polypeptide.

A number of pseudopeptide bonds have been described that in general do not affect peptide structure and biological activity. One example of this approach is to substitute retro-inverso pseudopeptide bonds ("Biologically active retro-inverso analogues of thymopentin", Sisto A. et al in Rivier, J. E. and Marshall, G. R. (eds) "Peptides, Chemistry, Structure and Biology", Escom, Leiden (1990), pp. 722-773) and Dalpozzo, et al. (1993), Int. J. Peptide Protein Res., 41:561-566, incorporated herein by reference). According to this modification, the amino acid sequences of the peptides may be identical to the sequences of a GIP described herein, except that one or more of the peptide bonds are replaced by a retro-inverso pseudopeptide bond. Preferably the most N-terminal peptide bond is substituted, since such a substitution will confer resistance to proteolysis by exopeptidases acting on the N-terminus. Further modifications also can be made by replacing chemical groups of the amino acids with other chemical groups of similar structure. Another suitable pseudopeptide bond that is known to enhance stability to enzymatic cleavage with no or little loss of biological activity is the reduced isostere pseudopeptide bond (Couder, et al. (1993), Int. J. Peptide Protein Res., 41:181-184, incorporated herein by reference in its entirety).

Thus, the amino acid sequences of these peptides may be identical to the sequences of a novel GIP analog and hybrid peptide, except that one or more of the peptide bonds are replaced by an isostere pseudopeptide bond. Preferably the most N-terminal peptide bond is substituted, since such a substitution would confer resistance to proteolysis by exopeptidases acting on the N-terminus. The synthesis of peptides with one or more reduced isostere pseudopeptide bonds is known in the art (Couder, et al. (1993), cited above). Other examples include the introduction of ketomethylene or methylsulfide bonds to replace peptide bonds.

In another embodiment the bond between the second and third residues that is a target for cleavage by DPP-IV is replaced to a peptidase-resistant bond as disclosed herein.

Peptoid derivatives of GIP analog and hybrid peptides represent another class of peptide mimetics that retain the important structural determinants for biological activity, yet eliminate the peptide bonds, thereby conferring resistance to proteolysis (Simon, et al., Proc. Natl. Acad. Sci. USA, 89:9367-9371 (1992), incorporated herein by reference in its entirety). Peptoids are oligomers of N-substituted glycines. A number of N-alkyl groups have been described, each corresponding to the side chain of a natural amino acid (Simon, et al. (1992), cited above). Some or all of the amino acids of the GIP peptides may be replaced with the N-substituted glycine corresponding to the replaced amino acid.

In one embodiment the novel GIP analog or hybrid polypeptides include combinations of the above-described modifications, i.e., deletion, insertion, and substitution.

Also included within the scope of the invention are GIP analog or hybrid polypeptides of the formulas wherein the indicated amino acid residue is chemical modified or derivitized (e.g., through fatty acid derivatization, PEGylation, amidation, glycolization, etc.). Exemplary embodiments include derivatization of a lysine residue, particularly at position 16 or 30. Also contemplated within the scope of the invention are D-amino acid residues of the indicated amino acids. In another embodiment, exemplary GIP analog or hybrid polypeptides include the polypeptides of the formulas with internal deletions, particularly in areas not corresponding to the active sites as described herein.

Exemplary GIP analog or hybrid polypeptides comprising substitutions of unnatural amino acids. Exemplary derivatives of the GIP analog or hybrid polypeptides of the invention include polymer-conjugated GIP analog or hybrid polypeptides, wherein the GIP analog or hybrid polypeptide includes any of the above-described insertions, deletions, substitutions, or combinations thereof, and the polymer molecule is conjugated at a lysine residue. Thus in one embodiment, the GIP analog or GIP-containing hybrid is a derivative or substitution of the methionine at position 14 and having a longer duration of action compared to human GIP or to the patent analog. For example, an octyl-glycine at the methionine position 14, as in 0601GIP4755, increases the duration of action of the compound in vivo. Duration of action was increased to at least 4 hours by this modification. Accordingly, in one embodiment are GIP analog and hybrid polypeptides conjugated at this position to one or more water soluble polymer molecules, such as polyethylene glycol ("PEG") or fatty acid chain of various lengths (e.g., stearyl, palmitoyl, octanoyl, etc.), or by the addition of polyamino acids, such as poly-his, poly-arg, poly-lys, poly-glu and poly-ala. Modifications to the polypeptides can also include small molecule substituents, such as short alkyls and constrained alkyls (e.g., branched, cyclic, fused, adamantyl), and aromatic groups.

Further specifically envisioned are D-Ala2 variants of each GIP sequence herein (e.g., see tables). In yet other embodiments envisioned are variants of each of the above sequences where the GIP portion is modified by one, two or three modifications as described herein. Exemplary modifications are those at the first, second or third N-terminal amino acid of GIP that impart DPP-IV resistance superior to that of native GIP. In yet a further embodiment the novel GIP compounds comprise a C-terminal amide.

In a further embodiment the novel GIP analog or a GIP hybrid comprises a half-life at least twice that of human GIP(1-30)amide. Further the half-life can be at least 6 hours.

In another embodiment is a pharmaceutically acceptable salt of a novel GIP analog or hybrid. The novel GIP analogs and hybrids can be formulated in a composition comprising a pharmaceutically acceptable carrier.

In one embodiment an analog of exenatide with leucine substituted for Met at position 14 is used either as a hybrid component or in adjunct therapy with a GIP hybrid:

(SEQ ID NO: 286)
HGEGTFTSDLSKQLEEEAVRLFIEWLKNGGPSSGAPPPS-NH2.

In one embodiment, the GIP analog or hybrid polypeptides of the invention retain at least about 25%, preferably about 30%, 40%, 50%, 60%, 70%, 80%, 90%, 95%, 98%, or 99% percent of the biological activity of native human GIP with regard to glucose lowering. In another embodiment, the GIP analog or hybrid polypeptides of the invention exhibit improved GIP agonist activity. In one embodiment, the GIP analog or hybrid polypeptides of the invention exhibits at least about 110%, 125%, 130%, 140%, 150%, 200%, or more of the biological activity of native human GIP. Conversely, the novel GIP analog or hybrids can be antagonists.

Exemplary GIP analog or hybrid polypeptide are those having a potency which is equal to or greater than the potency of GIP(1-42) or GIP(1-30) in that same assay. Alternatively, exemplary GIP analog or hybrid polypeptides of the invention may exhibit improved ease of manufacture, stability, and/or ease of formulation, as compared to GIP(1-42) or GIP(1-30).

It is also contemplated that the novel GIP analogs of the invention, as well as GIP analogs, can be administered with agents such as small molecules or antibodies that are agonists or antagonists, as may be the case, for the peptide hormones and growth factors mentioned herein.

In further embodiments and uses of the GIP hybrids having the naturally-occurring C-terminal amino acid sequence of exendin-4, particularly PSSGAPPPS (SEQ ID NO: 1) sequence, described herein, specifically excluded are those having a modification at the "P'1" position as described in WO2004/103390.

Further examples of the analog and hybrid polypeptides of the present invention are provided in the Sequence Listing, Tables and in the Examples section.

Further Uses of Hybrid Polypeptides in the Treatment or Prevention Disease Conditions or Disorders.

Metabolic diseases and disorders take on many forms, including obesity, diabetes, dyslipidemia, insulin resistance, cellular apoptosis, etc. Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, Nature 404: 635-43 (2000)). It reduces life-span and carries a serious risk of co-morbidities above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al., Br. Med. J. 301: 835-7 (1990)). Obesity is also a risk factor for the group of conditions called insulin resistance syndrome, or "Syndrome X." Recent estimate for the medical cost of obesity and associated disorders is $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder. A therapeutic drug useful in weight reduction of obese persons could have a profound beneficial effect on their health.

Diabetes is a disorder of carbohydrate metabolism characterized by hyperglycemia and glucosuria resulting from insufficient production or utilization of insulin. Diabetes severely affects the quality of life of large parts of the populations in developed countries. Insufficient production of insulin is characterized as type 1 diabetes and insufficient utilization of insulin is type 2 diabetes. However, it is now widely recognized that there are many distinct diabetes related diseases which have their onset long before patients are diagnosed as having overt diabetes. Also, the effects from the suboptimal control of glucose metabolism in diabetes gives rise to a wide spectrum of related lipid and cardiovascular disorders.

Dyslipidemia, or abnormal levels of lipoproteins in blood plasma, is a frequent occurrence among diabetics. Dyslipidemia is typically characterized by elevated plasma triglycerides, low HDL (High Density Lipoprotein) cholesterol, normal to elevated levels of LDL (Low Density Lipoprotein) cholesterol and increased levels of small dense, LDL (Low Density Lipoprotein) particles in the blood. Dyslipidemia is one of the main contributors to the increased incidence of coronary events and deaths among diabetic subjects. Epidemiological studies have confirmed this by showing a several-fold increase in coronary deaths among diabetic subjects when compared with non-diabetic subjects. Several lipoprotein abnormalities have been described among diabetic subjects.

Insulin resistance is the diminished ability of insulin to exert its biologically action across a broad range of concentrations. In insulin resistance, the body secretes abnormally high amounts of insulin to compensate for this defect and a state of impaired glucose tolerance develops. Failing to compensate for the defective insulin action, the plasma glucose concentration inevitable rises, resulting in the clinical state of diabetes. It is being recognized that insulin resistance and relative hyperinsulinemia have a contributory role in obesity, hypertension, atherosclerosis and type 2 diabetes. The association of insulin resistance with obesity, hypertension and angina has been described as a syndrome, Syndrome X, having insulin resistance as the common pathogenic link.

Apoptosis is an active process of cellular self-destruction that is regulated by extrinsic and intrinsic signals occurring during normal development. It is well documented that apoptosis plays a key role in regulation of pancreatic endocrine beta cells. There is increasing evidence that in adult mammals the beta-cell mass is subject to dynamic changes to adapt insulin production for maintaining euglycemia in particular conditions, such as pregnancy and obesity. The control of beta cell mass depends on a subtle balance between cell proliferation, growth and programmed cell death (apoptosis). A disturbance of this balance may lead to impairment of glucose homeostasis. For example, it is noteworthy that glucose intolerance develops with aging when beta cell replication rates are reduced and human autopsy studies repeatedly showed a 40-60% reduction of beta cell mass in patients with non-insulin-dependent-diabetes mellitus compared with nondiabetic subjects. It is generally agreed that insulin resistance is an invariable accompaniment of obesity but that normoglycemia is maintained by compensatory hyperinsulinemia until the beta cells become unable to meet the increased demand for insulin, at which point type 2 diabetes begins.

Attempts to treat the multiple abnormalities associated with diabetes have prompted for the administration of several anti-diabetic medicaments in order to address these abnormalities in the different patients. However, the GIP analogs, GIP hybrids and GIPR agonists as discussed herein find use, when administered at therapeutically effective amounts, either in monotherapy or in adjunct therapy, in treating or preventing these and other diseases and conditions discussed throughout.

Gastric inhibitory polypeptide (GIP) and glucagon-like peptide 1 (GLP-1) are gut peptide hormones that exert potent glucoregulatory action through their glucose-dependant stimulation of insulin secretion. Studies have shown that GIP and GLP-1 act in concert to exert their incretin effects [1-3]. Consequently, these incretin hormones have attracted considerable interest as potential anti-diabetic agents with reduced risk for hypoglycemia. Whereas GLP-1, GLP-1 analogs and mimetics such as exenatide have been shown to be efficacious in controlling glucose levels in type 2 diabetic patients, the insulinotropic effect of GIP is significantly reduced in diabetic subjects, compared to normal individuals [4-6]. The preservation of insulinotropic action of GLP-1 but not of GIP in the same diabetic subjects suggests that GIP signal transduction is impaired in type 2 diabetes. Reduced GIP receptor expression in pancreatic beta cells has been proposed to contribute to overall reduced incretin effects in diabetic subjects [7]. This hypothesis is supported by rodent studies showing decreased GIP receptor expression on beta-cells in diabetic fatty Zucker rats and reduced GIP incretin effect seen in first-degree relatives of patients with type 2 diabetes [8-9]. However, a recent study has shown significant increases in plasma insulin levels in type 2 diabetics to a bolus intravenous administration of GIP, that is in marked contrast to weak increase in insulin secretion with continuous GIP infusion [10]. The similar relative beta-cell sensitivity towards GIP bolus in type 2 diabetic patients and healthy control subjects suggest that a specific GIP receptor defect appears unlikely [10]. Rather, the differences in insulin secretion after acute and during continuous GIP administration indicate an impaired amplification of the late phase insulin response to glucose by GIP in type 2 diabetic patients, whereas the response in the early phase is almost preserved [11-12]. While not to be bound by theory, it is believed that while GIP's incretin effect is attenuated during persistent hyperglycemia, there is potential for GIP or its analogs to act with a similar potency in diabetic patients as their action in normal subjects once glucose control is improved in these individuals.

Amylin Pharmaceuticals, Inc. has conducted three pivotal clinical studies to evaluate the effects of exenatide in patients with type 2 diabetes not achieving target blood glucose concentrations using metformin alone, sulfonylureas alone, or using a combination of metformin and a sulfonylurea. All three studies met the primary glucose control endpoint as measured by HbA1c. The average reduction in HbA1c across the Phase 3 program in patients completing the studies on the highest dose of exenatide (10 µg twice daily) was approximately one percent. Additionally, approximately 40 percent of these patients achieved HbA1c measurements of 7 percent or less. The clinical data indicate that despite the efficacy of exenatide, some diabetic individuals fail to attain normal glucose concentrations.

In an embodiment of the invention, reduction of hyperglycemia (e.g., as by exenatide) in treated diabetic patients sets the stage for GIP intervention. Whereas the chronic hyperglycemic condition in type 2 diabetes patients attenuates GIP's insulinotropic response, improved glycemic control resulting from exenatide treatment would restore responsiveness of the pancreatic beta-cell to GIP stimulation. Therefore adjunct therapy, e.g. co-administration, GIP phybrids, of pharmacological doses of GIP or novel GIP analog or hybrids with exenatide (or other glucose lowering agents or agents or methods that reduce or inhibit gastric emptying) will lead to desired normoglycemia in diabetic patients or patients suffering from conditions associated with elevated glucose. Of note, GIP lacks the gastric emptying effect of GLP-1 [13-14] that is a possible contributing factor to the incidence of nausea during GLP-1 treatment and which limits the peptide's therapeutic window [15]. Thus, it should permit the use of higher GIP dosing regimens.

Since currently prescribed anti-diabetic agents (metformin, sulfonyureas, TZDs, etc) are able to achieve various degrees of glycemic control, the combination of GIP or novel GIP analog or hybrids with any of these therapies should also elicit an improved response that leads to normalization of glucose levels.

Accordingly, in one embodiment the methods of the present invention are based on the notion that patients can be primed for GIP therapy through prior glucose lowering with other anti-diabetic agents, such as GLP-1, a GLP-1 analog or exendin-4 or other agents, e.g. metformin, sulfonyureas, thiazolidinediones (TZDs), pramlintide, insulin, acarbose, dipeptidyl peptidase (DPP-IV) inhibitors. DPP-IV inhibitors are well-known and described for example in published application US20050004117, U.S. Pat. No. 6,710,040, and U.S. Pat. No. 6,645,995, which are incorporated herein by reference for their compounds. As example of a sulfonylureas (SFUs), which acts on the pancreatic tissue to produce insulin, is Glimepiride.

Adjunct therapy of a metabolically stable GIP analog or hybrid or novel GIP analog or hybrid with exenatide (or other antidiabetics) will provide for increased insulinotropic responses than either alone, in patients with conditions associated with elevated glucose, such as patients with type 2 diabetes. Such a treatment regimen leads to normalization of glucose concentrations, improvement in beta-cell function, and through their trophic activity on the β cells slows disease progression to obviate or lesson the need for insulin therapy.

GIP hybrids of the invention can be useful for reducing food intake, reducing appetite, reducing caloric intake, inducing satiety, reducing nutrient availability, causing weight loss, affecting body composition, altering body energy content or energy expenditure, improving lipid profile (including reducing LDL cholesterol and triglyceride levels and/or changing HDL cholesterol levels), slowing gastrointestinal motility, delay gastric emptying, moderating the postprandial blood glucose excursions, preventing or inhibiting glucagon secretion, and decreasing blood pressure. In one embodiment such GIP hybrids contain an exendin, GLP1, amylin and/or sCT portion.

Of particular interest as anti-obesity, weight reduction, food reduction, metabolic rate increasing, and body fat reduction and/or fat redistribution hybrids are those GIP-containing hybrids that contain an exendin, amylin (e.g. amylin-sCT-amylin chimera), leptin or PYY (e.g. PYY-NPY chimera) family module that can effectively reduce food intake, change body composition, redistribute fat and/or reduce body weight. In embodiments of particular interest for treating obesity and related diseases and conditions (body fat reduction) as discussed herein, are GIP hybrids comprising an exendin-4 or analog or derivative thereof, an amylin component such as pramlintide or an amylin-sCT-amylin chimera, an FN38 family member such as FN38 or an analog or derivative thereof, a PYY member such as a PYY-NPY chimera as described herein such as SEQ ID Nos. 266, 437, 438, 439, 442, 462, 469, 470, 471 and 472 of US 2006/013547A1 or the PYY-NPY chimera compound with the amino acid sequence CNTF agonists, peptide YY (PYY) and PYY agonists, exendin and exendin agonists, GLP-1 and GLP-1 agonist, ghrelin and ghrelin antagonists, cholecystokinin (CCK) and CCK agonists, and amylin and amylin agonists, including those described herein. Further peptide family components and clinical guidance can be found in applicant's co-pending patent application PCT/US06/17529, which is incorporated herein by reference.

| Individual anti-obesity targets and location | | | |
|---|---|---|---|
| Signaling System | CNS Region | Food Intake Role | Anti-obesity agents |
| Neuropeptide Y (NPY) | Forebrain (ARC/PVN) | Increases intake | NPY1 and NPY5 receptor antagonists |
| Leptin | Forebrain (ARC) | Decreases intake | Leptin, or agonists |
| Ciliary neurotrophic factor (CNTF) | Forebrain (ARC) | Decreases intake | CNTF |
| Peptide YY (PYY) | Forebrain (ARC) | Decrease intake | PYY(3-36) agonists |
| Glucagon-like peptide-1 (GLP-1) | Forebrain (PVN) | Decrease intake | Exenatide and other GLP-1 ligands, DPP-IV inhibitors |
| Ghrelin | Forebrain (ARC) | Increase intake | Ghrelin antagonists |
| Cholecystokinin (CCK) | Hindbrain (AP) | Decrease intake | CCK agonists |
| Amylin | Hindbrain (AP) | Decrease intake | Amylin agonists, Pramlintide, amylin analogs |
| Melanocortins (MC) | Forebrain (PVN/ARC) | Agonists decrease intake | MC4 agonists |

Ile, Lys, Pro, Glu, His, Pro, Gly, Glu, Asp, Ala, Ser, Pro, Glu, Glu, Leu, Ala, Arg, Tyr, Tyr, Ala, Ser, Leu, Arg, Ala, Tyr, Ile, Asn, Leu, Ile, Thr, Arg, Gln, Arg, Tyr (SEQ ID No. 456), for example. In another embodiment, the GIP hybrid can have at least one, preferably two components, which act on the CNS. Particular areas of the forebrain (telencephalonic- and diencephalonic-derived constituents of the brain) and hindbrain or brainstem (including the midbrain, pons and medulla) have been identified as being involved in controlling energy balance. Forebrain structures or nuclei residing in the hypothalamus involved in food intake and/or body weight modulation include, for example, the arcuate nucleus (ARC), the paraventricular nucleus (PVN), the dorsomedial hypothalamus (DMH), the ventromedial nucleus (VMH), and the lateral hypothalamus nucleus (LHA). Hindbrain structures or nuclei residing in the brainstem involved in food intake and/or body weight modulation include, for example, the nucleus of the solitary tract (NST), the area postrema (AP), and the lateral parabrachial nucleus (IPBN). Brainstem nuclei that control the elements of the consummatory motor control system are likely controlled by primary or second order projections from brainstem regions like the NST, AP, and IPBN. It is noteworthy that the AP, NST and IPBN have all been shown to (collectively and independently) possess their own integrative abilities.

A variety of CNS-directed anti-obesity agents act upon these forebrain structures residing in the hypothalamus involved in food intake and/or body weight modulation. In addition, CNS-directed anti-obesity agents act upon hindbrain structures residing in the brainstem involved in food intake and/or body weight modulation. Examples of such anti-obesity agents are described herein. See the table below for further examples of peptide family modules that can be combined with a GIP compound to form an anti-obesity agent hybrid, and can be combined to form an anti-obesity hybrid with activity on both the forebrain and hindbrain. Such components include, for example, neuropeptide Y1 (NPY1) receptor antagonists, NPY5 receptor antagonists, leptin and leptin agonists, ciliary neurotrophic factor (CNTF) and In certain embodiments, the GIP hybrid is an anti-obesity agent that can include one or more predominantly forebrain acting peptide family components in addition to a GIP compound. In other embodiments, the hybrid is an anti-obesity agent that can include one or more predominantly hindbrain acting anti-obesity agents. Exemplary peptide families and components are an NPY1 receptor antagonist, an NPY5 receptor antagonist, a leptin or a leptin agonist or analog, a CNTF, an NPY2 receptor agonist (e.g., a PYY(3-36) or a PYY(3-36) agonist), an exendin or an exendin agonist or analog, a GLP-1 or a GLP-1 agonist or analog, a ghrelin antagonist, a CCK or a CCK agonist or analog, and an amylin or an amylin agonist or analog.

In certain embodiments, the GIP hybrid and method for it use include a first component that predominantly targets the energy balance centers of the hypothalamus, such as the ARC, PVN, VM, and LH. In one embodiment the GIP hybrid further contains one or more other peptide family component that also target the hypothalamus but at a different location or via a different mechanism of action than the first component. When the GIP hybrid contains more than one other peptide family component and these also target the hypothalamus, the more than one other peptide family components may target the same location via the same mechanism of action as each other, or they may target different locations and/or different mechanisms of action. In another embodiment, the GIP hybrid then contains one or more other peptide family components that provide one or more additional beneficial therapeutic effects as desired, including an anti-obesity effect via a location or mechanism of action different than the first component and each other, control of blood glucose, cardioprotection, and/or control of hypertension. In certain embodiments, the additional peptide family component is one that predominantly targets the energy balance centers of the hindbrain such as the NST, the AP and the IPBN.

In certain embodiments, the GIP hybrid and method for it use include a first component that predominantly targets the energy balance centers of the hindbrain such as the NST, the AP and the IPBN. In one embodiment the GIP hybrid further contains one or more other peptide family component that also target the hypothalamus but at a different location or via a different mechanism of action than the first component and each other. In another embodiment, the GIP hybrid then contains one or more other peptide family components that provide one or more additional beneficial therapeutic effects as desired, including an anti-obesity effect via a location or mechanism of action different than the first component and each other, control of blood glucose, cardioprotection, and/or control of hypertension. In certain embodiments, the additional peptide family component is one that predominantly targets the energy balance centers of the hypothalamus, such as the ARC, PVN, VM, and LH.

As used herein, an anti-obesity agent that "acts on a forebrain structure involved in food intake and/or body weight modulation" stimulates or suppresses activity of a particular region, e.g., particular nuclei and/or neuronal circuits, in the forebrain. This forebrain stimulation or suppression leads to a reduction in nutrient availability to the body. An anti-obesity agent that "acts on a hindbrain structure involved in food intake and/or body weight modulation" stimulates or suppresses activity of a particular region, e.g., particular nuclei and/or neuronal circuits, in the hindbrain. This hindbrain stimulation or suppression results in a reduction in nutrient availability to the body.

In another aspect, methods for reducing fat mass by increasing the metabolic rate in a subject are provided, where the methods comprise administering an anti-obesity GIP hybrid in amounts effective to reduce fat mass by increasing the subject's metabolic rate. Fat mass can be expressed as a percentage of the total body mass. In some aspects, the fat mass is reduced by at least 1%, at least 5%, at least 10%, at least 15%, at least 20%, or at least 25% over the course of treatment. In one aspect, the subject's lean mass is not decreased over the course of the treatment. In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150, 200, 250, 300, 400, 500, 600, 700, 800, 900, or 1000 fewer calories per day.

In one embodiment, methods of use in altering fat distribution, reducing fat mass, or both in a subject are provided. Accordingly, subjects for whom altering body composition is of benefit can also benefit from the present methods. Altered body composition, as intended herein, includes loss or maintenance of body fat, with minimization of loss, maintenance, or gain of lean body mass. In such situations, weight may increase as well as decrease. Accordingly, subjects may be lean, overweight, or obese as these terms are generally used in the art. Methods provided may also include reducing fat in non-adipose tissue while sparing lean mass. Uses for this method include treating diseases such as nonalcoholic steatohepatitis (NASH) or lipodystrophy.

In one embodiment, a method for altering the fat distribution in a subject is provided where the method comprises administering an anti-obesity GIP hybrid in amounts effective to alter fat distribution in the subject. In one aspect, the alteration results from an increased metabolism of visceral or ectopic fat, or both in the subject. By "fat distribution" is meant the location of fat deposits in the body. Such locations of fat deposition include, for example, subcutaneous, visceral and ectopic fat depots. By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference. By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body. By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases. In some embodiments, the method involves the metabolism of visceral or ectopic fat or both at a rate of at least about 5%, 10%, 15%, 20%, 25%, 30%, 40%, or 50% greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass.

In another embodiment, methods for reducing the amount of subcutaneous fat in a subject are provided, wherein the method comprises administering, to a subject in need thereof, an anti-obesity GIP hybrid in amounts effective to reduce the amount of subcutaneous fat in the subject. In one instance, the amount of subcutaneous fat is reduced in a subject by at least about 5%. In other instances, the amount of subcutaneous fat is reduced by at least about 10%, 15%, 20%, 25%, 30% 40%, or 50% compared to the subject prior to administration of the anti-obesity hybrid.

The methods described herein can be used to reduce the amount of visceral fat in a subject. In one instance, the visceral fat is reduced in a subject by at least about 5%. In other instances, the visceral fat is reduced in the subject by at least about 10%, 15%, 20%, 25%, 30% 40%, or 50% compared to the subject prior to administration of the anti-obesity GIP hybrid. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In one embodiment, a method for preventing the accumulation of ectopic fat or reducing the amount of ectopic fat in a subject is provided, wherein the method comprises administering, to a subject in need thereof, an anti-obesity GIP hybrid in amounts effective to prevent accumulation of ectopic fat or to reduce the amount of ectopic fat in the subject. In one instance, the amount of ectopic fat is reduced in a subject by at least about 5% compared to the subject prior to administration of the anti-obesity hybrid. In other instances, the amount of ectopic fat is reduced in a subject by at least about 10%, or by at least about 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods are provided for producing a more favorable fat distribution in a subject, where the method comprises administering to a subject a GIP hybrid that is effective as an anti-obesity agent in an amount effective to produce a favorable fat distribution. In one embodiment, administration of an anti-obesity GIP hybrid reduces the amount of visceral fat or ectopic fat, or both, in a subject. In one embodiment is administered an anti-obesity hybrid that comprises at least one family module that acts upon forebrain structures involved in food intake or body weight modulation or both in combination with at least one family module that acts upon hindbrain structures involved in food intake or body weight modulation or both. In one embodiment, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combinations thereof. In one embodiment, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

Of particular interest for anti-obesity, body weight and fat composition related treatments as discussed herein are GIP hybrids containing an exendin, amylin (e.g. amylin-sCT-amylin chimera), leptin and/or PPF (e.g. PYY analogs or PPY/NPY chimera) family modules. In yet a further embodiment a GIP hybrid contains at least two of these peptide family modules. The GIP hybrid can be administered either alone or in combination with a second anti-obesity agent such as an amylin. Leptin, PYY or exendin family peptide.

In still another aspect, provided is a method for the administration of a therapeutically effective amount of a GIP hybrid effective as an anti-obesity agent administered in combination with glucocorticosteroids. Glucocorticosteroids have the adverse effect of increasing fat mass and decreasing lean mass. Accordingly, it is contemplated that the anti-obesity agent combination can be used in conjunction with glucocorticosteroids under conditions where glucocorticosteroid use is beneficial, in order to counteract the adverse effect of the glucocorticosteroid.

As discussed herein, a GIP hybrid of the invention can be administered separately or together with one or more other agents in order to obtain additional benefits or to enhance the effect of either the hybrid or the other agent. For example, an anti-obesity GIP hybrid can be administered with an anti-obesity agent or a cardioprotective or anti-hypertension agent, depending on the risk factors pertinent to the subject in need of treatment and desired treatment outcome. Exemplary anti-obesity agents for administration (either separately or mixed; either prior to, concomitantly or after) with a hybrid include serotonin (5HT) transport inhibitors, including, but not limited to, paroxetine, fluoxetine, fenfluramine, fluvoxamine, sertraline, and imipramine. Anti-obesity agents also include selective serotonin reuptake inhibitors, including, but not limited to dexfenfluramine, fluoxetine, sibutramine (e.g., MERIDIA®) and those described in U.S. Pat. No. 6,365,633 and PCT Patent Application Publication Nos. WO 01/27060 and WO 01/162341, which are hereby incorporated by reference in their entirety. Such 5HT transport inhibitors and serotonin reuptake inhibitors, analogs, derivatives, preparations, formulations, pharmaceutical compositions, doses, and administration routes have previously been described.

Anti-obesity agents also include selective serotonin agonists and selective 5-HT2C receptor agonists, including, but not limited to, U.S. Pat. No. 3,914,250; and PCT Application Publication Nos. WO 02/36596, WO 02/48124, WO 02/10169, WO 01/66548, WO 02/44152; WO 02/51844, WO 02/40456, and WO 02/40457, which are hereby incorporated by reference in their entirety. Such selective serotonin agonists and 5-HT2C receptor agonists, compositions containing such agonists, and administration routes appropriate for use in the methods provided are known in the art. See, for example, Halford et al. (2005) Curr. Drug Targets 6:201-213 and Weintraub et al. (1984) Arch. Intern. Med. 144:1143-1148.

Anti-obesity agents also include antagonists/inverse agonists of the central cannabinoid receptors (the CB-1 receptors), including, but not limited to, rimonabant (Sanofi Synthelabo), and SR-147778 (Sanofi Synthelabo). CB-1 antagonists/inverse agonsits, derivatives, preparations, formulations, pharmaceutical compositions, doses, and administration routes have previously been described, for example, in U.S. Pat. Nos. 6,344,474, 6,028,084, 5,747,524, 5,596,106, 5,532,237, 4,973,587, 5,013,837, 5,081,122, 5,112,820, 5,292,736, 5,624,941; European Patent Application Nos. EP-656 354 and EP-658546; and PCT Application Publication Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, and WO 02/076949, which are hereby incorporated by reference in their entirety.

Anti-obesity agents also include melanocortins and melanocortin agonists. The receptor MC4R appears to play a role in energy balance and obesity. See, for example, Anderson et al., Expert Opin. Ther. Patents 11:1583-1592 (2001), Speake et al., Expert Opin. Ther. Patents 12:1631-1638 (2002), Bednarek et al., Expert Opin. Ther. Patents 14:327-336 (2004). Melanocortin agonists, including, but not limited to, MC4R agonists, and composition containing such agonist appropriate for use in the methods provided are known in the art. MCR agonists, MC4R agonists, derivatives, preparations, formulation, pharmaceutical compositions, doses, and administration routes have previously been described, for example, in the following PCT patent applications, which are hereby incorporated by reference in their entirety: WO 03/007949, WO 02/068388, WO 02/068387, WO 02/067869, WO 03/040117, WO 03/066587, WO 03/068738, WO 03/094918, and WO 03/031410.

Anti-obesity agents also include metabotropic glutamate subtype 5 receptor (mGluR5) antagonists, including, but are not limited to, compounds such as 2-methyl-6-(phenylethynyl)-pyridine (MPEP) and (3-[(2-methyl-1,3-thiazol-4-yl) ethynyl]pyridine) (MTEP) and those compounds described in Anderson et al. J. Eur. J. Pharmacol. 473:35-40 (2003); Cosford et al. Bioorg. Med. Chem. Lett. 13(3):351-4 (2003); and Anderson et al. J. Pharmacol. Exp. Ther. 303:1044-1051 (2002).

Anti-obesity agents also include topiramate (TOPIMAX®) (Ortho McNeil Pharmaceuticals), indicated as an anti-convulsant and an anti-convulsant, but also shown to increase weight loss.

Anti-obesity agents also include neuropeptide Y1 (NPY1) antagonists and NPY5 antagonists. NPY1 and NPY5 antagonists are known in the art. See, for example Duhault et al. (2000) Can. J. Physiol. Pharm. 78:173-185, and U.S. Pat. Nos. 6,124,331, 6,214,853, and 6,340,683. NPY1 and NPY5 antagonists, derivatives, preparations, formulation, pharmaceutical compositions, doses, and administration routes have previously been described. NPY1 antagonists useful in the compositions and methods provided include: U.S. Pat. No. 6,001,836; and PCT Application Publication Nos. WO 96/14307, WO 01/23387, WO 99/51600, WO 01/85690, WO 01/85098, WO 01/85173, and WO 01/89528, which are hereby incorporated by reference in their entirety. NPY5 antagonists useful in compositions and methods of use provided herein, include, but are not limited to, the compounds described in: U.S. Pat. Nos. 6,140,354, 6,191,160, 6,258,837, 6,313,298, 6,337,332, 6,329,395, 6,340,683, 6,326,375, and 6,335,345; European Patent Nos. EP-01010691, and EP-01044970; and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, WO 02/49648, and WO 01/14376.

Anti-obesity agents also include melanin-concentrating hormone (MCH) antagonists including melanin-concentrating hormone 1 receptor (MCH1R) antagonists, such as T-226296 (Takeda) and melanin-concentrating hormone 2 receptor (MCH2R) antagonists. MCH receptor antagonists, derivatives, preparations, formulation, pharmaceutical compositions, doses, and administration routes have previously been described, for example, in U.S. Patent Application Publication Nos. 2005/0009815, 2005/0026915, 2004/0152742, 2004/0209865; PCT Patent Application Publication Nos. WO 01/82925, WO 01/87834, WO 02/06245, WO 02/04433, and WO 02/51809; and Japanese Patent Application No. JP 13226269, which are hereby incorporated by reference in their entirety.

Anti-obesity agents also include opioid antagonists, including, but not limited to those described in PCT Application No. WO 00/21509. Specific opioid antagonists useful in compositions and methods of use provided herein include, but are not limited to, nalmefene (REVEX®), 3-methoxynaltrexone naloxone, naltrexone, naloxonazine, beta-funaltrexamine, delta1 ([D-Ala2,Leu5,Cys6]-enkephalin (DALCE), naltrindole isothiocyanate, and nor-binaltorphamine.

Anti-obesity agents also include orexin antagonists, including, but not limited to, those described in PCT Patent Application Nos. WO 01/96302, WO 01/68609, WO 02/51232, and WO 02/51838. Specific orexin antagonists useful in compositions and methods of use provided include, but are not limited to, SB-334867-A.

Anti-obesity agents also include neuropeptide Y2 (NPY2) agonists, including, but not limited to, compounds such as PYY3-36 (e.g., Batterham et al. (2003) Nature 418:650-654), NPY3-36 and other Y2 agonists such as N acetyl [Leu(28,31)] NPY 24-36 (White-Smith et al. (1999) Neuropeptides 33:526-533, TASP-V (Malis et al. (1999) Br. J. Pharmacol. 126:989-996), cyclo-(28/32)-Ac-[Lys28-Glu32]-(25-36)-pNPY (Cabrele et al. (2000) J. Pept. Sci. 6:97-122), which can be either a hybrid component as discussed or administered separately. Anti-obesity agents provided also include neuropeptide Y4 (NPY4) agonists including, but not limited to, compounds such as pancreatic peptide (PP) (e.g., Batterham et al. (2003) J. Clin. Endocrinol. Metab. 88:3989-3992) and other Y4 agonists such as 1229U91 (Raposinho et al. (2000) Neuroendocrinology 71:2-7). NPY2 agonists and NPY4 agonsits, derivatives, preparations, formulations, pharmaceutical compositions, doses, and administration routes have previously been described, for example, in U.S. Pat. Publication No. 2002/0141985 and PCT Application Publication No. WO 2005/077094.

Anti-obesity agents also include histamine 3 (H3) antagonist/inverse agonists including but not limited to, those described in PCT Application No. WO 02/15905, O-[3-(1H-imidazol-4-yl)propanol]carbamates (Kiec-Kononowicz et al. (2000) Pharmazie 55:349-355), piperidine-containing histamine H3-receptor antagonists (Lazewska et al. (2001) Pharmazie 56:927-932), benzophenone derivatives and related compounds (Sasse et al. (2001) Arch. Pharm. (Weinheim) 334:45-52), substituted N-phenylcarbamates (Reidemeister et al. (2000) Pharmazie 55:83-86), and proxifan derivatives (Sasse et al. (2000) J. Med. Chem. 43:3335-3343). Specific H3 antagonists/inverse agonists useful in compositions and methods of use provided include, but are not limited to, thioperamide, 3-(1H-imidazol-4-yl)propyl N-(4-pentenyl)carbamate, clobenpropit, iodophenpropit, imoproxifan, and GT2394 (Gliatech).

Anti-obesity agents also include cholecystokinin (CCK) and CCK agonists. Cholecystokinin-A (CCK-A) agonists of use include, but are not limited to, those described in U.S. Pat. No. 5,739,106. Specific CCK-A agonists include, but are not limited to, AR-R 15849, GI 181771, JMV-180, A-71378, A-71623 and SR146131.

Anti-obesity agents also include ghrelin antagonists such as those described in PCT Application Publication Nos. WO 01/87335 and WO 02/08250. Ghrelin antagonists are also known as GHS (growth hormone secretagogue receptor) antagonists. The compositions and methods provided therefore contemplate the use GHS antagonists in place of ghrelin antagonists.

Anti-obesity agents include obestatin and obestatin analogs and agonists. Obestatin is a peptide derived from the same precursor from which ghrelin is derived, preproghrelin. See, for example, Zhang et al. (2005) Science 310: 996-999; Nogueiras et al. (2005) Science 310: 985-986; Pan et al. (2006) Peptides 27:911-916. In contrast to the activity of ghrelin, obestatin appears to act as an anorexic hormone by decreasing food intake, gastric emptying activities, jejunal motility, and body weight gain. Obestatin peptides of use include, but are not limited to those described in Zhang et al. (2005) Science 310: 996-999.

And the amylinomimetics, e.g. pramlintide, amylin-sCT-amylin, incretins, e.g. exendin-4, and PYY analogs, are anti-obesity agents that also can be administered as an anti-obesity agents with a GIP hybrid. For example, a GIP-leptin hybrid may be administered with exendin-4, a PYY analog, and/or an amylin analog.

Thus, in certain embodiments, the hybrids of the invention are useful for treating or preventing conditions or disorders which can be alleviated by reducing nutrient availability comprising administering to said subject a therapeutically or prophylactically effective amount of a compound of the invention. Such conditions and disorders include, but are not limited to, eating disorders, insulin-resistance, obesity, abnormal postprandial hyperglycemia, diabetes of any kind, including Type I, Type II, and gestational diabetes, Metabolic Syndrome, Dumping Syndrome, hypertension, dyslipidemia, cardiovascular disease, hyperlipidemia, sleep apnea, cancer, pulmonary hypertension, cholecystitis, and osteoarthritis. In one embodiment such hybrids contain an exendin, GLP1, amylin and/or sCT portion.

Non-limiting examples of a cardiovascular condition or disease are hypertension, myocardial ischemia, and myocardial reperfusion. Compounds of the invention may also be useful in treating or preventing other conditions associated with obesity including stroke, cancer (e.g., endometrial, breast, prostate, and colon cancer), gallbladder disease, sleep apnea, reduced fertility, and osteoarthritis, (see Lyznicki et al, Am. Fam. Phys. 63:2185, 2001). In other embodiments, compounds of the invention may be used to alter body composition for aesthetic reasons, to enhance one's physical capabilities, or to produce a leaner meat source. Hybrids are useful to change body composition by decreasing fat without significant decrease in muscle mass, thus producing a desirable loss of body fat while preserving lean body mass. In one embodiment such hybrids contain an exendin, GLP1, amylin and/or sCT portion.

In another aspect of the invention, methods for treating or preventing obesity are provided, wherein the method comprises administering a therapeutically or prophylactically effective amount of a hybrid polypeptide to a subject in need thereof. In a exemplary embodiment, the subject is an obese or overweight subject. While "obesity" is generally defined as a body mass index over 30, for purposes of this disclosure, any subject, including those with a body mass index of less than 30, who needs or wishes to reduce body weight is included in the scope of "obese." Subjects who are insulin resistant, glucose intolerant, or have any form of diabetes mellitus (e.g., type 1, 2 or gestational diabetes) can benefit from these hybrids. In one embodiment such GIP hybrids contain an exendin, PYY, GLP1, amylin and/or sCT portion.

In other aspects of the invention, methods of reducing food intake, reducing nutrient availability, causing weight loss, affecting body composition, and altering body energy content or increasing energy expenditure, treating diabetes mellitus, and improving lipid profile (including reducing LDL cholesterol and triglyceride levels and/or changing HDL cholesterol levels) are provided, wherein the methods comprise administering to a subject an effective amount of a hybrid polypeptide of the invention. In a exemplary embodiment, the methods of the invention are used to treat or prevent conditions or disorders which can be alleviated by reducing nutrient availability in a subject in need thereof, comprising administering to said subject a therapeutically or prophylactically effective amount of a hybrid polypeptide of the invention. Such conditions and disorders include, but are not limited to, hypertension, dyslipidemia, cardiovascular disease, eating disorders, insulin-resistance, obesity, and diabetes mellitus of any kind. In one embodiment such hybrids contain an exendin, PYY, GLP1, amylin and/or sCT portion.

In one embodiment in which a PPF or PYY family member comprises a GIP-hybrid component, and without intending to be limited by theory, it is believed that the effects of such peripherally-administered GIP hybrid polypeptides in the reduction of food intake, in the delay of gastric emptying, in the reduction of nutrient availability, and in the causation of weight loss are determined by interactions with one or more unique receptor classes in, or similar to, those in the PP family. More particularly, it appears that a receptor or receptors similar to the PYY-preferring (or Y7) receptors are involved.

Additional assays useful to the invention include those that can determine the effect of GIP hybrid compounds, particularly those containing an exendin, PPF, PYY, GLP1, amylin and/or sCT portion, on body composition. An exemplary assay can be one that involves utilization of a diet-induced obese (DIO) mouse model for metabolic disease. Prior to the treatment period, male C57BL/6J mice can be fed a high-fat diet (#D12331, 58% of calories from fat; Research Diets, Inc.,) for 6 weeks beginning at 4 weeks of age. During the study, the mice can continue to eat their high-fat diet. Water can be provided ad libitum throughout the study. One group of similarly-aged non-obese mice can be fed a low-fat diet (#D12329, 11% of calories from fat) for purposes of comparing metabolic parameters to DIO groups.

DIO mice can be implanted with subcutaneous (SC) intrascapular osmotic pumps to deliver either vehicle (50% dimethylsulfoxide (DMSO) in water) or a compound of the invention. The pumps of the latter group can be set to deliver any amount, e.g., 1000 μg/kg/d of a compound of the invention for 7-28 days. Body weights and food intake can be measured over regular intervals throughout the study periods. Respiratory quotient (RQ, defined as $CO_2$ production÷$O_2$ consumption) and metabolic rate can be determined using whole-animal indirect calorimetry (Oxymax, Columbus Instruments, Columbus, Ohio). The mice can be euthanized by isoflurane overdose, and an index of adiposity (bilateral epididymal fat pad weight) measured. Moreover, prior to determination of epididymal weight, body composition (lean mass, fat mass) for each mouse can be analyzed using a Dual Energy X-ray Absorptiometry (DEXA) instrument per manufacturer's instructions (Lunar Piximus, GE Imaging System). In the methods of the invention, GIP hybrids, particularly those comprising an exendin, PPF, PYY, GLP1, amylin and/or sCT portion having a potency in one of the assays described herein (preferably food intake, gastric emptying, pancreatic secretion, weight reduction or body composition assays) which is greater than the potency of a component peptide hormone in that same assay, can be identified.

In addition to the amelioration of hypertension in subjects in need thereof as a result of reduced food intake, weight loss, or treating obesity, compounds of the invention may be used to treat hypotension.

In another general aspect, hybrids of the invention may be used to inhibit the secretion of ghrelin. Accordingly, compounds of the invention may be utilize this mechanism to treat or prevent ghrelin related disorders such as Prader-Willi syndrome, diabetes of all types and its complications, obesity, hyperphagia, hyperlipidemia, or other disorders associated with hypernutrition. In one embodiment such hybrids contain an exendin, GLP1, amylin and/or sCT portion.

Compounds of the invention may also be useful for potentiating, inducing, enhancing or restoring glucose responsivity in pancreatic islets or cells. These actions may be useful for treating or preventing conditions associated with metabolic disorders such as those described above and in U.S. patent application no. US2004/0228846. Assays for determining such activity are known in the art. For example, in published U.S. patent application no. US2004/0228846 (incorporated by reference in its entirety), assays are described for islet isolation and culture as well as determining fetal islet maturation. In the examples of patent application US2004/0228846, intestine-derived hormone peptides including pancreatic polypeptide (PP), neuropeptide Y (NPY), neuropeptide K (NPK), PYY, secretin, glucagon-like peptide-1 (GLP-1) and bombesin were purchased from Sigma. Collagenase type XI was obtained from Sigma. RPMI 1640 culture medium and fetal bovine serum were obtained from Gibco. A radioimmunoassay kit containing anti-insulin antibody ([$^{125}$I]-RIA kit) was purchased from Linco, St Louis.

Post-partem rat islets were obtained from P-02 year old rats. Adult rat islets were obtained from 6-8 week old rats. Fetal rat islets were obtained as follows. Pregnant female rats were sacrificed on pregnancy day E21. Fetuses were removed from the uterus. 10-14 pancreata were dissected from each litter and washed twice in Hanks buffer. The pancreata were pooled, suspended in 6 ml 1 mg/ml collagenase (Type XI, Sigma) and incubated at 37° C. for 8-10 minutes with constant shaking. The digestion was stopped by adding 10 volumes of ice-cold Hanks buffer followed by three washes with Hanks buffer. The islets were then purified by Ficoll gradient and cultured in 10% fetal bovine serum (FBS)/RPMI medium with or without addition of 1 μM IBMX. At the end of five days, 20 islets were hand picked into each tube and assayed for static insulin release. Generally, islets were first washed with KRP buffer and then incubated with 1 ml of KRP buffer containing 3 mM (low) glucose for 30 minutes at 37° C. with constant shaking. After collecting the supernatant, the islets were then incubated with 17 mM (high) glucose for one hour at 37° C. The insulin released from low or high glucose stimulation were assayed by radioimmunoassay (RIA) using the [$^{125}$I]-RIA kit. E21 fetal islets were cultured for 5 days in the presence of 200 ng/ml PYY, PP, CCK, NPK, NPY, Secretin, GLP-1 or Bombesin.

An exemplary in vivo assay is also provided using the Zucker Diabetic Fatty (ZDF) male rat, an inbred (>F30 Generations) rat model that spontaneously expresses diabetes in all fa/fa males fed a standard rodent diet Purina 5008. In ZDF fa-fa males, hyperglycemia begins to develop at about seven weeks of age and glucose levels (fed) typically reach 500 mg/DL by 10 to 11 weeks of age. Insulin levels (fed) are high during the development of diabetes. However, by 19 weeks of age insulin drops to about the level of lean control litter mates. Triglyceride and cholesterol levels of obese rats are normally higher than those of leans. In the assay, three groups of 7-week old ZDF rats, with 6 rats per group, received the infusion treatment by ALZA pump for 14 days: 1) vehicle control, 2) and 3), PYY with two different doses, 100 pmol/kg/hr and 500 pmol/kg/hr respectively. Four measurements were taken before the infusion and after the infusion at day 7 and day 14: 1) plasma glucose level, 2) plasma insulin level, and 3) plasma triglycerides (TG) level, as well as oral glucose tolerance (OGTT) test. Accordingly, these assays can be used with compounds of the invention to test for desired activity.

Hybrids are also useful for the therapeutic and prophylactic treatment of neurological and nervous system disorders associated with neuronal loss or dysfunction, including, but not limited to, Parkinson's Disease, Alzheimer's Disease, Huntington's Disease, ALS, stroke, ADD, and neuropsychiatric syndromes, and to enhance or facilitate learning, memory and cognition in mammals. Particularly useful in this regard are GIP hybrids containing an exendin or GLP 1 active portion, more specifically comprising at least the N-terminal 7-15 amino acids or analog thereof, for example HSEGTFTSD (SEQ ID NO. 94).

Other uses contemplated for the hybrid polypeptides include methods for reducing aluminum (Al) concentrations in the central nervous system (see U.S. Pat. No. 6,734,166, incorporated by reference in its entirety) for treating, preventing, or delay the onset of Alzheimer's disease. Assays for determining effects on Al are known in the art and can be found in U.S. Pat. No. 6,734,166 using diploid and Ts mice. These mice were individually housed in Nalgene® brand metabolism or polypropylene cages and given three days to adjust to the cages before experimentation. Mice had free access to food (LabDiet® NIH Rat and Moust/Auto 6F5K52, St. Louis, Mo.) and water during the experiment except for the 16 hours prior to euthanasia when no food was provided. Mice were given daily subcutaneous injections of either active compound or saline. Mice were sacrificed at the end of day 13 for one experiment and day 3 for another, and samples were collected. Mice brain samples were weighted in clean teflon liners and prepared for analysis by microwave digestion in low trace element grade nitric acid. Samples were then analyzed for Al content using Inductively Coupled Plasma Mass Spectrometry (Nuttall et al., *Annals of Clinical and Laboratory Science* 25, 3, 264-271 (1995)). All tissue handling during analysis took place in a clean room environment utilizing HEPA air filtration systems to minimize background contamination.

Hybrids of the invention are useful for prevention and treatment of nephropathy, including hypertensive and diabetic nephropathy, and nephropathy associated with insulin resistance and metabolic syndrome. Hybrids achieve these ends by, among other things, improving or preventing worsening of hypertension, endothelial function, renal function, and glomerulosclerosis. In one embodiment, the invention provides a method for preventing or treating nephropathy, including hypertensive and diabetic nephropathy, or that related to insulin resistance, comprising administering a compound of the invention. Hybrids find further use for improving endothelial function in a patient having reduced vasodilatory capacity, or having glomerulosclerosis or any other reduction in glomerular flow. Such improvement in endothelial function serves both to reduce hypertension and to improve the function of the capillaries of the glomeruli. In additional embodiments, the molecules of the invention are useful to prevent progression of nephropathy to ESRD, to prevent, slow the progression of, treat or ameliorate proteinuria and/or glomerulosclerosis.

Hybrids are useful for reducing the risk of suffering from, preventing, or treating cardiac arrhythmias. Hybrids can provide anti-arrhythmic effects in patients with cardiac ischemia, cardiac ischemia-reperfusion, and congestive heart failure. For example, incretin GLP-1 has been found to reduce cardiac injury and enhance recovery in patients with these disorders. Incretins, including GLP-1, are glucose-dependent insulinotropic hormones. GLP-1 and exendin effectively enhance peripheral glucose uptake without inducing dangerous hypoglycemia. They also strongly suppress glucagon secretion, independent of its insulinotropic action, and thereby powerfully reduce plasma free fatty acid (FFA) levels substantially more than can be accomplished with insulin. High FFA levels have been implicated as a major toxic mechanism during myocardial ischemia. In another embodiment hybrids are useful for preventing and treating cardiac arrhythmias that reliably reduce injury associated with reperfusion and ischemia, and enhance patient recovery. In yet a further embodiment hybrid treatment after acute stroke or hemorrhage, preferably intravenous administration, provides a means for optimizing insulin secretion, increasing brain anabolism, enhancing insulin effectiveness by suppressing glucagon, and maintaining euglycemia or mild hypoglycemia with no risk of severe hypoglycemia or other adverse side effects. In one embodiment such GIP hybrids contain a GLP1 or exendin portion.

In yet a further embodiment, hybrids that are capable of lowering insulin resistance or increasing insulin sensitivity are useful to treat polycystic ovary syndrome (PCOS). Administering hybrids of the invention can reduce or prevent insulin resistance in a subject suffering from PCOS. In yet another embodiment hybrids prevent the onset of type-2 diabetes in a subject suffering from PCOS. Further hybrids can restore regular menses, ovulation, or fertility in a subject suffering from PCOS. In one embodiment such GIP hybrids contain a GLP1 or an exendin portion for binding and activating a GLP1 receptor.

By selection of hormone component modules the compounds of the invention can exhibit a broad range of biological activities, some related to their antisecretory and antimotility properties. The compounds may suppress gastrointestinal secretions by direct interaction with epithelial cells or, perhaps, by inhibiting secretion of hormones or neurotransmitters which stimulate intestinal secretion. Antisecretory properties include inhibition of gastric and/or pancreatic secretions and can be useful in the treatment or prevention of diseases and disorders including gastritis, pancreatitis, Barrett's esophagus, and Gastroesophageal Reflux Disease, as well as conditions associated therewith including heartburn, heartburn accompanied by regurgitation of gastric/intestinal contents into the mouth or the lungs, difficulty in swallowing, coughing, intermittent wheezing and vocal cord inflammation (conditions associated with GERD), esophageal erosion, esophageal ulcer, esophageal stricture, Barrett's metaplasia (replacement of normal esophageal epithelium with abnormal epithelium), Barrett's esophageal adenocarcinoma, and pulmonary aspiration. In another embodiment GIP hybrids containing amylin and/or sCT portions can be useful for treating or preventing these diseases and conditions, such as Barrett's esophagus, Gastroesophageal Reflux Disease (GERD) and conditions associated therewith as disclosed herein. Such hybrids have particularly effective anti-secretory properties, such as inhibition of gastric acids, inhibition of bile acids, and inhibition of pancreatic enzymes. Moreover, such hybrids can have a gastroprotective effect, which renders them particularly useful in the treatment or prevention of intestinal diseases and conditions and of Barrett's esophagus, and/or GERD and related or associated conditions as described herein.

Compounds of the invention are useful in the treatment of any number of gastrointestinal disorders (see e.g., Harrison's Principles of Internal Medicine, McGraw-Hill Inco, New York, 12th Ed.) that are associated with excess intestinal electrolyte and water secretion as well as decreased absorption, e.g., infectious diarrhea, inflammatory diarrhea, short bowel syndrome, or the diarrhea which typically occurs following surgical procedures, e.g., ileostomy. Examples of infectious diarrhea include, without limitation, acute viral diarrhea, acute bacterial diarrhea (e.g., *salmonella, campylobacter*, and *clostridium* or due to protozoal infections), or traveller's diarrhea (e.g., Norwalk virus or rotavirus). Examples of inflammatory diarrhea include, without limitation, malabsorption syndrome, tropical sprue, chronic pancreatitis, Crohn's disease, diarrhea, and irritable bowel syndrome. It has also been discovered that the peptides of the invention can be used to treat an emergency or life-threatening situation involving a gastrointestinal disorder, e.g., after surgery or due to cholera.

Compounds of the invention may also be useful for treating or preventing intestinal, including gastrointestinal, damage as opposed to merely treating the symptoms associated with the intestinal damage (for example, diarrhea). Such damage to the intestine may be, or a result of, ulcerative colitis, inflammatory bowel disease, bowel atrophy, loss bowel mucosa, and/or loss of bowel mucosal function (see WO 03/105763, incorporated herein by reference in its entirety). Assays for such activity, as described in WO 03/105763, include 11 week old male HSD rats, ranging 250-300 grams housed in a 12:12 light:dark cycle, and allowed ad libitum access to a standard rodent diet (Teklad LM 485, Madison, Wis.) and water. The animals were fasted for 24 hours before the experiment. A simple and reproducible rat model of chronic colonic inflammation has been previously described by Morris G P, et al., "Hapten-induced model of chronic inflammation and ulceration in the rat colon." Gastroenterology. 1989; 96:795-803. It exhibits a relatively long duration of inflammation and ulceration, affording an opportunity to study the pathophysiology of colonic inflammatory disease in a specifically controlled fashion, and to evaluate new treatments potentially applicable to inflammatory bowel disease in humans.

Rats were anesthetized with 3% isofluorane and placed on a regulated heating pad set at 37° C. A gavage needle was inserted rectally into the colon 7 cm. The hapten trinitrobenzenesulfonic acid (TNBS) dissolved in 50% ethanol (v/v) was delivered into the lumen of the colon through the gavage needle at a dose of 30 mg/kg, in a total volume of 0 0.4-0.6 mL, as described in Mazelin, et al., "Protective role of vagal afferents in experimentally-induced colitis in rats." *Juton Nerv Syst.* 73:38-45 (1998). Control groups received saline solution (NaCl 0.9%) intracolonically. Four days after induction of colitis, the colon was resected from anesthetized rats, which were then euthanized by decapitation. Weights of excised colon and spleen were measured, and the colons photographed for scoring of gross morphologic damage. Inflammation was defined as regions of hyperemia and bowel wall thickening.

In another aspect, GIP hybrids can be useful for treating or preventing pancreatitis, pancreatic carcinoma, and gastritis, particularly in the treatment and prevention of pancreatitis in patients who have undergone endoscopic retrograde cholangiopancreatography (ERCP). Amylin and/or sCT containing GIP hybrid agonists can have a surprisingly superior therapeutic effect when combined with somatostatin. Accordingly, in certain embodiments, methods for treating or preventing pancreatitis comprise administering such hybrids and administering somatostatin and somatostatin agonists to a subject. Hybrid polypeptides of the invention may also be used to treat or prevent Barrett's esophageal adenocarcinoma or pancreatic tumors (e.g., inhibit the proliferation of pancreatic tumors). Methods of the invention include reducing the proliferation of tumor cells. The types of benign pancreatic tumor cells which may be treated in accordance with the present invention include serous cyst adenomas, microcystic tumors, and solid-cystic tumors. The method is also effective in reducing the proliferation of malignant pancreatic tumor cells such as carcinomas arising from the ducts, acini, or islets of the pancreas. Particularly useful GIP hybrids in this regard are those comprising a hormone module component of the PYY or PPF family. U.S. Pat. No. 5,574,010 (incorporated by reference in its entirety) provides exemplary assays for testing anti-proliferative properties. For example, the '010 patent provides that PANC-1 and MiaPaCa-2 are two human pancreatic adenocarcinoma cancer cell lines which are available commercially from suppliers such as American Type Culture Collection, ATCC (Rockville, Md.). The two tumor cells were grown in RPMI-1640 culture media supplemented with 10% fetal bovine serum, 29.2 mg/L of glutamine, 25 µg gentamicin, 5 ml penicillin, streptomycin, and fungizone solution (JRH Biosciences, Lenexa, Kans.) at 37 degrees Celcius in a NAPCO water jacketed 5% $CO_2$ incubator. All cell lines were detached with 0.25% trypsin (Clonetics, San Diego, Calif.) once to twice a week when a confluent monolayer of tumor cells was achieved. Cells were pelleted for 7 minutes at 500 g in a refrigerated centrifuge at 4 degrees Celcius, and resuspended in trypsin free fortified RPMI 1640 culture media. Viable cells were counted on a hemocytometer slide with trypan blue.

Ten thousand, 20,000, 40,000 and 80,000 cells of each type were added to 96 well microculture plates (Costar, Cambridge, Mass.) in a total volume of 200 ul of culture media per well. Cells were allowed to adhere for 24 hours prior to addition of the PYY or test peptide. Fresh culture media was exchanged prior to addition of peptides. In vitro incubation of pancreatic tumor cells with either PYY or test compound was continued for 6 hours and 36 hours in length. PYY was added to cells at doses of 250 pmol, 25 pmol, and 2.5 pmol per well (N=14). Test compound was added to cells cultures at doses of 400 pmol, 40 pmol, and 4 pmol per well. Control wells received 2 ul of 0.9% saline to mimic the volume and physical disturbance upon adhered tumor cells. Each 96 well plate contained 18 control wells to allow for comparison within each plate during experimentation. Ninety-six (96) well plates were repeated 6 times with varying concentrations of PYY and test compound in both the PANC-1 and MiaPaCa-2 cells.

At the end of the incubation period, 3-(4,5-dimethylthiazolyl-2-yl)-2,5-diphenyltetrazolium bromide, MTr tetrazolium bromide (Sigma, St. Louis, Mo.) was added to fresh culture media at 0.5 mg/ml. Culture media was exchanged and tumor cells were incubated for 4 hours with MTT tetrazolium bromide at 37° C. At the end of incubation, culture media was aspirated. Formazon crystal precipitates were dissolved in 200 µl of dimethyl sulfoxide (Sigma, St. Louis, Mo.). Quantitation of solubilized formazon was performed by obtaining absorption readings at 500 nm wavelength on an ELISA reader (Molecular Devices, Menlo Park, Calif.). The MTT assay measures mitochondrial NADH dependent dehydrogenase activity, and it has been among the most sensitive and reliable method to quantitative in vitro chemotherapy responses of tumor cells. (Alley, M. C., et al., *Cancer Res.,* 48:589-601, 1988; Carmichael, J., et al., *Cancer Res.,* 47:936-942, 1987; McHale, A. P., et al., *Cancer Lett.,* 41:315-321, 1988; and Saxton, R. E., et al., *J. Clin. Laser Med. and Surg.,* 10(5):331-336, 1992.) Analysis of absorption readings at 550 nm were analyzed by grouping wells of the same test conditions and verifying differences occurring between control and the various peptide concentration treatments by one-way ANOVA.

An exemplary in vivo assay is also provided. The human pancreatic ductal adenocarcinoma Mia Paca-2 was examined for in vivo growth inhibition by peptide YY and test compound. Seventy thousand to 100,000 human Mia PaCa-2 cells were orthotopically transplanted into 48 male athymic mice. After one week, the animals were treated with either PYY or test compound at 200 pmol/kg/hr via mini-osmotic pumps for four weeks. The paired cultures received saline. At sacrifice, both tumor size and mass were measured. Control mice had significant human cancer growth within the pancreas as evidenced by histologic sections. At 9 weeks, ninety percent (90%) of control mice had substantial metastatic disease. Tumor mass was decreased by 60.5% in test treated mice and 27% in PYY treated mice.

In another general aspect, hybrids are useful for decreasing bone resorption, decreasing plasma calcium, and/or inducing an analgesic effect, particularly to treat bone disorders such as osteopenia and osteoporosis. In yet other embodiments, hybrids are useful to treat pain and painful neuropathy. In one embodiment such hybrids contain an exendin, GLP1, amylin and/or sCT portion. For example, a GIP-sCT or GIP-amylin/sCT hybrid compound of the invention can have a selectable property of a salmon calcitonin or amylin/sCT/Amylin chimera, such as decreasing bone loss and bone resorption or reducing cartilage turnover (chondroprotection), and a property of a GIP, such as plasma glucose lowering (concomitant with an anti-catabolic aspect as described herein) and/or inhibiting bone resorption and maintaining or increasing bone density. A GIP hybrid with such selectable properties can enhance treatment of osteoporosis or conditions of high cartilage turnover, particularly in those who can also benefit from glycemic control, such as subjects with diabetes or under going critical care.

GIP compounds, particularly GIP analogs, extended half-life GIP hybrids (e.g. DPP-IV cleavage resistant (such as a D-Ala2, N-Acetyl or N-pyroglutamyl analogs) optionally further comprising a peptidic enhancer such as a heterologous C-terminal tail, and GIP hybrids comprising other hormone modules known to provide beneficial cardiovascular effects, are useful to treat cardiovascular disease and related conditions. As demonstrated herein GIP compounds increase cardiac contractility (dP/dt), decrease blood pressure (for example by acute vasodilatation), decrease systolic pressure, decrease diastolic pressure, and can provide a direct beneficial action on cardiac cells. GIP compounds also improve cardiac function via metabolic actions, e.g. glucose lowering, insulin secretion, beta cell proliferation. By also providing direct effects on the cardiovascular system, the GIP compounds are surprisingly even more therapeutically beneficial.

Accordingly, provided herein are methods to treat, prevent or alleviate cardiovascular diseases and conditions by administering a therapeutically effective amount of a GIP compound, either alone or with another agent that provides cardiovascular benefit, to a patient in need of such treatment. As with the other conditions discussed throughout this specification, a GIP compound can be administered concurrently, sequentially or alternately with another agent.

Accordingly, in one embodiment the cardiovascular disease or condition is hypertension (including stage 1, stage 2 and stage 3 hypertension, diastolic or systolic), pulmonary hypertension, congestive heart failure, cardiac insufficiency, reduced stroke volume, cardiomyopathy (dilated, hypertrophic or restrictive), decreased cardiac contractility, pulmonary congestion associated with cardiovascular conditions, pulmonary and systemic edema, decreased cardiac output, abnormal left ventricular function, diastolic blood pressure abnormalities, renal failure associated with decreased cardiac contractility, increased cardiovascular risk (e.g. associated with elevated systolic pressure accompanied by normal diastolic pressure, associated with elevated diastolic pressure accompanied by normal systolic pressure, associated with elevated diastolic and systolic pressure, associated with elevated mean arterial blood pressure) and non-ischemic or ischemic heart tissue degeneration (such as from myocardial infarction). In one embodiment either or both the mortality or the morbidity associated with these diseases and conditions are reduced.

The patient in need of treatment includes those who are diabetic (e.g. suffering from diabetic cardiomyopathy), obese, undergoing intensive care, undergoing surgery, or a combination thereof, or who are otherwise normal. The patient may have had or be at risk of having such a disease or condition. For example, patients post myocardial infarction that are in need of preventing further heart failure can benefit from the methods herein.

Preventing a disease or condition, e.g., a cardiovascular disease or condition, includes preventing the initiation of, delaying the initiation of, preventing the progression or advancement of, slowing the progression or advancement of, delaying the progression or advancement of, and reversing the progression of the disease or condition from an advanced to a less advanced stage.

In one embodiment the method provides treating or delaying the onset of such diseases or conditions. For example, impaired contractility can decrease stroke volume which in turn can precipitate congestive heart failure. Thus in one embodiment treating heart failure refers to treating any one or more of the conditions underlying heart failure, including, without limitation, decreased cardiac contractility, abnormal diastolic compliance, reduced stroke volume, high blood pressure, pulmonary congestion, and decreased cardiac output.

In one embodiment is provided a method for inducing an inotropic response, for reducing blood pressure, for reducing diastolic pressure, for reducing diastolic pressure, increasing vasodilation, or a any combination of the above, with or without a concomitant beneficial metabolic action of a GIP such as glucose lowering, insulin secretion, or beta cell proliferation, comprising administration of a therapeutically effective amount of a GIP compound to provide such desired beneficial action. These methods are useful for treating conditions or disorders that can be alleviated by an increase in cardiac contractility, a reduction in blood pressure, a reduction in diastolic pressure, a reduction in diastolic pressure, an increase in vasodilation, or a combination of the above, in patients in need of such benefits.

Inotropic compounds are compounds that induce inotropic effects (e.g., increase of force of contraction of the heart) have been recognized as being useful for the treatment of, for example, congestive heart failure. Congestive heart failure, which is one of the most common causes of death and disability in industrialized nations, has a mortality rate of about 50% at five years (Goodman and Gilman's The Pharmacological Basis of Therapeutics, 9th Ed. McGraw Hill, N.Y., pp. 809-838). Criteria, testing and guidelines as established by the American Heart Association (AHA) are suitable for diagnosing the cardiovascular diseases and conditions discussed herein.

GIP compounds display a desired positive inotropic effect without a substantial, concomitant increase in blood pressure. Such blood pressure changes in subjects experiencing heart failure or cardiovascular disease or condition could cause further deterioration in heart function. In fact as demonstrated herein, GIP compounds can function to reduce blood pressure or the rate of change in blood pressure.

Issues with available inotropic agents illustrates the need for, and desirability of, therapies that are inotropic, with rapid onset of action, with prolonged duration of action (including a persistent effect, with absence of tachyphylaxis), with low toxicity (a high ratio of toxic to therapeutic dose), with absent or low nausea effect, and with a convenient (non-intravenous) route of administration. GIP compounds can provide these benefits.

Further beneficial action of GIP compounds of the invention, particularly the GIP hybrids comprising a DPP-IV resistant GIP analog with a peptidic enhancer such as an exendin tail (e.g. Compound G), arises from a lack of or reduced anorectic effect and an absence of or relatively insignificant nausea effect, which can be important in the patient populations discussed throughout.

Also provided is a method for treating critically ill patients, exemplified as those sufficiently ill to warrant admission to an intensive care unit (ICU) and that find benefit from anti- or non-catabolic therapy, which comprises administering a therapeutically effective amount of a GIP analog or hybrid to a patient in need of such treatment, alone or with another beneficial agent. Without being limited by theory, the methods are intended to benefit those patients in which the effect of GIP agonist analogs and hybrids to stimulate insulin secretion and incur the benefits associated with intensive insulin therapy (GIK therapy; glucose-insulin-potassium), without the hazards and complexity associated with insulin/glucose infusion and without the side effects reportedly associated with the use of some glucagon-like peptide-1 agonists. Further, it is now observed that GIP can favorably affect a patient's metabolic state in addition to simply indirectly regulating glucose levels in response to digestion of food. Accordingly GIP compounds are useful to reduce the mortality and morbidity that occurs in critically ill patients.

As demonstrated herein GIP compounds provide beneficial metabolic effects such as glucose lowering, insulin secretion and/or beta cell proliferation. GIP compounds also improve cardiac function by increasing cardiac contractility (dP/dt), decreasing blood pressure (for example by acute vasodilatation), and decreasing systolic pressure, decreasing diastolic pressure, and providing a direct beneficial action on cardiac cells. Since many critically ill patients have or are at risk for or are complicated by cardiovascular diseases or conditions, these cardiovascular effects can provided additional benefit. By also providing direct effects on the cardiovascular system, the GIP compounds, surprisingly, have added therapeutic value.

Accordingly, provided herein are methods to treat, prevent or alleviate conditions and diseases of critical care by administering a therapeutically effective amount of a GIP compound, either alone or with another agent that provides desired benefits, to a critically ill patient in need of such treatment. As with the other conditions discussed throughout this specification, a GIP compound can be administered concurrently, sequentially or alternately with another agent.

The "intensive care unit" can be a part of a hospital where critically ill patients are treated, and of course may not officially bear the name "Intensive Care Unit". ICU also includes a nursing home a clinic, for example, a private clinic, or the like if the same or similar activities are performed there.

The term a "critically ill patient" can be a patient who has sustained or are at risk of sustaining acutely life-threatening single or multiple organ system failure due to disease or injury, a patient who is being operated and where complications supervene, and a patient who has been operated in a vital organ within the last week or has been subject to major surgery within the last week. A critically ill patient can be a patient who needs vital organ support (either mechanically such as with mechanical ventilation or dialysis etc., or pharmacologically such as with inotropes or vasopressors) without which they would not survive. Expressions "critical care", "intensive care" and "critically ill" are used interchangeably. Critically ill patients are those who generally experience an unstable metabolic state. This unstable metabolic state, e.g. catabolic state, can be a result of changes in substrate metabolism which may lead to relative deficiencies in some nutrients and/or increased oxidation (e.g. wasting) of both fat and muscle, undesirable accelerated protein breakdown, hyperglycemia and high concentrations of serum triglycerides and other lipids. Non-limiting examples of a critically ill patient is a patient in need of cardiac surgery, cerebral surgery, thoracic surgery, abdominal surgery, vascular surgery, or transplantation, or a patient suffering from cerebral trauma, respiratory insufficiency, critical illness polyneuropathy, multiple traumas or severe burns, or a patient being mechanically ventilated.

Accordingly, in one embodiment the critical care disease or condition is classified as medical, surgical (e.g. trauma) or coronary care, and further can be classified as sepsis and respiratory care. Of particular interest are those classifications, such as septic shock or myocardial infarction, for which GIK therapy would be warranted.

Catabolic change (e.g., loss of body weight) is an adverse risk factor for the critically ill patient. Although most admissions to the ICU receive intravenous lines that deliver calories in some form, a Canadian study of nutritional support in ICU reported that typically only 58% of daily requirements were supplied and only 26% received parenteral nutrition. Thus a method is provided in which a critically ill patient in need of prevention or alleviating catabolic effects, such as weigh loss, is administered a therapeutically effective amount of a GIP compound as provided herein to prevent or alleviate the catabolism. The critically ill patient in need of treatment includes patients who are non-diabetic patient (not diagnosed as having diabetes or prediabetes), diabetic, prediabetic, and/or obese. The patient may have had or be at risk of having the disease or conditions indicated.

The use of GIP compounds can minimize or avoid risks associated with GLP-1 in invoking a GIK-like benefit. Slowing of gastric emptying can complicate the delivery of oral medicines, for example, by altering their kinetics, and decrease nutrient uptake; GLP-1 agonists, amylin agonists, CCK agonists, and secretin agonists, for example, slow gastric emptying. As shown herein, within therapeutic ranges, doses of GIP compounds do not slow gastric emptying or show only a weak effect, and in any event much less so than GLP1 and exendin 4. Typically such effect was blocked with a selective amylin antagonist, e.g. pramlintide, indicating that the effect was an indirect consequence of augmented beta-cell secretion of amylin, the latter being the most potent endogenous inhibitor of gastric emptying thus far identified. GIP administration is thus unassociated with a direct inhibition of gastric emptying. Importantly, it has been shown herein that GIP itself does not acutely inhibit food intake in mice. Neither does GIP cause weight loss in diet-induced-obese mice. Nor does the GIP analog hybrid 0601GIP3794. Further GIP was reported to exert a fat-sparing effect relative to GLP-1 agonists which are associated with a loss of body weight and adiposity. This fat-sparing effect is possibly attributable to an antilipolytic effect in adipocytes or to such effects as promotion of lipoprotein lipase, amplification of insulin signaling, and/or an increase of fatty acid incorporation into adipocyte lipid. Interestingly, 0601GIP3794 provided a slight decrease in percentage body fat with an increase in body protein without a concomitant reduction in body weight, indicating that body composition was affected. It is well recognized that loss of body energy stores predicts adverse outcomes in critical care whereas preservation of body energy stores promotes beneficial outcomes. The absence of or decreased anorexigenic effects, the absence of or decreased nausea and/or the absence of or reduction of weight loss, with or without the improvement in body composition, are advantageous in patients experiencing catabolic effects, such as critically ill patients. Although GIP receptor mRNA has been detected in heart tissue, hormone binding in heart has not been detected to date. However, as shown herein GIP binds to and activates cardiac myocytes and displays a positive inotropic effect in vivo. With regard to treatment of renal failure, particularly acute renal failure, in patients who remain oliguric despite attempts to enhance urine flow by approaches to establish urine output such as by the use of loop diuretics and osmotic diuretics, intervention by inotropic agents that increase cardiac contractility is generally attempted. Thus as discussed GIP compounds provide further benefit in patients with or at risk of compromised myocardium, and certain other conditions such as renal failure, independent of its insulinotropic action. Further the method includes administering to patients in need thereof a therapeutically effective amount of a GIP compound that provides a sparing of cardiac muscle, which otherwise tends to atrophy in catabolic states.

Accordingly, in one embodiment the critical care patient has a disease or condition of catabolic change associated with a critical illness, sepsis, post-traumatic, post-surgical, post-shock, comatose patients, stress-induced hyperglycemia (for example after a vascular event), stroke, myocardial infarction, acute mesenteric ischemia, respiratory distress, ventilator dependency, renal failure, congestive heart failure, edema, hibernating myocardium, cardiomyopathies (ischemic, diabetic), lowering of BNP, ejection dysfunction, hypertension, polyneuropathy, ischemia/reperfusion injury (for example post-thrombolytic therapy, post cardiac surgery), histoprotection of organ beds, myocardial infarction (mortality, function, symptomatology), acute coronary syndrome (stable/unstable angina, non-Q wave infarct, ECG positive), disturbances of conduction or rhythm, papillary dysfunction, and/or pulmonary edema. For example, in a one embodiment the method comprises attenuating, ameliorating or reducing such disease or conditions including pre- or post-surgical catabolic changes, comprising, administering to a patient in need thereof a GIP compound. The GIP compound is designed to provide a therapeutic benefit, for example a benefit measured for example as a reduction in APACHE score, a reduction in mortality, a reduction in days in hospital, a reduction in need for readmission, a reduction in hospitalization costs.

In one embodiment is a method for the treatment of a critically ill patient in need thereof, to prevent or decrease the incidence of blood stream infection, sepsis or septic shock, to reduce morbidity associated with the critical care, to reduce mortality (e.g. in-hospital mortality) associated with the critical care, to prevent or decrease the incidence of prolonged inflammation, to prevent or decrease the incidence of acute renal failure and/or renal replacement therapy, to prevent or decrease the incidence of critical care polyneuropathy, to reduce the use of antibiotics, to prevent or decrease the incidence of immune-mediated destruction of the beta cells, to reduce the likelihood of disturbance in markers of inflammation and/or inflammatory responses, to prevent or decrease the incidence of systemic inflammatory response syndrome (SIRS), to reduce the amount of red cell transfusion, to reduce stress-induced hyperglycemia, to protect from cholestasis, to reduce the need for invasive treatment, to prevent or decrease the incidence of endoneural edema, to decrease dialysis or hemofiltration, to reduce or eliminate a need of vital organ system support, to allow at least about one third of the caloric need through the normal enteral route, to reduce the risk or likelihood of multiple organ failure, to reduce the risk or likelihood of multiple organ failure associated with sepsis or septic shock, to reduce the use of mechanical ventilatory support, to reduce the likelihood of disturbed kidney function parameters, to reduce the likelihood of hyperbilirubinemia, or to treat, prevent or alleviate or reduce the incidence of one or more of the other critical care conditions mentioned herein, which comprises administering a therapeutically effective amount of a GIP compound. In a further embodiment administration achieves a normo- or euglycemia, a lowering of blood glucose, insulin secretion, a cardiovascular benefit as discussed herein, a reduction of catabolic effect, or any combination thereof.

Critical care patients can include those suffering from respiratory distress in which the patient has difficulty breathing as a result of pulmonary dysfunction. The patient may exhibit varying degrees of hypoxemia that that may or may not be controlled with supplemental oxygen. Respiratory distress may occur in patients with impaired pulmonary function due to direct lung injury, such as from pneumonia, aspiration of gastric contents, pulmonary contusion, fat emboli, near-drowning, inhalation injury, high altitude and reperfusion pulmonary edema, or from indirect lung injury as from sepsis, severe trauma with shock and multiple transfusions, cardiopulmonary bypass, drug overdose, and acute pancreatitis. A critically ill patient may have a pulmonary disorders associated with chronic hypoxemia, which can result in raised pressure within the pulmonary circulation called pulmonary hypertension. A critically ill patient may have cor pulmonale, which is a failure of the right side of the heart caused by prolonged high blood pressure in the pulmonary artery and right ventricle of the heart. A critically ill patient may have acute respiratory distress syndrome (ARDS) or chronic obstructive pulmonary diseases (COPDs) which include emphysema and chronic bronchitis, which also cause respiratory distress.

In another embodiment the critical care patient is one who with a disturbed glucose metabolism such as insulin resistance but no overt diabetes, as well as a patient who for any reason cannot receive nutrition through the alimentary canal. Such patients include surgery patients, comatose patients, patients in shock, patients with gastrointestinal disease, patients with digestive hormone disease, and the like. In particular, obese patients, atherosclerotic patients, vascular disease patients, patients with gestational diabetes, patients with liver disease such as liver cirrhosis, patients with acromegaly, patients with glucorticoid excess such as cortisol treatment or Cushings disease, patients with activated counter-regulatory hormones such as would occur after trauma, accidents and surgery and the like, patients with hypertriglyceridemia and patients with chronic pancreatitis can be readily and suitably nourished according to the invention without subjecting the patient to hypo- or hyperglycemia, while reducing undesirable catabolic changes and/or providing cardiovascular benefit.

In one embodiment the administration of a GIP compound, alone or with other agents, reduces morbidity or mortality in critically ill patients (who require intensive care) or the time they stay in the ICU. A reduction in morbidity means reducing the likelihood that the critically ill patient will develop additional illnesses, conditions, or symptoms or reducing the severity of additional illnesses, conditions or symptoms. For example reducing morbidity can be achieved by decreasing the incidence of bacteremia or sepsis or complications associated with multiple organ failure.

These indications need not be confined to those with dysglycemia, nor require that euglycemia be achieved. Neither are they restricted to an insulinotropic mechanism, or those individuals capable of responding with increased insulin secretion. Although GIP resistance has been reported in type 2 diabetes, resistance to the insulinotropic effects of GIP is not expected to be a feature of critically ill patients, including those with acute stress induced dysglycemia. Normal glucose-dependent stimulation of insulin secretion will occur in the majority of critically ill patients, and in those patients resistant to GIP efficacy can be attained with higher GIP doses or with the use of the GIP analogs and hybrids disclosed herein.

Thus in one embodiment is provided a method for inducing an insulinotropic response, for providing an anti- or non-catabolic effect (e.g. reducing a catabolic effect) or providing any one of the cardiovascular benefits discussed herein, or a any combination of the above, comprising administration of a therapeutically effective amount of a GIP compound to provide such desired beneficial action. These methods are useful for treating critical care conditions or disorders that can be alleviated by such effects, preferably in conjunction with a reduction of catabolic effect, in critically ill patients in need of such benefits.

The GIP compound includes GIP and GIP analogs and hybrids, particularly novel GIP analogs as described herein, extended half-life GIP hybrids (e.g. DPP-IV cleavage resistant (such as a D-Ala2, N-Acetyl or N-pyroglutamyl analogs) optionally further comprising a peptidic enhancer such as a heterologous C-terminal tail, and GIP hybrids comprising at least one hormone module known to provide beneficial benefit to a patient undergoing critical or intensive care. For example, GIP compounds of the invention particularly useful are the GIP hybrids comprising a DPP-IV resistant GIP analog with a peptidic enhancer such as an exendin tail (e.g. Compound G), or GIP hybrids comprising a GIP analog and a amylin family or salmon calcitonin hormone module, which are additionally beneficial by their lack of or reduced anorectic effect while maintaining a desirable glucose lowering, insulinotropic and/or cardiovascular benefit.

In one embodiment administering a GIP compound reduces the problems associated with parenteral nourishment. Very often it is not possible to infuse a desired amount of glucose even to people with healthy metabolism without provoking hyperglycemia. This can be exacerbated in critical care patients. Insulin secretion during parenteral nourishment in the presence of a GIP compound can be controlled such that the plasma glucose increase will be less than without the GIP compound. Therefore more glucose can be delivered over a 24-hour period than otherwise. The calorie deficit seen with parenterally nourished patients can thus be better satisfied. Accordingly, provided is a method for non-alimentary nutrition comprising administering by a parenteral route to a patient in need of parenteral nutrition, a nutritively effective amount of one or more nutrients selected from the group consisting of carbohydrates, ammo acids, lipids, free fatty acids, mono- or diglycerides, glycerol and any combination thereof, and a GIP compound, wherein the administration of the nutrient(s) produces a blood glucose level in the patient of from about 80 to 180 mg glucose per deciliter of blood, and the rate of administration is calculated to deliver up to about 1000 g of glucose or its equivalent per patient per day. In a further embodiment the patient receives at least about one third of the caloric need through the normal enteral route, at least about half of the caloric need through the normal enteral route, or at least about two third of the caloric need through the normal enteric route. When the nutrient source is carbohydrate, the source of carbohydrate can be present at a concentration of about a 2% to about a 50% by weight of glucose or its equivalent per liter. In a further embodiment enhance nutrient metabolism is achieved via the parenteral route in patients with a disturbed glucose metabolism, a surgery patient, a comatose patient, a patient in shock, a patient with gastrointestinal disease, a patient with digestive hormone disease, an obese patient, an atherosclerotic patient, a patient with vascular disease, a patient with gestational diabetes, a patient with liver disease, a patient with liver cirrhosis, a patient with glucocorticoid excess, a patient with Cushings disease, a patient with activated counter-regulatory hormones that occur after trauma or a disease, a patient with hypertriglyceridemia, or a patient with chronic pancreatitis, a nutritively effective amount of one or more nutrients or any combination thereof and one or more insulinotropic peptides. In yet a further embodiment the patient in need of enhanced parenteral nutrition via a non-alimentary route is a critical care patient.

In one embodiment for critical care use and parenteral nutrition enhancement use, a GIP compound is administered by continuous intravenous infusion to achieve blood glucose levels less than 200 mg/dl, or in the range of 80 to 150 mg/dl, or in the range of 80 to 110 mg/dl. For example, the GIP compound can be administered to maintain plasma glucose below the "renal threshold" of about 160 to 180 milligrams per deciliter. Patients not suffering from hyperglycemia can also be treated in view of the additional anti-catabolic and cardiovascular benefits provided by the GIP compounds.

As discussed herein, both acute and chronic administration by a range of routes is contemplated for critical care use and for enhancement of parenteral nutrition. In one embodiment for critical care use, a GIP compound is infused continuously at a rate of between about 0.1 and 100 pmol/kg/min, between about 0.1 and 50 pmol/kg/min, between about 0.5 and 30 pmol/kg/min, between about 0.1 and 10 pmol/kg/min, between about 0.5 and 5 pmol/kg/min, or between about 1.0 and 3.0 pmol/kg/min. As discussed elsewhere herein, the GIP compound can also be provided via a sustained release formulation, e.g. comprising microspheres or a gel matrix, and/ or administered via discrete or superimpositioning dosages, via subcutaneous, nasal, intravenous or other routes. The GIP compound can be administered prior to, during and/or after commencement of critical care, such as surgery.

The therapeutically effective dose of the GIP, GIP analog, novel GIP analog or GIP hybrid, or derivative thereof, will depend on a number of factors, including without limitation, the patient's sex, weight and age, the severity of inability to regulate blood glucose, the underlying cause(s) of inability to regulate blood glucose, whether glucose or another carbohydrate source is simultaneously administered, the route of administration and bioavailability, the persistence in the body, the formulation and the potency. It is within the skill of the ordinary physician to titrate the dose and rate of administration of a GIP compound to achieve the desired clinical result.

Polypeptide Production and Purification.

The polypeptides described herein may be prepared using standard recombinant techniques or chemical peptide synthesis techniques known in the art, e.g., using an automated or semi-automated peptide synthesizer, or both.

The polypeptides of the invention can be synthesized in solution or on a solid support in accordance with conventional techniques. Such methods are described, for example, herein and in U.S. Pat. No. 6,610,824 and U.S. Pat. No. 5,686,411 and in patent application Ser. No. 454,533 (filed Dec. 6, 1999), the entirety of which are incorporated herein by reference. Various automatic synthesizers are commercially available and can be used in accordance with known protocols. See, e.g., Stewart and Young, *Solid Phase Peptide Synthesis*, 2d. ed., Pierce Chemical Co. (1984); Tam et al, *J. Am. Chem. Soc.* 105: 6442 (1983); Merrifield, *Science* 232: 341-7 (1986); and Barany and Merrifield, *The Peptides*, Gross and Meienhofer, eds., Academic Press, New York, 1-284 (1979). Solid phase peptide synthesis may be carried out with an automatic peptide synthesizer (e.g., Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Peptides may also be assembled using an Advanced Chem Tech Synthesizer (Model MPS 350, Louisville, Ky.). Peptides may be purified by RP-HPLC (preparative and analytical) using, e.g., a Waters Delta Prep 3000 system and a C4, C8, or C18 preparative column (10µ, 2.2×25 cm; Vydac, Hesperia, Calif.). Polypeptides can be synthesized by convergent methods such as "native chemical ligation", and variations thereof, in which two or more peptide fragments with appropriate orthogonally reactive ends are ligated with native amide bond formation. The newly formed peptide can be further ligated to create even longer polypeptides. The individual starting peptides can be derivatized as desired or can be derivatized after a ligation step.

Peptides analogs were synthesized on a Pioneer continuous flow peptide synthesizer (Applied Biosystems) using PAL-PEG-PS resin (Applied Biosystems) with a loading of 0.2 mmol/g (0.25 mmole scale). Fmoc amino acid (4.0 eq, 1.0 mmol) residues were activated using 4.0 eq HBTU, 4.0 eq of HOBT, 8.0 eq DIEA and coupled to the resin for 1 hour. The Fmoc group was removed by treatment with 20% (v/v) piperidine in dimethylformamide. Final deprotection and cleavage of the peptide from the solid support was performed by treatment of the resin with reagent B (93% TFA, 3% phenol, 3% water and 1% triisopropylsilane) for 2-3 hours. The cleaved peptide was precipitated using tert-butyl methyl ether, pelleted by centrifugation and lyophilized. The pellet was re-dissolved in water (10-15 mL), filtered and purified via reverse phase HPLC using a C-18 column and an acetonitrile/water gradient containing 0.1% TFA. The purified product was lyophilized and analyzed by ESI-LC/MS and analytical HPLC and were demonstrated to be pure (>98%). Mass results all agreed with calculated values.

Alternatively, peptides were assembled on a Symphonyl peptide synthesizer (Protein Technologies, Inc., Woburn, Mass.) using Rink amide resin (Novabiochem, San Diego, Calif.) with a loading of 0.43-0.49 mmol/g at 0.050-0.100 mmol. Fmoc amino acid (Applied Biosystems, Inc. 5.0 eq, 0.250-0.500 mmol) residues were dissolved at a concentration of 0.10 M in 1-methyl-2-pyrrolidinone. All other reagents (HBTU, HOBT and N,N-diisopropylethylamine) were prepared as 0.55 M dimethylformamide solutions. The Fmoc protected amino acids were then coupled to the resin-bound amino acid using, HBTU (2.0 eq, 0.100-0.200 mmol), HOBT (1.8 eq, 0.090-0.18 mmol), N,N-diisopropylethylamine (2.4 eq, 0.120-0.240 mmol) for 2 hours. Following the last amino acid coupling, the peptide was deprotected using 20% (v/v) piperidine in dimethylformamide for 1 hour. Once peptide sequence is completed, the Symphonyl peptide synthesizer is programmed to cleave the resin. Trifluoroacetic acid (TFA) cleavage of the peptide from resin was carried out using a reagent mixture composed of 93% TFA, 3% phenol, 3% water and 1% triisopropylsilane. The cleaved peptide was precipitated using tert-butyl methyl ether, pelleted by centrifugation and lyophilized. The pellet was dissolved in acetic acid, lyophilized and then dissolved in water, filtered and purified via reverse phase HPLC using a C18 column and an acetonitrile/water gradient containing 0.1% TFA. Analytical HPLC was used to assess purity of peptide and identity was confirmed by LC/MS and MALDI-MS.

The active protein can be readily synthesized and then screened in screening assays designed to identify reactive peptides.

The analog and hybrid polypeptides of the present invention may alternatively be produced by recombinant techniques well known in the art. See, e.g., Sambrook et al., *Molecular Cloning: A Laboratory Manual*, 2d ed., Cold Spring Harbor (1989). These GIP analog or hybrid polypeptides produced by recombinant technologies may be expressed from a polynucleotide. One skilled in the art will appreciate that the polynucleotides, including DNA and RNA, that encode such GIP analog or hybrid polypeptides may be obtained from the wild-type cDNA, e.g. GIP, GLP1, amylin, taking into consideration the degeneracy of codon usage, or may be engineered as desired. These polynucleotide sequences may incorporate codons facilitating transcription and translation of mRNA in microbial hosts. Such manufacturing sequences may readily be constructed according to the methods well known in the art. See, e.g., WO 83/04053. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, *Bioorg. Chem.* 14: 356-77 (1986).

A variety of expression vector/host systems may be utilized to contain and express a GIP polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein.

As such, polynucleotide sequences provided by the invention are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present GIP polypeptides. The polynucleotide sequences encoding GIP analogs or hybrids herein may be useful for gene therapy in instances where underproduction of GIP or other component peptide hormone(s) of the hybrid would be alleviated, or the need for increased levels of such would be met.

The present invention also provides for processes for recombinant DNA production of the present GIP polypeptides. Provided is a process for producing the GIP polypeptides from a host cell containing nucleic acids encoding such GIP polypeptides comprising: (a) culturing said host cell containing polynucleotides encoding such GIP polypeptides under conditions facilitating the expression of such DNA molecule; and (b) obtaining such GIP polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, WI38, and the like, have specific cellular machinery and characteristic mechanisms for such post-translational activities, and may be chosen to ensure the correct modification and processing of the introduced foreign protein.

Alternatively, a yeast system may be employed to generate the GIP polypeptides of the present invention. The coding region of the GIP polypeptide cDNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, *Cell*, 30: 933-43 (1982)). The pre-pro-alpha leader coding sequence and GIP polypeptide coding sequence fragments are ligated into a plasmid containing the yeast alcohol dehydrogenase (ADH2) promoter, such that the promoter directs expression of a fusion protein consisting of the pre-pro-alpha factor fused to the mature GIP polypeptide. As taught by Rose and Broach, *Meth. Enz.* 185: 234-79, Goeddel ed., Academic Press, Inc., San Diego, Calif. (1990), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Stearns et al., *Meth. Enz.* 185: 280-97 (1990)). The ADH2 promoter is induced upon exhaustion of glucose in the growth media (Price et al., *Gene* 55: 287 (1987)). The pre-pro-alpha sequence effects secretion of the fusion protein from the cells. Concomitantly, the yeast KEX2 protein cleaves the pre-pro sequence from the mature GIP-polypeptides (Bitter et al., *Proc. Natl. Acad. Sci. USA* 81: 5330-4 (1984)).

GIP polypeptides of the invention may also be recombinantly expressed in yeast using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted GIP polypeptide is purified from the yeast growth medium by, e.g., the methods used to purify GIP polypeptide from bacterial and mammalian cell supernatants.

Alternatively, the cDNA encoding GIP polypeptides may be cloned into the baculovirus expression vector pVL1393 (PharMingen, San Diego, Calif.). This GIP-compound-encoding vector is then used according to the manufacturer's directions (PharMingen) to infect *Spodoptera frugiperda* cells in sF9 protein-free media and to produce recombinant protein. The protein is purified and concentrated from the media using a heparin-Sepharose column (Pharmacia, Piscataway, N.J.) and sequential molecular sizing columns (Amicon, Beverly, Mass.), and resuspended in PBS. SDS-PAGE analysis shows a single band and confirms the size of the protein, and Edman sequencing on a Proton 2090 Peptide Sequencer confirms its N-terminal sequence.

For example, the DNA sequence encoding the predicted mature GIP analog or hybrid polypeptide may be cloned into a plasmid containing a desired promoter and, optionally, a leader sequence (see, e.g., Better et al., Science 240: 1041-3 (1988)). The sequence of this construct may be confirmed by automated sequencing. The plasmid is then transformed into *E. coli*, strain MC1061, using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will affect secretion of the mature GIP analog or hybrid polypeptide and be cleaved during secretion. The secreted recombinant protein is purified from the bacterial culture media by the method described herein.

Alternatively, the GIP polypeptides of the invention may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The GIP polypeptide coding sequence is cloned into a nonessential region of the virus, such as the polyhedrin gene, and placed under control of the polyhedrin promoter. Successful insertion of GIP analog or hybrid polypeptide will render the polyhedrin gene inactive and produce recombinant virus lacking coat protein coat. The recombinant viruses are then used to infect *S. frugiperda* cells or *Trichoplusia larvae* in which GIP analog or hybrid polypeptide is expressed (Smith et al., *J. Virol* 46: 584 (1983); Engelhard et al., *Proc. Natl. Acad. Sci. USA* 91: 3224-7 (1994)).

In another example, the DNA sequence encoding the GIP polypeptide may be amplified by PCR and cloned into an appropriate vector, for example, pGEX-3X (Pharmacia, Piscataway, N.J.). The pGEX vector is designed to produce a fusion protein comprising glutathione-5-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3X/GIP analog polypeptide construct is transformed into *E. coli* XL-1 Blue cells (Stratagene, La Jolla, Calif.), and individual transformants are isolated and grown at 37° C. in LB medium (supplemented with carbenicillin) to an optical density at wavelength 600 nm of 0.4, followed by further incubation for 4 hours in the presence of 0.5 mM Isopropyl beta-D-Thiogalactopyranoside (Sigma Chemical Co., St. Louis, Mo.). Plasmid DNA from individual transformants is purified and partially sequenced using an automated sequencer to confirm the presence of the desired GIP polypeptide-encoding gene insert in the proper orientation.

The fusion protein, expected to be produced as an insoluble inclusion body in the bacteria, may be purified as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at room temperature. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/GIP polypeptide fusion protein is produced in bacteria as a soluble protein, it may be purified using the GST Purification Module (Pharmacia Biotech).

The fusion protein may be subjected to digestion to cleave the GST from the mature GIP analog or hybrid polypeptide. The digestion reaction (20-40 µg fusion protein, 20-30 units human thrombin (4000 U/mg (Sigma) in 0.5 mL PBS) is incubated 16-48 hrs. at room temperature and loaded on a denaturing SDS-PAGE gel to fractionate the reaction products. The gel is soaked in 0.4 M KCl to visualize the protein bands. The identity of the protein band corresponding to the expected molecular weight of the GIP analog or hybrid polypeptide may be confirmed by partial amino acid sequence analysis using an automated sequencer (Applied Biosystems Model 473A, Foster City, Calif.).

In a particularly exemplary method of recombinant expression of the GIP polypeptides of the present invention, 293 cells may be co-transfected with plasmids containing the GIP analog or hybrid polypeptide cDNA in the pCMV vector (5' CMV promoter, 3' HGH poly A sequence) and pSV2neo (containing the neo resistance gene) by the calcium phosphate method. In one embodiment, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for GIP analog or hybrid polypeptide expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

Many of the GIP polypeptides of the present invention may be produced using a combination of both automated peptide synthesis and recombinant techniques. For example, a GIP polypeptide of the present invention may contain a combination of modifications including deletion, substitution, and insertion by PEGylation. Such a GIP polypeptide may be produced in stages. In the first stage, an intermediate GIP polypeptide containing the modifications of deletion, substitution, insertion, and any combination thereof, may be produced by recombinant techniques as described. Then after an optional purification step as described herein, the intermediate GIP polypeptide is PEGylated through chemical modification with an appropriate PEGylating reagent (e.g., from NeKtar Transforming Therapeutics, San Carlos, Calif.) to yield the desired GIP polypeptide. One skilled in the art will appreciate that the above-described procedure may be generalized to apply to a GIP polypeptide containing a combination of modifications selected from deletion, substitution, insertion, derivation, and other means of modification well known in the art and contemplated by the present invention.

It may be desirable to purify the GIP polypeptides generated by the present invention. Peptide purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

Certain aspects of the present invention concern the purification, and in particular embodiments, the substantial purification, of an encoded protein or peptide. The term "purified peptide" as used herein, is intended to refer to a composition, isolatable from other components, wherein the peptide is purified to any degree relative to its naturally obtainable state. A purified peptide therefore also refers to a peptide, free from the environment in which it may naturally occur.

Generally, "purified" will refer to a peptide composition that has been subjected to fractionation to remove various other components, and which composition substantially retains its expressed biological activity. Where the term "substantially purified" is used, this designation will refer to a composition in which the peptide forms the major component of the composition, such as constituting about 50%, about 60%, about 70%, about 80%, about 90%, about 95% or more of the peptides in the composition.

Various techniques suitable for use in peptide purification will be well known to those of skill in the art. These include, for example, precipitation with ammonium sulphate, PEG, antibodies, and the like; heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein.

One may optionally purify and isolate such GIP polypeptides from other components obtained in the process. Methods for purifying a polypeptide can be found in U.S. Pat. No. 5,849,883. These documents describe specific exemplary methods for the isolation and purification of G-CSF compositions that may be useful in isolating and purifying the GIP polypeptides of the present invention. Given the disclosure of these patents, it is evident that one of skill in the art would be well aware of numerous purification techniques that may be used to purify GIP polypeptides from a given source.

Also it is contemplated that a combination of anion exchange and immunoaffinity chromatography may be employed to produce purified GIP polypeptide compositions of the present invention.

Pharmaceutical Compositions.

The present invention also relates to pharmaceutical compositions comprising a therapeutically or prophylactically effective amount of at least one GIP polypeptide of the invention, or a pharmaceutically acceptable salt thereof, together with pharmaceutically acceptable diluents, preservatives, solubilizers, emulsifiers, adjuvants and/or carriers useful in the delivery of the GIP polypeptides. Such compositions may include diluents of various buffer content (e.g., acetate, citrate, tartrate, phosphate, TRIS-HCl), pH and ionic strength; additives such as surfactants and solubilizing agents (e.g., sorbitan monooleate, lecithin, Pluronics, Tween 20 & 80, Polysorbate 20 & 80, propylene glycol, ethanol, PEG-40, sodium dodecyl sulfate), anti-oxidants (e.g., monothioglyercol, ascorbic acid, acetylcysteine, sulfurous acid salts (bisulfite and metabisulfite), preservatives (e.g., phenol, meta-cresol, benzyl alcohol, parabens (methyl, propyl, butyl), benzalkonium chloride, chlorobutanol, thimersol, phenylmercuric salts, (acetate, borate, nitrate), and tonicity/bulking agents (glycerine, sodium chloride, mannitol, sucrose, trehalose, dextrose); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present GIP analog polypeptides. See, e.g., Remington's Pharmaceutical Sciences 1435-712, 18th ed., Mack Publishing Co., Easton, Pa. (1990).

Optionally a GIP or a novel GIP analog can be formulated with (or alternatively administered in adjunct therapy with or alternatively covalently linked or fused to) a second active agent. Such agents can comprise activity that will complement or enhance a GIP effect. In one embodiment such agents have glucose lowering or anti-diabetic activity. In another embodiment the agent inhibits or reduces gastric emptying. In other embodiments the agent can comprise any other desirable activity, such as increasing bone density, reducing food intake, or the like.

In general, the present GIP analog and hybrid polypeptides will be useful in the same way that GIP and/or the individual component polypeptides (in the case of a hybrid) are useful in view of their pharmacological properties. Generally, the GIP polypeptides are peripherally administered for the treatment or prevention of metabolic conditions and disorders. In particular, the compounds of the invention possess activity as glucose lowering agents, insulinotropic agents, reducing or inhibiting gastric secretion, effecting weight loss, reducing nutrient availability, reducing food intake, suppressing appetite, ameliorating mortality and morbidity in critical (intensive) care applications, providing improved memory and other neurological benefits, increasing or maintaining bone density, effecting cardiovascular benefits, providing cardioprotection, and effecting other therapeutic benefits as discussed herein. In another embodiment, a exemplary use is to administer such hybrid polypeptides for the treatment of diabetes or diabetes related conditions and disorders, obesity, and cardiovascular diseases and conditions. The present GIP polypeptides may be formulated for peripheral administration, including formulation for injection, oral administration, nasal administration, pulmonary administration, topical administration, or other types of administration as one skilled in the art will recognize. More particularly, administration of the pharmaceutical compositions according to the present invention may be via any common route so long as the target tissue is available via that route. In a exemplary embodiment, the pharmaceutical compositions may be introduced into the subject by any conventional peripheral method, e.g., by intravenous, intradermal, intramusclar, subcutaneous, intramammary, intraperitoneal, intrathecal, retrobulbar, intrapulmonary (e.g., term release); by oral, sublingual, nasal, buccal, intratracheal, anal, vaginal, transmucosal, pulmonary or transdermal delivery, by suppository or by surgical implantation at a particular site. In one embodiment the administration is parenteral (including intravenous, intradermal, intraperitoneal, intramuscular and subcutaneous).

The treatment may consist of a single dose or a plurality of doses over a period of time. Controlled continual release of the compositions of the present invention is also contemplated.

Supplementary active ingredients also can be incorporated into the compositions. For use by the physician, the compounds will be provided in dosage unit form containing an amount of a GIP or novel GIP analog, with or without another therapeutic agent, for example, a glucose-lowering agent, a gastric emptying modulating agent, a lipid lowering agent, or a food intake inhibitor agent. Therapeutically effective amounts of a GIP or a novel GIP analog for example for use in the control of blood glucose or in the control of gastric emptying and in conditions in which gastric emptying is beneficially slowed or regulated are those that decrease post-prandial blood glucose levels, preferably to no more than about 8 or 9 mM or such that blood glucose levels are reduced as desired. In diabetic or glucose intolerant individuals, plasma glucose levels are higher than in normal individuals. In such individuals, beneficial reduction or "smoothing" of post-prandial blood glucose levels may be obtained. As will be recognized by those in the field, an effective amount of therapeutic agent will vary with many factors including the patient's physical condition, the blood sugar level or level of inhibition of gastric emptying to be obtained, or the desired level of food intake reduction, and other factors. In some cases, it will be convenient to provide a GIP polypeptide and at least one other active agent, for example another food-intake-reducing, plasma glucose-lowering or plasma lipid-altering agent, such as an exendin or GLP1 or agonist thereof, amylin, an amylin agonist analog, a CCK or CCK agonist, or a leptin or leptin agonist or a small molecule cannabinoid CB1 receptor antagonists, beta-hydroxysteroid dehydrogenase-1 inhibitors, sibutramine and other drugs marketed for treatment of diabetes or obesity, in a single composition or solution for administration together. As has been discussed throughout, the GIP polypeptide may be a GIP hybrid comprising the at least one other such active agent. In other cases, it may be more advantageous to administer the additional agent separately from said GIP polypeptide.

In one embodiment a GIP polypeptide may be administered separately or together with one or more other compounds and compositions that exhibit a long term or short-term action to lower blood glucose, reduce or inhibit gastric emptying or reduce or inhibit gastric secretions or reduce nutrient availability, including, but not limited to other compounds and compositions that comprise an amylin or amylin analog agonist, salmon calcitonin, a cholecystokinin (CCK) or CCK agonist, a leptin (OB protein) or leptin agonist, an exendin or exendin analog agonist, or a GLP-1 or GLP-1 analog agonist. Suitable amylin agonists include, for example, [$^{25,28,29}$Pro-] human amylin (also known as "pramlintide," and described in U.S. Pat. Nos. 5,686,511 and 5,998,367). The CCK used is preferably CCK octapeptide (CCK-8), more preferably its sulfated form. Leptin is discussed in, for example, (Pelleymounter et al., Science 269: 540-3 (1995); Halaas et al., Science 269: 543-6 (1995); Campfield et al., Science 269: 546-9 (1995)). Suitable exendins include exendin-3 and exendin-4, and exendin agonist compounds include, for example, those described in PCT Publications WO 99/07404, WO 99/25727, and WO 99/25728. Suitable agents also include various anti-diabetic agents, e.g. metformin, sulfonylureas, TZDs. In another embodiment is provided a combination therapy of a GIP analog or hybrid, e.g. 0601GIP3794, with an incretin mimetic, e.g., exenatide or liraglutide. In a further embodiment sub-therapeutic doses of the incretin mimetic are used, which provide a therapeutic benefit when combined with the GIP compound.

Accordingly, in one embodiment, particularly in patients subject to conditions associated with elevated glucose levels such as diabetic or glucose intolerant individuals, more particularly type 2 diabetic patients, where plasma glucose levels are higher than in normal individuals, GIP therapy in such individuals will benefit from a beneficial reduction or "smoothing" of post-prandial blood glucose levels prior to or concomitant with administration of a GIP or novel GIP analog.

In contrast to GLP-1, GLP-1 analogs and mimetics such as exenatide which have been shown to be efficacious in controlling glucose levels in type 2 diabetic patients, the insulinotropic effect of GIP is significantly reduced in diabetic subjects compared to normal individuals. While not to be bound by theory, it is believed that while GIP's incretin effect is attenuated during persistent hyperglycemia, GIP or its analogs will act with a similar potency in diabetic patients as their action in normal subjects once glucose control is improved in these individuals. Thus according to the present invention GIP insensitivity can be reduced by achieving in a patient in need thereof, a glucose-lowering or a reduction or "smoothing" of post-prandial blood glucose levels by appropriate agents or means, prior to or concomitant with administration of a GIP or novel GIP analog that will enable or prolong even further glucose-lowering. In one embodiment the agent or means is provided at least one day prior to GIP administration. In another embodiment the agent or means is provided and a sufficient glucose-lowering is observed prior to GIP administration.

As mentioned herein suitable agents include exenatide, metformin, sulfonylureas, or combinations thereof. Primary glucose control endpoint can be measured by means known in the art to clinicians. One method is simply to determine blood glucose levels post-prandially. Another is to measure HbA1c levels, as is known in the art.

A particularly suitable target population is those patients who fail to attain normal glucose concentrations during treatment with a glucose-lowering agent (such as exenatide). A type of hemoglobin called hemoglobin A1c (HbA1c) forms when glucose attaches to hemoglobin. This happens only when blood glucose levels are high. The hemoglobin A1c level can be used to measure a subject's past average blood sugar, e.g. over two to three months. Normal HbA1c values for non-diabetics are approximately 4.0-6.2 percent. The American Diabetes Association recommends that it should be below 7 percent for diabetics, to minimize the complications from diabetes. Despite glucose-lowering therapies, such as exenatide, significant numbers of patients may still remain with elevated Hb1Ac. Consequently, in one embodiment such subjects whose HbA1c level (despite treatment with a glucose-lowering agent) remains above normal, at least 7 percent, at least 8 percent, at least 9 percent or at least 10 percent, are suitable subjects for the GIP therapy and novel adjunct therapy treatments of the invention. In yet another embodiment the Hb1Ac level is greater than normal but no greater than 6.5%, no greater than 7%, no greater than 7.5%, no greater than 8.0%, no greater than 8.5%, no greater than 9.0%, no greater than 9.5%, or no greater than 10%. In yet another embodiment, while reduction of Hb1Ac levels is not reduced to normal levels with monotherapy, it is preferably reduced at least 10 percent, at least 20 percent, at least 30, 40, 50, 60, 70, 80 or at least 90 percent from pre-treatment levels, prior to GIP administration or application of a novel adjunct therapy of the invention. In such patients, adjunct therapy with GIP is indicated according to the invention since reduction of hyperglycemia (e.g., as by exenatide) in treated patients, e.g. diabetic patients, poises the patient for reduced GIP insensitivity. Whereas the chronic hyperglycemic condition in type 2 diabetes patients attenuates GIP's insulinotropic response, improved glycemic control resulting from exenatide treatment, for example, would restore responsiveness of the pancreatic beta-cell to GIP stimulation. Therefore GIP therapy or novel adjunct therapy (e.g. co-administration, GIP phybrid, GIP fusion protein) of pharmacological doses of GIP or novel GIP analogs with exenatide (or other glucose lowering agents or agents or methods that lower glucose or that reduce or inhibit gastric emptying) will attain GIP sensitivity and lead to desired normoglycemia in diabetic patients or patients suffering from conditions associated with elevated glucose. Since GIP lacks the gastric emptying effect of GLP1, nausea may be avoided, thus permitting the use of higher GIP dosing regimens than for GLP1. In yet another embodiment, GIP therapy or novel adjunct therapy will reduce Hb1Ac levels to at least normal levels, or at least 10 percent, at least 20 percent, at least 30, 40, 50, 60, 70, 80 or at least 90 percent from pre-treatment (pre GIP therapy or pre-novel-adjunct therapy) levels.

In yet a further embodiment, the GIP therapy or novel adjunct therapy can act at least additively, and preferably synergistically, to reduce the dose, dosing, amount, frequency or extent of treatment associated with another agent as mentioned herein. For example, such GIP or novel adjunct therapy can result in at least a 10, 20, 30, 40, 50, 60, 70, 80 or 90% reduction in the amount, dose, frequency of dosing, or length of treatment associated with a the other agent. The agent can be a glucose-lowering agent such a exendin-4, or any other agent, for diabetes or other conditions that benefit form the methods and compositions of the present invention.

The GIP polypeptide of the invention may be prepared for administration as solutions of free base, or pharmacologically acceptable salts in water suitably mixed with surface active agents (e.g., sorbitan monooleate, polyoxyethylene sorbitain monolaurate (Tween 20), polyoxyethylene sorbitan monooleate (Tween 80), lecithin, polyoxyethylene-polyoxypropylene copolymers (Pluronics), hydroxypropylcellulose,) or complexation agents (e.g., hydroxypropyl-b-cyclodextrin, sulfobutyether-b-cyclodextrin (Captisol), polyvinylpyrrolidone). Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like. Such products are readily prepared by procedures well known to those skilled in the art. Dispersions also can be prepared in glycerol, liquid polyethylene glycols, and mixtures thereof and in oils. Under ordinary conditions of storage and use, these preparations contain a preservative to prevent the growth of microorganisms.

In one embodiment, the pharmaceutical compositions of the present invention are formulated so as to be suitable for parenteral administration, e.g., via injection or infusion. In one embodiment, the GIP polypeptide is suspended in an aqueous carrier, for example, in an buffer solution at a pH of about 3.0 to about 8.0, preferably at a pH of about 3.5 to about 7.4, about 3.5 to about 6.0, about 3.5 to about 5.0 or about 3.7 to about 4.7. Useful buffers include sodium acetate/acetic acid, sodium lactate/lactic acid, ascorbic acid, sodium citrate-citric acid, sodium bicarbonate/carbonic acid, sodium succinate/succinic acid, Histidine, Sodium benzoate/benzoic acid, and sodium phosphates, and Tris(hydroxymethyl)aminomehane. A form of repository or "depot" slow release preparation may be used so that therapeutically effective amounts of the preparation are delivered into the bloodstream over many hours or days following transdermal injection or delivery.

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that is easily syringable. It is also desirable for the GIP polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In many cases, it will be preferable to include tonicity agents (for example, sugars, sodium chloride). Prolonged absorption of the injectable compositions can be brought about by the use in the compositions of agents delaying absorption (for example, aluminum monostearate and gelatin).

Sterile injectable solutions may be prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle that contains the basic dispersion medium and the required other ingredients from those enumerated above. In the case of sterile powders for the preparation of sterile injectable solutions, the exemplary methods of preparation are vacuum-drying and freeze-drying techniques that yield a powder of the active ingredient plus any additional desired ingredient from a previously sterile-filtered solution thereof.

Generally, a therapeutically or prophylactically effective amount of the present GIP polypeptides will be determined by the age, weight, and condition or severity of the diseases or metabolic conditions or disorders of the recipient. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2 S (1988). Typically, a dosage of between about 0.001 µg/kg body weight/day to about 1000 µg/kg body weight/day, may be used, but more or less, as a skilled practitioner will recognize, may be used. Dosing may be one, two, three, four or more times daily, or less frequently, such as once a week, once a month, or once a quarter, depending on the formulation, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

An effective dose will typically be in the range of about 0.5 to 30 µg to about 5 mg/day, preferably about 10 to 30 µg to about 2 mg/day and more preferably about 5 to 100 µg to about 1 mg/day, most preferably about 5 µg to about 500 µg/day, for a 50 kg patient, administered in a single or divided doses and/or controlled continual release, of two, three, four or more administrations. In one embodiment the GIP compound is administered peripherally at a dose of about 0.5 µg to about 5 mg per day in single or divided doses or controlled continual release, or at about 0.01 µg/kg to about 500 µg/kg per dose, more preferably about 0.05 µg/kg to about 250 µg/kg, most preferably below about 50 µg/kg.

Accordingly, exemplary doses can be derived from the total amount of drug to be given a day and the number doses administered a day. For example, exemplary doses can range from about 0.125 µg/dose (0.5 µg given four times a day) to about 2 mg/dose (2 mg given once a day). Other dosages can be between about 0.01 to about 100 µg/kg/dose. The exact dose to be administered may be determined by one of skill in the art and is dependent upon the potency of the particular compound, as well as upon the age, weight and condition of the individual. Administration should begin whenever the therapeutic benefit, e.g. suppression of nutrient availability, food intake, weight loss or control, blood glucose or plasma lipid lowering or modulation, is desired, for example, at the first sign of symptoms or shortly after diagnosis of obesity, diabetes mellitus, or insulin-resistance syndrome. In one embodiment the GIP compound is administered prophylactically. Administration may be by any route, e.g., injection, preferably subcutaneous or intramuscular, oral, nasal, transdermal, etc. Dosages for certain routes, for example oral administration, may be increased to account for decreased bioavailability, for example, by about 5-100 fold.

In general, the GIP compounds may be formulated into a stable, safe pharmaceutical composition for administration to a patient. Pharmaceutical formulations contemplated for use in the methods of the invention may comprise approximately 0.01 to 20% (w/v), preferably 0.05 to 10%, of the GIP compound. The GIP compounds may be in an acetate, phosphate, citrate or glutamate buffer allowing a pH of the final composition of about 3.0 to about 7.0; containing carbohydrate or polyhydric alcohol as tonicity modifier and, optionally, approximately 0.005 to 5.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In a particular embodiment of the present invention, a pharmaceutical formulation of the present invention may contain a range of concentrations of GIP compounds, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in this embodiment. A sufficient amount of water for injection may be used to obtain the desired concentration of solution. The pharmaceutical formulations described herein may be lyophilized. An exemplary formulation can be 1 mg/mL GIP compound in 10 mM sodium acetate buffer solution, pH 4.2, containing 9.3% sucrose as an osmolality modifier.

In one embodiment, where the pharmaceutical formulation is to be administered parenterally, the composition is formulation so as to deliver a dose of GIP polypeptide ranging from 0.1 µg/kg to 100 mg/kg body weight/day, preferably at doses ranging from 1 µg/kg to about 50 mg/kg body weight/day. Exemplary daily amounts may be in the range of a lower limit of 2, 5, 10, 20, 40, 60 or 80 to an upper limit of 80 100, 150, 200, or 250. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

In one embodiment the dose of GIP compound, either GIP analog, derivative or hybrid, for treatment of a human can be about 5 to about 50 fold lower than the dose used in a mouse to elicit a similar effect, such as the doses depicted herein. In a further embodiment, the dose for a human can be a 10 to 30-fold lower dose than that used in a mouse, or for example about 3 to 10 nmol/kg/d. In another embodiment, the dose in humans can be from about 0.1 to 20 ug/kg/day, and can be 0.5 to 10 ug/kg/d, and can be 1-2 ug/kg/d. These amounts may be achieved from either single or multiple dosing per day or from a sustained release delivery. For example, a sustained release composition if taken once weekly, can be provided at about 0.1 to 1.0 milligrams of GIP compound, depending factors as discussed herein and as would be known to a skilled practitioner. Once monthly or bimonthly dosing would be adjusted accordingly. Should nausea occur that would compromise patient compliance, an escalating dose scheme can be used, starting from a lower dose that does not elicit substantial nausea to increasing doses until the therapeutic effective dose is achieved.

The frequency of dosing will depend on the pharmacokinetic parameters of the agents and the routes of administration. The optimal pharmaceutical formulation will be determined by one of skill in the art depending on the route of administration and the desired dosage. See, e.g., Remington's Pharmaceutical Sciences, supra, pages 1435-1712. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein, as well as the pharmacokinetic data observed in animals or human clinical trials.

In one embodiment a formulation of the invention is a liquid, solid, or semi-solid depot, slow, or continuous release formulation capable of delivering an active ingredient of the invention (or multiple active ingredients as for use in the adjunct therapies mentioned herein) over a time period of at least one hour. The release can occur over a period of 24 hours to four months. Such slow or extended release formulations can, in some embodiments, comprise the active ingredient in a slow dissolving form or formulation, such as a slow-dissolving peptide crystal (such as disclosed in, for example, U.S. Pat. No. 6,380,357), in a matrix, or in a coating such as, e.g., an enteric coating or slow-dissolving coating (e.g., coated granules of active ingredient). Slow release matrices are commonly a biodegradable polymer, non-biodegradable polymer, wax, fatty material, etc., and are known in the art (e.g., see U.S. Pat. Nos. 6,368,630 and related patents, 6,379,704 and related patents). In addition, parenteral controlled release delivery can be achieved by forming polymeric microcapsules, matrices, solutions, implants and devices and administering them parenterally or by surgical means. These dosage forms would typically have a lower bioavailability due to entrapment of some of the peptide in the polymer matrix or device. (See e.g., U.S. Pat. Nos. 6,379,704, 6,379,703, and 6,296,842).

In one embodiment are microencapsulated GIP compounds, either a GIP analog, derivative or hybrid, for sustained delivery. Suitable polymer matrix and excipient formulations, and methods for making them, are provided for example, in US2005271702 published Dec. 8, 2005, for example. The matrix may be formulated as microspheres for injection or otherwise configured as an implantable device. Such a composition for the sustained release of biologically active GIP compound while comprise, preferably consist essentially of, a biocompatible polymer, the GIP compound and a sugar. The sugar can stabilize the peptide during manufacture, storage and use. The sustained release composition can comprise GIP compound from about 0.1% w/w to about 10% w/w of the total weight of the sustained release composition. The GIP polypeptide can be present from about 0.5% w/w to about 5% w/w of the total weight of the sustained release composition. In one embodiment the GIP compound will be present from about 2% to 5%. In one embodiment, to minimize initial burst and to increase the sustained release period, the sustained release composition can have a low porosity. In such embodiments, the sustained release composition has a total pore volume of about 0.1 mL/g or less. In addition the total pore volume can be from 0.0 to 0.1 mL/g and from 0.01 to less than 0.1 mL/g. For example, in one embodiment the total pore volume is about 0.1 mL/g or less as determined using mercury intrusion porosimetry. The sugar can be present from about 0.01% w/w to about 10% w/w of the total weight of the sustained release composition. In one embodiment the sugar is present from about 0.1% w/w to about 5% w/w of the total weight of the sustained release composition. In another embodiment the total combined percent weight of drug and excipient(s) is from about 2% to about 8%. The sugar can be selected from a monosaccharide, a disaccharide, a sugar alcohol or a combination thereof. In one embodiment the sugar is selected from sucrose, mannitol, trehalose, and combinations thereof. While any biocompatible, biodegradable polymer may be used, the polymer can be selected from the group consisting of poly(lactides), poly (glycolides), poly(lactide-co-glycolides), poly(lactic acid)s, poly(glycolic acid)s, poly(lactic acid co-glycolic acid)s, polycaprolactone, polycarbonates, polyesteramides, polyanhydrides, poly(amino acids), polyorthoesters, polycyanoacrylates, poly(p dioxanone), poly(alkylene oxalate)s, biodegradable polyurethanes, blends thereof and copolymers thereof. In one embodiment of particular interest the polymer comprises poly(lactide-co-glycolide), and further can be a 50:50 poly(lactide-co-glycolide), and further can have an inherent viscosity of between about 0.3 and 0.5 dL/g. In another embodiment when the sustained release compositions have a low porosity as described herein, which serves to both reduce initial release and to provide longer sustained release with a desirable Cmax to Cave ratio, additional excipients can be present. Such agents preferably will have little or no substantial effect on release rate. Such excipients can include those that provide or enhance agent stability, either during manufacturing, storage or release. Suitable stabilizers include, for example, carbohydrates, amino acids, fatty acids and surfactants and are known to those skilled in the art. Further, stabilizers include "antioxidants" such as methionine, vitamin C, vitamin E and maleic acid. The antioxidant can be present as part of a stabilized aqueous formulation or added into the polymer phase. Further a pH buffer can be added. Buffers are solutions containing either a weak acid and a related salt of the acid, or a weak base and a salt of the base. Buffers can maintain a desired pH to stabilize the formulation during any step of manufacturing, storage or release. For example, the buffer can be a monobasic phosphate salt or dibasic phosphate salt or combinations thereof or a volatile buffer such as ammonium bicarbonate. Other buffers include but are not limited to acetate, citrate, succinate and amino acids such as glycine, arginine and histidine. The buffer can be present in the formulation from about 0% to about 10% of the total weight, or less than about 10, 15, 20, 25 or 30 mM.

As discussed herein one of ordinary skill in the art can readily determine frequency, timing and dose of a GIP or novel GIP analog of the invention for treatment, particularly for conditions associated with elevated glucose, and further when used in adjunct therapy. For example a dose-response relationship over time for the glucose-lowering effect of agent of interest can be first determined, followed by determining a dose-response relationship with the added GIP or novel GIP analog in relation to the doses selected for the other agent. In one example patients with type 2 diabetes are treated and assessed following randomized, subcutaneous injection of placebo, and various amounts of agent on separate days following an overnight fast. Injections are given immediately before ingestion of a standardized Sustacal® meal (7 kcal/kg) followed by collection of plasma glucose samples at frequent intervals during the subsequent 300 minutes. Glycemic response can be quantified as the time-weighted mean (±SE) change in plasma glucose concentration during the 5-hr period. An $ED_{50}$ for the glucose lowering effect is determined, and appropriate dose of agent that lowers postprandial plasma glucose concentrations is selected. Subsequently, in a similar study, this dosage is administered to patients while administering varying doses of GIP or a novel GIP analog in order to determine an appropriate dose of GIP that will act in concert with the first agent to further lower or prolong glucose lowering.

Further, if desired, the timing of administration of the GIP dose relative to when or how long the first agent was administered is examined in order to identify an optimal dosing regimen. For example, a dose of exenatide can be given on day 1, followed by administration of GIP on day 2, preferably once a glucose lowering response is observed resulting from the exenatide alone. In another embodiment, alternating agent dosing with GIP dosing is provided. The agent may be administered every other period alternating with GIP administration. The period can be 1, 2, 3, 4, 5, 6, or 7 days, 1, 2, 3, or 4 weeks, or 1, 2, 3, 4, 5 or 6 months. The period can be varied, such as GIP administration 2 days after agent and agent administration 7 days after GIP treatment. Sustained release formulations or methods will extend the period in each case. Further, GIP or novel GIP analogs can be provided in adjunct therapy with (or after cessation of) beta cell neogenesis therapy or islet or beta cell transplantation, where beta cells are increased in number, thus providing a glucose-lowering post treatment. Consequently, in one embodiment such treatment, while not entirely creating a normoglycemia, nonetheless provides a patient with a sufficiently lowered glucose level, that resistance to GIP is attenuated such that further or more normal glucose levels are achieved post-prandially.

In one embodiment the agent will have been administered or the method will have been applied at least twenty-four hours prior to commencing GIP administration. More specifically the intervening period can be 24, 36, 48, 60 or 72 hours to 4, 5, 6, 7 or more days, to 2, 3, 4, 5, 6 or more weeks, or any particular intervening time in hours or minutes within the above range. Alternatively, blood glucose levels can be monitored regularly or post-prandially as would be known in the art to measure the effect of the glucose-lowering agent, using methods well known in the art, during and/or following administration of the agent. The administration of GIP can then be performed either at a time when the subject shows a level of response e.g., blood glucose level, indicative of reduced resistance to GIP, at which time or thereafter GIP or a novel GIP analog can be administered.

As discussed herein, in another embodiment of adjunct therapy with a GIP or novel GIP analog, the therapy comprises an agent or method that slows nutrient to the duodenum (or other more distal nutrient-sensing GIP-secreting sites) that results in lowering glucose levels compared to the absence of the agent or method. In yet another embodiment adjunct therapy comprises an agent or method that slows gastric emptying. In addition to the viscous decelerants, such as described herein (e.g., guar and fiber), the agent includes pharmacologic decelerants of gastric emptying, and includes gut hormones for which gastric slowing is a physiologic event. Such agents include agonists of amylin (e.g. pramlintide), agonists of GLP1 and exendin (e.g. exenatide, NN2211, ZP-10. liraglutide), agonists of CCK, agonists of PYY, agonists of secretin, agonists of GRP, agonists of neuromedins, and agonists of urocortin. In further embodiments are agents that directly or indirectly promote agonist signaling of the physiologic gastric decelerants. Such agents include secretagogues of endogenous gastric decelerants, and inhibitors of their degrading enzymes, including dipeptidyl dipeptidase inhibitors, or other inhibitors of their clearance, especially at the kidney. In other embodiments are therapeutic strategies that slow the appearance of nutrient stimulus at GIP-secreting cells. Examples include modulation of digestive functions through inhibition of digestive secretions (e.g. gastric acid, pancreatic enzymes, bile) or through inhibition of the digestive effect of such secretions (e.g. acid neutralization, enzyme inhibition, bile sequestration). Inhibiting digestive secretion can occur via agents that directly achieve this (e.g. somatostatin, amylin, calcitonins, PYY) or by agents that interfere with endogenous pro-secretory pathways (e.g. luminal CCK-releasing factor). In one embodiment the adjunct therapy comprises a method that achieves slower gastric emptying and lower nutrient uptake, e.g. diminishes nutrient drive at GIP secreting cells. In one such embodiment is gastric bypass surgery, for example Roux-En-Y Gastric Bypass Surgery, lap band, or physical devices that physically divert nutrient flow from the duodenum.

In yet other embodiments adjunct therapy comprises methods that stimulate secretion of, or slow degradation of, gastric decelerants. As mentioned guar gum ingestion is one example, for example 10 grams guar gum flour per meal. In Another agent is xanthum gum. Other decelerants of nutrient absorption include fiber, as for example provided in a high fiber diet, and as rough fiber in breads and bran. Another agent is a glucosidase inhibitor, such as acarbose, which slows the rate at which glucose (and fructose) is generated from sucrose at gut brush border disaccharidases. Yet another agent is Miglitol, another a glucosidase inhibitor.

In yet another embodiment gastric emptying is achieved or mediated by administering a peptide or peptide agonist. Based on the rat, doses of the following peptides have been determined to slow gastric emptying, and are entirely suitable as agents for adjunct therapies of the invention: amylin (e.g., pramlintide doses of 60-600 µg/day); GLP1 or exendin agonist (e.g., exenatide dose range of 10-50 µg/day); CCK and agonists (see Young et al. "Dose-responses for the slowing of gastric emptying in a rodent model by glucagon-like peptide (7-36)NH2, amylin, cholecystokinin, and other possible regulators of nutrient uptake." Metabolism 451-3 (1996); incorporated herein by reference). Other agents include Secretin and agonists, CGRP and agonists, Neuromedin agonists, Urocortin agonists, GRP and bombesin agonists, and PYY and agonists.

In the embodiments herein, a method of defining doses can be based on a desired degree of slowing, which can be readily determined. For example, therapeutic doses of pramlintide (30, 60 90 µg; see Kong et al. "The effect of single doses of pramlintide on gastric emptying of two meals in men with IDDM." Diabetologia. 41577-583 (1998)) approximately doubled the half-emptying time of the stomach. Accordingly, in one embodiment adjunct therapy comprises an agent or method that increases the half-emptying time of the stomach by about 200%, however in other embodiments the t ½ of stomach emptying can increased by more than about 25%, 50%, 75%, 100%, 200%, 300% and even 400% or more.

By example, an ED50 for exenatide slowing of gastric emptying has been reported at about 0.05 µg/kg (e.g., approximately currently used clinical dose) (see Kolterman et al. "Dose-response for inhibition of glucagon secretion and gastric emptying by synthetic exendin-4 (AC2993) in subjects with type 2 diabetes." Diabetes 49 (suppl 1)A114 Abstract 460-P (2000)). In adjunct therapy with a GIP or a novel GIP analog such slowing will provide a increased benefit to the subject. Consequently, in one embodiment agents or methods that provide an equivalent slowing of gastric emptying at pharmaceutically acceptable doses are suitable agents or methods. As discussed throughout, other embodiments of adjunct therapy comprise mammalian amylins, the (25,28,29)proline-human amylin analog (pramlintide), and salmon calcitonin, those being amongst the most potent. Additional suitable peptides and their EC50 (EC(50) nmol/kg_sem (EC(50) in µg): Pramlintide, 0.09_0.08 log (0.07 µg); Human amylin, 0.19_0.11 log (0.15 µg); Rat amylin, 0.23_0.08 log (0.18 µg); Salmon calcitonin, 0.28_0.07 log (0.19 µg); Rat calcitonin, 0.94_0.18 log (0.64 µg); Rat CGRP, 2.13_0.29 log (1.62 µg); GLP-1 (7-36)NH2, 2.76_ 0.12 log (1.82 µg); Secretin, 3.09_0.20 log (1.87 µg); CCK-8, 12.8_0.20 log (2.93 µg); Gastrin releasing peptide, 49.9_ 0.05 log (28.5 µg) (see Gedulin et al. "Comparison of 21 peptides on inhibition of gastric emptying in conscious rats." Dig. Dis. Week. A742 (abstract 2967) (1996); This study reported the potency and effect of 21 peptides to modulate gastric emptying in dose-response studies in conscious rats (n=~18 rats/peptide, rat weight ~200 g). Peptide was injected subcutaneously 5 min before gavage with an acaloric dye-labeled methyl cellulose gel. Animals were sacrificed 20 min later and the dye content of the stomach measured spectroscopically to assess emptying. Only 10 peptides were found to fully inhibit gastric emptying at doses up to 100 ug/rat. Peptides found to be either weakly active or inactive at doses of 100 µg were vasoactive intestinal peptide (VIP), gastric inhibitory peptide (GIP), pancreatic polypeptide, neuropeptide Y, glucagon, insulin (if plasma glucose was maintained constant), gastrin, somatostatin, pituitary adenylate cyclase activating peptide (PACAP38), adrenomedullin and deamidated pramlintide.). In other embodiments of the invention the agent comprise a agonist of any of the peptides mentioned herein, such as an antibody or antibody fragment agonist or small molecule agonist.

As described throughout, such agents (or their combination) can be administered either separately or together with GIP or can comprise a chimeric molecule with a GIP, e.g., either chemically linked or recombinant fusion. As described throughout (e.g., see times and periods mentioned herein), when administered separately GIP can be administered either at a designated time point after administration of the agent(s) or method, or it can be administered at or shortly after a desired effect has been obtained by prior administration of the agent or method, such effect associated with reducing the subject's GIP resistance.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit comprising a GIP analog or hybrid polypeptide of the invention, components suitable for preparing said GIP compound polypeptide of the invention for pharmaceutical application, and instructions for using GIP compound polypeptide and components for pharmaceutical application.

The following formulation method can be used with the GIP compounds, as well as with other suitable drug compounds. Generally, while screening for and formulating peptide or protein candidates for pharmaceutical applications, formulation scientists seek compounds where the solubility and physical stability and/or chemical stability are somewhat within the same pH range, making it easier to formulate and have sufficiently long shelf-life for clinical use. However, compounds that have solubility and stability maxima at different pH ranges present a formulation challenge. Because the solubility and stability of these drug candidates occur at different pH ranges, a common practice is to screen excipients to enhance the solubility where the peptide is most stable. Often times, however, the solubility increased only slightly by the solubility enhancer, but compromised the chemical stability of the peptide/protein. Exemplary bioactive GIP compounds where solubility and physical/chemical stability are at different ranges of pH include AC163794, AC164326. AC164850, AC164190, AC164847, AC164957, AC164947 and AC164948. For example, a drug compound that is a candidate for this method may have optimal physical/chemical stability at about pH 6, instability near the isoelectric point (e.g. pI ~5), and chemically stability, but lack desired solubility near the desired pH for formulation, e.g. pH 4. In contrast, exemplary compounds where the properties share the same pH range include AC164233, AC164815, AC164816, AC164853, AC164854, and AC164855.

Because the solubility and stability of peptides can occur at different pH ranges, a common practice is to screen excipients to enhance the solubility where the peptide is most stable. However, in many cases the solubility enhancer increases only slightly the solubility, but compromises the chemical stability of the peptide/protein. However, the present invention is based on a different approach to the problem. The method entails solubilizing the drug at a pH range at which the drug is maximally soluble, optimally soluble or at a sufficient and desirable concentration. Long-term physical or chemical stability (such as determine by an accelerated stability study, typically 40 degrees C. for 1 to 7 or more days) is not of concern at this step, since the drug need only be sufficiently stable until and during the subsequent processing step. By long-term stability is meant a period of time and under such conditions during which the drug is stored during transport and prior to therapeutic use. The concentrated drug solution (first solution) may be used as a bulk solution to fill commercial vials, etc. The drug solution is then dried to remove the aqueous phase. This is typically done in vial form or in the container for therapeutic use. Just prior to use or upon use, the dried material is reconstituted, and used for administration. In one embodiment, the drug solution pH is first optimized to attain the desired drug concentration (solubility, mg/mL) (i.e. the first solution). Secondly, the first solution is treated to remove the aqueous phase, as by lyophilization. The dried material provides a stable storage form. Thirdly, prior to or upon therapeutic use the lyophilized material is reconstituted with a buffered solution such that the dissolved drug is at a suitable dosing concentration that is stable during the use period.

A wide variety of buffers can be used at various pHs to provide the first solution where the protein has maximal, optimal or desired solubility, as would be known to the formulation chemist with regard to the drug compound of interest. In one embodiment the buffer is volatile, such as an acetate. In another embodiment, the buffer is not volatile but does not significantly affect the stability of the compound in the final formulation upon reconstitution prior to use. In yet another embodiment, the buffer comprises and contributes to the final formulation upon reconstitution.

In a further embodiment a tonicity modifier and/or lyo/cryoprotectant can be used as would be known by a formulation chemist with regard to the drug of interest. For peptide and polypeptide compounds, these excipients can include mannitol, sucrose, trehalose, or glycerol. These compounds can be included in the first solution, if solubility is not adversely affected, or can be included in the reconstitution vehicle or diluent.

The method can be used to formulate drug products containing biomolecules (e.g., peptides or proteins), that have low inherent solubility in the pH range where these compounds are optimally stable. Other examples of suitable biologically active agents that can have low inherent solubility in the pH range where these compounds are optimally stable include GLP-1 peptides and analogs, immunoglobulins, antibodies, cytokines (e.g. lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, enzymes (e.g., superoxide dismutase, tissue plasminogen activator), tumor suppressors, blood proteins, hormones and hormone analogs (e.g., growth hormone, adrenocorticotropic hormone and luteinizing hormone releasing hormone (LHRH)), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules; oligonucleotides; and ribozymes. Small molecular weight agents suitable for use in the method so long as they have low inherent solubility in the pH range where these compounds are optimally stable.

The following are examples present exemplary solutions and formulations, which can also be used with GIP analogs presented herein. In one embodiment, Formulation 1, the first solution is about 2 mg/mL drug (e.g. AC163794, AC164850, or AC164288 having a solubility range of about 0.5-5 mg/mL) in 10 mM Tris buffer (range: 10-50 mM) with about 5.07% mannitol at about pH 8.5 (range: ±0.5). The aqueous phase is removed, for example by lyophilization. Prior to use, the material is reconstituted with an (acidic) diluent to bring the pH to 7 (range: ±0.5). In another embodiment, Formulation 2, the first solution is about 2 mg/mL drug (e.g. AC163794, AC164850, or AC164288 (range: 0.5-5 mg/mL) in 10 mM glycylglycine buffer (range: 10-50 mM) with about 5.07% mannitol at about pH 8.5 (range: ±0.5). The aqueous phase is removed, for example by lyophilization. Prior to use, the material is reconstituted with an (acidic) diluent to bring the pH to 7 (range: ±0.5). In another embodiment, Formulation 3, the first solution is about 2 mg/mL drug (e.g. AC163794, AC164850, or AC164288 (range: 0.5-5 mg/mL) in 10 mM glycine (range: 10-50 mM) with 5.07% mannitol at pH 8.5 (range: ±0.5). The aqueous phase is removed, for example by lyophilization. Prior to use, the material is reconstituted with an (acidic) diluent to bring the pH to 7 (range: ±0.5). In another embodiment, Formulation 4, the first solution is about 2 mg/mL drug (e.g. AC163794, AC164850, or AC164288 (range: 0.5-5 mg/mL) in 10 mM Ethanolamine buffer (range: 10-50 mM) with about 5.07% mannitol at about pH 8.5 (range: ±0.5). The aqueous phase is removed, for example by lyophilization. Prior to use, the material is reconstituted with an (acidic) diluent to bring the pH to 7 (range: ±0.5). In another embodiment, Formulation 5, the first solution is about 2 mg/mL drug (e.g. AC163794, AC164850, or AC164288 (range: 0.5-5 mg/mL) in 10 mM phosphate buffer (range: 10-50 mM) with about 5.07% mannitol at about pH 8.0 (range: −1.0). The aqueous phase is removed, for example by lyophilization. Prior to use, the material is reconstituted with an (acidic) diluent to bring the pH to 7 (range: ±0.5).

The present application hereby incorporates by reference in their entirety commonly-owned: PCT/US05/04178 filed Feb. 11, 2005 and published as WO2005/077072; PCT/US2005/004351 filed Feb. 11, 2005; PCT/US2005/004631 filed Feb. 11, 2005; PCT/US2005/045471 filed Dec. 15, 2005; U.S. patent application Ser. No. 11/055,093; U.S. patent application Ser. No. 11/201,664 filed Aug. 10, 2005; and U.S. Ser. No. 206,903 filed Aug. 17, 2005. The applications teach compounds and uses related to and useful for the present invention. Also incorporated herein by reference is applicant's co-pending application PCT/US2006/005020 to Levy et al. An alternative embodiment to each of the embodiments disclosed herein is the proviso that the specific GIP peptides, analogs, and derivatives disclosed in PCT/US2006/005020 are specifically excluded. An alternative embodiment to each of the embodiments disclosed herein is the proviso that the specific GIP hybrids disclosed in PCT/US2006/005020 are specifically excluded. In yet another alternative embodiment to each of the embodiments disclosed herein is the proviso that the specific GIP peptides, analogs, and derivatives disclosed in PCT/US2006/005020 are specifically excluded, except when combined to generate a novel GIP hybrid not specifically mentioned in PCT/US2006/005020 or for uses and treatment methods for which they were not specifically mentioned in PCT/US2006/005020.

ADDITIONAL REFERENCES

1. Fehmann H C, Goke B, Goke R, Trautmann M E, Arnold R. Synergistic stimulatory effect of glucagon-like peptide-1 (7-36) amide and glucose-dependent insulin-releasing polypeptide on the endocrine rat pancreas. FEBS Lett. 1989 252:109-12
2. Nauck M A, Bartels E, Orskov C, Ebert R, Creutzfeldt W. Additive insulinotropic effects of exogenous synthetic human gastric inhibitory polypeptide and glucagon-like peptide-1-(7-36) amide infused at near-physiological insulinotropic hormone and glucose concentrations. J Clin Endocrinol Metab. 1993 76:912-7
3. Vilsboll T, Krarup T, Madsbad S, Holst J J. Both GLP-1 and GIP are insulinotropic at basal and postprandial glucose levels and contribute nearly equally to the incretin effect of a meal in healthy subjects. Regul Pept. 2003; 114:115-21
4. Jones I R, Owens D R, Moody A J, Luzio S D, Morris T, Hayes T M. The effects of glucose-dependent insulinotropic polypeptide infused at physiological concentrations in normal subjects and type 2 (non-insulin-dependent) diabetic patients on glucose tolerance and beta-cell secretion. Diabetologia. 1987 30:707-12.
5. Nauck M A, Heimesaat M M, Orskov C, Holst J J, Ebert R, Creutzfeldt W. Preserved incretin activity of glucagon-like peptide 1 [7-36 amide] but not of synthetic human gastric inhibitory polypeptide in patients with type-2 diabetes mellitus. J Clin Invest. 1993 91:301-7.
6. Elahi D, McAloon-Dyke M, Fukagawa N K, Meneilly G S, Sclater A L, Minaker K L, Habener J F, Andersen D K. The insulinotropic actions of glucose-dependent insulinotropic polypeptide (GIP) and glucagon-like peptide-1 (7-37) in normal and diabetic subjects. Regul Pept. 1994 Apr. 14; 51(1):63-74.
7. Holst J J, Gromada J, Nauck M A. The pathogenesis of NIDDM involves a defective expression of the GIP receptor. Diabetologia. 1997 40:984-6.
8. Lynn F C, Pamir N, Ng E H, McIntosh C H, Kieffer T J, Pederson R A. Defective glucose-dependent insulinotropic polypeptide receptor expression in diabetic fatty Zucker rats. Diabetes. 2001 50:1004-11
9. Meier J J, Hucking K, Hoist J J, Deacon C F, Schmiegel W H, Nauck M A. Reduced insulinotropic effect of gastric inhibitory polypeptide in first-degree relatives of patients with type 2 diabetes. Diabetes. 2001 50:2497-504.
10. Meier J J, Gallwitz B, Kask B, Deacon C F, Hoist J J, Schmidt W E, Nauck M A. Stimulation of insulin secretion by intravenous bolus injection and continuous infusion of gastric inhibitory polypeptide in patients with type 2 diabetes and healthy control subjects. Diabetes. 2004 53 Suppl 3:S220-4.
11. Vilsboll T, Knop F K, Krarup T, Johansen A, Madsbad S, Larsen S, Hansen T, Pedersen O, Hoist J J. The pathophysiology of diabetes involves a defective amplification of the late-phase insulin response to glucose by glucose-dependent insulinotropic polypeptide-regardless of etiology and phenotype. J Clin Endocrinol Metab. 2003 88:4897-903.
12. Vilsboll T, Krarup T, Madsbad S, Holst J J. Defective amplification of the late phase insulin response to glucose by GIP in obese Type II diabetic patients. Diabetologia. 2002 45:1111-9.
13. Young A A, Gedulin B R, Rink T J. Dose-responses for the slowing of gastric emptying in a rodent model by glucagon-like peptide (7-36) NH2, amylin, cholecystokinin, and other possible regulators of nutrient uptake. Metabolism. 1996 45:1-3.
14. Meier J J, Goetze O, Anstipp J, Hagemann D, Hoist J J, Schmidt W E, Gallwitz B, Nauck M A. Gastric inhibitory polypeptide does not inhibit gastric emptying in humans. Am J Physiol Endocrinol Metab. 2004 286:E621-5.

15. Kieffer T J. Gastro-intestinal hormones GIP and GLP-1. Ann Endocrinol 2004 65:13-21.
16. Jones I R, Owens D R, Moody A J, Luzio S D, Morris T, Hayes T M. The effects of glucose-dependent insulinotropic polypeptide infused at physiological concentrations in normal subjects and type 2 (non-insulin-dependent) diabetic patients on glucose tolerance and B-cell secretion. Diabetologia. 1987 30:707-12.
17. Nauck M A, Heimesaat M M, Orskov C, Hoist J J, Ebert R, Creutzfeldt W. Preserved incretin activity of glucagon-like peptide 1 [7-36 amide] but not of synthetic human gastric inhibitory polypeptide in patients with type-2 diabetes mellitus. J Clin Invest. 1993 91:301-7.
18. Elahi D, McAloon-Dyke M, Fukagawa N K, Meneilly G S, Sclater A L, Minaker K L, Habener J F, Andersen D K. The insulinotropic actions of glucose-dependent insulinotropic polypeptide (GIP) and glucagon-like peptide-1 (7-37) in normal and diabetic subjects. Regul Pept. 1994 Apr. 14; 51(1):63-74.
19. Hoist J J, Gromada J, Nauck M A. The pathogenesis of NIDDM involves a defective expression of the GIP receptor. Diabetologia. 1997 40:984-6.
20. Young A A, Gedulin B R, Rink T J. Dose-responses for the slowing of gastric emptying in a rodent model by glucagon-like peptide (7-36) NH2, amylin, cholecystokinin, and other possible regulators of nutrient uptake. Metabolism. 1996 45:1-3.
21. Kieffer T J. Gastro-intestinal hormones GIP and GLP-1. Ann Endocrinol 2004 65:13-21.
22. Deacon C F, Nauck M A, Toft-Nielsen M, Pridal L, Willms B, Holst J J. Both subcutaneously and intravenously administered glucagon-like peptide 1 are rapidly degraded from the NH2-terminus in type II diabetic patients and in healthy subjects. Diabetes 1995 44:1126-1131.
23. Deacon C F, Johnsen A H, Holst J J. Degradation of glucagon-like-peptide-1 by human plasma in vitro yields an N-terminally truncated peptide that is a major endogenous metabolite in vivo. J. Clin. Endocrinol. Metab. 1995 80:952-957.
24. Kieffer T J, McIntosh C H, Pederson R A. Degradation of glucose-dependent insulinotropic polypeptide and truncated glucagon-like peptide 1 in vitro and in vivo by dipeptidyl peptidase IV. Endocrinology. 1995 August; 136(8):3585-96.
25. Plamboeck A, Holst J J, Carr R D, Deacon C F. Neutral endopeptidase 24.11 and dipeptidyl peptidase IV are both involved in regulating the metabolic stability of glucagon-like peptide-1 in vivo. Adv Exp Med. Biol. 2003; 524:303-12.
26. Hupe-Sodmann K, McGregor G P, Bridenbaugh R, Goke R, Goke B, Thole H, Zimmermann B, Voigt K. Characterisation of the processing by human neutral endopeptidase 24.11 of GLP-1(7-36) amide and comparison of the substrate specificity of the enzyme for other glucagon-like peptides. Regul Pept. 1995 Aug. 22; 58(3):149-56.
27. Gault V A, Flatt P R, Harriott P, Mooney M H, Bailey C J, O'Harte FP. Improved biological activity of Gly2- and Ser2-substituted analogues of glucose-dependent insulinotrophic polypeptide. J Endocrinol. 2003 January; 176 (1):133-41.
28. Hinke S A, Gelling R W, Pederson R A, Manhart S, Nian C, Demuth H U, McIntosh C H. Dipeptidyl peptidase IV-resistant [D-Ala(2)]glucose-dependent insulinotropic polypeptide (GIP) improves glucose tolerance in normal and obese diabetic rats. Diabetes. 2002 March; 51(3):652-61.
29. Hudson F M, Andersen N H. Exenatide: NMR/CD evaluation of the medium dependence of conformation and aggregation state. Biopolymers. 2004 76:298-308.
30. Andersen N H, Brodsky Y, Neidigh J W, Prickett K S. Medium-dependence of the secondary structure of exendin-4 and glucagon-like-peptide-1. Bioorg Med. Chem. 2002 10:79-85.
31. Neidigh J W, Fesinmeyer R M, Prickett K S, Andersen N H. Exendin-4 and glucagon-like-peptide-1: NMR structural comparisons in the solution and micelle-associated states. Biochemistry. 2001 40:13188-200.
32. Thum A, Hupe-Sodmann K, Goke R, Voigt K, Goke B, McGregor GP. Endoproteolysis by isolated membrane peptidases reveal metabolic stability of glucagon-like peptide-1 analogs, exendins-3 and -4. Exp Clin Endocrinol Diabetes. 2002 110:113-8.
33. Fehmann H C, Goke B. Characterization of GIP(1-30) and GIP(1-42) as stimulators of proinsulin gene transcription. Peptides. 1995 16:1149-52.

Throughout this application various publications are referenced. The disclosures of these publications in their entirety are hereby incorporated by reference into this application in order to more fully describe the state of the art to which this invention pertains.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

The examples illustrate the preparation of the present GIP polypeptides, and the testing of these GIP polypeptides of the invention in vitro and/or in vivo.

Example 1

Preparation of GIP Polypeptides

Peptides of the invention may be assembled on a Symphony peptide synthesizer (Protein Technologies, Inc.) using Rink amide resin (Novabiochem) with a loading of 0.43-0.49 mmol/g at 0.050-0.100 mmol or a pre-loaded Wang Resin (Fmoc-Tyr(tBu)-Wang resin) 0.63 mmol/g (Novabiochem). Fmoc amino acid (5.0 eq, 0.250-0.500 mmol) residues are dissolved at a concentration of 0.10 M in 1-methyl-2-pyrrolidinone. All other reagents (HBTU, 1-hydroxybenzotriazole hydrate and N,N-Diisopropylethylamine) are prepared as 0.55 M dimethylformamide solutions. The Fmoc protected amino acids are then coupled to the resin-bound amino acid using, HBTU (2.0 eq, 0.100-0.200 mmol), 1-hydroxybenzotriazole hydrate (1.8 eq, 0.090-0.18 mmol), N,N-diisopropylethylamine (2.4 eq, 0.120-0.240 mmol) for 2 hours. Following the last amino acid coupling, the peptide is deprotected using 20% (v/v) piperidine in dimethylformamide for 1 hour. Once peptide sequence is complete, the Symphony peptide synthesizer is programmed to cleave the resin. Trifluoroacetic acid (TFA) cleavage of the peptide from resin is carried out using 93% TFA, 3% phenol, 3% water and 1% triisopropylsilane for 1 hour. The cleaved peptide is precipitated using tert-butyl methyl ether, pelleted by centrifugation and lyophilized. The pellet is re-dissolved in water (10-15 mL), filtered and purified via reverse phase HPLC using a C18 column and an acetonitrile/water gradient containing 0.1% TFA. The resulting peptides are purified to homogeneity by reverse phase HPLC and the purity is confirmed by LCMS.

A general procedure for N-capping the peptides of the invention with fatty acids (e.g., octanoic and stearic acids) is as follows: Peptide on rink amide resin (0.1 mmol) is suspended in NMP (5 mL). In a separate vial, HBTU (0.3 mmol), HOBt (0.3 mmol) is dissolved in DMF (5 mL) followed by the addition of DIEA (0.6 mmol). This solution is added to the resin and this suspension is shaken for 2 hrs. The solvent is filtered and washed thoroughly with NMP (5 mL×4) and $CH_2Cl_2$ (20 mL), dried and is subjected to the TFA cleavage for 1 hr. The yield of the desired peptide is ca. 40 mg after cleavage and purification.

PEG modification may be carried out in solution on a free epsilon-amino group of lysine or a terminal amino group of a purified peptide using commercially available activated PEG esters. The resulting PEGylated derivatives are purified to homogeneity by reverse phase HPLC and the purity is confirmed by LC/MS and MALDI-MS.

Example 2

Binding Assays

The GIP polypeptides of the invention may be tested in a variety of receptor, e.g. GIPR, GLP-1R, amylin receptor, binding assays using binding assay methodologies generally known to those skilled in the art. Such assays include those described herein.

GIP Receptor Binding Assay: To identify GIP analog peptides having affinity for the human GIP receptor the following assay was performed in a high throughput format. Cell membranes were prepared from confluent cultures of an HEK293 cell line stably expressing the human GIP receptor (HEK-GIPR), snap frozen, and stored at −80 degrees C. until use. At the time of assay, membranes were thawed on ice and diluted to 0.02 mg/mL in ice cold binding buffer (20 mM HEPES pH 7.4, 0.5% BSA, 5 mM MgCl2, 1 mM $CaCl_2$, 170 µM Phosphoramidon, 1.5 mM Bestatin-HCL, and 70 mM Bacitracin). Heterologous binding assays were initiated by combining membranes with 30 pM 125I-GIP and 10 nM individual unlabeled GIP analogs diluted in assay buffer. Reactions were allowed to proceed to equilibrium for 90' at room temperature with constant shaking. Binding was then terminated by rapid filtration through 96-well glass fiber filter plates separating bound and unbound fractions of radioligand. Displacement of radioligand for each analog was calculated relative maximal displacement by human GIP (100%), and non-specific binding (0%) in the absence of any competing ligand. Analog peptides displacing more than 50% of total ligand were segregated to a "positive" test group and re-tested for accurate IC50 determination using the aforementioned format with increasing concentrations of unlabeled analog (10 pM-1 uM final concentration). Analogs displacing more than 50% of total ligand were scored to have IC50 values less than 10 nM.

Amylin binding assay: Evaluation of the binding of some exemplary compounds of the invention to amylin receptors may be carried out as follows in nucleus accumbens membranes prepared from rat brain. Male Sprague-Dawley® rats (200-250) grams are sacrificed by decapitation. Brains are removed and place in cold phosphate-buffered saline (PBS). From the ventral surface, cuts are made rostral to the hypothalamus, bounded laterally by the olfactory tracts and extending at a 45° angle medially from these tracts. This basal forebrain tissue, containing the nucleus accumbens and surrounding regions, is weighed and homogenized in ice-cold 20 mM HEPES buffer (20 mM HEPES acid, pH adjusted to 7.4 with NaOH at 23° C.). Membranes are washed three times in fresh buffer by centrifugation for 15 minutes at 48,000×g. The final membrane pellet is resuspended in 20 mM HEPES buffer containing 0.2 mM phenylmethylsulfonyl fluoride (PMSF).

To measure $^{125}$I-amylin binding (see, Beaumont K et al. Can J Physiol Pharmacol. 1995 July; 73(7): 1025-9), membranes from 4 mg original wet weight of tissue are incubated with $^{125}$I-amylin at 12-16 pM in 20 mM HEPES buffer containing 0.5 mg/ml bacitracin, 0.5 mg/ml bovine serum albumin, and 0.2 mM PMSF. Solutions are incubated for 60 minutes at 2° C. Incubations are terminated by filtration through GF/B glass fiber filters (Whatman Inc., Clifton, N.J.) that are presoaked for 4 hours in 0.3% poylethyleneimine in order to reduce nonspecific binding of radiolabeled peptides. Filters are washed immediately before filtration with 5 ml cold PBS, and immediately after filtration with 15 ml cold PBS. Filters are removed and radioactivity assessed in a gamma-counter at a counting efficiency of 77%. Competition curves are generated by measuring binding in the presence of $10^{-12}$ to $10^{-6}$ M unlabeled test compound and are analyzed by nonlinear regression using a 4-parameter logistic equation (Inplot program; GraphPAD Software, San Diego).

CGRP receptor binding assay: Evaluation of the binding of compounds of the invention to CGRP receptors are essentially as described for amylin except using membranes prepared from SK-N-MC cells, known to express CGRP receptors (Muff, R. et. al, Ann NY *Acad. Sci.* 1992: 657, 106-16). Binding assays are performed as described for amylin except using 13,500 cpm 125I-hCGRP/well or 21.7 pM/well (Amersham).

Adrenomedullin binding assay: Binding to the adrenomedullin receptor may be investigated using HUWECs that contain the adrenomedullin receptor (Kato J et al., *Eur J Pharmacol* 1995, 289:383-5) using the Perkin Elmer AlphaScreen™ assay for cyclic AMP using an optimum of 25-30,000 cells per well. Elevation of cAMP levels is not large for HUVEC compared to CHO cells. As such, CHO cells may be chosen as a negative control since they do not express the adrenomedullin receptor if desired.

Calcitonin receptor binding assay: Binding to the calcitonin receptor may be investigated using CHO cells or T47D cells, which also express the calcitonin receptor (Muff R. et. al, *Ann NY Acad Sci.* 1992, 657:106-16 and Kuestner R. E. et. al. *Mol Pharmacol.* 1994, 46:246-55), as known in the art.

Leptin binding assay: Two in vitro bioassays are routinely used to assess leptin binding and receptor activation (see e.g., White, et al., 1997. Proc. Natl. Acad. Sci. U.S.A. 94: 10657-10662). An alkaline phosphatase("AP")-leptin ("OB") fusion protein ("AP-OB") may be used to measure inhibition of leptin binding in the absence or presence of recombinant mouse leptin (positive control) or peptide, by COS-7 cells transfected with the long (signaling) form of the mouse OB receptor ("OB-RL"). Signal transduction assays may be done in GT1-7 cells cotransfected with AP reporter and OB-RL constructs. Secreted alkaline phosphatase("SEAP") activity in response to stimulation with mouse leptin or peptide may be measured by chemiluminescence.

Y1 receptor binding assay: Membranes are prepared from confluent cultures of SK-N-MC cells that endogenously expresses the neuropeptide Y1 receptors. Membranes are incubated with 60 pM [125I]-human Peptide YY (2200 Ci/mmol, PerkinElmer Life Sciences), and with unlabeled test compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y2 receptor binding assay: Membranes are prepared from confluent cultures of SK-N-BE cells that endogenously expresses the neuropeptide Y2 receptors. Membranes are incubated with 30 pM [125I]-human Peptide YY (2200 Ci/mmol, PerkinElmer Life Sciences), and with unlabeled test compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y4 receptor binding assay: CHO-K1 cells are transiently transfected with cDNA encoding neuropeptide Y4 gene, and then forty-eight hours later membranes are prepared from confluent cell cultures. Membranes are incubated with 18 pM [125I]-human Pancreatic Polypeptide (2200 Ci/mmol, PerkinElmer Life Sciences), and with unlabeled test compound for 60 minutes at ambient temperature in a 96 well polystyrene plate. Then well contents are harvested onto a 96 well glass fiber plate using a Perkin Elmer plate harvestor. Dried glass fiber plates are combined with scintillant and counted on a Perkin Elmer scintillation counter.

Y5 receptor binding assay: CHO-K1 cells are transiently transfected with cDNA encoding neuropeptide Y5 gene, and then forty-eight hours later membranes are prepared from confluent cell cultures. Membranes are incubated with 44 pM [125I]-human Peptide YY (2200 Ci/mmol, PerkinElmer Life Sciences), and with unlabeled test compound for 60 minutes at ambient temperature in a 96 well polystyrene plate. Then well contents are harvested onto a 96 well glass fiber plate using a Perkin Elmer plate harvester. Dried glass fiber plates are combined with scintillant and counted on a Perkin Elmer scintillation counter.

GLP-1 receptor binding assay: GLP-1 receptor binding activity and affinity may be measured using a binding displacement assay in which the receptor source is RINm5F cell membranes, and the ligand is [125I]GLP-1. Homogenized RINm5F cell membranes are incubated in 20 mM HEPES buffer with 40,000 cpm [125I]GLP-1 tracer, and varying concentrations of test compound for 2 hours at 23° C. with constant mixing. Reaction mixtures are filtered through glass filter pads presoaked with 0.3% PEI solution and rinsed with ice-cold phosphate buffered saline. Bound counts are determined using a scintillation counter. Binding affinities are calculated using GraphPad Prism software (GraphPad Software, Inc., San Diego, Calif.).

Example 3

Mouse Food Intake Assay

The GIP hybrid polypeptides of the invention may be tested for appetite suppression in the mouse food intake assay and for their effect on body weight gain in diet-induced obesity (DIO) mice. The experimental protocols for the screens are described herein.

Female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage.

At time=0 min, all animals are given an intraperitoneal injection of vehicle or compound, typically in an amount ranging from about 10 nmol/kg to 75 nmol/kg, and immediately given a pre-weighed amount (10-15 g) of the standard chow. Food is removed and weighed, typically at 30, 60, and 120 minutes, to determine the amount of food consumed (Morley, Flood et al., *Am. J. Physiol* 267: R178-R184, 1994). Food intake is calculated by subtracting the weight of the food remaining at the e.g., 30, 60, 120, 180 and/or 240 minute time point, from the weight of the food provided initially at time=0, Significant treatment effects are identified by ANOVA (p<0.05). Where a significant difference exists, test means are compared to the control mean using Dunnett's test (Prism v. 2.01, GraphPad Software Inc., San Diego, Calif.).

Activity in the food intake assay and sequence of parent molecules used with GIP for the synthesis of hybrids herein include:

| Description | 60 min ED50 (nmol/kg) | Sequence | Mouse Food Intake, % basal | | | | Dose |
|---|---|---|---|---|---|---|---|
| | | | 30 min | 60 min | 120 min | 180 min | |
| PYY(3-36) (SEQ ID NO: 47) | 1 | 3 | IKPEAPGEDASPEELNR YYASLRHYLNLVTRQR Y-NH2 | -31 | -38 | -40 | -26 | 10 nmol/Kg |
| Exendin-4 (SEQ ID NO: 5) | | 5 | HGEGTFTSDLSKQMEEE AVRLFIEWLKNGGPSSG APPPS-NH2 | -41 | -60 | -61 | -60 | 4.8 nmol/Kg |
| Exendin-4 (1-28) (SEQ ID NO: 287) | 11 | 0.3 | HGEGTFTSDLSKQMEEE AVRLFIEWLKN-NH2 | -50 | -62 | -49 | -49 | 16.3 nmol/Kg |
| Exendin-4 (1-28) [Ala5, Leu14, Phe25] (SEQ ID NO: 288) | 12 | 13 | HGEGAFTSDLSKQLEEE AVRLFIEFLKN-NH2 | -53 | -61 | -50 | -53 | 16.7 nmol/Kg |
| Rat Amylin (SEQ ID No. 33) | | 9 | KCNTATCATQRLANFL VRSSNNLGPVLPPTNVG SNTY-NH2 | -58 | -40 | -36.5 | -35.5 | 25 nmol/Kg |

-continued

| Description | ED50 (nmol/kg) | Sequence | 30 min | 60 min | 120 min | 180 min | Dose |
|---|---|---|---|---|---|---|---|
| hAmylin(1-7)-<br>11,18Arg-sCT(8-27)-<br>Amylin(33-37)<br>(SEQ ID NO: 95) | 10 | 26 | KCNTATCVLGRLSQEL<br>HRLQTYPRTNTGSNTY-<br>NH2 | -60 | -47 | -42.5 | -32 | 25 nmol/Kg |
| CCK-8<br>(SEQ ID NO: 289) |  | 26 | DY(SO3) MGWMDF-NH2 | -92 | -56 | -27 |  | 10 nmol/Kg |

Example 4

Body Weight Gain in Fattened C57B1/6 (Diet-Induced-Obesity, or DIO) Mice

Male C57BL/6 mice (4 weeks old at start of study) are fed high fat (HF, 58% of dietary kcal as fat) or low fat (LF, 11% of dietary kcal as fat) chow. After 4 weeks on chow, each mouse is implanted with an osmotic pump (Alzet #2002) that subcutaneously delivers a predetermined dose of hybrid polypeptide continuously for two weeks. Body weight and food intake are measured weekly (Surwit et al., *Metabolism—Clinical and Experimental*, 44: 645-51, 1995). Effects of the test compound are expressed as the mean+/−sd of % body weight change (i.e., % change from starting weight) of at least 14 mice per treatment group (p<0.05 ANOVA, Dunnett's test, Prism v. 2.01, GraphPad Software Inc., San Diego, Calif.).

Example 5

Further Testing of GIP Compounds and Hybrids

Circular dichroism (CD) and NMR studies of Exendin-4 in aqueous media and in media containing organic cosolvents reveal that the C-terminal segment containing the sequence, LFIEWLKNGGPSSGAPPPS (SEQ ID NO: 183) (residue 21-39) forms a unique hydrophobic Trp-cage cluster resulting from interactions of Pro37 with Phe22 and Pro38 with Trp25 (14-16). Interestingly, there is no evidence of Trp-cage formation in water containing dodecylphosphocholine (DPC), a micellar state that mimics a biological membrane environment. NMR spectral data indicate rapid segmental motion of the eight C-terminal residues, presumably because the Trp-cage is destabilized due to energetically favorable association of the Trp residue with the phosphocholine head groups. This Trp-cage cluster motif is the first example of a protein-like tertiary structure displayed by a peptide, and could be responsible for imparting greater metabolic stability by masking protease-sensitive sites in the molecule in vivo (17).

Thus, in one embodiment GIP analog or hybrids were designed with the premise that these peptides could assume the Trp cage structure reported for Exendin-4 by appending the Exendin tail sequence to the C-termini of the truncated GIP peptides GIP-(1-30) and GIP-(1-26). In addition, substitutions of the Tyr and Ala residues at the N-terminus of GIP were also made to confer resistance to DPP-IV peptidase degradation. These metabolically stable GIP analog or hybrids can be used as monotherapy or as an adjunct therapy with Exendin-4 (or other GLP-1 agonists) or ant-diabetic drugs such as metformin, sulphonylureas, thiazolidinediones, pramlintide and insulin for treatment of type 2 diabetes.

Analogs can and were screened in GIP receptor binding and acute glucose lowering assays in NIH Swiss or diabetic db/db mice. See FIGS. 2-4. In vitro GLP-1 and glucagon receptor binding counterscreens were carried out to assess receptor specificity. The enzymatic stability of these GIP analog or hybrids are also being tested by incubation of the peptides with kidney brush-border membrane extract, membrane extract from RINm5F cells and purified neutral endopeptidase 24.11, followed by analysis of the cleavage products by LC-MS/MS (data not shown).

Figure 3B:
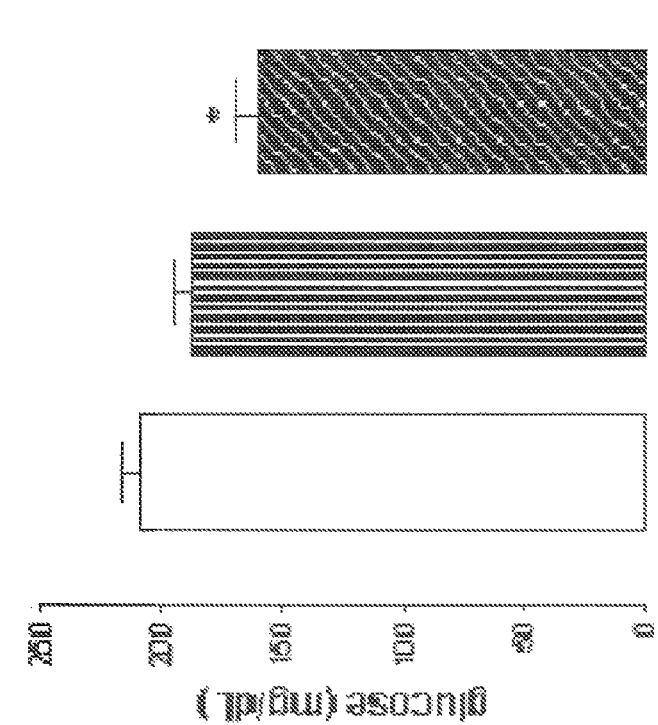
FIGS. 3A and 3B present suppression of glucose excursion following an OGTT, and basal glucose lowering activity of GIP and Compound G in NIH/Swiss mice.
Figure 3A:
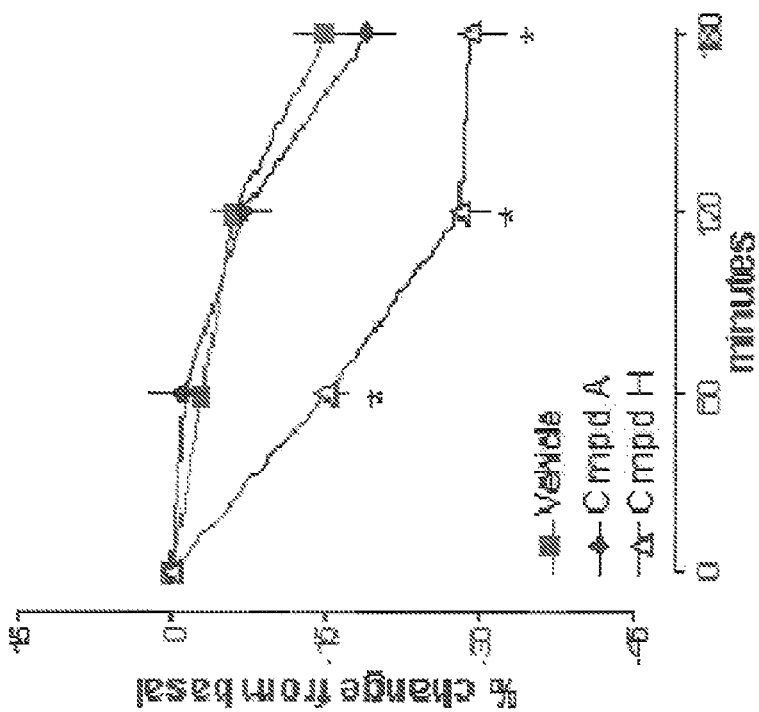
Figure 4:
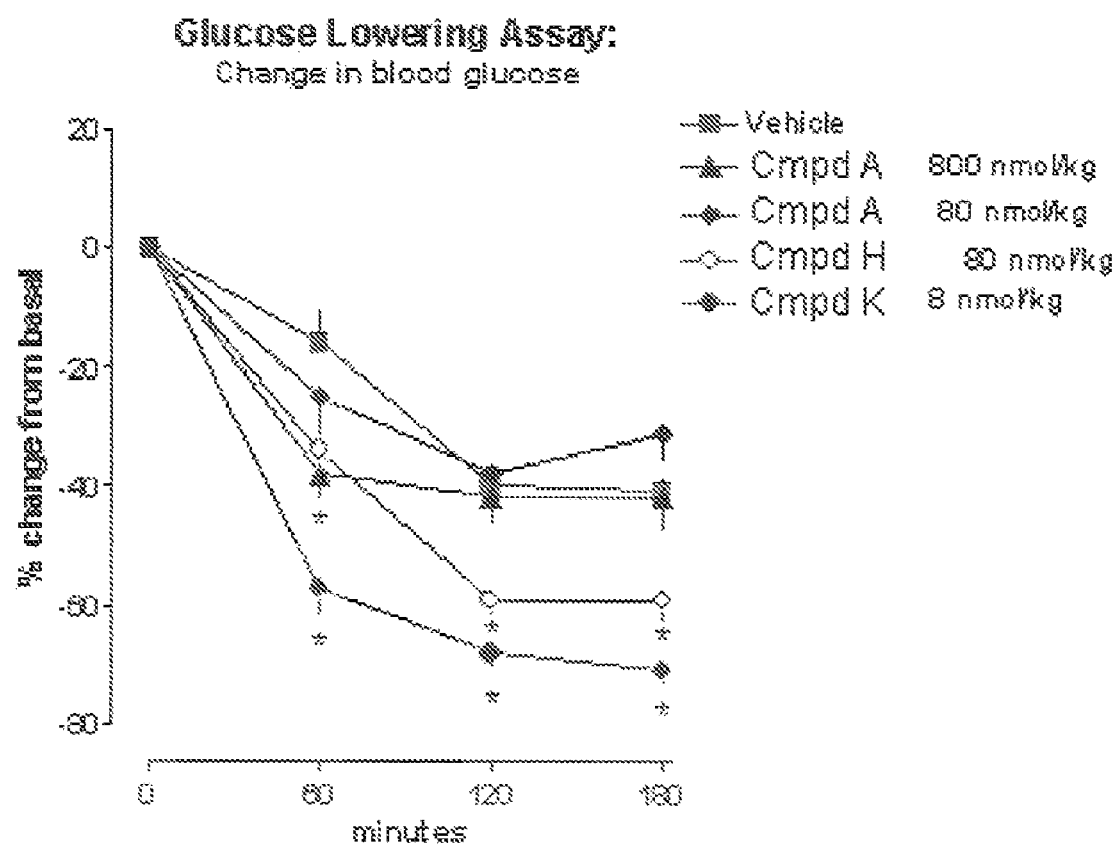
FIG. 4 presents a comparison of the glucose lowering action of Compound G with full length GIP and exendin-4 in diabetic db/db mice. Points represent mean±sem. n=6-10. Peptide was injected IP at t=0 immediately following baseline sample into 2-hour fasted db/db mice. Samples were taken at 60, 120, and 180 min. Blood glucose was measured with a OneTouch® Ultra® (LifeScan, Inc., a Johnson & Johnson Company, Milpitas, Calif.) * p<0.05 vs. vehicle control; ANOVA, Dunnett's test.

Analogs can be and were characterized further to assess their anti-diabetic effects, and in particular, the insulin secretion enhancement (insulinotropic effect) and glucose lowering action. For example, in normal mice Compound G was found to be significantly more efficacious than full length GIP (FIGS. 3A and 3B). As seen in FIG. 4, Compound G shows a pronounced and long-acting effect in lowering glucose in a diabetic mouse model, whereas the action of GIP at a 10 fold higher dose is modest and wanes over time. The glucose lowering profile of Compound G also differs from that of Exendin-4 (Compound K), which has a more rapid onset of action.

Example 6

Enhanced Glucose Lowering Effects of GIP Analogs and Hybrids

Glucose lowering effect in vivo of novel GIP analog or hybrids was determined. FIGS. 8A and 8b provide a result of one such study. Points represent mean±sem. Peptide was injected IP at t=0 immediately following baseline sample into 2-hour fasted NIH/Swiss mice. Samples were taken at t=60, 120, 180 and 240 minutes. Blood glucose was measured with a OneTouch® Ultra® (LifeScan, Inc., a Johnson & Johnson Company, Milpitas, Calif.). *p<0.05 vs. vehicle control; ANOVA, Dunnett's test.

Tested were:

```
                                          (SEQ ID NO: 2)
Compound Number A, human GIP acid form:
YAEGTFISDYSIAMDKIHQQDFVNWLLAQKGKKNDWKHNITQ-OH;

(SEQ ID No. 479)
Compound No. I, D-Ala2 GIP acid form:
Y(D-Ala)EGTFISDYSIAMDKIHQQDFVNWLLAQKGKKNDWKHNIT
Q-OH;
and (SEQ ID NO: 1)
Compound No. G, D-Ala2GIP(1-30)-PSSGAPPPS (SEQ ID No. 186)
amide form:
Y(D-Ala)EGTFISDYSIAMDKIHQQDFVNWLLAQKPSSGAPPPS-NH2.
```

The data demonstrates that a D-alanine substitution at position 2 in the novel GIP analog or hybrids herein improves glucose lowering ability in vivo. Addition of D-Ala even to full length improves glucose lowering compared to unmodified GIP: improved activity is seen in the first hour, but wanes over time. In contrast, a clearly superior and surprising profile is observed when both a protease resistant N-terminus and a Trp-cage C-terminal shield are present. For example, the profile an analog (see Compound G) comprising both aspects shows gradually increasing activity that peaks at t=120 min, and is more sustained than native GIP or its D-Ala2 version.

Figure 9:
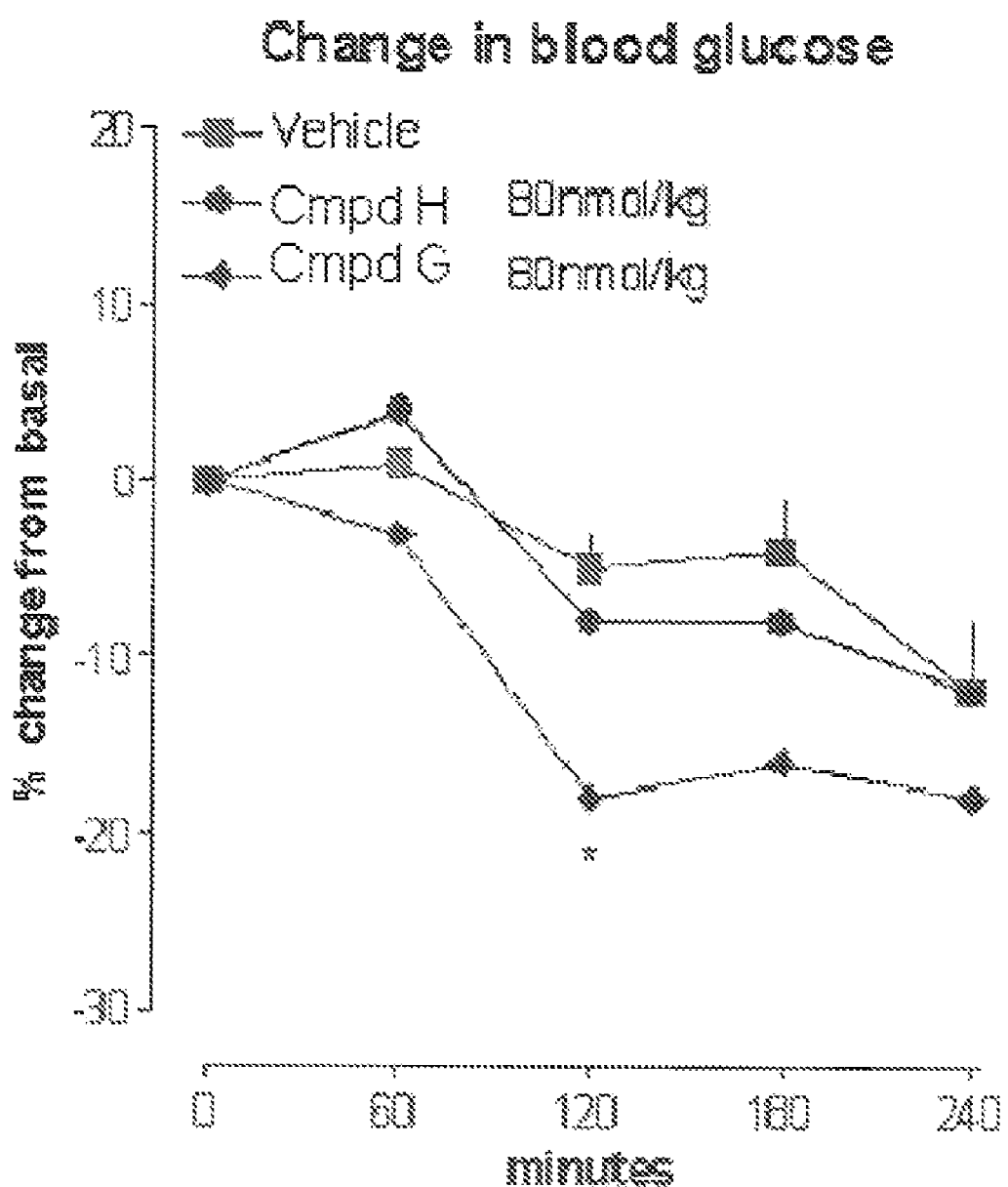
FIG. 9 depicts glucose lowering effect of novel GIP analogs, particularly the effect of a Trp-cage. Points represent mean±sem. Peptide was injected IP at t=0 immediately following baseline sample into 2-hour fasted NIH/Swiss mice. Samples were taken at t=60, 120, 180 and 240 min. Blood glucose was measured with a OneTouch® Ultra® (LifeScan, Inc., a Johnson & Johnson Company, Milpitas, Calif.). *p<0.05 vs. vehicle control; ANOVA, Dunnett's test.

FIG. 9 depicts glucose lowering effect of novel GIP analog or hybrids, particularly the effect of a Trp-cage. Points represent mean±sem. Peptide was injected IP at t=0 immediately following baseline sample into 2-hour fasted NIH/Swiss mice. Samples were taken at t=60, 120, 180 and 240 min. Blood glucose was measured with a OneTouch® Ultra® (LifeScan, Inc., a Johnson & Johnson Company, Milpitas, Calif.). *p<0.05 vs. vehicle control; ANOVA, Dunnett's test.

Tested were:

```

Compound No. H, (D-Ala2)GIP(1-30) amide form:
Y(D-Ala)EGTFISDYSIAMDKIHQQDFVNWLLAQK-NH2;
and
                                         (SEQ ID NO: 1)
Compound No. G, (D-Ala2)GIP(1-30)-PSSGAPPPS
                                       (SEQ ID No. 186)
amide form:
Y(D-Ala)EGTFISDYSIAMDKIHQQDFVNWLLAQKPSSGAPPPS-NH2.
```

The data demonstrates that the presence of a C-terminal Trp-cage sequence provides a significant and surprising benefit to GIP activity, particularly in truncated GIP analog or hybrids.

Figure 10:
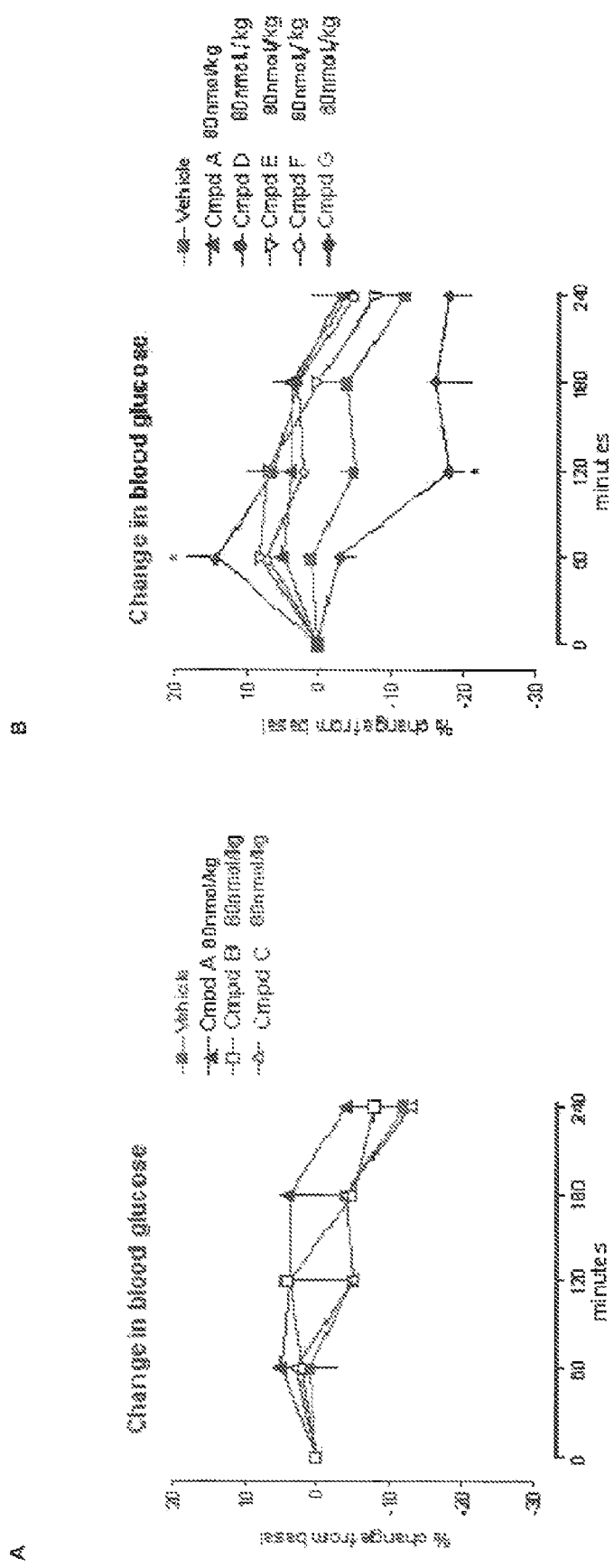
FIGS. 10A and 10B depict glucose lowering effect of various analogs. In this example, Ac modification and a Pro3 substitution did not significantly enhance glucose lowering ability. Points represent mean±sem. Peptide was injected IP at t=0 immediately following baseline sample into 2-hour fasted NIH/Swiss mice. Samples were taken at t=60, 120, 180 and 240 min. Blood glucose was measured with a OneTouch® Ultra® (LifeScan, Inc., a Johnson & Johnson Company, Milpitas, Calif.). *p<0.05 vs. vehicle control; ANOVA, Dunnett's test.

Glucose lowering effect in vivo of various analogs and hybrids was determined and shown in FIGS. 10A and 10B. In this example, Ac modification and a Pro3 substitution did not significantly enhance glucose lowering ability. Points represent mean±sem. Peptide was injected IP at t=0 immediately following baseline sample into 2-hour fasted NIH/Swiss mice. Samples were taken at t=60, 120, 180 and 240 min. Blood glucose was measured with a OneTouch® Ultra® (LifeScan, Inc., a Johnson & Johnson Company, Milpitas, Calif.). *p<0.05 vs. vehicle control; ANOVA, Dunnett's test.

Tested were:

```
                                         (SEQ ID NO: 2)
Cmpd. A, Human GIP acid form:
YAEGTFISDYSIAMDKIHQQDFVNWLLAQKGKKNDWKHNITQ;

(SEQ ID NO: 1)
Cmpd. B: (AcY)(D-Ala)GIP(1-30)-PSSGAPPPS
                                       (SEQ ID No. 455)
amide form:
Ac-Y(DAla)EGTFISDYSIAMDKIHQQDFVNWLLAQKPSSGAPPPS-NH2;

(SEQ ID NO: 290)
Cmpd. C: (Ac-Y)GIP acid form:
AcY-AEGTFISDYSIAMDKIHQQDFVNWLLAQKGKKNDWKHNITQPSSGAPPPS;

(SEQ ID NO: 1)
Cmpd. D, Pro3GIP(1-30)-PSSGAPPPS
                                       (SEQ ID NO: 245)
amide:
YAPGTFISDYSIAMDKIHQQDFVNWLLAQKPSSGAPPPS-NH2;

(SEQ ID NO: 291)
Cmpd E, Pro3GIP(1-42) acid form:
YAPGTFISDYSIAMDKIHQQDFVNWLLAQKGKKNDWKHNITQ;

(SEQ ID NO: 292)
Cmpd F, Pro3GIP(1-30) amide:
YAPGTFISDYSIAMDKIHQQDFVNWLLAQK-NH2;
and
                                         (SEQ ID NO: 1)
Cmpd G, (D-Ala2)GIP(1-30)-PSSGAPPPS
                                       (SEQ ID No. 186)
amide (also referred to as 0601GIP3794):
Y(D-Ala)EGTFISDYSIAMDKIHQQDFVNWLLAQKPSSGAPPPS-NH2.
```

To compare the insulinotropic effect of various GIP analog hybrids in response to an intravenous glucose challenge, GIP analog hybrids were tested in an intra venous glucose tolerance test (IVGTT assay) at 100 pmol/kg/min infusion dose in rats. GIP compounds were selected that displayed significant glucose lowering in vivo. For example, while native GIP displayed no or little activity in basal glucose lowering (basal glucose lowering (% maximal decrease) at 0% and OGTT response of −10%), the analog 0601GIP4042 and the analog hybrids 0601GIP 3794 and 0601GIP 4178 displayed, respectively, a very transient −11%, −20% and delayed onset −20% for basal glucose lowering, and "ND" (not determined), −21% and −20% decrease in the OGTT assay. The delayed onset with 0601GIP 4178 is consistent with the view that it binds to plasma proteins from which it is slowly released.

Duration of action of GIP compounds and hybrids was determined in an IVGTT assay. In the typical IVGTT assays the test sample was administered by IV infusion. The IV infusion of sample was initiated at t=−30 min and continued through t=90. IV glucose was given at t=0. To determine a duration of action using the IVGTT assay, the sample was injected SC as a single injection at one time point indicated (e.g., t=−240, −120, −60 or −30) prior to administration of glucose. IV glucose was given at t=0. Insulin levels were determined at 0-30 minutes as AUC. Exemplary activities in a rat IVGTT duration of action assay system are shown below.

| | Standard IVGTT assay | Duration of action in assay | | | |
|---|---|---|---|---|---|
| Compd # | IV infusion (100 pmol/min/kg) | SC inj T = −30 min | SC inj T = −60 min | SC inj T = −120 min | SC inj T = −240 min |
| Vehicle (saline) | 57 | — | — | — | — |
| Human GIP | 226 | 57 | — | — | — |
| 0601GIP3794 | 249 | 198 | 159 | 204 | 79 |
| 0601GIP4233 | 234 | 115 | — | 69 | — |
| 0601GIP4252 | 218 | — | — | 125 | 63 |

GIP, 0601GIP3794 and 0601GIP4042 (dAla2-GIP(1-42) acid form) produced significant enhancement of the insulinotropic response to an intravenous glucose challenge (IVGTT assay), similar in magnitude to the effects of exenatide and GLP-1 (data not shown). 0601GIP4178 (octylglycine-GIP(1-30)-Exendin-4-(31-39)), showed a diminished insulinotropic response, possibly due to its association with plasma proteins via the octylglycine group, which would however provide a compensating benefit of an even further extended duration of action. GIP, 0601GIP3794 and 0601GIP4178 produced a significant rise in insulin levels prior to the glucose challenge. All three analogs produced a significant lowering of the glucose excursion in response to the glucose challenge (data not shown). As described, fed, isoflurane anesthetized HSD male rats were intubated and cannulated via femoral artery and vein and allowed to stabilize for 1 hour. Following stabilization, an i.v. infusion of saline, GIP, or GIP analog hybrid was started (t=−30). At t=0, an i.v. bolus of 5.7 mmol/kg D-glucose was administered over 2 minutes. Samples for glucose measurement and insulin concentrations were taken at various time points before and after (0 to 90 minutes) glucose infusion.

Additional GIP hybrids that will be active in the IVGTT assay include: 0601GIP4252 [dAla2]GIP-(1-30)-[Octylglycine 34] Exendin-4 (31-39); 0601GIP4285 [dAla2, Leu14, Ala18, glu21] GIP-(1-30)-Exendin-4 (31-39); 0601GIP4233 [dAla2] GIP-(1-30)-fGLP-1v2-(31-37); and 0601GIP4179 [dAla2, Leu14, beta-Ala31, beta-Ala32] GIP-(1-32)-Exendin-4 (31-39).

Also performed were insulin secretion enhancement assays using mouse islet cells. Islet cells were isolated as follows. Mouse islets were isolated with technique described previously (Gotoh M, Maki T, Kiyoizumi T, Satomi S, Monaco A P (1985) An improved method for isolation of mouse pancreatic islets. Transplantation 40(4):437-438). Briefly, 0.35 mg/ml Liberase RI (Roche Applied Science) solution was injected into pancreatic duct and pancreas was digested for 18 min at 37° C. Islets were separated from exocrine tissue using Histopaque-1077 (Sigma-Aldrich, Inc.) discontinuous density gradient centrifugation for 20 min at 900 g. Before insulin secretion experiments, islets were cultured for 2 days in RPMI-1640 (Invitrogen) supplemented with 10% fetal calf serum, 10 mM Hepes, 100 U/ml penicillin, and 100 mg/ml streptomycin at 37° C. with 5% CO2. The insulin secretion in vitro assay was performed as follows. Glucose- and peptide-induced insulin secretion was performed according to previously described method with slight modifications (Tatarkiewicz k, Garcia M, Omer A, Van Schilfgaarde R, Weir G C, De Vos P (2001) C-peptide responses after meal challenge in mice transplanted with microencapsulated rat islets. Diabetologia 44(5):646-53). Before stimulation, islets were washed 3 times and preincubated with RPMI-1640 supplemented with 0.5% BSA and containing 1.67 mM glucose. After 1 hr preincubation, islets were washed again 3 times to remove residual insulin and islets were aliquoted into 24-well plates with culture inserts (Millicell-PCF, Millipore) containing stimulation medium. The static incubation was performed with approx. 10 islets per well in triplicates for 1 hr at 37 degrees C. Stimulatory medium contained 16.7 mM glucose with GIP analogs in doses of 1, 10, 100 nM. At the end of insulin secretion experiment, inserts with islets were removed, media were collected and frozen at −20 degrees C. for insulin ELISA assay (Crystal Chem, Inc.). Acid ethanol was applied for overnight extraction of insulin from remaining islets. Total islet insulin content per well was used to normalize insulin release results.

Example 7

Peptide Stability and Protease Resistance

Figure 11:
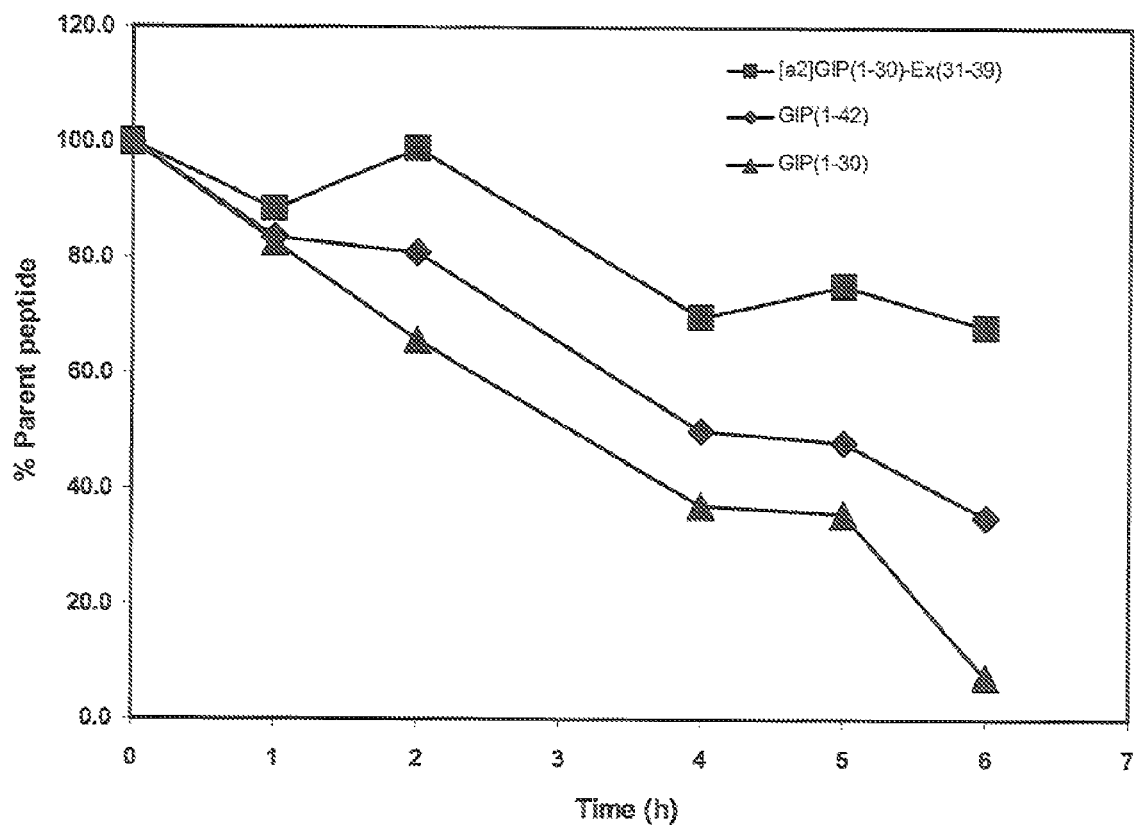
FIG. 11 demonstrates superior protease resistance of an exemplary GIP hybrid, 0601GIP3794 versus a native GIP.

Resistance to proteases was determined according to the protocol of Hupe-Sodmann et al. (Peptides 18(5):625-632 (1997)) using the cell line RINmF5. This well-differentiated cell line is generally accepted as a pancreatic beta-cell model. The indicated GIP compounds (30 μM) were incubated with RINm5F cell membrane extracts at 37° C., and degradation of peptides, in proportion to percentage of the parent peptide was monitored at different intervals for 6 hr using LC-MS. The data (see FIG. 11) indicate that the [DAla2]-GIP(1-30)-PSSGAPPPS GIP hybrid (Compound G (also designated 0601GIP3794); with C-terminally Trp-cage shield (e.g., exendin-4 tail)) is more stable than its parent molecule GIP (1-30) without the shield or the full length GIP(1-42). Accordingly the addition of a Trp-cage shield provides a surprisingly superior protease resistance compared to the absence of the cage or the presence of an alternate non-cage-forming sequence, such as the native GIP C-terminal sequence. Further the data indicates that a GIP(1-30) truncation can accommodate foreign sequences at its C-terminus and, in particular, can accommodate a Trp-cage shield sequence.

Analogs were also tested for stability in human plasma. Briefly, test compounds were dissolved water (or in very dilute DMSO as needed), added to human plasma or human kidney brush border membrane (hKBBM) preparations, incubated for 37° C. for time-points (0, 1, 2, 3, 4, and 5 hrs), extracted with methanol (1:4 ratio), and the supernatant analyze by LC/MS/MS. Typically, the GIP samples were prepared from a stock solution of peptides in water at 1 mg/mL concentration. The plasma stability samples were prepared by spiking a human plasma pool with the stock solution to a final concentration of 20 ug/mL. The hKBBM samples were prepared by adding 5 uL of kidney membrane proteins (at 10 mg/mL) to 650 uL of PBS, and then spiking stock solution of the peptides to a final concentration of 20 ug/mL. After incubation at different time points (0, 1, 2, 3, 4, 5 hrs) at 37 degrees C., 25 uL of each of the samples were diluted 1:4 with an aqueous solution of 1% formic acid using a BioTek™ Precision™ liquid handler. 50 μL of this diluted sample was injected into the Symbiosis Pharma™ system, and online solid phase extraction was performed. A 2 micron filter was used as a pre-column to prevent clogging of the Analytical (PLRPS, 1×20 mm) column. The HPLC pumps, Reliance™ autosampler and on-line solid phase extraction (SPE) were parts of an integrated system (Symbiosis Pharma™, Spark Holland, Inc.) controlled by a driver on the Mass Spectrometer (Analyst™) software. An Applied Biosystems API 4000™ Qtrap mass spectrometer provided MRM detection. The HPLC gradient form 95:5 to 5:95, combined solvent A that consisted of water and solvent B that consisted of acetonitrile, both with 0.05% trifluoroacetic acid (TFA) and 0.005% heptafluorobutyric acid (HFBA). Total analysis time was about 3.6 minutes per sample. A SPE cartridge (Hysphere GP resin, 2.0×4 mm, 10-15 μm) was used for sample extraction. After washing, samples were eluted with methanol for the analytical analysis. The integrated peak areas for the peptides were used to generate the following parameters: 1) normalized area counts for all time points to time zero for all peptides; 2) calculated Area Under the Curves (AUC) for all peptides, and 3) normalized all AUCs to AUC for exendin-4, which is given a value of 100% (the positive control).

In the human plasma stability assays, "stable" was scored as greater than about 90% remaining at 5 hours of treatment to human plasma, "intermediately stable" was scored as greater than about 75% remaining at 2 hours and less than about 90% remaining at 5 hours, and "unstable" was scored as less than about 75% remaining at 2 hours. Unstable analogs and hybrids would generally be unsuited in the methods presented herein. Exemplary compounds were tested. Compounds scored as stable were 0601GIP3794, 0601GIP 4150 and 0601GIP4233. Compounds scored as intermediately stable were 0601GIP4149, 0601GIP4152, 0601GIP4153, 0601GIP4176, 0601GIP4177, 0601GIP4215, 0601GIP4284, and 0601GIP4289. Compounds scored as unstable were 0601GIP154, 0601GIP4147, 0601GIP4292, 0601GIP4293, and 0601GIP4294. GIP Compound 0601GIP4178 which contains an octylglycine, was scored as unstable, however it is DPP-IV resistant, and binds to plasma proteins complicating its extraction and detection; it is nonetheless believed to be a stable compound for the purposes of the methods herein. The GIP analog hybrid 0601GIP3794 and GIP compounds having a C-terminal frog GLP-1 "tail" were surprisingly at least as stable or more stable than exendin-4.

Example 8

Further Exemplary GIP/Amylin-sCT Hybrids

Further exemplary GIP phybrids, amide forms, were prepared. (As used herein, lower case single amino acid code indicates a "D" amino acid. For example, YaE indicates a D-Alanine in position 2.)

The compounds were tested for receptor binding as described herein:

| Cmpd# | GIP RBA | GLP RBA | CT RBA (C1A) | AMY RBA | CGRP RBA | Cyclase |
|---|---|---|---|---|---|---|
| 3 | 0.10 | 448 | 0.15 | 0.20 | 108 | 199 |
| 4 | 0.13 | 664 | 0.12 | 0.30 | 110 | 215 |
| 10 | Nd | nd | 0.03 | 0.03 | 2.30 | 1.40 |
| 1 | 3.8 | 1000 | nd | nd | nd | 519 |

The hybrids effectively and selectively bound and activated the relevant receptors.

The compounds were also assayed in for food intake inhibition, lowering of blood glucose assay and Oral Glucose Tolerance Test (OGTT) as described herein. In the food intake assays (FIGS. 13A, 14, 15 and 16A-16B) points represent mean+/−sd of n=4 cages (3 mice/cage). Peptide was injected IP at t=0. Food was introduced immediately after injection and amount consumed measured at t=30, 60, 120, and 180 minutes. *p<0.05 versus vehicle control; ANOVA, Dunnett's test.

Figure 13A:
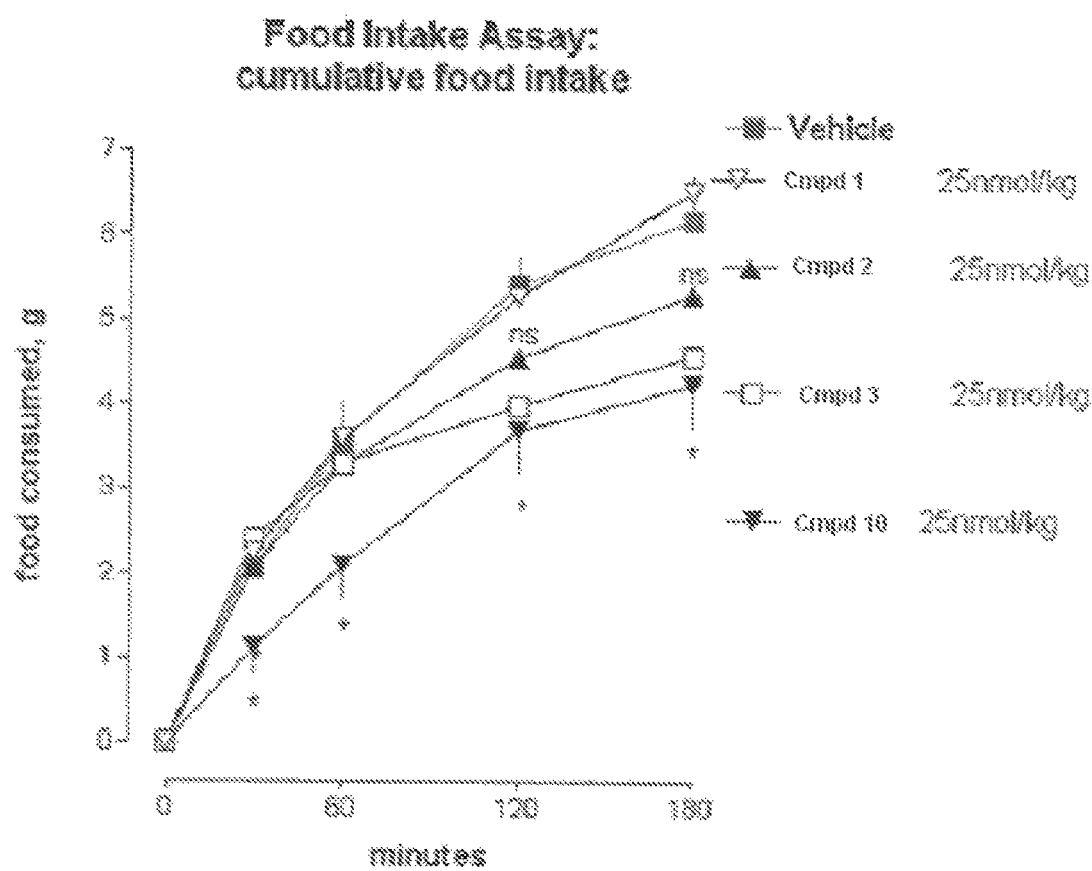
FIGS. 13A and 13B demonstrate food intake inhibition and lowering of blood glucose by GIP hybrids.
Figure 13B:
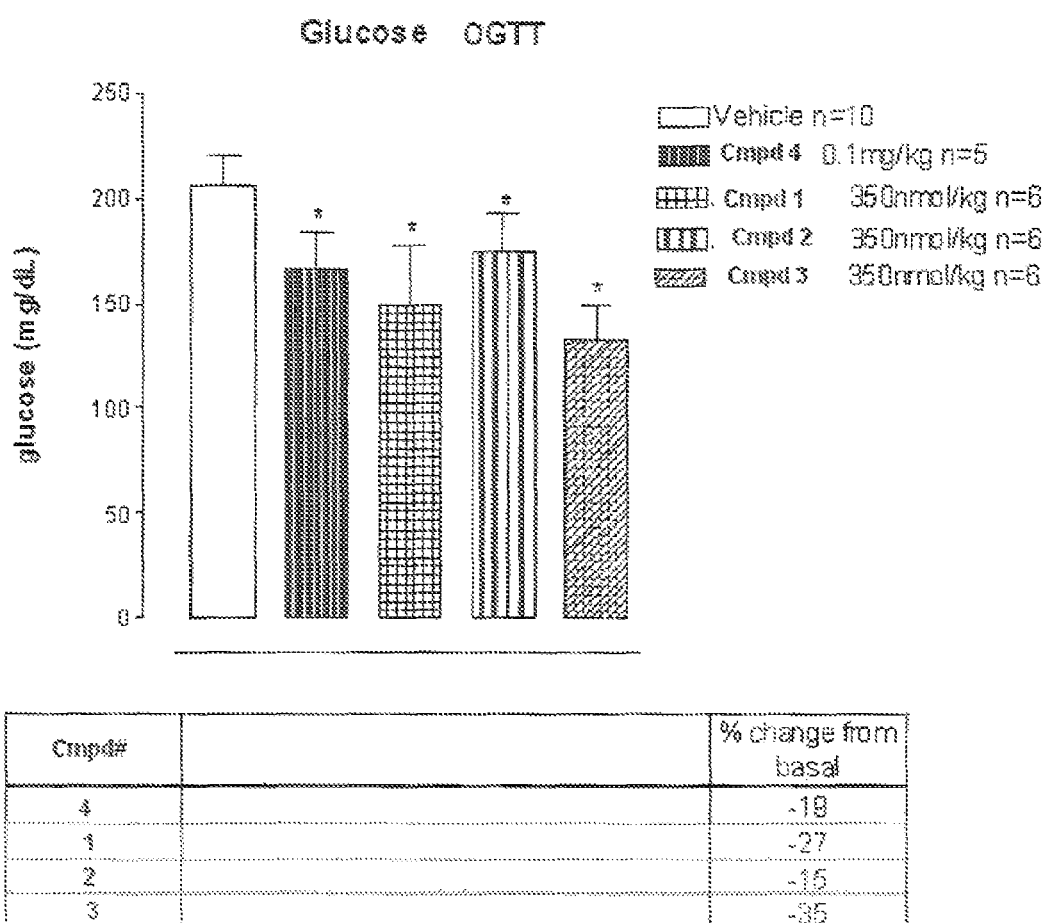
Figure 14:
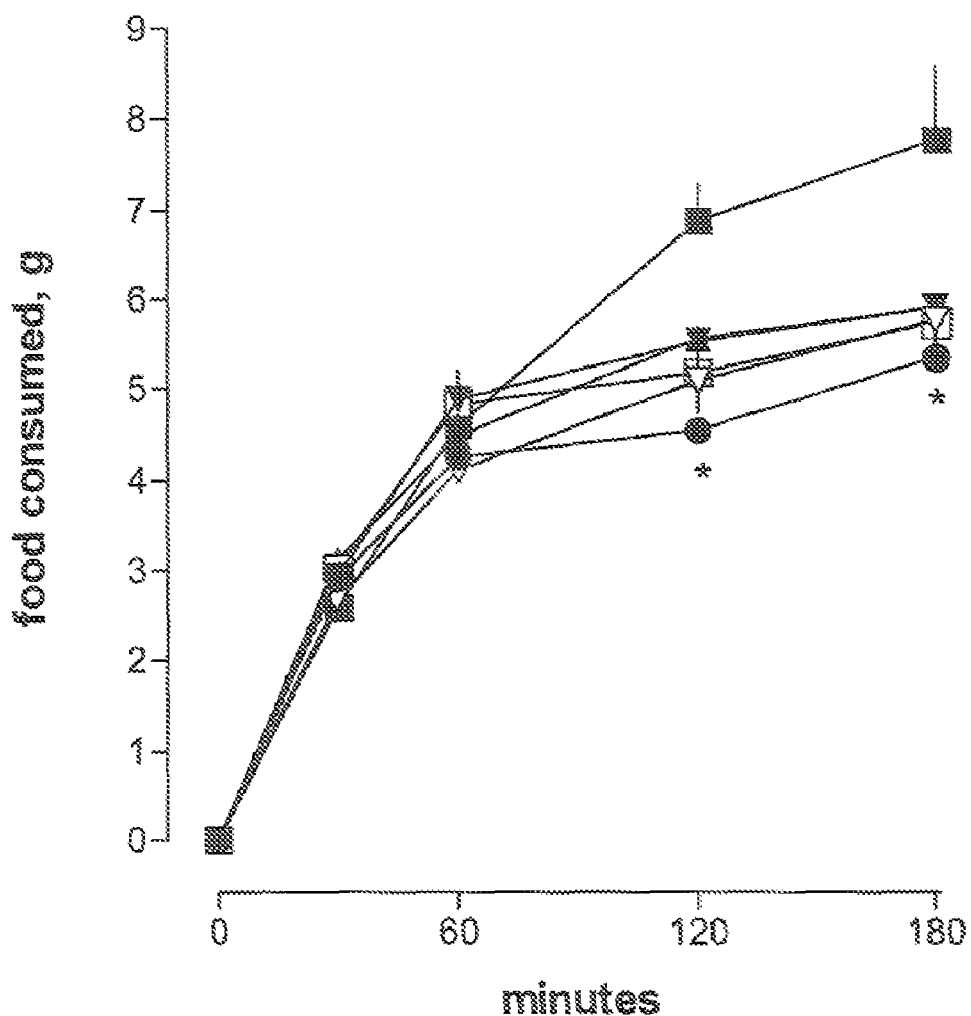
FIG. 14. Effect of GIP hybrids in food intake assay.
Figure 15:
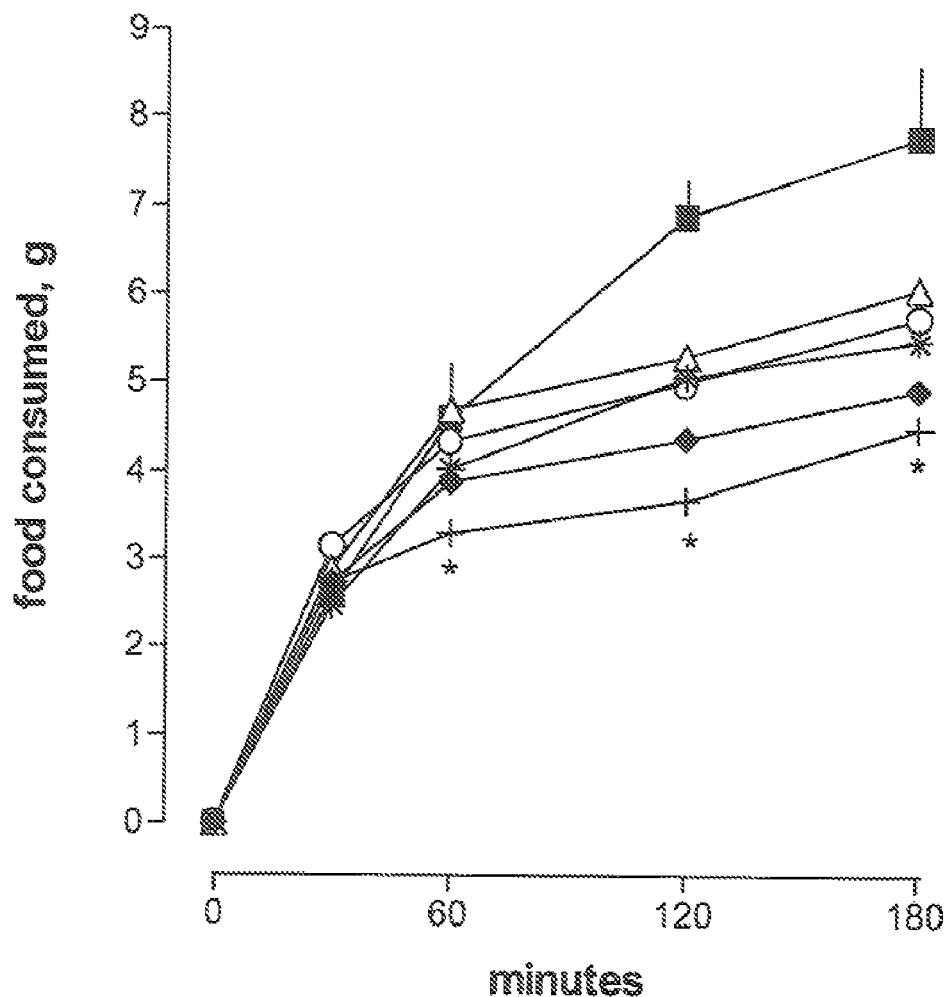
FIG. 15. Effect of GIP hybrid in food intake assay.
Figure 16A:
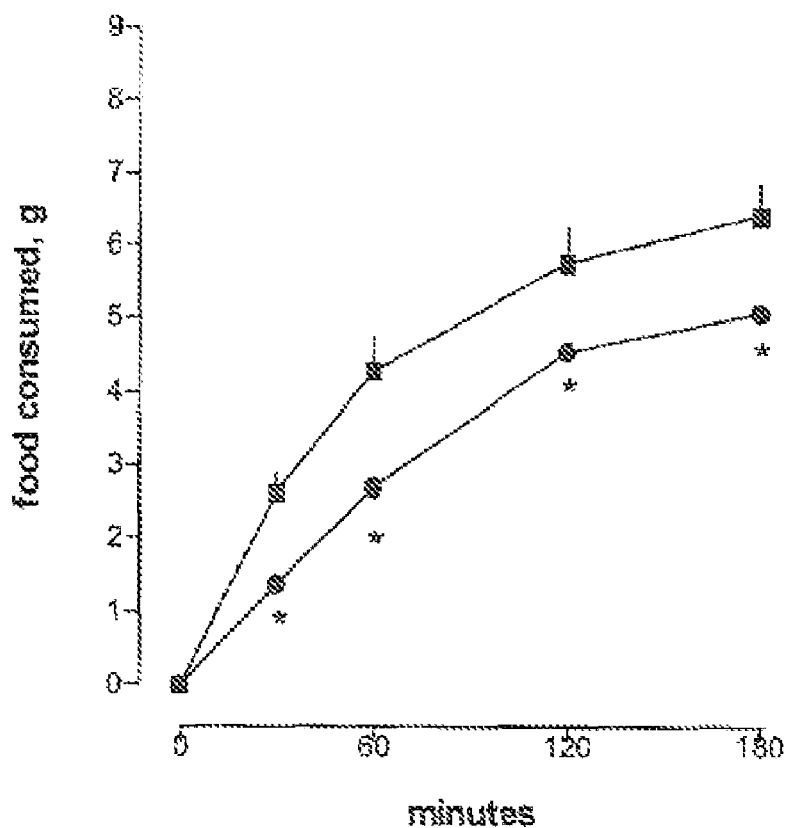
FIGS. 16A and 16B demonstrate effect of Compound 10 (also known as AC2307) (FIG. 16A) and sCT (FIG. 16B) in food intake assay.
Figure 16B:
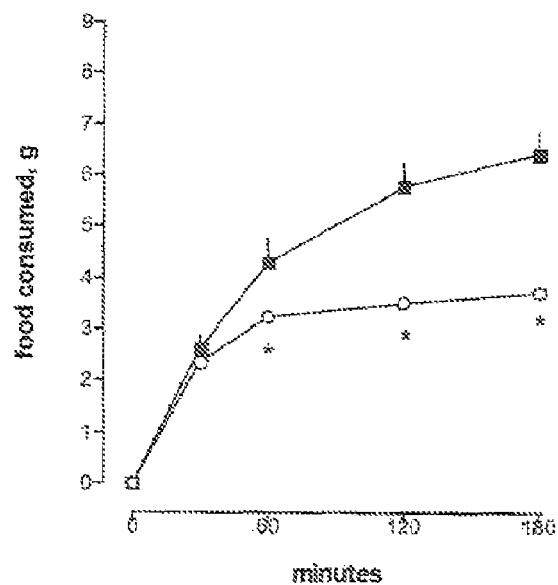
Figure 17:
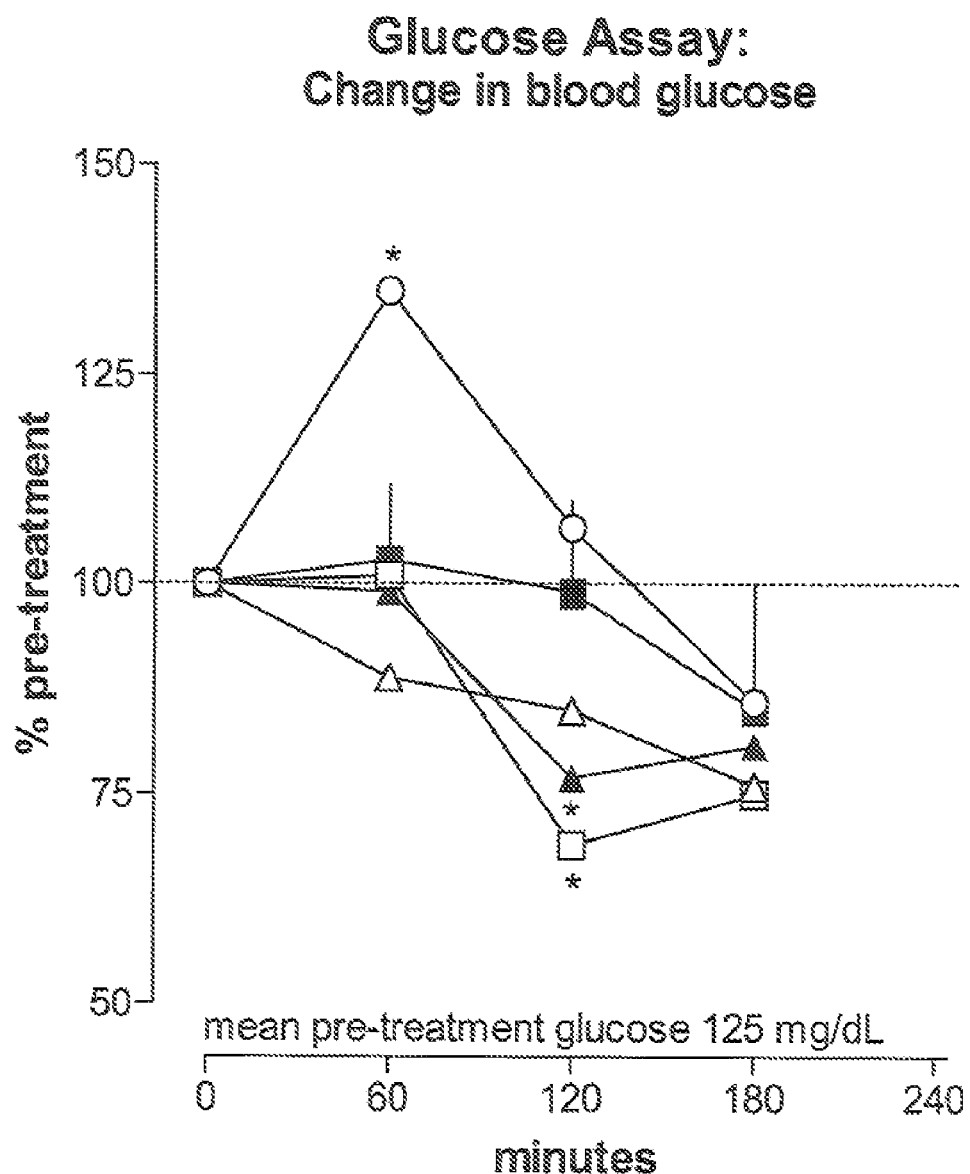
FIG. 17 demonstrates effect of GIP hybrids on lowering of blood glucose.
Figure 23A:
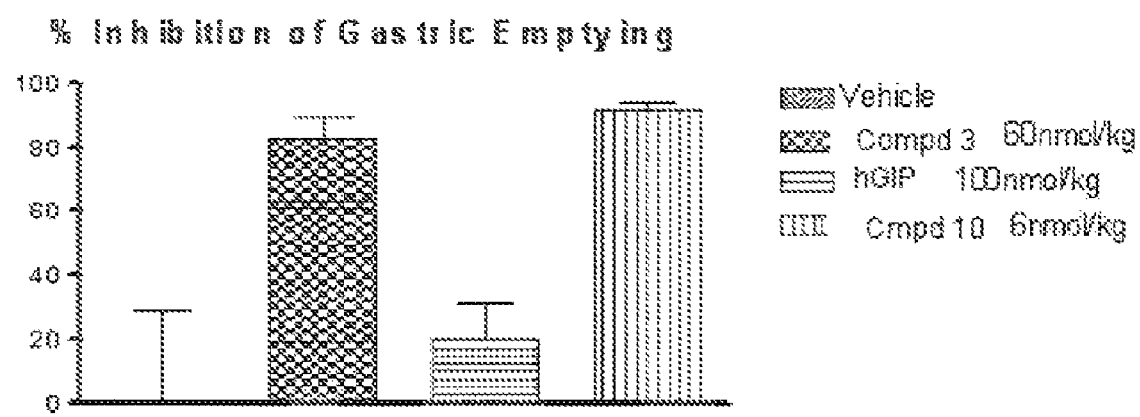
FIGS. 23A and B depict beneficial activity of a GIP-amylin/sCT/amylin hybrid in slowing of gastric emptying and reducing intracellular calcium levels.
Figure 23B:
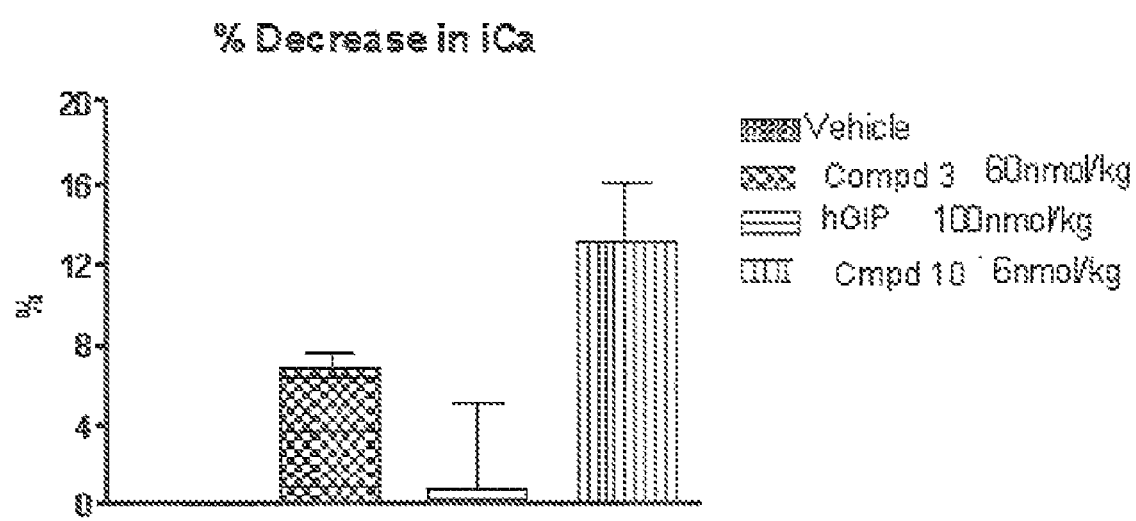
Figure 25:
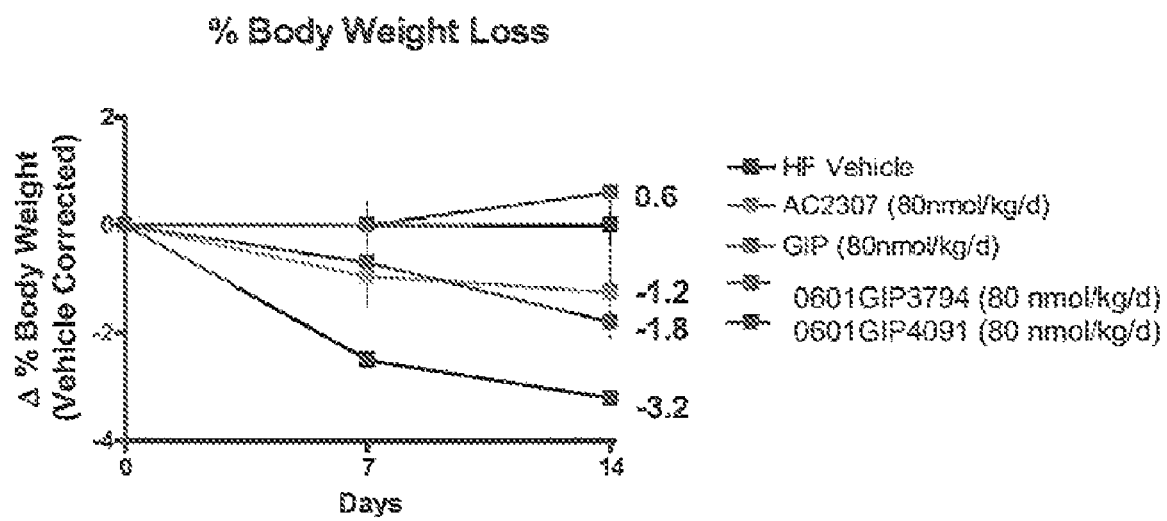
FIG. 25 depicts the reduction of body weight by GIP-amylin family hybrids of the invention.
Figure 26:
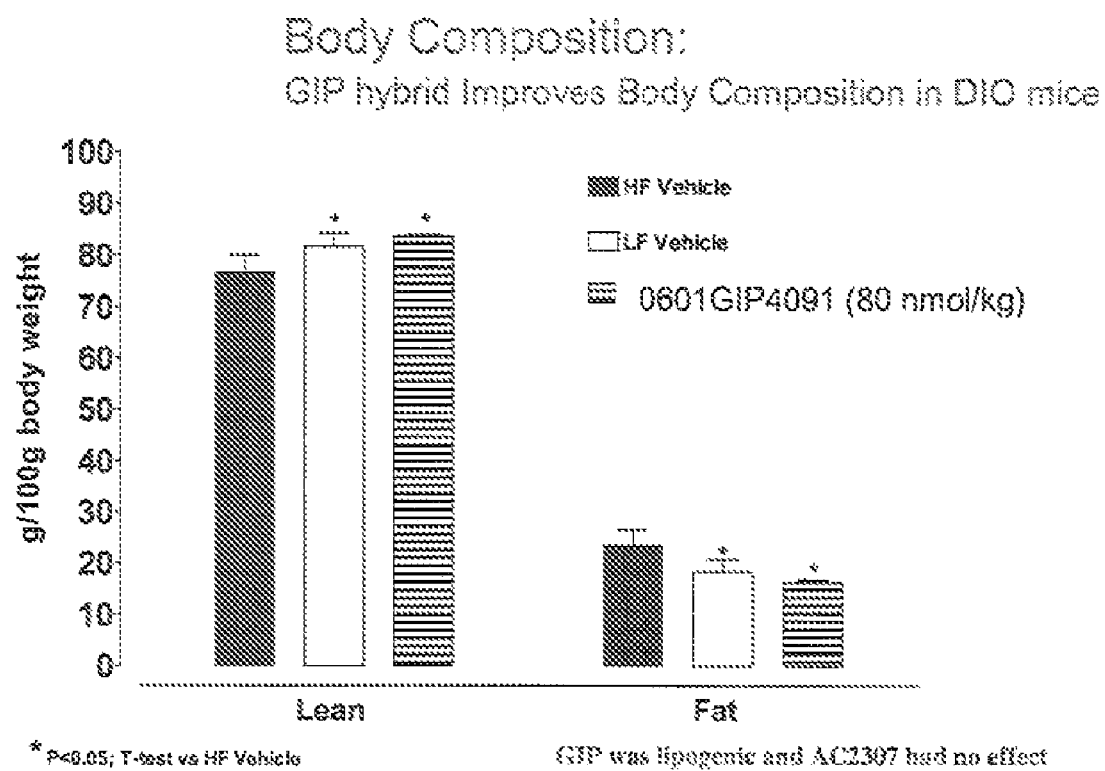
FIG. 26 depicts the improvement of body composition by a lean-sparing, fat reducing activity of by GIP-amylin family hybrids of the invention.

In FIG. 13B bars represent mean+/−sd. Peptide was injected IP at t=−5 minutes into 4-hour fasted NIH/Swiss female mice. Gavage (1.5 g/kg) was given at t=0, Sample was taken at t=30 minutes. *p<0.05 versus vehicle control; ANOVA, Dunnett's test. In FIG. 17 points represent mean+/−sem. Peptide was injected IP at t=) immediately following baseline sample into 2-hour fasted NIH/Swiss mice. Samples were taken at t=60, t=120 and t=180. Blood glucose was measured with a ONETOUCH ULTRA (LifeScan, Inc., Milpitas Calif.). *p<0.05 versus vehicle control; ANOVA, Dunnett's test. As shown in FIGS. 23A and 23B the GIP-amylin/sCT/amylin hybrid slows gastric emptying and reduces intracellular calcium, which are hallmarks of an amylin family hormone module. Thus these GIP hybrid compounds combine the insulinotropic action (and other actions) of a GIP

| SEQ ID No: | Cmpd# | Description | Sequence |
|---|---|---|---|
| 186 | 1 | GIP(1-30)dAla$^2$-exendin4(31-39) | YAEGTFISDYSIAMDKIHQQDFVNWLLAQKPSSGAPPPS |
| 480 | 2 | GIP(1-30)dAla$^2$-miniPEG(8)-hAmylin(1-7)-$^{11,18}$Arg-sCT(8-27)-Amylin(33-37) | YaEGTFISDYSIAMDKIHQQDFVNWLLAQK-miniPEG(8)-K(CNTATC)VLGRLSQELHRLQTYPRTNTGSNTY-NH2 |
| 481 | 3 | GIP(1-30)dAla$^2$-Ala-bAla-hAmylin(1-7)-$^{11,18}$Arg-sCT(8-27)-Amylin(33-37) | YaEGTFISDYSIAMDKIHQQDFVNWLLAQK-bAla-bAla-K(CNTATC)VLGRLSQELHRLQTYPRTNTGSNTY-NH2 |
| 51 | 4 | GLP(7-36) | HAEGTFTSDVSSYLEGQAALEFIAWLVKGR |
| 95 | 10 | hAmylin(1-7)-$^{11,18}$Arg-sCT(8-27)-Amylin(33-37) | KCNTATCVLGRLSQELHRLQTYPRTNTGSNTY-NH2 |
| 482 | | GIP(1-30)dAla$^2$-GlyGlyGly-hAmylin(1-7)-$^{11,18}$Arg-sCT(8-27)-Amylin(33-37) | YaEGTFISDYSIAMDKIHQQDFVNWLLAQK-Gly-Gly-Gly-K(CNTATC)VLGRLSQELHRLQTYPRTNTGSNTY-NH2 | analog with a gastric emptying effect or beneficial calcium modulation effect (e.g. as for bone density maintenance) of an amylin mimetic. In one embodiment for each of these GIP hybrids a Gly linker is used, e.g. GlyGlyGly. While the amylin-sCT-amylin chimera did not lower blood glucose compared to vehicle, the GIP hybrids containing the amylin-sCT-amylin chimera effectively lowered blood glucose. Exemplary compounds of GIP and an amylin family module with this activity include 0601GIP4090 and 0601GIP4091. Compared to the parent compounds these compounds displayed the following properties:

|  | GIP | Amylin-sCT-amylin chimera | Hybrid |
| --- | --- | --- | --- |
| Food Intake | not active | active | active |
| OGTT | decreases | increases | decreases |
| Glucose mice | weak | increases | decreases |
| Glucose rats | not active | increases | not active |
| Gastric Emptying | not active | active | active |
| iCa | not active | active | active |
| BWt (mDIO) | not active | not active | active |
| Body Comp (mDIO) | No effect on lean mass | not active | improves |
| Heart Rate (rat) | increases | increases | increases |
| MAP (rat) | not active | not active | not active |

GIP hybrids bind and activate desired receptors as well as display in vivo properties consistent with the selected properties of the GIP hybrid. This is further shown below. Column RBA1 indicates "GIP RBA(RIN) or (% Inh10 nM, GIP-LF)"; column A1 indicates "AUC Change in Insulin Pre IVGTT"; column A2 the "AUC Change in Insulin Post IVGTT"; column B1 "Basal Glucose Lowering 80 nmol/Kg"; column IV1 the "IVGTT activity compared to 0601GIP3794"; column C1 the "GLP/GIP/CT CYCLASE(RIN) V.2 activity"

digestion buffer (Cellutron D1 buffer) to dissociate cells. For 15 rat hearts, 8 digestions with 6 mls of buffer (Cellutron D2 buffer) were sufficient. The resuspended cells incubated in buffer (Cellutron D3 buffer) for sufficient time to allow optimal dispersion and minimize the need for pipetting to break up clumps. Cells released from the first 2 digestions were discarded since a significant portion of these is red blood cells. Resuspended cells were filtered and allowed to pre-plate for 1 hour on plastic in an incubator in NS media (Cellutron, NJ) in order to remove fibroblasts. After 1 hour of pre-plating, floating cells are removed and the flask rinsed with NS media. The floating cells and the cells in the rinse media were combined and counted. Residual red blood cells, which are smaller that the cardiac myocytes, were not counted.

Cell Plating. At Day 0 of an experiment, the cells were isolated and plated in NS media at 8,000/384 well, 50,000/96 well or 500,000/12 well for 24 hours. At Day 1, the NS media was replaced with fresh NS media. It was observed that the recommended NW (Cellutron, NJ) media did not typically support adequate cell growth or morphology.

cAMP Assay. GIP compounds were tested for cAMP induction on the isolated, cultured cardiomyocytes. Test-compound induced cAMP levels were determined using a commercially available CisBio (Bedford Mass.) HRTF® (homogeneous time-resolved fluorescence) cAMP dynamic assay in a Gs/Gi 384-well adherent format, essentially as described by the manufacture (see also Gabriel et al., High throughput screening technologies for direct cyclic AMP measurement, Assay & Drug Dev. Technol. 2:291-303 (2003) and Cenni et al., HTRF® cyclic AMP assay: new optimized cell-based assay for better investigation of Gi coupled receptors, in Smart assays for screening, IIR Congress, Zurich (CH) (2003)). Dose response was determined.

For Gs assays the positive control was 10 uM forskolin and negative control was buffer. For Gi assays the positive control

| Cmpd# | RBA1 | OGTT/ GL (%) 350 nmol/Kg | B1 | A1 | A2 | IV1 | C1 | GLP RBA | CT cyclase | CGRP RBA | CT RBA |
| --- | --- | --- | --- | --- | --- | --- | --- | --- | --- | --- | --- |
| 0601GIP4091 | 0.1 | −35 | −9%, AUC 180 | 31.8 +− 5.8 | 153.2 +− 9.9 | < | 199 | 448 | 40 | 108 | 0.15 |
| 0601GIP4090 | 0.13 | −15 | −13%, AUC 180 | | | | 215 | 664 | 57 | 110 | 0.12 |
| 0601GIP4501 | | | | | | | | 332 | | 21.3 | |

Example 9

Direct Action of GIP Compounds on Cardiomyocytes

Cyclic AMP (adenosine 3',5'-cyclic monophosphate) is a key second messenger in the G-Protein Coupled Receptor (GPCR) signaling pathway. The binding of a ligand to the receptor leads to G protein activation which in turns regulates Adenylyl Cyclase, the enzyme responsible for modulating intracellular levels of cAMP. Measurement of cAMP levels is widely used as an indicator of receptor function. Activation of cardiomyocyte Gs- and Gi-coupled receptors was determined as a measure of cAMP production.

Figure 18A:
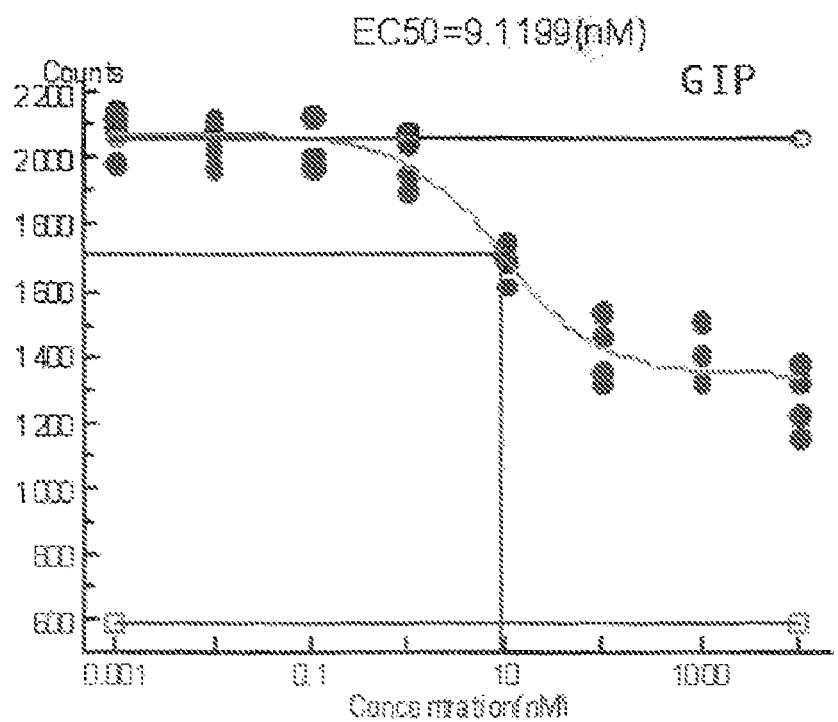
FIGS. 18A and 18B depict cAMP production in whole cardiomyocytes from receptor activation in response to varying doses of test compound, human GIP(1-42) free acid form (FIG. 18A) and GIP hybrid compound G (FIG. 18B).
Figure 18B:
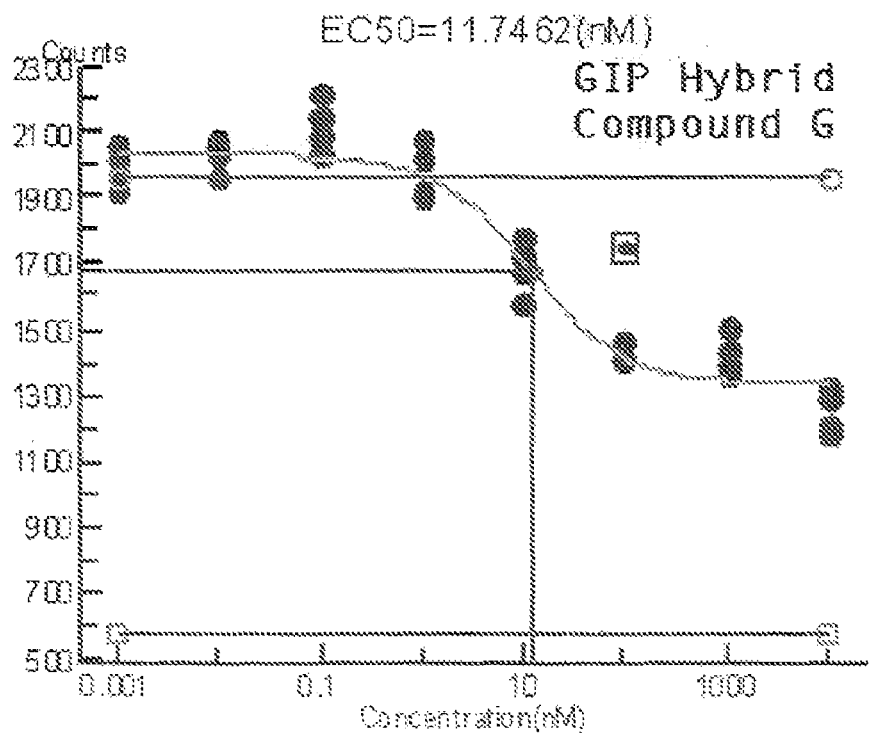

Cell Isolation. Neonatal cardiomyocytes were isolated using a commercially available system. The Cellutron Isolation kit (nc-6031) (Cellutron, NJ) and protocol was used for cell isolation. Sprague Dawley neonatal rats (1-2 days old) were decapitated and the beating heart dissected out into was buffer and the negative control was 10 uM forskolin. Test compound was incubated with cells for 30 minutes at 37 degrees C. in stimulation buffer ((200 mls contains 198.3 ml 1×HBSS, 1 ml 1M Hepes, 670 ul 30% BSA titrated to pH 7.4 with 1M NaOH). To measure cAMP produced, cells were lysed and cAMP assayed according to the manufacturers protocol. Exemplary results are shown in FIGS. 18A (GIP: human GIP(1-42) acid form) and 18B (GIP hybrid Compound G). The Y-axis is a ratio of time resolved fluorescence measurements taken at 665 nM divided by measurements taken at 620 nM. In this experiment the EC50 was 11.7 nM for the GIP hybrid and 9.1 nM for GIP. GLP-1 and exendin-4 displayed very low to no significant activity (data not shown). Further, from three independent experiments of cardiomyocyte Gs-coupled receptor activation, the EC50 (nM) was 15.6 for GIP, 0.7 for urocortin and 29.8 for the GIP hybrid Compound G. Urocortin is a known cardiac myocyte Gs-coupled receptor activator used as a positive control. GIP and the GIP hybrid typically gave receptor activation responses greater than 50%. Usdin et al. (Endocrinology 133:2861-2870 (1993)) reported cloning of a rat GIP receptor and its in situ hybridization to RNA in various rat tissues, including the heart, particularly the cardiac endothelium, which was consistent with labeling of the endothelium of major blood vessels. The results indicate that GIP compounds can provide a direct action on the heart.

Example 10

Measurement of Circulatory System Effects in Conscious Rats by Telemetry after Administration of GIP Compounds Male Harlan Sprague Dawley rats housed at 22.8±0.8° C. in a 12:12 hour light:dark cycle were used to study the effects of test compounds on the circulatory system through the use of telemetry. The experiments were performed during the light cycle. Telemetry allows for real-time hemodynamic readings including arterial blood pressure, heart rate and arterial dP/dt, via an implanted radio transmitter in conscious, non-anesthetized, unrestrained rats. In the present Example, rats were injected with either vehicle, 80 nmol/kg GIP (human GIP(1-42) acid form), or 80 nmol/kg of 0601GIP3794 by remote intravenous dosing. Remote intravenous dosing was achieved through in-dwelling vascular access ports (Access Technologies (Skokie, Ill.). The port is secured to the underlying muscle just below the skin between the scapulae. The catheter resides in the jugular vein. Data were collected for up to 60 minutes following injection.

Figure 19A:
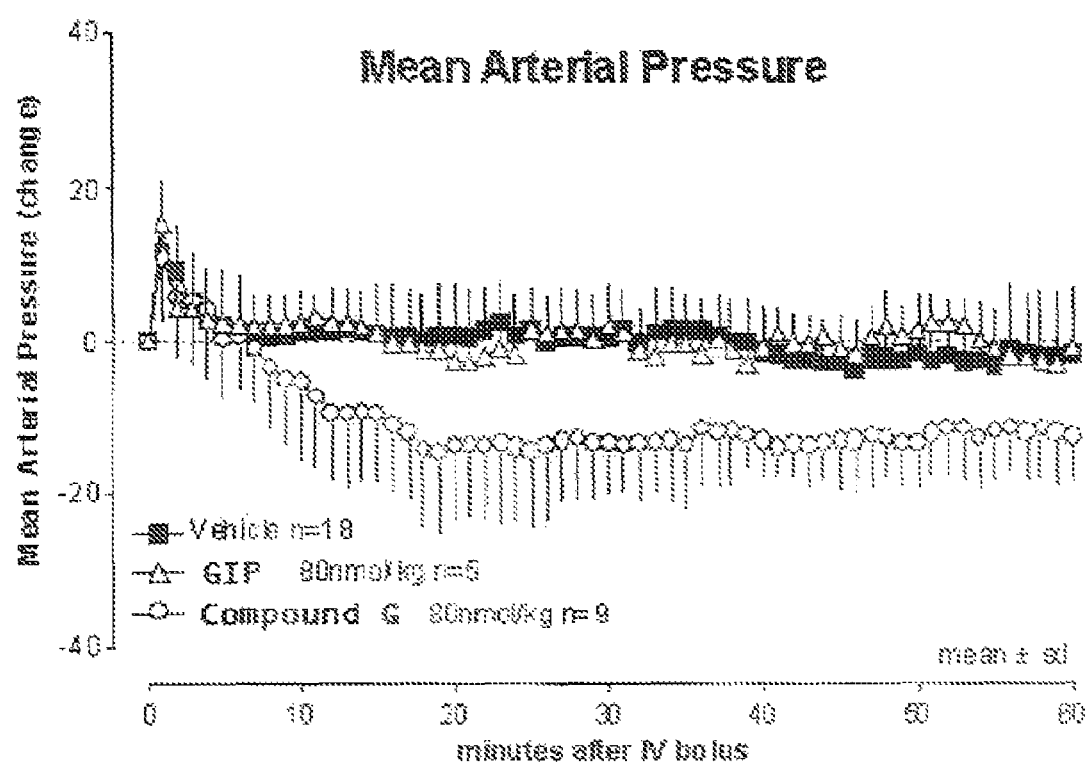
FIGS. 19A to 19E depict the response of mean arterial pressure (FIG. 19A), heart rate (FIG. 19B), and rate of change in blood pressure (dP/dt, FIG. 19C), systolic pressure (FIG.
Figure 19B:
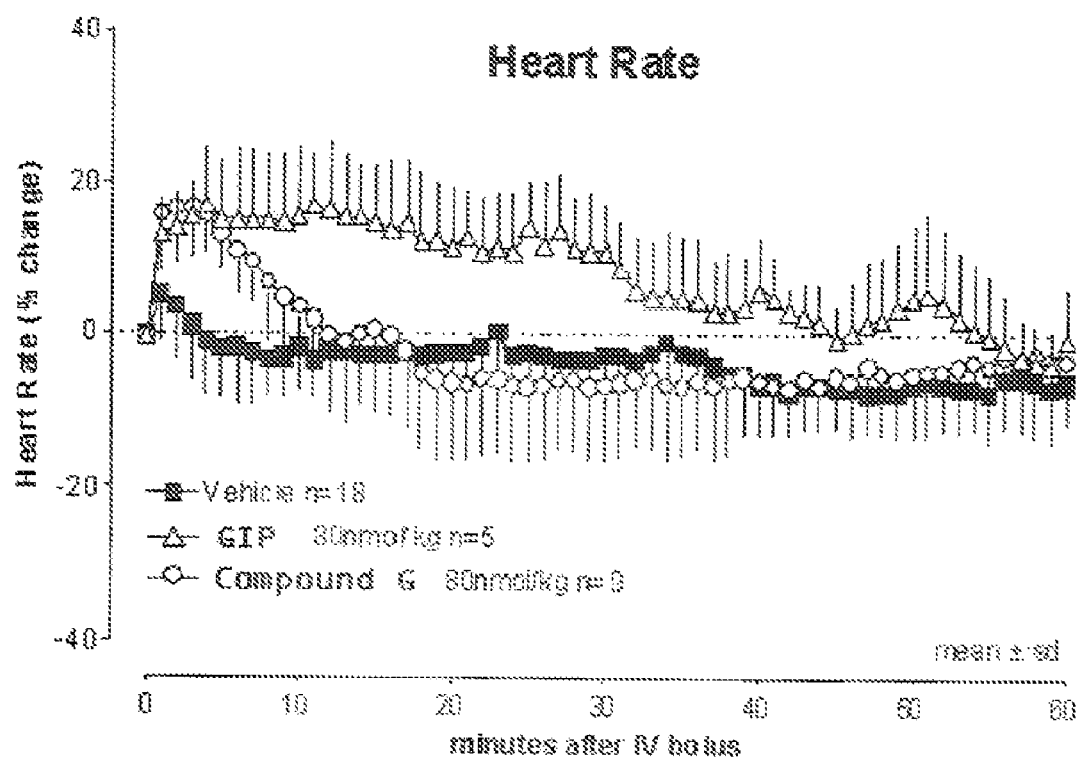
Figure 19C:
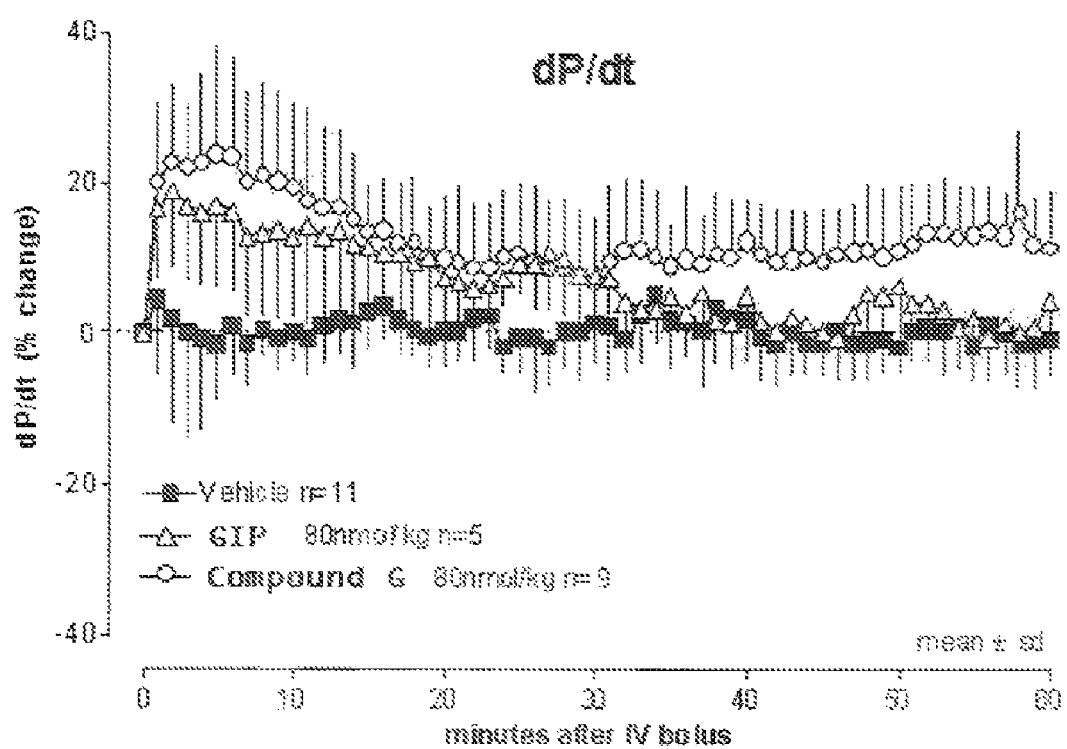
Figure 19D:
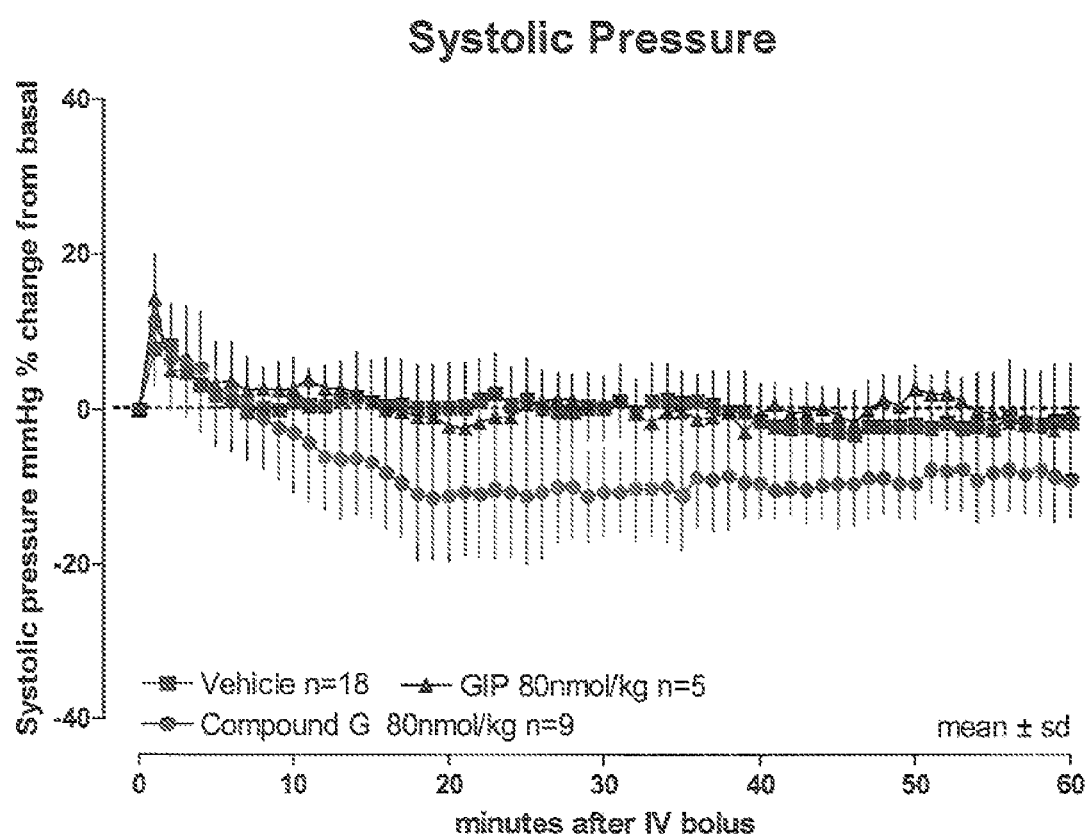
Figure 19E:
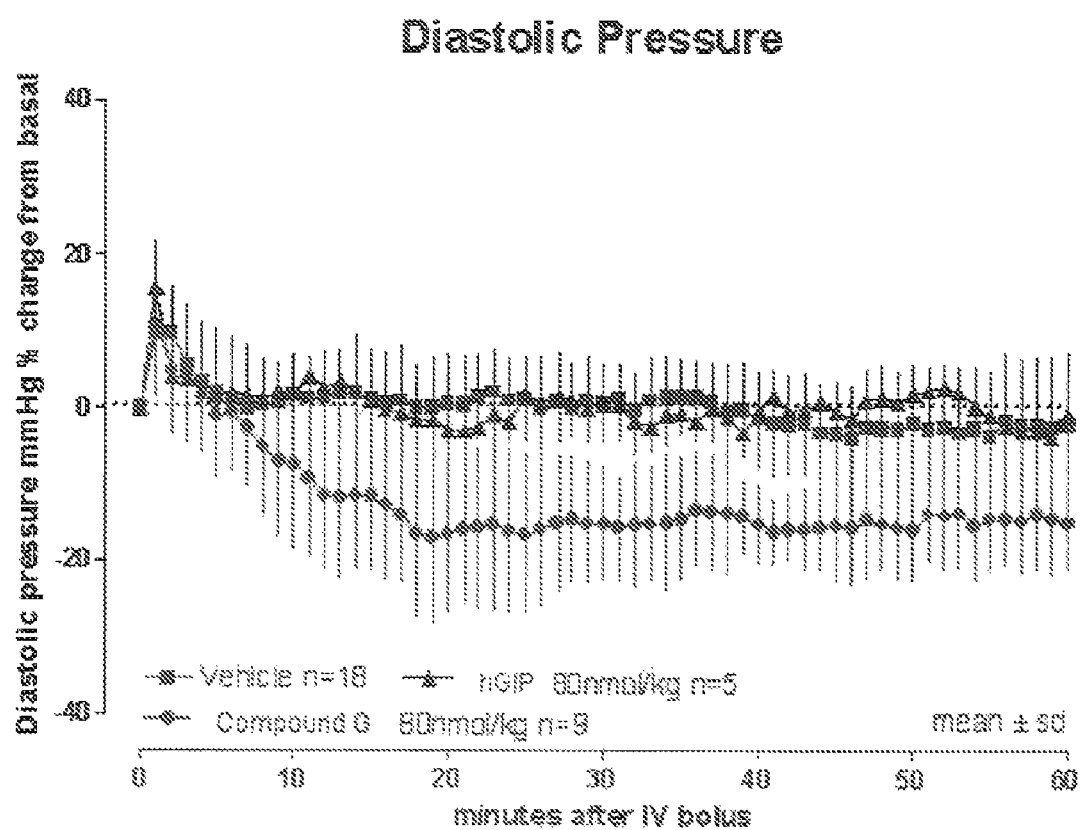

As shown in FIGS. 19A-E the effect of the GIP hybrid to increase heart rate was transient relative to GIP (human GIP (1-42) acid form) (FIG. 19B), that that the GIP hybrid decreased mean arterial pressure while GIP had no effect (FIG. 19A), and that both compounds increased dP/dt similarly (FIG. 19C). FIGS. 19D and 19E demonstrate that the GIP hybrid provides a sustained lowering of systolic and diastolic pressures compared to either vehicle or GIP. Hybrid 0601GIP4091 had a beneficial effect on these cardiovascular parameters, similar to that of GIP and the amylin-sCT-amylin chimera Compound 10 (also referred to AC2307).

From the data it can be seen that GIP displays a positive inotropic effect in intact rats without elevating arterial pressure. GIP also displayed a chronotropic (heart rate elevating) effect. The GIP hybrid displayed a prolonged inotropic effect (shown here as peak rate of increase in arterial pressure; dP/dt), compared to GIP, without causing cardiac acceleration, and invoked a decrease in arterial pressure. Accordingly, GIP hybrids can display vasodilation and perfusion benefits that are not associated with an increase in cardiac work. In addition the sustained lowering of either systolic pressure or diastolic pressure, including both, is a recognized beneficial cardiovascular effect linked to reducing hypertension and cardiovascular-associated morbidity and mortality events.

Example 11

Lack of Effect of GIP on Weight Loss

Figure 20A:
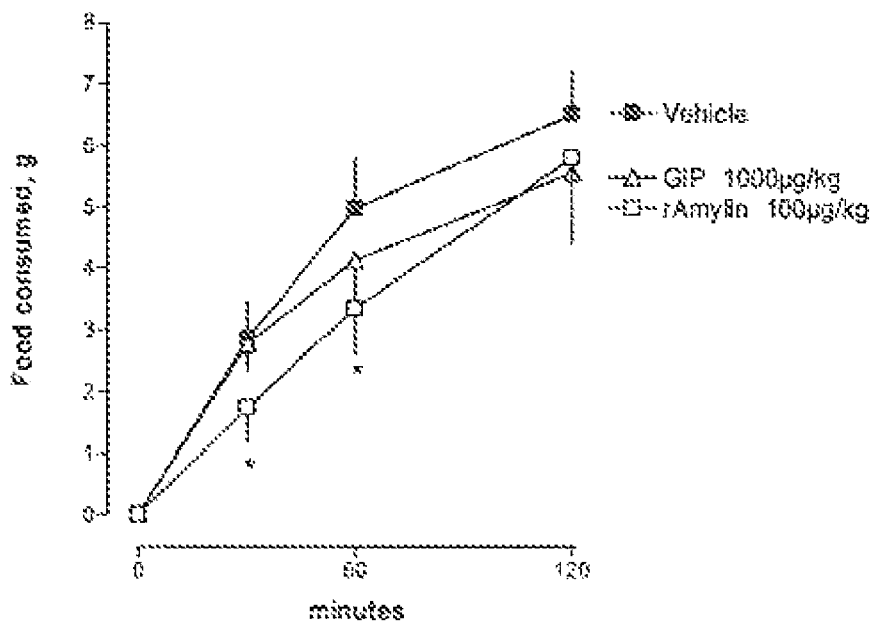
FIGS. 20A, 20B and 20C depict the lack an acute effect of GIP(1-42) and a GIP DPP-IV-resistant-analog/exendin-tail hybrid on food intake in contrast to exendin-4. The pancreatic hormone amylin produced a significant effect as expected.
Figure 20B:
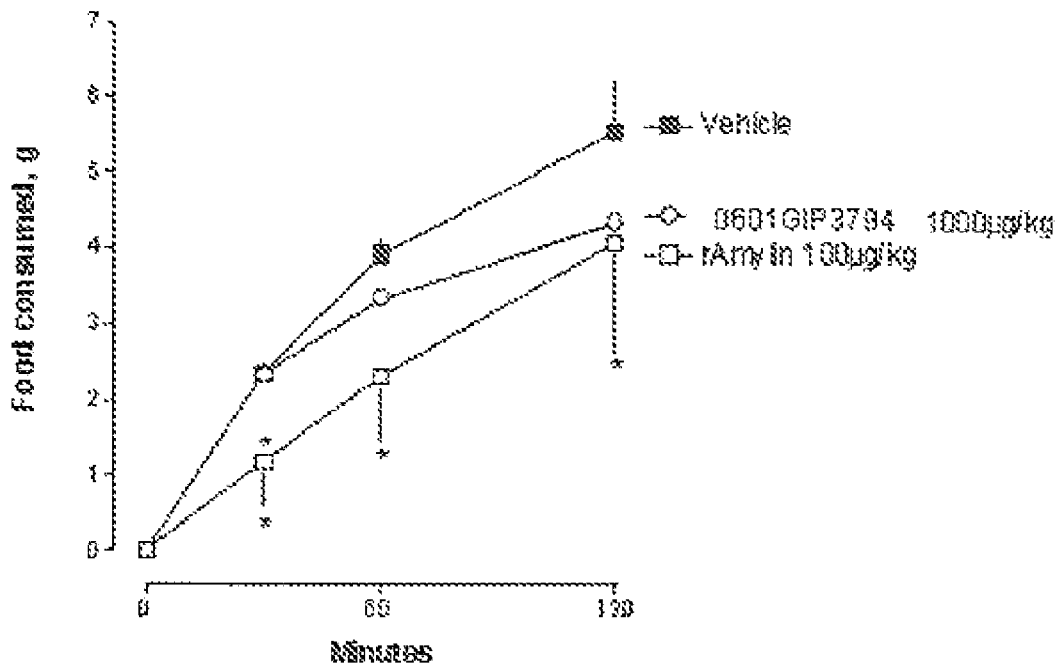
Figure 20C:
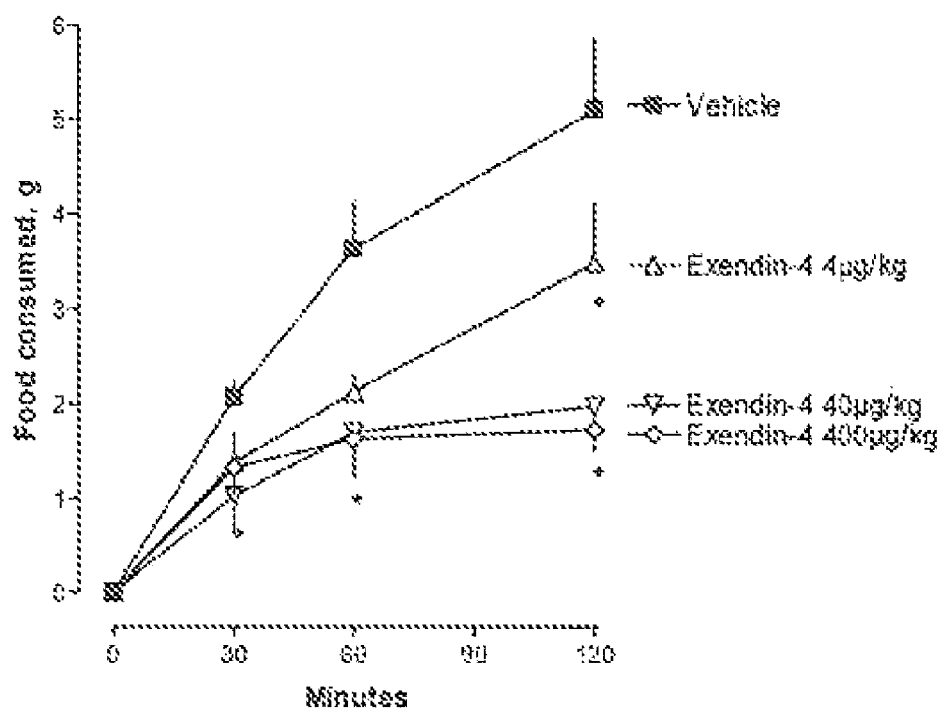

The effect of GIP(1-42) and a GIP DPP-IV resistant analog/exendin tail hybrid (0601GIP3794) were tested for effect on food intake and on weight loss in DIO mice as described herein. As shown in FIG. 20A, it was observed that GIP did not acutely inhibit food intake in mice. In comparison, rat amylin at one tenth the dose caused a significant decrease in food intake within 30 min, relative to control. A trend for GIP to decrease food intake at later time points (60, 120 min) may have been an indirect effect due to its stimulation of amylin secretion. Points represent mean±sd of n=4 cages (3 mice/cage). Peptide was injected IP at t=0. Food was introduced immediately after injection and amount consumed measured at t=30, 60, and 120 min. * p<0.05 vs. vehicle control; ANOVA, Dunnett's test. Similarly the DPP-IV resistant GIP analog hybrid comprising an exendin tail, Compound 0601GIP3794, did not acutely inhibit food intake as reflected by no difference from vehicle control intake at 30 min (FIG. 20B). As with GIP, a trend for this compound to decrease food intake at later time points (60, 120 min) may have been due to its stimulation of amylin secretion. Points represent mean±sd of n=4 cages (3 mice/cage). Peptide was injected IP at t=0. Food was introduced immediately after injection and amount consumed measured at t=30, 60, and 120 min. * p<0.05 vs. vehicle control; ANOVA, Dunnett's test. In contrast to GIP and GIP agonists, exenatide and GLP 1 agonists directly and acutely inhibit food intake, independent of their effect to stimulate amylin secretion. A reduction in food intake is apparent at the first time point (FIG. 20C). Similarly, effects of GLP-1 and exenatide on gastric emptying and post-prandial glucose profiles have been reported in type 1 diabetic subjects, indicating the effect is not dependent upon the presence of b cells or amylin.

Figure 21:
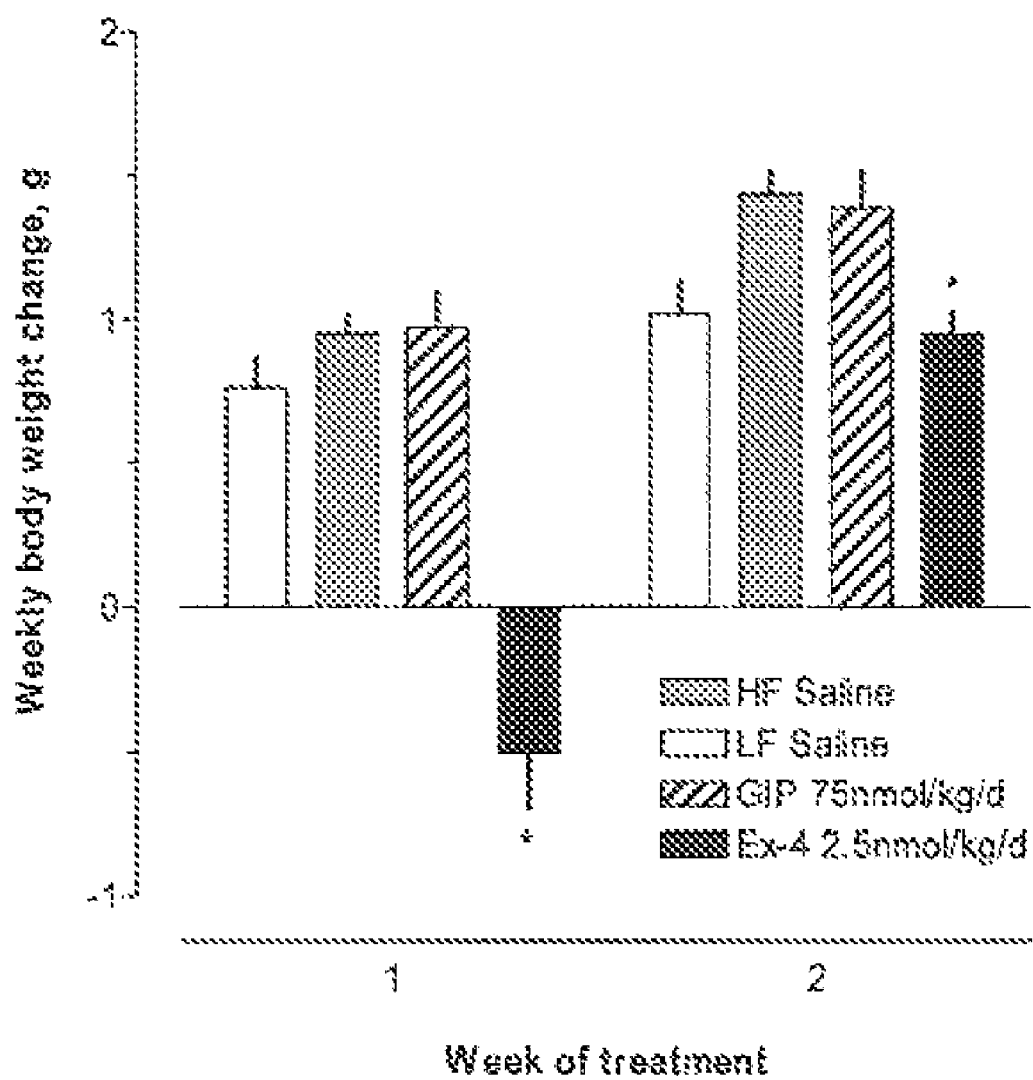
FIG. 21 depicts the lack of effect on weight loss in diet-induced obesity mice, in contrast to the effect of exendin-4.

As shown in FIG. 21, GIP did not cause weight loss in diet-induced-obese mice. In mice in which body weight had been increased by feed a high-fat diet (HF Saline group), GIP infused via min-osmotic pump for 2 weeks had no effect on body weight change. In contrast, exenatide infused at a 30-fold lower rate reduced body weight change to that observed in mice fed a low fat diet (LF group). * P<0.05; ANOVA vs HF Saline. This demonstrates an anti- or non-catabolic effect of GIP. In contrast, it was observed herein that a GIP hybrid having an appropriate choice of a second hormone module, such as an amylin/sCT/amylin chimera, did cause a reduction in food intake and weight loss. Further a GIP hybrid containing an exendin family module also resulted in weight loss. The exendin-GIP hybrid 0601GIP4526 [HGEGTFTSDLSKQMEEEAVR-LFIEWLKN(beta-A)(beta-A)K(#C)-NH2] (SEQ ID NO: 484) [YaEGTFISDYSIAMDKIHQQDFVNWLLAQK(beta-A)(beta-A)K#] (SEQ ID No. 483) in which the two molecules were linked C-terminal to C-terminal displayed reduction of body weight sustained to day 7. This hybrid also reduced food intake in a mouse model. This hybrid bound to and activated both the GIP and the GLP-1 receptor.

Example 12

Solubility and Physical Stability

GIP analogs comprising the modifications described here have surprisingly good solubility (at least about 1 mg/ml or at least about 2.5 mg/ml or even at least about 5 mg/ml) at least several pHs relevant for pharmaceutical formulation, storage and administration, while retaining superior bioactivity, duration of action and/or physical stability, as compared to human GIP or to a parent GIP compound such as 0601GIP3794. The following method can be used to compare solubility and physical and chemical stability at various pHs. The following exemplary pH and buffers can be used: pH 3.0 in 30 mM citrate, pH 4.0 in 30 mM acetate, pH 5.0 in 30 mM acetate, pH 6.0 in 30 mM histidine, pH 7.0 in 30 mM histidine, pH 8.0 in 30 mM phosphate and pH 9.0 in 30 mM borate. Two hundred ml of buffer is added to a vial containing the test peptide to achieve a 10 mg/ml or a 5 mg/ml solution. After vortexing for approximate 30 seconds, the appearance of the solution is observed under a Fiber-Lite. Buffer is continued added in 200 ml aliquots until the total volume of the solution reaches 1000 ml. The appearance of the solution is recorded after each 200 ml of buffer is added. The appearance versus the peptide concentration is recorded as clear, slightly hazy, hazy or cloudy. In one embodiment the GIP analog achieves a clear solution at least 2.5 mg/ml concentration at pH 4-8 or pH 5-7, and further at least 5.0 mg/ml at pH 4-8 or at pH 5-7.

To assess stability at a pH, the solution above is filtered into a 2-mL Schott vial, and equally divided into 3 vials. Each vial is stoppered and tightly sealed. A first vial is incubated at 5° C. for 7 days, the second at 40° C. for 3 days, and the third at 40° C. for 7 days. After incubation, the appearance of all samples is recorded under the Fiber-Lite. If the peptide solution becomes cloudy or precipitated, the solution is filtered prior to HPLC analysis (reverse-phase HPLC method using Vydac C18 column) to determine amount of intact peptide remaining in solution. Alternatively, bioactivity can be measured. Stability is recorded as percent potency loss using the calculation [(% peptide at test day−% peptide at T0 at 5 C)/% peptide at T0 at 5 C] times 100. FIG. 27 presents an exemplary pH versus solubility profile and a pH versus stability profile of 0601GIP5082.

While the present invention has been described in terms of exemplary examples and embodiments, it is understood that variations and modifications will occur to those skilled in the art. Therefore, it is intended that the appended claims cover all such equivalent variations which come within the scope of the invention as claimed.

What is claimed is:

1. A gastric inhibitory peptide (GIP) compound that is a GIP hybrid polypeptide exhibiting at least two hormonal activities, said polypeptide comprising a first bio-active GIP peptide hormone modified for resistance to DPP-IV that exhibits at least one hormonal activity of the human GIP and comprises at least 28 amino acids and has at least 85% sequence identity to the human GIP 1-30 covalently linked to at least one additional bio-active peptide hormone that exhibits at least one hormonal activity of its parent peptide hormone with the proviso that serum albumin is not present, and wherein the GIP compound comprises the sequence of SEQ. ID NO: 481.

2. A gastric inhibitory peptide (GIP) compound that is a GIP hybrid polypeptide exhibiting at least two hormonal activities, said polypeptide comprising a first bio-active GIP peptide hormone modified for resistance to DPP-IV that exhibits at least one hormonal activity of the human GIP and comprises at least 28 amino acids and has at least 85% sequence identity to the human GIP (1-30) covalently linked to at least one additional bio-active peptide hormone that exhibits at least one hormonal activity of its parent peptide hormone with the proviso that serum albumin is not present, wherein the GIP compound comprises the sequence of SEQ. ID. NO: 481 or the pegylated derivative thereof.

3. A gastric inhibitory peptide (GIP) compound that is a GIP hybrid polypeptide exhibiting at least two hormonal activities, said polypeptide comprising a first bio-active GIP peptide hormone modified for resistance to DPP-IV that exhibits at least one hormonal activity of the human GIP and comprises at least 28 amino acids and has at least 85% sequence identity to the human GIP (1-30) covalently linked to at least one additional bio-active peptide hormone that exhibits at least one hormonal activity of its parent peptide hormone with the proviso that serum albumin is not present, wherein the GIP compound comprises the sequence of an analog of SEQ. ID. NO: 481 wherein the analog of sequence of SEQ. ID. NO: 481 has a first bio-active GIP peptide hormone that is at least 30 amino acids long and has at leas 85% sequence identity to the first bio-active GIP peptide hormone of SEQ. ID. NO: 481, or pegylated derivatives thereof.

* * * * *

UNITED STATES PATENT AND TRADEMARK OFFICE
CERTIFICATE OF CORRECTION

PATENT NO. : 8,263,545 B2  
APPLICATION NO. : 11/840921  
DATED : September 11, 2012  
INVENTOR(S) : Levy et al.

Page 1 of 1

It is certified that error appears in the above-identified patent and that said Letters Patent is hereby corrected as shown below:

Title Page, Insert the Following:

--(60) U.S. Provisional Application No. 60/652,662 filed February 11, 2005;
U.S. Provisional Application No. 60/653,433 filed February 15, 2005;
U.S. Provisional Application No. 60/651,647 filed February 11, 2005;
U.S. Provisional Application No. 60/707,244 filed August 11, 2005:
U.S. Provisional Application No. 60/707,369 filed August 11, 2005;
U.S. Provisional Application No. 60/709,320 filed August 17, 2005;
U.S. Provisional Application No. 60/709,316 filed August 17, 2005.--.

Signed and Sealed this

Thirteenth Day of November, 2012

David J. Kappos
*Director of the United States Patent and Trademark Office*